(12) United States Patent
Ushio et al.

(10) Patent No.: US 9,150,555 B2
(45) Date of Patent: Oct. 6, 2015

(54) AMIDE DERIVATIVE AND USE THEREOF

(75) Inventors: Hiroyuki Ushio, Osaka (JP); Maiko Hamada, Osaka (JP); Masayuki Watanabe, Osaka (JP); Atsushi Numata, Osaka (JP); Naoto Fujie, Osaka (JP); Tooru Takashima, Yokohama (JP); Hiroyuki Furukawa, Osaka (JP); Junki Ando, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 149 days.

(21) Appl. No.: 13/879,475

(22) PCT Filed: Oct. 13, 2011

(86) PCT No.: PCT/JP2011/073532
§ 371 (c)(1),
(2), (4) Date: Apr. 15, 2013

(87) PCT Pub. No.: WO2012/050159
PCT Pub. Date: Apr. 19, 2012

(65) Prior Publication Data
US 2013/0211075 A1    Aug. 15, 2013

(30) Foreign Application Priority Data

Oct. 14, 2010    (JP) ................. 2010-231479

(51) Int. Cl.
| | | |
|---|---|---|
| A61K 31/47 | (2006.01) | |
| C07D 211/14 | (2006.01) | |
| C07D 405/14 | (2006.01) | |
| C07D 401/12 | (2006.01) | |
| C07D 401/14 | (2006.01) | |
| C07D 405/12 | (2006.01) | |
| C07D 417/12 | (2006.01) | |
| C07D 495/04 | (2006.01) | |

(52) U.S. Cl.
CPC ............ *C07D 405/14* (2013.01); *C07D 401/12* (2013.01); *C07D 401/14* (2013.01); *C07D 405/12* (2013.01); *C07D 417/12* (2013.01); *C07D 495/04* (2013.01)

(58) Field of Classification Search
CPC .................................................. C07D 211/14
USPC .......................................... 546/229; 514/318
See application file for complete search history.

(56) References Cited

U.S. PATENT DOCUMENTS

| 7,015,218 | B1 | 3/2006 | Ushio et al. |
| 2003/0203909 | A1 | 10/2003 | Ushio et al. |
| 2007/0123504 | A1 | 5/2007 | Bolin et al. |
| 2009/0093497 | A1 | 4/2009 | Bolin et al. |
| 2009/0099201 | A1 | 4/2009 | Bolin et al. |
| 2009/0105273 | A1 | 4/2009 | Bolin et al. |
| 2010/0093733 | A1 | 4/2010 | Barba et al. |
| 2010/0168419 | A1 | 7/2010 | Bolin et al. |
| 2010/0190979 | A1 | 7/2010 | Bolin et al. |

FOREIGN PATENT DOCUMENTS

| CN | 1346348 A | 4/2002 |
| CN | 101835757 A | 9/2010 |
| EP | 1 176 140 A1 | 1/2002 |
| EP | 1 310 488 A1 | 5/2003 |
| JP | 2002-338537 | 11/2002 |
| JP | 2003/176273 | 6/2003 |
| JP | 2009-517428 | 4/2009 |
| WO | WO 00/47558 A1 | 8/2000 |
| WO | WO 02/12189 A1 | 2/2002 |
| WO | WO 2004/002948 A1 | 1/2004 |
| WO | WO 2007/060140 A2 | 5/2007 |
| WO | WO 2007/060140 A3 | 5/2007 |
| WO | WO 2008/099221 A1 | 8/2008 |
| WO | WO 2008/141976 A1 | 11/2008 |

OTHER PUBLICATIONS

International Search Report issued Nov. 8, 2011 in PCT/JP2011/073532.
Written Opinion issued Nov. 8, 2011 in PCT/JP2011/073532 filed Oct. 13, 2011.
International Preliminary Report on Patentability issued May 16, 2013 in PCT/JP2011/073532 filed Oct. 13, 2011.
Maria Ziolkowska, et al., "High Levels of IL-17 in Rheumatoid Arthritis Patient:IL-15 Triggers in Vitro IL-17 Production Via Cyclosporin A-Sensitive Mechanism", The Journal of Immunology, 164, 2000, pp. 2823-2838.

(Continued)

*Primary Examiner* — John Mabry
(74) *Attorney, Agent, or Firm* — Oblon, McClelland, Maier & Neustadt, L.L.P.

(57) ABSTRACT

The present invention relates to a novel amide derivative. More specifically, the present invention provides a medicinal agent useful as a prophylactic or therapeutic agent for diseases, which relies on the production of cytokines from T cells, and which comprises an amide derivative or a pharmacologically acceptable salt thereof or a solvate of the derivative or the pharmacologically acceptable salt as an active ingredient. Provided is an amide derivative represented by general formula (I)

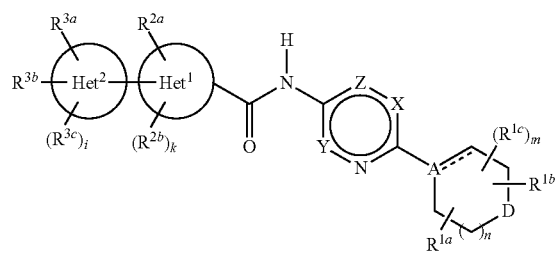

[wherein each symbol is as defined in the description] or a pharmacologically acceptable salt thereof, or a solvate of the derivative or the pharmacologically acceptable salt.

12 Claims, 1 Drawing Sheet

(56) References Cited

OTHER PUBLICATIONS

Susumu Nakae, et al., "Suppression of Immune Induction of Collagen-Induced Arthritis in IL-17-Deficient Mice", The Journal of Immunology, 2003, 171, pp. 6173-6177.

Erik Lubberts, et al., "Treatment With a Neutralizing Anti-Murine Interleukin-17 Antibody After the Onset of Collagen-Induced Arthritis Reduces Joint Inflammation, Cartilage Destruction, and Bone Erosion", Arthritis & Rheumatism, vol. 50, No. 2, Feb. 2004, pp. 650-659.

Erik Lubberts, "The Role of IL-17 and Family Members in the Pathogenesis of Arthritis", Current Opinion in Investigational Drugs, vol. 4, No. 5, 2003, pp. 572-577.

B. Afzali, et al., "The role of T helper 17 (Th17) and regulatory T cells (Treg) in human organ transplantation and autoimmune disease", Clinical and Experimental Immunology, 148, 2007, pp. 32-46.

Yutaka Komiyama, et al., "IL-17 Plays an Important Role in the Development of Experimental Autoimmune Encephalomyelitis", The Journal of Immunology, 2006, 177, pp. 566-573.

Zili Zhang, et al., "Critical Role of IL-17 Receptor Signaling in Acute TNBS-induced Colitis", Inflamm. Bowel Dis, vol. 12, No. 5, May 2006, pp. 382-388.

Susumu Nakae, et al.., "Antigen-Specific T Cell Sensitization Is Impaired in IL-17-Deficient Mice, Causing Suppression of Allergic Cellular and Humoral Responses", Immunity, vol. 17, 375-387, Sep. 2002, pp. 375-387.

Mi-La Cho, et al., "Cyclosporine a Inhibits IL-15-Induced IL-17 Production in CD4* T Cells Via Down-Regulation of PI3K/Akt and $Nf_{\kappa}b$", Immunology Letters, 108, 2007, pp. 88-96.

Cai Zhang, et al., "Cyclosporin A inhibits the production of IL-17 by memory Th17 cells from healthy individuals and patients with rheumatoid arthritis", Cytokine, Cytokine 42, 2008, pp. 345-352.

Hiroyuki Ushio, et al., "Phenylpyazoleanilides as Potent Inhibitor of IL-15 Dependent T Cell Proliferation. Part 2: Discovery of a New Drug Candidate, Y-320", Letters in Drug Design & Discovery, 2008, vol. 5, No. 4, pp. 292-296.

David A. Nugiel, et al., "De Novo Design of a Picomolar Nonbasic $5\text{-}HT_{1B}$ Receptor Antagonist", Journal of Medicinal Chemistry, 2010, vol. 53, No. 4, pp. 1876-1880.

Combined Chinese Office Action and Search Report issued Mar. 5, 2014, in Patent Application No. 201180057889.1 (with English-language translation).

U.S. Appl. No. 14/391,998, filed Oct. 10, 2014, Watanabe, et al.

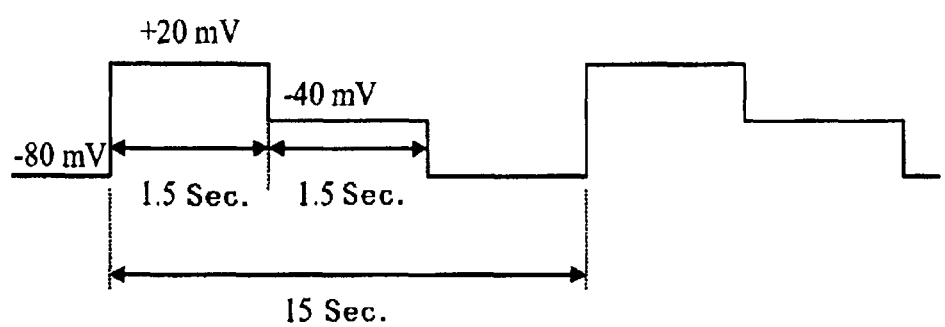

AMIDE DERIVATIVE AND USE THEREOF

CROSS-REFERENCE TO RELATED APPLICATIONS

This application is a National Stage of PCT/JP2011/073532 filed on Oct. 13, 2011. This application is based upon and claims the benefit of priority to Japanese Application No. 2010-231479 filed on Oct. 14, 2010.

BACKGROUND OF THE INVENTION

Technical Field

The present invention relates to novel amide derivatives. More specifically, the present invention relates to inhibitors for activated lymphocyte proliferation comprising as the active ingredient a novel amide derivative or a pharmacologically acceptable salt thereof, or a solvate thereof.

The present invention relates to useful amide compounds which enable the prophylaxis or treatment of autoimmune diseases and inflammatory/allergic diseases by inhibiting the production of cytokines from T cells, especially the production of Interleukin 17 (also referred to as "IL-17" hereinafter), and their medical use.

BACKGROUND ART

Autoimmune diseases are believed to be induced by the incomplete removal of self-reactive lymphocytes in thymus glands. Among them, rheumatoid arthritis (also referred to as "RA" hereinafter) is a progressive inflammatory disease where joint pain•swelling•inflammation spread systemically for unknown reasons, and subsequently deformity•destruction of joint becomes advanced as these conditions continue, and finally physical disability is triggered. A major pathology of RA is synovium, and synoviocytes that compose synovium are proliferated which gradually affects the surrounding cartilage•bone to cause destruction and deformity of joint.

IL-17, and IL-15 which induces the same have been confirmed in high concentrations in synovial fluid of RA patients, and have been indicated to be involved in inflammation, bone destruction (Nonpatent document 1). It has been also reported that the incidence of arthritis in IL-17-deficient mice is significantly suppressed compared to wild-type mice in type II collagen-induced arthritis model (Nonpatent document 2), and that the arthritis scores are significantly suppressed when anti-mouse IL-17-neutralizing antibody is prophylactically or therapeutically administered to type H collagen-induced mouse arthritis model (Nonpatent document 3), etc. IL-17 activates synoviocytes and chondrocytes to promote the production of cytokines or chemokines such as IL-1, TNF-γ and osteoclast differentiation factor (RANKL). Further, it has been considered to be involved in the induction of collagenolytic enzymes from these cells to induce joint destruction (Nonpatent document 4). Accordingly, it is considered that IL-17 is closely involved in the development and progress of rheumatoid arthritis.

In addition to rheumatoid arthritis, it has been recognized that IL-17 was produced or its expression was increased in multiple sclerosis, systemic lupus erythematosus, psoriasis, inflammatory bowel disease, transplantation rejection, asthma, etc. (Nonpatent document 5). It has been also reported that pathogenesis of mouse experimental encephalomyelitis (EAE) in IL-17-deficient mice is significantly suppressed compared to wild-type mice in EAE model (Nonpatent document 6), and inflammation of bowel in IL-17R-deficient mice is also reduced in TNBS-induced mouse enteritis model as well (Nonpatent document 7). Further, each reaction in IL-17-deficient mice was also reduced compared to wild-type mice in trinitrochlorobenzene-induced contact-type hypersensitivity, methylated bovine serum albumin-induced delayed-type hypersensitivity and ovalbumin-induced reactive airway disease (Nonpatent document 8). These facts indicated that IL-17 is also involved in autoimmune diseases and inflammatory/allergic diseases such as multiple sclerosis, systemic lupus erythematosus, psoriasis, inflammatory bowel disease.

Accordingly, it is considered that controlling the production of IL-17 from T cells would be useful for a prophylactic or therapeutic agent for autoimmune diseases and inflammatory/allergic diseases such as multiple sclerosis, systemic lupus erythematosus, psoriasis, inflammatory bowel disease as well as rheumatoid arthritis.

As mentioned above, it has been indicated that IL-17 generated from T cells is deeply involved in various autoimmune diseases and inflammatory/allergic diseases including rheumatoid arthritis. Hence, it is believed that compounds controlling the production of IL-17 from T cells would show remarkable effects on prophylaxis or treatment of various autoimmune diseases and inflammatory/allergic diseases.

Cyclosporin has been known as a compound controlling the production of IL-17 (Nonpatent documents 9, 10). Cyclosporin inhibits the activation of calcineurin by forming a complex with intracellular binding protein, cyclopholin. As a result, the translocation to a nuclear by dephosphorylation of transcription factor NF-AT of IL-2, etc. is inhibited, and the production of cytokines from T cells is suppressed. Therapeutic effects for autoimmune diseases have been already recognized, but side effects such as renal disorder have been seen as a problem. A therapeutic agent for autoimmune diseases with showing more remarkable therapeutic effects and with fewer side effects has been desired especially in RA area, etc. for which prolonged administration is required.

On the other hand, specific amide derivatives with lymphocytic antiproliferative effects have been reported in Nonpatent document 11 and Patent documents 1 to 4, nevertheless, they have different structures from the present invention. In Patent documents 5 to 7, no lymphocytic antiproliferative effects are mentioned, and compounds with different structures from the present invention are reported.

BACKGROUND ART DOCUMENTS

Patent Documents

[Patent document 1] WO 00/047558
[Patent document 2] WO 02/012189
[Patent document 3] JP-A-2002-338537
[Patent document 4] WO 04/002948
[Patent document 5] WO 07/060,140
[Patent document 6] WO 08/099,221
[Patent document 7] WO 08/141,976

Nonpatent Documents

[Nonpatent document 1] J. Immunol. vol. 164, pp. 2832-2838, 2000
[Nonpatent document 2] J. Immunol. vol. 171, pp. 6173-6177, 2003
[Nonpatent document 3] Arithritis & Rheum. vol. 50, pp. 650-659, 2004

[Nonpatent document 4] Current Opinion in Investigtional Drugs, vol. 4, pp. 572-577, 2003
[Nonpatent document 5] Clinical and Experimental Immunol. vol. 148, pp. 32-46, 2007
[Nonpatent document 6] J. Immunol. vol. 177, pp. 566-573, 2006
[Nonpatent document 7] Inflamm. Bowel Dis. vol. 12, pp. 382-388, 2006
[Nonpatent document 8] Immunity vol. 17, pp. 375-387, 2002
[Nonpatent document 9] Immunol Lett. vol. 108, pp. 88-96, 2007
[Nonpatent document 10] Cytokine vol. 42, pp. 345-352, 2008
[Nonpatent document 11] Letters in Drug Design & Discovery, vol. 5, pp. 292-296, 2008

SUMMARY OF INVENTION

Problems to be Solved by the Invention

The problem to be solved by the present invention is the provision of amide derivatives or pharmacologically acceptable salts thereof or solvates thereof as well as IL-17 production inhibitors which are useful for prevention or treatment of diseases involving IL-17 production.

Means of Solving the Problems

The present inventors have made intensive studies to solve the above problems, and then have found that specific amide derivatives may achieve the desired objects such as inhibition of IL-17 production from T cells and avoidance of toxicities typified by hERG inhibitory activity and have achieved the present invention.

Specifically, the present invention relates to the following amide derivatives or pharmacologically acceptable salts thereof, or solvates thereof, and their use.

The present invention relates to pharmaceuticals, especially to useful amide compounds which enable the prophylaxis or treatment of autoimmune diseases and inflammatory/allergic diseases by controlling or inhibiting the production of Interleukin 17 (IL-17), and their medical use.

(1) An amide derivative of the following general formula (I):

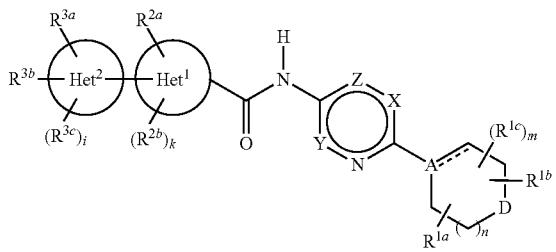

wherein $R^{1a}$, $R^{1b}$ and $R^{1c}$ are each independently selected from hydrogen atom, halogen atom, cyano group, hydroxy group, amino group, alkylamino group, optionally substituted alkyl group, or optionally substituted alkoxy group, n is an integer of 0 to 3,
m is an integer of 0 to 3, $Het^1$ is thiazolyl group, isothiazolyl group, isoxazolyl group, thiadiazolyl group, oxadiazolyl group, furyl group, thienyl group, pyrrolyl group, pyrazolyl group, imidazolyl group, triazolyl group, pyridyl group, pyridazinyl group, pyrimidinyl group, pyrazinyl group, triazinyl group, cycloalkyl group, heterocycle group, indolyl group, indazolyl group, benzimidazolyl group, benzisoxazolyl group, benzisothiazolyl group, benzoxazolyl group, benzothiazolyl group, quinolyl group, quinazolyl group, isoquinolyl group, quinoxalyl group, cinnolyl group, pyrrolopyrimidinyl group, pyrrolopyridyl group, imidazopyridyl group, or imidazopyrimidyl group, $Het^2$ is cycloalkyl group, aryl group, heterocycle group, or heteroaryl group, alternatively, $Het^1$ may be optionally combined with $Het^2$ to form a condensed ring, $R^{2a}$, $R^{2b}$, $R^{3a}$, $R^{3b}$ and $R^{3c}$ are each independently selected from hydrogen atom, halogen atom, cyano group, hydroxy group, optionally substituted alkyl group, optionally substituted alkenyl group, optionally substituted alkynyl group, optionally substituted cycloalkyl group, optionally substituted heterocycle group, optionally substituted aryl group, optionally substituted heteroaryl group, —O—$R^{4a}$, —$NR^{4a}R^{4b}$, —CO—$R^{4a}$, —NHCO—$R^{4a}$, —SO—$R^{4a}$, —S—$R^{4a}$, —$SO_2$—$R^{4a}$, —$CONR^{4a}R^{4b}$, —NH—CO—$NR^{4a}R^{4b}$, —NH—CO—O—$R^{4a}$, or —O—CO—$NR^{4a}R^{4b}$ (in which $R^{4a}$ and $R^{4b}$ are each independently selected from hydrogen atom, alkyl group, alkoxyalkyl group, hydroxyalkyl group, haloalkyl group, aminoalkyl group, optionally substituted cycloalkyl group, optionally substituted aryl group, optionally substituted heterocycle group, or optionally substituted heteroaryl, or $R^{4a}$ and $R^{4b}$ are optionally combined together to form an optionally substituted heterocycle group), i is an integer of 0 to 3,
k is an integer of 0 to 2,
X is N or C—$R^5$, $R^5$ is hydrogen atom, halogen atom, hydroxy group, cyano group, optionally substituted alkyl group, optionally substituted alkenyl group, optionally substituted alkynyl group, optionally substituted cycloalkyl group, optionally substituted aryl group, optionally substituted heterocycle group, optionally substituted heteroaryl group, —O—$R^{6a}$, —$NR^{6a}R^{6b}$, —CO—$R^{6a}$, —CO—O—$R^{6a}$, —$N(R^{6c})$—CO—$R^{6a}$, —$SO_2$—$R^{6a}$, —S—$R^{6a}$, —SO—$R^{6a}$, —CO—$NR^{6a}R^{6b}$, —$N(R^{6c})$—CO—$NR^{6a}R^{6b}$, or —$N(R^{6c})$—CO—O—$R^{6a}$ (in which $R^{6a}$, $R^{6b}$ and $R^{6c}$ are each independently selected from hydrogen atom, alkyl group, haloalkyl group, aminoalkyl group, hydroxyalkyl group, alkenyl group, alkynyl group, optionally substituted cycloalkyl group, optionally substituted heterocycle group, optionally substituted cycloalkylalkyl group, or optionally substituted heterocyclic alkyl group, or $R^{6a}$ and $R^{6b}$ are optionally combined together to form an optionally substituted heterocycle group), Y and Z are each independently selected from N or C—$R^7$ (in which $R^7$ is hydrogen atom, halogen atom, cyano group, optionally substituted alkyl group, or optionally substituted alkoxy group), ⸺ is a single bond or a double bond, A is carbon atom or C—$R^8$, $R^8$ is hydrogen atom, halogen atom, hydroxy group, cyano group, optionally substituted alkyl group, optionally substituted alkenyl group, optionally substituted alkynyl group, optionally substituted cycloalkyl group, optionally substituted aryl group, optionally substituted heterocycle group, optionally substituted heteroaryl group, —O—$R^{9a}$, —$NR^{9a}R^{9b}$, —CO—$R^{9a}$, —CO—O—$R^{9a}$, —$NR^{9c}$—CO—$R^{9a}$, —$SO_2$—$R^{9a}$, —S—$R^{9a}$, —SO—$R^{9a}$, —CO—$NR^{9a}R^{9b}$, —$NR^{9c}$—CO—$NR^{9a}R^{9b}$, or —$NR^{9c}$—CO—O—$R^{9a}$ (in which $R^{9a}$, $R^{9b}$ and $R^{9c}$ are each independently selected from hydrogen atom, alkyl group, haloalkyl group, aminoalkyl group, hydroxyalkyl group, alkenyl group, alkynyl group, optionally substituted cycloalkyl group, optionally substituted heterocycle group, optionally substituted cycloalkylalkyl group or optionally substituted heterocyclic alkyl group, or $R^{9a}$ and $R^{9b}$ are optionally combined together to form an optionally substituted heterocycle group), D is any one of groups of the following general formulae:

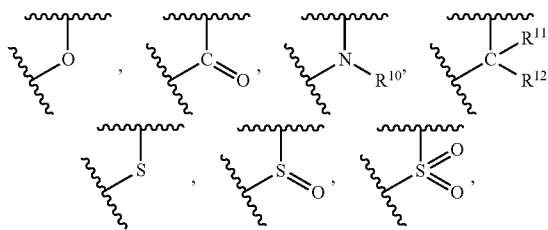

$R^{10}$ is hydrogen atom, alkyl group, haloalkyl group, alkoxyalkyl group, hydroxyalkyl group, carboxyalkyl group, aminoalkyl group, -$L^{1a}$-$R^{13}$ (in which $R^{13}$ is optionally substituted cycloalkyl group, optionally substituted aryl group, optionally substituted heterocycle group, or optionally substituted heteroaryl group), -$L^{1b}$-O—$R^{14}$, -$L^{1b}$-O—CO—$R^{14}$, -$L^{1b}$-O—Si($R^{15}R^{16}$)—$R^{14}$, -$L^{1a}$-SO$_2$—$R^{14}$, -$L^{1a}$-SO$_2$-NR$^{14}R^{15}$, -$L^{1a}$-SO—$R^{14}$, -$L^{1b}$-S—$R^{14}$, -$L^{1b}$-NR$^{14}R^{15}$, -$L^{1b}$-N($R^{16}$)—CO—$R^{14}$, -$L^{1a}$-CO—$R^{14}$, -$L^{1a}$-CO—O—$R^{14}$, -$L^{1a}$-CO—NR$^{14}R^{15}$, -$L^{1b}$-N($R^{16}$)—CO—O—$R^{14}$, -$L^{1b}$-O—CO—NR$^{14}R^{15}$, or -$L^{1b}$-N($R^{16}$)—CO—NR$^{14}R^{15}$

[in which $L^{1a}$ is a bond, or —(CR$_A$R$_B$)$_j$— (in which j is an integer of 1-4, R$_A$ and R$_B$ are each independently selected from hydrogen atom or alkyl group), $L^{1b}$ is —(CR$_A$R$_B$)$_j$— (in which j, R$_A$ and R$_B$ are the same as defined above), $R^{14}$, $R^{15}$ and $R^{16}$ are each independently selected from hydrogen atom, alkyl group, alkoxyalkyl group, hydroxyalkyl group, haloalkyl group, aminoalkyl group, optionally substituted cycloalkyl group, optionally substituted aryl group, optionally substituted heterocycle group, hydroxyalkyloxyalkyl group, haloalkyloxyalkyl group, carboxylalkyl group, alkyloxycarbonylalkyl group, alkylcarbonylalkyl group, alkylaminoalkyl group, amidealkyl group, alkylamideakyl group, alkylcarbonylaminoalkyl group, alkylsulfonylalkyl group, alkylsulfoxyalkyl group, alkylsulfidealkyl group, optionally substituted cycloalkyloxyalkyl group, optionally substituted heterocyclic oxyalkyl group, optionally substituted cycloalkylalkoxyalkyl group, or optionally substituted heterocyclic alkoxyalkyl group, or $R^{14}$ and $R^{15}$ are optionally combined together to form an optionally substituted heterocycle group], $R^{11}$ and $R^{12}$ are each independently selected from hydrogen atom, halogen atom, hydroxy group, alkyl group, haloalkyl group, alkoxyalkyl group, hydroxyalkyl group, carboxylalkyl group, aminoalkyl group, alkenyl group, -$L^{1a}$-$R^{13}$ (in which $R^{13}$ is the same as defined above), -$L^{1a}$-O—$R^{14}$, -$L^{1a}$-O—Si($R^{15}R^{16}$)—$R^{14}$, -$L^{1a}$-O—CO—NR$^{14}R^{15}$, -$L^{1a}$-CO—$R^{14}$, -$L^{1a}$-CO—NR$^{14}R^{15}$, -$L^{1a}$-SO$_2$—$R^{14}$, -$L^{1a}$-SO$_2$-NR$^{14}R^{15}$, -$L^{1a}$-SO—$R^{14}$, -$L^{1a}$-S—$R^{14}$, -$L^{1a}$-NR$^{14}R^{15}$, -$L^{1a}$-NR$^{16}$)—CO—$R^{14}$, -$L^{1a}$-N($R^{16}$)—CO—O—$R^{14}$, or -$L^{1a}$-N($R^{16}$)—CO—NR$^{14}R^{15}$ (in which $L^{1a}$, $L^{1b}$, $R^{14}$, $R^{15}$ and $R^{16}$ are the same as defined above), or $R^{11}$ and $R^{12}$ are optionally combined together to form an optionally substituted cycloalkyl group, or optionally substituted heterocycle group, or a pharmacologically acceptable salt thereof.

(2) The amide derivative of the above (1), wherein Het$^1$ is a group selected from thiazolyl group, furyl group, thienyl group, pyrrolyl group, pyrazolyl group, imidazolyl group, triazolyl group, pyridyl group, or indolyl group, or a pharmacologically acceptable salt thereof.

(3) The amide derivative of the above (2), wherein Y and Z are C—R$^7$, or a pharmacologically acceptable salt thereof.

(4) The amide derivative of the above (3), wherein X is C—R$^5$, or a pharmacologically acceptable salt thereof.

(5) The amide derivative of the above (4), wherein Het$^2$ is aryl group or heteroaryl group, or a pharmacologically acceptable salt thereof (6) The amide derivative of the above (5), wherein ---- in the general formula (I) is a single bond, and A is C—R$^8$, or a pharmacologically acceptable salt thereof.

(7) The amide derivative of the above (5), wherein ---- in the general formula (I) is a double bond, and A is carbon atom, or a pharmacologically acceptable salt thereof (8) A compound selected from the following group:
N-{6-[1-cyano-4-(morpholin-4-yl)cyclohexyl]pyridin-3-yl}-5-methyl-1-[5-(trifluoromethyl)-pyridin-2-yl]-1H-pyrazole-4-carboxamide;
N-{6-[1-cyano-4-(morpholin-4-yl)cyclohexyl]pyridin-3-yl}-5-methyl-1-(4-methylphenyl)-1H-pyrazole-4-carboxamide;
N-{6-[1-cyano-4-(methoxymethoxy)cyclohexyl]pyridin-3-yl}-5-methyl-1-(4-methylphenyl)-1H-pyrazole-4-carboxamide;
5-methyl-N-{6-[4-(morpholin-4-yl)cyclohexyl]pyridin-3-yl}-1-[5-(trifluoromethyl)pyridin-2-yl]-1H-pyrazole-4-carboxamide;
N-{6-[1-cyano-4-(morpholin-4-yl)cyclohexyl]pyridin-3-yl}-1-(3,5-dichloropyridin-2-yl)-5-methyl-1H-pyrazole-4-carboxamide;
N-{6-[4-cyano-1-(2-methyltetrahydrofuran-3-yl)piperidin-4-yl]pyridin-3-yl}-5-methyl-1-[5-(trifluoromethyl)pyridin-2-yl]-1H-pyrazole-4-carboxamide;
N-{6-[4-cyano-1-(2-methyltetrahydrofuran-3-yl)piperidin-4-yl]pyridin-3-yl}-1-(5-cyclopropylpyridin-2-yl)-5-methyl-1H-pyrazole-4-carboxamide;
N-{6-[4-cyano-1-(2-methyltetrahydrofuran-3-yl)piperidin-4-yl]pyridin-3-yl}-5-methyl-1-[4-(trifluoromethyl)phenyl]-1H-pyrazole-4-carboxamide;
N-{6-[1-cyano-4-(3-hydroxypyrrolidin-1-yl)cyclohexyl]pyridin-3-yl}-5-methyl-1-[5-(trifluoromethyl)pyridin-2-yl]-1H-pyrazole-4-carboxamide;
N-{6-[1-cyano-4-(morpholin-4-yl)cyclohexyl]pyridin-3-yl}-1-[3-fluoro-5-(trifluoromethyl)-pyridin-2-yl]-5-methyl-1H-pyrazole-4-carboxamide;
N-{6-[1-cyano-4-methoxycyclohexyl]pyridin-3-yl}-5-methyl-1-(4-methylphenyl)-1H-pyrazole-4-carboxamide;
5-methyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide;
N-{6-[1-cyano-4-(morpholin-4-yl)cyclohexyl]pyridin-3-yl}-1-(5-isopropylpyridin-2-yl)-5-methyl-1H-pyrazole-4-carboxamide;
N-{6-[1-hydroxy-4-(morpholin-4-yl)cyclohexyl]pyridin-3-yl}-5-methyl-1-[5-(trifluoromethyl)-pyridin-2-yl]-1H-pyrazole-4-carboxamide;
1-(4-chlorophenyl)-N-[6-(1-cyano-4-hydroxycyclohexyl)pyridin-3-yl]-5-methyl-1H-pyrazole-4-carboxamide;
N-[6-(1-cyano-4-hydroxycyclohexyl)pyridin-3-yl]-1-(4-fluorophenyl)-5-methyl-1H-pyrazole-4-carboxamide;
N-[6-(1-cyano-4-hydroxycyclohexyl)pyridin-3-yl]-5-methyl-1-(4-methylphenyl)-1H-pyrazole-4-carboxamide;

1-(4-tert-butylphenyl)-N-[6-(4-hydroxycyclohexyl)pyridin-3-yl]-5-methyl-1H-pyrazole-4-carboxamide;

N-[6-(4-hydroxycyclohexyl)-5-methylpyridin-3-yl]-5-methyl-1-[5-(trifluoromethyl)pyridin-2-yl]-1H-pyrazole-4-carboxamide;

N-{6-[1-cyano-4-(2-hydroxyethoxy)cyclohexyl]pyridin-3-yl}-5-methyl-1-(4-methylphenyl)-1H-pyrazole-4-carboxamide;

N-[6-(8-cyano-1-oxaspiro[4.5]dec-8-yl)pyridin-3-yl]-5-methyl-1-[5-(trifluoromethyl)pyridin-2-yl]-1H-pyrazole-4-carboxamide;

N-(6-{1-cyano-4-[N-(2,2-dimethylpropanoyl)-N-methylamino]cyclohexan-1-yl}pyridin-3-yl)-5-methyl-1-[5-(trifluoromethyl)pyridin-2-yl]-1H-pyrazole-4-carboxamide;

N-{6-[1-cyano-4-(N-isobutyryl-N-methylamino)cyclohexan-1-yl]pyridin-3-yl}-5-methyl-1-[5-(trifluoromethyl)pyridin-2-yl]-1H-pyrazole-4-carboxamide;

N-{6-[1-cyano-4-(3-hydroxypyrrolidin-1-yl)cyclohex-1-yl]pyridin-3-yl}-5-methyl-1-[4-(trifluoromethyl)phenyl]-1H-pyrazole-4-carboxamide;

N-{6-[1-cyano-4-(morpholin-4-yl)cyclohexyl]pyridin-3-yl}-5-isopropyl-1-[5-(trifluoromethyl)pyridin-2-yl]-1H-pyrazole-4-carboxamide;

N-[6-(1-cyano-4-ethoxycyclohex-1-yl)pyridin-3-yl]-5-methyl-1-[5-(trifluoromethyl)pyridin-2-yl]-1H-pyrazole-4-carboxamide;

1-[3-fluoro-5-(trifluoromethyl)pyridin-2-yl]-N-[6-(1-hydroxycyclohexan-4-yl)-5-methylpyridin-3-yl]-5-methyl-1H-pyrazole-4-carboxamide;

1-[3-chloro-5-(trifluoromethyl)pyridin-2-yl]-N-[6-(1-hydroxycyclohexan-4-yl)-5-methylpyridin-3-yl]-5-methyl-1H-pyrazole-4-carboxamide;

N-[6-(1-fluoro-4-hydroxycyclohexan-1-yl)pyridin-3-yl]-5-methyl-1-[5-(trifluoromethyl)-pyridin-2-yl]-1H-pyrazole-4-carboxamide;

N-[6-(4-hydroxycyclohexan-1-yl)pyridin-3-yl]-5-methyl-1-[5-(trifluoromethyl)pyridin-2-yl]-1H-pyrazole-4-carboxamide; and N-[6-(1-cyano-4-ethyl-4-hydroxycyclohexan-1-yl)pyridin-3-yl]-1-(4-fluorophenyl)-5-methyl-1H-pyrazole-4-carboxamide, or a pharmacologically acceptable salt thereof.

(9) A compound selected from the following group:

N-{6-[r-1-cyano-c-4-(morpholin-4-yl)cyclohexyl]pyridin-3-yl}-5-methyl-1-[5-(trifluoromethyl)pyridin-2-yl]-1H-pyrazole-4-carboxamide;

N-{6-[r-1-cyano-c-4-(morpholin-4-yl)cyclohexyl]pyridin-3-yl}-5-methyl-1-(4-methylphenyl)-1H-pyrazole-4-carboxamide;

N-{6-[r-1-cyano-c-4-(methoxymethoxy)cyclohexyl]pyridin-3-yl}-5-methyl-1-(4-methylphenyl)-1H-pyrazole-4-carboxamide;

1-(5-cyclopropylpyridin-2-yl)-5-methyl-N-{6-[4-(morpholin-4-yl)cyclohex-1-en-1-yl]pyridin-3-yl}-1H-pyrazole-4-carboxamide;

trans-5-methyl-N-{6-[4-(morpholin-4-yl)cyclohexyl]pyridin-3-yl}-1-[5-(trifluoromethyl)-pyridin-2-yl]-1H-pyrazole-4-carboxamide;

N-{6-[r-1-cyano-c-4-(morpholin-4-yl)cyclohexyl]pyridin-3-yl}-1-(3,5-dichloropyridin-2-yl)-5-methyl-1H-pyrazole-4-carboxamide;

cis-N-{6-[4-cyano-1-(2-methyltetrahydrofuran-3-yl)piperidin-4-yl]pyridin-3-yl}-5-methyl-1-[5-(trifluoromethyl)pyridin-2-yl]-1H-pyrazole-4-carboxamide;

N-{6-[4-cyano-1-(2-hydroxy-2-methylpropyl)piperidin-4-yl]pyridin-3-yl}-5-methyl-1-[5-(trifluoromethyl)pyridin-2-yl]-1H-pyrazole-4-carboxamide;

cis-N-{6-[4-cyano-1-(2-methyltetrahydrofuran-3-yl)piperidin-4-yl]pyridin-3-yl}-1-(5-cyclopropylpyridin-2-yl)-5-methyl-1H-pyrazole-4-carboxamide;

cis-N-{6-[4-cyano-1-(2-methyltetrahydrofuran-3-yl)piperidin-4-yl]pyridin-3-yl}-5-methyl-1-[4-(trifluoromethyl)phenyl]-1H-pyrazole-4-carboxamide;

N-{6-[4-cyano-1-(2-hydroxy-2-methylpropyl)piperidin-4-yl]pyridin-3-yl}-1-(5-cyclopropylpyridin-2-yl)-5-methyl-1H-pyrazole-4-carboxamide;

N-{6-[r-1-cyano-c-4-(3-hydroxypyrrolidin-1-yl)cyclohexyl]pyridin-3-yl}-5-methyl-1-[5-(trifluoromethyl)pyridin-2-yl]-1H-pyrazole-4-carboxamide;

N-{6-[r-1-cyano-c-4-(morpholin-4-yl)cyclohexyl]pyridin-3-yl}-1-[3-fluoro-5-(trifluoromethyl)pyridin-2-yl]-5-methyl-1H-pyrazole-4-carboxamide;

N-{6-[r-1-cyano-c-4-methoxycyclohexyl]pyridin-3-yl}-5-methyl-1-(4-methylphenyl)-1H-pyrazole-4-carboxamide;

1-[5-chloro-3-fluoropyridin-2-yl]-5-methyl-N-{5-methyl-6-[4-(morpholin-4-yl)cyclohex-1-en-1-yl]pyridin-3-yl}-1H-pyrazole-4-carboxamide;

5-methyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide;

(R)-5-methyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide;

(S)-5-methyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide;

N-[6-(4-hydroxycyclohex-1-en-1-yl)-5-methyl-pyridin-3-yl]-5-methyl-1-[5-(trifluoromethyl)-pyridin-2-yl]-1H-pyrazole-4-carboxamide;

1-[3-fluoro-5-(trifluoromethyl)pyridin-2-yl]-5-methyl-N-{5-methyl-6-[4-(morpholin-4-yl)cyclohex-1-en-1-yl]pyridin-3-yl}-1H-pyrazole-4-carboxamide;

1-[3-fluoro-5-(trifluoromethyl)pyridin-2-yl]-5-methyl-N-[5-methyl-6-(4-hydroxycyclohex-1-en-1-yl)pyridin-3-yl]-1H-pyrazole-4-carboxamide;

N-{6-[r-1-cyano-c-4-(morpholin-4-yl)cyclohexyl]pyridin-3-yl}-1-(5-isopropylpyridin-2-yl)-5-methyl-1H-pyrazole-4-carboxamide;

5-methyl-N-{6-[4-(morpholin-4-yl)cyclohex-1-en-1-yl]pyridin-3-yl}-1-[5-(trifluoromethyl)-pyridin-2-yl]-1H-pyrazole-4-carboxamide;

N-{6-[r-1-hydroxy-c-4-(morpholin-4-yl)cyclohexyl]pyridin-3-yl}-5-methyl-1-[5-(trifluoromethyl)pyridin-2-yl]-1H-pyrazole-4-carboxamide;

N-[6-(1-cyano-4-oxocyclohexyl)pyridin-3-yl]-5-methyl-1-[5-(trifluoromethyl)pyridin-2-yl]-1H-pyrazole-4-carboxamide;

1-(4-chlorophenyl)-N-[6-(r-1-cyano-c-4-hydroxycyclohexyl)pyridin-3-yl]-5-methyl-1H-pyrazole-4-carboxamide;

N-[6-(r-1-cyano-c-4-hydroxycyclohexyl)pyridin-3-yl]-1-(4-fluorophenyl)-5-methyl-1-pyrazole-4-carboxamide;

N-[6-(r-1-cyano-c-4-hydroxycyclohexyl)pyridin-3-yl]-5-methyl-1-(4-methylphenyl)-1H-pyrazole-4-carboxamide;

trans-1-(4-tert-butylphenyl)-N-[6-(4-hydroxycyclohexyl)pyridin-3-yl]-5-methyl-1H-pyrazole-4-carboxamide;

N-[6-(4-hydroxycyclohex-1-en-1-yl)-5-methylpyridin-3-yl]-5-methyl-1-[4-(trifluoromethyl)-phenyl]-1H-pyrazole-4-carboxamide;

trans-N-[6-(4-hydroxycyclohexyl)-5-methylpyridin-3-yl]-5-methyl-1-[5-(trifluoromethyl)-pyridin-2-yl]-1H-pyrazole-4-carboxamide;

N-{6-[r-1-cyano-c-4-(2-hydroxyethoxy)cyclohexyl]pyridin-3-yl}-5-methyl-1-(4-methylphenyl)-1H-pyrazole-4-carboxamide;

N-[6-(3,6-dihydro-2H-pyran-4-yl)-5-methylpyridin-3-yl]-5-methyl-1-[4-(trifluoromethyl)phenyl]-1H-pyrazole-4-carboxamide;

N-{6-[4-(N-isobutyryl-N-methylamino)cyclohex-1-en-1-yl]-5-methylpyridin-3-yl}-5-methyl-1-[5-(trifluoromethyl)pyridin-2-yl]-1H-pyrazole-4-carboxamide;

N-(6-{4-[N-(2,2-dimethylpropion-1-yl)-N-methylamino]cyclohex-1-en-1-yl}-5-methylpyridin-3-yl)-5-methyl-1-(pyridin-2-yl)-1H-pyrazole-4-carboxamide;

1-(4-fluorophenyl)-N-{6-[4-(N-isobutyryl-N-methylamino)cyclohex-1-en-1-yl]-5-methylpyridin-3-yl}-5-methyl-1H-pyrazole-4-carboxamide;

N-[6-(4-N,N-dimethylcarbamoylcyclohex-1-en-1-yl)-5-methylpyridin-3-yl]-5-methyl-1-[5-(trifluoromethyl)pyridin-2-yl]-1H-pyrazole-4-carboxamide;

1-(5-cyclopropylpyridin-2-yl)-N-[6-(4-N,N-dimethylcarbamoylcyclohex-1-en-1-yl)-5-methylpyridin-3-yl]-5-methyl-1H-pyrazole-4-carboxamide;

3-methyl-N-{5-methyl-6-[4-(morpholin-4-yl)cyclohex-1-en-1-yl]pyridin-3-yl}-2-[4-(trifluoromethyl)phenyl]-3H-imidazole-4-carboxamide;

N-{5-methyl-6-[4-(morpholin-4-yl)cyclohex-1-en-1-yl]pyridin-3-yl}-2-[4-(trifluoromethyl)-phenyl]thiazole-4-carboxamide;

5-methyl-N-(5-methyl-6-{4-[N-methyl-N-(2,2,2-trifluoroacetyl)amino]cyclohex-1-en-1-yl}pyridin-3-yl)-1-[5-(trifluoromethyl)pyridin-2-yl]-1H-pyrazole-4-carboxamide;

N-[6-(c-8-cyano-r-1-oxaspiro[4.5]dec-8-yl)pyridin-3-yl]-5-methyl-1-[5-(trifluoromethyl)-pyridin-2-yl]-1H-pyrazole-4-carboxamide;

N-(6-{r-1-cyano-c-4-[N-(2,2-dimethylpropanoyl)-N-methylamino]cyclohexan-1-yl}pyridin-3-yl)-5-methyl-1-[5-(trifluoromethyl)pyridin-2-yl]-1H-pyrazole-4-carboxamide;

N-{6-[r-1-cyano-c-4-(N-isobutyryl-N-methylamino)cyclohexan-1-yl]pyridin-3-yl}-5-methyl-1-[5-(trifluoromethyl)pyridin-2-yl]-1H-pyrazole-4-carboxamide;

5-methyl-N-{5-methyl-6-[4-(morpholin-4-yl)cyclohex-1-en-1-yl]pyridin-3-yl}-1-[4-methyl-5-(trifluoromethyl)pyridin-2-yl]-1H-pyrazole-4-carboxamide;

N-{6-[r-1-cyano-c-4-(3-hydroxypyrrolidin-1-yl)cyclohex-1-yl]pyridin-3-yl}-5-methyl-1-[4-(trifluoromethyl)phenyl]-1H-pyrazole-4-carboxamide;

N-{6-[r-1-cyano-c-4-(morpholin-4-yl)cyclohexyl]pyridin-3-yl}-5-isopropyl-1-[5-(trifluoromethyl)pyridin-2-yl]-1H-pyrazole-4-carboxamide;

5-isopropyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide;

5-methyl-N-{5-methyl-6-[4-(3-oxomorpholin-4-yl)cyclohex-1-en-1-yl]pyridin-3-yl}-1-[5-(trifluoromethyl)pyridin-2-yl]-1H-pyrazole-4-carboxamide;

N-[6-(r-1-cyano-c-4-ethoxycyclohex-1-yl)pyridin-3-yl]-5-methyl-1-[5-(trifluoromethyl)-pyridin-2-yl]-1H-pyrazole-4-carboxamide;

1-[3-fluoro-5-(trifluoromethyl)pyridin-2-yl]-5-methyl-N-[5-methyl-6-(4-oxocyclohex-1-yl)pyridin-3-yl]-1H-pyrazole-4-carboxamide;

1-[3-chloro-5-(trifluoromethyl)pyridin-2-yl]-5-methyl-N-[5-methyl-6-(4-oxocyclohex-1-yl)pyridin-3-yl]-1H-pyrazole-4-carboxamide;

N-[6-(1-fluoro-4-oxocyclohexan-1-yl)pyridin-3-yl]-5-methyl-1-[5-(trifluoromethyl)pyridin-2-yl]-1H-pyrazole-4-carboxamide;

trans-1-[3-fluoro-5-(trifluoromethyl)pyridin-2-yl]-N-[6-(1-hydroxycyclohexan-4-yl)-5-methylpyridin-3-yl]-5-methyl-1H-pyrazole-4-carboxamide;

trans-1-[3-chloro-5-(trifluoromethyl)pyridin-2-yl]-N-[6-(1-hydroxycyclohexan-4-yl)-5-methylpyridin-3-yl]-5-methyl-1H-pyrazole-4-carboxamide;

N-[6-(c-1-fluoro-r-4-hydroxycyclohexan-1-yl)pyridin-3-yl]-5-methyl-1-[5-(trifluoromethyl)-pyridin-2-yl]-1H-pyrazole-4-carboxamide;

trans-N-[6-(4-hydroxycyclohexan-1-yl)pyridin-3-yl]-5-methyl-1-[5-(trifluoromethyl)pyridin-2-yl]-1H-pyrazole-4-carboxamide;

N-(6-{4-[N-(2,2-dimethylpropion-1-yl)-N-methylamino]cyclohex-1-en-1-yl}-5-methylpyridin-3-yl)-5-methyl-1-[5-(trifluoromethyl)pyridin-2-yl]-1H-pyrazole-4-carboxamide;

N-{6-[4-(1-hydroxy-1-methylethyl)cyclohex-1-en-1-yl]-5-methylpyridin-3-yl}-5-methyl-1-[5-(trifluoromethyl)pyridin-2-yl]-1H-pyrazole-4-carboxamide;

N-[6-(r-1-cyano-4-ethyl-c-4-hydroxycyclohexan-1-yl)pyridin-3-yl]-1-(4-fluorophenyl)-5-methyl-1H-pyrazole-4-carboxamide;

5-methyl-N-{5-[4-(morpholin-4-yl)cyclohex-1-en-1-yl]pyrazin-2-yl}-1-[5-(trifluoromethyl)-pyridin-2-yl]-1H-pyrazole-4-carboxamide;

N-{5-cyano-6-[4-(morpholin-4-yl)cyclohex-1-en-1-yl]pyridin-3-yl}-5-methyl-1-[5-(trifluoromethyl)pyridin-2-yl]-1H-pyrazole-4-carboxamide;

N-{6-[1-(2,2-dimethylpropanoyl)-1,2,3,6-tetrahydropyridin-4-yl]-5-methylpyridin-3-yl}-5-methyl-1-[5-(trifluoromethyl)pyridin-2-yl]-1H-pyrazole-4-carboxamide;

5-methyl-N-{5-methyl-6-[1-(propane-2-sulfonyl)-1,2,3,6-tetrahydropyridin-4-yl]pyridin-3-yl}-1-[5-(trifluoromethyl)pyridin-2-yl]-1H-pyrazole-4-carboxamide;

5-methyl-N-[5-methyl-6-(1,2,3,6-tetrahydro-1-trifluoroacetylpyridin-4-yl)pyridin-3-yl]-1-[5-(trifluoromethyl)pyridin-2-yl]-1H-pyrazole-4-carboxamide;

N-{6-[4-cyano-1-(propane-2-sulfonyl)piperidin-4-yl]pyridin-3-yl}-5-methyl-1-[5-(trifluoromethyl)pyridin-2-yl]-1H-pyrazole-4-carboxamide;

5-methyl-N-{5-methyl-1-(pyrrolidin-1-ylcarbonyl)-6-[1,2,3,6-tetrahydropyridin-4-yl]pyridin-3-yl}-1-[5-(trifluoromethyl)pyridin-2-yl]-1H-pyrazole-4-carboxamide;

5-methyl-N-{5-methyl-6-[1-(propane-2-sulfonyl)piperidin-4-yl]pyridin-3-yl}-1-[5-(trifluoromethyl)pyridin-2-yl]-1H-pyrazole-4-carboxamide;

N-{6-[4-cyano-1-(cyclopropanesulfonyl)piperidin-4-yl]pyridin-3-yl}-5-methyl-1-[5-(trifluoromethyl)pyridin-2-yl]-1H-pyrazole-4-carboxamide;

N-{6-[4-cyano-1-(dimethylsulfamoyl)piperidin-4-yl]pyridin-3-yl}-5-methyl-1-[5-(trifluoromethyl)pyridin-2-yl]-1H-pyrazole-4-carboxamide;

5-methyl-N-{5-methyl-6-[1-(trifluoroacetyl)piperidin-4-yl]pyridin-3-yl}-1-[5-(trifluoromethyl)pyridin-2-yl]-1H-pyrazole-4-carboxamide;

N-[6-(4-cyano-1-trifluoromethanesulfonylpiperidin-4-yl)pyridin-3-yl]-5-methyl-1-[5-(trifluoromethyl)pyridin-2-yl]-1H-pyrazole-4-carboxamide;

N-(5-{4-[N-(2,2-dimethylpropion-1-yl)-N-methylamino]cyclohex-1-en-1-yl}pyrazin-2-yl)-5-methyl-1-[5-(trifluoromethyl)pyridin-2-yl]-1H-pyrazole-4-carboxamide;

N-(6-{4-[N-(2,2-dimethylpropion-1-yl)-N-methylamino]cyclohex-1-en-1-yl}-5-methoxypyridin-3-yl)-5-methyl-1-[5-(trifluoromethyl)pyridin-2-yl]-1H-pyrazole-4-carboxamide;

N-{5-methoxy-6-[4-(morpholin-4-yl)cyclohex-1-en-1-yl] pyridin-3-yl}-5-methyl-1-[5-(trifluoromethyl)pyridin-2-yl]-1H-pyrazole-4-carboxamide;

N-(6-{4-[N-(2,2-dimethylpropion-1-yl)-N-methylamino] cyclohex-1-en-1-yl}-5-(trifluoromethyl)pyridin-3-yl)-5-methyl-1-[5-(trifluoromethyl)pyridin-2-yl]-1H-pyrazole-4-carboxamide;

N-{6-[1-(dimethylsulfamoyl)piperidin-4-yl]-5-methylpyridin-3-yl}-5-methyl-1-[5-(trifluoromethyl)pyridin-2-yl]-1H-pyrazole-4-carboxamide;

5-methyl-N-{6-[1-(propane-2-sulfonyl)piperidin-4-yl]pyridin-3-yl}-1-[5-(trifluoromethyl)-pyridin-2-yl]-1H-pyrazole-4-carboxamide; and 5-methyl-N-{6-[1-(trifluoromethanesulfonyl)piperidin-4-yl]pyridin-3-yl}-1-[5-(trifluoromethyl)pyridin-2-yl]-1H-pyrazole-4-carboxamide, or a pharmacologically acceptable salt thereof.

(10) A solvate of the amide derivative of any one of the above (1) to (9) or a pharmacologically acceptable salt thereof.

(11) An IL-17 production inhibitor, comprising as the active ingredient the amide derivative of any one of the above (1) to (10) or a pharmacologically acceptable salt thereof, or a solvate thereof.

(12) A prophylactic and/or therapeutic agent for autoimmune disease, comprising as the active ingredient the amide derivative of any one of the above (1) to (10) or a pharmacologically acceptable salt thereof, or a solvate thereof.

(13) A prophylactic and/or therapeutic agent for rheumatoid arthritis, comprising as the active ingredient the amide derivative of any one of the above (1) to (10) or a pharmacologically acceptable salt thereof, or a solvate thereof.

Effect of the Invention

The amide derivatives of the present invention may suppress the cytokine production of T cells and may become a medicament which is effective for the prevention or treatment of diseases involved in the cytokine production from T cells.

The amide derivatives of the present invention may avoid toxicities typified by hERG inhibitory activity, for example, and may become a medicament which is effective for the prevention or treatment of diseases involved in the cytokine production from T cells.

BRIEF DESCRIPTION OF THE DRAWINGS

FIG. 1 shows the test pulse applied in Test Example 2.

DESCRIPTION OF EMBODIMENTS

Herein, "halogen atom" refers to fluorine atom, chlorine atom, bromine atom or iodine atom.

Herein, "alkyl group" may preferably have 1 to 10 of straight- or branched-chain carbon atoms, more preferably 1 to 6 of carbon atoms, and includes, for example, methyl group, ethyl group, normal-propyl group, isopropyl group, normal-butyl group, isobutyl group, tert-butyl group, normal-pentyl group, normal-hexyl group, etc.

Herein, "alkenyl group" may preferably have 2 to 10 of straight- or branched-chain carbon atoms, more preferably 2 to 6 of carbon atoms, and has at least one carbon double bond, and includes, for example, ethenyl group, propenyl group, butenyl group, etc.

Herein, "alkynyl group" may have 2 to 10 of straight- or branched-chain carbon atoms, more preferably 2 to 6 of carbon atoms, and has at least one carbon triple bond, and includes, for example, ethynyl group, propynyl group, butynyl group, etc.

Herein, "haloalkyl group" may preferably have 1 to 6 of straight- or branched-chain carbon atoms, and includes, for example, fluoromethyl group, difluoromethyl group, trifluoromethyl group, trifluoroethyl group, pentafluoroethyl group, heptafluoroisopropyl group, chloromethyl group, bromomethyl group, etc.

Herein, "alkoxy group" refers to a monovalent group generated by loss of hydrogen atom of hydroxyl group of alcohols, and may preferably have 1 to 6 of straight- or branched-chain carbon atoms, and includes, for example, methoxy group, ethoxy group, normal-propoxy group, isopropoxy group, normal-butoxy group, isobutoxy group, tert-butoxy group, normal-pentyloxy group, normal-hexyloxy group, etc.

Herein, "alkoxyalkyl group" refers to a monovalent group wherein the "alkoxy group" defined herein binds via alkyl group, and preferably, the carbon atoms of "alkoxyalkyl group" are 2 to 10, more preferably 2 to 6, and each alkyl moiety may preferably have 1 to 4 of straight- or branched-chain carbon atoms. For example, it includes methoxymethyl group, ethoxymethyl group, methoxyethyl group, tert-butoxymethyl group, etc.

Herein, "hydroxyalkyl group" refers to a monovalent group wherein "alkyl group" defined herein is substituted by hydroxyl group, preferably 1 to 6 of straight- or branched-chain carbon atoms, and includes, for example, hydroxymethyl group, hydroxyethyl group, hydroxypropyl group, etc.

Herein, "aminoalkyl group" refers to a monovalent group wherein "alkyl group" defined herein is substituted by amino group, preferably 1 to 6 of straight- or branched-chain carbon atoms, and includes, for example, aminomethyl group, aminoethyl group, aminopropyl group, etc.

Herein, "alkylamino group" refers to a group wherein 1 or 2 hydrogen atom(s) in amino group is substituted by alkyl group and the alkyl moiety may be preferably 1 to 4 of straight- or branched-chain carbon atoms, for example alkylamino group, or dialkylamino group. "Alkylamino group" includes, for example, methylamino group, ethylamino group, isopropylamino group, etc. "Dialkylamino group" includes, for example, dimethylamino group, diethylamino group, isopropyl(methyl)amino group, etc.

Herein, "hydroxyalkyloxyalkyl group" refers to a monovalent group wherein "alkoxyalkyl" defined herein is substituted by hydroxyl group, preferably 2 to 10 of straight- or branched-chain carbon atoms, and each alkyl moiety may be preferably 1 to 4 of straight- or branched-chain carbon atoms, for example hydroxymethyloxyethyl group.

Herein, "haloalkyloxyalkyl group" refers to a monovalent group wherein "alkoxyalkyl" defined herein is substituted by halogen, preferably 2 to 10 of straight- or branched-chain carbon atoms, and each alkyl moiety may be preferably 1 to 4 of straight- or branched-chain carbon atoms, for example trifluoromethyloxyethyl group.

Herein, "carboxylalkyl group" refers to a monovalent group wherein "alkyl group" defined herein is substituted by carboxyl group, preferably 2 to 6 of straight- or branched-chain carbon atoms, for example carboxylethyl group.

Herein, "alkyloxycarbonylalkyl group" has preferably 2 to 10 of carbon atoms, and each alkyl moiety may be preferably 1 to 4 of straight- or branched-chain carbon atoms, for example methyloxycarbonylethyl group.

Herein, "alkylcarbonylalkyl group" has preferably 2 to 10 of carbon atoms, and each alkyl moiety may be preferably 1 to 4 of straight- or branched-chain carbon atoms, for example methylcarbonylethyl group.

Herein, "alkylaminoalkyl group" refers to a group wherein 1 or 2 hydrogen atom(s) in amino group in "aminoalkyl group" defined herein is substituted by alkyl group, and each alkyl moiety may be preferably 1 to 4 of straight- or branched-chain carbon atoms, for example methylaminoethyl group, dimethylaminoethyl group.

Herein, "amidealkyl group" refers to a monovalent group wherein "alkyl group" defined herein is substituted by amide group, and has preferably 2 to 10, more preferably 2 to 6, of carbon atoms, and each alkyl moiety may be preferably 1 to 4 of straight- or branched-chain carbon atoms, for example amidoethyl group.

Herein, "alkylamidealkyl group" refers to a group wherein 1 or 2 hydrogen atom(s) in amino group in "amidealkyl group" defined herein is substituted by alkyl group, and has preferably 2 to 10, more preferably 2 to 6, of carbon atoms, and each alkyl moiety may be preferably 1 to 4 of straight- or branched-chain carbon atoms, for example methylamideethyl group.

Herein, "alkylcarbonylaminoalkyl group" has preferably 2 to 10, more preferably 2 to 6, of carbon atoms, and each alkyl moiety may be preferably 1 to 4 of straight- or branched-chain carbon atoms, for example methylcarbonylaminoethyl group.

Herein, "alkylsulfonylalkyl group" has preferably 2 to 10, more preferably 2 to 6 of carbon atoms, and each alkyl moiety may be preferably 1 to 4 of straight- or branched-chain carbon atoms, for example methylsulfonylethyl group.

Herein, "alkylsulfoxyalkyl group" has preferably 2 to 10, more preferably 2 to 6, of carbon atoms, and each alkyl moiety may be preferably 1 to 4 of straight- or branched-chain carbon atoms, for example methylsulfoxyethyl group.

Herein, "alkylsulfidealkyl group" has preferably 2 to 10, more preferably 2 to 6, of carbon atoms, and each alkyl moiety may be preferably 1 to 4 of straight- or branched-chain carbon atoms, for example methylsulfideethyl group.

Herein, "cycloalkyl group" refers to a whole saturated alicyclic hydrocarbon ring, and includes monocyclic hydrocarbon ring, condensed polycyclic hydrocarbon ring, and bridged hydrocarbon ring. The number of carbon atoms generally prefers to 3 to 11, more preferably 3 to 8, but is not limited thereto. The carbon atoms on the cycloalkyl group may be partially substituted by oxo group or thioxo group. The cycloalkyl group includes cyclopropyl group, cyclobutyl group, cyclopentyl group, cyclohexyl group, cycloheptyl group, cyclooctyl group, perhydronaphthyl group, adamantyl group, etc.

Herein, "aryl group" refers to a monovalent group of monocyclic aromatic hydrocarbon ring or polycyclic aromatic hydrocarbon ring, and includes, for example, phenyl group, biphenyl group, naphthyl group, anthracenyl group, phenanthryl group, indenyl group, fluorenyl group, azulenyl group, etc. Herein, "aryl group" also refers to a monovalent group of partially saturated aromatic hydrocarbon, and includes, for example, 1,2,3,4-tetrahydronaphthyl group, indanyl group, etc.

Herein, "heteroaryl group" refers to a monovalent group of aromatic cyclic compound having at least one heteroatom (e.g., nitrogen, oxygen or sulfur) and carbon atom(s), and includes a monovalent group of 5 to 6-membered monocyclic compound, or 8 to 12-membered condensed cyclic compound condensed or fused with other heterocycle, heteroaryl, cycloalkyl or aryl. The cyclic compound wherein a cyclic compound forming heteroaryl group is condensed includes a partially saturated cyclic compound.

The heteroaryl group includes thienyl group, pyrrolyl group, isoxazolyl group, isothiazolyl group, pyrazolyl group, oxazolyl group, oxadiazolyl group, thiazolyl group, thiadiazolyl group, imidazolyl group, triazolyl group, tetrazolyl group, furyl group, triazinyl group, pyrimidinyl group, pyridyl group, benzisooxazolyl group, benzoxazolyl group, benzothiazolyl group, benzisothiazolyl group, benzofuranyl group, dihydrobenzofuranyl group, indolinyl group, isoindolinyl group, pyridazinyl group, indazolyl group, isoindolyl group, indolyl group, indolizinyl group, benzothiophenyl group, dihydrobenzothiophenyl group, benzimidazolyl group, benzotriazolyl group, quinolyl group, quinolizinyl group, phthalazinyl group, naphthyridinyl group, quinoxalinyl group, quinaquizolinyl group, cinnolinyl group, carbazolyl group, dihydrobenzimidazolyl group, indazolyl group, benzisoxazolyl group, benzisothiazolyl group, benzoxazolyl group, benzothiazolyl group, quinazolyl group, isoquinolyl group, quinoxalyl group, pyrrolopyrimidinyl group, pyrrolopyridyl group, imidazopyridyl group, imidazopyrimidyl group, etc.

Herein, "heterocycle group" includes a monovalent group of saturated or partially unsaturated 3 to 6-membered monocyclic compound having at least one heteroatom (e.g., nitrogen, oxygen or sulfur) and carbon atom(s), or 8 to 12-membered condensed cyclic compound condensed or fused with other heterocycle, heteroaryl, cycloalkyl or aryl. The carbon atom(s) or heteroatom(s) on the heterocycle group herein may be partially substituted by oxo group or thioxo group. The heterocycle group includes pyrrolidinyl group, imidazolinyl group, oxazolinyl group, imidazolidinyl group, oxazolidinyl group, pyrazolidinyl group, piperidyl group, piperazyl group, morpholino group, morpholinyl group, dihydrofuryl group, tetrahydrofuryl group, dihydropyryl group, tetrahydropyranyl group, oxetanyl group, oxylanyl group, aziridinyl group, dihydropyrrolyl group, 1,3-dioxolanyl group, 2-oxopyrrolidinyl group, indenyl group, tetrahydroquinolyl group, etc.

Herein, "cycloalkylalkyl group" refers to a monovalent group wherein "alkyl group" defined herein is substituted by "cycloalkyl group", and each alkyl moiety may be preferably 1 to 4, more preferably 1 to 3, of straight- or branched-chain carbon atoms, and the cycloalkyl group moiety may be optionally substituted. For example, it is cyclopropylethyl group.

Herein, "heterocyclic alkyl group" refers to a monovalent group wherein "alkyl group" defined herein is substituted by "heterocycle group", and the alkyl moiety may be preferably 1 to 4, more preferably 1 to 3, of straight- or branched-chain carbon atoms, and the heterocycle group moiety may be optionally substituted. For example, pyrrolidinylethyl group is included.

Herein, "cycloalkyloxyalkyl group" refers to a monovalent group wherein hydrogen atom in hydroxyl group in "hydroxyalkyl group" defined herein is substituted by "cycloalkyl group", and the alkyl moiety may be preferably 1 to 4, more preferably 1 to 3, of straight- or branched-chain carbon atoms, and the cycloalkyl group moiety may be optionally substituted. For example, it is cyclopropyloxyethyl group.

Herein, "heterocyclic oxyalkyl group" refers to a monovalent group wherein hydrogen atom in hydroxyl group in "hydroxyalkyl group" defined herein is substituted by "heterocycle group", and the alkyl moiety may be preferably 1 to 4, more preferably 1 to 3, of straight- or branched-chain carbon atoms, and the heterocycle group moiety may be optionally substituted. For example, pyrrolidinyloxyethyl group is included.

Herein, "cycloalkylalkoxyalkyl group" refers to a monovalent group wherein the alkyl moiety in "alkoxyalkyl group" defined herein is substituted by "cycloalkyl group", and the alkyl moiety may be preferably 1 to 4, more preferably 1 to 3, of straight- or branched-chain carbon atoms, and the cycloalkyl group moiety may be optionally substituted. For example, cyclopropylmethoxyethyl group is included.

Herein, "heterocyclic alkoxyalkyl group" refers to a monovalent group wherein the alkyl moiety in "alkoxyalkyl group" defined herein is substituted by "heterocycle group", and the alkyl moiety may be preferably 1 to 4, more preferably 1 to 3, of straight- or branched-chain carbon atoms, and the heterocycle group moiety may be optionally substituted. For example, pyrrolidinylmethoxyethyl group is included.

The "condensed ring" which $Het^1$ and $Het^2$ are combined together to form includes a monovalent group of 8 to 12-membered condensed cyclic compound wherein 2 or more and same or different heterocycle, heteroaryl, cycloalkyl or aryl are condensed or fused. The condensed cyclic compound includes a partially saturated condensed cyclic compound. Preferably, it is an aromatic condensed cyclic compound having at least one heteroatom (e.g., nitrogen, oxygen or sulfur) and carbon atom(s). The condensed cyclic compound includes indolyl group, benzofuryl group, benzothiophenyl group, benzimidazolyl group, benzoxazolyl group, quinolyl group, tetrahydroquinolyl group, isoquinolyl group, pyridinothiophenyl group, thienopyridyl group, indazolyl group, benzisoxazolyl group, benzisothiazolyl group, benzothiazolyl group, quinolyl group, quinazolyl group, isoquinolyl group, quinoxalyl group, cinnolyl group, pyrrolopyrimidinyl group, pyrrolopyridyl group, imidazopyridyl group, imidazopyrimidyl group, etc.

Substituent(s) of "optionally substituted alkyl group" in $R^{1a}$, $R^{1b}$ and $R^{1c}$ include halogen atom, hydroxyl group, cyano group, $C_1$-$C_6$ haloalkyl group, $C_1$-$C_6$ alkoxy group, amino group, carboxyl group, etc.

Substituent(s) of "optionally substituted alkoxy group" in $R^{1a}$, $R^{1b}$ and $R^{1c}$ include halogen atom, hydroxyl group, cyano group, $C_1$-$C_6$ haloalkyl group, $C_1$-$C_6$ alkoxy group, amino group, carboxyl group, etc.

Substituent(s) of "optionally substituted alkyl group", "optionally substituted alkenyl group" and "optionally substituted alkynyl group" in $R^{2a}$, $R^{2b}$, $R^{3a}$, $R^{3b}$ and $R^{3c}$ include halogen atom, hydroxyl group, cyano group, $C_1$-$C_6$ haloalkyl group, $C_1$-$C_6$ alkoxy group, amino group, $C_1$-$C_6$ thioalkyl group, $C_1$-$C_6$ alkylsulfide group, $C_1$-$C_6$ alkylsulfoxy group, $C_1$-$C_6$ alkylsulfonyl group, $C_1$-$C_6$ alkylamino group, $C_2$-$C_6$ alkylcarbonyl group, $C_2$-$C_6$ alkylaminocarbonyl group, $C_2$-$C_6$ alkylcarbonylamino group, $C_2$-$C_6$ alkyloxycarbonyl group, $C_2$-$C_6$ alkylcarbonyloxy group, etc.

Substituent(s) of "optionally substituted cycloalkyl group", "optionally substituted heterocycle group", "optionally substituted aryl group" and "optionally substituted heteroaryl group" in $R^{2a}$, $R^{2b}$, $R^{3a}$, $R^{3b}$ and $R^{3c}$ include halogen atom, hydroxyl group, cyano group, $C_1$-$C_6$ alkyl group, $C_1$-$C_6$ haloalkyl group, $C_1$-$C_6$ alkoxy group, amino group, $C_1$-$C_6$ thioalkyl group, $C_1$-$C_6$ alkylsulfide group, $C_1$-$C_6$ alkylsulfoxy group, $C_1$-$C_6$ alkylsulfonyl group, $C_1$-$C_6$ alkylamino group, $C_2$-$C_6$ alkylcarbonyl group, $C_2$-$C_6$ alkylaminocarbonyl group, $C_2$-$C_6$ alkylcarbonylamino group, $C_2$-$C_6$ alkyloxycarbonyl group, $C_2$-$C_6$ alkylcarbonyloxy group.

Substituent(s) of "optionally substituted cycloalkyl group", "optionally substituted aryl group", "optionally substituted heterocycle group" and "optionally substituted heteroaryl group" in $R^{4a}$ and $R^{4b}$ include halogen atom, hydroxyl group, cyano group, $C_1$-$C_6$ alkyl group, $C_1$-$C_6$ haloalkyl group, $C_1$-$C_6$ alkoxy group, etc.

The "heterocycle group" which $R^{4a}$ and $R^{4b}$ are combined together to form is preferably pyrrolidinyl group, imidazolinyl group, oxazolinyl group, imidazolidinyl group, oxazolidinyl group, pyrazolidinyl group, piperidyl group, piperazyl group, morpholino group, morpholinyl group, dihydropyryl group or 2-oxopyrrolidinyl group, and the heterocycle group which $R^{4a}$ and $R^{4b}$ are combined together to form may be further substituted by halogen atom, $C_1$-$C_3$ alkyl group, amino group, alkylamino group, hydroxyl group, cyano group, $C_1$-$C_3$ haloalkyl group or $C_1$-$C_3$ alkoxy group.

Substituent(s) of "optionally substituted alkyl group", "optionally substituted alkenyl group" and "optionally substituted alkynyl group" in $R^5$ include halogen atom, hydroxyl group, cyano group, $C_1$-$C_6$ haloalkyl group, $C_1$-$C_6$ alkoxy group, amino group, carboxyl group, $C_1$-$C_6$ thioalkyl group, $C_1$-$C_6$ alkylsulfide group, $C_1$-$C_6$ alkylsulfoxy group, $C_1$-$C_6$ alkylsulfonyl group, $C_1$-$C_6$ alkylamino group, $C_1$-$C_6$ alkylcarbonyl group, $C_2$-$C_6$ alkylaminocarbonyl group, $C_2$-$C_6$ alkylcarbonylamino group, $C_2$-$C_6$ alkyloxycarbonyl group, $C_2$-$C_6$ alkylcarbonyloxy group, etc.

Substituent(s) of "optionally substituted cycloalkyl group", "optionally substituted aryl group", "optionally substituted heterocycle group" and "optionally substituted heteroaryl group" in $R^5$ include halogen atom, hydroxyl group, cyano group, $C_1$-$C_6$ alkyl group, $C_1$-$C_6$ haloalkyl group, $C_1$-$C_6$ alkoxy group, amino group, $C_2$-$C_6$ alkylaminocarbonyl group, $C_1$-$C_6$ thioalkyl group, $C_1$-$C_6$ alkylsulfide group, $C_1$-$C_6$ alkylsulfoxy group, $C_1$-$C_6$ alkylsulfonyl group, $C_1$-$C_6$ alkylamino group, $C_2$-$C_6$ alkyloxycarbonyl group, etc.

Substituent(s) of "optionally substituted cycloalkyl group", "optionally substituted heterocycle group", "optionally substituted cycloalkylalkyl group" and "optionally substituted heterocyclic alkyl group" in $R^{6a}$, $R^{6b}$ and $R^{6c}$ include halogen atom, hydroxyl group, cyano group, $C_1$-$C_6$ alkyl group, $C_1$-$C_6$ haloalkyl group, $C_1$-$C_6$ alkoxy group, etc.

The "heterocycle group" which $R^{6a}$ and $R^{6b}$ are combined together to form is preferably pyrrolidinyl group, imidazolinyl group, oxazolinyl group, imidazolidinyl group, oxazolidinyl group, pyrazolidinyl group, piperidyl group, piperazyl group, morpholino group, morpholinyl group, dihydropyryl group or 2-oxopyrrolidinyl group, and the heterocycle group which $R^{6a}$ and $R^{6b}$ are combined together to form may be further substituted by halogen atom, $C_1$-$C_3$ alkyl group, amino group, alkylamino group, hydroxyl group, cyano group, $C_1$-$C_3$ haloalkyl group or $C_1$-$C_3$ alkoxy group.

Substituent(s) of "optionally substituted alkyl group" and "optionally substituted alkoxy group" in $R^7$ include halogen atom, cyano group, $C_1$-$C_6$ haloalkyl group, $C_1$-$C_6$ alkoxy group, etc.

Substituent(s) of "optionally substituted alkyl group", "optionally substituted alkenyl group" and "optionally substituted alkynyl group" in $R^8$ include halogen atom, hydroxyl group, cyano group, $C_1$-$C_6$ haloalkyl group, $C_1$-$C_6$ alkoxy group, amino group, $C_1$-$C_6$ thioalkyl group, $C_1$-$C_6$ alkylsulfide group, $C_1$-$C_6$ alkylsulfoxy group, $C_1$-$C_6$ alkylsulfonyl group, $C_1$-$C_6$ alkylamino group, $C_1$-$C_6$ alkylcarbonyl group, $C_2$-$C_6$ alkylaminocarbonyl group, $C_2$-$C_6$ alkylcarbonylamino group, $C_2$-$C_6$ alkyloxycarbonyl group, $C_2$-$C_6$ alkylcarbonyloxy group, etc.

Substituent(s) of "optionally substituted cycloalkyl group", "optionally substituted aryl group", "optionally substituted heterocycle group" and "optionally substituted heteroaryl group" in $R^8$ include halogen atom, hydroxyl group, cyano group, $C_1$-$C_6$ alkyl group, $C_1$-$C_6$ haloalkyl group, $C_1$-$C_6$ alkoxy group, amino group, $C_1$-$C_6$ alkylamino group, etc.

Substituent(s) of "optionally substituted cycloalkyl group", "optionally substituted heterocycle group", "optionally substituted cycloalkylalkyl group" and "optionally substituted heterocyclic alkyl group" in $R^{9a}$, $R^{9b}$ and $R^{9c}$ include halogen atom, hydroxyl group, cyano group, $C_1$-$C_6$ alkyl group, $C_1$-$C_6$ haloalkyl group, $C_1$-$C_6$ alkoxy group, amino group, $C_1$-$C_6$ alkylamino group, etc.

The "heterocycle group" which $R^{9a}$ and $R^{9b}$ are combined together to form is preferably pyrrolidinyl group, imidazolinyl group, oxazolinyl group, imidazolidinyl group, oxazolidinyl group, pyrazolidinyl group, piperidyl group, piperazyl group, morpholino group, morpholinyl group, dihydropyryl group or 2-oxopyrrolidinyl group, and the heterocycle group which $R^{9a}$ and $R^{9b}$ are combined together to form includes halogen atom, hydroxyl group, cyano group, $C_1$-$C_6$ alkyl group, $C_1$-$C_6$ haloalkyl group, $C_1$-$C_6$ alkoxy group, amino group, $C_1$-$C_6$ alkylamino group, etc.

The "optionally substituted cycloalkyl group" and "optionally substituted heterocycle group" which $R^{11}$ and $R^{12}$ are combined together to form are preferably cyclopropyl group, cyclobutyl group, cyclopentyl group, cyclohexyl group, pyrrolidinyl group, imidazolinyl group, oxazolinyl group, imidazolidinyl group, oxazolidinyl group, pyrazolidinyl group, piperidyl group, piperazyl group, morpholino group, morpholinyl group, dihydrofuryl group, tetrahydrofuryl group, dihydropyryl group, 1,3-dioxolanyl group, 2-oxopyrrolidinyl group, tetrahydropyranyl group, oxazolidinonyl group, 2-oxopiperidinyl group, piperidinedionyl group, 2-oxooxazolidinyl group or 2-oxoimidazolidinyl group, and the "cycloalkyl group" and "heterocycle group" which $R^{11}$ and $R^{12}$ are combined together to form may be further optionally substituted by halogen atom, hydroxyl group, cyano group, $C_1$-$C_6$ alkyl group, $C_1$-$C_6$ haloalkyl group, $C_1$-$C_6$ alkoxy group, $C_1$-$C_6$ hydroxyalkyl group, $C_2$-$C_6$ alkoxyalkyl group, $C_2$-$C_6$ alkylaminoalkyl group, $C_2$-$C_6$ alkylcarbonyl group, $C_1$-$C_6$ alkylsulfonyl group, $C_1$-$C_6$ alkylamino group, $C_2$-$C_6$ alkyloxycarbonyl group, etc.

Substituent(s) of "optionally substituted cycloalkyl group", "optionally substituted aryl group", "optionally substituted heterocycle group" and "optionally substituted heteroaryl group" in $R^{13}$ include halogen atom, hydroxyl group, cyano group, $C_1$-$C_6$ alkyl group, $C_1$-$C_6$ haloalkyl group, $C_1$-$C_6$ alkoxy group, amino group, carboxyl group, $C_1$-$C_6$ thioalkyl group, $C_1$-$C_6$ alkylsulfide group, $C_1$-$C_6$ alkylsulfonyl group, $C_1$-$C_6$ alkylamino group, $C_1$-$C_6$ alkyloxycarbonyl group, etc.

Substituent(s) of "optionally substituted cycloalkyl group", "optionally substituted aryl group", "optionally substituted heterocycle group", "optionally substituted cycloalkyloxyalkyl group", "optionally substituted heterocyclic oxyalkyl group", "optionally substituted cycloalkylalkoxyalkyl group" and "optionally substituted heterocyclic alkoxyalkyl group" in $R^{14}$, $R^{15}$ and $R^{16}$ include halogen atom, hydroxyl group, cyano group, $C_1$-$C_6$ alkyl group, $C_1$-$C_6$ haloalkyl group, $C_1$-$C_6$ alkoxy group, amino group, carboxyl group, $C_1$-$C_6$ thioalkyl group, $C_1$-$C_6$ alkylsulfide group, $C_1$-$C_6$ alkylsulfonyl group, $C_1$-$C_6$ alkylamino group, $C_2$-$C_6$ alkyloxycarbonyl group, etc.

The "heterocycle group" which $R^{14}$ and $R^{15}$ are combined together to form is preferably pyrrolidinyl group, imidazolinyl group, oxazolinyl group, imidazolidinyl group, oxazolidinyl group, pyrazolidinyl group, piperidyl group, piperazyl group, morpholino group, morpholinyl group, dihydropyryl group, 2-oxopyrrolidinyl group, 2-oxoimidazolidinyl group, 2-oxooxazolidinyl group, 2-oxopiperidinyl group or 2-oxopiperazinyl group, and the heterocycle group which $R^{14}$ and $R^{15}$ are combined together to form may be further optionally substituted by halogen atom, hydroxyl group, cyano group, $C_1$-$C_6$ alkyl group, $C_1$-$C_6$ haloalkyl group, $C_1$-$C_6$ alkoxy group, amino group, carboxyl group, $C_1$-$C_6$ alkylsulfide group, $C_1$-$C_6$ alkylsulfonyl group, $C_1$-$C_6$ alkylamino group, $C_2$-$C_6$ alkyloxycarbonyl group, etc.

If ---- is a single bond, then A is C—$R^8$, and if ---- is a double bond, then A is carbon atom.

The "alkyl group" in $R_A$ and $R_B$ is preferably alkyl group with 1 to 6 of carbon atom(s), more preferably alkyl group with 1 to 3 of carbon atom(s). For example, it is methyl group, ethyl group or normal-propyl group.

n is preferably an integer of 1 to 2, more preferably an integer of 1.

$Het^1$ is preferably thiazolyl group, furyl group, thienyl group, pyrrolyl group, pyrazolyl group, imidazolyl group, triazolyl group, pyridyl group, or indolyl group, more preferably any one of groups of the following general formulae:

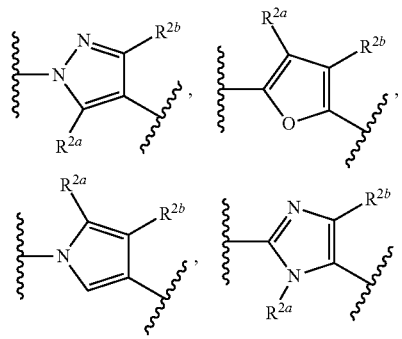

$R^{2a}$ is preferably hydrogen atom, optionally substituted alkyl group, or optionally substituted cycloalkyl group, more preferably hydrogen atom or alkyl group.

$R^{2b}$ is preferably hydrogen atom, or alkyl group.

k is preferably an integer of 0 to 1.

$Het^2$ is preferably aryl group or heteroaryl group, more preferably any one of groups of the following general formulae:

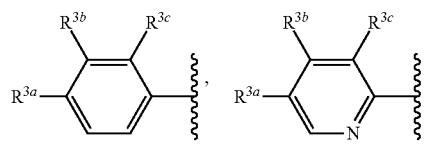

$R^{3a}$ is preferably hydrogen atom, halogen atom, cyano group, optionally substituted alkyl group, optionally substituted alkenyl group, optionally substituted cycloalkyl group, —O—$R^{4a}$, —CO—$R^{4a}$, or —SO$_2$—$R^{4a}$, more preferably hydrogen atom, halogen atom, cyano group, alkyl group, haloalkyl group, cycloalkyl group, or —O—$R^{4a}$.

$R^{3b}$ and $R^{3c}$ are preferably hydrogen atom, halogen atom, cyano group, optionally substituted alkyl group, optionally substituted alkenyl group, optionally substituted cycloalkyl group, —O—$R^{4a}$, —CO—$R^{4a}$, or —SO$_2$—$R^{4a}$, more preferably hydrogen atom, halogen atom, alkyl group, or —O—$R^{4a}$.

$R^{4a}$ and $R^{4b}$ are preferably hydrogen atom, alkyl group, alkoxyalkyl group, hydroxyalkyl group, haloalkyl group, or optionally substituted heteroaryl group, more preferably hydrogen atom, alkyl group, alkoxyalkyl group, or haloalkyl group.

The condensed ring which $Het^1$ and $Het^2$ are optionally combined together to form is preferably indolyl group, benzimidazolyl group, or thienopyridyl group, more preferably indolyl group.

i is preferably an integer of 0 to 1.

k is preferably an integer of 0 to 1.

X is preferably C—$R^5$.

$R^5$ is preferably hydrogen atom, halogen atom, cyano group, optionally substituted alkyl group, or —O—$R^{6a}$, more preferably hydrogen atom, cyano group, alkyl group, haloalkyl group, or —O—$R^{6a}$.

$R^{6a}$ and $R^{6b}$ are preferably hydrogen atom or alkyl group.

$R^7$ is preferably hydrogen atom or alkyl group.

$R^8$ is preferably hydrogen atom, halogen atom, hydroxy group, cyano group, optionally substituted alkyl group, —O—$R^{9a}$ or —CO—O—$R^{9a}$, more preferably hydrogen atom, halogen atom, hydroxy group, cyano group, alkyl group, or —CO—O—$R^{9a}$.

$R^{9a}$ is preferably hydrogen atom or alkyl group.

D is preferably any one of groups of the following general formulae:

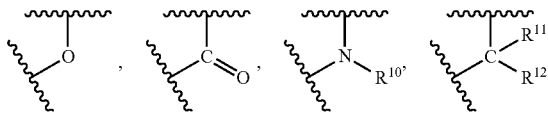

$R^{10}$ is preferably alkoxyalkyl group, hydroxyalkyl group, -$L^{1a}$-$R^{13}$, optionally substituted heterocycle group, -$L^{1a}$-$SO_2$—$R^{14}$, -$L^{1a}$-$SO_2$—$NR^{14}R^{15}$, -$L^{1a}$-SO—$R^{14}$, -$L^{1a}$-CO—$R^{14}$, or -$L^{1a}$-CO—$NR^{14}R^{15}$, more preferably alkoxyalkyl group, hydroxyalkyl group, -$L^{1a}$-$R^{13}$, optionally substituted heterocycle group, -$L^{1a}$-$SO_2$—$R^{14}$, -$L^{1a}$-$SO_2$—$NR^{14}R^{15}$, -$L^{1a}$-CO—$R^{14}$, or -$L^{1a}$-CO—$NR^{14}R^{15}$.

$R^{11}$ is preferably hydrogen atom, hydroxy group, alkyl group, haloalkyl group, alkoxyalkyl group, hydroxyalkyl group, alkenyl group, -$L^{1a}$-$R^{13}$, -$L^{1a}$-O—$R^{14}$, -$L^{1a}$-CO—$R^{14}$, -$L^{1a}$-O—Si($R^{15}R^{16}$)—$R^{14}$, -$L^{1a}$-CO—$NR^{14}R^{15}$, -$L^{1a}$-$NR^{14}R^{15}$, -$L^{1a}$-N($R^{16}$)—CO—$R^{14}$, or -$L^{1a}$-N($R^{16}$)—CO—O—$R^{14}$, more preferably hydrogen atom, hydroxy group, alkyl group, haloalkyl group, hydroxyalkyl group, alkenyl group, -$L^{1a}$-$R^{13}$, -$L^{1a}$-O—$R^{14}$, -$L^{1a}$-CO—$NR^{14}R^{15}$, -$L^{1a}$-$NR^{14}R^{15}$, -$L^{1a}$-N($R^{16}$)—CO—$R^{14}$, or -$L^{1a}$-N($R^{16}$)—CO—O—$R^{14}$.

$R^{12}$ is preferably hydrogen atom, hydroxy group, alkyl group, haloalkyl group, alkoxyalkyl group, hydroxyalkyl group, alkenyl group, -$L^{1a}$-$R^{13}$, -$L^{1a}$-O—$R^{14}$, -$L^{1a}$-CO—$R^{14}$, -$L^{1a}$-O—Si($R^{15}R^{16}$)—$R^{14}$, -$L^{1a}$-CO—$NR^{14}R^{15}$, -$L^{1a}$-$NR^{14}R^{15}$, -$L^{1a}$-N($R^{16}$)—CO—$R^{14}$, or -$L^{1a}$-N($R^{16}$)—CO—O—$R^{14}$, more preferably hydrogen atom, hydroxy group, alkyl group, or alkenyl group.

The group which $R^{11}$ and $R^{12}$ are optionally combined together to form is preferably optionally substituted heterocycle group, more preferably tetrahydrofuryl group, dihydrofuryl group, or 1,3-dioxolanyl group.

$R^{13}$ is preferably optionally substituted heterocycle group, more preferably optionally substituted pyrrolidinyl group, optionally substituted morpholino group, optionally substituted morpholinyl group, optionally substituted tetrahydropyryl group, or optionally substituted tetrahydrofuryl group.

$R^{14}$ is preferably hydrogen atom, alkyl group, alkoxyalkyl group, hydroxyalkyl group, haloalkyl group, optionally substituted cycloalkyl group, optionally substituted aryl group, optionally substituted heterocycle group, carboxyalkyl group or optionally substituted heterocyclic oxyalkyl group, more preferably hydrogen atom, alkyl group, alkoxyalkyl group, hydroxyalkyl group, haloalkyl group, or optionally substituted heterocycle group.

$R^{15}$ and $R^{16}$ are preferably hydrogen atom, or alkyl group.

$L^{1a}$ is preferably a bond, or —$CH_2$—, more preferably a bond.

$L^{1b}$ is preferably —$CH_2$—.

A compound of the general formula (I) or a salt thereof may be synthesized by utilizing characteristics based on its basic skeleton or type of substituents and adjusting various known synthetic methods. Preparation methods of the condensed pyridazine derivative of the general formula (I) are illustrated as below, but the present invention is not intended to be limited thereto.

Depending on the type of functional groups, it may be useful in view of the processing technology that said functional groups may be preliminarily converted at the stage of starting materials or intermediate compounds into appropriate protecting groups, i.e. groups which may be easily reconverted into said functional groups, and the protecting groups may be optionally deprotected to give the desired compounds.

[Preparation Method] Synthetic Methods of the Amide Derivatives of the Present Invention Method 1: Compound (I) of the Present Invention May be Prepared According to the Following Method.

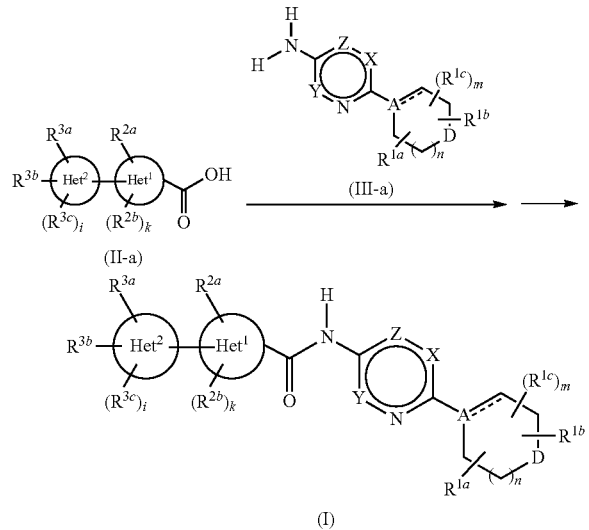

(in which each symbol has the same meaning as defined above.)

The condensation reaction of Compound (II-a) and Compound (III-a) may be carried out according to the following three processes.

(1) Compound (II-a) is treated by the conventional method using a halogenating agent and converted into the corresponding acid halide, followed by reacting with Compound (III-a) to give the corresponding compound of the general formula (I). The reaction proceeds in an appropriate solvent usually in the range from −20° C. to reflux temperature of the solvent with a base. The reaction time varies depending on starting materials or a solvent to be used and reaction temperature, etc., and is usually in the range from 30 minutes to 24 hours. The halogenating agent includes, for example, thionyl chloride, oxalyl chloride, etc. The base includes, for example, triethylamine, pyridine, etc. The solvent includes, for example, dichloromethane, dichloroethane, chloroform, N-methylpyrrolidone, pyridine, toluene, etc. In this reaction, a base to be used may be used as a solvent.

(2) Compound (II-a) is condensed with Compound (III-a) in the presence of a condensing agent to give the corresponding compound of the general formula (I). The reaction temperature is usually in the range from 0° C. to 100° C. The reaction time varies depending on starting materials or a solvent to be used and reaction temperature, etc., and is usually in the range from 30 minutes to 24 hours. The condensing agent includes 1,3-dicyclohexylcarbodiimide, 1-ethyl-3-(3-dimethylaminopropyl)carbo diimide hydrochloride, carbonyldiimidazole, 4-(4,6-dimethoxy[1,3,5]triazin-2-yl)-4-methylmorpholinium chloride hydrate (DMT-MM)), etc. The solvent includes N,N-dimethylformamide, dimethyl sulfoxide, tetrahydrofuran, dichloromethane, chloroform, 1,4-dioxane, methanol, ethanol, isopropyl alcohol, butanol, etc. The reaction may be accelerated by the addition of 1-hydroxybenzotriazole (HOBt). In case that Compound (III-a) forms a salt with an acid, the reaction proceeds by the neutralization by the addition of a base. Alternatively, the condensing agent of the reaction includes, for example, diethyl cyanophosphonate, diphenylphosphoryl azide, etc. The reaction proceeds in an appropriate solvent such as N,N-dimethylformamide, dimethyl sulfoxide in the presence of a base (e.g., triethylamine, pyridine, etc.). The reaction temperature is usually in the range from 0° C. to 100° C. The reaction time varies depending on starting materials or solvent to be used and reaction temperature, etc., and is usually in the range from 30 minutes to 24 hours.

(3) Compound (II-a) is converted into a mixed anhydride such as methyl chlorocarbonate, ethyl chlorocarbonate, isobutyloxycarbonyl chloride, pivaloyl chloride, followed by reacting with Compound (III-a) in a solvent in the presence of a base or in a base as a solvent to give a compound of the general formula (I). The solvent includes, for example, methanol, ethanol, isopropyl alcohol, butanol, ethylene glycol, tetrahydrofuran, chloroform, N,N-dimethylformamide, toluene, etc. The base includes, for example, triethylamine, pyridine, N-methylmorpholine, etc. The reaction temperature is usually in the range from 0° C. to 100° C. The reaction time varies depending on starting materials or a solvent to be used and reaction temperature, etc., and is usually in the range from 30 minutes to 24 hours.

Method 2: Compound (I) May be Synthesized According to the Following Method Using Amide Compound (II-b) and Compound (III-b).

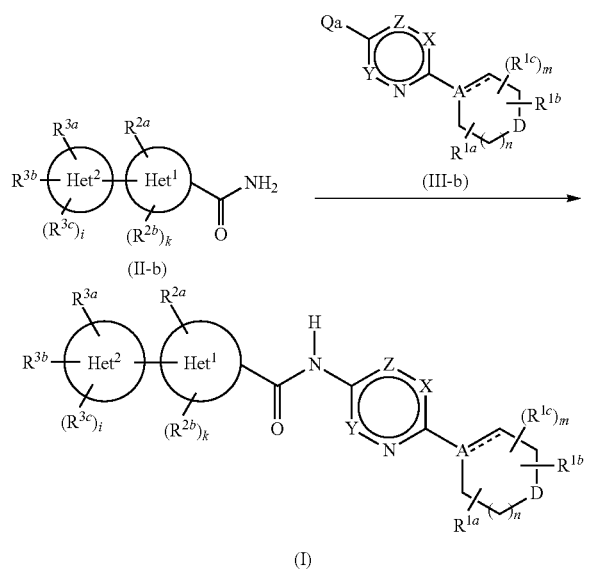

(in which Qa is chlorine atom, bromine atom, iodine atom, trifluoromethanesulfonyloxy group or p-toluenesulfonyloxy group, and other symbols have the same meanings as defined above.)

Compound (II-b) which is obtained by treating Compound (II-a) according to Method 1-(1) to convert into an acid halide, followed by treating with ammonium hydroxide is reacted with Compound (III-b) in an appropriate solvent under nitrogen atmosphere in the presence of a base, a copper catalyst and a ligand to give the corresponding compound of the general formula (I). The solvent used in the reaction includes, for example, dimethylformamide, dimethyl sulfoxide, 1,4-dioxane, N-methylpyrrolidone, toluene, tetrahydrofuran, cyclopentyl methyl ether, xylene, 1,2-dimethoxyethane, tert-butanol, etc. The base includes, for example, potassium carbonate, cesium carbonate, potassium acetate, tripotassium phosphate, diisopropylethylamine, sodium tert-butoxide, etc. The copper catalyst includes copper (I) iodide, copper (I) bromide, etc. The ligand includes N,N'-dimethylethylenediamine, trans-N,N'-dimethylcyclohexanediamine, trans-1,2-cyclohexanediamine 1,10-phenanthroline, etc.

The reaction also proceeds in an appropriate solvent under nitrogen atmosphere using a palladium catalyst, a phosphine ligand and a base with heating. The solvent used in the reaction includes, for example, dimethylformamide, dimethyl sulfoxide, dioxane, N-methylpyrrolidone, toluene, tetrahydrofuran, cyclopentyl methyl ether, xylene, 1,2-dimethoxyethane, tert-butanol, etc. The base includes, for example, potassium carbonate, cesium carbonate, potassium acetate, tripotassium phosphate, diisopropylethylamine, sodium tert-butoxide, etc. The palladium catalyst includes, for example, palladium (II) acetate, tris(dibenzylideneacetone)dipalladium (0), etc. The ligand includes 4,5-bis(diphenylphosphino)-9,9-dimethylxanthene, 2-dicyclohexylphosphinobiphenyl, 2-di-tert-butylphosphinobiphenyl, 2-(di-tert-butylphosphino)-3,4,5,6-tetramethyl-2',4',6'-triisopropyl-1,1'-biphenyl, 2-(dicyclohexylphosphino)-2',4',6'-triisopropyl-1,1'-biphenyl, etc.

The reaction temperature is usually in the range from room temperature to reflux temperature of solvent. The reaction time varies depending on starting materials or a solvent to be used and reaction temperature, etc., and is usually in the range from 1 hour to 72 hours.

Method 3: Compound (I) May be Synthesized According to the Following Method Using Compound (II-c) and Compound (IV-a).

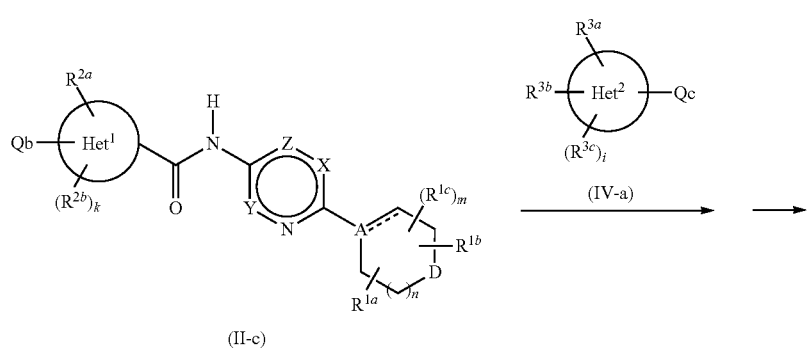

-continued

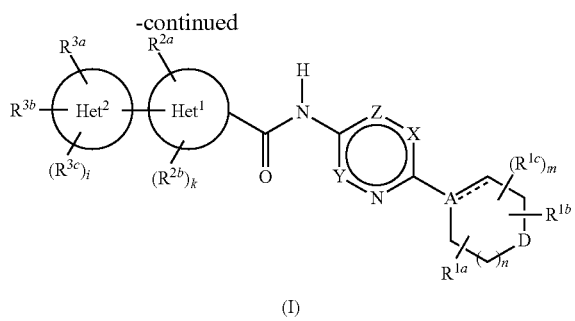

(I)

(in which Qb is bromine atom, chlorine atom, iodine atom, trifluoromethanesulfonyloxy group or p-toluenesulfonyloxy group, Qc is an active group having boron atom such as boron acid, boron acid ester, for example. Other symbols have the same meanings as defined above.)

Compound (II-c) is coupled with Compound (IV-a) under Suzuki reaction to give the corresponding compound of the general formula (I). The reaction proceeds under nitrogen atmosphere using a palladium catalyst, a phosphine ligand and a base in an appropriate solvent with heating. The solvent used in the reaction includes, for example, tetrahydrofuran, toluene, acetonitrile, N-methylpyrrolidone, dimethylformamide, dimethyl sulfoxide, 1,4-dioxane, 1,2-dimethoxyethane, tert-butanol, isopropanol, ethanol, methanol or a mixed solvent of the same with water, etc. The base includes, for example, potassium carbonate, cesium carbonate, sodium carbonate, potassium acetate, tripotassium phosphate, diisopropylethylamine, sodium tert-butoxide, etc. The palladium catalyst includes, for example, palladium (II) acetate, tris(dibenzylideneacetone)dipalladium (0), etc. The ligand includes 2-dicyclohexylphosphino-2,6-dimethoxybiphenyl, 2-dicyclohexylphosphinobiphenyl, 2-(di-tert-butylphosphino)biphenyl, 2-(di-tert-butylphosphino)-3,4,5,6-tetramethyl-2',4',6'-triisopropyl-1,1'-biphenyl, 2-(dicyclohexylphosphino)-2',4',6'-triisopropyl-1,1'-biphenyl, 4,5-bis(diphenylphosphino)-9,9-dimethylxanthene, etc. A complex formed by a palladium catalyst and a phosphine ligand may be used, and for example, includes [1,1'-bis(diphenylphosphino)ferrocene]palladium (II) dichloride-dichloromethane complex, dichlorobis(tricyclohexylphosphine)palladium (II), tetrakis(triphenylphosphine)palladium (0), [1,1'-bis(diphenylphosphino)ferrocene]palladium (II) dichloride, dichlorobis(tricyclohexylphosphine)palladium (II), bis(triphenylphosphine)palladium (II) dichloride, etc. The reaction temperature is usually in the range from room temperature to reflux temperature of solvent. The reaction time varies depending on starting materials or solvent to be used and reaction temperature, etc., and is usually in the range from 1 hour to 24 hours.

Method 4: Compound (I) Wherein Het¹ has Nitrogen and Binds to Het² Via Nitrogen of Het¹ May be Synthesized According to the Following Method Using Compound (II-d) and Compound (IV-b).

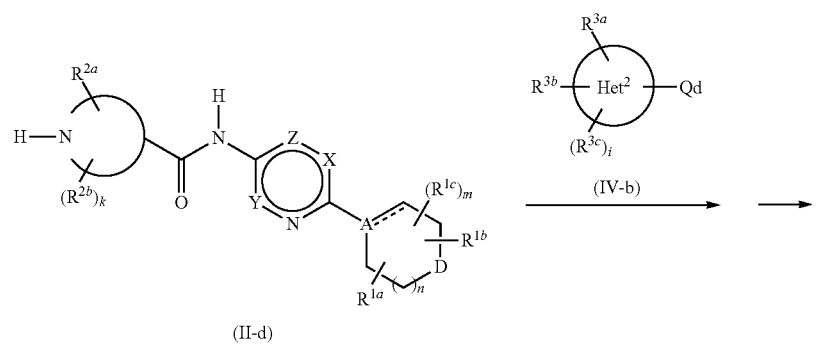

(II-d)    (IV-b)

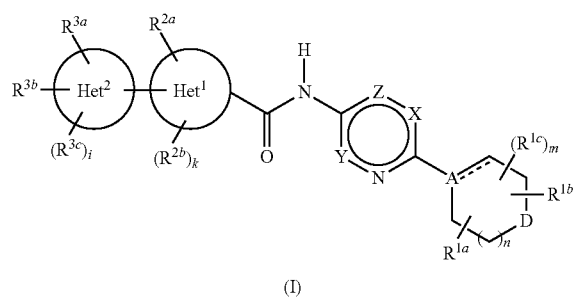

(I)

(in which

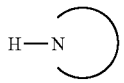

is a group having nitrogen atom among the group defined by Het¹, Qd is bromine atom, chlorine atom, iodine atom, trifluoromethanesulfonyloxy group, boric acid or boric acid ester, Het$^{1a}$ is a group having nitrogen atom which binds to Het² via nitrogen atom among the group defined by Het¹. Other symbols have the same meanings as defined above.)

(1) In case that Qd is bromine atom, chlorine atom or iodine atom, Compound (II-d) is reacted with Compound (IV-b) under nitrogen atmosphere in the presence of a base, a copper catalyst and a ligand to give the corresponding compound of the general formula (I). The solvent used in the reaction includes, for example, dimethylformamide, dimethyl sulfoxide, 1,4-dioxane, N-methylpyrrolidone, toluene, tetrahydrofuran, cyclopentyl methyl ether, xylene, 1,2-dimethoxyethane, tert-butanol, etc. The base includes, for example, potassium carbonate, cesium carbonate, potassium acetate, tripotassium phosphate, diisopropylethylamine, sodium tert-butoxide, etc. The copper catalyst includes, for example, copper (I) iodide, copper (I) bromide, etc. The ligand includes N,N'-dimethylethylenediamine, trans-N,N'-dimethylcyclohexanediamine, trans-1,2-cyclohexanediamine, 1,10-phenanthroline, etc.

(2) In case that Qd is trifluoromethanesulfonyloxy group, Compound (II-d) is reacted with Compound (IV-b) under nitrogen atmosphere in an appropriate solvent in the presence of a base, a palladium catalyst and a ligand to give the corresponding compound of the general formula (I). The solvent used in the reaction includes, for example, toluene, 1,4-dioxane, tetrahydrofuran, dimethylformamide and a mixed solvent thereof, etc. The base includes, for example, potassium carbonate, cesium carbonate, tripotassium phosphate, etc. The palladium catalyst includes, for example, tris(dibenzylideneacetone)dipalladium (0), etc. The ligand includes 2,2'-bis(dicyclohexylphosphino)-1,1'-binaphthyl, 2-(dicyclohexylphosphino)-2',4',6'-triisopropyl-1,1'-biphenyl, etc.

(3) In case that Qd is boric acid or boric acid ester, Compound (II-d) is reacted with Compound (IV-b) under nitrogen atmosphere in an appropriate solvent in the presence of a base, a palladium catalyst and a ligand to give the corresponding compound of the general formula (I). The solvent used in the reaction includes, for example, dimethylformamide, dimethyl sulfoxide, 1,4-dioxane, N-methylpyrrolidone, toluene, tetrahydrofuran, cyclopentyl methyl ether, xylene, 1,2-dimethoxyethane, tert-butanol, etc. The base includes, for example, potassium carbonate, cesium carbonate, potassium acetate, tripotassium phosphate, diisopropylethylamine, sodium tert-butoxide, potassium tert-butoxide, etc. The palladium catalyst includes, for example, palladium (II) acetate, tris(dibenzylideneacetone)dipalladium (0), etc. The ligand includes 4,5-bis(diphenylphosphino)-9,9-dimethylxanthene, 2-dicyclohexylphosphinobiphenyl, 2-di-tert-butylphosphinobiphenyl, 2-(di-tert-butylphosphino)3,4,5,6-tetramethyl-2',4',6'-triisopropyl-1,1'-biphenyl, 2-(dicyclohexylphosphino)-2',4',6'-triisopropyl-1,1'-biphenyl, etc. A complex formed by a palladium catalyst and a phosphine ligand may be used, and includes, for example [1,1'-bis(diphenylphosphino)ferrocene]palladium (II) dichloride-dichloromethane complex, dichlorobis(tricyclohexylphosphine)palladium (II), tetrakis(triphenylphosphine)palladium (0), [1,1'-bis(diphenylphosphino)ferrocene]palladium (II) dichloride, dichlorobis(tricyclohexylphosphine)palladium (II), bis(triphenylphosphine)palladium (II) dichloride, etc.

The reaction temperature is usually in the range from room temperature to reflux temperature of solvent. The reaction time varies depending on starting materials or solvent to be used and reaction temperature, etc., and is usually in the range from 1 hour to 72 hours.

Method 5: Compound (II-a-1) Wherein Het¹ is Pyrrole and Substituted by Het² on 1-Position of the Pyrrole, R$^{2a}$ and R$^{2b}$ are Hydrogen, and Pyrrole is Substituted by Carboxyl Group on the 3-Position Among Compound (II-a) May be Synthesized According to the Following Methods.

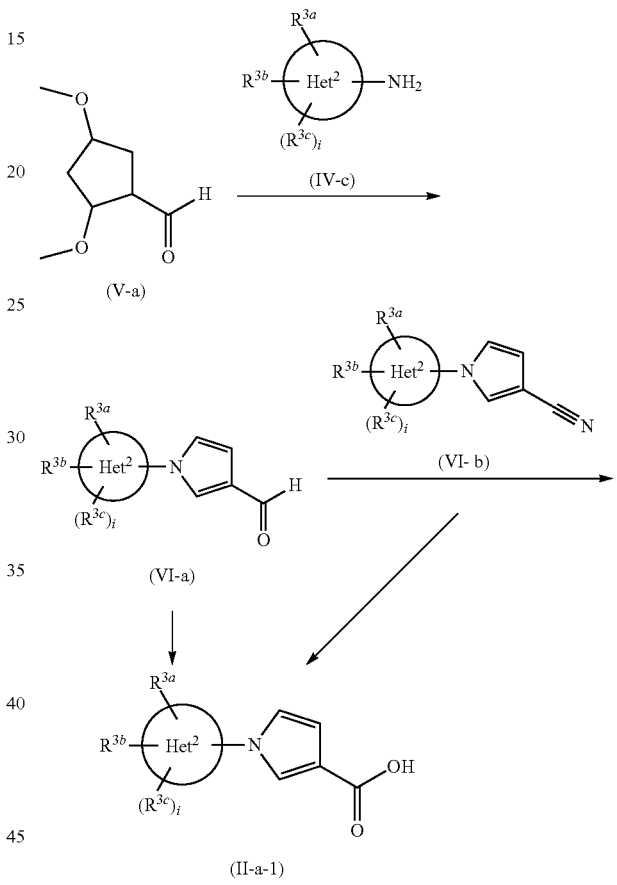

(in which each symbol has the same meaning as defined above.)

(1) Compound (V-a) is reacted with Compound (IV-c) in an appropriate solvent (e.g., acetic acid, water, methanol or a mixed solvent thereof) in the range from room temperature to reflux temperature of solvent for 1 to 24 hours to give Compound (VI-a). Compound (VI-a) is oxidized in the presence of a base (including sodium hydroxide, potassium hydroxide, triethylamine, pyridine) by an oxidizing agent (including manganese dioxide, potassium permanganate, peroxides (including hydrogen peroxide, meta-chloroperoxybenzoic acid)) to give Compound (II-a-1).

(2) Compound (II-a-1) is also obtained according the following method. Compound (VI-a) is treated by hydroxylamine hydrochloride in an appropriate solvent (e.g., water, methanol, ethanol, acetonitrile, tetrahydrofuran or a mixed solvent thereof) in the presence of a base (including sodium acetate, sodium hydroxide, sodium hydrogen carbonate, potassium carbonate, triethylamine), followed by treatment by an acid anhydride (including acetic anhydride, phthalic acid anhydride) to give Compound (VI-b), and then reacted with a base (including sodium hydroxide, potassium hydroxide) in an appropriate solvent (e.g., ethanol, water, tetrahydrofuran or a mixed solvent thereof) at a reflux temperature of a solvent to give Compound (II-a-1).

Method 6: Compound (II-a-1) May be Also Synthesized According to the Following Method.

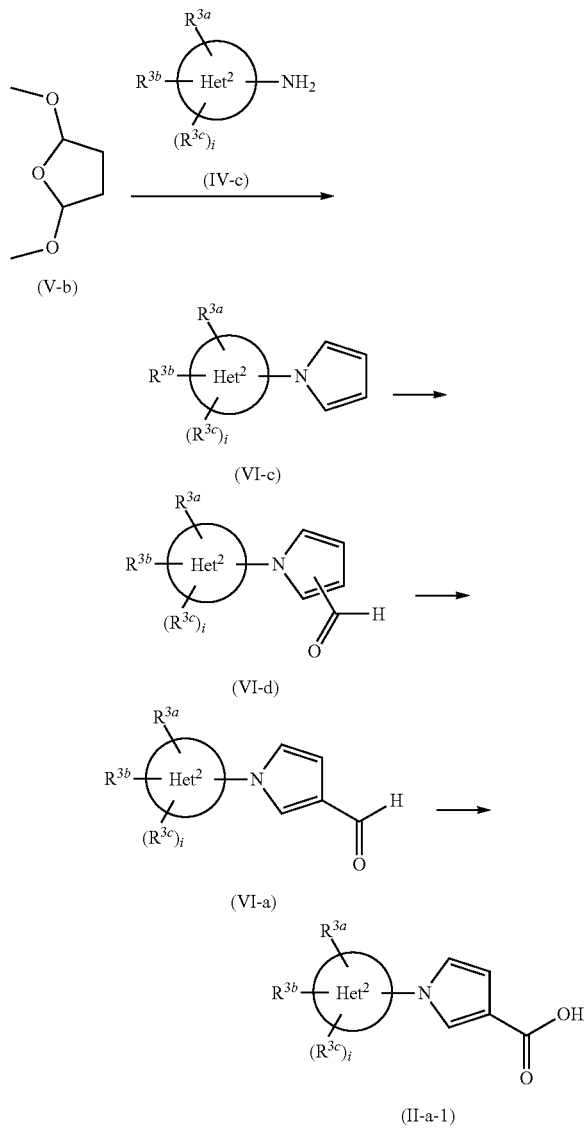

(in which each symbol has the same meaning as defined above.)

Compound (V-b) is reacted with Compound (IV-c) in an appropriate solvent (e.g., acetic acid, water, methanol or a mixed solvent thereof) in the range from room temperature to reflux temperature of solvent for 1 to 24 hours to give Compound (VI-c). Compound (VI-c) is treated with phosphorus oxychloride in Vilsmeier reaction in the presence of N,N-dimethylformamide or N-methylformanilide in the range from room temperature to 100° C. for 1 to 24 hours to give Compound (VI-d). Compound (VI-d) may be reacted with trifluoromethanesulfonic acid in an appropriate solvent (including methylene chloride, chloroform, dichloroethane, benzene, toluene, xylene) in the range from room temperature to reflux temperature of solvent for 1 to 24 hours to give Compound (VI-a). Compound (VI-a) is oxidized by an oxidizing agent (including manganese dioxide, potassium permanganate, peroxides (including hydrogen peroxide, meta-chloroperbenzoic acid)) in the presence of a base (including sodium hydroxide, potassium hydroxide, triethylamine, pyridine) to give Compound (II-a-1).

Method 7: Compound (II-a-2) Wherein Het$^1$ is Pyrrole and the Pyrrole is Substituted with Het$^2$ at the 1-Position, and the Pyrrole is Substituted with Methyl Groups at the 2- and 5-positions and a carboxyl group at the 3-position among compound (II-a) may be synthesized According to the Following Method.

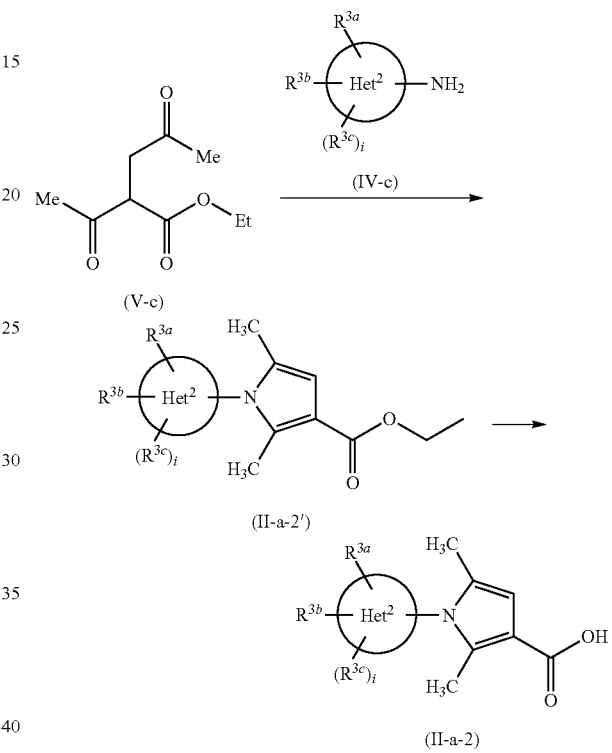

(in which each symbol has the same meaning as defined above.)

Compound (V-c) may be reacted with Compound (IV-c) in an appropriate solvent (e.g., methanol, ethanol, water or a mixed solvent thereof) in the presence or absence of an acid (including hydrochloric acid, sulfuric acid, nitric acid) in the range from room temperature to 100° C. for 1 to 24 hours to give Compound (II-a-2'), followed by hydrolysis according to the conventional method to give Compound (II-a-2).

Method 8: Compound (II-a-1) Wherein Het$^1$ is Pyrrole and the Pyrrole is Substituted with Het$^2$ at the 1-position and a carboxyl group at the 3-position among Compound (II-a) may be also synthesized according to the following method.

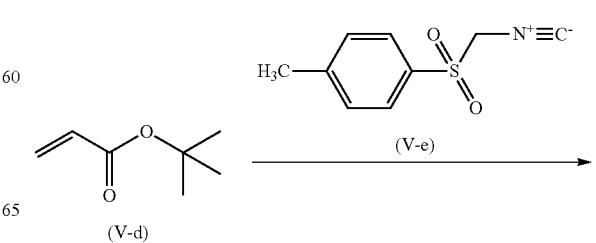

Method 9: Compound (II-a) May be Obtained According to the Following Method from a Carboxylic Acid Ester of Formula (VI-e).

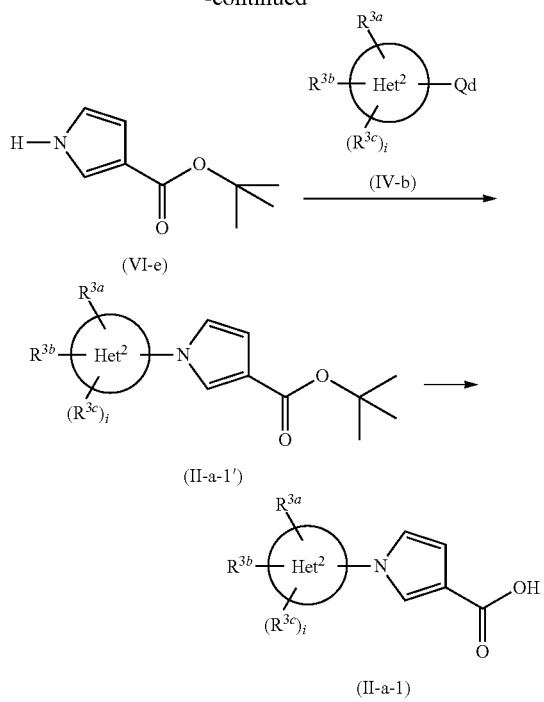

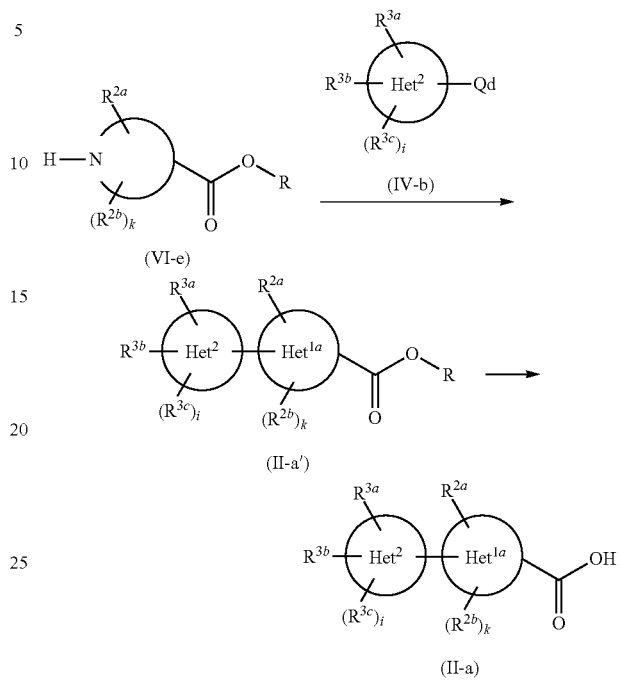

(in which Qd is a bromine atom, a chlorine atom, an iodine atom, a trifluoromethanesulfonyloxy group or boric acid or boric acid ester, and other symbols have the same meanings as defined above, respectively.)

Acrylic acid tert-butyl ester (V-d) is reacted with p-toluenesulfonylmethyl isocyanide (V-e) in an appropriate solvent in the presence of a base to give Compound (VI-e). The solvent used in the reaction includes, for example, tetrahydrofuran, 1,4-dioxane, etc. The base includes, for example, sodium hydride, etc. The reaction temperature is usually in the range from room temperature to 80° C. The reaction time varies depending on starting materials or a solvent to be used and reaction temperature, etc., and is usually in the range from 30 minutes to 12 hours.

In case that Qd is a bromine atom, a chlorine atom or an iodine atom, Compound (VI-e) is reacted with Compound (IV-b) under nitrogen atmosphere in the presence of a base, a copper catalyst and a ligand to give the corresponding Compound (II-a-1'). This reaction proceeds in the similar manner to Method 4-(1).

In case that Qd is a trifluoromethanesulfonyloxy group, Compound (VI-e) is reacted with Compound (IV-b) under nitrogen atmosphere in an appropriate solvent in the presence of a base, a palladium catalyst and a ligand to give the corresponding Compound (II-a-1'). This reaction proceeds in the similar manner to Method 4-(2).

In case that Qd is boric acid or boric acid ester, Compound (VI-e) is reacted with Compound (IV-b) under nitrogen atmosphere in an appropriate solvent in the presence of a base, a palladium catalyst and a ligand to give the corresponding Compound (II-a-1'). This reaction proceeds in the similar manner to Method 4-(3).

The obtained Compound (II-a-1') may be hydrolyzed according to the conventional method to give Compound (II-a-1).

(in which Qd is a fluorine atom, a chlorine a atom, a bromine atom, an iodine atom, a trifluoromethanesulfonyloxy group or boric acid or boric acid ester, R is alkyl and includes, for example methyl, ethyl or tert-butyl. Other symbols have the same meanings as defined above, respectively.)

(1) In case that Qd is a fluorine atom, a chlorine atom or a bromine atom, Compound (VI-e) may be treated with a base in an appropriate solvent, followed by the reaction with Compound (IV-b) to give Compound (II-a'), and then hydrolysis according to the conventional method to give Compound (II-a). The solvent includes, for example, tetrahydrofuran, N,N-dimethylformamide, etc. The base includes, for example, sodium hydride, potassium carbonate, diisopropylethylamine, sodium tert-butoxide, potassium tert-butoxide, etc. The reaction temperature is usually in the range from 0° C. to the reflux temperature of a solvent. The reaction time varies depending on starting materials or a solvent to be used and reaction temperature, etc., and is usually in the range from 1 to 24 hours.

(2) In case that Qd is a chlorine atom, a bromine atom or an iodine atom, Compound (VI-e) is reacted with Compound (IV-b) under nitrogen atmosphere in the presence of a base, a copper catalyst and a ligand to give the corresponding Compound (II-a'). This reaction proceeds in the similar manner to Method 4-(1).

In case that Qd is a trifluoromethanesulfonyloxy group, Compound (VI-e) is reacted with Compound (IV-b) under nitrogen atmosphere in an appropriate solvent in the presence of a base, a palladium catalyst and a ligand to give the corresponding Compound (II-a'). This reaction proceeds in the similar manner to Method 4-(2).

In case that Qd is boric acid or boric acid ester, Compound (VI-e) is reacted with Compound (IV-b) under nitrogen atmosphere in an appropriate solvent in the presence of a base, a palladium catalyst and a ligand to give the corresponding Compound (II-a'). This reaction proceeds in the similar manner to Method 4-(3).

The obtained Compound (II-a') may be hydrolyzed according to the conventional method to give Compound (II-a).

Method 10: Compound (II-a) May be Obtained by Coupling of Compound (VI-f) and Compound (IV-a) to Give Compound (II-a'), Followed by Hydrolysis According to the Conventional Method.

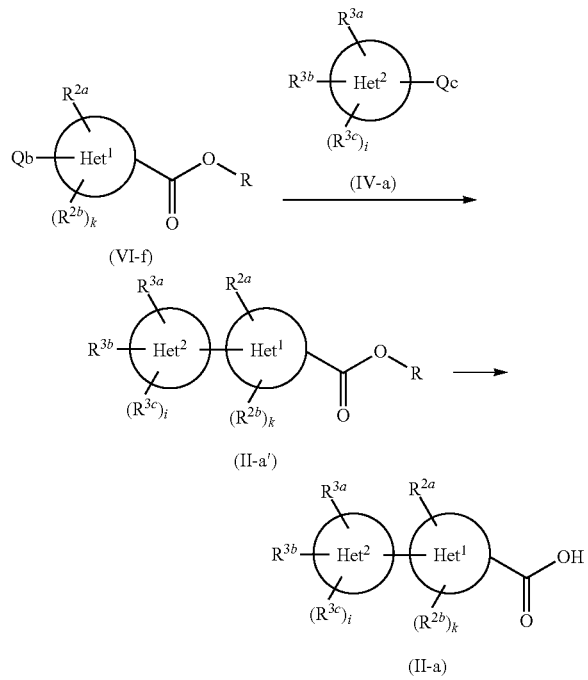

(in which Qb is a bromine atom, a chlorine atom, an iodine atom, a trifluoromethanesulfonyloxy group or a p-toluenesulfonyloxy group, Qc is an active group having a boron atom and includes, for example, boron acid, boron acid ester, etc. R is alkyl and includes, for example, methyl, ethyl or tert-butyl. Other symbols have the same meanings as defined above, respectively.)

Compound (VI-f) is coupled with Compound (IV-a) by Suzuki reaction to give the corresponding Compound (II-a'). This reaction proceeds in the similar manner to Method 3. The obtained Compound (II-a') may be hydrolyzed according to the conventional method to give Compound (II-a).

Method 11: Compound (II-a-3) Wherein $Het^1$ is Pyrazole and the Pyrazole is Substituted with $Het^2$ at the 1-Position, and is Substituted with Alkyl, Haloalkyl or Cycloalkyl at the 5-Position and by a Carboxyl Group at the 4-Position Among Compound (II-a) May be Synthesized According to the Following Method.

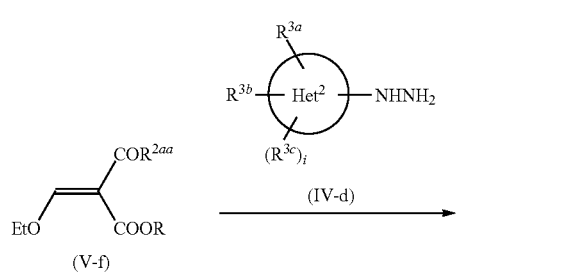

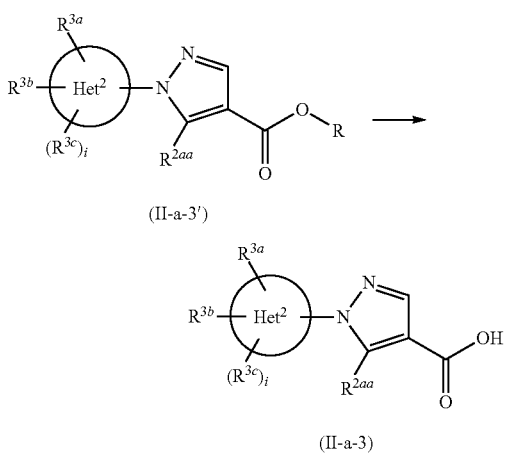

(in which $R^{2aa}$ is alkyl with 1 to 6 carbon atom(s), haloalkyl with 1 to 6 carbon atom(s) or cycloalkyl with 3 to 6 carbon atoms, and other symbols have the same meanings as defined above.)

Compound (V-f) may be reacted with Compound (IV-d) in an appropriate solvent (e.g., water, methanol, ethanol, isopropyl alcohol, butanol, ethylene glycol, acetic acid or a mixed solvent thereof) in the range from room temperature to the reflux temperature of a solvent for 1 to 24 hours to give Compound (II-a-3'). Compound (II-a-3') may be treated with an acid (including hydrochloric acid, sulfuric acid) or a base (including sodium hydroxide, potassium hydroxide) in an appropriate solvent (e.g., water, methanol, ethanol, tetrahydrofuran or a mixed solvent thereof) in the range from room temperature to the reflux temperature of a solvent for 1 to 24 hours to give Compound (II-a-3).

Compound (V-f) may be prepared according to *J. Chem. Soc. Perkin Trans I, p.* 1875 (1988).

Method 12: Compound (II-a-4) Wherein $Het^1$ is Pyrazole and the Pyrazole is Substituted with $Het^2$ on the 1-position, and an amino group on the 5-position, a carboxyl group on the 4-position and hydrogen, alkyl, haloalkyl or cycloalkyl on the 3-position among Compound (II-a) may be synthesized according to the following method.

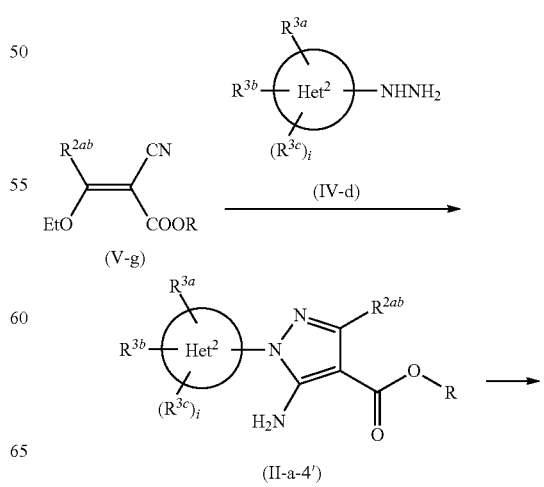

-continued

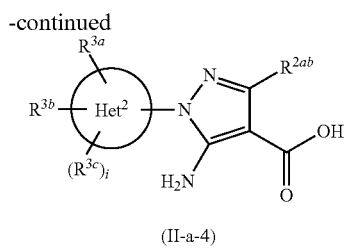

(II-a-4)

(in which $R^{2ab}$ is hydrogen, alkyl with 1 to 6 carbon atom(s), haloalkyl with 1 to 6 carbon atom(s) or cycloalkyl with 3 to 6 carbon atoms, and each symbol has the same meaning as defined above.)

Compound (V-g) may be reacted with Compound (IV-d) in an appropriate solvent (e.g., water, methanol, ethanol, isopropyl alcohol, butanol, ethylene glycol, acetic acid or a mixed solvent thereof) in the range from room temperature to the reflux temperature of a solvent for 1 to 24 hours to give Compound (II-a-4'). Compound (II-a-4') may be treated with an acid (including hydrochloric acid, sulfuric acid) or a base (including sodium hydroxide, potassium hydroxide) in an appropriate solvent (e.g., water, methanol, ethanol or a mixed solvent thereof) in the range from room temperature to the reflux temperature of a solvent for 1 to 24 hours to give Compound (II-a-4).

Compound (V-g) may be prepared according to *J. Chem. Soc. Perkin Trans I*, p. 1875 (1988).

Method 13: Compound (II-a-5) Wherein Het¹ is Pyrazole and Substituted by Het² on the 1-Position of the Pyrazole, and is Substituted by Hydrogen or Alkyl on the 3-Position, by Hydrogen on the 5-Position and by a Carboxyl Group on the 4-Position of the Pyrazole Among Compound (II-a) May be Synthesized According to the Following Method.

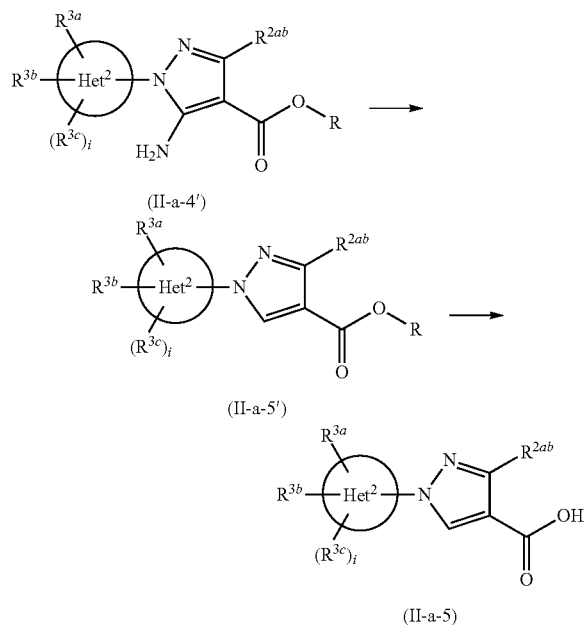

(in which each symbol has the same meaning as defined above.)

Compound (II-a-4') may be reacted with isoamyl nitrite, etc. in an appropriate solvent (e.g., water, acetic acid, methanol, ethanol, isopropyl alcohol, butanol, ethylene glycol, tetrahydrofuran or a mixed solvent thereof) in the presence or absence of aqueous hypophosphorous acid solution at 0° C. to 5° C. for 1 to 3 hours, followed by reaction at room temperature for 4 to 12 hours to give Compound (II-a-5'). Compound (II-a-5') may be reacted with an acid (including hydrochloric acid, sulfuric acid) or an alkali (including sodium hydroxide, potassium hydroxide) in an appropriate solvent (e.g., water, methanol, ethanol, tetrahydrofuran or a mixed solvent thereof) in the range from room temperature to the reflux temperature of a solvent for 1 to 24 hours to give Compound (II-a-5).

Method 14: Compound (II-a-6) Wherein Het¹ is Pyrazole Ring and is Substituted by Alkyl Groups on the 3- and 5-Positions and by a Carboxyl Group on the 4-Position Thereof Among Compound (II-a) May be Prepared According to the Following Method.

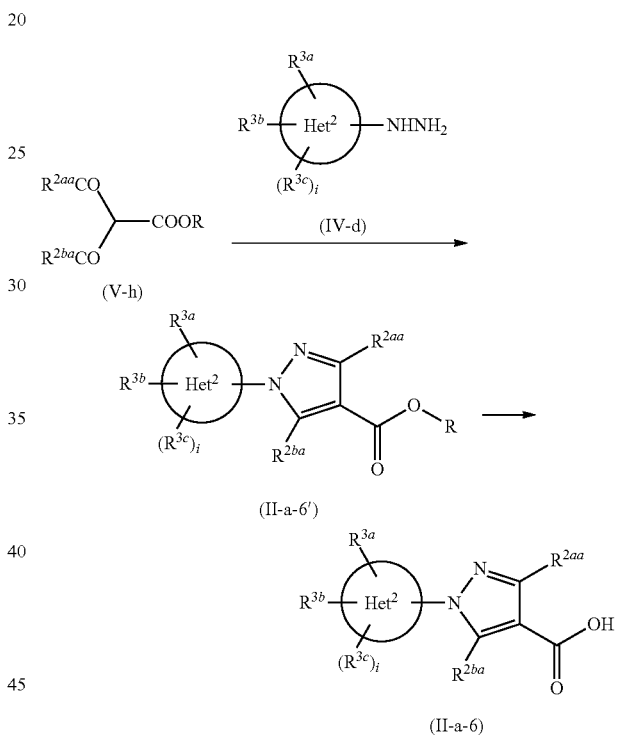

(in which $R^{2ba}$ is alkyl with 1 to 6 carbon atom(s), haloalkyl with 1 to 6 carbon atom(s) or cycloalkyl with 3 to 6 carbon atoms, and other symbols have the same meanings as defined above. Each symbol has the same meaning as defined above.)

Compound (V-h) may be reacted with Compound (IV-d) in an appropriate solvent (e.g., water, methanol, ethanol, isopropyl alcohol, butanol, ethylene glycol, acetic acid or a mixed solvent thereof) in the range from −20° C. to the reflux temperature of a solvent for 1 to 24 hours to give Compound (II-a-6'). Compound (II-a-6') may be reacted with an acid (including hydrochloric acid, sulfuric acid) or an alkali (including sodium hydroxide, potassium hydroxide) in an appropriate solvent (e.g., water, methanol, ethanol, tetrahydrofuran or a mixed solvent thereof) in the range from room temperature to the reflux temperature of a solvent for 1 to 24 hours to give Compound (II-a-6).

Method 15: Compound (III-a) May be Synthesized According to the Following Method.

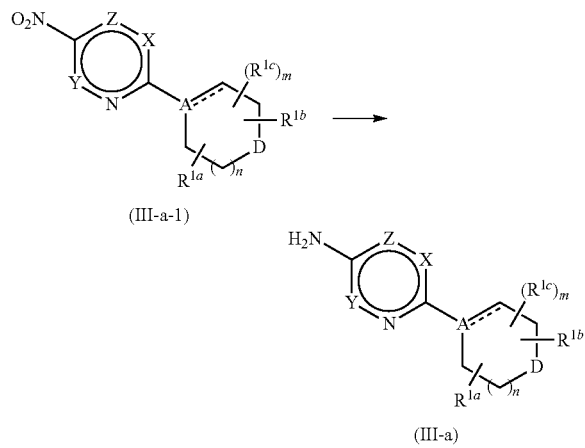

(in which each symbol has the same meaning as defined above.)

Compound (III-a-1) is treated according to the conventional reduction method in the organic synthetic chemistry, for example a method treated by diluted hydrochloric acid using iron powder as a catalyst or catalytic amounts of ammonium chloride in an appropriate solvent (including water, methanol, ethanol, propanol, butanol, ethylene glycol or a mixed solvent thereof), or a catalytic reduction method hydrogenated in the presence of a catalyst such as nickel, palladium, platinum, to give Compound (III-a). The reaction temperature is usually in the range from room temperature to the reflux temperature of a solvent, and the reaction time is usually in the range from 1 to 24 hours.

Method 16: Compound (III-a) May be Also Synthesized According to the Following Method.

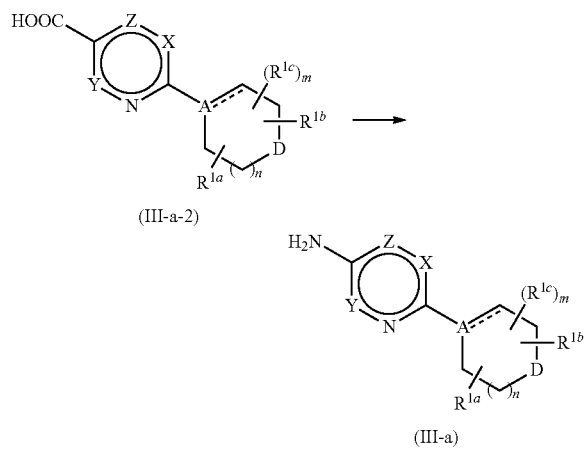

(in which each symbol has the same meaning as defined above.)

Compound (III-c) is treated with sodium azide and a strong acid (including sulfuric acid, trifluoroacetic acid) in an appropriate solvent (e.g., water, methanol, ethanol, propanol, butanol, tertiary butylalcohol, ethylene glycol, benzene, toluene, xylene, etc., preferably benzene) in the range from room temperature to the reflux temperature of a solvent for 1 to 24 hours in Curtius rearrangement or Schmidt rearrangement, or treated with triethylamine and diphenylphosphoryl azide in an appropriate solvent (e.g., methanol, ethanol, isopropyl alcohol, butanol, tertiary butanol, etc., preferably tert-butanol) in the range from room temperature to the reflux temperature of a solvent for 1 to 24 hours, followed by an acid (including hydrochloric acid, sulfuric acid) to give Compound (III-a).

Method 17: Compound (III-a) May be Also Synthesized According to the Following Method.

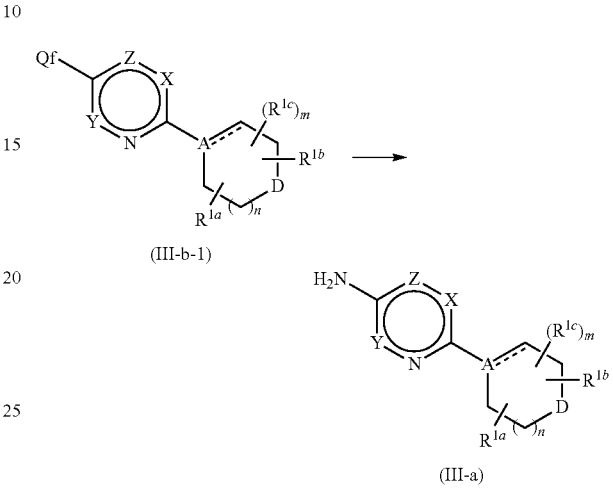

(in which Qf is a bromine atom or a chlorine atom, and other symbols have the same meanings as defined above, respectively.)

Compound (III-b-1) is treated according to the method of *Organic Letters*, vol. 3, p. 2729 (2001) in an appropriate solvent (including toluene, tetrahydrofuran, dioxane) in the presence of a catalyst (including dibenzylideneacetonepalladium, palladium acetate), a ligand (including triphenylphosphine, tris(tertiary-butyl)phosphine) and lithium bis(trimethylsilyl)amide in the range from −20° C. to the reflux temperature of a solvent, followed by treatment by tributyl ammonium fluoride, potassium fluoride, etc. to give Compound (III-a).

Method 18: Compound (III-a) May be Also Synthesized According to the Following Method.

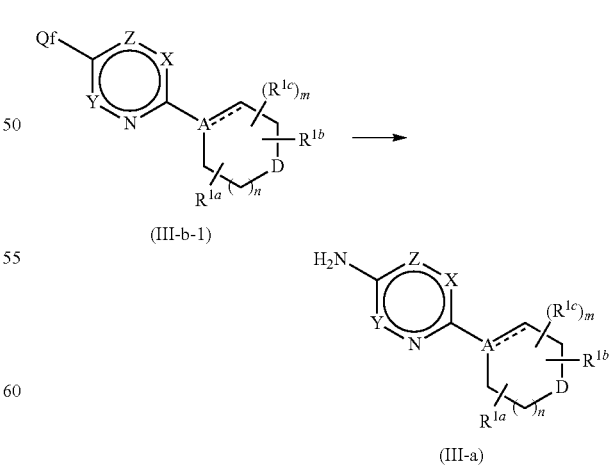

(in which Qf is a bromine atom or a chlorine atom, and other symbols have the same meanings as defined above, respectively.)

Compound (III-b-1) is treated under the condition using a catalyst (including tris(dibenzylideneacetone)dipalladium (0), palladium acetate), a ligand (including 2,2'-bis(diphenylphosphino)-1,1'-binaphthyl, 2-di-tert-butylphosphino-2', 4',6'-triisopropylbiphenyltriphenylphosphine), benzophenone imine and a base (including sodium tert-butoxide, tripotassium phosphate) in an appropriate solvent (including toluene, tetrahydrofuran, 1,4-dioxane, 1,2-dimethoxyethane) in the range from room temperature to the reflux temperature of a solvent for 1 to 24 hours, followed by treatment by an acid such as 1N aqueous hydrochloric acid solution in an appropriate solvent (e.g., toluene, 1,4-dioxane, 1,2-dimethoxyethane, tetrahydrofuran, etc.) to give Compound (III-a).

Method 19: Compound (III-a) May be Also Synthesized According to the Following Method.

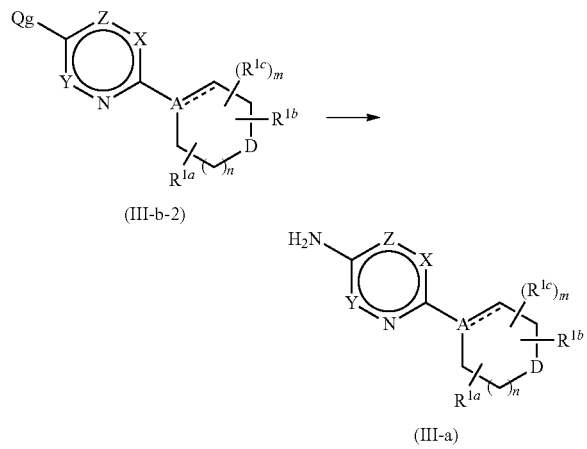

(in which Qg is a bromine atom or an iodine atom, and other symbols have the same meanings as defined above, respectively.)

According to the method of *Angewandte Chemie International Edition*, vol. 48, p. 337 (2009), Compound (III-b-2) is treated in an appropriate solvent (including N,N-dimethylformamide) in the presence of a catalyst (including copper (II) acetylacetonate), acetylacetone, ammonium hydroxide and cesium carbonate as a base in a sealed tube at 60° C. to 150° C. for 3 to 60 hours to give Compound (III-a).

Method 20: Compound (III-b-4) May be Synthesized According to the Following Method.

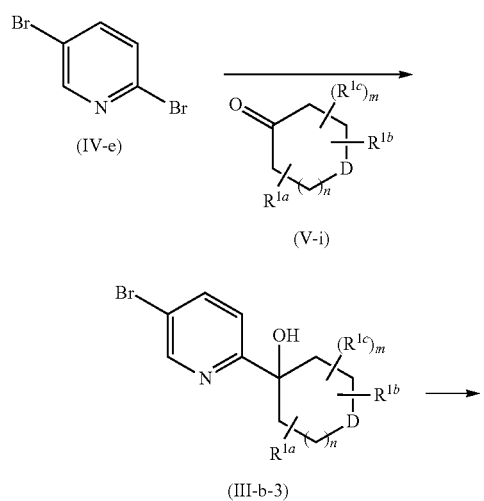

(in which each symbol has the same meaning as defined above.)

Compound (IV-e) is reacted with n-BuLi in toluene at −60° C. to −78° C. for 30 minutes to 2 hours, and then thereto is added appropriate ketone derivative (V-i), and the mixture is treated at the same temperature for 1 to 2 hours, then at room temperature for 3 to 24 hours, and then treated with water or aqueous sodium carbonate solution, etc. in an appropriate way to give Compound (III-b-3). If necessary, conventional post-treatment procedures are carried out. Then, Compound (III-b-3) is reacted in pyridine (if necessary, dichloromethane, etc. is added) with addition of thionyl chloride at 0° C. to room temperature for 30 minutes to 24 hours to give Compound (III-b-4).

Method 21: Compound (III-b-4) May be Also Synthesized According to the Following Method.

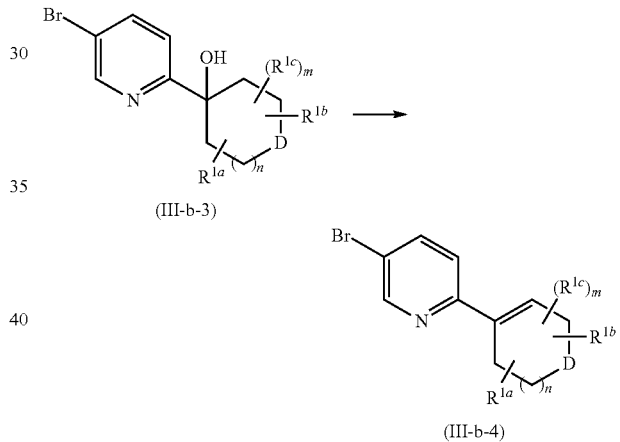

(in which each symbol has the same meaning as defined above.)

Compound (III-b-3) is reacted with addition of polyphosphoric acid, for example, at 100° C. to 200° C. for 30 minutes to 5 hours to give Compound (III-b-4).

Method 22: Compound (III-a-1') May be Synthesized According to the Following Method.

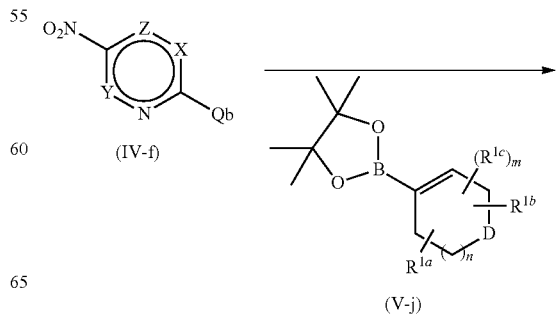

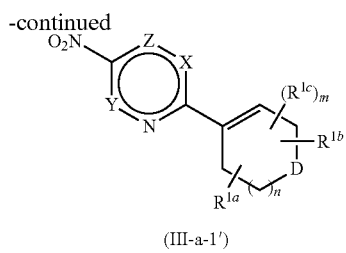

(III-a-1')

(in which each symbol has the same meaning as defined above.)

Compound (IV-f) is coupled with Compound (V-j) in Suzuki reaction to give the corresponding Compound (III-a-1'). This reaction proceeds by heating under nitrogen atmosphere using a palladium catalyst, a phosphine ligand and a base in an appropriate solvent. The solvent used in the reaction includes, for example, tetrahydrofuran, toluene, N-methylpyrrolidone, N,N-dimethylformamide, 1,4-dioxane, 1,2-dimethoxyethane, tert-butanol or a mixed solvent of these organic solvents with water, etc. The base includes, for example, potassium carbonate, cesium carbonate, sodium carbonate, potassium acetate, tripotassium phosphate, diisopropylethylamine, sodium tert-butoxide, etc. The palladium catalyst includes, for example, palladium (II) acetate, tris(dibenzylideneacetone)dipalladium (0), etc. The ligand includes 2-dicyclohexylphosphino-2,6-dimethoxybiphenyl, 2-(di-t-butylphosphino)biphenyl, 2-dicyclohexylphosphino-biphenyl, 2-di-tert-butylphosphinobiphenyl, 2-(di-tert-butylphosphino)3,4,5,6-tetramethyl-2',4',6'-triisopropyl-1,1'-biphenyl, 2-(dicyclohexylphosphino)-2',4',6'-triisopropyl-1,1'-biphenyl, etc. A complex formed by a palladium catalyst and a phosphine ligand may be used, and includes, for example, [1,1'-bis(diphenylphosphino)ferrocene]palladium (II) dichloride-dichloromethane complex, dichlorobis(tricyclohexylphosphine)palladium (II), tetrakis(triphenylphosphine)palladium (0), [1,1'-bis(diphenylphosphino)ferrocene] palladium dichloride, bis(triphenylphosphine)palladium (II) dichloride, etc. The reaction temperature is usually in the range from room temperature to the reflux temperature of a solvent. The reaction time varies depending on starting materials or a solvent to be used and the reaction temperature, etc., and is usually in the range from 1 to 24 hours.

Method 23: Compound (V-j) May be Synthesized According to the Following Method.

Compound (V-i) is reacted with a triflating agent in the presence of a base to give Compound (V-k). This reaction proceeds by enolation using a base under nitrogen atmosphere in an appropriate solvent, and then by addition of a triflating agent. The solvent used in the reaction includes, for example, tetrahydrofuran, toluene, dichloromethane, 1,4-dioxane, 1,2-dimethoxyethane, 1,2-dichloroethane, dimethylether, etc. The base includes, for example, lithium diisopropylamide, lithium bis(trimethylsilyl)amide, sodium hydride, pyridine, 2,6-di-tert-butyl-4-methylpyridine, 2,6-di-tert-butylpyridine, sodium carbonate, diisopropylethylamine, etc. The triflating agent includes, for example, N-phenyl-bis(trifluoromethanesulfonimide), trifluoromethanesulfonic anhydride, etc. The reaction temperature is usually in the range from −78° C. to the reflux temperature of a solvent. The reaction time varies depending on starting materials or a solvent to be used and the reaction temperature, etc., and is usually in the range from 30 minutes to 24 hours.

Then, Compound (V-k) may be converted into borane derivative (V-j) in the presence of a palladium catalyst. This reaction proceeds by heating with addition of a palladium catalyst and a borylating agent using a base under nitrogen atmosphere in an appropriate solvent. The solvent used in the reaction includes, for example, tetrahydrofuran, toluene, 1,4-dioxane, etc. The base includes, for example, potassium carbonate, triethylamine, potassium acetate, phenoxypotassium, diisopropylethylamine, etc. The borylating agent includes, for example, 4,4,5,5-tetramethyl-1,3,2-dioxaborolane(pinacolborane), bis(pinacolate)diborane, etc. The palladium catalyst includes, for example, [1,1'-bis(diphenylphosphino)ferrocene]palladium (II) dichloride-dichloromethane complex, bis(triphenylphosphine)palladium (II) dichloride, etc., and the ligand added, if necessary, includes, for example, triphenylphosphine, 1,1'-bis(diphenylphosphino)ferrocene, etc. The reaction temperature is usually in the range from room temperature to the reflux temperature of a solvent. The reaction time varies depending on starting materials or a solvent to be used and the reaction temperature, etc., and is usually in the range from 1 to 24 hours.

Method 24: Compound (III-b-5) May be Synthesized According to the Following Method.

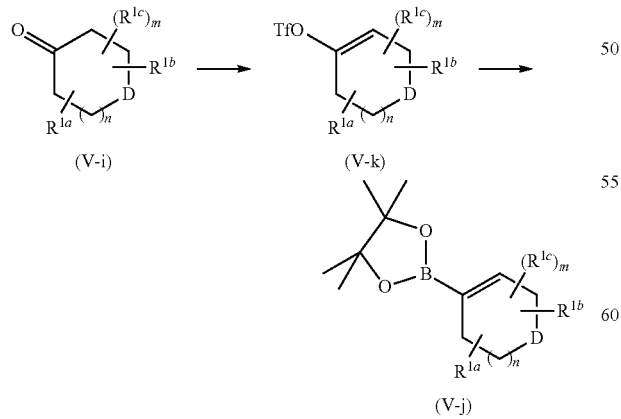

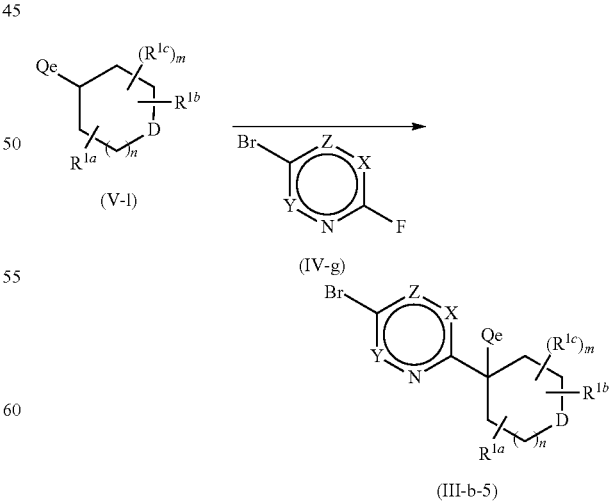

(in which each symbol has the same meaning as defined above.)

(in which Qe is ester or cyano, and other symbols have the same meanings as defined above, respectively.)

Compound (V-l) may be treated with a base in an appropriate solvent, and then reacted with Compound (IV-g) to give Compound (III-b-5). The solvent used in the reaction includes, for example, tetrahydrofuran, toluene, etc. The base includes, for example, lithium bis(trimethylsilyl)amide, etc. The reaction temperature is usually in the range from −20° C. to the reflux temperature of a solvent. The reaction time varies depending on starting materials or a solvent to be used and the reaction temperature, etc., and is usually in the range from 30 minutes to 24 hours.

Method 25: Compound (III-c-1) May be Synthesized According to the Following Method.

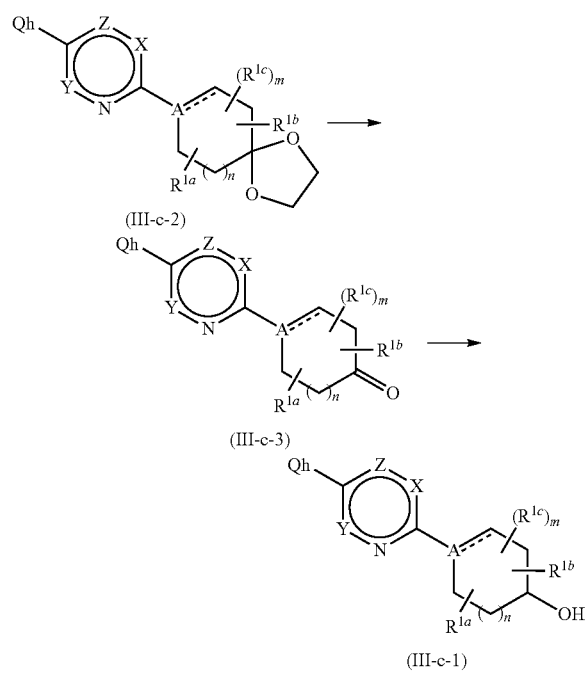

(in which Qh is a bromine atom, a chlorine atom or an iodine atom, and other symbols have the same meanings as defined above, respectively.)

Compound (III-c-2) may be reacted with an acid to give Compound (III-c-3). The acid used in the reaction includes trifluoroacetic acid, trifluoroacetic acid-water, aqueous hydrochloric acid solution, etc. If necessary, tetrahydrofuran, etc. may be added as a solvent, for example. If necessary, conventional post-treatment procedures are carried out. The reaction temperature is usually in the range from 0° C. to the reflux temperature of a solvent. The reaction time varies depending on starting materials or a solvent to be used and the reaction temperature, etc., and is usually in the range from 1 to 24 hours. Then, Compound (III-c-3) may be reacted with addition of a reducing agent in an appropriate solvent to give Compound (III-c-1). The solvent used in the reaction includes, for example, methanol, ethanol, tetrahydrofuran, etc. The reducing agent includes, for example, sodium borohydride, lithium borohydride, lithium aluminum hydride, etc. The reaction temperature is usually in the range from −78° C. to the reflux temperature of a solvent. The reaction time varies depending on starting materials or a solvent to be used and the reaction temperature, etc., and is usually in the range from 10 minutes to 24 hours.

Method 26: Compound (III-c-4) May be Synthesized According to the Following Method.

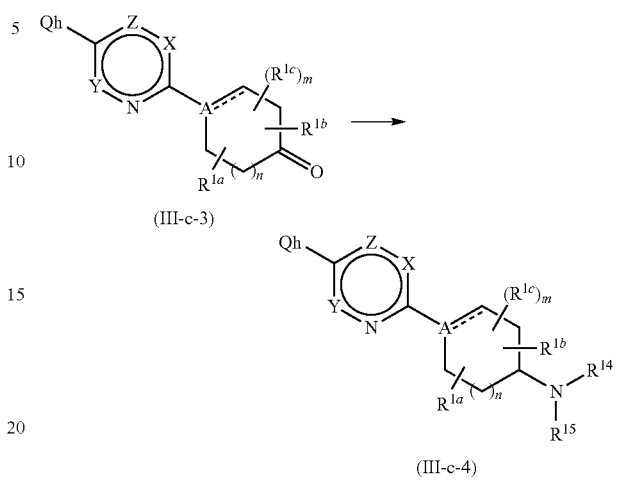

(in which each symbol has the same meaning as defined above.)

Compound (III-c-3) may be treated in an appropriate solvent by reductive amination using the corresponding amine to give Compound (III-c-4). The solvent used in the reaction includes, for example, dichloromethane, toluene, tetrahydrofuran, etc. The reducing agent includes, for example, sodium triacetoxyborohydride, etc. The reaction temperature is usually in the range from 0° C. to the reflux temperature of a solvent. The reaction time varies depending on starting materials or a solvent to be used and the reaction temperature, etc., and is usually in the range from 1 to 48 hours.

Method 27: Compound (III-c-6) May be Synthesized According to the Following Method.

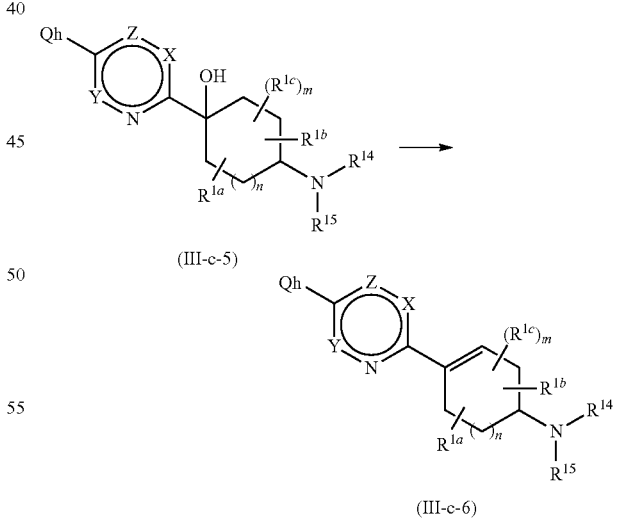

(in which each symbol has the same meaning as defined above.)

Compound (III-c-5) may be treated in pyridine (if necessary, dichloromethane, etc. is added) with addition of thionyl chloride at 0° C. to room temperature for 30 minutes to 24 hours to give Compound (III-c-6). Alternatively, treatment by addition of an acid such as polyphosphoric acid at 100° C. to 200° C. for 30 minutes to 5 hours also gives Compound (III-c-6).

Method 28: Compound (III-c-8) May be Synthesized According to the Following Method.

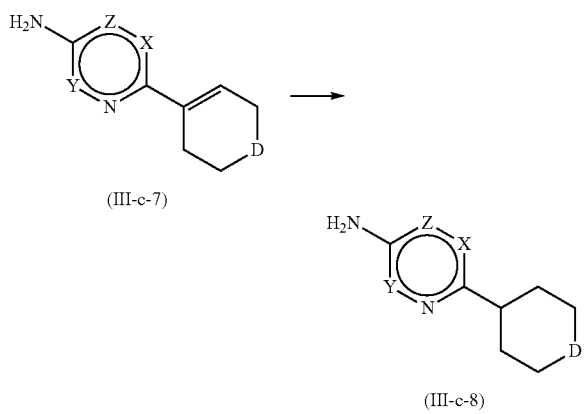

(in which each symbol has the same meaning as defined above.)

Compound (III-c-7) may be reduced by catalytic hydrogenation in an appropriate solvent to give Compound (III-c-8). The solvent used in the reaction includes, for example, ethanol, methanol, ethyl acetate, N,N-dimethylformamide, 1,4-dioxane, toluene, acetic acid or a mixed solvent thereof, etc. The catalyst includes, for example, palladium carbon, etc. The reaction temperature is usually in the range from room temperature to the reflux temperature of a solvent, and a hydrogen pressure is in the range from 1 to 20 atm. The reaction time varies depending on starting materials or a solvent to be used and the reaction temperature, etc., and is usually in the range from 1 to 48 hours. According to the method of *Organic Letters, vol.* 7, p. 5087 (2005), the reduction reaction proceeds by using tetrahydrofuran, 1,4-dioxane, water or a mixed solvent thereof, etc. in the presence of potassium fluoride, etc. using palladium acetate, etc. as a catalyst, and adding polymethylhydrosiloxane, etc. The reaction temperature is usually in the range from 0° C. to the reflux temperature of a solvent. The reaction time varies depending on starting materials or a solvent to be used and the reaction temperature, etc., and is usually in the range from 1 to 48 hours.

The compounds or salts thereof of the present invention include both solvates and hydrates thereof, etc. The compounds of the present invention may be treated with an inorganic acid or an organic acid by the conventional method to give acid addition salts, and may be treated with an inorganic base or an organic base by the conventional method to give base addition salts, in an appropriate solvent, if necessary. The compounds of the present invention may be treated with an alkali metal salt and an alkaline-earth metal salt, etc. by the conventional method to give the corresponding metal salts. The compounds of the present invention may be treated with water, an aqueous solvent or other solvent by the conventional method to give hydrates or solvates thereof. The compounds of the present invention may be converted into N-oxide compound by treating with an oxidizing agent such as hydrogen peroxide, meta-chloroperbenzoic acid by the conventional method.

The compound of the general formula (I) and each intermediate obtained in the above are isolated and purified by conventional chemical operations or known methods in the organic synthetic chemistry such as extraction, crystallization, recrystallization, various chromatography methods.

An acid addition salt or a base addition salt may be used as a salt of the compound of the general formula (I), and types of salts are not intended to be limited if they are physiologically acceptable.

A salt of the compound of the general formula (I), or a solvate thereof may be prepared by known methods from an amide derivative of the general formula (I).

In case that the compound of the general formula (I), or a salt thereof is a racemate, or includes optically active compounds, it may be isolated into each optically active isomer by conventional optical resolution methods. For example, it may be divided into the desired optically active compounds by fractional crystallization by a salt with an optically active acid or base, or by passing through a column loaded with optically active carriers. Alternatively, an optically active compound of the compound of the general formula (I), or a salt thereof may be synthesized by using optically pure starting materials or compounds which configurations are known.

One or more of the compound or a pharmacologically acceptable salt thereof, or a solvate thereof in the present invention may be directly administered to patients, and may be preferably provided in the form of a formulation well known to a skilled person comprising the active ingredient and pharmacologically and pharmaceutically acceptable additives.

The compound or a pharmacologically acceptable salt thereof, or a solvate thereof in the present invention is useful for prevention or treatment of autoimmune diseases or inflammatory/allergic diseases, since it inhibits the production of cytokines from T cells (e.g., productions of IL-17 or other inflammatory cytokines (including IFN-γ), etc.). The autoimmune disease includes rheumatoid arthritis, multiple sclerosis, systemic lupus erythematosus, psoriasis, inflammatory bowel disease, transplantation rejection, asthma, etc.

The compound or a pharmacologically acceptable salt thereof, or a solvate thereof in the present invention may be optionally used in combination with other immunosuppressants, steroid drugs, anti-allergic drugs, etc.

Timing of administration of the compound or a pharmacologically acceptable salt thereof, or a solvate thereof in the present invention and concomitant medication is not intended to be limited, and they may be administered to subjects concurrently or with temporal intervals. Further, the compound of the present invention and concomitant medication may be administered as two types of formulations each of which contains each active ingredient or as a single formulation compositing both active ingredients.

Dosage amounts of the concomitant medication may be optionally selected on the basis of clinically used dosage amounts. Combination ratios of the compound of the present invention and the concomitant medication may be optionally selected depending on administration subjects, administration routes, subject diseases, conditions, a combination thereof, etc. For example, when the administration subject is human, 0.01 to 100% by weight of the concomitant medication to 1 part by weight of the compound of the present invention may be used.

The compound of the present invention may be prepared in an appropriate dosage form (including powders, injections, tablets, capsules or topical external preparations) together with appropriate usual diluents and other additives, followed by administered to human or animals by appropriate administration routes depending on its dosage form (e.g., intravenous administration, oral administration, cutaneous administration or topical administration).

As the pharmacologically and pharmaceutically acceptable additive, excipients, disintegrants, binders, lubricants, coating agents, pigments, diluents, bases and tonicity agents may be used.

A preparation appropriate for oral administration may include tablets, capsules, powders, fine granules, granules, liquids or syrups, and a preparation appropriate for parenteral administration may include injections, drops or suppositories.

In the preparation appropriate for oral administration, additives such as excipients, disintegrants, binders, lubricants, coating agents or bases may be used. When the compound of the present invention is administered to patients as a therapeutic target, other drugs appropriate for treating the target disease may be used concurrently with the compound of the present invention.

An administration route of the medicine of the present invention is not limited specifically, and it may be either orally or parenterally administered. Dosage amounts are determined by conditions depending on age, weight, general health condition, sex, diet, administration time, administration method, excretory time, combination of medicines, condition of disease under treatment at the time, or other factors. The compounds, optical isomers thereof or pharmaceutically acceptable salts thereof in the present invention may be used with low toxicity and safely. The dosage amounts per day differ depending on conditions and weight of patients, kinds of the compounds, administration routes, etc., and, for example, about 0.1 to 1000 mg/person/day, preferably 1 to 500 mg/person/day are parenterally administered via subcutaneously, intravenously, intramuscularly or rectally, and about 0.1 to 1000 mg/person/day, preferably 1 to 500 mg/person/day are orally administered.

The present invention is explained by Examples of the present invention in more detail as below, but the scope of the present invention is not intended to be limited thereto.

The "room temperature" in the following Examples refers to 10 to 30° C. The solvent ratios in a mixed solvent refer to volume ratios.

Mass spectra were determined by LCMS (liquid chromatograph mass spectrometer) using the following (1), (2) or (3) instrument, and conditions. ESI (electrospray ionization) method, or APCI (atmospheric pressure chemical ionization) method was used as a MS measurement mode. Unless otherwise specified, each compound was determined by ESI method. Unless otherwise specified, each compound was determined by ESI method.

(1) LC-2010 (manufactured by Shimadzu Corporation) was used as the instrument, and Chromolith SpeedROD RP-18e (4.6 mmϕ×50 mm) (manufactured by Merck) was used as the column. For the measurement conditions, a gradient elution was carried out under 2.0 ml/min of a flow rate and a mixed solvent of solution A (0.05% trifluoroacetic acid/water) and solution B (0.05% trifluoroacetic acid/acetonitrile) as a solvent from solution A:solution B=95:5 to solution A:solution B=0:100 for 4 minutes;

(2) Acquity/ZQ (manufactured by Waters) or SQD was used as the instrument, and Acquity UPLC BEH C18 (2.1 mmϕ×50 mm) (manufactured by Waters) was used as the column. For the measurement conditions, a gradient elution was carried out under 0.6 ml/min of a flow rate and a mixed solvent of solution A (0.05% trifluoroacetic acid/water) and solution B (0.05% trifluoroacetic acid/acetonitrile) or a mixed solvent of solution A (0.05% formic acid/water) and solution B (0.05% formic acid/acetonitrile) as a solvent from solution A:solution B=95:5 to solution A:solution B=2:98 for 1 minute.

(3) LXQ (manufactured by Thermo Fisher Scientific) was used as the instrument, and the measurement conditions were 0.2 ml/min of a flow rate and a mixed solvent of 80% methanol/water, and samples were injected by flow injection method using a LC instrument without separation by column chromatography.

$^1$H-NMR (proton nuclear magnetic resonance spectra) was measured at 400 MHz or 300 MHz. Relative delta ($\delta$) values of chemical shifts of $^1$H-NMR were represented as ppm using tetramethylsilane (TMS) as an internal standard. s refers to singlet, d refers to doublet, t refers to triplet, q refers to quartet, m refers to multiplet, broad refers to a broad absorption peak, and brs refers to a broad singlet.

Other abbreviations used herein refer to the following meanings.

CDCl$_3$: deuterochloroform

DMSO-d$_6$: hexadeuterodimethyl sulfoxide

As to a nomenclature of compounds, in case that a compound has benzimidazole as a substituent group, for example, tautomers may exist. In such case, substituent positions are described as "-5(6)-yl", for example.

EXAMPLES

The present inventions are illustrated in more detail by Reference Example, Example, Formulation example and Test Example, but they should not be construed to be limited thereto.

Reference Example 1

1-(4-Fluorophenyl)-5-methyl-1H-pyrazole-4-carboxylic acid

To an ethanol (75 ml) solution of ethyl 2-(ethoxymethylene)acetoacetate (28.63 g) prepared according to a method described in *J. Chem. Soc. Perkin trans. I*, 1875 (1988), was added 1N hydrochloric acid aqueous solution (75 ml) of 4-fluorophenylhydrazine hydrochloride (25 g) and the mixture was stirred at reflux temperature for three hours. After evaporation of ethanol, sodium hydroxide (12 g) was added to the residue and stirred at reflux temperature for three hours. After completion of the reaction, the solvent was evaporated, diluted hydrochloric acid was added to the residue, and the precipitated solid was washed with ethyl acetate to give the titled compound (16.08 g).

MS (ESI) m/z: 221 (M+H)$^+$.

Reference Example 2

1-(2,4-Difluorophenyl)-5-methyl-1H-pyrazole-4-carboxylic acid 2,4-Difluorophenylhydrazine hydrochloride was used in place of 4-fluorophenylhydrazine hydrochloride in Reference Example 1 and reacted and treated in a similar manner to give the titled compound.

MS (ESI) m/z: 239 (M+H)$^+$.

Reference Example 3

1-(4-Chlorophenyl)-5-methyl-1H-pyrazole-4-carboxylic acid

4-Chlorophenylhydrazine sulfate was used in place of 4-fluorophenylhydrazine hydrochloride in Reference Example 1 and reacted and treated in a similar manner to give the titled compound.
MS (ESI) m/z: 237 (M+H)$^+$.

Reference Example 4

5-Methyl-1-(4-methylphenyl)-1H-pyrazole-4-carboxylic acid

To an ethanol (70 ml) and water (70 ml) solution of ethyl 2-(ethoxymethylene)acetoacetate (16.67 g) prepared according to a method described in *J. Chem. Soc. Perkin trans. I,* 1875 (1988), was added 4-methylphenylhydrazine hydrochloride (14.2 g) and the mixture was stirred at reflux temperature for 7.5 hours. Sodium hydroxide (8.5 g) was added and the mixture was further stirred at reflux temperature for an hour. After completion of the reaction, the solvent was evaporated, diluted hydrochloric acid was added to the residue, and the mixture was extracted with ethyl acetate. The organic layer was dried over anhydrous magnesium sulfate and the solvent was evaporated. The residue was washed with n-hexane to give the titled compound (11.17 g).
MS (ESI) m/z: 217 (M+H)$^+$.

Reference Example 5

1-(4-Methoxyphenyl)-5-methyl-1H-pyrazole-4-carboxylic acid

4-Methoxyphenyl hydrazine hydrochloride was used in place of 4-fluorophenylhydrazine hydrochloride in Reference Example 1 and reacted and treated in a similar manner to give the titled compound.
MS (ESI) m/z: 233 (M+H)$^+$.

Reference Example 6

5-Methyl-1-[3-(trifluoromethyl)phenyl]-1H-pyrazole-4-carboxylic acid 3-(Trifluoromethyl)phenylhydrazine hydrochloride was used in place of 4-fluorophenylhydrazine hydrochloride in Reference Example 1 and reacted and treated in a similar manner to give the titled compound.
MS (ESI) m/z: 271 (M+H)$^+$.

Reference Example 7

5-Methyl-1-phenyl-1H-pyrazole-4-carboxylic acid

Phenylhydrazine was used in place of 4-fluorophenylhydrazine hydrochloride in Reference Example 1 and reacted and treated in a similar manner to give the titled compound.
MS (ESI) m/z: 203 (M+H)$^+$.

Reference Example 8

5-Methyl-1-[5-(trifluoromethyl)pyridin-2-yl]-1H-pyrazole-4-carboxylic acid (1) 2-Chloro-5-(trifluoromethyl)pyridine (25 g) and hydrazine monohydrate (100%) (100 ml) were added to ethanol (60 ml) and stirred at 100° C. for three hours. The reaction solution was concentrated in vacuo, chloroform and water were added to the residue, the organic layer was separated and dried over anhydrous sodium sulfate. The solvent was exaporated in vacuo and 4N hydrochloric acid ethanol solution was added to the residue to give 5-trifluoromethylpyridin-2-ylhydrazine hydrochloride (15.4 g).
MS (ESI) m/z: 178 (M+H)$^+$.

(2) Next, ethyl 2-(ethoxymethylene)acetoacetate (6.11 g), which was prepared according to a method described in *J. Chem. Soc. Perkin trans. I,* 1875 (1988), and 5-trifluoromethylpyridin-2-ylhydrazine hydrochloride (7.0 g) described above were added to a mixed solvent of water (40 ml) and ethanol (40 ml). The mixture was stirred at refluxing temperature for three hours, sodium hydroxide (2.6 g) was added to the reaction solution and the mixture was stirred additionally for an hour. The reaction solution was treated with 1N hydrochloric acid aqueous solution and the precipitated solid was purified with a mixture of ethyl acetate and n-hexane to give the titled compound (6.5 g).
MS (ESI) m/z: 272 (M+H)$^+$.

Reference Example 9

5-Methyl-1-[6-(trifluoromethyl)pyridin-2-yl]-1H-pyrazole-4-carboxylic acid

2-Chloro-6-(trifluoromethyl)pyridine was used in place of 2-chloro-5-(trifluoromethyl)pyridine in Reference Example 8, and reacted and treated in a similar manner to give the titled compound.
MS (ESI) m/z: 272 (M+H)$^+$.

Reference Example 10

5-Methyl-1-[4-(trifluoromethyl)pyridin-2-yl]-1H-pyrazole-4-carboxylic acid

2-Chloro-4-(trifluoromethyl)pyridine was used in place of 2-chloro-5-(trifluoromethyl)pyridine in Reference Example 8, and reacted and treated in a similar manner to give the titled compound.
MS (ESI) m/z: 272 (M+H)$^+$.

Reference Example 11

1-(3,4-Dichlorophenyl)-5-methyl-1H-pyrazole-4-carboxylic acid 3,4-Dichlorophenylhydrazine hydrochloride was used in pace of 4-fluorophenylhydrazine hydrochloride in Reference Example 1, and reacted and treated in a similar manner to give the titled compound.
MS (ESI) m/z: 270 (M)$^+$.

Reference Example 12

1-(3,4-Difluorophenyl)-5-methyl-1H-pyrazole-4-carboxylic acid 3,4-Difluorophenylhydrazine was used in pace of 4-fluorophenylhydrazine hydrochloride in Reference Example 1, and reacted and treated in a similar manner to give the titled compound.
MS (ESI) m/z: 239 (M+H)$^+$.

Reference Example 13

1-(4-Bromophenyl)-5-methyl-1H-pyrazole-4-carboxylic acid

4-Bromophenylhydrazine hydrochloride was used in pace of 4-fluorophenylhydrazine hydrochloride in Reference Example 1, and reacted and treated in a similar manner to give the titled compound.
MS (ESI) m/z: 281, 283 (M+H)$^+$.

Reference Example 14

5-Methyl-1-[5-(trifluoromethyl)pyridin-2-yl]-1H-pyrazole-3-carboxylic acid

Ethyl 2,4-dioxopentanoate was used in place of ethyl 2-(ethoxymethylene)acetoacetate in Reference Example 8, and reacted and treated in a similar manner to give the titled compound.
MS (ESI) m/z: 272 (M+H)$^+$.

Reference Example 15

3,5-Dimethyl-1-[5-(trifluoromethyl)pyridin-2-yl]-1H-pyrazole-4-carboxylic acid Ethyl diacetoacetate was used in place of ethyl 2-(ethoxymethylene)acetoacetate in Reference Example 8, and reacted and treated in a similar manner to give the titled compound.
MS (ESI) m/z: 286 (M+H)$^+$.

Reference Example 16

3-Methyl-1-[5-(trifluoromethyl)pyridin-2-yl]-1H-pyrazole-4-carboxylic acid 5-(Trifluoromethyl)pyridin-2-ylhydrazine (10.0 g) described in Reference Example 8 and ethyl 2-cyano-3-ethoxy-3-methylacrylate (10.3 g) were added to a mixed solvent of ethanol (40 ml) and 1N hydrochloric acid aqueous solution (40 ml), and the mixture was stirred at reflux temperature for three hours. Water was added to the reaction solution to give ethyl 5-amino-3-methyl-1-[5-(trifluoromethyl)pyridin-2-yl]-1H-pyrazole-4-carboxylate (9.6 g). Next, the compound was added to tetrahydrofuran (50 ml), isoamyl nitrite (20 g) was added and the mixture was stirred at reflux temperature for five hours. The reaction solution was concentrated, a mixed solvent of ethanol (40 ml) and water (40 ml) and sodium hydroxide (5 g) were added and the mixture was stirred at reflux temperature for two hours. Ethanol was evaporated, diluted hydrochloric acid was added and the precipitated solid was recrystallized from aqueous methanol to give the titled compound.
MS (ESI) m/z: 272 (M+H)$^+$.

Reference Example 17

1-(4-tert-Butylphenyl)-5-methyl-1H-pyrazole-4-carboxylic acid

Ethyl 2-(ethoxymethylene)acetoacetate (13.92 g), which was prepared according to a method described in *J. Chem. Soc. Perkin trans. I*, 1875 (1988), was dissolved in ethanol (45 ml), an aqueous solution (45 ml) of 4-tert-butylphenylhydrazine hydrochloride (15.0 g) was added therein and the mixture was stirred at reflux temperature for four hours. To the reaction mixture was added water, and the mixture was extracted with ethyl acetate. The extract layers were washed with saturated brine and evaporated in vacuo. To the residue was added sodium hydroxide (5.9 g), water (45 ml) and ethanol (45 ml) and the resulting mixture was stirred at reflux temperature for two hours. After completion of the reaction, the organic solvent was evaporated and the aqueous residue was washed with toluene, and then the aqueous layer was acidified by the addition of diluted hydrochloric acid, extracted with ethyl acetate, dried over anhydrous magnesium sulfate and concentrated in vacuo. The precipitated solid was repurified with ethyl acetate/n-hexane to give the titled compound (4.50 g).
MS (ESI) m/z: 259 (M+H)$^+$.

Reference Example 18

1-(2,4-Dichlorophenyl)-5-methyl-1H-pyrazole-4-carboxylic acid 2,4-Dichlorophenylhydrazine hydrochloride was used in place of 4-fluorophenylhydrazine hydrochloride in Reference Example 1 and reacted and treated in a similar manner to give the titled compound.
MS (ESI) m/z: 271 (M+H)$^+$.

Reference Example 19

1-(2,3,4-Trifluorophenyl)-5-methyl-1H-pyrazole-4-carboxylic acid (1) 2,3,4-Trifluoroaniline (25 g) was added to concentrated hydrochloric acid (125 ml), and an aqueous solution (20 ml) of sodium nitrite (12.9 g) was added dropwise under ice-cooling. A solution of tin (II) chloride (114.6 g) in concentrated hydrochloric acid (50 ml) was separately prepared and it was added dropwise to the reaction solution. The precipitated solid was collected by filtration, added to an aqueous solution of sodium hydroxide and the aqueous solution was extracted with toluene to give 2,3,4-trifluorophenylhydrazine (9.3 g).

(2) To a mixed solvent of 1N hydrochloric acid aqueous solution (120 ml) and ethanol (120 ml), were added 2,3,4-trifluorophenylhydrazine (9.3 g) and ethyl 2-(ethoxymethylene)acetoacetate (10.7 g) prepared according to a method described in *J. Chem. Soc. Perkin trans. I*, 1875 (1988), and the mixture was stirred at reflux temperature for three hours. Next, sodium hydroxide (2.8 g) was added and the mixture was further stirred for an hour. Ethanol was evaporated in vacuo, the organic layer was separated with toluene, hydrochloric acid was added to the aqueous layer and the precipitated solid was collected by filtration to give the titled compound (10 g).
MS (ESI) m/z: 257 (M+H)$^+$.

Reference Example 20

1-(5-Chloropyridin-2-yl)-5-methyl-1H-pyrazole-4-carboxylic acid 2,5-Dichloropyridine was used in place of 2-chloro-5-(trifluoromethyl)pyridine in Reference Example 8, and reacted and treated in a similar manner to give the titled compound.
MS (ESI) m/z: 238 (M+H)$^+$.

Reference Example 21

1-(5-Fluoropyridin-2-yl)-5-methyl-1H-pyrazole-4-carboxylic acid 2,5-Difluoropyridine was used in place of 2-chloro-5-(trifluoromethyl)pyridine in Reference Example 8, and reacted and treated in a similar manner to give the titled compound.
MS (ESI) m/z: 222 (M+H)$^+$.

Reference Example 22

1-(3,5-Dichloropyridin-2-yl)-5-methyl-1H-pyrazole-4-carboxylic acid (1) 2,3,5-Trichloropyridine (25 g) and hydrazine monohydrate (109.8 g) were added to ethanol (20 ml), stirred at 100° C. and left to stand at room temperature. The precipitated solid was collected by filtration to give 3,5-dichloropyridin-2-ylhydrazine (24.07 g).

(2) To ethyl 2-(ethoxymethylene)acetoacetate (25.1 g) prepared according to a method described in *J. Chem. Soc. Perkin trans. I*, 1875 (1988), were added 1N hydrochloric acid aqueous solution (135 ml) and an ethanol solution (135 ml) of 3,5-dichloropyridin-2-ylhydrazine (24.02 g) described above, stirred at reflux temperature for three hours and left to stand at room temperature. Water was added to the reaction solution, the precipitated solid was collected by filtration and purified with a mixed solvent of ethyl acetate and n-hexane to give 1-(3,5-dichloropyridin-2-yl)-5-methyl-1H-pyrazole-4-carboxylic acid ethyl ester.

(3) 4N Aqueous solution of sodium hydroxide (10 ml) and water (10 ml) were added to 1-(3,5-dichloropyridin-2-yl)-5-methyl-1H-pyrazole-4-carboxylic acid ethyl ester (1.0 g) and stirred at 80° C. for 2.5 hours. The reaction solution was washed with ethyl acetate and 1N hydrochloric acid aqueous solution was added to the aqueous layer at 0° C. The precipitated solid was collected by filtration and washed with water to give the titled compound (680 mg) as a white solid.
MS (ESI) m/z: 272 (M+H)$^+$.

Reference Example 23

5-Methyl-1-[4-(trifluoromethyl)phenyl]-1H-pyrazole-4-carboxylic acid 4-(Trifluoromethyl)aniline was used in place of 2,3,4-trifluoroaniline in, Reference Example 19, and reacted and treated in a similar manner to give the titled compound.
MS (ESI) m/z: 271 (M+H)$^+$.

Reference Example 24

1-(5-Bromopyridine-2-yl)-5-methyl-1H-pyrazole-4-carboxylic acid (1) 5-Bromo-2-fluoropyridine (25.12 g) and hydrazine monohydrate (100%) (91 g) were added to ethanol (75 ml), stirred under reflux for four hours, and then water was added thereto and the precipitated solid was washed with water to give 5-bromopyridin-2-ylhydrazine (25.3 g) as a white solid.
MS (ESI) m/z: 188, 190 (M+H)$^+$.

(2) Next, 5-bromopyridin-2-ylhydrazine (25.3 g) and ethyl 2-ethoxymethyleneacetoacetate (25.1 g) prepared according to a method described in *J. Chem. Soc. Perkin trans. I*, 1875 (1988), were added to a mixed solvent of 1N hydrochloric acid aqueous solution (320 ml) and ethanol (370 ml), stirred at reflux temperature for 4.5 hours and the solvent was evaporated in vacuo. Water was added to the residue, the precipitated solid was washed with water and recrystallized from a mixed solvent of ethyl acetate and n-hexane to give 1-(5-bromopyridin-2-yl)-5-methyl-1H-pyrazole-4-carboxylic acid ethyl ester (30.6 g) as a pale yellow solid.
MS (ESI) m/z: 310, 312 (M+H)$^+$.

(3) 1-(5-Bromopyridin-2-yl)-5-methyl-1H-pyrazole-4-carboxylic acid ethyl ester (3.1 g) was added to ethanol (20 ml), water (10 ml) and 4N aqueous solution of sodium hydroxide (10 ml), stirred at 80° C. for five hours, and the solvent was evaporated in vacuo. 1N Hydrochloric acid aqueous solution was added to the residue at 0° C. and the precipitated solid was washed with water to give the titled compound (1.78 g) as a white solid.
MS (ESI) m/z: 282, 284 (M+H)$^+$.

Formulae of the Reference Example 1 to 24 were listed in the next table.

| Reference Example No | Structure |
|---|---|
| 1 | *1-(4-fluorophenyl)-5-methyl-1H-pyrazole-4-carboxylic acid* |
| 2 | *1-(2,4-difluorophenyl)-5-methyl-1H-pyrazole-4-carboxylic acid* |
| 3 | *1-(4-chlorophenyl)-5-methyl-1H-pyrazole-4-carboxylic acid* |
| 4 | *1-(4-methylphenyl)-5-methyl-1H-pyrazole-4-carboxylic acid* |
| 5 | *1-(4-methoxyphenyl)-5-methyl-1H-pyrazole-4-carboxylic acid* |
| 6 | *1-[3-(trifluoromethyl)phenyl]-5-methyl-1H-pyrazole-4-carboxylic acid* |
| 7 | *1-phenyl-5-methyl-1H-pyrazole-4-carboxylic acid* |

| Reference Example No | Structure |
|---|---|
| 8 | (5-trifluoromethylpyridin-2-yl)-5-methyl-1H-pyrazole-4-carboxylic acid |
| 9 | (6-trifluoromethylpyridin-2-yl)-5-methyl-1H-pyrazole-4-carboxylic acid |
| 10 | (4-trifluoromethylpyridin-2-yl)-5-methyl-1H-pyrazole-4-carboxylic acid |
| 11 | 1-(3,4-dichlorophenyl)-5-methyl-1H-pyrazole-4-carboxylic acid |
| 12 | 1-(3,4-difluorophenyl)-5-methyl-1H-pyrazole-4-carboxylic acid |
| 13 | 1-(4-bromophenyl)-5-methyl-1H-pyrazole-4-carboxylic acid |
| 14 | 1-(5-trifluoromethylpyridin-2-yl)-5-methyl-1H-pyrazole-3-carboxylic acid |
| 15 | 1-(5-trifluoromethylpyridin-2-yl)-3,5-dimethyl-1H-pyrazole-4-carboxylic acid |
| 16 | 1-(5-trifluoromethylpyridin-2-yl)-3-methyl-1H-pyrazole-4-carboxylic acid |

| Reference Example No | Structure |
|---|---|
| 17 | 1-(4-tert-butylphenyl)-5-methyl-1H-pyrazole-4-carboxylic acid |
| 18 | 1-(2,4-dichlorophenyl)-1H-pyrazole-4-carboxylic acid |
| 19 | 1-(2,3,4-trifluorophenyl)-5-methyl-1H-pyrazole-4-carboxylic acid |
| 20 | 1-(5-chloropyridin-2-yl)-5-methyl-1H-pyrazole-4-carboxylic acid |
| 21 | 1-(5-fluoropyridin-2-yl)-5-methyl-1H-pyrazole-4-carboxylic acid |
| 22 | 1-(3,5-dichloropyridin-2-yl)-5-methyl-1H-pyrazole-4-carboxylic acid |
| 23 | 1-(4-trifluoromethylphenyl)-5-methyl-1H-pyrazole-4-carboxylic acid |
| 24 | 1-(5-bromopyridin-2-yl)-5-methyl-1H-pyrazole-4-carboxylic acid |

Reference Example 25

1-{5-[(1E)-3-Methoxy-1-propenyl]pyridin-2-yl}-5-methyl-1H-pyrazole-4-carboxylic acid Tetrahydrofuran (4 ml) was added to 1-(5-bromopyridin-2-yl)-5-methyl-1H-pyrazole-4-carboxylic acid ethyl ester (620 mg) described in Reference Example 24(2), palladium (II) acetate (45 mg), 2-dicyclohexylphosphino-2',6'-dimethoxybiphenyl (S-Phos) (82 mg), 3-methoxy-1-propenylboronic acid pinacol ester (594 μl) and tripotassium phosphate (1.0 g), and stirred at 100° C. for 4.5 hours. Then, water (5 ml), 4N aqueous solution of sodium hydroxide (5 ml) and ethanol (5 ml) were added to the reaction solution and the mixture was stirred at 80° C. for two hours. The reaction solution was acidified by the addition of water and 1N hydrochloric acid aqueous solution, extracted with ethyl acetate and the solvent was evaporated in vacuo. The resulting solid was washed with water to give the titled compound (300 mg) as a white solid.

MS (ESI) m/z: 274 (M+H)$^+$.

Reference Example 26

1-(4-Cyclopropylphenyl)-5-methyl-1H-pyrazole-4-carboxylic acid (1) Toluene (40 ml) and thionyl chloride (8.0 ml) were added to 1-(4-bromophenyl)-5-methyl-1H-pyrazole-4-carboxylic acid (20.50 g) described in reference Example 13, stirred under reflux and the solvent was evaporated in vacuo. Pyridine (20 ml) and ethanol (40 ml) were added to the residue, and the mixture was stirred again under reflux and then the solvent was evaporated in vacuo. A saturated aqueous solution of sodium bicarbonate was added to the residue, and the mixture was extracted with ethyl acetate and the organic layer was washed with saturated brine, dried over anhydrous magnesium sulfate and concentrated in vacuo. The resulting solid was washed with n-hexane to give 1-(4-bromophenyl)-5-methyl-1H-pyrazole-4-carboxylic acid ethyl ester (15.83 g).

MS (ESI) m/z: 309, 311 (M+H)$^+$.

(2) Tetrahydrofuran (10 ml) was added to 1-(4-bromophenyl)-5-methyl-1H-pyrazole-4-carboxylic acid ethyl ester (1.5 g) obtained above, palladium (II) acetate (108 mg), 2-dicyclohexylphosphino-2',6'-dimethoxybiphenyl (S-Phos) (198 mg), cyclopropylboronic acid (582 mg) and tripotassium phosphate (2.6 g), and stirred at 100° C. for 8 hours. Water was added to the reaction solution, extracted with ethyl acetate and the organic layer was washed with saturated brine, dried over anhydrous sodium sulfate and concentrated in vacuo. The resulting residue was purified with silica gel column chromatography (n-hexane/ethyl acetate). 4N aqueous solution of sodium hydroxide (4 ml) and ethanol (10 ml) were added to the purified oily product, stirred at 80° C. for four hours, and the reaction solution was washed with ethyl acetate. 1N Hydrochloric acid aqueous solution was added to the aqueous layer at 0° C. and the precipitated solid was washed with diethyl ether and water to give the titled compound (915 mg) as a white solid.

MS (ESI) m/z: 243 (M+H)$^+$.

Reference Example 27

1-(4-Ethylphenyl)-5-methyl-1H-pyrazole-4-carboxylic acid (1) Tetrahydrofuran (10 ml) was added to 1-(4-bromophenyl)-5-methyl-1H-pyrazole-4-carboxylic acid ethyl ester (1.5 g) described in Reference Example 26(1), palladium (II) acetate (108 mg), 2-dicyclohexylphosphino-2',6'-dimethoxybiphenyl (S-Phos) (198 mg), vinylboronic acid pinacol ester (1.04 g) and tripotassium phosphate (2.6 g), and stirred at 100° C. for 7 hours. Water was added to the reaction solution, extracted with ethyl acetate, and the organic layer was washed with water and saturated brine, dried over anhydrous sodium sulfate and concentrated in vacuo. The resulting residue was purified with silica gel column chromatography (n-hexane/ethyl acetate). 4N Aqueous solution of sodium hydroxide (4 ml) and ethanol (10 ml) were added to the purified yellow oily product, stirred at 80° C. for two hours and the reaction solution was washed with ethyl acetate. 1N Hydrochloric acid aqueous solution was added to the aqueous layer at 0° C., and the precipitated solid was washed with diethyl ether and water to give 5-methyl-1-(4-vinylphenyl)-1H-pyrazole-4-carboxylic acid (508 mg).

MS (ESI) m/z: 229 (M+H)$^+$.

(2) 5-Methyl-1-(4-vinylphenyl)-1H-pyrazole-4-carboxylic acid (508 mg) obtained above was dissolved in methanol (5 ml) and tetrahydrofuran (2 ml), 10% palladium-carbon (containing ca. 50% of water; 100 mg) was added and the mixture was stirred under hydrogen atmosphere at room temperature for 3.5 hours. The reaction solution was filtered through Celite and the filtrate was concentrated in vacuo. Water was added to the residue and the precipitated solid was washed with diethyl ether and water to give the titled compound (423 mg) as a white solid.

MS (ESI) m/z: 231 (M+H)$^+$.

Reference Example 28

1-(5-Ethylpyridin-2-yl)-5-methyl-1H-pyrazole-4-carboxylic acid

Vinylboronic acid pinacol ester (2.4 ml) was added to 1-(5-bromopyridin-2-yl)-5-methyl-1H-pyrazole-4-carboxylic acid ethyl ester (3.1 g) described in Reference Example 24(2), palladium (II) acetate (224 mg), 2-dicyclohexylphosphino-2',6'-dimethoxybiphenyl (S-Phos) (410 mg), tripotassium phosphate (5.3 g) and tetrahydrofuran (20 ml), and stirred at 100° C. for 6.5 hours. Then palladium (II) acetate (22.4 mg), 2-dicyclohexylphosphino-2',6'-dimethoxybiphenyl (S-Phos) (41 mg), vinylboronic acid pinacol ester (240 μl) and tripotassium phosphate (530 mg) were added therein, and stirred at 100° C. for 8.5 hours. Water was added and the mixture was extracted with ethyl acetate. The organic layer was washed with water and saturated brine, dried over anhydrous sodium sulfate and concentrated in vacuo. The resulting residue was purified with silica gel column chromatography (n-hexane/ethyl acetate). 1,4-Dioxane (28 ml) and 10% palladium-carbon (containing ca. 50% of water; 700 mg) were added to the purified yellow oily product and the mixture was stirred under hydrogen atmosphere at room temperature for 6 hours. The reaction solution was filtered through Celite, concentrated in vacuo and the residue was purified with silica gel column chromatography (n-hexane/ethyl acetate). 4N Aqueous solution of sodium hydroxide (5 ml), water (5 ml) and ethanol (10 ml) were added to the purified oily product and the mixture was stirred at 80° C. for 4.5 hours. The reaction solution was concentrated in vacuo and 1N hydrochloric acid aqueous solution was added to the residue at 0° C. and then the precipitated solid was washed with water to give the titled compound (1.16 g) as a gray solid.

MS (ESI) m/z: 232 (M+H)$^+$.

Reference Example 29

1-(5-Bromo-2-chloropyridin-3-yl)-5-methyl-1H-pyrazole-4-carboxylic acid ethyl ester 5-Bromo-2-chloro-3-fluoropyridine was used in place of 5-bromo-2-fluoropyridine in Reference Example 24, and reacted and treated in a similar manner as (1) and (2) to give 1-(5-bromo-2-chloropyridin-3-yl)-5-methyl-1H-pyrazole-4-carboxylic acid ethyl ester (9.6 g) as a white solid.

MS (ESI) m/z: 344, 346 (M+H)$^+$.

Reference Example 30

1-(5-Isopropylpyridin-2-yl)-5-methyl-1H-pyrazole-4-carboxylic acid

Isopropenylboronic acid pinacol ester (5.2 ml) was added to 1-(5-bromopyridin-2-yl)-5-methyl-1H-pyrazole-4-carboxylic acid ethyl ester (6.2 g) described in Reference Example 24(2), palladium (II) acetate (448 mg), 2-dicyclohexylphosphino-2',6'-dimethoxybiphenyl (S-Phos) (820 mg), tripotassium phosphate (0.6 g) and tetrahydrofuran (20 ml), and the mixture was stirred at 100° C. for 8 hours. Water was added and the reaction mixture was extracted with ethyl acetate and the organic layer was washed with saturated brine, dried over anhydrous sodium sulfate and concentrated in vacuo. To the resultant yellow oil was added 1,4-Dioxane (25 ml) and 10% palladium-carbon (containing ca. 50% of water; 500 mg), and the mixture was stirred under hydrogen atmosphere at room temperature for 5 hours. The reaction solution was filtered through Celite, the filtrate was concentrated in vacuo and the residue was purified with silica gel column chromatography (n-hexane/ethyl acetate). 4N Aqueous solution of sodium hydroxide (5 ml), water (5 ml) and ethanol (10 ml) were added to the resulting oily residue and stirred at 80° C. for 4 hours. The reaction solution was concentrated in vacuo, 1N hydrochloric acid aqueous solution was added to the resulting residue at 0° C., and the precipitated solid was washed with water to give the titled compound (1.56 g) as a pale red solid.

MS (ESI) m/z: 246 (M+H)$^+$.

Reference Example 31

1-(5-Iodo-6-methylpyridin-2-yl)-5-methyl-1H-pyrazole-4-carboxylic acid ethyl ester (1) 6-Chloro-2-methyl-3-nitropyridine was used in place of 5-bromo-2-fluoropyridine in Reference Example 24, and reacted at room temperature in a similar manner as (1) to give 1-(6-methyl-5-nitropyridin-2-yl)hydrazine.

MS (ESI) m/z: 169 (M+H)$^+$.

(2) 1-(6-Methyl-5-nitropyridin-2-yl)hydrazine was reacted and treated in a similar manner as Reference Example 24(2) to give 5-methyl-1-(6-methyl-5-nitropyridin-2-yl)-1H-pyrazole-4-carboxylic acid ethyl ester as a yellow solid.

MS (ESI) m/z: 291 (M+H)$^+$.

(3) Methanol (50 ml), 1,4-dioxane (200 ml) and 10% palladium-carbon (containing ca. 50% water; 5 g) were added to 5-methyl-1-(6-methyl-5-nitropyridin-2-yl)-1H-pyrazole-4-carboxylic acid ethyl ester (15 g) and the mixture was stirred under hydrogen atmosphere at room temperature for four hours. The reaction solution was filtered through Celite, the filtrate was concentrated in vacuo and the resulting solid was washed with n-hexane to give 1-(5-amino-6-methyl-pyridin-2-yl)-5-methyl-1H-pyrazol-4-carboxylic acid ethyl ester as a pale yellow solid.

MS (ESI) m/z: 261 (M+H)$^+$.

(4) After concentrated sulfuric acid (20 ml) were added to 1-(5-amino-6-methylpyridin-2-yl)-5-methyl-1H-pyrazole-4-carboxylic acid ethyl ester (7.8 g) and water (80 ml) at 0° C., sodium nitrite (3.0 g) was added therein in several portions. After stirring for 0.5 hour, potassium iodide (9.96 g) was added in several portions and the mixture was stirred for 2.5 hours at room temperature. A saturated aqueous solution of sodium bicarbonate was added in several portions at 0° C. and then an aqueous solution of sodium sulfite was added and the aqueous solution was extracted with ethyl acetate. The organic layer was washed with water and saturated brine, dried over anhydrous sodium sulfate and concentrated in vacuo. The resulting solid was washed with ethyl acetate and n-hexane to give the titled compound (7.76 g) as a yellow solid.

MS (ESI) m/z: 372 (M+H)$^+$.

Reference Example 32

1-(5-tert-Butylpyridin-2-yl)-5-methyl-1H-pyrazole-4-carboxylic acid (1) tert-Butyl magnesium bromide (2M tetrahydrofuran solution; 35 ml) was added to a suspension of copper cyanide (3.1 g) in tetrahydrofuran (35 ml) at −78° C., stirred for 20 minutes, and then 1-(5-bromopyridin-2-yl)-5-methyl-1H-pyrazole-4-carboxylic acid ethyl ester (3.1 g) described in Reference example 24(2) was added and the mixture was stirred at −78° C. for two hours. It was further stirred at room temperature for 16 hours. Ammonium hydroxide was added to the reaction solution and extracted with ethyl acetate. The organic layer was washed with water and saturated brine, dried over anhydrous sodium sulfate and concentrated in vacuo. The resulting residue was purified with silica gel column chromatography (n-hexane/ethyl acetate) to give 1-(5-tert-butylpyridin-2-yl)-5-methyl-1H-pyrazole-4-carboxylic acid ethyl ester (320 mg) as a yellow oil.

MS (ESI) m/z: 288 (M+H)$^+$.

(2) The resulting 1-(5-tert-butylpyridin-2-yl)-5-methyl-1H-pyrazole-4-carb oxyl ic acid ethyl ester (320 mg) was reacted and treated in a similar manner as Reference Example 24(3) to give the titled compound (270 mg) as a white solid.

MS (ESI) m/z: 260 (M+H)$^+$.

Reference Example 33

1-(5-Isopropyloxypyridin-2-yl)-5-methyl-1H-pyrazole-4-carboxylic acid (1) Benzyl alcohol (6.67 ml) was added to a suspension of 1-(5-bromopyridin-2-yl)-5-methyl-1H-pyrazole-4-carboxylic acid ethyl ester (10 g) described in Reference example 24(2), palladium (II) acetate (217 mg), racemic-2-(di-tert-butylphosphino)-1,1'-binaphthyl (482 mg) and cesium carbonate (26.3 g) in toluene (65 ml) and stirred at 80° C. for 2.5 hours. Then, benzyl alcohol (3.34 ml) was added and the mixture was stirred at 130° C. for 1.5 hours. Water was added to the reaction mixture and extracted with ethyl acetate. The organic layer was washed with water and saturated brine, dried over anhydrous sodium sulfate and concentrated in vacuo. A 4N sodium hydroxide aqueous solution (50 ml), water (50 ml) and ethanol (100 ml) were added to the resulting residue and stirred at 80° C. for 4.5 hours. The reaction solution was concentrated in vacuo, 1N hydrochloric acid aqueous solution was added to the resulting residue at 0° C. and the precipitated solid was washed with water to give a mixture of 1-(5-benzyloxypyridin-2-yl)-1H-pyrazole-4-carboxylic acid and 5-methyl-1-(pyridin-2-yl)-1H-pyrazol-4-carboxylic acid as a yellow oil.

MS (ESI) m/z: 204, 310 (M+H)$^+$.

(2) N,N-dimethylformamide (107 ml) and ethyl iodide (3.8 ml) were added to the obtained mixture and potassium carbonate (13.3 g) and the mixture was stirred at room temperature for five hours. Water was added to the reaction solution and extracted with ethyl acetate. The organic layer was washed with water and saturated brine, dried over anhydrous sodium sulfate and concentrated in vacuo. 1,4-Dioxane (50 ml) and 10% palladium carbon (containing ca. 50% water; 1.0 g) were added to the resulting residue, and stirred at room temperature under hydrogen atmosphere for five hours. The reaction solution was filtered through celite and the filtrate was concentrated in vacuo. The residue was purified with silica gel column chromatography (n-hexane/ethyl acetate) to give 1-(5-hydroxypyridin-2-yl)-5-methyl-1H-pyrazole-4-carboxylic acid ethyl ester (333 mg) as a yellow oil.

MS (ESI) m/z: 248 (M+H)$^+$.

(3) Isopropylbromide (164 μl) was added to a suspension of 1-(5-hydroxypyridin-2-yl)-5-methyl-1H-pyrazole-4-carboxylic acid ethyl ester (333 mg) and potassium carbonate (558 mg) in N,N-dimethylformamide (1.5 ml) and stirred at 80° C. for 2.5 hours. Water was added to the reaction solution and extracted with ethyl acetate. The organic layer was washed with water and saturated brine, dried over anhydrous sodium sulfate and concentrated in vacuo. The resulting residue was reacted and treated in a similar manner as Reference Example 24(3) to give the titled compound (152 mg) as a white solid.

MS (ESI) m/z: 262 (M+H)$^+$.

Reference Example 34

1-(5-Cyclopropyl-6-methylpyridin-2-yl)-5-methyl-1H-pyrazole-4-carboxylic acid 1-(5-Iodo-6-methylpyridin-2-yl)-5-methyl-1H-pyrazole-4-carboxylic acid ethyl ester described in Reference Example 31 was used in place of 1-(4-bromophenyl)-5-methyl-1H-pyrazole-4-carboxylic acid ethyl ester in Reference Example 26(2), and reacted and treated in a similar manner to give the titled compound.

MS (ESI) m/z: 258 (M+H)$^+$.

Reference Example 35

1-(5-Chloro-6-methylpyridin-2-yl)-5-methyl-1H-pyrazole-4-carboxylic acid

Water (4 ml) and concentrated hydrochloric acid (1 ml) were added to 1-(5-amino-6-methylpyridin-2-yl)-5-methyl-1H-pyrazole-4-carboxylic acid ethyl ester (260 mg) described in Reference Example 31(3), and then sodium nitrite (83 mg) was added therein at 0° C. After stirring for 0.5 hour, sodium nitrite (83 mg) was added again and stirred for an hour. Then copper (I) chloride (485 mg) was added and stirred in a water bath for 20 minutes. The reaction solution was added to a saturated aqueous solution of sodium bicarbonate and filtered through Celite. Water was added to the filtrate, extracted with ethyl acetate and the organic layer was dried over anhydrous sodium sulfate and concentrated in vacuo. The resulting residue was reacted and treated in a similar manner as Reference Example 24(3) to give the titled compound (112 mg) as a brown solid.

MS (ESI) m/z: 252 (M+H)$^+$.

Reference Example 36

1-(5-Ethyl-6-methylpyridin-2-yl)-5-methyl-1H-pyrazole-4-carboxylic acid 1-(5-Iodo-6-methylpyridin-2-yl)-5-methyl-1H-pyrazole-4-carboxylic acid ethyl ester described n Reference Example 31 was used in place of 1-(5-bromopyridin-2-yl)-5-methyl-1H-pyrazole-4-carboxylic acid ethyl ester in Reference Example 28, and reacted and treated in a similar manner to give the titled compound.

MS (ESI) m/z: 246 (M+H)$^+$.

Reference Example 37

1-[4-(Methoxymethyl)phenyl]-5-methyl-1H-pyrazole-4-carboxylic acid (1) 4-Hydrazinobenzoic acid was used in place of 5-bromopyridin-2-ylhydrazine in Reference Example 24(2), and reacted and treated in a similar manner to give 4-[4-(ethoxycarbonyl)-5-methyl-1H-pyrazol-1-yl]benzoic acid.

(2) 0.93M Tetrahydrofuran solution of borane (18 ml) was added dropwise to a solution of 4-[4-(ethoxycarbonyl)-5-methyl-1H-pyrazol-1-yl]benzoic acid (3.0 g) in tetrahydrofuran (50 ml) at 0° C. and stirred at room temperature for three hours. After completion of the reaction, a saturated aqueous solution of sodium bicarbonate was added therein and extracted with ethyl acetate three times. The organic layer was washed with saturated brine, dried oner anhydrous sodium sulfate and concentrated in vacuo. The resulting residue was purified with NH silica gel column chromatography (n-hexene/ethyl acetate) to give 1-[4-(hydroxymethyl)phenyl]-5-methyl-1H-pyrazole-4-carboxylic acid ethyl ester (1.93 g) as a white solid.

(3) Sodium hydride (129 mg) was added to a solution of 1-[4-(hydroxymethyl)phenyl]-5-methyl-1H-pyrazole-4-carboxylic acid ethyl ester (700 mg) in N,N-dimethylformamide (13 ml) at room temperature and stirred at the same temperature for 0.5 hour. Methyl iodide (0.3 ml) was added therein and stirred at 80° C. for two hours. Methyl iodide (0.2 ml) was further added and stirred at the same temperature for an hour. After completion of the reaction, the reaction solution was cooled to room temperature, water was added therein and extracted with ethyl acetate three times. The organic layer was dried over anhydrous sodium sulfate and concentrated in vacuo. The resulting residue was purified with silica gel column chromatography (n-hexane/ethyl acetate) to give 1-[4-(methoxymethyl)phenyl]-5-methyl-1H-pyrazol-4-carboxylic acid ethyl ester (401 mg) as a white solid.

(4) 1N Aqueous solution of sodium hydroxide (7.0 ml) was added at room temperature to a solution of 1-[4-(methoxymethyl)phenyl]-5-methyl-1H-pyrazole-4-carboxylic acid ethyl ester (401 mg) in ethanol (14 ml) and stirred at 70° C. for two hours. After completion of the reaction, ethanol was evaporated, water and 1N hydrochloric acid aqueous solution was added therein and the precipitated solid was collected by filtration to give the titled compound (314 mg) as a white solid.

MS (ESI) m/z: 247 (M+H)$^+$.

Reference Example 38

1-[4-(Ethoxymethyl)phenyl]-5-methyl-1H-pyrazole-4-carboxylic acid

Ethyl iodide was used in place of methyl iodide in Reference Example 37, and reacted and treated in a similar manner to give the titled compound as a white solid.

MS (ESI) m/z: 261 (M+H)$^+$.

Reference Example 39

1-(4-Ethoxyphenyl)-5-methyl-1H-pyrazole-4-carboxylic acid (1) Thionyl chloride (3.84 g) was added to a solution of 1-(4-methoxyphenyl)-5-methyl-1H-pyrazole-4-carboxylic acid (5.0 g) described in Reference Example 5 in toluene (20 ml) at room temperature, stirred at 80° C. for an hour and the solvent and an excess amount of thionyl chloride were evaporated. Pyridine (10 ml) and ethanol (20 ml) were added to the resulting residue and stirred at 40° C. for 0.5 hour. After completion of the reaction, the solvent was evaporated and ethyl acetate and 1N aqueous solution of sodium hydroxide were added. The mixture was extracted with ethyl acetate three times and the organic layer was dried over anhydrous sodium sulfate and concentrated to give 1-(4-methoxyphenyl)-5-methyl-1H-pyrazole-4-carboxylic acid ethyl ester (5.2 g).

(2) 1.0M Solution of borone tribromide in dichloromethane (35 ml) was added to a solution of 1-(4-methoxyphenyl)-5-methyl-1H-pyrazole-4-carboxylic acid ethyl ester (3.0 g) in dichloromethane (12 ml) under ice cooling, and the mixture was stirred at the same temperature for three hours. After completion of the reaction, the reaction mixture was added to a saturated aqueous solution of sodium bicarbonate under ice cooling, a saturated aqueous solution of sodium bicarbonate was further added until the mixture was neutralized to pH 7 and extracted with chloroform three times. The organic layer was dried over anhydrous sodium sulfate and concentrated. The resulting residue was purified with silica gel column chromatography (chloroform/methanol) to give 1-(4-hydroxyphenyl)-5-methyl-1H-pyrazole-4-carboxylic acid ethyl ester (2.33 g) as a white solid.

(3) Sodium hydride (234 mg) was added to a solution of 1-(4-hydroxyphenyl)-5-methyl-1H-pyrazole-4-carboxylic acid ethyl ester (1.2 g) in N,N-dimethylformamide (12 ml) at room temperature, stirred at the same temperature for 30 minutes, then ethyl iodide (0.8 ml) was added therein and the mixture was stirred at 80° C. for an hour. After completion of the reaction, the reaction solution was cooled to room temperature, water was added therein and extracted with ethyl acetate three times. The organic layer was dried over anhydrous sodium sulfate and concentrated. The resulting residue was purified with silica gel column chromatography (n-hexane/ethyl acetate) to give 1-(4-ethoxyphenyl)-5-methyl-1H-pyrazole-4-carboxylic acid ethyl ester (1.32 g) as a white solid.

(4) 1N Aqueous solution of sodium hydroxide (4.8 ml) was added to a solution of 1-(4-ethoxyphenyl)-5-methyl-1H-pyrazole-4-carboxylic acid ethyl ester (1.3 g) in ethanol (24 ml) at room temperature and stirred at 70° C. for three hours. After completion of the reaction, the reaction solution was cooled to room temperature, 1N hydrochloric acid aqueous solution was added and the precipitated solid was collected by filtration to give the titled compound (1.12 g) as a white solid.

MS (ESI) m/z: 247 (M+H)$^+$.

Reference Example 40

1-[4-(Difluoromethyl)phenyl]-5-methyl-1H-pyrazole-4-carboxylic acid (1) Dess-Martin Reagent (3.77 g) was added at 0° C. to a solution of 1-[4-(hydroxymethyl)phenyl]-5-methyl-1H-pyrazole-4-carboxylic acid ethyl ester (1.93 g) described in Reference Example 37(2) in dichloromethane (74 ml), and stirred at the same temperature for an hour. After completion of the reaction, a saturated aqueous solution of sodium bicarbonate was added and the reaction solution was filtered through Celite. The filtrate was extracted with chloroform three times, the organic layer was dried over anhydrous sodium sulfate and concentrated.

(2) Dimethylamino sulfur trifluoride (6.0 g) was added to a solution of the resulting residue in dichloromethane (37 ml) at −78° C., and the reaction solution was warmed to room temperature over 12 hours.

After completion of the reaction, a saturated aqueous solution of sodium bicarbonate was added and extracted with chloroform three times. The organic layer was washed with saturated brine, dried over anhydrous sodium sulfate and concentrated in vacuo. The resulting residue was purified with silica gel column chromatography (n-hexane/ethyl acetate) to give 1-[4-(difluoromethyl)phenyl]-5-methyl-1H-pyrazole-4-carboxylic acid ethyl ester (1.18 g) as a colorless oil.

MS (ESI) m/z: 281 (M+H)$^+$.

(3) 2N Aqueous solution of sodium hydroxide (32 ml) was added to a solution of 1-[4-(difluoromethyl)phenyl]-5-methyl-1H-pyrazole-4-carboxylic acid ethyl ester (1.8 g) in ethanol (32 ml) at room temperature and stirred at the same temperature for 12 hours. After completion of the reaction, 1N hydrochloric acid aqueous solution was added and the precipitated solid was filtered to give the titled compound (1.46 g) as a white solid.

MS (ESI) m/z: 253 (M+H)$^+$.

Reference Example 41

1-[5-(Difluoromethyl)pyridin-2-yl]-5-methyl-1H-pyrazole-4-carboxylic acid (1) Hydrazine monohydrate (101 g) was added to a solution of 6-chloronicotinic acid (20 g) in ethanol (20 ml) at room temperature and stirred under reflux. After completion of the reaction, the solvent was evaporated, ethanol was added and the solid was collected by filtration to give 6-hydrazinonicotinic acid (13.8 g).

(2) To 4N hydrochloric acid aqueous solution (35 ml) of 6-hydrazinonicotinic acid (3.9 g), was added an ethanol solution (35 ml) of ethyl 2-(ethoxymethylene)acetylacetate (5.0 g), which was prepared according to a method described in *J. Chem. Soc. Perkin trans. I*, 1875 (1988), at 120° C., and stirred at the same temperature for five hours. After completion of the reaction, the reaction solution was cooled to room temperature, the precipitated solid was filtered and washed with water.

(3) A solution of borane (0.93M tetrahydrofuran solution; 123 ml) was added dropwise at 0° C. to a solution of the resulting residue in tetrahydrofuran (50 ml), and stirred at room temperature for three hours. After completion of the reaction, a saturated aqueous solution of sodium bicarbonate was added and extracted with ethyl acetate four times. The organic layer was washed with saturated brine, dried over anhydrous sodium sulfate and concentrated in vacuo. The resulting residue was purified with NH silica gel column chromatography (n-hexane/ethyl acetate) to give 1-[5-(hydroxymethyl)pyridin-2-yl]-5-methyl-1H-pyrazole-4-carboxylic acid ethyl ester (2.13 g) as a white solid.

(4) Dess-Martin Reagent (4.15 g) was added at 0° C. to a solution of 1-[5-(hydroxymethyl)pyridin-2-yl]-5-methyl-1H-pyrazole-4-carboxylic acid ethyl ester (2.13 g) in dichloromethane (40 ml), and the mixture was stirred at the same temperature for an hour. After completion of the reaction, a saturated aqueous solution of sodium bicarbonate was added, the mixture was filtered through Celite and the filtrate was extracted with chloroform three times. The organic layer was dried over anhydrous sodium sulfate and concentrated.

(5) Diethylamino sulfur trifluoride (7.9 g) was added to the solution of the resulting residue in dichloromethane (40 ml) at −78° C. and warmed up to room temperature over 14 hours. After completion of the reaction, a saturated aqueous solution of sodium bicarbonate was added and extracted with chloroform three times. The organic layer was washed with saturated brine, dried over anhydrous sodium sulfate and concentrated. The resulting residue was purified with silica gel column chromatography (n-hexane/ethyl acetate) to give 1-[5-difluoromethyl)pyridin-2-yl]-5-methyl-1H-pyrazole-4-carboxylic acid ethyl ester (1.68 g) as a pale yellow solid.

(6) 2N Aqueous solution of sodium hydroxide (30 ml) was added at room temperature to a solution of 1-[5-difluoromethyl)pyridin-2-yl]-5-methyl-1H-pyrazole-4-carboxylic acid ethyl ester (1.68 g) in ethanol (30 ml) and tetrahydrofuran (15 ml), and stirred at 40° C. for an hour. After completion of the reaction, the reaction solution was cooled to room temperature, 6N hydrochloric acid aqueous solution was added and the precipitated solid was collected by filtration to give the titled compound (1.43 g) as a white solid.
MS (ESI) m/z: 254 (M+H)$^+$.

Reference Example 42

5-Methyl-1-[6-(trifluoromethyl)pyridin-3-yl]-1H-pyrazole-4-carboxylic acid

5-Bromo-2-(trifluoromethyl)pyridine was used in place of 2-chloro-5-(trifluoromethyl)pyridine in Reference Example 8, and reacted and treated in a similar manner to give the titled compound.
MS (ESI) m/z: 272 (M+H)$^+$.

Reference Example 43

1-(2-Chloro-5-ethylpyridin-3-yl)-5-methyl-1H-pyrazole-4-carboxylic acid (1) Tetrahydrofuran (75 ml) was added to 1-(5-bromo-2-chloropyridin-3-yl)-5-methyl-1H-pyrazole-4-carboxylic acid ethyl ester (3 g) described in Reference Example 29, vinylboronic acid pinacol ester (2.01 g), tetrakis(triphenylphosphine)palladium (504 mg) and 2M aqueous solution of sodium carbonate (15.2 ml) and stirred at 90° C. for 4 hours. The reaction solution was cooled to 0° C., and a saturated aqueous solution of ammonium chloride and ethyl acetate were added therein. The organic layer was separated, dried over anhydrous sodium sulfate and concentrated in vacuo. The residue was purified with column chromatography (n-hexane/ethyl acetate) to give 1-(2-chloro-5-vinylpyridin-3-yl)-5-methyl-1H-pyrazole-4-carboxylic acid ethyl ester (1.84 g).
MS (ESI) m/z: 292 (M+H)$^+$.

(2) Next, 1-(2-chloro-5-vinylpyridin-3-yl)-5-methyl-1H-pyrazole-4-carboxylic acid ethyl ester (0.902 g) was added to a mixed solvent of ethanol (10 ml) and 1,4-dioxane (8 ml), the atmosphere in the flask was substituted with nitrogen gas, 10% palladium-carbon (containing ca. 50% water; 0.20 g) was added and the mixture was stirred under hydrogen atmosphere at room temperature for three hours. The reaction mixture was filtered through Celite to remove palladium-carbon, the filtrate was concentrated and the residue was purified with column chromatography (n-hexane/ethyl acetate) to give 1-(2-chloro-5-ethylpyridin-3-yl)-5-methyl-1H-pyrazole-4-carboxylic acid ethyl ester (0.639 g).
MS (ESI) m/z: 294 (M+H)$^+$.

(3) 1-(2-Chloro-5-ethylpyridin-3-yl)-5-methyl-1H-pyrazole-4-carboxylic acid ethyl ester (0.639 g) and 4N aqueous solution of sodium hydroxide (5 ml) were added to a mixed solvent of ethanol (10 ml) and water (5 ml) and stirred at room temperature for an hour. The reaction solution was cooled to 0° C., 1N hydrochloric acid aqueous solution (30 ml) was added dropwise and the precipitated solid was filtered to give the titled compound (0.488 g).
MS (ESI) m/z: 266 (M+H)$^+$.

Reference Example 44

1-(5-Bromo-3-chloropyridin-2-yl)-5-methyl-1H-pyrazole-4-carboxylic acid (1) Hydrazine monohydrate (50 ml) was stirred at 100° C., a solution of 5-bromo-2,3-dichloropyridine (15.0 g) in ethanol (25 ml) was added therein dropwise over an hour and the mixture was stirred at the same temperature. After completion of the reaction, the reaction solution was cooled to room temperature, water (150 ml) was added and stirred at the room temperature. The precipitated solid was collected by filtration to give (5-bromo-3-chloropyridin-2-yl)hydrazine (14.78 g) as a white solid.

(2) To a suspension of (5-bromo-3-chloropyridin-2-yl)hydrazine (14.78 g) in water (15 ml) and concentrated hydrochloric acid (15 ml), was added an ethanol solution (30 ml) of ethyl 2-(ethoxymethylene)acetoacetate (30 ml), prepared according to a method described in *J. Chem. Soc. Perkin trans. I*, 1875 (1988), and the mixture was stirred at 100° C. for 1.5 hours. The reaction solution was cooled to room temperature, water (100 ml) was added and extracted with ethyl acetate three times. The organic layer was dried over anhydrous sodium sulfate and concentrated in vacuo. n-Hexane (150 ml) was added, and ethyl acetate was further added little by little at 80° C. to completely dissolve the residue. The solution was cooled to room temperature and the precipitated solid was filtered. The filtrate was concentrated and a similar handling was repeated four times to give 1-(5-bromo-3-chloropyridin-2-yl)-5-methyl-1H-pyrazole-4-carboxylic acid ethyl ester (15.93 g) as a pale yellow solid.

(3) Water (7 ml) and 4N aqueous solution of sodium hydroxide (7 ml) were added at room temperature to a solution of 1-(5-bromo-3-chloropyridin-2-yl)-5-methyl-1H-pyrazole-4-carboxylic acid ethyl ester (1.00 mg) in ethanol (14 ml) and stirred at 80° C. for five hours. After completion of the reaction, the reaction solution was cooled to 0° C. and 1N hydrochloric acid aqueous solution (29 ml) was added. The precipitated solid was collected by filtration to give the titled compound (723 mg) as a light brown solid.
MS (ESI) m/z: 316, 318 (M+H)$^+$.

Reference Example 45

1-(4-Isopropylphenyl)-5-methyl-1H-pyrazole-4-carboxylic acid (1) Potassium carbonate (8.76 g) and methyl iodide (3.15 ml) were added to a N,N-dimethylformamide solution (42 ml) of 1-(4-chlorophenyl)-5-methyl-1H-pyrazole-4-carboxylic acid (10.0 g) in Reference Example 3 at room temperature and stirred for five hours. Potassium carbonate (4.08 g) and methyl iodide (2.1 ml) were subsequently added and the mixture was stirred further for three hours at room temperature. After completion of the reaction, water (200 ml) was added and the precipitated solid was collected by filtration to give 1-(4-chlorophenyl)-5-methyl-1H-pyrazole-4-carboxylic acid methyl ester (10.5 g) as a pale yellow solid.

(2) Tripotassium phosphate (5.31 g), 2-dicyclohexylphosphino-2',6'-dimethoxybiphenyl (S-Phos) (420 mg), isopropenylboronic acid pinacol ester (2.44 ml) and palladium (II) acetate (227 mg) were added to a solution of 1-(4-chlorophenyl)-5-methyl-1H-pyrazole-4-carboxylic acid methyl ester (2.50 g) in tetrahydrofuran (20 ml) and stirred at 100° C. for nine hours. The reaction solution was left to stand at room temperature for 15 hours, and 2-dicyclohexylphosphino-2',6'-dimethoxybiphenyl (S-Phos) (414 mg), isopropenylboronic acid pinacol ester (2.44 ml) and palladium (II) acetate (216 mg) were subsequently added and further stirred at 100° C. for eight hours. The reaction solution was cooled to room temperature, water was added and extracted with ethyl acetate three times. The organic layer was dried over sodium sulfate and concentrated. The resulting residue was dissolved again in tetrahydrofuran (20 ml) and tripotassium phosphate (5.30 g), 2-dicyclohexylphosphino-2',6'-dimethoxybiphenyl (S-Phos) (206 mg), isopropenylboronic acid pinacol ester (2.22 ml) and palladium (II) acetate (114 mg) were added to the solution and the mixture was further stirred at 100° C. for seven hours. Then, the reaction solution was cooled to room temperature, water was added and extracted with ethyl acetate three times. The organic layer was dried over anhydrous sodium sulfate and concentrate. The resulting residue was purified with silica gel column chromatography (n-hexane/ethyl acetate) to give 1-(4-isopropenyllphenyl)-5-methyl-1H-pyrazole-4-carboxylic acid methyl ester (2.05 g) as a white solid.

(3) 10% palladium carbon (containing ca. 50% water; 1.00 g) was added to a solution of 1-(4-isopropenylphenyl)-5-methyl-1H-pyrazole-4-carboxylic acid methyl ester (2.05 g) in 1,4-dioxane (40 ml) and the mixture was stirred under hydrogen atmosphere at room temperature for seven hours. The reaction solution was filtered through Celite and the filtrate was concentrated. Ethanol (40 ml), water (20 ml) and 4N aqueous solution of sodium hydroxide (20 ml) were added to the resultant residue and the mixture was stirred at 80° C. for two hours. After completion of the reaction, the reaction solution was cooled to 0° C. and 1N hydrochloric acid aqueous solution was added therein, the precipitated solid was collected by filtration to give the titled compound (1.77 g) as a white solid.

MS (ESI) m/z: 245 (M+H)$^+$.

Reference Example 46

1-(3-Chloro-5-cyclopropylpyridin-2-yl)-5-methyl-1H-pyrazole-4-carboxylic acid (1) Cyclopropylboronic acid (269 mg), tripotassium phosphate (1.61 g) and 1,1'-bis(diphenylphosphino)ferrocene-palladium (II) dichloride dichloromethane complex (124 mg) were added to a N,N-dimethylformamide solution (15 ml) of 1-(5-bromo-3-chloropyridin-2-yl)-5-methyl-1H-pyrazole-4-carboxylic acid ethyl ester (1.03 g) described in Reference Example 44(2), and the mixture was stirred at 100° C. for six hours. The reaction solution was cooled to room temperature, diluted with water, filtered through Celite and the filtrate was extracted with ethyl acetate three times. The organic layer was washed with water and saturated brine, dried over anhydrous sodium sulfate and concentrated. The resulting residue was purified with silica gel column chromatography (n-hexane/ethyl acetate) to give 1-(3-chloro-5-cyclopropylpyridin-2-yl)-5-methyl-1H-pyrazole-4-carboxylic acid ethyl ester (240 mg) as a pale yellow solid.

(2) Water (2 ml) and 4N aqueous solution of sodium hydroxide (2 ml) were added to a solution of 1-(3-chloro-5-cyclopropylpyridin-2-yl)-5-methyl-1H-pyrazole-4-carboxylic acid ethyl ester (240 mg) in ethanol (4 ml) at room temperature, and stirred at 90° C. for six hours. After completion of the reaction, the reaction solution was cooled to 0° C. and 1N hydrochloric acid aqueous solution (9 ml) was added. The precipitated solid was collected by filtration to give the titled compound (157 mg) as a light brown solid.

MS (ESI) m/z: 278 (M+H)$^+$.

Reference Example 47

1-(3-Chloro-5-methylpyridin-2-yl)-5-methyl-1H-pyrazole-4-carboxylic acid (1) Methylboronic acid (457 mg), tripotassium phosphate (3.40 g) and 1,1'-bis(diphenylphosphino)ferrocene-palladium (II) dichloride dichloromethane complex (296 mg) were added to a N,N-dimethylformamide solution (36 ml) of 1-(5-bromo-3-chloropyridin-2-yl)-5-methyl-1H-pyrazole-4-carboxylic acid ethyl ester (2.50 g) described in Reference Example 44(2), and the mixture was stirred at 100° C. for three hours. Methylboronic acid (154 mg) and 1,1'-bis(diphenylphosphino)ferrocene-palladium (II) dichloride dichloromethane complex (103 mg) were subsequently added and the mixture was further stirred for three hours. The reaction solution was cooled to room temperature and left stand for 16 hours, and methylboronic acid (153 mg) and 1,1'-bis(diphenylphosphino)ferrocene-palladium (II) dichloride dichloromethane complex (114 mg) were further added and the mixture was stirred again at 100° C. for five hours. After completion of the reaction, the reaction solution was cooled to room temperature, diluted with water and extracted with ethyl acetate three times. The organic layer was washed with water, dried over anhydrous sodium sulfate and concentrated. The resulting residue was purified with silica gel column chromatography (n-hexane/ethyl acetate) to give 1-(3-chloro-5-methylpyridin-2-yl)-5-methyl-1H-pyrazole-4-carboxylic acid ethyl ester (1.03 g).

(2) Water (9 ml) and 4N aqueous solution of sodium hydroxide (9 ml) were added to a solution of 1-(3-chloro-5-methylpyridin-2-yl)-5-methyl-1H-pyrazole-4-carboxylic acid ethyl ester (1.03 g) in ethanol (18 ml) at room temperature, and the mixture was stirred at 80° C. for 3.5 hours. After completion of the reaction, the reaction solution was cooled to 0° C. and 1N hydrochloric acid aqueous solution (38 ml) was added. The precipitated solid was collected by filtration to give the titled compound (654 mg) as a light brown solid.

MS (ESI) m/z: 252 (M+H)$^+$.

Reference Example 48

1-(3-Chloro-5-ethylpyridin-2-yl)-5-methyl-1H-pyrazole-4-carboxylic acid (1) Vinylboronic acid pinacol ester (1.37 ml), tripotassium phosphate (3.85 g) and 1,1'-bis(diphenylphosphino)ferrocene-palladium (II) dichloride dichloromethane complex (301 mg) were added to a solution of 1-(5-bromo-3-chloropyridin-2-yl)-5-methyl-1H-pyrazole-4-carboxylic acid ethyl ester (2.52 g) described in Reference Example 44(2) in N,N-dimethylformamide (36 ml), and the mixture was stirred at 100° C. for seven hours. The reaction solution was cooled to room temperature, diluted with water, filtered through Celite and the filtrate was extracted with ethyl acetate three times. The organic layer was washed with water and saturated brine, dried over anhydrous sodium sulfate and concentrated. The resulting residue was purified with silica gel column chromatography (n-hexane/ethyl acetate) to give 1-(3-chloro-5-vinylpyridin-2-yl)-5-methyl-1H-pyrazole-4-carboxylic acid ethyl ester (1.67 g).

(2) 10% Palladium-carbon (containing ca. 50% water; 281 mg) was added to a solution of 1-(3-chloro-5-vinylpyridin-2-yl)-5-methyl-1H-pyrazole-4-carboxylic acid ethyl ester (567 mg) in 1,4-dioxane (19 ml), and stirred under hydrogen atmosphere at room temperature for an hour. The reaction solution was filtered through Celite and the filtrate was concentrated. The resulting residue was purified with silica gel column chromatography (n-hexane/ethyl acetate) to give 1-(3-chloro-5-ethylpyridin-2-yl)-5-methyl-1H-pyrazole-4-carboxylic acid ethyl ester (459 mg).

(3) Water (4 ml) and 4N aqueous solution of sodium hydroxide (4 ml) were added at room temperature to a solution of 1-(3-chloro-5-ethylpyridin-2-yl)-5-methyl-1H-pyrazole-4-carboxylic acid ethyl ester (454 mg), and stirred at room temperature for 15 hours. After completion of the reaction, the reaction solution was cooled to 0° C. and 1N hydrochloric acid aqueous solution was added. The precipitated solid was collected by filtration to give the titled compound (314 mg) as a white solid.

MS (ESI) m/z: 266 (M+H)$^+$.

Structures of Reference Examples 25 to 48 are shown in the next table.

| Reference Example No | Structure |
|---|---|
| 38 | (structure) |
| 39 | (structure) |
| 40 | (structure) |
| 41 | (structure) |
| 42 | (structure) |
| 43 | (structure) |
| 44 | (structure) |
| 45 | (structure) |
| 46 | (structure) |
| 47 | (structure) |
| 48 | (structure) |

Reference Example 49

1-[5-(Trifluoromethyl)pyridin-2-yl]-1H-pyrazole-4-carboxylic acid

Copper (I) iodide (2.87 g), tripotassium phosphate (15.89 g) and N,N'-dimethylethylenediamine (4.8 ml) were added to a solution of 1H-pyrazole-4-carboxylic acid ethyl ester (2.1 g) and 2-chloro-5-(trifluoromethyl)pyridine (3.26 g) in 1,4-dioxane (150 ml), and the mixture was stirred at 120° C. for three hours. After completion of the reaction, the reaction solution was cooled to room temperature, water was added therein and extracted with ethyl acetate three times. The organic layer was washed with water and saturated brine, dried over anhydrous sodium sulfate and concentrated. The resulting residue was purified with silica gel column chromatography (n-hexane/ethyl acetate) to give 1-[5-(trifluoromethyl)pyridin-2-yl]-1H-pyrazole-4-carboxylic acid ethyl ester (544 mg) as a white solid.

(2) Water (5 ml) and 4N aqueous solution of sodium hydroxide (5 ml) were added at room temperature to a solution of 1-[5-(trifluoromethyl)pyridin-2-yl]-1H-pyrazole-4-carboxylic acid ethyl ester (544 mg) in ethanol (10 ml), and stirred at 80° C. for 3.5 hours. After completion of the reaction, the reaction solution was cooled to 0° C. and 1N hydrochloric acid aqueous solution (21 ml) was added. The precipitated solid was collected by filtration to give the titled compound (356 mg) as a white solid.

MS (ESI) m/z: 258 (M+H)$^+$.

Reference Example 50

1H-Pyrrole-3-carboxylic acid tert-butyl ester

A solution of tert-butyl acrylate (10.5 g) and toluenesulfonylisocyanate (16 g) in tetrahydrofuran (210 ml) was added dropwise at 70° C. to a suspension of sodium hydride (3.9 g) in tetrahydrofuran (200 ml) over 0.5 hour and stirred at the same temperature for two hours. After completion of the reaction, the solvent was evaporated, water was added to the residue and extracted with ethyl acetate three times. The organic layer was dried over anhydrous magnesium sulfate and concentrated. The resulting residue was purified with silica gel column chromatography (n-hexane/ethyl acetate)

and recrystallized (n-hexane/ethyl acetate) to give the titled compound (5.27 g) as a white solid.

MS (ESI)(m/z): 168 (M+H)$^+$.

Reference Example 51

1-[5-(Difluoromethyl)pyridin-2-yl]-1H-pyrrole-3-carboxylic acid (1) Diethylaminosulfur trifluoride (50 g) was added to a solution of 6-bromonicotinaldehyde (10 g) in dichloromethane (100 ml) at −78° C. and warmed up to room temperature over 15 hours. After completion of the reaction, 4N aqueous solution of sodium hydroxide was added and extracted with chloroform three times. The organic layer was washed with saturated brine, dried over anhydrous sodium sulfate and concentrated. The resulting residue was purified with silica gel column chromatography (n-hexane/ethyl acetate) to give 2-bromo-5-(difluoromethyl)pyridine (8.12 g) as a pale yellow solid.

(2) Sodium hydride (230 mg) was added to a solution of 1H-pyrrole-3-carboxylic acid tert-butyl ester (804 mg) in N,N-dimethylformamide (9.6 ml) at room temperature and stirred at the same temperature for 0.5 hour. 2-Bromo-5-(difluoromethyl)pyridine (1.0 g) was added and stirred at 60° C. for an hour. After completion of the reaction, the reaction solution was cooled to room temperature, water was added and the precipitated solid was filtered. The resulting residue was purified with silica gel column chromatography (n-hexane/ethyl acetate) to give 1-[5-(difluoromethyl)pyridin-2-yl]-1H-pyrrole-3-carboxylic acid tert-butyl ester (1.01 g) as a white solid.

MS (ESI) m/z: 295 (M+H)$^+$.

(3) Trifluoroacetic acid (13.6 ml) was added at room temperature to a solution of 1-[5-(difluoromethyl)pyridin-2-yl]-1H-pyrrole-3-carboxylic acid tert-butyl ester (1.01 g) in tetrahydrofuran (3.4 ml) and stirred at the same temperature for an hour. After completion of the reaction, water was added to the reaction solution and the precipitated solid was collected by filtration to give the titled compound (790 mg) as a white solid.

MS (ESI) m/z: 239 (M+H)$^+$.

Reference Example 52

5-Bromo-1-methyl-1H-indole-3-carboxylic acid (1) Trifluoroacetic anhydride (8.5 ml) was added to a solution of 5-bromoindole (10.0 g) in N,N-dimethylformamide (50 ml) at 0° C., and stirred at the same temperature for three hours. After completion of the reaction, water was added to the reaction solution and the precipitated crystalline was collected by filtration. Water (250 ml) and sodium hydroxide (50 g) were added to a solution of the resulting residue in ethanol (50 ml) and the mixture was stirred at 120° C. for eight hours. After completion of the reaction, the reaction solution was cooled to room temperature, concentrated hydrochloric acid was added and the precipitated solid was collected by filtration. To a solution of the resulting residue in ethanol (250 ml), was added concentrated sulfuric acid (5.0 ml) and the mixture was stirred at 90° C. for three hours. Concentrated sulfuric acid (5.0 ml) was further added and stirred at the same temperature for four hours. After completion of the reaction, the reaction solution was cooled to room temperature, and 4N aqueous solution of sodium hydroxide was added until the solution becomes pH 7. Ethanol was evaporated, the precipitated solid was collected and the resulting residue was purified with silica gel column chromatography (n-hexane/ethyl acetate) to give 5-bromo-1H-indole-3-carboxylic acid ethyl ester (5.40 g) as a white solid.

(2) Sodium hydride (537 mg) was added to a solution of 5-bromo-1H-indole-3-carboxylic acid ethyl ester (3.00 g) in N,N-dimethylformamide (22 ml) at room temperature, and stirred at the same temperature for 0.5 hour. Methyl iodide (2.1 ml) was added and the mixture was stirred at the same temperature for two hours. After completion of the reaction, water was added and the precipitated solid was collected by filtration. The resulting residue was purified with silica gel column chromatography (n-hexane/ethyl acetate) to give 5-bromo-1-methyl-1H-indole-3-carboxylic acid ethyl ester (3.10 g) as a white solid.

(3) 1N Aqueous solution of sodium hydroxide (10 ml) was added at room temperature to a solution of 5-bromo-1-methyl-1H-indole-3-carboxylic acid ethyl ester (605 mg) in ethanol (10 ml) and stirred at 70° C. for three hours. After completion of the reaction, the reaction solution was cooled to room temperature, water and 1N hydrochloric acid aqueous solution were added and the precipitated solid was collected by filtration to give the titled compound (530 mg) as a white solid.

MS (ESI) m/z: 253, 255 (M+H)$^+$.

Reference Example 53

5-Cyclopropyl-1-methyl-1H-indole-3-carboxylic acid (1) Cyclopropylboronic acid (457 mg), palladium (II) acetate (79.5 mg), 2-dicyclohexylphosphino-2',6'-dimethoxybiphenyl (S-Phos) (290 mg) and tripotassium phosphate (1.88 g) were added at room temperature to a solution of 5-bromo-1-methyl-1H-indole-3-carboxylic acid ethyl ester (1.0 g) described in Reference Example 52(2) in tetrahydrofuran (14 ml), and the mixture was stirred at 75° C. for five hours. After completion of the reaction, the reaction solution was cooled to room temperature, water was added and filtered through Celite. The filtrate was extracted with ethyl acetate three times. The organic layer was dried over anhydrous sodium sulfate and concentrated. The resulting residue was purified with silica gel column chromatography (n-hexane/ethyl acetate) to give 5-cyclopropyl-1-methyl-1H-indole-3-carboxylic acid ethyl ester (802 mg) as a yellow solid.

MS (ESI) m/z: 244 (M+H)$^+$.

(2) 1N Aqueous solution of sodium hydroxide (16 ml) was added at room temperature to a solution of 5-cyclopropyl-1-methyl-1H-indole-3-carboxylic acid ethyl ester (802 mg) in ethanol (16 ml) and stirred at 70° C. for 12 hours. After completion of the reaction, the reaction solution was cooled to room temperature and 1N hydrochloric acid aqueous solution was added until the solution became pH 1-2. The precipitated solid was collected by filtration to give the titled compound (615 mg) as a brown solid.

MS (ESI) m/z: 216 (M+H)$^+$.

Reference Example 54

6-Cyclopropyl-1-methyl-1H-indole-3-carboxylic acid

6-Bromoindole was used in place of 5-bromoindole in Reference Example 52(1), and reacted and treated in a similar manner as Reference Example 52(1), (2) and 53 to give the titled compound as a white solid.

MS (ESI) m/z: 216 (M+H)$^+$.

Reference Example 55

1-(5-Chloropyridin-2-yl)pyrrole-3-carboxylic acid (1) N,N-dimethylethylenediamine (1.9 ml) was added to 1H-pyrrole-3-carboxylic acid tert-butyl ester (2.0 g) described in Reference Example 50, copper iodide (2.28 g), tripotassium phosphate (12.7 g) and 2-bromo-5-chloropyridine (2.78 g) in 1,4-dioxane (120 ml), and stirred at 120° C. for four hours. Water was added to the reaction solution, extracted with ethyl acetate, dried over anhydrous sodium sulfate and concentrated in vacuo. n-Hexane was added to the resulting residue and the precipitated solid was washed with n-hexane to give 1-(5-chloropyridin-2-yl)pyrrole-3-carboxylic acid tert-butyl ester (3.0 g) as a gray solid.

MS (ESI) m/z: 279 (M+H)$^+$, 223 (M-tert-Bu+H)$^+$.

(2) Trifluoroacetic acid (3 ml) was added to a solution of 1-(5-chloropyridin-2-yl)pyrrole-3-carboxylic acid tert-butyl ester (1.0 g) in dichloromethane (10 ml) and stirred at room temperature for four hours. Water was added to the reaction solution and the precipitated solid was washed with water to give the titled compound (775 mg) as a gray solid.

MS (ESI) m/z: 223 (M+H)$^+$.

Reference Example 56

1-(4-Methoxyphenyl)pyrrole-3-carboxylic acid 2,5-Dimethoxytetrahydrofuran-3-carbaldehyde (7.31 g) and p-anisidine hydrochloride (7.28 g) were added to water (100 ml) and stirred at 60° C. for three hours. The precipitated yellow solid were filtered at the same temperature, washed with water (50 ml), saturated aqueous solution of sodium bicarbonate (50 ml), and further water (50 ml) to give 1-(4-methoxyphenyl)pyrrole-3-carb aldehyde.

Next, 1-(4-methoxyphenyl)pyrrole-3-carbaldehyde was added to an aqueous solution (100 ml) of sodium hydroxide (4.38 g) and an aqueous pyridine solution (water 100 ml and pyridine 180 ml) of potassium permanganate (8.65 g) at 20-30° C., and stirred at room temperature for six hours. After completion of the reaction, the reaction solution was filtered through Celite, the filtrate was acidified by the addition of hydrochloric acid and extracted with ethyl acetate. The organic layer was dried over anhydrous magnesium sulfate, concentrated in vacuo and the precipitated solid was purified with ethyl acetate/n-hexane to give the titled compound (8.52 g).

MS (ESI) m/z: 218 (M+H)$^+$.

Reference Example 57

1-(5-Ethylpyridin-2-yl)pyrrole-3-carboxylic acid

Tetrahydrofuran (7.2 ml) was added to 1-(5-chloropyridin-2-yl)pyrrole-3-carboxylic acid tert-butyl ester (1.0 g) described in Reference Example 55(1), palladium (II) acetate (80 mg), 2-dicyclohexylphosphino-2',6'-dimethoxybiphenyl (S-Phos) (147 mg), vinylboronic acid pinacol ester (860 μl) and tripotassium phosphate (1.9 g) and stirred at 100° C. for 8.5 hours. Water was added to the reaction solution and extracted with ethyl acetate. The organic layer was washed with water and saturated brine, dried over anhydrous sodium sulfate and concentrated in vacuo. 1,4-Dioxane (15 ml) and 10% palladium-carbon (containing ca. 50% water; 200 mg) was added to the resulting residue and the mixture was stirred under hydrogen atmosphere at room temperature for six hours. The reaction solution was filtered through Celite and the filtrate was concentrated in vacuo. The residue was purified with silica gel column chromatography (n-hexane/ethyl acetate). To the resulting residue was added Dichloromethane (10 ml) and trifluoroacetic acid (3 ml) and the mixture was stirred at room temperature for 4.5 hours. Water was added to the reaction solution and the precipitated solid was washed with water. The resulting solid was dissolved in ethyl acetate, extracted with 4N aqueous solution of sodium hydroxide and the aqueous layer was acidified by the addition of 1N hydrochloric acid aqueous solution and extracted with ethyl acetate. The organic layer was dried over anhydrous sodium sulfate, concentrated in vacuo to give the titled compound (153 mg) as a white solid.

MS (ESI) m/z: 217 (M+H)$^+$.

Reference Example 58

2-Bromo-5-isopropyloxypyridine

2-Bromopropane (701 μl) was added to a suspension of 2-bromo-5-hydroxypyridine (1.0 g) and potassium carbonate (2.38 g) in N,N-dimethylformamide (19 ml), and stirred at 80° C. for four hours. Water was added to the reaction solution and extracted with ethyl acetate. The organic layer was washed with water and saturated brine, dried over anhydrous sodium sulfate and concentrated in vacuo. The residue was purified with silica gel column chromatography (n-hexane/ethyl acetate) to give the titled compound (1.05 g) as a yellow oil.

MS (ESI) m/z: 216 (M+H)$^+$.

Reference Example 59

5-Methyl-1-(3-methylphenyl)-1H-pyrazole-4-carboxylic acid

3-Methylphenylhydrazine hydrochloride was used in place of 4-fluorophenylhydrazine hydrochloride in Reference Example 1, and reacted and treated in a similar manner to give the titled compound.

MS (ESI) m/z: 217 (M+H)$^+$.

Reference Example 60

1-(4-Methanesulfonylphenyl)pyrrole-3-carboxylic acid 2,5-Dimethoxytetrahydrofuran-3-carbaldehyde (16.7 g) and 4-methanesulfonylaniline hydrochloride (21.67 g) were added to water (110 ml) and stirred at 60° C. for six hours. The precipitated yellow brown solid was filtered at the same temperature, washed with water (70 ml), a saturated aqueous solution of sodium bicarbonate (50 ml), and further water (70 ml) to give 1-(4-methoxyphenyl)pyrrole-3-carbaldehyde. Next, triethylamine (11.58 g) was added to a solution of hydroxylamine hydrochloride (7.95 g) in acetonitrile (390 ml) under ice cooling, and then, all of 1-(4-methoxyphenyl)pyrrole-3-carbaldehyde obtained above and phthalic anhydride (16.9 g) were added thereto. The mixture was stirred at reflux temperature of the solvent for three hours and the reaction solution was quenched with water. It was extracted with ethyl acetate, the organic layer was washed with saturated brine and concentrated in vacuo. Ethyleneglycol (130 ml), water (130 ml) and 85% potassium hydroxide (27.5 g) were added to the residue and stirred at 120° C. for six hours. Water (500 ml) and activated charcoal (2 g) were added to the reaction solution and stirred at room temperature for 20 minutes. The mixture was filtered through Celite, ethyl acetate (5 ml) was added to the filtrate and hydrochloric acid was added under stirring. The precipitated solid was dried under air blower at 70° C. for eight hours to give the titled compound (13.6 g).
MS (ESI) m/z: 264(M−H)+.

Reference Example 61

3-Methyl-1-(4-mesylphenyl)-1H-pyrazole-4-carboxylic acid

4-Mesylphenylhydrazine hydrochloride was used in place of [5-(trifluoromethyl)pyridin-2-yl]hydrazine in Reference Example 16, and reacted and treated in a similar manner to give the titled compound.
MS (ESI) m/z: 281 (M+H)+.

Reference Example 62

1-(4-methylphenyl)pyrrole-3-carboxylic acid p-Toluidine hydrochloride was used in place of p-anisidine hydrochloride in Example 56, and reacted and treated in a similar manner to give the titled compound.
MS (ESI) m/z: 202 (M+H)+.

Reference Example 63

1-(2,4-Dimethylphenyl)pyrrole-3-carboxylic acid 2,4-Dimethylaniline was used in place of 4-mesylaniline hydrochloride in Reference Example 60, and reacted and treated in a similar manner to give the titled compound.
MS (ESI) m/z: 216 (M+H)+.

Reference Example 64

1-(3-Methylphenyl)pyrrole-3-carboxylic acid

3-Methylaniline was used in place of 4-mesylaniline hydrochloride in Reference Example 60, and reacted and treated in a similar manner to give the titled compound.
MS (ESI) m/z: 202 (M+H)+.

Reference Example 65

1-(2-Methylphenyl)pyrrole-3-carboxylic acid

2-Methylaniline was used in place of 4-mesylaniline hydrochloride in Reference Example 60, and reacted and treated in a similar manner to give the titled compound.
MS (ESI) m/z: 202 (M+H)+.

Reference Example 66

1-(3,4-Dimethylphenyl)pyrrole-3-carboxylic acid 3,4-Dimethylaniline was used in place of 4-mesylaniline hydrochloride in Reference Example 60, and reacted and treated in a similar manner to give the titled compound.
MS (ESI) m/z: 216 (M+H)+.

Reference Example 67

1-(4-Fluorophenyl)pyrrole-3-carboxylic acid (1) 4-Fluoroaniline (117 g) and 2,5-dimethoxytetrahydrofuran (139 g) were added to acetic acid (120 ml), stirred at reflux temperature for an hour and then the reaction solution was poured into ice water (1 l). The precipitated solid was filtered, dissolved in methanol and water was added therein. The precipitated solid was collected again by filtration to give 1-(4-fluorophenyl)pyrrole (122.7 g).

(2) Phosphoryl chloride (136.3 g) was slowly added dropwise to a solution of 1-(4-fluorophenyl)pyrrole (136.3 g) in N,N-dimethylformamide (250 ml) under ice cooling so as to keep the temperature of the reaction solution under 50° C., and then the mixture was stirred at room temperature for 24 hours. The reaction solution was made alkaline by pouring into an aqueous solution of potassium carbonate under ice cooling and the mixture was extracted with ethyl acetate. The organic layer was washed with water and saturated brine and concentrated in vacuo. n-Hexane was added to the residue and the resulting precipitated solid was collected by filtration to give 1-(4-fluorophenyl)-2-formylpyrrole (152 g).

(3) Trifluoromethanesulfonic acid (100 g) was added dropwise at room temperature into a dichloromethane solution (680 ml) containing 1-(4-fluorophenyl)-2-formylpyrrole (50.4 g), and stirred at reflux temperature for 13 hours. The reaction solution was poured into ice water, made alkaline with the addition of potassium carbonate and extracted with chloroform. The organic layer was dried over anhydrous magnesium sulfate and concentrated in vacuo. The residue was purified with silica gel column chromatography (n-hexane/ethyl acetate) to give 1-(4-fluorophenyl)-3-formylpyrrole (34.5 g).

(4) N,N-Dimethylformamide (300 ml) and water (100 ml) were added to potassium permanganate (28.7 g), and 1-(4-fluorophenyl)-3-formylpyrrole (34.4 g) was added under ice cooling. Potassium permanganate (14.4 g) was further added and the mixture was warmed up to room temperature and stirred for two hours. 1N Aqueous solution of sodium hydroxide (300 ml) was added to the reaction solution and stirred at room temperature for 0.5 hour. The reaction solution was washed with ethyl acetate, neutralized by the addition of hydrochloric acid and extracted with ethyl acetate. The organic layer was concentrated, isopropylether was added to the residue and the precipitated solid was collected by filtration to give the titled compound (15.2 g).
MS (ESI) m/z: 205 (M+H)+.

Reference Example 68

1-(4-Chlorophenyl)pyrrole-3-carboxylic acid

4-Chloroaniline hydrochloride was used in place of 4-fluoroaniline in Reference Example 67, and reacted and treated in a similar manner to give the titled compound.
MS (ESI) m/z: 222 (M+H)+.

Reference Example 69

1-(4-Chlorophenyl)-5-cyclopropyl-1H-pyrazole-4-carboxylic acid (1) N,N-Dimethylformamide dimethylacetal (4.31 g) was added to a solution of 3-cyclopropyl-3-oxopropanoic acid methyl ester (4.9 g) in ethyl acetate (50 ml) at room temperature, and stirred at 75° C. for three hours. Next, the reaction solution was cooled to room temperature, 4-chlorophenylhydrazine hydrochloride (7.52 g) and triethylamine (7.0 ml) were added, and stirred at 75° C. for four hours. After completion of the reaction, to the reaction mixture was added water and extracted with ethyl acetate. The organic layer was washed with water twice, dried and concentrated and the residue was purified with silica gel column chromatography (chloroform/methanol) to give the mixture (7.7 g).

(2) 4N Aqueous solution of sodium hydroxide (8.4 ml) was added to a solution of the resulting mixture (7.7 g) in methanol (45 ml), and stirred under reflux for an hour. After completion of the reaction, the reaction solution was cooled to room temperature, water (100 ml) and activated charcoal (1 g) were added and stirred at room temperature for 0.25 hour. After completion of the reaction, the mixture was filtered, 1N hydrochloric acid aqueous solution was added to the filtrate until pH was about 3 and extracted with ethyl acetate twice. The organic layer was washed with saturated brine, dried over anhydrous sodium sulfate and concentrated to some extent. n-Hexane was added to the solution, stirred at 0° C. and filtered to give the titled compound (5.8 g) as a white solid.

MS (ESI) m/z: 263 (M+H)$^+$.

Reference Example 70

6-Isopropylthieno[2,3-b]pyridine-2-carboxylic acid

6-Isopropylthieno[2,3-b]pyridine-2-carboxylic acid can be prepared according to example 17 preparing a starting material in WO 2002/12189.

MS (ESI) m/z: 222 (M+H)$^+$.

Reference Example 71

5-Methyl-1-(4-trifluoromethoxyphenyl)-1H-pyrazole-4-carboxylic acid

4-Trifluoromethoxyphenylhydrazine hydrochloride (4.0 g) and ethyl 2-ethoxymethylene-acetoacetate (3.26 g) prepared according to a method described in J. Chem. Soc. Perkin trans. I, 1875 (1988), were added to a mixed solvent of water (10 ml) and ethanol (10 ml), and stirred at 76° C. for two hours. Sodium hydroxide (1.40 g) was added to the reaction solution and the mixture was further stirred at the same temperature for an hour. Ethanol was evaporated in vacuo, hydrochloric acid (1 mole/1) was added to the aqueous solution and the precipitated solid was recrystallized from ethyl acetate to give the titled compound (3.56 g).

MS (ESI) m/z: 287 (M+H)$^+$.

Reference Example 72

1-(4-Methylphenyl)-indole-3-carboxylic acid

Indole-3-carboxylic acid methyl ester (2.50 g), 4-methyliodobenzene (3.72 g), copper (I) iodide (136 mg), N,N'-dimethyl-1,2-cyclohexanediamine (0.5 ml) and potassium carbonate (4.06 g) were stirred at 120° C. for 48 hours. After completion of the reaction, water was added and extracted with ethyl acetate. The organic layer was dried over anhydrous magnesium sulfate and concentrated. The residue was dissolved in ethanol (10 ml), sodium hydroxide (1.17 g) was added and stirred at room temperature overnight. The reaction solution was concentrated with an evaporator, the aqueous layer was acidified by the addition of 1N hydrochloric acid aqueous solution and extracted with ethyl acetate. The organic layer was dried over anhydrous magnesium sulfate and concentrated to give the titled compound (184 mg) as a dark brown solid.

Structures of Reference Examples 49-72 are shown in the next table.

| Reference Example No | Structure |
|---|---|
| 49 | [structure] |
| 50 | [structure] |
| 51 | [structure] |
| 52 | [structure] |
| 53 | [structure] |
| 54 | [structure] |
| 55 | [structure] |
| 56 | [structure] |
| 57 | [structure] |

| Reference Example No | Structure |
|---|---|
| 58 | 5-(1-methoxyethoxy)-2-bromopyridine |
| 59 | 1-(3-methylphenyl)-5-methyl-1H-pyrazole-4-carboxylic acid |
| 60 | 1-(4-(methylsulfonyl)phenyl)-1H-pyrrole-3-carboxylic acid |
| 61 | 1-(4-(methylsulfonyl)phenyl)-3-methyl-1H-pyrazole-4-carboxylic acid |
| 62 | 1-(4-methylphenyl)-1H-pyrrole-3-carboxylic acid |
| 63 | 1-(2,4-dimethylphenyl)-1H-pyrrole-3-carboxylic acid |
| 64 | 1-(3-methylphenyl)-1H-pyrrole-3-carboxylic acid |
| 65 | 1-(2-methylphenyl)-1H-pyrrole-3-carboxylic acid |
| 66 | 1-(3,4-dimethylphenyl)-1H-pyrrole-3-carboxylic acid |
| 67 | 1-(4-fluorophenyl)-1H-pyrrole-3-carboxylic acid |
| 68 | 1-(4-chlorophenyl)-1H-pyrrole-3-carboxylic acid |
| 69 | 1-(4-chlorophenyl)-5-cyclopropyl-1H-pyrazole-4-carboxylic acid |
| 70 | 6-isopropylthieno[2,3-b]pyridine-2-carboxylic acid |
| 71 | 1-(4-(trifluoromethoxy)phenyl)-5-methyl-1H-pyrazole-4-carboxylic acid |
| 72 | 1-(4-methylphenyl)-1H-indole-3-carboxylic acid |

Reference Example 73

1-(3,5-Dimethylphenyl)-1H-pyrazole-4-carboxylic acid

A solution of 1H-pyrazole-4-carboxylic acid ethyl ester (1.65 g), 5-iodo-m-xylene (1.65 g), copper (I) iodide (68 mg), N,N'-dimethyl-1,2-cyclohexanediamine (222 mg) and potassium carbonate (2.06 g) in toluene (2 ml) was stirred at 110° C. for 48 hours. After completion of the reaction, water was added and extracted with ethyl acetate. The organic layer was dried over anhydrous magnesium sulfate and concentrated. The residue was dissolved in ethanol (10 ml), 1N aqueous solution of sodium hydroxide (10 ml) was added and the mixture was stirred at room temperature overnight. The reaction solution was concentrated by an evaporator, the aqueous solution was acidified by the addition of 1N hydrochloric acid aqueous solution and extracted with ethyl acetate. The organic layer was dried over anhydrous magnesium sulfate and concentrated to give the titled compound (438 mg) as a dark brown solid.

Reference Example 74

1-(5-Iodopyridin-2-yl)-1H-pyrazole-4-carboxylic acid

A mixture of 1H-pyrazole-4-carboxylic acid ethyl ester (2.00 g), 5-iodo-2-fluoropyridine (1.68 g), copper (I) iodide (136 mg), N,N'-dimethyl-1,2-cyclohexanediamine (5 ml) and potassium carbonate (4.06 g) was stirred at 120° C. for 48 hours. After completion of the reaction, water was added and extracted with ethyl acetate. The organic layer was dried over anhydrous magnesium sulfate and concentrated. The residue was dissolved in ethanol (10 ml), sodium hydroxide (568 mg) was added and the mixture was stirred at room temperature overnight. The reaction solution was concentrated by an evaporator, the aqueous solution was acidified by the addition of 1N hydrochloric acid aqueous solution and extracted with ethyl acetate. The organic layer was dried over anhydrous magnesium sulfate and concentrated to give the titled compound (207 mg) as a dark brown solid.

Reference Example 75

6-(Tetrahydro-2H-pyran-4-yl)pyridin-3-amine (1) 1.0 M Tetrahydrofuran solution (28 ml) of lithium bis(trimethylsilyl)amide was added dropwise to a solution of tetrahydro-2H-pyrane-4-carboxylic acid methyl ester (2.87 g) in tetrahydrofuran (40 ml) at −78° C., and the mixture was stirred at the same temperature for an hour. And then a solution of 5-bromo-2-fluoropyridine (3.5 g) was added dropwise, and the reaction mixture was stirred at room temperature for two hours. After completion of the reaction, a saturated aqueous solution of ammonium chloride was added and extracted with ethyl acetate. The organic layer was dried over anhydrous sodium sulfate and concentrated in vacuo. The resulting residue was purified with silica gel column chromatography (n-hexane/ethyl acetate) to give 4-(5-bromopyridin-2-yl)tetrahydro-2H-pyrane-4-carboxylic acid methyl ester (4.14 g) as a colorless oil.

MS (ESI) m/z: 300, 302 (M+H)$^+$.

(2) 1N Aqueous solution of sodium hydroxide (40 ml) was added to a solution of 4-(5-bromopyridin-2-yl)tetrahydro-2H-pyrane-4-carboxylic acid methyl ester (3.43 g) in ethanol (10 ml) at room temperature and stirred at 80° C. for three hours. After completion of the reaction, the reaction solution was cooled to room temperature, 1N hydrochloric acid aqueous solution was added and the precipitated solid was collected by filtration to give a white solid.

(3) A solution of the resulting white solid in dimethylsulfoxide (10 ml) was stirred at 150° C. for an hour. After completion of the reaction, the reaction solution was cooled to room temperature, water was added and the precipitated solid was collected by filtration to give 5-bromo-2-(tetrahydro-2H-pyran-4-yl)pyridine (1.97 g) as a white solid.

MS (ESI) m/z: 242, 244 (M+H)$^+$.

(4) After 1.0M toluene-solution (9.8 ml) of lithium bis(trimethylsilyl)amide was added to bis(dibenzylideneacetone)palladium (0) (67 mg) and tri-tert-butylphosphine tetrafluoroborate (118 mg) at 70° C. under an atmosphere of nitrogen, a toluene solution (8.2 ml) of 5-bromo-2-(tetrahydro-2H-pyran-4-yl)pyridine (1.97 g) was added dropwise and stirred at the same temperature for 0.5 hour. Next, the reaction solution was cooled to room temperature, 1.0M tetrahydrofuran-solution (7.0 ml) of tetrabutylammonium fluoride was added and stirred at the same temperature for 1.5 hours. After completion of the reaction, a saturated aqueous solution of sodium bicarbonate was added and extracted with ethyl acetate. The organic layer was dried over anhydrous sodium sulfate and concentrated. The resulting residue was purified with silica gel column chromatography (n-hexane/ethyl acetate) to give the titled compound (1.1 g) as a white solid.

MS (ESI) m/z: 179 (M+H)$^+$.

Reference Example 76

1-(5-Bromopyridin-2-yl)-c-4-(morpholin-4-yl)-r-1-cyclohexanol (1) 1.6M n-Hexane solution of n-butyl lithium (66 ml) was added dropwise to a solution of 2,5-dibromopyridine (23.9 g) in toluene (420 ml) at −78° C., and stirred at the same temperature for an hour. Next, a solution of 1,4-cyclohexanedione monoethyleneketal (15 g) in dichloromethane (60 ml) was added dropwise, and the reaction solution was warmed up to room temperature over 7 hours. After completion of the reaction, a saturated aqueous solution of ammonium chloride and extracted with ethyl acetate three times. The organic solution was dried over anhydrous sodium sulfate and concentrated. The resulting residue was purified with silica gel column chromatography (n-hexane/ethyl acetate) and recrystallized from n-hexane/diethyl ether to give 8-(5-bromopyridin-2-yl)-1,4-dioxaspiro[4,5]decan-8-ol (16.2 g) as a white solid.

MS (ESI) m/z: 314, 316 (M+H)$^+$.

(2) 3N Hydrochloric acid aqueous solution (100 ml) was added to 8-(5-bromopyridin-2-yl)-1,4-dioxaspiro[4,5]decan-8-ol (16.2 g) at room temperature and stirred at the same temperature for two hours. After completion of the reaction, a saturated aqueous solution of sodium bicarbonate was added under ice cooling and the precipitated solid was collected by filtration.

(3) Morpholine (4.92 g) and sodium triacetoxyborohydride (14.4 g) was added to a solution of the solid in dichloromethane (170 ml) at room temperature, and stirred at the same temperature for 3.5 hours. After completion of the reaction, a saturated aqueous solution of sodium bicarbonate was added and extracted with chloroform three times. The organic solution was dried over anhydrous sodium sulfate and concentrated. The resulting residue was purified with silica gel column chromatography (chloroform/methanol) and recrystallized from n-hexane/diethyl ether to give the titled compound (7.88 g) as a white solid.

MS (ESI) m/z: 341, 343 (M+H)$^+$.

Reference Example 77

4-[4-(5-Bromopyridin-2-yl)cyclohex-3-en-1-yl]morpholine

Pyridine (3.84 ml) was added to a solution of the crude solid (3.69 g) in Reference Example 76(3) in dichloromethane (30 ml) at room temperature, thionyl chloride (3.22 g) was added dropwise and stirred at the same temperature for an hour. After completion of the reaction, a saturated aqueous solution of sodium bicarbonate was added and extracted with chloroform three times. The organic solution was washed with saturated brine, dried over anhydrous sodium sulfate and concentrated. The resulting residue was purified with silica gel column chromatography (chloroform/methanol) and recrystallized from n-hexane/diethyl ether to give the titled compound (1.95 g) as a white solid.

MS (ESI) m/z: 323, 325 (M+H)$^+$.

Reference Example 78

6-[4-(Morpholin-4-yl)cyclohex-1-en-1-yl]pyridin-3-amine

Palladium (II) acetate (65 mg), benzophenonimine (4.1 ml), (±)-2,2'-bis(diphenylphosphino)-1,1'-binaphthyl (180 mg) and sodium tert-butoxide (3.33 g) were added to a toluene solution (51 ml) of 4-[4-(5-bromopyridin-2-yl)cyclohex-3-en-1-yl]morpholine (7.46 g) described in Reference Example 77, and stirred at 120° C. for two hours. After completion of the reaction, the reaction vessel was taken out from an oil bath, 3N hydrochloric acid aqueous solution (50 ml) was added and the mixture was stirred at room temperature for two hours. Next, the reaction solution was filtered through Celite, the aqueous layer of the filtrate was separated from the organic layer with a separating funnel. The resulting aqueous layer was cooled to 0° C., 1N aqueous solution of sodium hydroxide was added and the precipitated solid was filtered. The resulting residue was purified with NH silica gel column chromatography (n-hexane/ethyl acetate) to give the titled compound (5.73 g) as a white solid.
MS (ESI) m/z: 260 (M+H)$^+$.

Reference Example 79

1-(5-Aminopyridin-2-yl)-c-4-(morpholin-4-yl)-r-1-cyclohexanol 1-(5-Bromopyridin-2-yl)-c-4-(morpholin-4-yl)-r-1-cyclohexanol described in Reference Example 76 was used in place of 4-[4-(5-bromopyridin-2-yl)cyclohex-3-en-1-yl]morpholine in Reference Example 78, and reacted and treated in a similar manner to give the titled compound as a white solid.
MS (ESI) m/z: 278 (M+H)$^+$.

Reference Example 80A cis-6-[(4-Morpholin-4-yl)cyclohexyl]pyridin-3-amine

Reference Example 80B trans-6-[(4-Morpholin-4-yl)cyclohexyl]pyridin-3-amine

Palladium (II) acetate (519 mg) and an aqueous solution (23 ml) of potassium fluoride (2.69 g) was added at room temperature to a solution of 6-[4-(morpholin-4-yl)cyclohex-1-en-1-yl]pyridin-3-amine (3.0 g) described in Reference Example 78 in tetrahydrofuran (115 ml), poly(methylhydrosiloxane) (2.8 ml) was added dropwise and the mixture was stirred at the same temperature for an hour. After completion of the reaction, diethyl ether (115 ml) was added, the reaction solution was filtered through Celite and the filtrate was concentrated. Saturated brine was added to the resulting solution and extracted with ethyl acetate three times. The organic layer was dried over anhydrous sodium sulfate and concentrated. The resulting residue was purified with NH silica gel column chromatography (n-hexane/ethyl acetate) to give cis-6-[4-(morpholin-4-yl)cyclohexyl]pyridin-3-amine (1.45 g) and trans-6-[4-(morpholin-4-yl)cyclohexyl]pyridin-3-amine (906 mg) as a white solid respectively.
MS (ESI) m/z: 262 (M+H)$^+$.

Reference Example 81

8-(5-Aminopyridin-2-yl)-1,4-dioxaspiro[4,5]decane-8-carboxylic acid ethyl ester (1) Ethylene glycol (18.2 g) and p-toluenesulfonic acid monohydrate (2.37 g) were added to a solution of 4-cyclohexanonecarboxylic acid ethyl ester (25 g) in toluene (500 ml) and stirred under reflux for 10 hours. After completion of the reaction, the reaction mixture was cooled to room temperature, diluted with diethyl ether and washed with saturated brine. The organic layer was dried over anhydrous sodium sulfate and concentrated. The resulting residue was purified with silica gel column chromatography (n-hexane/ethyl acetate) to give 1,4-dioxaspiro[4,5]decane-8-carboxylic acid ethyl ester (23 g) as a colorless oil.

(2) A solution of 1,4-dioxaspiro[4,5]decane-8-carboxylic acid ethyl ester (6.09 g) in tetrahydrofuran (14 ml) was added dropwise to a tetrahydrofuran solution (32 ml) of 1.0M tetrahydrofuran solution of lithium bis(trimethylsilyl)amide (39.8 ml) at −78° C., and stirred at the same temperature for 1.5 hours. Next, a solution of 5-bromo-2-fluoropyridine (5.0 g) in tetrahydrofuran (14 ml) was added dropwise and stirred at the same temperature for 0.5 hour and at room temperature for an hour. After completion of the reaction, water was added to the reaction solution and extracted with ethyl acetate twice. The organic layer was dried over anhydrous sodium sulfate and concentrated. The resulting residue was purified with silica gel column chromatography (n-hexane/ethyl acetate) to give 8-(5-bromopyridin-2-yl)-1,4-dioxaspiro[4,5]decane-8-carboxylic acid ethyl ester (6.9 g) as a colorless oil.

(3) 1.0M Toluene-solution of lithium bis(trimethylsilyl)amide (1.89 ml) was added to bis(dibenzylideneacetone)palladium (0) (39 mg) and tri-tert-butylphosphine tetrafluoroborate (20 mg) at 70° C. under an atmosphere of nitrogen, a solution of 8-(5-bromopyridin-2-yl)-1,4-dioxaspiro[4,5]decane-8-carboxylic acid ethyl ester (500 mg) in toluene (1.4 ml) was added dropwise and stirred at the same temperature for 0.5 hours. After completion of the reaction, the reaction solution was cooled to room temperature, tetrabutylammonium fluoride (4.7 ml) was added and stirred at the same temperature for an hour. Then, a saturated aqueous solution of sodium bicarbonate was added and extracted with ethyl acetate. The organic layer was dried over anhydrous sodium sulfate and concentrated. The resulting residue was purified with silica gel column chromatography (n-hexane/ethyl acetate) to give the titled compound (312 mg) as a yellow oil.
MS (ESI) m/z: 307 (M+H)$^+$.

Reference Example 82

8-(5-Bromopyridin-2-yl)-1,4-dioxaspiro[4,5]decane-8-carbonitrile (1) p-Toluenesulfonylmethylisocyanide (27.0 g) was added at room temperature to a solution of 1,4-cyclohexanedione monoethyleneketal (16.6 g) in 1,2-dimethoxyethane (133 ml) and ethanol (13 ml). Then, potassium tert-butoxide was added under ice cooling over an hour, and stirred at room temperature for three hours. After completion of the reaction, water was added and extracted with ethyl acetate three times. The organic layer was dried over anhydrous sodium sulfate and concentrated. The resulting residue was purified with silica gel column chromatography (n-hexane/ethyl acetate) to give 1,4-dioxaspiro[4,5]decane-8-carbonitrile (12.8 g) as a colorless oil.

(2) After 1,4-dioxaspiro[4,5]decane-8-carbonitrile (2.5 g) was dissolved in tetrahydrofuran (8 ml), 1M tetrahydrofuran-solution of lithium bis(trimethylsilyl)amide (15 ml) was added at 0° C. and stirred for 30 minutes. 5-Bromo-2-fluoropyridine (2.64 g) was further added and stirred at room temperature for two hours. Water was added to the reaction solution, extracted with ethyl acetate and concentrated in vacuo. The residue was purified with silica gel chromatography (n-hexane/ethyl acetate) and the resulting solid was washed with n-hexane to give the titled compound (3.32 g).

MS (ESI) m/z: 323, 325 (M+H)$^+$.

Reference Example 83

1-(5-Aminopyridin-2-yl)cyclohexanecarbonitrile (1) Cyclohexanecarbonitrile was used in place of 1,4-dioxaspiro[4,5]decane-8-carbonitrile in Reference Example 82(2), and reacted and treated in a similar manner to give 1-(5-bromopyridin-2-yl)cyclohexanecarbonitrile as a solid (2) Palladium (II) acetate (90 mg), 2-(di-tert-butylphosphino)biphenyl (240 mg), sodium tert-butoxide (1.35 g), toluene (20 ml) and p-methoxybenzylamine (1.81 g) were added to 1-(5-bromopyridin-2-yl)cyclohexanecarbonitrile (2.5 g), and stirred at 100° C. for two hours. Water was added to the reaction solution, the resulting precipitate was filtered, the filtrate was extracted with ethyl acetate and the organic layer was concentrated. The residue was purified with silica gel chromatography (n-hexane/ethyl acetate) to give 1-{5-[(4-methoxybenzyl)amino]pyridin-2-yl}cyclohexanecarbonitrile (650 mg) as a solid.

(3) Trifluoroacetc acid (4 ml) and thioanisole (1.2 ml) were added to 1-{5-[(4-methoxybenzyl)amino]pyridin-2-yl}cyclohexanecarbonitrile (632 mg) and stirred at 40° C. for 1.5 hours. An aqueous solution of sodium hydroxide was added and the mixture was adjusted to pH 10. The solution was extracted with ethyl acetate, the organic layer was dried over anhydrous magnesium sulfate and concentrated. The residue was purified with silica gel chromatography (n-hexane/ethyl acetate) to give the titled compound (360 mg) as a solid.

$^1$H-NMR (DMSO-d$_6$) δ(ppm): 1.24 (1H, m), 1.53-1.85 (7H, m), 2.04 (2H, d, J=12.9 Hz), 5.40 (2H, brs), 6.94 (1H, dd, J=3.0, 8.4 Hz), 7.19 (1H, d, J=8.4 Hz), 7.91 (1H, d, J=3.0 Hz).

Reference Example 84

5-Methyl-1-(5-n-propylpyridin-2-yl)-1H-pyrazole-4-carboxylic acid trans-1-Propen-1-ylboronic acid was used in place of vinylboronic acid pinacol ester in Reference Example 28, and reacted and treated in a similar manner to give the titled compound.

MS (ESI) m/z: 246 (M+H)$^+$.

Reference Example 85

1-(5-Aminopyridin-2-yl)-c-4-(methoxymethoxy)-r-1-cyclohexanecarbonitrile (1) Trifluoroacetic acid (4.1 ml) was added to 8-(5-bromopyridin-2-yl)-1,4-dioxaspiro[4,5]decane-8-carbonitrile (3.4 g) described in Reference Example 82 at room temperature, and stirred at the same temperature for 22 hours. After completion of the reaction, the solvent and trifluoroacetic acid were evaporated and the resulting residue was purified with silica gel column chromatography (n-hexane/ethyl acetate) to give 1-(5-bromopyridin-2-yl)-4-oxocyclohexanecarbonitrile (2.78 g) as a white solid.

(2) Sodium borohydride (980 mg) was added to a solution of 1-(5-bromopyridin-2-yl)-4-oxocyclohexanecarbonitrile (1.8 g) in methanol (44 ml) and chloroform (22 ml) at −78° C., and stirred at the same temperature for 1.5 hours. After completion of the reaction, water was added, the solvent was evaporated and the aqueous solution was extracted with ethyl acetate three times. The organic layer was dried over anhydrous sodium sulfate and concentrated. The resulting residue was purified with silica gel column chromatography (n-hexane/ethyl acetate) to give 1-(5-bromopyridin-2-yl)-c-4-hydroxy-r-1-cyclohexanecarbonitrile (1.58 g) as a white solid.

(3) Diisopropylamine (5.0 ml) and chloromethylmethylether (1.7 ml) were added to a solution of 1-(5-bromopyridin-2-yl)-c-4-hydroxy-r-1-cyclohexanecarbonitrile (2.0 g) in dichloromethane (14 ml) at room temperature, and stirred at the same temperature for two hours. After completion of the reaction, water was added and extracted with chloroform twice. The organic layer was dried over anhydrous sodium sulfate and concentrated. The resulting residue was purified with silica gel column chromatography (n-hexane/ethyl acetate) to give 1-(5-bromopyridin-2-yl)-c-4-(methoxymethoxy)-r-1-cyclohexanecarbonitrile (2.26 g) as a colorless oil.

(4) After 1.0M toluene-solution of lithium bis(trimethylsilyl)amide (7.5 ml) was added to bis(dibenzylideneacetone) palladium (0) (153 mg) and tri-tert-butylphosphine tetrafluoroborate (78 mg) at 70° C. under an atmosphere of nitrogen, a solution of 1-(5-bromopyridin-2-yl)-c-4-(methoxymethoxy)-r-1-cyclohexanecarbonitrile (1.73 g) in toluene (5.3 ml) was added dropwise, and stirred at the same temperature for 0.5 hours. Then, the reaction solution was cooled to room temperature, 1.0M tetrahydrofuran-solution of tetrabutylammonium fluoride (16 ml) was added and stirred at the same temperature for an hour. After completion of the reaction, a saturated aqueous solution of sodium bicarbonate was added and extracted with ethyl acetate three times. The organic layer was dried over anhydrous sodium sulfate and concentrated. The resulting residue was purified with silica gel column chromatography (n-hexane/ethyl acetate) to give the titled compound (1.1 g) as a white solid.

MS (ESI) m/z: 262 (M+H)$^+$.

Reference Example 86

8-(5-Aminopyridin-2-yl)-1,4-dioxaspiro[4,5]decane-8-carbonitrile

In Reference Example 75(4), 8-(5-bromopyridin-2-yl)-1,4-dioxaspiro[4,5]decane-8-carbonitrile described in Reference Example 82 was used in place of 5-bromo-2-(tetrahydro-2H-pyran-4-yl)pyridine, and reacted and treated in a similar manner to give the titled compound.

MS (ESI) m/z: 260 (M+H)$^+$.

Reference Example 87

4-(5-Bromopyridin-2-yl)tetrahydro-2H-pyrane-4-carbonitrile

Tetrahydro-4H-pyran-one was used in place of 1,4-cyclohexanedione monoethyleneketal in Reference Example 82, and reacted and treated in a similar manner to give the titled compound.

¹H-NMR (CDCl₃) δ(ppm): 2.00-2.06 (2H, m), 2.30-2.37 (2H, m), 3.84-3.91 (2H, m), 4.07-4.14 (2H, m), 7.49 (1H, d, J=8.4 Hz), 7.88 (1H, dd, J=8.4, 2.3 Hz), 8.68 (1H, d, J=2.3 Hz).

Reference Example 88 cis-4-(5-Aminopyridin-2-yl)-1-(2-methyltetrahydrofuran-3-yl)piperidine-4-carbonitrile (1) 1-tert-Butyloxycarbonyl-4-piperidone (13 g) and p-toluenesulfonylmethylisocyanate (16.6 g) were added to 1,2-dimethoxyethane (90 ml) and ethanol (10 ml). The solution was cooled in ice, potassium tert-butoxide (8.3 g) was added thereto under stirring and the mixture was stirred at room temperature for 6.5 hours. Water was added to the reaction solution and extracted with ethyl acetate. The organic layer was dried over anhydrous sodium sulfate, concentrated in vacuo and the resulting residue was purified with silica gel column chromatography (n-hexane/ethyl acetate) to give 4-cyanopiperidine-1-carboxylic acid tert-butyl ester (8.0 g) as a solid.

(2) 1.0M Tetrahydrofuran-solution of sodium bis(trimethylsilyl)amide (19 ml) was added to 4-cyanopiperidine-1-carboxylic acid tert-butyl ester (3.23 g) at 0° C. and stirred for 50 minutes. A solution of 5-bromo-2-fluoropyridine (2.57 g) in tetrahydrofuran (5 ml) was added thereto and stirred at room temperature for 7.5 hours. An aqueous solution of potassium carbonate was added to the reaction solution and extracted with ethyl acetate. The organic layer was dried over anhydrous sodium sulfate and concentrated in vacuo. 2N Hydrochloric acid-ethanol solution (30 ml) was added to the residue and stirred for 4.5 hours. An aqueous solution of sodium bicarbonate was added to the reaction solution, extracted with ethyl acetate, and then with chloroform, washed with saturated brine dried over anhydrous sodium sulfate and concentrated in vacuo. The resulting solid was washed with isopropylether to give 4-(5-bromopyridin-2-yl)piperidine-4-carbonitrile (2.73 g) as a pale orange solid
MS (ESI) m/z: 266, 268 (M+H)⁺.

(3) To a solution of 4-(5-bromopyridin-2-yl)piperidine-4-carbonitrile (1.15 g) in toluene (14.4 ml), was added 2-methyltetrahydrofuran-3-one (526 mg), and then, sodium triacetoxyborohydride (1.37 g), and the mixture was stirred at room temperature for five hours. Water and 1N aqueous solution of sodium hydroxide were added to the reaction solution at 0° C., and extracted with ethyl acetate. The organic layer was washed with saturated brine, dried over anhydrous sodium sulfate and concentrated in vacuo. The residue was purified with NH silica gel chromatography (n-hexane/ethyl acetate) to give cis-4-(5-bromopyridin-2-yl)-1-(2-methyltetrahydrofuran-3-yl)piperidine-4-carbonitrile (1.05 g) as a yellow solid.
MS (ESI) m/z: 350, 352 (M+H)⁺.

(4) Benzophenonimine (570 mg) was added to a suspension of cis-4-(5-bromopyridin-2-yl)-1-(2-methyltetrahydrofuran-3-yl)piperidine-4-carbonitrile (1.05 g), palladium (II) acetate (17 mg), racemic-2-(di-tert-butylphosphino)-1,1'-binaphthyl (47 mg) and sodium tert-butoxide (432 mg) in toluene (7.5 ml) and stirred at 120° C. for 7 hours. It was left stand and a mixture of concentrated hydrochloric acid (2 ml) and water (6 ml) was added at 60-80° C. and stirred at room temperature for 24 hours. The reaction solution was filtered through Celite and washed with water and ethyl acetate. The filtrate was washed with ethyl acetate, 1N aqueous solution of sodium hydroxide was added to the aqueous layer and extracted with ethyl acetate. The organic layer was washed with saturated brine, dried over anhydrous sodium sulfate and concentrated in vacuo. The resulting solid was washed with ethyl acetate and n-hexane to give the titled compound as a pale yellow solid.
MS (ESI) m/z: 287 (M+H)⁺.

Reference Example 89

4-(5-Aminopyridin-2-yl)-1-(tetrahydrofuran-3-yl)piperidine-4-carbonitrile

3-Oxoterahydrofuran was used in place of 2-methyltetrahydrofuran-3-one in Reference Example 88, and reacted and treated Ma similar manner as (1)-(3) to give the titled compound.
MS (ESI) m/z: 273 (M+H)⁺.

Reference Example 90

4-(5-Bromopyridin-2-yl)-1-(tetrahydro-2H-pyran-4-yl)piperidine-4-carbonitrile

Tetrahydro-4H-pyrane-4-one was used in place of 2-methyltetrahydrofuran-3-one in Reference Example 88, and reacted and treated in a similar manner to give the titled compound.
MS (ESI) m/z: 350, 352 (M+H)⁺.

Reference Example 91A

5-Methyl-1-[6-methyl-5-(trifluoromethyl)pyridin-2-yl]-1H-pyrazole-4-carboxylic acid Reference Example 91B 5-Methyl-1-[6-methyl-5-(pentafluoroethyl)pyridin-2-yl]-1H-pyrazole-4-carboxylic acid (1) (Trifluoromethyl)trimethylsilane (828 µl) was added to 1-(5-iodo-6-methylpyridin-2-yl)-5-methyl-1H-pyrazole-4-carboxylic acid ethyl ester (1.37 g) described in Reference Example 31, potassium fluoride (1.07 g), copper (I) iodide (3.51 g), N,N-dimethylformamide (3.7 ml) and N-methylmorpholine (3.7 ml), and stirred at 80° C. for 3.5 hours. (Trifluoromethyl)trimethylsilane (828 µl) was further added and stirred at 80° C. for 4.5 hours. Potassium fluoride (214 mg), copper (I) iodide (702 mg) and (trifluoromethyl)trimethylsilane (828 µl) were added and stirred at 80° C. for five hours, and then, (trifluoromethyl)trimethylsilane (497 µl) was further added and stirred for three hours. Water and a saturated aqueous solution of sodium bicarbonate were added to the reaction solution, the mixture was filtered through Celite and washed with ethyl acetate and water. The filtrate was extracted with ethyl acetate, and the organic layer was washed with saturated brine, dried over anhydrous sodium sulfate and concentrated in vacuo. The residue was purified with silica gel chromatography (n-hexane/ethyl acetate) to give 5-methyl-1-[6-methyl-5-(trifluoromethyl)pyridin-2-yl]-1H-pyrazole-4-carboxylic acid ethyl ester [560 mg; MS (ESI) m/z: 314 (M+H)⁺] and 5-methyl-1-[6-methyl-5-(pentafluoroethyl)pyridin-2-yl]-1H-pyrazole-4-carboxylic acid ethyl ester [95 mg, MS (ESI) m/z: 364 (M+H)⁺] as a white solid respectively.

(2) 5-Methyl-1-[6-methyl-5-(trifluoromethyl)pyridin-2-yl]-1H-pyrazole-4-carboxylic acid ethyl ester was reacted and treated in a similar manner as Reference Example 24(3)

to give 5-methyl-1-[6-methyl-5-(trifluoromethyl)pyridin-2-yl]-1H-pyrazole-4-carboxylic acid as a white solid.

MS (ESI) m/z: 286 (M+H)+.

(3) 5-Methyl-1-[6-methyl-5-(pentafluoroethyl)pyridin-2-yl]-1H-pyrazole-4-carboxylic acid ethyl ester prepared in the previous step (1), was reacted and treated in a similar manner as Reference Example 24(3) to give 5-methyl-1-[6-methyl-5-(pentafluoroethyl)pyridin-2-yl]-1H-pyrazole-4-carboxylic acid as a white solid.

MS (ESI) m/z: 336 (M+H)+.

Reference Example 92

4-(5-Bromopyridin-2-yl)cyclohexan-1-one 8-(5-Bromopyridin-2-yl)-1,4-dioxaspiro[4,5]decane-8-carbonitrile (1 g) described in Reference Example 82 was stirred in concentrated hydrochloric acid (5 ml) at 100° C. for eight hours. After completion of the reaction, the reaction solution was made alkaline by the addition of a saturated aqueous solution of potassium carbonate and extracted with ethyl acetate. The organic layer was dried over anhydrous magnesium sulfate and concentrated in vacuo to give the titled compound (85 mg) as a white solid.

$^1$H-NMR (DMSO-$d_6$) δ(ppm): 1.87-1.98 (2H, m), 2.11-2.16 (2H, m), 2.27-2.30 (2H, m), 2.53-2.60 (2H, m), 3.19-3.30 (1H, m), 7.36 (1H, d, J=8.4 Hz), 7.98 (1H, dd, J=8.4, 2.3 Hz), 8.62 (1H, d, J=2.3 Hz).

Reference Example 93

1-(5-Bromopyridin-2-yl)-c-4-(morpholin-4-yl)-r-1-cyclohexanecarbonitrile 1,4-Dioxaspiro[4,5]decane-8-carbonitrile (47.2 g) described in Reference Example 82(1) was added to 1M tetrahydrofurane solution (360 ml) of sodium bis(trimethylsilyl)amide, stirred at room temperature for 30 minutes, then a tetrahydrofuran solution (100 ml) containing 5-bromo-2-fluoropyridine (38.2 g) was added and the mixture was further stirred for an hour. 6N Hydrochloric acid aqueous solution (40 ml) was added to the reaction solution, stirred at 60° C. for an hour and extracted with ethyl acetate. The organic layer was dried over anhydrous sodium sulfate and concentrated in vacuo. Toluene (540 ml) and morpholine (24.6 g) were added to the residue, and to the solution were added sodium triacetoxyborohydride (60 g) and acetic acid (1 ml) and stirred for six hours. The reaction solution was treated with 1N aqueous solution of sodium hydroxide and extracted with ethyl acetate. The organic layer was dried over anhydrous magnesium sulfate, concentrated in vacuo, and the residue was purified with silica gel column chromatography (n-hexane:ethyl acetate=2:1) to give the titled compound (34 g).

MS (ESI) m/z: 350, 352 (M+H)+.

Reference Example 94

1-(5-Aminopyridin-2-yl)-c-4-(morpholin-4-yl)-r-1-cyclohexanecarbonitrile 1-(5-Bromopyridin-2-yl)-c-4-(morpholin-4-yl)-r-1-cyclohexanecarbonitrile (34 g) described in Reference Example 93 was added to 1M toluene-solution (100 ml) of sodium bis(trimethylsilyl)amide containing bis(dibenzylideneacetone)palladium (0) (2.8 g) and tri-tert-butylphosphine tetrafluoroborate (1.4 g) at 70° C. and stirred for three hours under an atmosphere of nitrogen. The reaction solution was treated with 1M tetrahydrofuran-solution of tetrabutylammonium fluoride and filtered through Celite. The filtrate was washed with saturated brine, dried over anhydrous sodium sulfate, concentrated in vacuo and the residue was purified with silica gel column chromatography (chloroform/methanol=95:5) to give the titled compound (17.2 g).

MS (ESI) m/z: 287 (M+H)+.

Structures of Reference Examples 73-94 are shown in the next table.

| Reference Example No | Structure |
|---|---|
| 73 | ![structure] |
| 74 | ![structure] |
| 75 | ![structure] |
| 76 | ![structure] |
| 77 | ![structure] |
| 78 | ![structure] |

-continued
| Reference Example No | Structure |
|---|---|
| 79 | 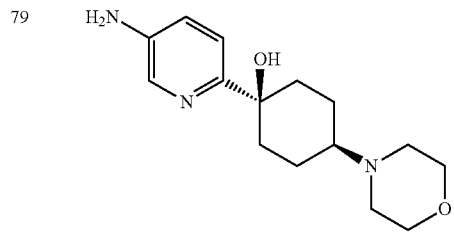 |
| 80A | 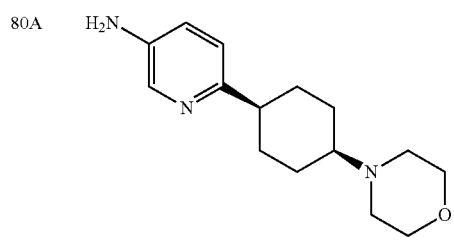 |
| 80B | 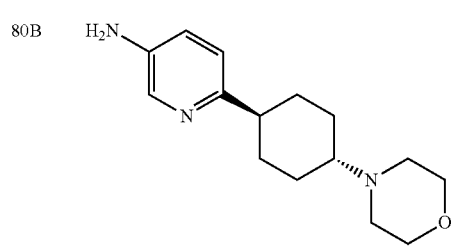 |
| 81 | 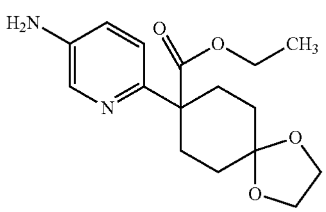 [SMILES: CCOC(=O)C1(c2ccc(N)cn2)CCC2(CC1)OCCO2] |
| 82 | 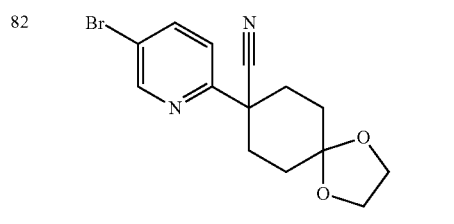 |
| 83 | 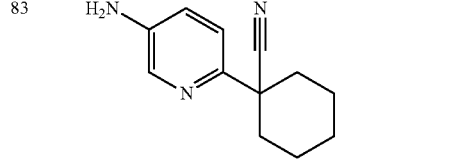 |
| 84 | 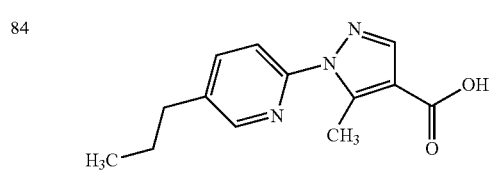 |
-continued
| Reference Example No | Structure |
|---|---|
| 85 | 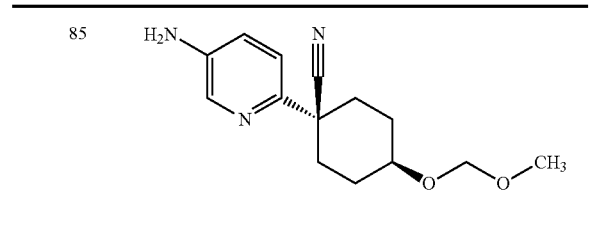 |
| 86 | 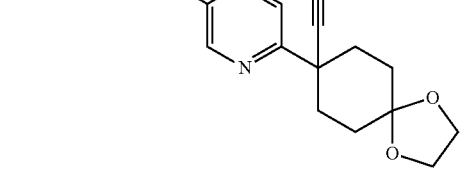 |
| 87 | 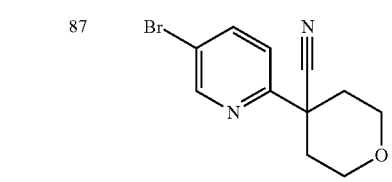 |
| 88 | 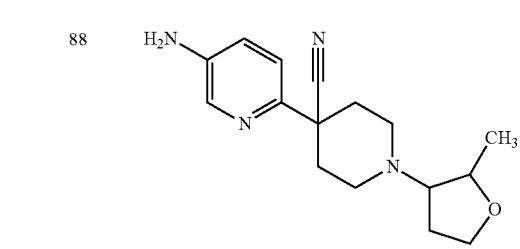 |
| 89 | 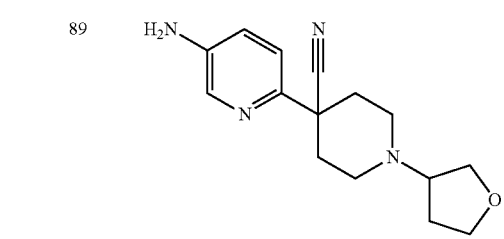 |
| 90 | 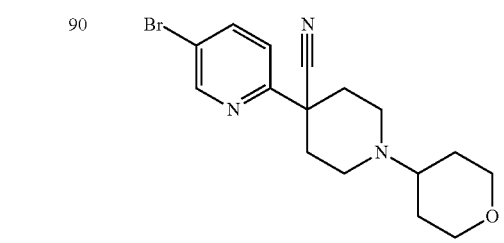 |
| 91A | 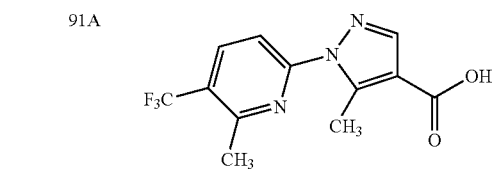 |

-continued

| Reference Example No | Structure |
|---|---|
| 91B | F₃C-CF₂ pyridine (CH₃, CH₃) linked to pyrazole (CH₃) with COOH |
| 92 | Br-pyridine linked to cyclohexanone |
| 93 | Br-pyridine linked to cyclohexane with CN and morpholine |
| 94 | H₂N-pyridine linked to cyclohexane with CN and morpholine |

Reference Example 95

1-(5-Bromo-3-methylpyridin-2-yl)-c-4-(morpholin-4-yl)-r-1-cyclohexanecarbonitrile (1) 1M Solution of sodium bis(trimethylsilyl)amide (77 ml) was added under ice cooling to 1,4-dioxaspiro[4,5]decane-8-carbonitrile (11.0 g) described in Reference Example 82(1) and stirred for 30 minutes. Then, 2,5-dibromo-3-methylpyridine (15 g) was added, stirred for 30 minutes and further stirred at room temperature for an hour. The reaction solution was treated with water and extracted with ethyl acetate. The organic layer was washed with saturated brine and concentrated in vacuo. To the residue, were added trifluoroacetic acid (20 ml) and water (5 ml), and the mixture was stirred at 40° C. for two hours. The reaction solution was treated with an aqueous solution of sodium carbonate and extracted with ethyl acetate. The organic layer was dried over anhydrous magnesium sulfate, concentrated in vacuo and the residue was purified with silica gel column chromatography (ethyl acetate:n-hexane=5:1) to give 1-(5-bromo-3-methylpyridin-2-yl)-4-oxocyclohexanecarbonitrile (17.1 g).

MS (ESI) m/z: 293, 295 (M+H)⁺.

(2) 1-(5-Bromo-3-methylpyridin-2-yl)-4-oxocyclohexanecarbonitrile (3.7 g) and morpholine (1.3 g) were added to toluene (20 ml), sodium triacetoxyborohydride (3.2 g) was added under stirring, and the mixture was stirred at 80° C. for three hours. The reaction solution was treated with 1N aqueous solution of sodium hydroxide and extracted with ethyl acetate. The organic layer was washed with saturated brine, concentrated in vacuo and the residue was purified with silica gel column chromatography (ethyl acetate:n-hexane=5:1) to give the titled compound (1.13 g).

MS (ESI) m/z: 364, 366 (M+H)⁺.

Reference Example 96

4-(5-Aminopyridin-2-yl)-1-(2-hydroxy-2-methylpropyl)piperidine-4-carbonitrile (1) Morpholine (catalytic amount) and isobutylene oxide (2.84 g) were added to 4-(5-bromopyridin-2-yl)piperidine-4-carbonitrile (3.4 g) of Reference Example 88(2) and water (35 ml), and the mixture was stirred at 100° C. for 4.5 hours. A saturated aqueous solution of sodium bicarbonate was added to the reaction solution and extracted with ethyl acetate. The organic layer was washed with saturated brine dried over anhydrous sodium sulfate and concentrated in vacuo. Water was added to the residue and the precipitated solid was washed with water to give 4-(5-bromopyridin-2-yl)-1-(2-hydroxy-2-methylpropyl)piperidine-4-carbonitrile (3.95 g) as a light brown solid.

MS (ESI) m/z: 348, 340 (M+H)⁺.

(2) Benzophenonimine (2.22 g) was added to a suspension of 4-(5-bromopyridin-2-yl)-1-(2-hydroxy-2-methylpropyl)piperidine-4-carbonitrile (3.95 g), palladium (II) acetate (328 mg), racemic-2-(di-tert-butylphosphino)-1,1'-binaphthyl (909 mg) and sodium tert-butoxide (1.68 g) in toluene (29 ml), and stirred at 120° C. for 2.5 hours. The reaction solution was left stand, a mixture of concentrated hydrochloric acid (2 ml) and water (6 ml) were added at 60-80° C. and stirred at room temperature. A saturated aqueous solution of sodium bicarbonate was added to the reaction solution and extracted with ethyl acetate. The organic layer was dried over anhydrous sodium sulfate and concentrated in vacuo. The residue was purified with basic silica gel column chromatography (n-hexane/ethyl acetate) to give the titled compound (2.6 g) as a pale yellow solid.

MS (ESI) m/z: 275 (M+H)⁺.

Reference Example 97

4-(5-Aminopyridin-2-yl)-1-(tetrahydro-2H-pyran-4-yl)piperidine-4-carbonitrile 4-(5-Bromopyridin-2-yl)-1-(tetrahydro-2H-pyran-4-yl)piperidine-4-carbonitrile of Reference Example 90 was used in place of 1-(5-bromopyridin-2-yl)-c-4-(morpholin-4-yl)-r-1-cyclohexanecarbonitrile in Reference Example 94, and reacted and treated in a similar manner to give the titled compound.

MS (ESI) m/z: 287 (M+H)⁺.

Reference Example 98

1-(5-Aminopyridin-2-yl)-c-4-methoxy-r-1-cyclohexanecarbonitrile (1) 60% Sodium hydride (94 mg) was added little by little to a solution of 1-(5-bromopyridin-2-yl)-c-4-hydroxy-r-1-cyclohexanecarbonitrile (600 mg) described in Reference Example 85(2) in N,N-dimethylformamide (3 ml) under ice cooling, and stirred at room temperature for 30 minutes. Then, methyl iodide (0.139 ml) was added and the mixture was stirred at room temperature. After completion of the reaction, water was added and extracted with chloroform. The organic layer was dried over anhydrous sodium sulfate, concentrated and the resulting residue was purified with silica gel column chromatography (n-hexane/ethyl acetate) to give 1-(5-bromopyridin-2-yl)-c-4-methoxy-r-1-cyclohexanecarbonitrile (410 mg) as a white solid.

MS (ESI) m/z: 295, 297 (M+H)+.

(2) Under nitrogen atmosphere, bis(dibenzylideneacetone) palladium (0) (39.1 mg), tri-tert-butylphosphine tetrafluoroborate (19.7 mg) and 1.0M toluene-solution of lithium bis (trimethylsilyl)amide (1.9 ml) were successively added to a reaction vessel, and a solution of 1-(5-bromopyridin-2-yl)-c-4-methoxy-r-1-cyclohexanecarbonitrile (400 mg) in toluene (1.4 ml) was added dropwise thereto. Then, the mixture was stirred at 85° C. for 1.5 hours. After completion of the reaction, the reaction solution was cooled to room temperature, 1.0M solution of tetra-n-butylammonium fluoride in tetrahydrofuran (4.76 ml) was added and stirred at room temperature for three hours. After completion of the reaction, a saturated aqueous solution of sodium bicarbonate was added to the reaction solution and extracted with ethyl acetate. The organic layer was dried over anhydrous sodium sulfate and concentrated. The resulting residue was purified with silica gel column chromatography (n-hexane/ethyl acetate) to give the titles compound (114 mg) as a ple yellow solid.

MS (ESI) m/z: 232 (M+H)+.

Reference Example 99

1-(5-Aminopyridin-2-yl)-c-4-[2-(tetrahydro-2H-pyran-2-yloxy)ethoxy]-r-1-cyclohexanecarbonitrile (1) 2-(2-bromoethoxy)tetrahydro-2H-pyrane was used in place of methyliodide in Reference Example 98(1), and reacted and treated in a similar manner to give 1-(5-bromopyridin-2-yl)-c-4-[2-(tetrahydro-2H-pyran-2-yloxy)ethoxy]-r-1-cyclohexanecarbonitrile as a colorless oil.

MS (ESI) m/z: 409, 411 (M+H)+.

(2) 1-(5-bromopyridin-2-yl)-c-4-[2-(tetrahydro-2H-pyran-2-yloxy)ethoxy]-r-1-cyclohexanecarbonitrile was used in place of 1-(5-bromopyridin-2-yl)-c-4-methoxy-r-1-cyclohexanecarbonitrile in Reference Example 98(2), and reacted and treated in a similar manner to give the titled compound as a brown oil.

MS (ESI) m/z: 346 (M+H)+.

Reference Example 100

1-(5-Aminopyridin-2-yl)-c-4-(2-methoxyethoxy)-r-1-cyclohexanecarbonitrile (1) Methanesulfonic acid 2-methoxyethyl ester was used in place of methyliodide in Reference Example 98(1), and reacted and treated in a similar manner to give 1-(5-bromopyridin-2-yl)-c-4-(2-methoxyethoxy)-r-1-cyclohexanecarbonitrile as a colorless oil.

MS (ESI) m/z: 339, 341 (M+H)+.

(2) 1-(5-Bromopyridin-2-yl)-c-4-(2-methoxyethoxy)-r-1-cyclohexanecarbonitrile was used in place of 1-(5-bromopyridin-2-yl)-c-4-methoxy-r-1-cyclohexanecarbonitrile in Reference Example 98(2), and reacted and treated in a similar manner to give the titled compound as a brown solid.

MS (ESI) m/z: 276 (M+H)+.

Reference Example 101

1-(5-Aminopyridin-2-yl)-c-4-methoxy-r-1-cyclohexanecarboxylic acid ethyl ester (1) Water was removed using a Dean-Stark apparatus while a solution of cis/tarns mixture of 4-hydroxycyclohexane-1-carboxylic acid (25 g) and concentrated sulfuric acid (0.8 ml) in ethanol (300 ml) was heated under reflux for an hour. After completion of the reaction, solvent was evaporated and the resulting residue was diluted with diethyl ether. The organic layer was washed with water, a saturated aqueous solution of sodium bicarbonate and saturated brine successively, dried over anhydrous sodium sulfate and concentrated to give a colorless oil (27.1 g).

(2) 60% Sodium hydride (6.92 g) was added little by little to a solution of the colorless oil (27 g) in N,N-dimethylformamide (150 ml) under ice cooling, and stirred at room temperature for 30 minutes. Then, methyl iodide (10.3 ml) was added under ice-cooling and stirred at room temperature. After completion of the reaction, water was added to the reaction solution and extracted with chloroform. The organic layer was dried over anhydrous sodium sulfate and concentrated. The resulting residue was purified with silica gel column chromatography (n-hexane/ethyl acetate) to give a colorless oil (4.46 g).

(3) Under nitrogen atmosphere, 1.0M tetrahydrofuran-solution (23.9 ml) of lithium bis(trimethylsilyl)amide was added under ice cooling to a solution of the colorless oil (4.45 g) obtained in the previous step (2) in tetrahydrofuran (10 ml), and stirred at the same temperature for an hour. Then, a solution of 6-chloronicotinic acid ethyl ester (4.44 g) in tetrahydrofuran (10 ml) was added dropwise under ice cooling. After the addition, the reaction solution was gradually warmed up to room temperature and stirred. After completion of the reaction, water was added to the reaction solution under ice cooling and extracted with chloroform. The organic solution was dried over anhydrous sodium sulfate and concentrated. The resulting oil was purified with silica gel column chromatography (n-hexane/ethyl acetate) to give 1-(5-methoxycarbonylpyridin-2-yl)-4-methoxy-1-cyclohexanecarboxylic acid ethyl ester (1.3 g) as a cis/trans mixture of colorless oil.

MS (ESI) m/z: 336 (M+H)+.

(4) 1N Aqueous solution of sodium hydroxide (20 ml) was added to a solution of cis/trans mixture of 1-(5-methoxycarbonylpyridin-2-yl)-4-methoxy-1-cyclohexanecarboxylic acid ethyl ester (1.28 g) in methanol (20 ml) and tetrahydrofuran (20 ml), and stirred at room temperature. After completion of the reaction, the organic solvent was evaporated and the aqueous layer was washed with diethyl ether. Concentrated hydrochloric acid was added to the aqueous layer under ice cooling and pH was adjusted to 4, and extracted with chloroform. The organic layer was dried over anhydrous sodium sulfate and concentrated to give a cis/trans mixture of 6-[4-methoxy-1-(methoxycarbonyl)cyclohexyl]nicotinic acid ethyl ester (1.0 g) as a colorless oil.

MS (ESI) m/z: 308 (M+H)+.

(5) Diphenylphosphorylazide (0.91 ml) and triethylamine (0.59 ml) were added to a solution of 6-[4-methoxy-1-(methoxycarbonyl)cyclohexyl]nicotinic acid ethyl ester (cis/trans mixture) (1.0 g) in tert-butanol (20 ml) and stirred at 80° C. for two hours. After completion of the reaction, the reaction solution was cooled to room temperature, water was added and extracted with chloroform. The organic solution was dried over anhydrous sodium sulfate and concentrated. The resulting residue was purified with silica gel column chromatography (n-hexane/ethyl acetate) to give 1-{5-[(tert-butoxycarbonyl)amino]pyridin-2-yl}-c-4-methoxy-r-1-cyclohexanecarboxylic acid ethyl ester (533 mg) as a colorless oil.

MS (ESI) m/z: 379 (M+H)$^+$.

(6) 4N Hydrochloric acid-ethyl acetate (10 ml) was added to 1-{5-[(tert-butoxycarbonyl)amino]pyridin-2-yl}-c-4-methoxy-r-1-cyclohexanecarboxylic acid ethyl ester (530 mg) and stirred at room temperature. After completion of the reaction, the reaction solution was neutralized by the addition of 1N aqueous solution of sodium hydroxide and extracted with ethyl acetate. The organic layer was dried over anhydrous sodium sulfate and concentrated to give the titled compound (395 mg) as a pale yellow oil.

MS (ESI) m/z: 279 (M+H)$^+$.

Reference Example 102

6-(1,4-Dioxaspiro[4,5]decane-8-yl)pyridin-3-amine (1) 4N Aqueous solution of sodium hydroxide (5 ml) and water (5 ml) were added to a solution of 8-(5-bromopyridin-2-yl)-1,4-dioxaspiro[4,5]decane-8-carboxylic acid ethyl ester (1.0 g) described in Reference Example 81(2) in methanol (10 ml) and tetrahydrofuran (10 ml), and stirred at 80° C. for eight hours. After completion of the reaction, the organic solvent was evaporated and the aqueous layer was washed with diethyl ether. Concentrated hydrochloric acid was added to the aqueous layer under ice cooling, pH was adjusted to 4-5, and extracted with chloroform. The organic layer was dried over anhydrous sodium sulfate and concentrated to give 8-(5-bromopyridin-2-yl)-1,4-dioxaspiro[4,5]decane-8-carboxylic acid (864 mg) as a colorless solid.

MS (ESI) m/z: 342, 344 (M+H)$^+$.

(2) A solution of 8-(5-bromopyridin-2-yl)-1,4-dioxaspiro[4,5]decane-8-carboxylic acid (776 mg) in dimethylsulfoxide (3 ml) was stirred at 150° C. for 1.5 hours. After completion of the reaction, the reaction solution was left stand to room temperature, water was added and extracted with ethyl acetate. The organic solution was washed with water and saturated brine successively, dried over anhydrous sodium sulfate and concentrated. The resulting residue was purified with silica gel column chromatography (n-hexane/ethyl acetate) to give 5-bromo-2-(1,4-dioxaspiro[4,5]decane-8-yl)pyridine (646 mg) as a colorless oil.

MS (ESI) m/z: 298, 300 (M+H)$^+$.

(3) 5-Bromo-2-(1,4-dioxaspiro[4,5]decane-8-yl)pyridine was used in place of 1-(5-bromopyridin-2-yl)-c-4-methoxy-r-1-cyclohexanecarbonitrile in Reference Example 98(2), and reacted and treated in a similar manner to give the titled compound as a pale yellow oil.

MS (ESI) m/z: 235 (M+H)$^+$.

Reference Example 103 trans-4-(5-Aminopyridin-2-yl)cyclohexanol (1) 5-Bromo-2-(1,4-dioxaspiro[4,5]decane-8-yl)pyridine (9.0 g) described in Reference Example 102(2) was dissolved in trifluoroacetic acid (15 ml) and stirred at room temperature overnight. After completion of the reaction, water was added under ice cooling, neutralized by the addition of 4N aqueous solution of sodium hydroxide and extracted with ethyl acetate. The organic layer was washed with saturated brine, dried over anhydrous sodium sulfate and concentrated to give 4-(5-bromopyridin-2-yl)cyclohexanone (7.9 g) as a pale yellow solid.

MS (ESI) m/z: 254, 256 (M+H)$^+$.

(2) Sodium borohydride (4.58 g) was added under ice cooling to a solution of 4-(5-bromopyridin-2-yl)cyclohexanone (7.9 g) in ethanol (120 ml), and stirred at the same temperature for an hour. After completion of the reaction, water was added under ice cooling, the organic solvent was evaporated and extracted with ethyl acetate. The organic layer was washed with saturated brine, dried over anhydrous sodium sulfate and concentrated. The resulting residue was purified with silica gel column chromatography (n-hexane/ethyl acetate) to give trans-4-(5-bromopyridin-2-yl)cyclohexanol (4.94 g) as a white solid, and cis-4-(5-bromopyridin-2-yl)cyclohexanol (1.16 g) as a colorless oil.

MS (ESI) m/z: 256, 258 (M+H)$^+$.

(3) tert-Butyldimethylsilylchloride (2.35 g) and imidazole (1.06 g) were added to a solution of trans-4-(5-bromopyridin-2-yl)cyclohexanol (2.0 g) in dichloromethane (50 ml) and stirred at room temperature for an hour. After completion of the reaction, water was added to the reaction solution and extracted with dichloromethane. The organic layer was washed with saturated brine, dried over anhydrous sodium sulfate and concentrated. The resulting residue was purified with silica gel column chromatography (n-hexane/ethyl acetate) to give trans-5-bromo-[4-(tert-butyldimethylsilyloxy)cyclohexa-1-yl]pyridine (2.84 g) as a colorless oil.

(4) trans-5-Bromo-[4-(tert-butyldimethylsilyloxy)cyclohex-1-yl]pyridine (2.84 g) was used in place of 1-(5-bromopyridin-2-yl)-c-4-methoxy-r-1-cyclohexanecarbonitrile in Reference Example 98(2), and reacted and treated in a similar manner to give the titled compound (193 mg) as a yellow solid.

MS (ESI) m/z: 193 (M+H)$^+$.

Reference Example 104

1-[3-Methoxy-5-(trifluoromethyl)pyridin-2-yl]-5-methyl-1H-pyrazole-4-carboxylic acid (1) A solution of 2,3-difluoro-5-(trifluoromethyl)pyridine (4.45 g) in ethanol (50 ml) was added dropwise to a solution of hydrazine hydrate (100%) (3.54 ml) in ethanol (150 ml) at room temperature, stirred for two hours and then under reflux for two hours. After completion of the reaction, the reaction solution was left stand to room temperature, water was added and concentrated in vacuo. The precipitated solid was filtered and washed with water to give a white solid.

(2) The white solid obtained above and ethyl 2-ethoxymethyleneacetoacetate (4.52 g), which was prepared according to a method described in J. Chem. Soc. Perkin trans. I, 1875 (1988), were added to a mixed solvent of 1N hydrochloric acid aqueous solution (110 ml) and ethanol (166 ml) and stirred under reflux for three hours. After completion of the reaction, the reaction solution was left stand, water was added and the precipitated solid was collected by filtration, washed with water and dried at 60° C. under air blow to give 1-[3-fluoro-5-(trifluoromethyl)pyridin-2-yl]-5-methyl-1H-pyrazole-4-carboxylic acid ethyl ester (5.16 g) as a white solid.

MS (ESI) m/z: 318 (M+H)$^+$.

(3) 4N Aqueous solution of sodium hydroxide (20 ml) and water (20 ml) were added to a solution of 1-[3-fluoro-5-(trifluromethyl)pyridin-2-yl]-5-methyl-1H-pyrazole-4-carboxylic acid ethyl ester (3 g) in methanol (20 ml) and tetrahydrofuran (20 ml), and stirred at room temperature for five hours. After completion of the reaction, the organic solvent was evaporated, diethylether and water was added to the residue. The aqueous layer was separated, pH was adjusted to 5 by the addition of concentrated hydrochloric acid under ice cooling, and the precipitated solid was collected by filtration dried at 60° C. under air blow to give the titled compound (1.17 g) as a white solid.

MS (ESI) m/z: 302 (M+H)$^+$.

Reference Example 105

5-Bromo-2-(1,4-dioxaspiro[4,5]decan-7-en-8-yl)-3-methylpyridine (1) 1.6M n-Hexane solution of n-butyl lithium (100 ml) was added dropwise under nitrogen atmosphere at −78° C. to a solution of 2,5-dibromo-3-picoline (38.3 g) in toluene (300 ml), and stirred at the same temperature for two hours. Then, a solution of 1,4-cyclohexanedione monoethyleneketal (25 g) in toluene (200 ml) was added slowly dropwise, and after the addition the mixture was stirred at the same temperature for an hour. Then, the reaction solution was warmed up slowly to room temperature under stirring. After completion of the reaction, water was added and extracted with ethyl acetate. The organic layer was washed with water and saturated brine successively, dried over anhydrous sodium sulfate and concentrated. Acetonitrile and water were added to the residue and the precipitate was filtered and dried at 60° C. under air blow to give 8-(5-bromo-3-methylpyridin-2-yl)-1,4-dioxaspiro[4,5]decan-8-ol (28 g) as a light brown solid.

MS (ESI) m/z: 328, 330 (M+H)$^+$.

(2) Pyridine (42.7 ml) was added to a solution of 8-(5-bromo-3-methylpyridin-2-yl)-1,4-dioxaspiro[4,5]decan-8-ol (28 g) in dichloromethane (300 ml), thionyl chloride (19 ml) was added dropwise under ice cooling and the reaction solution was warmed to room temperature and stirred for an hour. After completion of the reaction, the reaction solution was poured into 10% aqueous solution of sodium carbonate, stirred and the resulting precipitate was collected by filtration and dried at 60° C. under air blow to give the titled compound (13.1 g) as a pale yellow solid.

MS (ESI) m/z: 310, 312 (M+H)$^+$.

Reference Example 106

6-(1,4-dioxaspiro[4,5]decan-7-en-8-yl)-5-methylpyridin-3-amine (1) 1.0M Toluene-solution of lithium bis(trimethylsilyl) amide (13.4 ml) was added at room temperature under nitrogen atmosphere to a solution of 5-bromo-2-(1,4-dioxaspiro[4,5]decane-7-ene-8-yl)-3-methylpyridine (2.78 g) of Reference Example 105, bis(dibenzylideneacetone) palladium (0) (258 mg) and tri-tert-butylphosphine tetrafluoroborate (130 mg) in toluene (12 ml), and stirred at 70° C. for two hours. Then, the reaction solution was cooled to room temperature, 1.0M tetrahydrofuran-solution of tetrabutylammonium fluoride (40.3 ml) was added and stirred at the same temperature for an hour. After completion of the reaction, water was added to the reaction solution and extracted with ethyl acetate. The organic layer was washed with water and saturated brine successively, dried over anhydrous sodium sulfate and concentrated. The resulting residue was purified with basic silica gel column chromatography (n-hexane/ethyl acetate) to give the titled compound (773 mg) as a pale yellow solid.

MS (ESI) m/z: 247 (M+H)$^+$.

Reference Example 107

4-[4-(5-Bromo-3-methylpyridin-2-yl)cyclohex-3-en-1-yl]morpholine (1) Trifluoroacetic acid (11 ml) and water (1 ml) were added to 8-(5-bromo-3-methylpyridin-2-yl)-1,4-dioxaspiro[4,5]decan-8-ol (7.45 g) described in Reference Example 105(1) and stirred at room temperature. After completion of the reaction, water was added and neutralized by the addition of 1N aqueous solution of sodium hydroxide and extracted with chloroform. The organic layer was washed with a saturated aqueous solution of sodium bicarbonate and saturated brine successively, dried over anhydrous sodium sulfate and concentrated. The resulting residue was purified with silica gel column chromatography (n-hexane/ethyl acetate) to give 4-(5-bromo-3-methylpyridin-2-yl)-4-hydroxy-cyclohexanone (2.69 g) as a white solid.

MS (ESI) m/z: 284, 286 (M+H)$^+$.

(2) Sodium triacetoxyborohydride (4.01 g) was added at room temperature to a solution of 1-(5-bromo-3-methylpyridin-2-yl)-4-hydroxy-cyclohexanone (2.69 g) and morpholine (0.87 ml) in tetrahydrofuran (80 ml), and stirred at the same temperature. After completion of the reaction, the reaction solution was poured into ice water and extracted with chloroform. The organic layer was dried over anhydrous sodium sulfate and concentrated to give a cis/trans mixture of 4-(5-bromo-3-methylpyridin-2-yl)-4-(morpholin-4-yl)-1-cyclohexanol (3.22 g) as a crude product.

MS (ESI) m/z: 355, 357 (M+H)$^+$.

(3) Thionyl chloride (3.65 ml) was added dropwise to a solution of a cis/trans mixture of 1-(5-bromo-3-methylpyridin-2-yl)-4-(morpholin-4-yl)-1-cyclohexanone (3.22 g) in pyridine (30 ml) under ice cooling, the mixture was warmed to room temperature and stirred for an hour. After completion of the reaction, water was added to the reaction solution under ice cooling and extracted with chloroform. The organic layer was washed with saturated brine, dried over anhydrous sodium sulfate and concentrated. The resulting residue was purified with silica gel column chromatography (chloroform/methanol) to give the titled compound (1.82 g) as a yellow solid.

MS (ESI) m/z: 337, 339 (M+H)$^+$.

Reference Example 108

5-Methyl-6-[4-(morpholin-4-yl)cyclohex-1-en-1-yl]pyridin-3-amine

Acetylacetone (0.31 ml) and 28% ammonia water (1.78 ml) were added to a suspension of 4-[4-(5-bromo-3-methylpyridin-2-yl)cyclohex-3-en-1-yl]morpholine (2 g), copper acetylacetonate (466 mg) and cesium carbonate (3.86 g) in N,N-dimethylformamide (12 ml), sealed in a tube under nitrogen atmosphere and stirred at 100° C. for 20 hours. After completion of the reaction, the reaction solution was left stand to room temperature and concentrated. The resulting residue was diluted with water and extracted with chloroform. The organic layer was dried over anhydrous sodium sulfate and concentrated. The resulting residue was purified with silica gel column chromatography (chlorofolin/methanol) to give the titled compound (1.31 g) as a pale yellow solid.

MS (ESI) m/z: 274 (M+H)$^+$.

Two enantioisomers were separated by chiral HPLC;
Column: Chiralpac IC 4.6×250 mm,
eluent: n-hexane:ethanol:diethylamine=50:50:0.1
Flow rate: 0.5 ml/min
RT: R-isomer 23.8 min, S-isomer 29.6 min

Reference Example 109

3-Methyl-1'-(tetrahydro-2H-pyran-4-yl)-1',2',3',6'-tetrahydro-2,4'-bipyridine-5-amine (1) Under nitrogen atmosphere, 1.6M n-hexane solution of n-butyl lithium (65.6 ml) was added dropwise to a solution of 2,5-dibromo-3-picoline (25.1 g) in toluene (200 ml) at −78° C. and stirred at the same temperature for two hours. Next, a solution of 1-(tert-butoxycarbonyl)-4-piperidone (20.9 g) in toluene (200 ml) was added slowly dropwise. After the addition, the mixture was stirred at the same temperature for an hour. Then, the reaction solution was gradually warmed up to room temperature under stirring. After completion of the reaction, water was added and extracted with ethyl acetate. The organic layer was dried over anhydrous sodium sulfate and concentrated. The resulting residue was purified with silica gel column chromatography (n-hexane/ethyl acetate) and the product was solidified with n-hexane to give 4-(5-bromo-3-methylpyridin-2-yl)-4-hydroxy-piperidine-1-carboxylic acid tert-butyl ester (11.4 g) as a white solid.

MS (ESI) m/z: 371, 373 (M+H)$^+$.

(2) Thionyl chloride (9.04 ml) was added dropwise under ice cooling to a solution of 4-(5-bromo-3-methylpyridin-2-yl)-4-hydroxy-piperidine-1-carboxylic acid tert-butyl ester (11.4 g) in pyridine (110 ml), and stirred at the same temperature for an hour. The reaction solution was then warmed up to room temperature and stirred for an hour. After completion of the reaction, 4N aqueous solution of sodium hydroxide was added under ice cooling and extracted with chloroform. The organic layer was dried over anhydrous sodium sulfate and concentrated. The resulting residue was purified with silica gel column chromatography (n-hexane/ethyl acetate) to give 5-bromo-3-methyl-3',6'-dihydro-2,4'-bipyridine-1'(2H')-carboxylic acid tert-butyl ester (6.75 g) as a colorless oil.

Next, concentrated hydrochloric acid (5 ml) was added to a solution of 5-bromo-3-methyl-3',6'-dihydro-2,4'-bipyridine-1'(2H')-carboxylic acid tert-butyl ester (6.75 g) in tetrahydrofuran (20 ml) and stirred at room temperature. After completion of the reaction, the reaction solution was neutralized by the addition of 4N aqueous solution of sodium hydroxide under ice cooling and extracted with chloroform. The organic layer was dried over anhydrous sodium sulfate and concentrated to give 5-bromo-3-methyl-1',2',3',6'-tetrahydro-2,4'-bipyridine (5.23 g) as a brown oil.

MS (ESI) m/z: 253, 255 (M+H)$^+$.

(3) Sodium triacetoxyborohydride (5.25 g) was added at room temperature to a solutions of 5-bromo-3-methyl-1',2',3',6'-tetrahydro-2,4'-bipyridine (5.23 g) and tetrahydro-4H-pyran-4-one (2.07 g) in tetrahydrofuran (50 ml) and n-hexane (20 ml), and stirred at the same temperature. After completion of the reaction, 1N aqueous solution of sodium hydroxide was added under ice cooling and extracted with chloroform. The organic layer was dried over anhydrous sodium sulfate and concentrated. The resulting residue was purified with silica gel column chromatography (chloroform/methanol) and washed with diethyl ether and n-hexane to give 5-bromo-3-methyl-1'-(tetrahydro-2H-pyran-4-yl)-1',2',3',6'-tetrahydro-2,4'-bipyridine (3.1 g) as a pale yellow solid.

MS (ESI) m/z: 337, 339 (M+H)$^+$.

(4) 5-Bromo-3-methyl-1'-(tetrahydro-2H-pyran-4-yl)-1',2',3',6'-tetrahydro-2,4'-bipyridine was used in place of 4-[4-(5-bromo-3-methylpyridin-2-yl)cyclohex-3-en-1-yl]morpholine in Reference Example 108, and reacted and treated in a similar manner to give the titled compound as a yellow solid.

MS (ESI) m/z: 274 (M+H)$^+$.

Reference Example 110

6-(4-{[tert-Butyl(dimethyl)silyl]oxy}cyclohex-1-en-1-yl)-5-methylpyridin-3-amine (1) Sodium borohydride (1.04 g) was added under ice cooling to a solution of 4-(5-bromo-3-methylpyridin-2-yl)-4-hydroxycyclohexanone (7.8 g) described in Reference Example 107(1) in methanol (100 ml), and stirred at the same temperature for an hour. After completion of the reaction, water was added under ice cooling and extracted with chloroform. The organic layer was washed with saturated brine, dried over anhydrous sodium sulfate and concentrated. The resulting residue was dissolved in dichloromethane (150 ml), imidazole (3.74 g) and tert-butyldimethylsilylchloride (5.4 g) were added and stirred at room temperature for an hour. After completion of the reaction, the reaction solution was diluted with ice water, 1N aqueous solution of sodium hydroxide was added and extracted with chloroform. The organic layer was dried over anhydrous sodium sulfate and concentrated. The resulting residue was dissolved in pyridine (40 ml), thionyl chloride (6.02 ml) was added dropwise under ice cooling and the mixture was warmed up to room temperature and stirred for two hours. After completion of the reaction, 10% aqueous solution of sodium carbonate was added under ice cooling, the solution was adjusted to pH>11 by the addition of 4N aqueous solution of sodium hydroxide and extracted with chloroform. The organic layer was dried over anhydrous sodium sulfate and concentrated. The resulting residue was purified with silica gel column chromatography (n-hexane/ethyl acetate) to give 5-bromo-2-(4-{[tert-butyl(dimethyl)silyl]oxy}cyclohex-1-en-1-yl)-3-methylpyridine (8.44 g) as a colorless oil.

(2) 5-Bromo-2-(4-{[tert-butyl(dimethyl) silyl]oxy}cyclohex-1-en-1-yl)-3-methylpyridine (8.4 g) was used inn place of 4-[4-(5-bromo-3-methylpyridin-2-yl)cyclohex-3-en-1-yl]morpholine in Reference Example 108, and reacted and treated in a similar manner to give the titled compound (5.76 g) as a brown solid.

MS (ESI) m/z: 319 (M+H)$^+$.

Reference Example 111

4-(5-Amino-3-methylpyridin-2-yl)cyclohex-3-en-1-ol (1) A suspension of 5-bromo-2-(4-{[tert-butyl(dimethyl)silyl]oxy}cyclohex-1-en-1-yl)-3-methylpyridine (5.59 g) of Reference Example 110(1), benzophenonimine (2.77 g), palladium acetate (41 mg), (±)-2,2'-bis(diphenylphosphino)-1,1'-binaphthyl (114 mg) and sodium tert-butoxide (2.1 g) in toluene (30 ml) was stirred under reflux for two hours. After completion of the reaction, the reaction solution was left stand, concentrated hydrochloric acid (20 ml) and water (60 ml) were added and stirred at room temperature for two hours. Then, diethyl ether was added and extracted with 1N hydrochloric acid aqueous solution. The resulting aqueous layer was cooled with ice, adjusted to pH>10 by the addition of 4N aqueous solution of sodium hydroxide and extracted with chloroform. The organic layer was dried over anhydrous sodium sulfate and concentrated to give the titled compound (2.52 g) as a yellow solid.

MS (ESI) m/z: 205 (M+H)$^+$.

Reference Example 112

1-(5-Amino-3-methyl-3',6'-dihydro-2,4'-bipyridin-1'(2H')-yl)-2-methylpropan-2-ol (1) In a sealed tube, morpholine (catalytic amount) and isobutylene oxide (3.81 g) were added to 5-bromo-3-methyl-1',2',3',6'-tetrahydro-2,4'-bipyridine (3.4 g) of Reference Example 109(2) and water (10 ml), and stirred at 100° C. for 20 hours. After being left stand, water was added and extracted with chloroform. The organic layer was dried over anhydrous sodium sulfate and concentrated in vacuo to give 1-(5-bromo-3-methyl-3',6'-dihydro-2,4'-bipyridin-1'(2H')-yl)-2-methylpropan-2-ol as a brown oil.

MS (ESI) m/z: 325, 327 (M+H)$^+$.

(2) 1-(5-Bromo-3-methyl-3',6'-dihydro-2,4'-bipyridin-1'(2H')-yl)-2-methylpropan-2-ol (3.65 g) was used in place of 4-[4-(5-bromo-3-methylpyridin-2-yl)cyclohex-3-en-1-yl]morpholine in Reference Example 108, and reacted and treated in a similar manner to give the titled compound (1.59 g) as a yellow oil.

MS (ESI) m/z: 262 (M+H)'.

Reference Example 113

1-[4-(5-Amino-3-methylpyridin-2-yl)piperidin-1-yl]-2-methylpropan-2-ol

To a solution of 1-(5-amino-3-methyl-3',6'-dihydro-2,4'-bipyridin-1'(2H')-yl)-2-methylpropan-2-ol (500 mg) described in Reference Example 112, palladium acetate (86 mg) and potassium fluoride (444 mg) in tetrahydrofuran (10 ml) and water (4 ml) was slowly added dropwise polymethylhydrosiloxane (PMHS) (0.46 ml) at room temperature with stirring, and then stirred at room temperature for 3 hours. After completion of the reaction, the reaction solution was diluted with diethyl ether, filtered through Celite, and then the filtrate was concentrated to half of the volume. Then, saturated brine was added thereto, the mixture was extracted with ethyl acetate, the obtained organic layer was dried over anhydrous sodium sulfate, and then the solvent was evaporated in vacuo. The obtained residue was purified with silica gel column chromatography (chloroform/methanol) to give the titled compound (457 mg) as a pale yellow oil. MS (ESI) m/z: 264 (M+H)$^+$.

Reference Example 114 cis/trans-6-(4-{[tert-Butyl(dimethyl)silyl]oxy}cyclohexyl)-5-methylpyridine-3-amine To a solution of 6-(4-{[tert-butyl(dimethyl)silyl]oxy}-cyclohex-1-en-1-yl)-5-methylpyridin-3-amine (1.5 g) described in Reference Example 110, palladium acetate (211 mg) and potassium fluoride (1.09 g) in tetrahydrofuran (24 ml) and water (10 ml) was slowly added dropwise polymethylhydrosiloxane (PMHS) (1.12 ml) at room temperature with stirring, and then stirred at room temperature for 2 hours. After completion of the reaction, the reaction solution was diluted with diethyl ether, filtered through Celite, and then the filtrate was concentrated to half of the volume. Then, saturated brine was added thereto, the mixture was extracted with ethyl acetate, the obtained organic layer was dried over anhydrous sodium sulfate, and then the solvent was evaporated in vacuo. The obtained residue was purified with silica gel column chromatography (n-hexane/ethyl acetate) to give the titled compound (1.35 g) as a light brown solid. MS (ESI) m/z: 321 (M+H)$^+$.

Reference Example 115 A cis-4-(5-Amino-3-methylpyridin-2-yl)-1-(2-methyltetrahydrofuran-3-yl)-1,2,3,6-tetrahydropyridine,
and

Reference Example 115B trans-4-(5-amino-3-methylpyridin-2-yl)-1-(2-methyltetrahydrofuran-3-yl)-1,2,3,6-tetrahydropyridine (1) To a solution of 5-bromo-3-methyl-1',2',3',6'-tetrahydro-2,4'-bipyridine (2.26 g) described in Reference Example 109 (2) and 2-methyltetrahydrofuran-3-one (1.1 ml) in dichloromethane (25 ml) was added sodium triacetoxyborohydride (2.77 g), and stirred at room temperature for 6 hours. To the reaction solution was added 1 N aqueous solution of sodium hydroxide, and extracted with chloroform. The obtained organic layer was dried over anhydrous sodium sulfate, and the solvent was evaporated in vacuo. The obtained residue was purified with silica gel chromatography (n-hexane/ethyl acetate) to give cis-4-(5-bromo-3-methylpyridin-2-yl)-1-(2-methyltetrahydrofuran-3-yl)-1,2,3,6-tetrahydropyridine (2.43 g) and trans-4-(5-bromo-3-methylpyridin-2-yl)-1-(2-methyltetrahydrofuran-3-yl)-1,2,3,6-tetrahydropyridine (193 mg) as brown oils respectively. MS (ESI) m/z: 337, 339 (M+H)$^+$.

(2) cis-4-(5-Bromo-3-methylpyridin-2-yl)-1-(2-methyltetrahydrofuran-3-yl)-1,2,3,6-tetrahydropyridine (2.43 g) and trans-4-(5-bromo-3-methylpyridin-2-yl)-1-(2-methyltetrahydrofuran-3-yl)-1,2,3,6-tetrahydropyridine (193 mg) were used in place of 5-bromo-2-(4-{[tert-butyl(dimethyl)silyl]oxy}cyclohex-1-en-1-yl)-3-methylpyridine in Reference Example 111, and reacted and treated in a similar manner to give the titled compounds; cis-4-(5-amino-3-methylpyridin-2-yl)-1-(2-methyltetrahydrofuran-3-yl)-1,2,3,6-tetrahydropyridine (991 mg), and trans-4-(5-amino-3-methylpyridin-2-yl)-1-(2-methyl-tetrahydrofuran-3-yl)-1,2,3,6-tetrahydropyridine (67 mg) as brown solids respectively. MS (ESI) m/z: 274 (M+H)$^+$.

Reference Example 116 cis-4-(5-Amino-3-methylpyridin-2-yl)-1-(2-methyltetrahydrofuran-3-yl)piperidine (1) cis-4-(5-Amino-3-methylpyridin-2-yl)-1-(2-methyltetrahydrofuran-3-yl)-1,2,3,6-tetrahydropyridine (557 mg) in Reference Example 115 (2) was used in place of 1-(5-amino-3-methyl-3',6'-dihydro-2,4'-bipyridin-1'(2H')-yl)-2-methylpropan-2-ol in Reference Example 113, and reacted and treated in a similar manner to give the titled compound (480 mg) as a brown solid. MS (ESI) m/z: 276 (M+H)$^+$.

Reference Example 117

6-(1,4-Dioxaspiro[4.5]decan-8-yl)-5-methylpyridin-3-amine (1) A suspension of 5-bromo-2-(1,4-dioxaspiro[4.5]decan-7-en-8-yl)-3-methylpyridine (22.5 g) in Reference Example 105, benzophenone imine (13.9 g), palladium acetate (204 mg), (±)-2,2'-bis(diphenylphosphino)-1,1'-binaphthyl (567 mg) and sodium tert-butoxide (10.5 g) in toluene (150 ml) was stirred for 6 hours under heating to reflux. After completion of the reaction, the mixture was allowed to cool, ice water was added thereto, and the mixture was extracted with chloroform. The organic layer was dried over anhydrous sodium sulfate, and then the solvent was evaporated to give 6-(1,4-dioxaspiro[4.5]decan-8-yl)-N-(diphenylmethylene)-5-methylpyridin-3-amine (28 g) as a brown oil. MS (ESI) m/z: 411 (M+H)$^+$.

(2) To a solution of 6-(1,4-dioxaspiro[4.5]decan-8-yl)-N-(diphenylmethylene)-5-methylpyridin-3-amine (2.87 g), palladium acetate (314 mg) and potassium fluoride (1.63 g) in tetrahydrofuran (35 ml) and water (16 ml) was slowly added dropwise polymethylhydrosiloxane (PMHS) (1.67 ml) at room temperature with stirring, and then stirred at room temperature for 5 hours. During that time, polymethylhydrosiloxane (PMHS) (1.67 ml) was added twice. After completion of the reaction, water was added thereto, the mixture was extracted with chloroform, the organic layer was dried over anhydrous sodium sulfate, and then the solvent was evaporated in vacuo. The obtained residue was purified with silica gel column chromatography (chloroform/methanol) to give the titled compound (1.28 g) as a gray solid. MS (ESI) m/z: 249 (M+H)$^+$.

The structural formulae of Reference Examples 95-117 are shown below.

| Reference Example No | Structure |
|---|---|
| 95 | 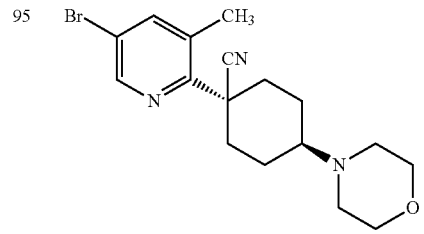 |
| 96 | 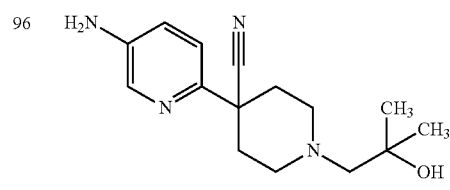 |
| 97 | 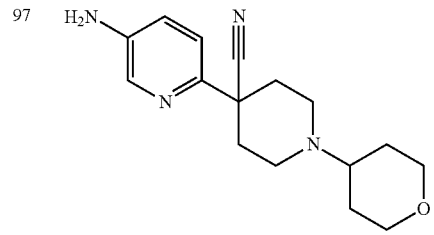 |
| 98 | 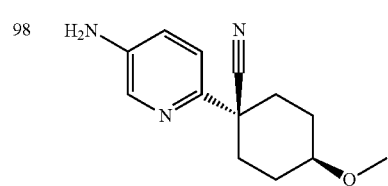 |
| 99 | H$_2$N-pyridine-CN-cyclohexyl-O-CH$_2$CH$_2$-O-tetrahydropyranyl |
| 100 | H$_2$N-pyridine-CN-cyclohexyl-O-CH$_2$CH$_2$-O-CH$_3$ |
| 101 | H$_2$N-pyridine-COOEt-cyclohexyl-OMe |
| 102 | H$_2$N-pyridine-(1,4-dioxaspiro[4.5]decane) |
| 103 | H$_2$N-pyridine-cyclohexyl-OH |
| 104 | F$_3$C-pyridine(OMe)-N-pyrazole(CH$_3$)-COOH |
| 105 | Br-pyridine(CH$_3$)-cyclohexenyl-1,3-dioxolane |

| Reference Example No | Structure |
|---|---|
| 106 | 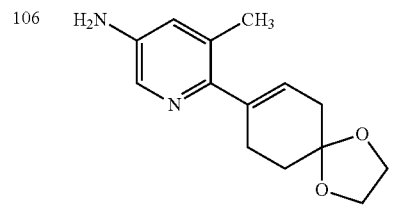 |
| 107 | 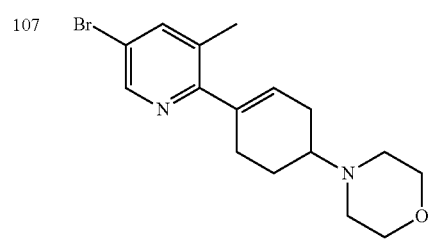 |
| 108 | 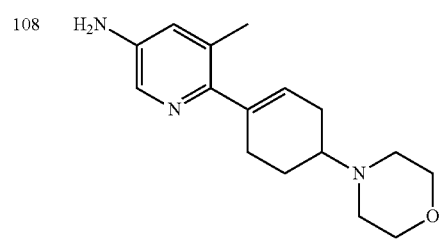 |
| 109 | 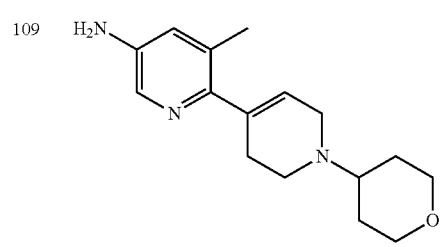 |
| 110 | 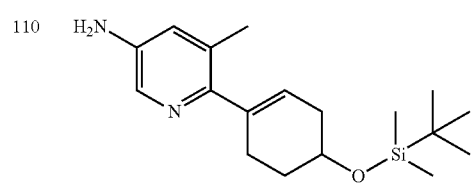 |
| 111 | 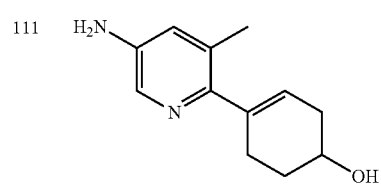 |
| 112 | 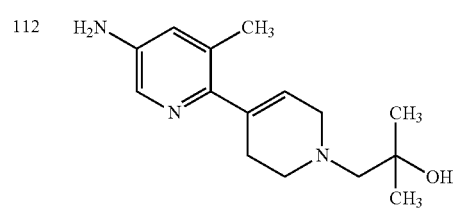 |
| 113 | 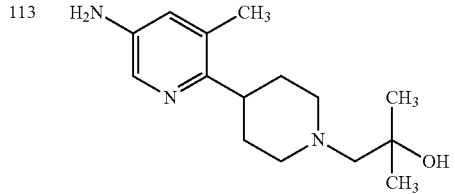 |
| 114 | 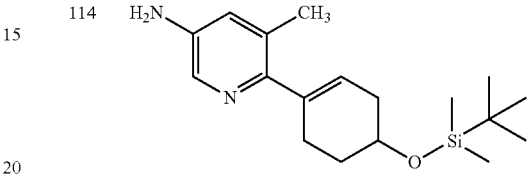 |
| 115A | 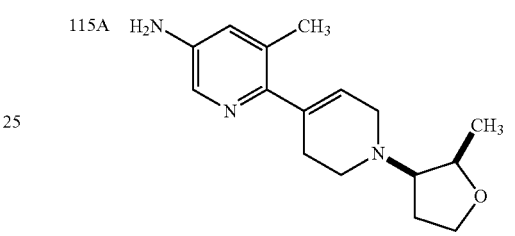 |
| 115B | 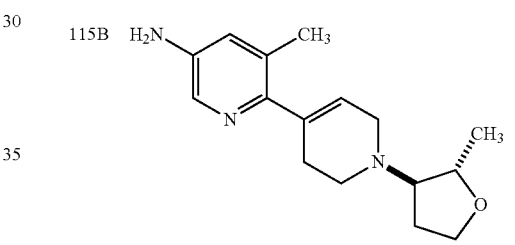 |
| 116 | 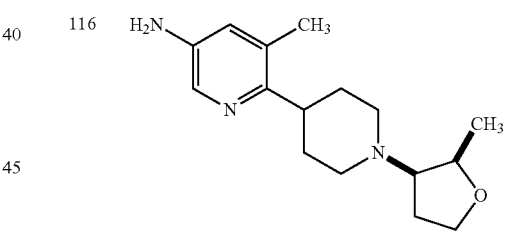 |
| 117 | 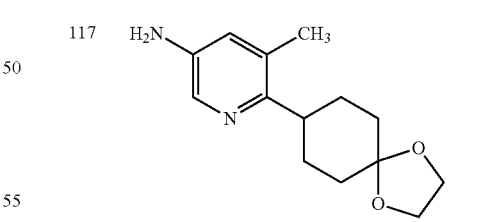 |
Reference Example 118
1-(5-Cyclopropylpyridin-2-yl)-5-methyl-1H-pyrazole-4-carboxylic acid
(1) A suspension of 1-(5-bromopyridin-2-yl)-5-methyl-1H-pyrazole-4-carboxylic acid ethyl ester (18 g) described in Reference Example 24 (2), cyclopropylboronic acid (9.96 g), dichlorobis(tricyclohexylphosphine)palladium (II) (2.14 g)

and tripotassium phosphate (49.2 g) in 1,4-dioxane (120 ml) was stirred at 110° C. for 3 hours. After completion of the reaction, the mixture was allowed to cool, chloroform was added thereto, filtered through Celite, then, to the filtrate was added a saturated aqueous solution of ammonium chloride, and the mixture was extracted with chloroform. The organic layer was dried over anhydrous sodium sulfate, and the solvent was evaporated in vacuo. The obtained residue was purified with silica gel chromatography (n-hexane/ethyl acetate) to give 1-(5-cyclopropylpyridin-2-yl)-5-methyl-1H-pyrazole-4-carboxylic acid ethyl ester (14 g) as a yellow solid. MS (ESI) m/z: 272 (M+H)+.

(2) To a solution of 1-(5-cyclopropylpyridin-2-yl)-5-methyl-1H-pyrazole-4-carboxylic acid ethyl ester (14 g) in methanol (70 ml) and tetrahydrofuran (70 ml) were added 4 N aqueous solution of sodium hydroxide (70 ml) and water (50 ml), and stirred at room temperature overnight. After completion of the reaction, the organic solvent was evaporated in vacuo, then water and diethyl ether were added thereto, and the aqueous layer was separated. To the aqueous layer was added concentrated hydrochloric acid under ice-cooling to adjust the layer to pH 5, the precipitated solid was collected by filtration, and dried at 60° C. under air blow to give the titled compound (12.4 g) as a white solid. MS (ESI) m/z: 244 (M+H)+.

Reference Example 119

5-Methyl-1-(5-methylpyridin-2-yl)-1H-pyrazole-4-carboxylic acid (1) A suspension of 1-(5-bromopyridin-2-yl)-5-methyl-1H-pyrazole-4-carboxylic acid ethyl ester (4 g) in Reference Example 24 (2), methylboronic acid (1.54 g), 1,1'-bis(di-tert-butylphosphino)ferrocene (306 mg), palladium acetate (145 mg) and tripotassium phosphate (11 g) in 1,4-dioxane (30 ml) was stirred under reflux. After completion of the reaction, the mixture was allowed to cool, ice water and a saturated aqueous solution of ammonium chloride were added thereto, and extracted with ethyl acetate. The organic layer was dried over anhydrous sodium sulfate, and the solvent was evaporated in vacuo. The obtained residue was purified with silica gel chromatography (n-hexane/ethyl acetate) to give 5-methyl-1-(5-methylpyridin-2-yl)-1H-pyrazole-4-carboxylic acid ethyl ester (2.81 g) as a white solid. MS (ESI) m/z: 246 (M+H)+.

(2) 5-Methyl-1-(5-methylpyridin-2-yl)-1H-pyrazole-4-carboxylic acid ethyl ester (2.81 g) was used in place of 1-(5-cyclopropylpyridin-2-yl)-5-methyl-1H-pyrazole-4-carboxylic acid ethyl ester in Reference Example 118 (2), and reacted and treated in a similar manner to give the titled compound (2.19 g) as a white solid. MS (ESI) m/z: 218 (M+H)+.

Reference Example 120

5-Methyl-1-[5-(trifluoromethyl)pyridin-2-yl]-1H-pyrazole-4-carboxamide

To a solution of 5-methyl-1-[5-(trifluoromethyl)pyridin-2-yl]-1H-pyrazole-4-carboxylic acid (2.07 g) described in Reference Example 8 in dichloromethane (50 ml) were added oxalyl chloride (2.62 ml) and N,N-dimethylformamide (catalytic amount) at room temperature, stirred at room temperature for 2 hours, and then the solvent and an excess amount of oxalyl chloride were evaporated. To the obtained reaction mixture was added tetrahydrofuran (50 ml), then 28% ammonia aqueous solution (30 ml) was added thereto under ice-cooling, and stirred at room temperature overnight. After completion of the reaction, the organic solvent was evaporated in vacuo, then 1 N aqueous solution of sodium hydroxide was added thereto, the precipitated solid was collected by filtration, and dried at 60° C. under air blow to give the titled compound (1.8 g) as a pale yellow solid. MS (ESI) m/z: 271 (M+H)+.

Reference Example 121

1-(2-Chloro-5-cyclopropylpyridin-3-yl)-5-methyl-1H-pyrazole-4-carboxylic acid (1) To 1-(5-bromo-2-chloropyridin-3-yl)-5-methyl-1H-pyrazole-4-carboxylic acid ethyl ester (2 g) in Reference Example 29 (1), cyclopropylboronic acid (724 mg), tetrakis(triphenylphosphine)palladium (0) (670 mg) and 2 M sodium carbonate aqueous solution (8.7 ml) was added tetrahydrofuran (12 ml), and stirred under reflux. After completion of the reaction, a saturated aqueous solution of ammonium chloride was added to the reaction solution under ice-cooling, and extracted with chloroform. The organic layer was dried over anhydrous sodium sulfate, and the solvent was evaporated in vacuo. The obtained residue was purified with silica gel chromatography (n-hexane/ethyl acetate) to give 1-(2-chloro-5-cyclopropylpyridin-3-yl)-5-methyl-1H-pyrazole-4-carboxylic acid ethyl ester (1.13 g) as a white solid. MS (ESI) m/z: 306 (M+H)+.

(2) To a solution of 1-(2-chloro-5-cyclopropylpyridin-3-yl)-5-methyl-1H-pyrazole-4-carboxylic acid ethyl ester (1.13 g) in tetrahydrofuran (30 ml) were added 4 N aqueous solution of sodium hydroxide (30 ml) and water (20 ml), and stirred at room temperature overnight. After completion of the reaction, the organic solvent was evaporated in vacuo, then water and diethyl ether were added thereto, and the aqueous layer was separated. To the aqueous layer was added concentrated hydrochloric acid under ice-cooling to adjust the layer to pH 5, the precipitated solid was collected by filtration, washed, and then dried at 60° C. under air blow to give the titled compound (922 mg) as a white solid. MS (ESI) m/z: 278 (M+H)+.

Reference Example 122

1-(5-Cyclopropylpyridin-3-yl)-5-methyl-1H-pyrazole-4-carboxylic acid

Under hydrogen atmosphere, a mixed solution of 1-(5-cyclopropyl-2-chloropyridin-3-yl)-5-methyl-1H-pyrazole-4-carboxylic acid (400 mg) in Reference Example 121 and palladium-activated carbon ethylenediamine complex (100 mg) in ethanol (50 ml) was stirred at room temperature. After completion of the reaction, the solution was filtered through Celite, and the solvent was evaporated in vacuo. The obtained residue was purified with silica gel chromatography (chloroform/methanol) to give the titled compound (184 mg) as a white solid.
MS (ESI) m/z: 244 (M+H)+.

Reference Example 123

1-[3-Chloro-5-(trifluoromethyl)pyridin-2-yl]-5-methyl-1H-pyrazole-4-carboxylic acid (1) To a solution of 2,3-dichloro-5-(trifluoromethyl)pyridine (25 g) in ethanol (75 ml) was added hydrazine hydrate (100%) (16.9 ml) at room temperature, and stirred. After completion of the reaction, water was added thereto, the organic solvent was evaporated in vacuo, the precipitated solid was collected by filtration, and washed with water to give 3-chloro-5-(trifluoromethyl)pyridin-2-ylhydrazine (24 g) as a white solid.

(2) Then, [3-chloro-5-(trifluoromethyl)pyridin-2-yl]hydrazine (10 g) and ethyl (2-ethoxymethylene)acetoacetate (8.8 g) synthesized according to the method described in J. Chem. Soc. Perkin trans. I, p. 1875 (1988) were added to a mixed solvent of 1 N hydrochloric acid aqueous solution (150 ml) and ethanol (150 ml), and stirred under reflux. After completion of the reaction, the mixture was allowed to cool, and the organic solvent was evaporated in vacuo. Then, the mixture was extracted with ethyl acetate, the organic layer was dried over anhydrous sodium sulfate, and then the solvent was evaporated in vacuo. The obtained residue was purified with silica gel column chromatography (n-hexane/ethyl acetate) to give 1-[3-chloro-5-(trifluoromethyl)pyridin-2-yl]-5-methyl-1H-pyrazole-4-carboxylic acid ethyl ester (13.6 g) as a light brown oil. MS (ESI) m/z: 334 (M+H)+.

(3) 1-[3-Chloro-5-(trifluoromethyl)pyridin-2-yl]-5-methyl-1H-pyrazole-4-carboxylic acid ethyl ester (7.6 g) was used in place of 1-(2-chloro-5-cyclopropylpyridin-3-yl)-5-methyl-1H-pyrazole-4-carboxylic acid ethyl ester in Reference Example 121 (2), and reacted and treated in a similar manner to give the titled compound (6.11 g) as a white solid. MS (ESI) m/z: 306 (M+H)+.

Reference Example 124

1-(5-Chloro-3-fluoropyridin-2-yl)-5-methyl-1H-pyrazole-4-carboxylic acid (1) 5-Chloro-3-fluoro-2-hydrazinylpyridine (5 g) and ethyl (2-ethoxymethylene)-acetoacetate (5.76 g) synthesized according to the method described in J. Chem. Soc. Perkin trans. I, p. 1875 (1988) were added to a mixed solvent of 1 N hydrochloric acid aqueous solution (150 ml) and ethanol (100 ml), and stirred under reflux. After completion of the reaction, the mixture was allowed to cool, and the organic solvent was evaporated in vacuo. Then, the mixture was extracted with ethyl acetate, the organic layer was dried over anhydrous sodium sulfate, and then the solvent was evaporated in vacuo. The obtained residue was purified with silica gel column chromatography (n-hexane/ethyl acetate) to give 1-(5-chloro-3-fluoropyridin-2-yl)-5-methyl-1H-pyrazole-4-carboxylic acid ethyl ester (6.95 g) as a pale yellow solid. MS (ESI) m/z: 284 (M+H)+.

(2) To a solution of 1-(5-chloro-3-fluoropyridin-2-yl)-5-methyl-1H-pyrazole-4-carboxylic acid ethyl ester (1 g) in tetrahydrofuran (5 ml) were added 4 N aqueous solution of sodium hydroxide (5 ml) and water (5 ml), and stirred at room temperature overnight. After completion of the reaction, the organic solvent was evaporated in vacuo, then water and diethyl ether were added thereto, and the aqueous layer was separated. To the aqueous layer was added concentrated hydrochloric acid under ice-cooling to adjust the layer to pH 5, the precipitated solid was collected by filtration, and dried at 60° C. under air blow to give the titled compound (710 mg) as a white solid. MS (ESI) m/z: 256 (M+H)+.

Reference Example 125

1-(5-Cyclopropyl-3-fluoropyridin-2-yl)-5-methyl-1H-pyrazole-4-carboxylic acid (1) A suspension of 1-(5-chloro-3-fluoropyridin-2-yl)-5-methyl-1H-pyrazole-4-carboxylic acid ethyl ester (2 g) in Reference Example 124 (1), cyclopropylboronic acid (911 mg), 1,1'-bis(di-tert-butylphosphino)ferrocene (167 mg), palladium acetate (79 mg) and tripotassium phosphate (4.49 g) in 1,4-dioxane (16 ml) was stirred under reflux. After completion of the reaction, the mixture was allowed to cool, ice water and a saturated aqueous solution of ammonium chloride were added thereto, and the mixture was extracted with ethyl acetate. The organic layer was dried over anhydrous sodium sulfate, and the solvent was evaporated in vacuo. The obtained residue was purified with silica gel chromatography (n-hexane/ethyl acetate) to give 1-(5-cyclopropyl-3-fluoropyridin-2-yl)-5-methyl-1H-pyrazole-4-carboxylic acid ethyl ester (1.88 g) as a light brown oil. MS (ESI) m/z: 290 (M+H)+.

(2) 1-(5-Cyclopropyl-3-fluoropyridin-2-yl)-5-methyl-1H-pyrazole-4-carboxylic acid ethyl ester (1.87 g) was used in place of 1-(5-cyclopropyl-2-chloropyridin-3-yl)-5-methyl-1H-pyrazole-4-carboxylic acid ethyl ester in Reference Example 121 (2), and reacted and treated in a similar manner to give the titled compound (1.33 g) as a white solid. MS (ESI) m/z: 262 (M+H)+.

Reference Example 126

5-Methyl-1-[3-methyl-5-(trifluoromethyl)pyridin-2-yl]-1H-pyrazole-4-carboxylic acid (1) A suspension of 1-[3-chloro-5-(trifluoromethyl)pyridin-2-yl-5-methyl-1H-pyrazole-4-carboxylic acid ethyl ester (3 g) in Reference Example 123 (2), methylboronic acid (807 mg), 2-dicyclohexylphosphino-2',6'-dimethoxybiphenyl (185 mg), palladium acetate (101 mg) and tripotassium phosphate (5.72 g) in 1,4-dioxane (20 ml) was stirred at 120° C. After completion of the reaction, the mixture was allowed to cool to room temperature, 4 N aqueous solution of sodium hydroxide (30 ml), water (30 ml), tetrahydrofuran (10 ml) and methanol (20 ml) were added thereto, and stirred at room temperature overnight. The organic solvent was evaporated in vacuo, then water and diethyl ether were added thereto, and the aqueous layer was separated. To the aqueous layer was added concentrated hydrochloric acid under ice-cooling to adjust the layer to pH 5, and extracted with chloroform. The organic layer was dried over anhydrous sodium sulfate, and the solvent was evaporated in vacuo. The obtained residue was purified with silica gel chromatography (chloroform/methanol) to give the titled compound (697 mg) as a brown solid. MS (ESI) m/z: 286 (M+H)+.

Reference Example 127

1-(6-Cyclopropylpyridin-3-yl)-5-methyl-1H-pyrazole-4-carboxylic acid (1) To hydrazine monohydrate (400 ml) heated at 100° C. with stirring was added dropwise a solution of 2-chloro-5-fluoropyridine (25.0 g) in ethanol (100 ml) over 2 hours, and then stirred at the same temperature. After completion of the reaction, the mixture was cooled to room temperature, 1 N aqueous solution of sodium hydroxide was added thereto, and extracted with chloroform. The organic layer was dried over anhydrous sodium sulfate, and then the solvent was evaporated. To the obtained residue were added water (100 ml) and concentrated hydrochloric acid (30 ml), a solution of ethyl (2-ethoxymethylene)acetoacetate (34.7 g) synthesized according to the method described in J. Chem. Soc. Perkin trans. I, p. 1875 (1988) in ethanol (100 ml) was added thereto with stirring, and stirred at 100° C. for 1.5 hours. The reaction solution was cooled to room temperature, then diluted with water (100 ml), and extracted with ethyl acetate three times. The organic layer was dried over anhydrous sodium sulfate, and then the solvent was evaporated. The obtained residue was purified with silica gel column chromatography (chloroform/methanol) to give 1-(6-chloropyridin-3-yl)-5-methyl-1H-pyrazole-4-carboxylic acid ethyl ester (2.81 g) as a white solid.

(2) A suspension of 1-(6-chloropyridin-3-yl)-5-methyl-1H-pyrazole-4-carboxylic acid ethyl ester (1.6 g), cyclopropylboronic acid (776 mg), 2-dicyclohexylphosphino-2',6'-dimethoxybiphenyl (124 mg), palladium acetate (67.6 mg) and tripotassium phosphate (3.83 g) in 1,4-dioxane (13 ml) was stirred under reflux. After completion of the reaction, the mixture was allowed to cool, ice water and a saturated aqueous solution of ammonium chloride were added thereto, and extracted with chloroform. The organic layer was dried over anhydrous sodium sulfate, and the solvent was evaporated in vacuo. The obtained residue was purified with silica gel chromatography (n-hexane/ethyl acetate) to give 1-(6-cyclopropylpyridin-3-yl)-5-methyl-1H-pyrazole-4-carboxylic acid ethyl ester (911 mg) as a brown oil. MS (ESI) m/z: 272 (M+H)$^+$.

(3) To a solution of 1-(6-cyclopropylpyridin-3-yl)-5-methyl-1H-pyrazole-4-carboxylic acid ethyl ester (910 mg) in methanol (3 ml) and tetrahydrofuran (5 ml) were added 4 N aqueous solution of sodium hydroxide (7 ml) and water (3 ml), and stirred at room temperature overnight. After completion of the reaction, the organic solvent was evaporated in vacuo, then water and diethyl ether were added thereto, and the aqueous layer was separated. To the aqueous layer was added concentrated hydrochloric acid under ice-cooling to adjust the layer to pH 5, and extracted with chloroform. The organic layer was dried over anhydrous sodium sulfate, and the solvent was evaporated in vacuo. To the obtained residue were added ethyl acetate and n-hexane, the precipitated solid was collected by filtration, washed with ethyl acetate/n-hexane solution, and heat-dried in vacuo at 60° C. to give the titled compound (321 mg) as a pale yellow solid. MS (ESI) m/z: 244 (M+H)$^+$.

Reference Example 128

1-(3,5-Dimethylpyridin-2-yl)-5-methyl-1H-pyrazole-4-carboxylic acid (1) A suspension of 1-(3,5-dichloropyridin-2-yl)-5-methyl-1H-pyrazole-4-carboxylic acid ethyl ester (4 g) in Reference Example 22 (2), methylboronic acid (3.19 g), 1,1'-bis(di-tert-butylphosphino)ferrocene (315 mg), palladium acetate (149 mg) and tripotassium phosphate (22.6 g) in 1,4-dioxane (30 ml) was stirred with reflux. After completion of the reaction, the mixture was allowed to cool, and ice water and a saturated aqueous solution of ammonium chloride were added thereto, and extracted with ethyl acetate. The organic layer was dried over anhydrous sodium sulfate, and the solvent was evaporated in vacuo. The obtained residue was purified with silica gel chromatography (n-hexane/ethyl acetate) to give 1-(3,5-dimethylpyridin-2-yl)-5-methyl-1H-pyrazole-4-carboxylic acid ethyl ester (2.45 g) as a yellow oil. MS (ESI) m/z: 260 (M+H)$^+$.

(2) 1-(3,5-Dimethylpyridin-2-yl)-5-methyl-1H-pyrazole-4-carboxylic acid ethyl ester (2.45 g) was used in place of 1-(5-cyclopropylpyridin-2-yl)-5-methyl-1H-pyrazole-4-carboxylic acid ethyl ester in Reference Example 118 (2), and reacted and treated in a similar manner to give the titled compound (862 mg) as a white solid. MS (ESI) m/z: 232 (M+H)$^+$.

Reference Example 129

1-(5-Cyclopropyl-3-methylpyridin-2-yl)-5-methyl-1H-pyrazole-4-carboxylic acid (1) A suspension of 1-(3,5-dichloropyridin-2-yl)-5-methyl-1H-pyrazole-4-carboxylic acid ethyl ester (2.0 g) in Reference Example 22 (2), methylboronic acid (419 mg), 1,1'-bis(di-tert-butylphosphino)ferrocene (631 mg), palladium acetate (299 mg) and tripotassium phosphate (2.97 g) in 1,4-dioxane (35 ml) was stirred with reflux for 8 hours. After completion of the reaction, the mixture was allowed to cool, and ice water and a saturated aqueous solution of ammonium chloride were added thereto, and extracted with chloroform. The organic layer was dried over anhydrous sodium sulfate, and the solvent was evaporated in vacuo. The obtained residue was purified with silica gel chromatography (n-hexane/ethyl acetate) to give 1-(5-chloro-3-methylpyridin-2-yl)-5-methyl-1H-pyrazole-4-carboxylic acid ethyl ester (1.07 g) as a yellow solid. MS (ESI) m/z: 230 (M+H)$^+$.

(2) A suspension of 1-(5-chloro-3-methylpyridin-2-yl)-5-methyl-1H-pyrazole-4-carboxylic acid ethyl ester (600 mg), cyclopropylboronic acid (369 mg), 1,1'-bis(di-tert-butylphosphino)ferrocene (51 mg), palladium acetate (24 mg) and tripotassium phosphate (1.83 g) in 1,4-dioxane (5 ml) was stirred under reflux for 6 hours. After completion of the reaction, the mixture was allowed to cool, and chloroform was added, filtered through Celite, and then the filtrate was evaporated in vacuo. The obtained residue was purified with silica gel chromatography (n-hexane/ethyl acetate) to give 1-(5-cyclopropyl-3-methylpyridin-2-yl)-5-methyl-1H-pyrazole-4-carboxylic acid ethyl ester (462 mg) as a yellow solid. MS (ESI) m/z: 286 (M+H)$^+$.

(3) 1-(5-Cyclopropyl-3-methylpyridin-2-yl)-5-methyl-1H-pyrazole-4-carboxylic acid ethyl ester (460 mg) was used in place of 1-(5-cyclopropylpyridin-2-yl)-5-methyl-1H-pyrazole-4-carboxylic acid ethyl ester in Reference Example 118 (2), and reacted and treated in a similar manner to give the titled compound as a white solid (278 mg). MS (ESI) m/z: 258 (M+H)$^+$.

Reference Example 130

1-[3-Fluoro-5-(trifluoromethyl)pyridin-2-yl]-5-methyl-1H-pyrazole-4-carboxylic acid (1) To a solution of hydrazine hydrate (100%) (3.45 ml) in ethanol (150 ml) was added dropwise a solution of 2,3-difluoro-5-(trifluoromethyl)pyridine (4.45 g) in ethanol (50 ml) at room temperature, stirred at the same temperature for 2 hours, and then additionally stirred at 80° C. for 2 hours. Then, the mixture was allowed to cool, water was added thereto, and the organic solvent was evaporated in vacuo. The precipitated solid was collected by filtration, and washed with water to give 3-fluoro-5-(trifluoromethyl)pyridin-2-ylhydrazine as a white solid.

(2) To a solution of 3-fluoro-5-(trifluoromethyl)pyridin-2-ylhydrazine in ethanol (166 ml) were added ethyl (2-ethoxymethylene)acetoacetate (4.52 g) synthesized according to the method described in J. Chem. Soc. Perkin trans. I, p. 1875 (1988) and 1 N hydrochloric acid aqueous solution (110 ml), and stirred under reflux for 3 hours. After the mixture was allowed to cool, to the reaction solution was added water, the precipitated solid was collected by filtration, washed with water, and then dried at 60° C. under air blow to give 1-[3-fluoro-5-(trifluoromethyl)pyridin-2-yl]-5-methyl-1H-pyrazole-4-carboxylic acid ethyl ester (5.16 g) as a white solid. MS (ESI) m/z: 318 (M+H)$^+$.

(3) To a solution of 1-[3-fluoro-5-(trifluoromethyl)pyridin-2-yl]-5-methyl-1H-pyrazole-4-carboxylic acid ethyl ester (2.17 g) in tetrahydrofuran (10 ml) was added 1 N aqueous solution of sodium hydroxide (10 ml), and stirred at room temperature overnight. After completion of the reaction, the organic solvent was evaporated in vacuo, then water and diethyl ether were added thereto, and the aqueous layer was separated. To the aqueous layer was added 1 N hydrochloric acid aqueous solution under ice-cooling to adjust the layer to pH 5, the precipitated solid was collected by filtration, and dried at 60° C. under air blow to give the titled compound (1.7 g) as a white solid. MS (ESI) m/z: 290 (M+H)$^+$.

Reference Example 131

1-(5-Aminopyridin-2-yl)-c-4-(methoxymethoxy)-r-1-cyclohexanecarboxylic acid ethyl ester (1) To 8-(5-bromopyridin-2-yl)-1,4-dioxaspiro[4.5]decane-8-carboxylic acid ethyl ester (1.0 g) described in Reference Example 81 (2) was added trifluoroacetic acid (1.1 ml) at room temperature, and stirred at the same temperature for 2 hours. After completion of the reaction, the solvent and trifluoroacetic acid were evaporated. The obtained residue was purified with silica gel column chromatography (n-hexane/ethyl acetate) to give 1-(5-bromopyridin-2-yl)-4-oxocyclohexanecarboxylic acid ethyl ester (803 mg) as a colorless oil.

(2) To a solution of 1-(5-bromopyridin-2-yl)-4-oxocyclohexanecarboxylic acid ethyl ester (789 mg) in methanol (16 ml) and chloroform (8.0 ml) was added sodium borohydride (366 mg) at −78° C., and stirred at the same temperature for 3 hours. After completion of the reaction, a saturated aqueous solution of ammonium chloride was added thereto, the solvent was evaporated, and then extracted with ethyl acetate twice. The organic layer was dried over anhydrous sodium sulfate, and then the solvent was evaporated. The obtained residue was purified with silica gel column chromatography (n-hexane/ethyl acetate) to give 1-(5-bromopyridin-2-yl)-c-4-hydroxy-r-1-cyclohexanecarboxylic acid ethyl ester (614 mg) as a colorless oil.

(3) To a solution of 1-(5-bromopyridin-2-yl)-c-4-hydroxy-r-1-cyclohexanecarboxylic acid ethyl ester (590 mg) in dichloromethane (9.0 ml) were added diisopropylethylamine (0.9 ml) and chloromethyl methyl ether (0.3 ml) at room temperature, and stirred at the same temperature for 3 hours. After completion of the reaction, a saturated aqueous solution of ammonium chloride was added thereto, and extracted with dichloromethane twice. The organic layer was dried over anhydrous sodium sulfate, and then the solvent was evaporated.

(4) Under nitrogen gas flow, to bis(dibenzylideneacetone)palladium (0) (46 mg) and tri-tert-butylphosphine tetrafluoroborate (24 mg) was added a 1.0 M solution of lithium bis(trimethylsilyl)amide in toluene (2.3 ml) at 70° C., and then a solution of 1-(5-bromopyridin-2-yl)-c-4-(methoxymethoxy)-r-1-cyclohexanecarboxylic acid ethyl ester (595 mg) in toluene (1.6 ml) was added dropwise, and stirred at the same temperature for 0.5 hours. Then, the mixture was cooled to room temperature, a 1.0 M solution of tetrabutylammonium fluoride in tetrahydrofuran (4.8 ml) was added thereto, and stirred at the same temperature for 1 hour. After completion of the reaction, a saturated aqueous solution of sodium hydrogen carbonate was added thereto, and extracted with ethyl acetate twice. The organic layer was dried over anhydrous sodium sulfate, and then the solvent was evaporated. The obtained residue was purified with silica gel column chromatography (n-hexane/ethyl acetate) to give the titled compound (466 mg) as a yellow oil. MS (ESI) m/z: 309 (M+H)$^+$.

Reference Example 132 A 1-(5-Aminopyridin-2-yl)-t-4-(3-hydroxylpyrrolidin-1-yl)-r-1-cyclohexanecarbonitrile Reference Example 132 B 1-(5-Aminopyridin-2-yl)-c-4-(3-hydroxylpyrrolidin-1-yl)-r-1-cyclohexanecarbonitrile (1) To 1,4-dioxaspiro[4.5]decane-8-carbonitrile (13.4 g) described in Reference Example 82 (1) was added a 1 M solution of sodium bis(trimethylsilyl)amide in tetrahydrofuran (100 ml), stirred at 0° C., then a solution of 5-bromo-2-fluoropyridine (12.8 g) in tetrahydrofuran (20 ml) was added thereto, and stirred at room temperature for 1 hour. Tetrahydrofuran (20 ml) was added thereto, additionally stirred for 1 hour, then to the reaction solution was added an aqueous solution of potassium carbonate, extracted with ethyl acetate, washed with saturated brine, dried over anhydrous sodium sulfate, and then the solvent was evaporated in vacuo. To the residue were added water (10 ml) and trifluoroacetic acid (50 ml), and stirred at room temperature for 6 hours. The reaction solution was added to an aqueous solution of potassium carbonate, the mixture was extracted with ethyl acetate, the organic layer was washed with saturated brine, dried over anhydrous magnesium sulfate, and then the solvent was evaporated in vacuo. The residue was purified with silica gel column chromatography (n-hexane/ethyl acetate) to give 1-(5-bromopyridin-2-yl)-4-oxocyclohexanecarbonitrile (13.08 g) as a pale yellow solid. MS (ESI) m/z: 279, 281 (M+H)$^+$.

(2) To a solution of 1-(5-bromopyridin-2-yl)-4-oxocyclohexanecarbonitrile (4.0 g) in dichloromethane (48 ml) was added 3-pyrrolidinol (1.3 g), then sodium triacetoxyborohydride (3.95 g) and acetic acid (820 µl) were added thereto at 0° C., and stirred at room temperature for 6.5 hours. To the reaction solution were added water and 1N aqueous solution of sodium hydroxide, extracted with dichloromethane, the organic layer was washed with saturated brine, dried over anhydrous sodium sulfate, and then the solvent was evaporated in vacuo. The residue was purified with basic silica gel chromatography (chloroform/methanol) to give 1-(5-bromopyridin-2-yl)-t-4-(3-hydroxylpyrrolidin-1-yl)-r-1-cyclohexanecarbonitrile (1.95 g, MS (ESI) m/z: 350, 352 (M+H)$^+$) and 1-(5-bromopyridin-2-yl)-c-4-(3-hydroxylpyrrolidin-1-yl)-r-1-cyclohexanecarbonitrile (2.50 g, MS (ESI) m/z: 350, 352 (M+H)$^+$ as white solids respectively.

(3) To a solution of 1-(5-bromopyridin-2-yl)-t-4-(3-hydroxylpyrrolidin-1-yl)-r-1-cyclohexanecarbonitrile (1.95 g) in dichloromethane (30 ml) were added imidazole (502 mg) and tert-butyldimethylsilyl chloride (1.0 g), stirred at room temperature for 2.5 hours, then additionally, tert-butyldimethylsilyl chloride (252 mg) was added thereto, and stirred for 5 hours. To the reaction solution was added water, extracted with dichloromethane, the organic layer was washed with saturated brine, dried over anhydrous sodium sulfate, and the solvent was evaporated in vacuo. The residue was purified with basic silica gel chromatography (n-hexane/ethyl acetate)

to give 1-(5-bromopyridin-2-yl)-t-4-(3-{[tert-butyl(dimethyl)silyl]oxy}pyrrolidin-1-yl)-r-1-cyclohexanecarbonitrile (1.77 g) as a white solid.

MS (ESI) m/z: 464, 466 (M+H)$^+$.

(4) To a suspension of 1-(5-bromopyridin-2-yl)-t-4-(3-{[tert-butyl(dimethyl)silyl]oxy}pyrrolidin-1-yl)-r-1-cyclohexanecarbonitrile (1.77 g), palladium (II) acetate (107 mg), 2-(di-tert-butylphosphino)-1,1'-binaphthyl (296 mg) and tert-butoxysodium (549 mg) in toluene (9.5 ml) was added benzophenone imine (725 mg), stirred at 120° C. for 4.5 hours, then a mixed solution of concentrated hydrochloric acid (2 ml) and water (5 ml) was added thereto at 60° C., and stirred for 1 hour. Then, to the reaction solution was added tetrabutylammonium fluoride (5 ml), and stirred for 3 hours. To the reaction solution was added saturated sodium bicarbonate water at 0° C., extracted with ethyl acetate, additionally, extracted with dichloromethane, then dried over anhydrous sodium sulfate, and the solvent was evaporated in vacuo. The residue was purified with basic silica gel chromatography (n-hexane/ethyl acetate) to give the titled compound; 1-(5-aminopyridin-2-yl)-t-4-(3-hydroxylpyrrolidin-1-yl)-r-1-cyclohexanecarbonitrile (520 mg) as a pale yellow solid.

MS (ESI) m/z: 287 (M+H)$^+$.

(5) 1-(5-Bromopyridin-2-yl)-c-4-(3-hydroxylpyrrolidin-1-yl)-r-1-cyclohexanecarbonitrile was used in place of 1-(5-bromopyridin-2-yl)-t-4-(3-hydroxylpyrrolidin-1-yl)-r-1-cyclohexanecarbonitrile in Reference Example 132 (3), and reacted and treated in a similar manner to give 1-(5-bromopyridin-2-yl)-c-4-(3-{[tert-butyl(dimethyl)silyl]oxy}pyrrolidin-1-yl)-r-1-cyclohexanecarbonitrile.

MS (ESI) m/z: 464, 466 (M+H)$^+$.

(6) 1-(5-Bromopyridin-2-yl)-c-4-(3-{[tert-butyl(dimethyl)silyl]oxy}pyrrolidin-1-yl)-r-1-cyclohexanecarbonitrile was used in place of 1-(5-bromopyridin-2-yl)-t-4-(3-{[tert-butyl(dimethyl)silyl]oxy}pyrrolidin-1-yl)-r-1-cyclohexanecarbonitrile in Reference Example 132 (4), and reacted and treated in a similar manner to give the titled compound; 1-(5-aminopyridin-2-yl)-c-4-(3-hydroxylpyrrolidin-1-yl)-r-1-cyclohexanecarbonitrile.

MS (ESI) m/z: 287 (M+H)$^+$.

Reference Example 133

1-(4-tert-Butoxyethoxyphenyl)-5-methyl-1H-pyrazole-4-carboxylic acid

To a solution of 1-(4-Hydroxyphenyl)-5-methyl-1H-pyrazole-4-carboxylic acid ethyl ester (500 mg) in Reference Example 39 (2), 2-tert-butoxyethanol (480 mg) and triphenylphosphine (1.06 g) in tetrahydrofuran (20 ml) was added dropwise a solution of 40% azodicarboxylic acid diisopropylester in toluene (2.14 ml) under ice-cooling, and then stirred at room temperature overnight. After completion of the reaction, water was added thereto, extracted with ethyl acetate, the organic layer was dried over anhydrous sodium sulfate, and the solvent was evaporated in vacuo. The obtained residue was purified with silica gel chromatography (n-hexane/ethyl acetate) to give 1-(4-tert-butoxyethoxyphenyl)-5-methyl-1H-pyrazole-4-carboxylic acid ethyl ester (870 mg) as a pale yellow oil.

MS (ESI) m/z: 347 (M+H)$^+$.

(2) To a solution of 1-(4-tert-butoxyethoxyphenyl)-5-methyl-1H-pyrazole-4-carboxylic acid ethyl ester (870 mg) in methanol (30 ml) was added 4 N aqueous solution of sodium hydroxide (10 ml), and stirred at room temperature overnight. After completion of the reaction, the organic solvent was evaporated in vacuo, then water and diethyl ether were added thereto, and the aqueous layer was separated. To the aqueous layer was added concentrated hydrochloric acid under ice-cooling to adjust the layer to pH 5, and extracted with chloroform. The organic layer was dried over anhydrous sodium sulfate, and the solvent was evaporated in vacuo. The obtained residue was purified with silica gel chromatography (chloroform/methanol), isopropylether was added thereto, the precipitated solid was collected by filtration, and heat-dried at 60° C. in vacuo to give the titled compound (363 mg) as a white solid.

$^1$H-NMR (DMSO-d$_6$) δ (ppm): 1.17 (9H, s), 2.45 (3H, s), 3.65-3.68 (2H, m), 4.09-4.12 (2H, m), 7.07-7.09 (2H, m), 7.40-7.44 (2H, m), 7.92 (1H, s), 12.4 (1H, brs).

Reference Example 134

4-(5-Bromopyridin-2-yl)tetrahydro-2H-pyran 4-(5-Bromopyridin-2-yl)tetrahydro-2H-pyran-4-carbonitrile (2 g) described in Reference Example 87 in concentrated hydrochloric acid (10 ml) was stirred at 100° C. for 3 days. After completion of the reaction, a saturated aqueous solution of potassium carbonate was added to alkalify the mixture, and extracted with ethyl acetate. The organic layer was dried over anhydrous magnesium sulfate, and then the solvent was evaporated to give the titled compound (1.05 g) as a white solid.

$^1$H-NMR (CDCl$_3$) δ (ppm): 1.85-1.95 (4H, m), 2.88-2.96 (1H, m), 3.51-3.59 (2H, m), 4.07-4.15 (2H, m), 7.08 (1H, d, J=8.4 Hz), 7.75 (1H, dd, J=8.4, 2.3 Hz), 8.66 (1H, d, J=2.3 Hz).

Reference Example 135

5-Bromo-2-(3,6-dihydro-2H-pyran-4-yl)-3-methylpyridine (1) Tetrahydro-4H-pyran-4-one (2.39 g) was used in place of 1-(tert-butoxycarbonyl)-4-piperidone in Reference Example 109 (1), and reacted and treated in a similar manner to give 4-(5-bromo-3-methylpyridin-2-yl)tetrahydro-2H-pyran-4-ol (2.95 g) as a white solid.

MS (ESI) m/z: 272, 274 (M+H)$^+$.

(2) 4-(5-Bromo-3-methylpyridin-2-yl)-tetrahydro-2H-pyran-4-ol (2.95 g), triethylamine (3 ml) and trimethylamine monohydrochloride (103 mg) were suspended in toluene (50 ml), mesyl chloride (1.26 ml) was added thereto under ice-cooling, then warmed to room temperature, and stirred for 72 hours. After completion of the reaction, water was added thereto, extracted with chloroform, the organic layer was dried over anhydrous sodium sulfate, and then the solvent was evaporated in vacuo. The obtained residue was purified with silica gel column chromatography (n-hexane/ethyl acetate) to give the titled compound (2.39 g) as a white solid. MS (ESI) m/z: 254, 256 (M+H)$^+$.

Reference Example 136

5-Bromo-3-methyl-2-(tetrahydro-2H-pyran-4-yl) pyridine (1) To a solution of tetrahydro-2H-pyran-4-carboxylic acid methyl ester (759 mg) in toluene (5 ml) was added dropwise a 1.0 M solution of sodium bis(trimethylsilyl)amide in tetrahydrofuran (5.26 ml) under ice-cooling, and stirred at the same temperature for 1 hour. Then, a solution of 5-bromo-2-fluoro-3-methylpyridine (1 g) in toluene (5 ml) was added dropwise thereto, and stirred at room temperature for 2 hours. After completion of the reaction, a saturated aqueous solution of ammonium chloride was added thereto, and extracted with ethyl acetate. The organic layer was dried over anhydrous sodium sulfate, and then the solvent was evaporated. The obtained residue was purified with silica gel column chromatography (n-hexane/ethyl acetate) to give 4-(5-bromo-3-methylpyridin-2-yl)tetrahydro-2H-pyran-4-carboxylic acid methyl ester (753 mg) as a pale yellow oil. MS (ESI) m/z: 314, 316 (M+H)$^+$.

(2) To a solution of 4-(5-bromo-3-methylpyridin-2-yl)tetrahydro-2H-pyran-4-carboxylic acid methyl ester (745 mg) in tetrahydrofuran (5 ml) and methanol (5 ml) was added 4 N aqueous solution of sodium hydroxide (5 ml) at room temperature, and stirred overnight. After completion of the reaction, the organic solvent was evaporated, diluted with 1 N aqueous solution of sodium hydroxide and water, diethyl ether was added thereto, and the aqueous layer was separated. The aqueous layer was ice-cooled, concentrated hydrochloric acid was added thereto to adjust the layer to pH 4, extracted with chloroform, the organic layer was dried over anhydrous sodium sulfate, and then the solvent was evaporated to give 4-(5-bromo-3-methylpyridin-2-yl)tetrahydro-2H-pyran-4-carboxylic acid (421 mg) as a white solid. MS (ESI) m/z: 300, 302 (M+H)$^+$.

(3) A solution of 4-(5-bromo-3-methylpyridin-2-yl)tetrahydro-2H-pyran-4-carboxylic acid (420 mg) in dimethylsulfoxide (1 ml) was stirred at 150° C. for 1.5 hours. After completion of the reaction, the mixture was cooled to room temperature, water was added thereto, and extracted with chloroform. The organic layer was washed with water and saturated brine sequentially, then dried over anhydrous sodium sulfate, and the solvent was evaporated. The obtained residue was purified with silica gel column chromatography (n-hexane/ethyl acetate) to give the titled compound (316 mg) as a white solid. MS (ESI) m/z: 256, 258 (M+H)$^+$.

Reference Example 137

1-(5-Acetylpyridin-2-yl)pyrrole-3-carboxylic acid (1) A suspension of 1H-pyrrole-3-carboxylic acid tert-butyl ester (700 mg) described in Reference Example 50, 1,1'-bis(diphenylphosphino)ferrocene (35 mg), palladium acetate (9.4 mg), cesium carbonate (1.64 g) and 5-acetyl-2-bromopyridine (921 mg) in toluene (10 ml) was stirred at 100° C. for 8 hours. After completion of the reaction, the mixture was allowed to cool to room temperature, ice water was added thereto, and extracted with chloroform. The organic layer was dried over anhydrous sodium sulfate, and the solvent was evaporated in vacuo. The obtained residue was purified with silica gel column chromatography (n-hexane/ethyl acetate) to give 1-(5-acetylpyridin-2-yl)pyrrole-3-carboxylic acid tert-butyl ester (380 mg) as a white solid.

(2) To a solution of 1-(5-acetylpyridin-2-yl)pyrrole-3-carboxylic acid tert-butyl ester (380 mg) in dichloromethane (5 ml) were added trifluoroacetic acid (3 ml) and water (0.3 ml), and stirred at room temperature. After completion of the reaction, the solvent was evaporated in vacuo, to the residue was added water, 1 N aqueous solution of sodium hydroxide was added thereto under ice-cooling to adjust the mixture to pH 10, diethyl ether was added thereto, and the aqueous layer was separated. To the aqueous layer was added concentrated hydrochloric acid under ice-cooling, the precipitated solid was collected by filtration, and dried at 60° C. under air blow to give the titled compound (300 mg) as a white solid. MS (ESI) m/z: 231 (M+H)$^+$.

Reference Example 138 A cis-5-Methyl-6-[4-(morpholin-4-yl)cyclohexyl]pyridin-3-amine Reference Example 138 B trans-5-Methyl-6-[4-(morpholin-4-yl)cyclohexyl]pyridin-3-amine To a mixed solution of 5-methyl-6-[4-(morpholin-4-yl]cyclohex-1-en-1-yl)pyridin-3-amine (9.5 g) described in Reference Example 108, potassium fluoride (8.07 g), palladium(II) acetate (1.56 g), water (35 ml) and tetrahydrofuran (81 ml) was added poly(methylhydrosiloxane) (6.4 ml) at water temperature, and then stirred at room temperature for 2 hours. The solvent of the reaction solution was evaporated in vacuo, and the residue was purified with silica gel chromatography (n-hexane/ethyl acetate) to give the titled compounds cis-5-methyl-6-[4-(morpholin-4-yl)cyclohexyl]pyridin-3-amine (3.4 g, MS (ESI) m/z: 276 (M+H)$^+$) and trans-5-methyl-6-[4-(morpholin-4-yl)cyclohexyl]pyridin-3-amine (2.4 g, MS (ESI) m/z: 276 (M+H)$^+$) as white solids respectively.

The structural formulae of Reference Examples 118-138 are shown below.

| Reference Example No | Structure |
|---|---|
| 118 | 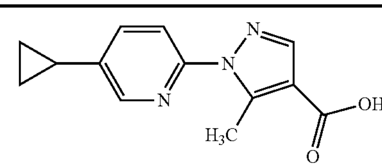 |
| 119 | 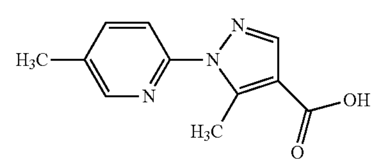 [SMILES: Cc1ccc(-n2ncc(C(=O)O)c2C)nc1] |
| 120 | 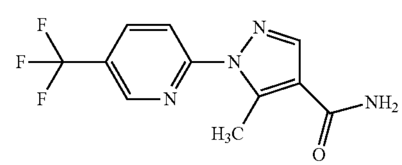 [SMILES: Cc1c(C(N)=O)cnn1-c1ccc(C(F)(F)F)cn1] |
| 121 | 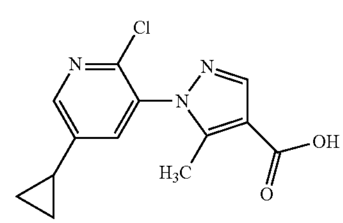 [SMILES: Cc1c(C(=O)O)cnn1-c1cc(C2CC2)cnc1Cl] |

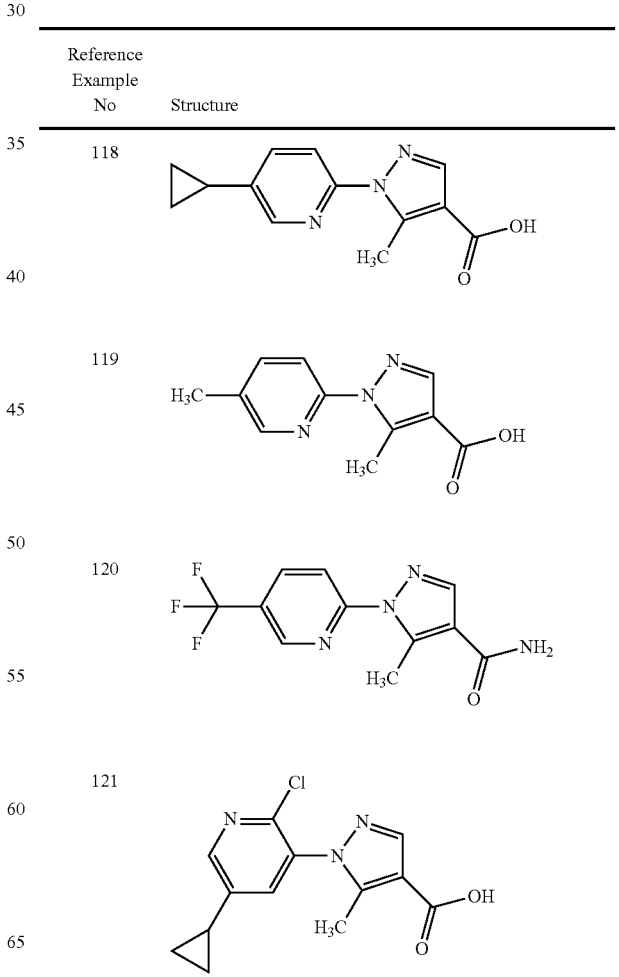

-continued
| Reference Example No | Structure |
|---|---|
| 122 | 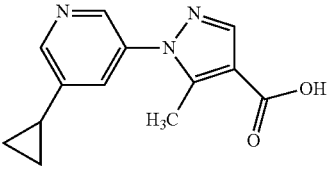 [SMILES: Cc1c(C(=O)O)cnn1-c1cncc(C2CC2)c1] |
| 123 | 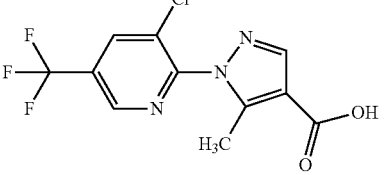 |
| 124 | 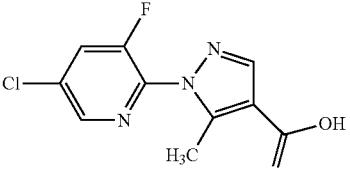 |
| 125 | 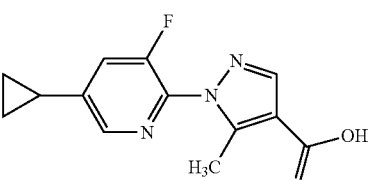 |
| 126 | 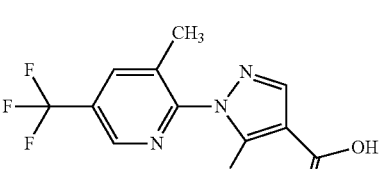 |
| 127 | 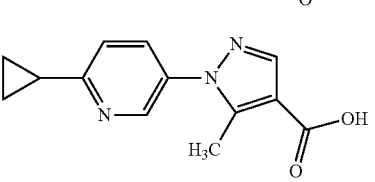 |
| 128 | 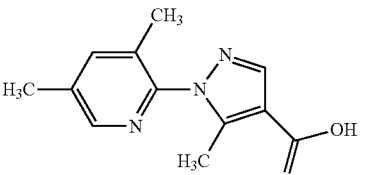 |
| 129 | 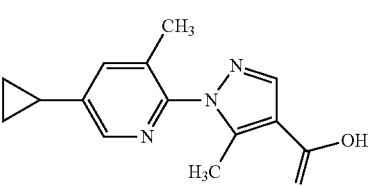 |
-continued
| Reference Example No | Structure |
|---|---|
| 130 | 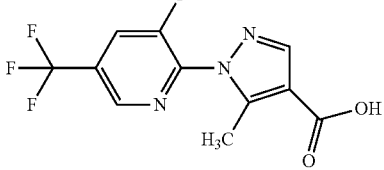 |
| 131 | 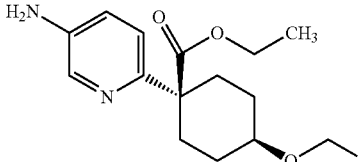 |
| 132A | 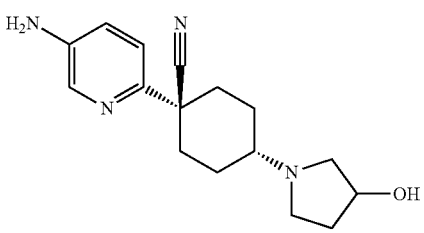 [SMILES: N#C[C@]1(c2ccc(N)cn2)CC[C@@H](N2CCC(O)C2)CC1] |
| 132B | 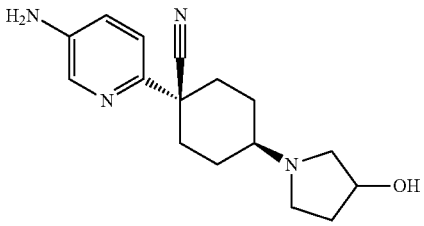 [SMILES: N#C[C@]1(c2ccc(N)cn2)CC[C@H](N2CCC(O)C2)CC1] |
| 133 | 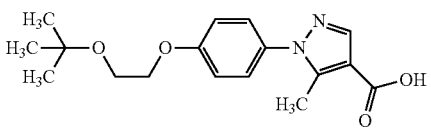 [SMILES: Cc1c(C(=O)O)cnn1-c1ccc(OCCOC(C)(C)C)cc1] |
| 134 | 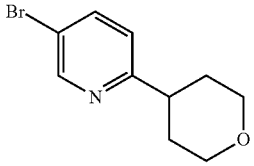 |
| 135 | 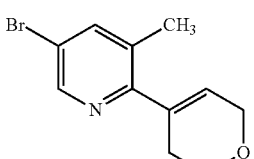 |
| 136 | 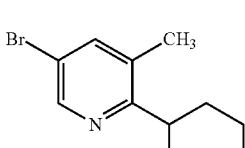 |

| Reference Example No | Structure |
|---|---|
| 137 | ![structure: acetyl-pyridine-pyrrole-carboxylic acid] |
| 138A | ![structure: H2N-aminopyridine-methyl-cyclohexyl-morpholine] |
| 138B | ![structure: H2N-aminopyridine-methyl-cyclohexyl-morpholine isomer] |

Reference Example 139 cis-6-[4-(2,6-Dimethylmorpholin-4-yl)cyclohex-1-en-1-yl]-5-methylpyridin-3-amine (1) cis-2,6-Dimethylmorpholine (1.46 g) was used in place of morpholine in Reference Example 107 (2) and (3), and reacted and treated in a similar manner to give cis-4-[4-(5-bromo-3-methylpyridin-2-yl)cyclohex-3-en-1-yl]-2,6-dimethylmorpholine (1.62 g). MS (ESI) m/z: 365, 367 (M+H)$^+$.

(2) cis-4-[4-(5-Bromo-3-methylpyridin-2-yl)cyclohex-3-en-1-yl]-2,6-dimethylmorpholine (1.6 g) was used in place of 4-[4-(5-bromopyridin-2-yl)cyclohex-3-en-1-yl]morpholine in Reference Example 78, and reacted and treated in a similar manner to give the titled compound (1.02 g) as a white solid. MS (ESI) m/z: 302 (M+H)$^+$.

Reference Example 140

5-Ethyl-1-methyl-1H-indole-3-carboxylic acid (1) To a solution of 5-bromo-1-methyl-1H-indole-3-carboxylic acid ethyl ester (1.2 g) described in Reference Example 52 (2) in tetrahydrofuran (14 ml) were added 4,4,5,5-tetramethyl-2-vinyl-1,3,2-dioxaborolane (983 mg), 2-dicyclohexylphosphino-2',6'-dimethoxybiphenyl (S-Phos) (349 mg), palladium acetate (96 mg) and tripotassium phosphate (2.26 g) at room temperature, and stirred at 75° C. for 4 hours. After completion of the reaction, the mixture was cooled to room temperature, water was added thereto, and extracted with ethyl acetate. The organic layer was dried over anhydrous sodium sulfate, and then the solvent was evaporated. The obtained residue was purified with silica gel column chromatography (n-hexane/ethyl acetate) to give 1-methyl-5-vinyl-1H-indole-3-carboxylic acid ethyl ester (934 mg) as a yellow solid.

(2) To a solution of 1-methyl-5-vinyl-1H-indole-3-carboxylic acid ethyl ester (934 mg) in ethanol (40 ml) was added 10% palladium carbon (containing about 50% water) (95 mg) at room temperature, and stirred at the same temperature for 4 hours under hydrogen gas flow. After completion of the reaction, the mixture was filtered through Celite, and then the filtrate was concentrated. The obtained residue was dissolved in ethanol (20 ml), 1N aqueous solution of sodium hydroxide (20 ml) was added thereto at room temperature, and stirred at 70° C. for 3 hours. After completion of the reaction, the mixture was cooled to room temperature, filtered through Celite, and then the solvent was evaporated. The obtained residue was extracted with ethyl acetate. To the aqueous layer was added 1 N hydrochloric acid aqueous solution, and the precipitated solid was collected by filtration to give the titled compound (797 mg) as a white solid. MS (ESI) m/z: 204 (M+H)$^+$.

Reference Example 141

6-Ethyl-1-methyl-1H-indole-3-carboxylic acid

6-Bromoindole was used in place of 5-bromoindole in Reference Example 52, and reacted and treated in a similar manner as Reference Example 52 and Reference Example 140 to give the titled compound as a white solid. MS (ESI) m/z: 204 (M+H)$^+$.

Reference Example 142

1-(5-Aminopyridin-2-yl)-c-4-(morpholin-4-yl)-r-1-cyclohexanecarboxylic acid ethyl ester (1) To a solution of 4-cyclohexanone carboxylic acid ethyl ester (5.0 g) in dichloromethane (58 ml) were added morpholine (2.56 g) and sodium triacetoxyborohydride (7.47 g) at room temperature, and stirred at the same temperature for 3.5 hours. After completion of the reaction, saturated sodium bicarbonate water was added thereto, and extracted with 10% methanol/chloroform solution. The organic layer was dried over anhydrous sodium sulfate, and then the solvent was evaporated.

(2) The obtained mixture (7.09 g) was used in place of 1,4-dioxaspiro[4.5]decane-8-carboxylic acid ethyl ester in Reference Example 81 (2), and reacted and treated in a similar manner to give a yellow oil.

(3) The obtained yellow oil (4.99 g) was used in place of 4-[4-(5-bromopyridin-2-yl)cyclohex-3-en-1-yl]morpholine in Reference Example 78, and reacted and treated in a similar manner to give the titled compound (2.15 g) as a white solid. MS (ESI) (m/z): 334 (M+H)$^+$.

Reference Example 143

N-[4-(5-Amino-3-methylpyridin-2-yl)cyclohex-3-en-1-yl]-N-methylcarbamic acid tert-butyl ester (1) To 8-(5-bromo-3-methylpyridin-2-yl)-1,4-dioxaspiro[4.5]decan-8-ol (23.2 g) described in Reference Example 105 (1) was added 3 N hydrochloric acid aqueous solution (140 ml), and stirred at room temperature for 16 hours. After completion of the reaction, a saturated aqueous solution of sodium hydrogen carbonate was added thereto, the precipitated solid was collected by filtration, and then washed with ethanol to give 4-(5-bromo-3-methylpyridin-2-yl)-4-hydroxycyclohexanone (18.3 g) as a pale yellow solid. MS (ESI) m/z: 284, 286 (M+H)$^+$.

(2) To a solution of 4-(5-bromo-3-methylpyridin-2-yl)-4-hydroxycyclohexanone (18.3 g) in methanol (213 ml) were added ammonium formate (40.6 g) and sodium triacetoxyborohydride (16.4 g) at room temperature, and stirred at the same temperature for 24 hours. After completion of the reaction, methanol was evaporated, and the obtained residue was purified with basic silica gel column chromatography (chloroform/methanol).

(3) To a solution of the obtained compound (18.4 g) in tetrahydrofuran (128 ml) were added triethylamine (9.9 ml) and di-tert-butyl dicarbonate (14.1 g) at room temperature, and stirred at the same temperature for 24 hours. After completion of the reaction, water was added thereto, and extracted with ethyl acetate. The organic layer was dried over anhydrous sodium sulfate, and then the solvent was evaporated. The obtained residue was purified with silica gel column chromatography (chloroform/methanol) to give a mixture (18.9 g) of N-[4-(5-bromo-3-methylpyridin-2-yl)-c-4-hydroxycyclohexan-1-yl]-r-carbamic acid-tert-butyl ester and N-[4-(5-bromo-3-methylpyridin-2-yl)-t-4-hydroxycyclohexan-1-yl]-r-carbamic acid-tert-butyl ester as a pale yellow solid.

MS (ESI) m/z: 385, 387 (M+H)$^+$.

(4) To a solution of the mixture (18.9 g) of N-[4-(5-bromo-3-methylpyridin-2-yl)-c-4-hydroxycyclohexan-1-yl]-r-carbamic acid-tert-butyl ester and N-[4-(5-bromo-3-methylpyridin-2-yl)-t-4-hydroxycyclohexan-1-yl]-r-carbamic acid-tert-butyl ester in pyridine (100 ml) was added thionyl chloride (14.6 g) under ice-cooling, and stirred at the same temperature for 10 minutes. After completion of the reaction, a saturated aqueous solution of sodium hydrogen carbonate was added thereto, the precipitated solid was collected by filtration, and then washed with ethyl acetate to give N-[4-(5-bromo-3-methylpyridin-2-yl)cyclohex-3-en-1-yl]carbamic acid-tert-butyl ester (11.2 g) as a white solid.

MS (ESI) m/z: 367, 369 (M+H)$^+$.

(5) To a solution of N-[4-(5-bromo-3-methylpyridin-2-yl)cyclohex-3-en-1-yl]carbamic acid-tert-butyl ester (11.2 g) in N,N-dimethylformamide (90 ml) was added sodium hydride (1.46 g) under ice-cooling, and stirred at the same temperature for 0.5 hours. Then methyl iodide (5.7 ml) was added thereto, and stirred at the same temperature for 2 hours. After completion of the reaction, water was added thereto, and the precipitated solid was collected by filtration to give N-[4-(5-bromo-3-methylpyridin-2-yl)cyclohex-3-en-1-yl]-N-methylcarbamic acid-tert-butyl ester.

(6) To a solution of N-[4-(5-bromo-3-methylpyridin-2-yl)cyclohex-3-en-1-yl]-N-methylcarbamic acid-tert-butyl ester (1.25 g) in toluene (17 ml) were added palladium acetate (18 mg), benzophenone imine (0.6 ml), (±)-2,2'-bis(diphenylphosphino)-1,1'-binaphthyl (51 mg) and sodium tert-butoxide (473 mg) at room temperature, and stirred at 120° C. for 0.5 hours. Then, after the mixture was cooled to room temperature, hydroxyamine monohydrochloride (683 mg) and sodium acetate (1.6 g) were added thereto, and stirred at the same temperature for 4 hours. After completion of the reaction, a saturated aqueous solution of sodium hydrogen carbonate was added thereto, and extracted with 10% methanol/chloroform solution. The organic layer was dried over anhydrous sodium sulfate, and then the solvent was evaporated. The obtained residue was purified with basic silica gel column chromatography (n-hexane/ethyl acetate) to give the titled compound (987 mg) as a pale yellow solid.

MS (ESI) m/z: 318 (M+H)$^+$.

Reference Example 144

1-(5-Aminopyridin-2-yl)-c-4-(tert-butyl dimethylsilanyloxy)-r-1-cyclohexanecarbonitrile (1) To a solution of 1-(5-bromopyridin-2-yl)-c-4-hydroxy-r-1-cyclohexanecarbonitrile (5.04 g) described in Reference Example 85 (2) in dichloromethane (60 ml) were added imidazole (1.34 g) and tert-butyldimethylchlorosilane (2.97 g) at room temperature, and stirred at the same temperature for 6 hours. After completion of the reaction, water was added thereto, and extracted with chloroform. The organic layer was dried over anhydrous sodium sulfate, and then the solvent was evaporated. The obtained residue was purified with basic silica gel column chromatography (n-hexane/ethyl acetate) to give 1-(5-bromopyridin-2-yl)-c-4-(tert-butyldimethylsilanyloxy)-r-1-cyclohexanecarbonitrile (6.33 g) as a white solid.

(2) To a solution of 1-(5-bromopyridin-2-yl)-c-4-(tert-butyldimethylsilanyloxy)-r-1-cyclohexanecarbonitrile (1.50 g) in toluene (19 ml) were added palladium acetate (11 mg), benzophenone imine (0.67 ml), (±)-2,2'-bis(diphenylphosphino)-1,1'-binaphthyl (30 mg) and sodium tert-butoxide (547 mg) at room temperature, and stirred at 120° C. for 1 hour. Then, after the mixture was cooled to room temperature, water was added thereto, and extracted with ethyl acetate. The organic layer was dried over anhydrous sodium sulfate, and then the solvent was evaporated.

(3) To a solution of the obtained residue in methanol (38 ml) were added hydroxyamine monohydrochloride (475 mg) and sodium acetate (747 mg), and stirred at the same temperature for 1 hour. After completion of the reaction, a saturated aqueous solution of sodium hydrogen carbonate was added thereto, and extracted with ethyl acetate. The organic layer was dried over anhydrous sodium sulfate, and then the solvent was evaporated. The obtained residue was purified with silica gel column chromatography (n-hexane/ethyl acetate) to give the titled compound (1.06 g) as a pale yellow solid. MS (ESI) m/z: 332 (M+H)$^+$.

Reference Example 145

N-[4-(5-Amino-3-methylpyridin-2-yl)cyclohex-3-en-1-yl]-2,2,N-trimethylpropionic acid amide (1) To a solution of N-[4-(5-bromo-3-methylpyridin-2-yl)cyclohex-3-en-1-yl]-N-methylcarbamic acid tert-butyl ester (11.6 g) described in Reference Example 143 (5) in dichloromethane (30 ml) was added trifluoroacetic acid (10 ml) at room temperature, and stirred at 50° C. for 4 hours. After completion of the reaction, a saturated aqueous solution of sodium hydrogen carbonate was added thereto under ice-cooling, and extracted with 10% methanol/chloroform. The organic layer was dried over anhydrous sodium sulfate, and then the solvent was evaporated. The obtained residue was purified with basic silica gel column chromatography (chloroform) to give N-[4-(5-bromo-3-methylpyridin-2-yl)cyclohex-3-en-1-yl]-N-methylamine (8.13 g) as a brown oil.

MS (ESI) m/z: 281, 283 (M+H)$^+$.

(2) To a solution of N-[4-(5-bromo-3-methylpyridin-2-yl)cyclohex-3-en-1-yl]-N-methylamine (4.5 g) in pyridine (32 ml) were added pivalic acid anhydride (5.96 g) and 4-dimethylaminopyridine (391 mg) at room temperature, and stirred at 70° C. for 3 hours. After completion of the reaction, the mixture was cooled to room temperature, water was added thereto, and extracted with ethyl acetate. The organic layer was dried over anhydrous sodium sulfate, and then the solvent was evaporated. The obtained residue was purified with silica gel column chromatography (n-hexane/ethyl acetate) to give N-[4-(5-bromo-3-methylpyridin-2-yl)cyclohex-3-en-1-yl]-2,2,N-trimethylpropionic acid amide (5.07 g) as a white solid.

MS (ESI) m/z: 365, 367 (M+H)$^+$.

(3) To a solution of N-[4-(5-bromo-3-methylpyridin-2-yl)cyclohex-3-en-1-yl]-2,2,N-trimethylpropionic acid amide (5.07 g) in toluene (28 ml) were added palladium acetate (39 mg), benzophenone imine (2.5 ml), (±)-2,2'-bis(diphenylphosphino)-1,1'-binaphthyl (108 mg) and sodium tert-butoxide (2.0 g) at room temperature, and stirred at 120° C. for 1 hour. After completion of the reaction, the mixture was cooled to room temperature, water was added thereto, and extracted with ethyl acetate. The organic layer was dried over anhydrous sodium sulfate, and then the solvent was evaporated.

(4) To a solution of the obtained residue in methanol (70 ml) were added hydroxyamine monohydrochloride (2.31 g) and sodium acetate (3.42 g) at room temperature, and stirred at the same temperature for 3 hours. After completion of the reaction, a saturated aqueous solution of sodium hydrogen carbonate was added thereto, and extracted with ethyl acetate. The organic layer was dried over anhydrous sodium sulfate, and then the solvent was evaporated. The obtained residue was purified with basic silica gel column chromatography (n-hexane/ethyl acetate) to give the titled compound (3.89 g) as a pale yellow solid. MS (ESI) m/z: 302 (M+H)$^+$.

Reference Example 146

N-[4-(5-Amino-3-methylpyridin-2-yl)cyclohex-3-en-1-yl]-2,2,2-trifluoro-N-methylacetamide (1) To a solution of N-[4-(5-bromo-3-methylpyridin-2-yl)cyclohex-3-en-1-yl]-N-methylamine (1.5 g) described in Reference Example 145 (1) in pyridine (10 ml) were added trifluoroacetic acid anhydride (1.50 ml) and 4-dimethylaminopyridine (130 mg) at room temperature, and stirred at 70° C. for 2 hours. After completion of the reaction, the mixture was cooled to room temperature, water and triethylamine were added thereto, and extracted with ethyl acetate. The organic layer was dried over anhydrous sodium sulfate, and then the solvent was evaporated. The obtained residue was purified with silica gel column chromatography (n-hexane/ethyl acetate) to give N-[4-(5-bromo-3-methylpyridin-2-yl)cyclohex-3-en-1-yl]-2,2,2-trifluoro-N-methylacetamide (1.76 g) as a white solid.

MS (ESI) m/z: 377, 379 (M+H)$^+$.

(2) To a solution of N-[4-(5-bromo-3-methylpyridin-2-yl)cyclohex-3-en-1-yl]-2,2,2-trifluoro-N-methylacetamide (1.71 g) in toluene (22 ml) were added palladium acetate (13 mg), benzophenone imine (0.80 ml), (±)-2,2'-bis(diphenylphosphino)-1,1'-binaphthyl (36 mg) and sodium tert-butoxide (653 mg) at room temperature, and stirred at 120° C. for 1 hour. After completion of the reaction, the mixture was cooled to room temperature, water was added thereto, and extracted with ethyl acetate. The organic layer was dried over anhydrous sodium sulfate, and then the solvent was evaporated.

(3) To a solution of the obtained residue in methanol (23 ml) were added hydroxyamine monohydrochloride (756 mg) and sodium acetate (1.12 g) at room temperature, and stirred at the same temperature for 4 hours. After completion of the reaction, a saturated aqueous solution of sodium hydrogen carbonate was added thereto, and extracted with 10% methanol/chloroform solution. The organic layer was dried over anhydrous sodium sulfate, and then the solvent was evaporated. The obtained residue was purified with basic silica gel column chromatography (n-hexane/ethyl acetate) to give the titled compound (1.05 g) as a yellow solid.

MS (ESI) m/z: 314 (M+H)$^+$.

Reference Example 147

N-[4-(5-Amino-3-methylpyridin-2-yl)cyclohex-3-en-1-yl]-N-methylisobutyl amide (1) To a solution of N-[4-(5-bromo-3-methylpyridin-2-yl)cyclohex-3-en-1-yl]-N-methylamine (1.5 g) described in Reference Example 145 (1) in pyridine (10 ml) was added isobutyryl chloride (1.13 ml) at room temperature, and stirred at 70° C. for 2 hours. After completion of the reaction, the mixture was cooled to room temperature, water and triethylamine were added thereto, and the precipitated solid was collected by filtration. The obtained residue was purified with silica gel column chromatography (n-hexane/ethyl acetate) to give N-[4-(5-bromo-3-methylpyridin-2-yl)cyclohex-3-en-1-yl]-N-methylisobutylamide (1.5 g) as a white solid. MS (ESI) m/z: 351, 353 (M+H)$^+$.

(2) To a solution of N-[4-(5-bromo-3-methylpyridin-2-yl)cyclohex-3-en-1-yl]-N-methylisobutylamide (1.47 g) in toluene (21 ml) were added palladium acetate (12 mg), benzophenone imine (0.75 ml), (±)-2,2'-bis(diphenylphosphino)-1,1'-binaphthyl (33 mg) and sodium tert-butoxide (605 mg) at room temperature, and stirred at 120° C. for 1 hour. After completion of the reaction, the mixture was cooled to room temperature, water was added thereto, and extracted with ethyl acetate. The organic layer was dried over anhydrous sodium sulfate, and then the solvent was evaporated.

(3) To a solution of the obtained residue in methanol (21 ml) were added hydroxyamine monohydrochloride (700 mg) and sodium acetate (1.03 g) at room temperature, and stirred at the same temperature for 4 hours. After completion of the reaction, a saturated aqueous solution of sodium hydrogen carbonate was added thereto, and extracted with 10% methanol/chloroform solution. The organic layer was dried over anhydrous sodium sulfate, and then the solvent was evaporated. The obtained residue was purified with basic silica gel column chromatography (n-hexane/ethyl acetate) to give the titled compound (1.05 g) as a yellow solid.

MS (ESI) m/z: 288 (M+H)$^+$.

Reference Example 148

1-(5-Aminopyridin-2-yl)-c-4-hydroxy-4-methyl-r-1-cyclohexanecarbonitrile (1) To a solution of 8-(5-bromopyridin-2-yl)-1,4-dioxaspiro[4.5]decane-8-carbonitrile (20 g) in Reference Example 82 in toluene (124 ml) were added palladium acetate (174 mg), benzophenone imine (10.9 ml), (±)-2,2'-bis(diphenylphosphino)-1,1'-binaphthyl (483 mg) and sodium tert-butoxide (8.93 g) at room temperature, and stirred at 120° C. for 1 hour. After completion of the reaction, the mixture was cooled to room temperature, water was added thereto, and extracted with ethyl acetate. The organic layer was dried over anhydrous sodium sulfate, and then the solvent was evaporated.

(2) To a solution of the obtained residue in methanol (200 ml) were added hydroxyamine monohydrochloride (7.75 g) and sodium acetate (12.2 g) at room temperature, and stirred at the same temperature for 1 hour. After completion of the reaction, a saturated aqueous solution of sodium hydrogen carbonate was added thereto, and extracted with ethyl acetate. The organic layer was dried over anhydrous sodium sulfate, and then the solvent was evaporated. The obtained residue was purified with silica gel column chromatography (n-hexane/ethyl acetate) to give 8-(5-aminopyridin-2-yl)-1,4-dioxaspiro[4.5]decane-8-carbonitrile (14.5 g) as a light brown solid.

MS (ESI) m/z: 260 (M+H)$^+$.

(3) To a solution of 8-(5-aminopyridin-2-yl)-1,4-dioxaspiro[4.5]decane-8-carbonitrile (14.5 g) in pyridine (55 ml) was added acetic anhydride (5.0 ml) at room temperature, and stirred at the same temperature for 3 hours. After completion of the reaction, water was added thereto, and the precipitated solid was collected by filtration.

(4) To a solution of the obtained solid in tetrahydrofuran (10 ml) was added 3 N hydrochloric acid aqueous solution (110 ml) at room temperature, and stirred at the same temperature for 28 hours. After completion of the reaction, the solvent was evaporated, and 1N aqueous solution of sodium hydroxide was added thereto. The precipitated solid was collected by filtration, and suspended and washed with diethyl ether to give N-[6-(1-cyano-4-oxocyclohexan-1-yl)pyridin-3-yl]acetamide (8.89 g) as a white solid. MS (ESI) m/z: 258 (M+H)$^+$.

(5) To a suspension of N-[6-(1-cyano-4-oxocyclohexan-1-yl)pyridin-3-yl]acetamide (2.0 g) in tetrahydrofuran (39 ml) was added dropwise a 1.0 M solution of methylmagnesium bromide in tetrahydrofuran (17.1 ml) at room temperature, and then stirred at the same temperature for 12 hours. After completion of the reaction, a saturated aqueous solution of ammonium chloride was added thereto, and extracted with ethyl acetate. The organic layer was dried over anhydrous sodium sulfate, and then the solvent was evaporated. The obtained residue was purified with silica gel column chromatography (n-hexane/ethyl acetate). Then, the purified residue was purified with preparative HPLC (water:acetonitrile) to give N-[6-(r-1-cyano-c-4-hydroxy-4-methylcyclohexyl)pyridin-3-yl]acetamide (454 mg) as a white solid.

MS (ESI) m/z: 274 (M+H)$^+$.

Furthermore, N-[6-(r-1-cyano-t-4-hydroxy-4-methylcyclohexyl)pyridin-3-yl]acetamide (421 mg) was also obtained as a white solid.

MS (ESI) m/z: 274 (M+H)$^+$.

(6) To a solution of N-[6-(r-1-cyano-c-4-hydroxy-4-methylcyclohexan-1-yl)pyridin-3-yl]acetamide (454 mg) in methanol (25.5 ml) and tetrahydrofuran (8.5 ml) were added lithium hydroxide monohydrate (3.48 g) and water (17 ml) at room temperature, and stirred at 100° C. for 1 hour. Additionally, lithium hydroxide monohydrate (1.74 g) was added thereto at room temperature, and stirred at 100° C. for 2 hours. After completion of the reaction, the solvent was evaporated, and the obtained residue was extracted with chloroform. The organic layer was dried over anhydrous sodium sulfate, and then the solvent was evaporated. The obtained residue was purified with silica gel column chromatography (chloroform/methanol) to give the titled compound (277 mg) as a white solid.

MS (ESI) m/z: 232 (M+H)$^+$.

Reference Example 149

1-(5-Aminopyridin-2-yl)-t-4-hydroxy-4-methyl-r-1-cyclohexanecarbonitrile

N-[6-(r-1-cyano-t-4-hydroxy-4-methylcyclohexan-1-yl)pyridin-3-yl]acetamide (421 mg) described in Reference Example 148 (5) was used in place of N-[6-(r-1-cyano-c-4-hydroxy-4-methylcyclohexan-1-yl)pyridin-3-yl]acetamide in Reference Example 148 (6), and reacted and treated in a similar manner to give the titled compound (303 mg) as a white solid.

MS (ESI) m/z: 232 (M+H)$^+$.

Reference Example 150

1-(5-Aminopyridin-2-yl)-t-4-hydroxy-4-vinyl-r-1-cyclohexanecarbonitrile (1) To a suspension of N-[6-(1-cyano-4-oxocyclohexan-1-yl)pyridin-3-yl]acetamide (2.0 g) described in Reference Example 148 (4) in tetrahydrofuran (39 ml) was added dropwise a 1.0 M solution of vinylmagnesium bromide in tetrahydrofuran (17.1 ml) at room temperature, and then stirred at the same temperature for 12 hours. After completion of the reaction, a saturated aqueous solution of ammonium chloride was added thereto, and extracted with ethyl acetate. The organic layer was dried over anhydrous sodium sulfate, and then the solvent was evaporated. The obtained residue was purified with basic silica gel column chromatography (n-hexane/ethyl acetate). Then, the purified residue was purified with silica gel column chromatography (chloroform/methanol) to give N-[6-(r-1-cyano-t-4-hydroxy-4-vinylcyclohexan-1-yl)pyridin-3-yl]acetamide (474 mg) as a white solid. MS (ESI) m/z: 286 (M+H)$^+$.

Furthermore, N-[6-(r-1-cyano-c-4-hydroxy-4-vinylcyclohexan-1-yl)pyridin-3-yl]acetamide (244 mg) was also obtained as a white solid.

MS (ESI) m/z: 286 (M+H)$^+$.

(2) To a solution of N-[6-(r-1-cyano-t-4-hydroxy-4-vinylcyclohexan-1-yl)pyridin-3-yl]acetamide (474 mg) in methanol (25.5 ml) and tetrahydrofuran (8.5 ml) were added lithium hydroxide monohydrate (5.23 g) and water (17 ml) at room temperature, and stirred at 100° C. for 1 hour. Additionally, lithium hydroxide monohydrate (1.74 g) was added thereto at room temperature, and stirred at 100° C. for 4 hours. After completion of the reaction, the solvent was evaporated, and the obtained residue was extracted with chloroform. The organic layer was dried over anhydrous sodium sulfate, and then the solvent was evaporated. The obtained residue was purified with silica gel column chromatography (chloroform/methanol) to give the titled compound (210 mg) as a white solid.

MS (ESI) m/z: 244 (M+H)$^+$.

Reference Example 151

1-(5-Aminopyridin-2-yl)-c-4-hydroxy-4-vinyl-r-1-cyclohexanecarbonitrile

N-[6-(r-1-cyano-c-4-hydroxy-4-vinyl cyclohexan-1-yl)pyridin-3-yl]acetamide (244 mg) described in Reference Example 150 (1) was used in place of N-[6-(r-1-cyano-t-4-hydroxy-4-vinylcyclohexan-1-yl)pyridin-3-yl]acetamide in Reference Example 150 (2), and reacted and treated in a similar manner to give the titled compound (174 mg) as a white solid.

MS (ESI) m/z: 244 (M+H)$^+$.

Reference Example 152

N-[4-(5-amino-3-methylpyridin-2-yl)cyclohex-3-en-1-yl]carboxylic acid-tert-butylamide (1) To a solution of 2,5-dibromo-3-methylpyridine (22.4 g) in toluene (300 ml) was added dropwise a 1.6 M solution of n-butyllithium in n-hexane (64 ml) at −78° C., and stirred at the same temperature for 1 hour. Then, a solution of 4-cyclohexanone carboxylic acid ethyl ester (14.5 g) in dichloromethane (42.5 ml) was added dropwise thereto, and warmed to room temperature over 18 hours. After completion of the reaction, a saturated aqueous solution of ammonium chloride was added thereto, and extracted with ethyl acetate. The organic layer was dried over anhydrous sodium sulfate, and then the solvent was evaporated.

(2) To a solution of the obtained compound in pyridine (170 ml) was added dropwise thionyl chloride (25.3 g) under ice-cooling, and stirred at the same temperature for 10 minutes. After completion of the reaction, a saturated aqueous solution of sodium hydrogen carbonate was added thereto, and extracted with ethyl acetate. The organic layer was dried over anhydrous sodium sulfate, and then the solvent was evaporated. The obtained residue was purified twice with silica gel column chromatography (n-hexane/ethyl acetate) to give [4-(5-bromo-3-methylpyridin-2-yl)cyclohex-3-en-1-yl]carboxylic acid ethyl ester (15.3 g) as a yellow oil.

MS (ESI) m/z: 324, 326 (M+H)$^+$.

(3) To a solution of [4-(5-bromo-3-methylpyridin-2-yl)cyclohex-3-en-1-yl]carboxylic acid ethyl ester (8.57 g) in ethanol (26 ml) and tetrahydrofuran (26 ml) was added 2N aqueous solution of sodium hydroxide (52 ml) at room temperature, and stirred at 70° C. for 1 hour. After completion of the reaction, the mixture was cooled to room temperature, and extracted with diethyl ether. To the obtained aqueous layer was added 1 N hydrochloric acid aqueous solution under ice-cooling, and the precipitated solid was collected by filtration to give [4-(5-bromo-3-methylpyridin-2-yl)cyclohex-3-en-1-yl]carboxylic acid (5.37 g) as a pale yellow solid.

MS (ESI) m/z: 296, 298 (M+H)$^+$.

(4) To a solution of [4-(5-bromo-3-methylpyridin-2-yl)cyclohex-3-en-1-yl]carboxylic acid (3.5 g) in toluene (24 ml) were added thionyl chloride (2.81 g) and a catalytic amount of N,N-dimethylformamide at room temperature, stirred at 80° C. for 1 hour, and then the solvent and excessive thionyl chloride were evaporated. To a solution of the obtained residue in pyridine (12 ml) was added a solution of tert-butylamine (6.26 ml) in pyridine (12 ml) at room temperature, and stirred at 50° C. for 1 hour. After completion of the reaction, the mixture was cooled to room temperature, water was added thereto, and then extracted with ethyl acetate. The organic layer was dried over anhydrous sodium sulfate, and then the solvent was evaporated. The obtained residue was purified with silica gel column chromatography (n-hexane/ethyl acetate) to give N-[4-(5-bromo-3-methylpyridin-2-yl)cyclohex-3-en-1-yl]carboxylic acid-tert-butylamide (3.46 g) as a white solid.

MS (ESI) m/z: 351, 353 (M+H)$^+$.

(5) N-[4-(5-bromo-3-methylpyridin-2-yl)cyclohex-3-en-1-yl]carboxylic acid-tert-butylamide (1.40 g) was used in place of 1-(5-bromopyridin-2-yl)-c-4-(tert-butyldimethylsilanyloxy)-r-1-cyclohexanecarbonitrile in Reference Examples 144 (2) and (3), and reacted and treated in a similar manner to give the titled compound (750 mg) as a white solid.

MS (ESI) m/z: 288 (M+H)$^+$.

Reference Example 153

8-(5-Aminopyridin-2-yl)-r-1-oxaspiro[4.5]dec-3-ene-c-8-carbonitrile (1) To a solution of 1-(5-bromopyridin-2-yl)-4-oxocyclohexanecarbonitrile (3.0 g) described in Reference Example 85 (1) in tetrahydrofuran (20 ml) was added dropwise a 1.0 M solution of vinylmagnesium bromide in tetrahydrofuran (25.8 ml) at −78° C., and then stirred at the same temperature for 3 hours. Additionally, a 1.0 M solution of vinylmagnesium bromide in tetrahydrofuran (5.4 ml) was added dropwise thereto, and then stirred at the same temperature for 1 hour. After completion of the reaction, a saturated aqueous solution of ammonium chloride was added thereto, and extracted with ethyl acetate. The organic layer was dried over anhydrous sodium sulfate, and then the solvent was evaporated. The obtained residue was purified with silica gel column chromatography (n-hexane/ethyl acetate) to give 1-(5-bromopyridin-2-yl)-c-4-hydroxy-4-vinyl-r-1-cyclohexanecarbonitrile (1.24 g) as a white solid.

MS (ESI) m/z: 307, 309 (M+H)$^+$.

(2) To a solution of 1-(5-bromopyridin-2-yl)-c-4-hydroxy-4-vinyl-r-1-cyclohexanecarbonitrile (1.96 g) in N,N-dimethylformamide (21 ml) was added sodium hydride (306 mg) at room temperature, and stirred at the same temperature for 1 hour. Then, allyl bromide (1.3 ml) was added thereto, and stirred at 80° C. for 8 hours. After completion of the reaction, the mixture was cooled to room temperature, water was added thereto, and extracted with ethyl acetate. The organic layer was dried over anhydrous sodium sulfate, and then the solvent was evaporated. The obtained residue was purified with silica gel column chromatography (n-hexane/ethyl acetate) to give c-4-allyloxy-1-(5-bromopyridin-2-yl)-4-vinyl-r-1-cyclohexanecarbonitrile (1.35 g) as a white solid.

MS (ESI) m/z: 347, 349 (M+H)$^+$.

(3) To a solution of c-4-allyloxy-1-(5-bromopyridin-2-yl)-4-vinyl-r-1-cyclohexanecarbonitrile (1.28 g) in dichloromethane (370 ml) was added Grubbs catalyst 2nd generation (93.9 mg) at room temperature, and stirred at the same temperature for 4 hours. After completion of the reaction, the solvent was evaporated. The obtained residue was purified with silica gel column chromatography (n-hexane/ethyl acetate) to give 8-(5-bromopyridin-2-yl)-r-1-oxaspiro[4.5]dec-3-ene-c-8-carbonitrile (1.07 g) as a white solid.

MS (ESI) m/z: 319, 321 (M+H)$^+$.

(4) 8-(5-Bromopyridin-2-yl)-r-1-oxaspiro[4.5]dec-3-ene-c-8-carbonitrile (1.30 g) was used in place of 1-(5-bromopyridin-2-yl)-c-4-(tert-butyldimethylsilanyloxy)-r-1-cyclohexanecarbonitrile in Reference Example 144 (2) and (3), and reacted and treated in a similar manner to give the titled compound (502 mg) as a yellow solid.

MS (ESI) m/z: 256 (M+H)$^+$.

Reference Example 154

5-Fluoro-6-[4-(morpholin-4-yl)cyclohex-1-en-1-yl]pyridin-3-amine (1) 2,5-Dibromo-3-fluoropyridine was used in place of 2,5-dibromopyridine in Reference Example 76, and reacted and treated in a similar manner as Reference Examples 76 and 77 to give 4-[4-(5-bromo-3-fluoropyridin-2-yl)cyclohex-3-en-1-yl]morpholine as a light brown solid.

MS (ESI) m/z: 341, 343 (M+H)$^+$.

(2) 4-[4-(5-Bromo-3-fluoropyridin-2-yl)cyclohex-3-en-1-yl]morpholine (2.28 g) was used in place of 1-(5-bromopyridin-2-yl)-c-4-(tert-butyldimethyl silanyloxy)-r-1-cyclohexanecarbonitrile in Reference Example 144 (2) and (3), and reacted and treated in a similar manner to give the titled compound (1.68 g) as a pale yellow solid. MS (ESI) m/z: 278 (M+H)$^+$.

Reference Example 155

N-[4-(5-Aminopyridin-2-yl)-t-4-cyanocyclohexan-1-yl]-r-2,2,N-trimethylpropionamide (1) To a solution of 1-(5-bromopyridin-2-yl)-4-oxocyclohexanecarbonitrile (15.0 g) described in Reference Example 85 (1) in methanol (270 ml) were added ammonium formate (33.9 g) and sodium triacetoxyborohydride (13.7 g) at room temperature, and stirred at the same temperature for 18 hours. Additionally, ammonium formate (10.2 g) and sodium triacetoxyborohydride (4.56 g) were added thereto, and stirred at the same temperature for 19 hours. After completion of the reaction, the solvent was evaporated, saturated sodium bicarbonate water was added thereto, and extracted with a mixed solution of ethyl acetate/tetrahydrofuran (1:1). The organic layer was dried over anhydrous sodium sulfate, and then the solvent was evaporated.

(2) To a solution of the obtained residue (15.1 g) in dichloromethane (270 ml) were added di-tert-butyl dicarbonate (11.7 g), 4-dimethylaminopyridine (1.31 g) and triethylamine (7.50 ml) at room temperature, and stirred at the same temperature for 8 hours. Subsequently, the mixture was stirred at 55° C. for 8 hours. After completion of the reaction, the mixture was cooled to room temperature, a saturated aqueous solution of ammonium chloride was added thereto, and extracted with chloroform. The organic layer was dried over anhydrous sodium sulfate, and then the solvent was evaporated. The obtained residue was purified with silica gel column chromatography (n-hexane/ethyl acetate) to give a mixture (6.53 g) of N-[4-(5-bromopyridin-2-yl)-c-4-cyanocyclohexan-1-yl]-r-carbamic acid tert-butyl ester and N-[4-(5-bromopyridin-2-yl)-t-4-cyanocyclohexan-1-yl]-r-carbamic acid tert-butyl ester as a pale yellow solid.

MS (ESI) m/z: 380, 382 (M+H)$^+$.

(3) To a solution of the mixture (5.53 g) of N-[4-(5-bromopyridin-2-yl)-c-4-cyanocyclohexan-1-yl]-r-carbamic acid tert-butyl ester and N-[4-(5-bromopyridin-2-yl)-t-4-cyanocyclohexan-1-yl]-r-carbamic acid tert-butyl ester in N,N-dimethylformamide (30 ml) was added sodium hydride (700 mg) under ice-cooling, and stirred at the same temperature for 0.5 hours. Subsequently, methyl iodide (1.1 ml) was added thereto at the same temperature, and stirred for 4 hours. After completion of the reaction, water was added thereto, and the precipitated solid was collected by filtration. The obtained residue was purified with silica gel column chromatography (n-hexane/ethyl acetate) to give N-[4-(5-bromopyridin-2-yl)-c-4-cyanocyclohexan-1-yl]-r-N-methylcarbamic acid tert-butyl ester (3.28 g) as a pale yellow solid.

MS (ESI) m/z: 394, 396 (M+H)$^+$.

Additionally, N-[4-(5-bromopyridin-2-yl)-t-4-cyanocyclohexan-1-yl]-r-N-methylcarbamic acid tert-butyl ester (2.01 g) was obtained as a pale yellow solid.

MS (ESI) m/z: 394, 396 (M+H)$^+$.

(4) To a solution of N-[4-(5-bromopyridin-2-yl)-t-4-cyanocyclohexan-1-yl]-r-N-methylcarbamic acid tert-butyl ester (2.32 g) in 1,4-dioxane (6.0 ml) was added 3 N hydrochloric acid aqueous solution (6.0 ml) at room temperature, and stirred at the same temperature for 1 hour. Subsequently, the mixture was stirred at 60° C. for 1 hour. After completion of the reaction, the mixture was cooled to room temperature, 1N aqueous solution of sodium hydroxide was added thereto, and extracted with ethyl acetate. The organic layer was dried over anhydrous sodium sulfate, and then the solvent was evaporated. The obtained residue was purified with silica gel column chromatography (n-hexane/ethyl acetate) to give 1-(5-bromopyridin-2-yl)-t-4-methylaminocyclohexane-r-1-carbonitrile (1.63 g) as a pale yellow solid.

MS (ESI) m/z: 294, 296 (M+H)$^+$.

(5) To a solution of 1-(5-bromopyridin-2-yl)-t-4-methylaminocyclohexane-r-1-carbonitrile (1.63 g) in pyridine (11 ml) were added pivalic acid anhydride (2.06 g) and 4-dimethylaminopyridine (135 mg) at room temperature, and stirred at 70° C. for 3 hours. After completion of the reaction, the mixture was cooled to room temperature, water was added thereto, and extracted with ethyl acetate. The organic layer was washed with saturated brine, dried over anhydrous sodium sulfate, and then the solvent was evaporated. The obtained residue was purified with silica gel column chromatography (n-hexane/ethyl acetate) to give N-[4-(5-bromopyridin-2-yl)-t-4-cyanocyclohexan-1-yl]-r-2,2,N-trimethylpropionamide (1.25 g) as a white solid.

MS (ESI) m/z: 378, 380 (M+H)$^+$.

(6) N-[4-(5-bromopyridin-2-yl)-t-4-cyanocyclohexan-1-yl]-r-2,2,N-trimethylpropionamide (1.25 g) was used in place of 1-(5-bromopyridin-2-yl)-c-4-(tert-butyldimethylsilanyloxy)-r-1-cyclohexanecarbonitrile in Reference Example 144 (2) and (3), and reacted and treated in a similar manner to give the titled compound (865 mg) as a pale yellow solid.

MS (ESI) m/z: 315 (M+H)$^+$.

Reference Example 156

N-[4-(5-Aminopyridin-2-yl)-c-4-cyanocyclohexan-1-yl]-r-2,2,N-trimethylpropionamide (1) N-[4-(5-bromopyridin-2-yl)-c-4-cyanocyclohexan-1-yl]-r-N-methylcarbamic acid tert-butyl ester (3.90 g) described in Reference Example 155 (3) was used, and reacted and treated in a similar manner as Reference Example 155 (4) to give 1-(5-bromopyridin-2-yl)-c-4-methylaminocyclohexane-r-1-carbonitrile (2.44 g) as a white solid.

MS (ESI) m/z: 294, 296 (M+H)$^+$.

(2) 1-(5-Bromopyridin-2-yl)-c-4-methylaminocyclohexane-r-1-carbonitrile (1.20 g) was used in place of 1-(5-bromopyridin-2-yl)-t-4-methylaminocyclohexane-r-1-carbonitrile in Reference Example 155 (5) and (6), and reacted and treated in a similar manner to give the titled compound (835 mg) as a white solid.

MS (ESI) m/z: 315 (M+H)$^+$.

Reference Example 157

N-[4-(5-Aminopyridin-2-yl)-c-4-cyanocyclohexan-1-yl]-r-N-methylisobutylamide (1) To a solution of 1-(5-bromopyridin-2-yl)-c-4-methylaminocyclohexane-r-1-carbonitrile (1.17 g) described in Reference Example 156 (1) in pyridine (8.0 ml) was added isobutylcarboxylic acid chloride (0.84 ml) at room temperature, and stirred at 70° C. for 1 hour. After completion of the reaction, the mixture was cooled to room temperature, water was added thereto, and then extracted with ethyl acetate. The organic layer was washed with saturated brine, dried over anhydrous sodium sulfate, and then the solvent was evaporated. The obtained residue was purified with silica gel column chromatography (n-hexane/ethyl acetate) to give N-[4-(5-bromopyridin-2-yl)-c-4-cyanocyclohexan-1-yl]-r-N-methylisobutylamide (995 mg) as a white solid.

MS (ESI) m/z: 364, 366 (M+H)$^+$.

(2) N-[4-(5-bromopyridin-2-yl)-c-4-cyanocyclohexan-1-yl]-r-N-methylisobutylamide (995 mg) was used in place of 1-(5-bromopyridin-2-yl)-c-4-(tert-butyldimethylsilanyloxy)-r-1-cyclohexanecarbonitrile in Reference Example 144 (2) and (3), and reacted and treated in a similar manner to give the titled compound (688 mg) as a pale yellow solid.

MS (ESI) m/z: 301 (M+H)+.

Reference Example 158

1-(5-Aminopyridin-2-yl)-t-4-ethyl-4-hydroxy-r-1-cyclohexanecarbonitrile

To a solution of 1-(5-aminopyridin-2-yl)-c-4-hydroxy-4-vinyl-r-1-cyclohexanecarbonitrile (1.3 g) described in Reference Example 151 in methanol (27 ml) was added 10% palladium carbon (containing about 50% water) (130 mg) at room temperature, and stirred at the same temperature for 0.5 hours under hydrogen gas flow. After completion of the reaction, the mixture was filtered through Celite, and the solvent was evaporated. The obtained residue was purified with silica gel column chromatography (chloroform/methanol) to give the titled compound (1.14 g) as a white solid.

MS (ESI) m/z: 246 (M+H)+.

Reference Example 159

8-(5-Aminopyridin-2-yl)-r-1-oxaspiro[4.5]decane-c-8-carbonitrile 8-(5-Aminopyridin-2-yl)-r-1-oxaspiro[4.5]dec-3-ene-c-8-carbonitrile (398 mg) described in Reference Example 153 was used in place of 1-(5-aminopyridin-2-yl)-c-4-hydroxy-t-4-vinyl-r-1-cyclohexanecarbonitrile in Reference Example 158, and reacted and treated in a similar manner to give the titled compound (352 mg) as a white solid.

MS (ESI) m/z: 258 (M+H)+.

Reference Example 160

1-(5-Aminopyridin-2-yl)-c-4-(tert-butyldimethyl silanyloxy)cyclohexan-r-1-ol (1) To 8-(5-bromopyridin-2-yl)-1,4-dioxaspiro[4.5]decan-8-ol (21.5 g) described in Reference Example 76 (1) was added 3 N hydrochloric acid aqueous solution (140 ml) at room temperature, and stirred at the same temperature for 2 hours. After completion of the reaction, a saturated aqueous solution of sodium bicarbonate was added thereto under ice-cooling, and the precipitated solid was collected by filtration.

(2) To a solution of the obtained solid (5.0 g) in methanol (60 ml) and chloroform (30 ml) was slowly added sodium borohydride (2.8 g) at −78° C., and warmed to room temperature over 6 hours with stirring. After completion of the reaction, a saturated aqueous solution of ammonium chloride was added thereto, the solvent was evaporated, and then extracted with ethyl acetate. The organic layer was washed with saturated brine, dried over anhydrous sodium sulfate, and then the solvent was evaporated. The obtained residue was purified with silica gel column chromatography (chloroform/methanol) to give 1-(5-bromopyridin-2-yl)cyclohexane-r-1,c-4-diol (4.22 g) as a white solid.

MS (ESI) m/z: 272, 274 (M+H)+.

(3) To a solution of 1-(5-bromopyridin-2-yl)cyclohexane-r-1,c-4-diol (4.21 g) in pyridine (30 ml) was added anhydrous acetic acid (15 ml) at room temperature, and stirred at the same temperature for 3 hours. After completion of the reaction, 1 N aqueous solution of sodium hydroxide was added thereto until the mixture became about pH 7, additionally water was added thereto, and then the precipitated solid was collected by filtration.

(4) To a solution of the obtained solid (1.8 g) in 1,4-dioxane (28 ml) was added 1 N aqueous solution of sodium hydroxide (28 ml) at room temperature, and stirred at the same temperature for 16 hours. After completion of the reaction, 1 N hydrochloric acid aqueous solution was added thereto, and extracted with ethyl acetate. The organic layer was dried over anhydrous sodium sulfate, and then the solvent was evaporated. To a solution of the obtained residue in dichloromethane (28 ml) and 1,4-dioxane (28 ml) were added 4-dimethylaminopyridine (140 mg) and tert-butyldimethylsilyl chloride (1.04 g) at room temperature, and stirred at the same temperature for 2 hours. Additionally, 4-dimethylaminopyridine (700 mg) was added thereto, and stirred at the same temperature for 28 hours. After completion of the reaction, a saturated aqueous solution of ammonium chloride was added thereto, and extracted with chloroform. The organic layer was dried over anhydrous sodium sulfate, and then the solvent was evaporated. The obtained residue was purified with silica gel column chromatography (n-hexane/ethyl acetate) to give 1-(5-bromopyridin-2-yl)-c-4-(tert-butyldimethylsilanyloxy)cyclohexan-r-1-ol (1.99 g) as a white solid.

(5) 1-(5-Bromopyridin-2-yl)-c-4-(tert-butyldimethylsilanyloxy)cyclohexan-r-1-ol (1.98 g) was used in place of 1-(5-bromopyridin-2-yl)-c-4-(tert-butyldimethylsilanyloxy)-r-1-cyclohexanecarbonitrile in Reference Example 144 (2) and (3), and reacted and treated in a similar manner to give the titled compound (1.08 g) as a white solid.

MS (ESI) m/z: 323 (M+H)+.

Reference Example 161

1-(5-Aminopyridin-2-yl)-c-4-(tert-butyldimethylsilanyloxy)cyclohexane-r-1-carboxylic acid ethyl ester and 1-(5-aminopyridin-2-yl)-t-4-(tert-butyldimethylsilanyloxy)cyclohexane-r-1-carboxylic acid ethyl ester (1) To a solution of 1-(5-bromopyridin-2-yl)-4-oxocyclohexanecarboxylic acid ethyl ester (3.4 g) described in Reference Example 131 (1) in methanol (36 ml) and chloroform (18 ml) was slowly added sodium borohydride (1.58 g) at −78° C., and stirred at the same temperature for 6 hours. After completion of the reaction, a saturated aqueous solution of ammonium chloride was added thereto, and extracted with chloroform. The organic layer was dried over anhydrous sodium sulfate, and then the solvent was evaporated. The obtained residue was purified with silica gel column chromatography (n-hexane/ethyl acetate) to give a mixture (3.31 g) of 1-(5-bromopyridin-2-yl)-c-4-hydroxycyclohexane-r-1-carboxylic acid ethyl ester and 1-(5-bromopyridin-2-yl)-t-4-hydroxycyclohexane-r-1-carboxylic acid ethyl ester as a colorless clear oil.

MS (ESI) m/z: 328, 330 (M+H)+.

(2) To a solution of the mixture (3.31 g) of 1-(5-bromopyridin-2-yl)-c-4-hydroxycyclohexane-r-1-carboxylic acid ethyl ester and 1-(5-bromopyridin-2-yl)-t-4-hydroxycyclohexane-r-1-carboxylic acid ethyl ester in dichloromethane (40 ml) were added 4-dimethylaminopyridine (247 mg) and tert-butyldimethylsilyl chloride (1.82 g) at room temperature, and stirred at the same temperature for 4 hours. Additionally, tert-butyldimethylsilyl chloride (456 mg) was added thereto, and stirred at 50° C. for 1 hour. Then, 4-dimethylaminopyridine (1.23 g) was added thereto, and stirred at the same temperature for 1 hour. After completion of the reaction, the mixture was cooled to room temperature, a saturated aqueous solution of ammonium chloride was added thereto, and extracted with chloroform. The organic layer was dried over anhydrous sodium sulfate, and then the solvent was evaporated. The obtained residue was purified with silica gel column chromatography (n-hexane/ethyl acetate) to give a mixture (4.23 g) of 1-(5-bromopyridin-2-yl)-c-4-(tert-butyldimethylsilanyloxy)cyclohexane-r-1-carboxylic acid ethyl ester and 1-(5-bromopyridin-2-yl)-t-4-(tert-butyldimethylsilanyloxy)cyclohexane-r-1-carboxylic acid ethyl ester as a colorless clear oil.

MS (ESI) m/z: 442, 444 (M+H)$^+$.

(3) A mixture (4.21 g) of 1-(5-bromopyridin-2-yl)-c-4-(tert-butyldimethylsilanyloxy)cyclohexane-r-1-carboxylic acid ethyl ester and 1-(5-bromopyridin-2-yl)-t-4-(tert-butyldimethylsilanyloxy)cyclohexane-r-1-carboxylic acid ethyl ester was used in place of 1-(5-bromopyridin-2-yl)-c-4-(tert-butyldimethylsilanyloxy)-r-1-cyclohexanecarbonitrile in Reference Example 144 (2) and (3), and reacted and treated in a similar manner to give the titled compound (2.32 g) as a pale yellow oil.

MS (ESI) m/z: 379 (M+H)$^+$.

Reference Example 162 trans-6-[4-(tert-Butyldimethylsilanyloxy)cyclohex-1-yl]pyridin-3-amine trans-5-Bromo-2-[4-(tert-butyldimethylsilyloxy)cyclohex-1-yl]pyridine (1.54 g) described in Reference Example 103 (3) was used in place of 1-(5-bromopyridin-2-yl)-c-4-(tert-butyldimethylsilanyloxy)-r-1-cyclohexanecarbonitrile in Reference Example 144 (2) and (3), and reacted and treated in a similar manner to give the titled compound (1.11 g) as a white solid.

MS (ESI) m/z: 307 (M+H)$^+$.

Reference Example 163

4-(5-Amino-3-methylpyridin-2-yl)azepane-1-carboxylic acid tert-butyl ester (1) To a solution of 2,5-dibromo-3-methylpyridine (3.88 g) in toluene (70 ml) was added dropwise a 1.6 M solution of n-butyllithium in n-hexane (10.6 ml) at −78° C., and stirred at the same temperature for 1 hour. Then, a solution of N-tert-butoxycarbonyl-hexahydroazepin-4-one (3.0 g) in toluene (16 ml) was added dropwise thereto, and stirred at the same temperature for 5 hours. After completion of the reaction, a saturated aqueous solution of ammonium chloride was added thereto, and extracted with ethyl acetate. The organic layer was dried over anhydrous sodium sulfate, and then the solvent was evaporated. The obtained residue was purified with silica gel column chromatography (n-hexane/ethyl acetate) to give 4-(5-bromo-3-methylpyridin-2-yl)-4-hydroxyazepane-1-carboxylic acid tert-butyl ester (2.14 g) as a colorless clear oil.

MS (ESI) m/z: 385, 387 (M+H)$^+$.

(2) To a solution of 4-(5-bromo-3-methylpyridin-2-yl)-4-hydroxyazepane-1-carboxylic acid tert-butyl ester (1.90 g) in pyridine (20 ml) was added thionyl chloride (1.47 g) under ice-cooling, and stirred at the same temperature for 1 hour. After completion of the reaction, saturated sodium bicarbonate water was added thereto, and extracted with ethyl acetate. The organic layer was dried over anhydrous sodium sulfate, and then the solvent was evaporated. The obtained residue was purified with silica gel column chromatography (n-hexane/ethyl acetate) to give a mixture (1.02 g) of 4-(5-bromo-3-methylpyridin-2-yl)-2,3,6,7-tetrahydroazepine-1-carboxylic acid tert-butyl ester and 4-(5-bromo-3-methylpyridin-2-yl)-2,3,4,7-tetrahydroazepine-1-carboxylic acid tert-butyl ester as a colorless clear oil.

MS (ESI) m/z: 367, 369 (M+H)$^+$.

(3) The mixture (1.65 g) of 4-(5-bromo-3-methylpyridin-2-yl)-2,3,6,7-tetrahydroazepine-1-carboxylic acid tert-butyl ester and 4-(5-bromo-3-methylpyridin-2-yl)-2,3,4,7-tetrahydroazepine-1-carboxylic acid tert-butyl ester was used in place of 1-(5-bromopyridin-2-yl)-c-4-(tert-butyldimethylsilanyloxy)-r-1-cyclohexanecarbonitrile in Reference Example 144 (2) and (3), and reacted and treated in a similar manner to give a yellow oil (1.14 g).

(4) To a solution of the obtained oil (1.14 g) in 1,4-dioxane (19 ml) was added 10% palladium carbon (containing about 50% water) (342 mg), and stirred for 2 hours under hydrogen gas flow. Subsequently, 10% palladium carbon (containing about 50% water) (798 mg) was added thereto, and stirred for 5.5 hours under hydrogen gas flow. After completion of the reaction, the mixture was filtered through Celite, and the solvent was evaporated. The obtained residue was purified with basic silica gel column chromatography (n-hexane/ethyl acetate) to give the titled compound (768 mg) as a brown oil.

MS (ESI) m/z: 306 (M+H)$^+$.

Reference Example 164

N-[4-(5-Amino-3-methylpyridin-2-yl)cyclohex-3-en-1-yl]carboxylic acid-N,N-dimethylamide (1) To a solution of [4-(5-bromo-3-methylpyridin-2-yl)cyclohex-3-en-1-yl]carboxylic acid (1.2 g) described in Reference Example 152 (3) in toluene (20 ml) were added thionyl chloride (1.45 g) and catalyst quantity of N,N-dimethylformamide, stirred at 80° C. for 1 hour, and then the solvent and an excess amount of thionyl chloride were evaporated. To a solution of the obtained residue in pyridine (20 ml) was added a 2.0 M solution of dimethylamine in tetrahydrofuran (20.2 ml) at room temperature, and stirred at 50° C. for 1 hour. After completion of the reaction, the mixture was cooled to room temperature, water was added thereto, and then extracted with ethyl acetate. The organic layer was dried over anhydrous sodium sulfate, and then the solvent was evaporated. The obtained residue was purified with basic silica gel column chromatography (n-hexane/ethyl acetate) to give N-[4-(5-bromo-3-methylpyridin-2-yl)cyclohex-3-en-1-yl]carboxylic acid-N,N-dimethylamide (856 mg) as an orange oil.

MS (ESI) m/z: 323, 325 (M+H)$^+$.

(2) N-[4-(5-bromo-3-methylpyridin-2-yl)cyclohex-3-en-1-yl]carboxylic acid-N,N-dimethylamide (855 mg) was used in place of 1-(5-bromopyridin-2-yl)-c-4-(tert-butyldimethylsilanyloxy)-r-1-cyclohexanecarbonitrile in Reference Example 144 (2) and (3), and reacted and treated in a similar manner to give the titled compound (501 mg) as a white solid.

MS (ESI) m/z: 260 (M+H)$^+$.

Reference Example 165

8-(5-Aminopyridin-2-yl)-1,4-dioxaspiro[4.5]decan-8-ol 8-(5-Bromopyridin-2-yl)-1,4-dioxaspiro[4.5]decan-8-ol (3.0 g) described in Reference Example 76 (1) was used in place of 1-(5-bromopyridin-2-yl)-c-4-(tert-butyldimethylsilanyloxy)-r-1-cyclohexanecarbonitrile in Reference Example 144 (2) and (3), and reacted and treated in a similar manner to give the titled compound (1.28 g) as a white solid.

MS (ESI) m/z: 251 (M+H)$^+$.

Reference Example 166

4-[4-(4,4,5,5-Tetramethyl-[1,3,2] dioxaborolan-2-yl) cyclohex-3-en-1-yl] morpholine (1) To a solution of 1,4-cyclohexanedionemonoethyl-eneketal (25.0 g), morpholine (13.8 ml), and acetic acid (9.1 ml) in dichloromethane (320 ml) was added sodium triacetoxyborohydride (40.8 g) at 0° C., and stirred at room temperature for 3 hours. To the reaction solution was added 2.5 N aqueous solution of sodium hydroxide (160 ml), extracted with dichloromethane, the organic layer was washed with saturated brine, dried over anhydrous sodium sulfate, and then the solvent was evaporated in vacuo. To the residue were added tetrahydrofuran (300 ml) and 7N HCl aqueous solution (120 ml), and stirred at room temperature for 3.5 hours. To the reaction solution was added saturated sodium hydrogen carbonate (1.5 l), extracted with ethyl acetate and dichloromethane, and the solvent was evaporated in vacuo. The obtained residue was purified with basic silica gel column chromatography (n-hexane/ethyl acetate) to give 4-(morpholin-4-yl)cyclohexanone (14.85 g) as a colorless oil.

MS (ESI) m/z: 184 (M+H)$^+$.

(2) To a solution of 4-(morpholin-4-yl)cyclohexanone (14.85 g) in tetrahydrofuran (270 ml) was added dropwise a 1 M solution of lithium bis(trimethylsilyl)amide in tetrahydrofuran (97 ml) at −78° C., stirred at the same temperature for 1 hour, then N-phenylbis(trifluoromethanesulfonimide) (30.6 g) was added thereto, stirred at −78° C. for 1 hour, and stirred at room temperature for 3.5 hours. The reaction solution was concentrated in vacuo, and the obtained residue was purified with basic silica gel column chromatography (n-hexane/ethyl acetate) to give trifluoromethanesulfonic acid 4-morpholin-4-yl-cyclohex-1-en-1-yl ester (15.7 g) as a pale yellow oil.

MS (ESI) m/z: 316 (M+H)$^+$.

(3) A suspension of trifluoromethanesulfonic acid [4-(morpholin-4-yl)cyclohex-1-en-1-yl]ester (10.48 g), bis(pinacolatediborane) (12.7 g), potassium acetate (9.8 g), and [1,1'-bis(diphenylphosphino)ferrocene]palladium(II) dichloridedichloromethane complex (1.36 g) in N,N-dimethylformamide (133 ml) was stirred at 85° C. for 4.5 hours. To the reaction solution was added toluene, and the solvent was evaporated in vacuo. The residue was filtered through Celite, and then purified with basic silica gel column chromatography (n-hexane/ethyl acetate) to give the titled compound (4.8 g) as a white solid.

MS (ESI) m/z: 294 (M+H)$^+$.

Reference Example 167

2,2,N-Trimethyl-N-{4-(4,4,5,5-tetramethyl[1,3,2] dioxaborolan-2-yl)cyclohex-3-en-1-yl}propionamide (1) To a solution of 2,2,N-trimethyl-N-(4-oxocyclohex-1-yl)propionamide (7.25 g) in Reference Example 186 in tetrahydrofuran (170 ml) was added dropwise a solution of lithium hexamethyldisilazide in tetrahydrofuran (1 M, 40 ml) at −78° C., and stirred at the same temperature for 1 hour. To the reaction solution was added N-phenylbis(trifluoromethanesulfonimide) (13.0 g), warmed to 10° C., and stirred for 1 hour. After completion of the reaction, ethyl acetate was added thereto, and washed with water and saturated brine. The organic layer was dried over sodium sulfate, the solvent was evaporated, and the obtained residue was purified with silica gel column chromatography (n-hexane/ethyl acetate) to give trifluoromethanesulfonic acid 14-[(2,2-dimethylpropionyl)methylamino]cyclohex-1-en-1-yl) ester (9.14 g) as a white solid.

(2) To a solution of trifluoromethanesulfonic acid {4-[(2,2-dimethylpropionyl)methylamino]cyclohex-1-en-1-yl}ester (5.0 g) in dimethylformamide (73 ml) were added bis(pinacolate)diboron (5.55 g), potassium acetate (4.29 g) and 1,1-bis(diphenylphosphino)ferrocene-palladium(II) dichloride-dichloromethane complex (595 mg), and stirred at 100° C. for 1 hour. After completion of the reaction, ethyl acetate was added thereto, washed with water and saturated brine, and the solvent was evaporated. The obtained residue was purified with silica gel column chromatography (n-hexane/ethyl acetate), then n-hexane was added thereto, and the insoluble matter was collected by filtration to give the titled compound (2.13 g) as a white solid.

MS (ESI) m/z: 322 (M+H)$^+$.

Reference Example 168

1-(5-Bromopyridin-2-yl)-c-4-ethoxy-r-1-cyclohexanecarbonitrile (1) To 8-(5-bromopyridin-2-yl)-1,4-dioxaspiro[4.5]decane-8-carbonitrile (3.4 g) described in Reference Example 82 was added trifluoroacetic acid (4.1 ml) at room temperature, and stirred at the same temperature for 22 hours. After completion of the reaction, the solvent and trifluoroacetic acid were evaporated. The obtained residue was purified with silica gel column chromatography (n-hexane:ethyl acetate) to give 1-(5-bromopyridin-2-yl)-4-oxocyclohexanecarbonitrile (2.78 g) as a white solid.

MS (ESI) m/z: 279, 281 (M+H)$^+$.

(2) To a solution of 1-(5-bromopyridin-2-yl)-4-oxocyclohexanecarbonitrile (1.8 g) in methanol (44 ml) and chloroform (22 ml) was added sodium borohydride (980 mg) at −78° C., and stirred at the same temperature for 1.5 hours. After completion of the reaction, water was added thereto, the solvent was evaporated, and then extracted with ethyl acetate. The organic layer was dried over anhydrous sodium sulfate, and then the solvent was evaporated. The obtained residue was purified with silica gel column chromatography (n-hexane/ethyl acetate) to give 1-(5-bromopyridin-2-yl)-c-4-hydroxy-r-1-cyclohexanecarbonitrile (1.58 g) as a white solid.

MS (ESI) m/z: 281, 283 (M+H)$^+$.

(3) To a solution of 1-(5-bromopyridin-2-yl)-c-4-hydroxy-r-1-cyclohexanecarbonitrile (100 mg) in N,N-dimethylformamide (4 ml) was added sodium hydride (21 mg) at 0° C., and stirred at the same temperature for 1.5 hours. Additionally, ethyl iodide (43 µl) was added thereto, and stirred at room temperature for 2 hours. Additionally, ethyl iodide (86 µl) was added thereto, and stirred at room temperature for 18 hours. Additionally, ethyl iodide (43 µl) was added thereto, and stirred at room temperature for 2 hours. After completion of the reaction, the solvent was evaporated. The obtained residue was purified with silica gel column chromatography (hexane:ethyl acetate) to give the titled compound (67 mg) as a white solid.

MS (ESI) m/z: 309, 311 (M+H)$^+$.

Reference Example 169

N-[6-(4-Cyanopiperidin-4-yl)pyridin-3-yl]-5-methyl-1-[5-(trifluoromethyl)pyridin-2-yl]-1H-pyrazole-4-carboxamide (1) To a solution of 4-cyanopiperidine-1-carboxylic acid tert-butyl ester (6.24 g) described in Reference Example 88

(1) in tetrahydrofuran (20 ml) was added a 1.9 M solution of sodium bis(trimethylsilyl)amide in tetrahydrofuran (21.2 ml) at 0° C., stirred for 45 minutes, then a solution of 5-bromo-2-fluoropyridine (2.76 g) in tetrahydrofuran (10 ml) was added thereto, and stirred at room temperature for 5 hours. To the reaction solution was added 10% potassium carbonate aqueous solution, extracted with ethyl acetate, washed with saturated brine, dried over anhydrous sodium sulfate, and then the solvent was evaporated in vacuo. The obtained residue was purified with silica gel chromatography (n-hexane/ethyl acetate) to give 4-(5-bromopyridin-2-yl)-4-cyanopiperidine-1-carboxylic acid tert-butyl ester (7.1 g) as a pale yellow oil.

$^1$H-NMR (DMSO-$d_6$) δ (ppm): 1.40 (9H, s), 1.92-2.00 (2H, m), 2.15 (2H, J=12.3 Hz), 3.02 (2H, brs), 4.07 (2H, J=12.8 Hz), 7.61 (1H, d, J=8.2 Hz), 8.16 (1H, dd, J=8.2, 2.1 Hz), 8.76 (1H, d, J=2.7 Hz).

(2) To a suspension of 4-(5-bromopyridin-2-yl)-4-cyanopiperidine-1-carboxylic acid tert-butyl ester (7.1 g), palladium(II) acetate (554 mg), (±)-2-(di-tert-butylphosphino)-1,1'-binaphthyl (1.51 g), and tert-butoxysodium (2.79 g) in toluene (48 ml) was added benzophenone imine (3.42 ml), stirred at 120° C. for 7 hours, then ethanol (48 ml), hydroxylamine monohydrate (5.4 g), and sodium acetate (9.54 g) were added thereto at room temperature, and stirred for 3.5 hours. To the reaction solution was added water (48 ml), stirred, then an aqueous solution of sodium hydrogen carbonate was added thereto, extracted with ethyl acetate, dried over anhydrous sodium sulfate, and then the solvent was evaporated in vacuo. The obtained residue was purified with basic silica gel chromatography (n-hexane/ethyl acetate) to give 4-(5-aminopyridin-2-yl)-4-cyanopiperidine-1-carboxylic acid tert-butyl ester (4.0 g) as a white solid. $^1$H-NMR (DMSO-$d_6$) δ (ppm): 1.40 (9H, s), 1.82-1.89 (2H, m), 2.08 (2H, J=12.8 Hz), 3.00 (2H, brs), 4.04 (2H, J=12.8 Hz), 6.96 (1H, dd, J=8.7, 3.1 Hz), 7.21 (1H, d, J=8.2 Hz), 7.92 (1H, d, J=2.6 Hz).

(3) To a suspension of 5-methyl-1-[5-(trifluoromethyl)pyridin-2-yl]-1H-pyrazole-4-carboxylic acid (3.23 g) described in Reference Example 8 in toluene (30 ml) were added N,N-dimethylformamide (catalytic amount) and thionyl chloride (2.2 ml), stirred at 80° C. for 5 hours, and then the solvent was evaporated in vacuo. To a solution of the residue in pyridine (25 ml) was added a solution of 4-(5-aminopyridin-2-yl)-4-cyanopiperidine-1-carboxylic acid tert-butyl ester (3.0 g) in pyridine (25 ml), and stirred at 40° C. for 1.5 hours. To the reaction solution was added triethylamine (7.0 ml), then water was added thereto, and the precipitated solid was washed with ethanol and water to give N-[6-(1-tert-butyloxycarbonylpiperidine-4-cyano-4-yl)pyridin-3-yl]-5-methyl-1-[5-(trifluoromethyl)pyridin-2-yl]-1H-pyrazole-4-carboxamide (5.48 g). MS (ESI) m/z: 456 (M-Boc+H)$^+$, 556 (M+H)$^+$.

(4) To N-[6-(1-tert-butyloxycarbonylpiperidine-4-cyano-4-yl)pyridin-3-yl]-5-methyl-1-[5-(trifluoromethyl)pyridin-2-yl]-1H-pyrazole-4-carboxamide (5.43 g) were added dichloromethane (100 ml) and trifluoroacetic acid (20 ml), stirred at room temperature for 4 hours, and then to the reaction solution was added 4 N aqueous solution of sodium hydroxide under ice-cooling. The precipitated solid was washed with ethanol and water to give the titled compound (4.29 g). MS (ESI) m/z: 456 (M+H)$^+$.

Reference Example 170

5-Methyl-N-[5-methyl-6-(1,2,3,6-tetrahydropyridin-4-yl)pyridin-3-yl]-1-[5-(trifluoromethyl)pyridin-2-yl]-1H-pyrazole-4-carboxamide (1) To 2,5-dibromo-3-methylpyridine (5.0 g), tetrakis(triphenylphosphine)palladium(0) (1.15 g), and N-tert-butyloxycarbonyl-1,2,3,6-tetrahydropyridine-4-boronic acid pinacol ester (6.16 g) were added 1,4-dioxane (40 ml) and 2M aqueous solution of sodium carbonate (25 ml), stirred at 90° C. for 6 hours, then tetrakis(triphenylphosphine)palladium (0) (115 mg) was added thereto, and stirred at 90° C. for 1 hour. To the reaction solution was added water, extracted with ethyl acetate, the organic layer was washed with saturated brine, dried over anhydrous sodium sulfate, and then the solvent was evaporated in vacuo. The obtained residue was purified with silica gel chromatography (n-hexane/ethyl acetate) to give 4-(5-bromo-3-methylpyridin-2-yl)-1,2,3,6-tetrahydropyridine-1-carboxylic acid tert-butyl ester (4.83 g) as a pale yellow oil.

$^1$H-NMR (DMSO-$d_6$) δ (ppm): 1.43 (9H, s), 2.32 (3H, s), 2.40-2.43 (2H, m), 3.53 (2H, m), 3.99 (2H, brs), 5.88 (1H, brs), 7.93 (1H, d, J=2.1 Hz), 8.47 (1H, d, J=1.7 Hz).

(2) To a suspension of 4-(5-bromo-3-methylpyridin-2-yl)-1,2,3,6-tetrahydropyridine-1-carboxylic acid tert-butyl ester (4.83 g), palladium(II) acetate (384 mg), (±)-2-(di-tert-butylphosphino)-1,1'-binaphthyl (1.06 g), and tert-butoxysodium (1.97 g) in toluene (34 ml) was added benzophenone imine (2.29 ml), stirred at 120° C. for 3.5 hours, then ethanol (34 ml), water (34 ml), hydroxylamine monohydrate (4.0 g), and sodium acetate (6.73 g) were added thereto at room temperature, and stirred at room temperature for 4 hours. To the reaction solution was added a saturated aqueous solution of sodium hydrogen carbonate, extracted with ethyl acetate, washed with saturated brine, dried over anhydrous sodium sulfate, and then the solvent was evaporated in vacuo. The obtained residue was purified with basic silica gel chromatography (n-hexane/ethyl acetate) to give 4-(5-amino-3-methylpyridin-2-yl)-1,2,3,6-tetrahydropyridine-1-carboxylic acid tert-butyl ester (2.4 g) as a yellow oil.

$^1$H-NMR (DMSO-$d_6$) δ (ppm): 1.43 (9H, s), 2.19 (3H, s), 2.38 (2H, m), 3.48-3.50 (2H, m), 3.95 (2H, brs), 5.21 (2H, s), 5.64 (1H, brs), 6.73 (1H, d, Hz), 7.74 (1H, d, J=2.6 Hz).

(3) To a suspension of 5-methyl-1-[5-(trifluoromethyl)pyridin-2-yl]-1H-pyrazole-4-carboxylic acid (2.7 g) described in Reference Example 8 in toluene (33 ml) were added N,N-dimethylformamide (0.25 ml) and thionyl chloride (1.8 ml), stirred at 80° C. for 2.5 hours, and then the solvent was evaporated in vacuo. To a solution of the residue in pyridine (15 ml) was added a solution of 4-(5-amino-3-methylpyridin-2-yl)-1,2,3,6-tetrahydropyridine-1-carboxylic acid tert-butyl ester (2.4 g) in pyridine (15 ml), and stirred at 40° C. for 3 hours. To the reaction solution was added triethylamine (5.8 ml), then water was added thereto, and the precipitated solid was washed with ethanol and water to give N-[6-(1-tert-butyloxycarbonyl-1,2,3,6-tetrahydropyridin-4-yl)-5-methylpyridin-3-yl]-5-methyl-1-[5-(trifluoromethyl)pyridin-2-yl]-1H-pyrazole-4-carboxamide (3.56 g) as a white solid.

MS (ESI) m/z: 543 (M+H)$^+$.

(4) To N-[6-(1-tert-butyloxycarbonyl-1,2,3,6-tetrahydropyridin-4-yl)-5-methylpyridin-3-yl]-5-methyl-1-[5-(trifluoromethyl)pyridin-2-yl]-1H-pyrazole-4-carboxamide (3.4 g) were added dichloromethane (63 ml) and trifluoroacetic acid (13 ml), stirred at room temperature for 2 hours, and then to the reaction solution was added 4 N aqueous solution of sodium hydroxide under ice-cooling. The precipitated solid was washed with ethanol and water to give the titled compound (2.6 g) as a white solid.

MS (ESI) m/z: 443 (M+H)$^+$.

Reference Example 171

5-Methyl-N-[5-methyl-6-(piperidin-4-yl)pyridin-3-yl]-1-[5-(trifluoromethyl)pyridin-2-yl]-1H-pyrazole-4-carboxamide (1) A mixture of 2-bromo-3-methyl-5-nitropyridine (10.0 g), cesium carbonate (42 g), [1,1'-bis(diphenylphosphino)

ferrocene]palladium(II)dichloridedichloromethane complex (1.88 g), and N-tert-butyloxycarbonyl-1,2,3,6-tetrahydropyridine-4-boronic acid pinacol ester (15 g) in 1,4-dioxane (150 ml) and water (50 ml) was stirred at 110° C. for 2.5 hours. To the reaction solution was added water, extracted with chloroform, the organic layer was washed with water, dried over anhydrous sodium sulfate, and then the solvent was evaporated in vacuo. The obtained solid was washed with a mixed solution of n-hexane and ethyl acetate to give 4-(3-methyl-5-nitropyridin-2-yl)-1,2,3,6-tetrahydropyridine-1-carboxylic acid tert-butyl ester (13.25 g) as a red solid.

MS (ESI) m/z: 220 (M-Boc+H)$^+$.

(2) To 4-(3-methyl-5-nitropyridin-2-yl)-1,2,3,6-tetrahydropyridine-1-carboxylic acid tert-butyl ester (5.0 g) were added 1,4-dioxane (50 ml) and 10% palladium carbon (containing about 50% water, 2.0 g), stirred at room temperature for 9 hours under hydrogen atmosphere, then 10% palladium carbon (containing about 50% water, 1.5 g) was additionally added thereto, and stirred at 40° C. for 8.5 hours under hydrogen atmosphere. The reaction solution was filtered through Celite, and then the solvent was evaporated in vacuo to give 4-(5-amino-3-methylpyridin-2-yl)piperidine-1-carboxylic acid tert-butyl ester (4.4 g) as a yellow oil.

MS (ESI) m/z: 292 (M+H)$^+$.

(3) To a solution of 4-(5-amino-3-methylpyridin-2-yl)piperidine-1-carboxylic acid tert-butyl ester (4.4 g) in pyridine (50 ml) was added 5-methyl-1-[5-(trifluoromethyl)pyridin-2-yl]-1H-pyrazole-4-carboxylic acid chloride (5.16 g) described in Reference Example 180 at 0° C., and stirred at room temperature for 1 hour. To the reaction solution was added triethylamine (6.33 ml), then water was added thereto, and the precipitated solid was washed with water and ethyl acetate to give N-[6-(1-tert-butyloxycarbonylpiperidin-4-yl)-5-methylpyridin-3-yl]-5-methyl-1-[5-(trifluoromethyl)pyridin-2-yl]-1H-pyrazole-4-carboxamide (7.0 g) as a pale yellow solid.

MS (ESI) m/z: 545 (M+H)$^+$.

(4) To N-[6-(1-tert-butyloxycarbonylpiperidin-4-yl)-5-methylpyridin-3-yl]-5-methyl-1-[5-(trifluoromethyl)pyridin-2-yl]-1H-pyrazole-4-carboxamide (7.0 g) were added dichloromethane (128 ml) and trifluoroacetic acid (26 ml), stirred at room temperature for 2 hours, and then to the reaction solution was added 4 N aqueous solution of sodium hydroxide under ice-cooling. The precipitated solid was washed with n-hexane and water, the obtained solid was dissolved in chloroform, water was added thereto, extracted with chloroform and ethyl acetate, dried over anhydrous sodium sulfate, and then the solvent was evaporated in vacuo. The precipitated solid was washed with ethyl acetate to give the titled compound (5.39 g) as a white solid.

MS (ESI) m/z: 445 (M+H)$^+$.

Reference Example 172

5-Methyl-N-[6-(1,2,3,6-tetrahydropyridin-4-yl)pyridin-3-yl]-1-[5-(trifluoromethyl)pyridin-2-yl]-1H-pyrazole-4-carboxamide (1) To a suspension of 5-methyl-1-[5-(trifluoromethyl)pyridin-2-yl]-1H-pyrazole-4-carboxylic acid (6.51 g) described in Reference Example 8 in toluene (67 ml) were added N,N-dimethylformamide (0.50 ml) and thionyl chloride (4.4 ml), stirred at 80° C. for 1.5 hours, and then the solvent was evaporated in vacuo. To a solution of the residue in pyridine (30 ml) was added a solution of 5-amino-2-bromopyridine (3.46 g) in pyridine (30 ml), and stirred at 40° C. for 3 hours. To the reaction solution was added triethylamine (14 ml), then water was added thereto, and the precipitated solid was washed with ethanol and water to give N-(6-bromopyridin-3-yl)-5-methyl-1-[5-(trifluoromethyl)pyridin-2-yl]-1H-pyrazole-4-carboxamide (7.96 g) as a gray solid. MS (ESI) m/z: 426, 428 (M+H)$^+$.

(2) To N-(6-bromopyridin-3-yl)-5-methyl-1-[5-(trifluoromethyl)pyridin-2-yl]-1H-pyrazole-4-carboxamide (3.0 g), cesium carbonate (6.4 g), [1,1'-bis(diphenylphosphino)ferrocene]palladium(II)dichloridedichloromethane complex (287 mg), and N-tert-butyloxycarbonyl-1,2,3,6-tetrahydropyridine-4-boronic acid pinacol ester (2.28 g) were added 1,4-dioxane (26 ml) and water (7 ml), and stirred at 110° C. for 6.5 hours. To the reaction solution was added water, and the obtained solid was washed with a mixed solution of n-hexane and ethyl acetate to give N-[6-(1-tert-butyloxycarbonyl-1,2,3,6-tetrahydropyridin-4-yl)pyridin-3-yl]-5-methyl-1-[5-(trifluoromethyl)pyridin-2-yl]-1H-pyrazole-4-carboxamide (3.53 g) as a brown solid.

MS (ESI) m/z: 529 (M+H)$^+$.

(3) To N-[6-(1-tert-butyloxycarbonyl-1,2,3,6-tetrahydropyridin-4-yl)pyridin-3-yl]-5-methyl-1-[5-(trifluoromethyl)pyridin-2-yl]-1H-pyrazole-4-carboxamide (3.53 g) were added dichloromethane (70 ml) and trifluoroacetic acid (14 ml), and stirred at room temperature for 4.5 hours. To the reaction solution was added 4 N aqueous solution of sodium hydroxide under ice-cooling, and the precipitated solid was purified with basic silica gel chromatography (chloroform/methanol) to give the titled compound (1.8 g) as a yellow solid. MS (ESI) m/z: 429 (M+H)$^+$.

Reference Example 173

5-Methyl-N-[6-(piperidin-4-yl)pyridin-3-yl]-1-[5-(trifluoromethyl)pyridin-2-yl]-1H-pyrazole-4-carboxamide (1) To 2,5-dibromopyridine (5.0 g), tetrakis(triphenylphosphine)palladium(0) (1.22 g), and N-tert-butyloxycarbonyl-1,2,3,6-tetrahydropyridine-4-boronic acid pinacol ester (8.16 g) were added 1,4-dioxane (42 ml) and 2M aqueous solution of sodium carbonate (26 ml), and stirred at 90° C. for 7 hours. To the reaction solution was added saturated sodium bicarbonate water, extracted with ethyl acetate, the organic layer was dried over anhydrous sodium sulfate, and then the solvent was evaporated in vacuo. The obtained residue was purified with basic silica gel chromatography (n-hexane/ethyl acetate) to give 4-(5-bromopyridin-2-yl)-1,2,3,6-tetrahydropyridine-1-carboxylic acid tert-butyl ester (6.45 g) as a pale yellow oil.

MS (ESI) m/z: 339, 341 (M+H)$^+$.

(2) To a suspension of 4-(5-bromopyridin-2-yl)-1,2,3,6-tetrahydropyridine-1-carboxylic acid tert-butyl ester (6.45 g), palladium(II) acetate (533 mg), (±)-2-(di-tert-butylphosphino)-1,1'-binaphthyl (1.48 g), and tert-butoxysodium (2.74 g) in toluene (47 ml) was added benzophenone imine (3.35 ml), stirred at 120° C. for 3 hours, then ethanol (50 ml), water (50 ml), hydroxylamine monohydrate (5.28 g), and sodium acetate (9.35 g) were added thereto at room temperature, and stirred at room temperature for 2.5 hours. To the reaction solution was added a saturated aqueous solution of sodium hydrogen carbonate, extracted with ethyl acetate, the organic layer was dried over anhydrous sodium sulfate, and then the solvent was evaporated in vacuo. The obtained residue was purified with basic silica gel chromatography (n-hexane/ethyl acetate) to give a mixture of 4-(5-aminopyridin-2-yl)-1,2,3,6-tetrahydropyridine-1-carboxylic acid tert-butyl ester and 4-(5-diphenylaminopyridin-2-yl)-1,2,3,6-tetrahydropyridine-1-carboxylic acid tert-butyl ester. To the obtained mixture were added ethanol (100 ml), water (50 ml), hydroxylamine monohydrate (2.64 g), and sodium acetate (4.67 g), and stirred at room temperature for 6.5 hours. To the reaction solution was added a saturated aqueous solution of sodium hydrogen carbonate, extracted with ethyl acetate, dried over anhydrous sodium sulfate, and then the solvent was evaporated in vacuo. The obtained residue was purified with basic silica gel chromatography (n-hexane/ethyl acetate). To the obtained oil were added 1,4-dioxane (15 ml) and 10% palladium carbon (containing about 50% water, 1.7 g), stirred at room temperature for 3.5 hours under hydrogen atmosphere, and then stirred at 40° C. for 12 hours. The reaction solution was filtered through Celite, then the solvent was evaporated in vacuo, and the obtained residue was purified with basic silica gel chromatography (chloroform/methanol) to give 4-(5-aminopyridin-2-yl)piperidine-1-carboxylic acid tert-butyl ester (2.8 g) as a yellow oil.

MS (ESI) m/z: 278 (M+H)⁺.

(3) To a suspension of 5-methyl-1-[5-(trifluoromethyl)pyridin-2-yl]-1H-pyrazole-4-carboxylic acid (3.0 g) described in Reference Example 8 in toluene (37 ml) were added N,N-dimethylformamide (catalytic amount) and thionyl chloride (2.2 ml), stirred at 80° C. for 8.5 hours, and then the solvent was evaporated in vacuo. To a solution of the residue in pyridine (20 ml) was added a solution of 4-(5-aminopyridin-2-yl)piperidine-1-carboxylic acid tert-butyl ester (2.8 g) in pyridine (17 ml), stirred at 80° C. for 5 hours, then additionally, 5-methyl-1-[5-(trifluoromethyl)pyridin-2-yl]-1H-pyrazole-4-carboxylic acid chloride (980 mg) described in Reference Example 180 was added thereto, and stirred at 80° C. for 2 hours. To the reaction solution was added triethylamine (4.2 ml), then water was added thereto, and the precipitated solid was washed with water and ethyl acetate to give N-[6-O-tert-butyloxycarbonylpiperidin-4-yl)pyridin-3-yl]-5-methyl-1-[5-(trifluoromethyl)pyridin-2-yl]-1H-pyrazole-4-carboxamide (4.0 g) as a yellow solid.

MS (ESI) m/z: 531 (M+H)⁺.

(4) To N-[6-(1-tert-butyloxycarbonylpiperidin-4-yl)pyridin-3-yl]-5-methyl-1-[5-(trifluoromethyl)pyridin-2-yl]-1H-pyrazole-4-carboxamide (4.0 g) were added dichloromethane (75 ml) and trifluoroacetic acid (15 ml), stirred at room temperature for 2.5 hours, and then to the reaction solution was added 4 N aqueous solution of sodium hydroxide under ice-cooling. The precipitated solid was washed with water and ethyl acetate to give the titled compound (2.9 g) as a pale yellow solid.

MS (ESI) m/z: 431 (M+H)⁺.

Reference Example 174

5-Methyl-1-(pyridin-2-yl)-1H-pyrazole-4-carboxylic acid

To a solution of 1-(5-bromopyridin-2-yl)-5-methyl-1H-pyrazole-4-carboxylic acid (30 mg) described in Reference Example 24 in N,N-dimethylformamide (1 ml) was added 10% palladium carbon (containing about 50% water) (10 mg) at room temperature, and stirred at the same temperature for 30 minutes under hydrogen atmosphere. After completion of the reaction, the reaction solution was filtered through Celite, then the solvent was evaporated in vacuo, azeotropically concentrated together with toluene to give the titled compound (23 mg) as a white solid.

MS (ESI) m/z: 204 (M+H)⁺.

Reference Example 175

5-Methyl-1-[4-methyl-5-(trifluoromethyl)pyridin-2-yl]-1H-pyrazole-4-carboxylic acid (1) To a solution of hydrazine hydrate (100%) (12.7 ml) in ethanol (600 ml) was added dropwise a solution of 2-chloro-4-methyl-5-nitropyridine (16.5 g) in ethanol (200 ml), and stirred at room temperature for 2 hours. After completion of the reaction, water (500 ml) was added thereto, and the solvent was evaporated in vacuo. The precipitated solid was collected by filtration, and washed with water to give a yellow solid.

(2) The obtained yellow solid and ethyl (2-ethoxymethylene)acetoacetate (17.8 g) synthesized according to the method described in J. Chem. Soc. Perkin trans. I, p. 1875 (1988) were added to a mixed solvent of 1 N hydrochloric acid aqueous solution (430 ml) and ethanol (650 ml), and stirred for 3 hours under reflux. After completion of the reaction, the mixture was allowed to cool, the precipitated solid was collected by filtration, washed with ethanol, and then heat-dried in vacuo at 60° C. to give 5-methyl-1-(4-methyl-5-nitropyridin-2-yl)-1H-pyrazole-4-carboxylic acid ethyl ester (22.4 g) as a pale yellow solid.

MS (ESI) m/z: 291 (M+H)⁺.

(3) To a solution of 5-methyl-1-(4-methyl-5-nitropyridin-2-yl)-1H-pyrazole-4-carboxylic acid ethyl ester (22.3 g) in ethanol (600 ml) and acetic acid (50 ml) was added palladium carbon (1.0 g), and stirred at room temperature for 6 hours under hydrogen atmosphere (1 atm). After completion of the reaction, the mixture was filtered through Celite, then the filtrate was concentrated, and the obtained residue was dissolved in chloroform. The organic layer was washed with saturated sodium bicarbonate water and water sequentially, dried over anhydrous sodium sulfate, and then the solvent was evaporated. To the obtained residue was added a small amount of diethyl ether and n-hexane, the precipitated solid was collected by filtration, and heat-dried in vacuo at 60° C. to give 1-(5-amino-4-methylpyridin-2-yl)-5-methyl-1H-pyrazole-4-carboxylic acid ethyl ester (18.3 g) as a pale yellow solid.

MS (ESI) m/z: 261 (M+H)⁺.

(4) 1-(5-Amino-4-methylpyridin-2-yl)-5-methyl-1H-pyrazole-4-carboxylic acid ethyl ester (1.0 g) was suspended in 20% (v/v) sulfuric acid aqueous solution (75 ml), sodium nitrite (318 mg) was added thereto little by little under ice-cooling with stirring, and then stirred for 40 minutes under ice-cooling. Then, potassium iodide (1.27 g) was dissolved in water (12 ml), and the obtained aqueous solution was slowly added dropwise to the reaction solution under ice-cooling with stirring. After the completion of adding dropwise, the solution was stirred for 3 hours under ice-cooling, and then gradually warmed to room temperature. The reaction solution was poured into 10% sodium carbonate aqueous solution, the precipitated solid was collected by filtration, and dissolved in ethyl acetate. The organic layer was sequentially washed with sodium thiosulfate aqueous solution, water, and saturated brine, dried over anhydrous sodium sulfate, and then the solvent was evaporated to give 1-(5-iodo-4-methylpyridin-2-yl)-5-methyl-1H-pyrazole-4-carboxylic acid ethyl ester (1.16 g) as a brown solid.

MS (ESI) m/z: 372 (M+H)⁺.

(5) 1-(5-Iodo-4-methylpyridin-2-yl)-5-methyl-1H-pyrazole-4-carboxylic acid ethyl ester (395 mg), copper(I) iodide (1.13 g), triethyl(trifluoromethyl)silane (1.11 ml), and potassium fluoride (345 mg) were suspended in N,N-dimethylformamide (6.2 ml) and N-methylpyrrolidone (6.2 ml), and stirred at 70° C. for 9 hours. After completion of the reaction, the mixture was allowed to cool, extracted with ethyl acetate, the obtained organic layer was sequentially washed with 28% ammonia water, water, and saturated brine, dried over anhydrous sodium sulfate, and then the solvent was evaporated. The obtained residue was purified with silica gel column chromatography (n-hexane/ethyl acetate) to give 5-methyl-1-[4-methyl-5-(trifluoromethyl)pyridin-2-yl]-1H-pyrazole-4-carboxylic acid ethyl ester (271 mg) as a white solid.

MS (ESI) m/z: 314 (M+H)$^+$.

(6) 5-Methyl-1-[4-methyl-5-(trifluoromethyl)pyridin-2-yl]-1H-pyrazole-4-carboxylic acid ethyl ester (270 mg) was dissolved in tetrahydrofuran (5 ml), 1 N aqueous solution of sodium hydroxide (5 ml) was added thereto, and stirred at 80° C. for 4 hours. After completion of the reaction, the solvent was evaporated, to the aqueous layer was added concentrated hydrochloric acid under ice-cooling to adjust the layer to pH 5, the precipitated solid was collected by filtration, and dried at 60° C. under air blow to give the titled compound (204 mg) as a white solid.

MS (ESI) m/z: 286 (M+H)$^+$.

Reference Example 176

5-Methyl-1-[5-(trifluoromethyl)pyridin-2-yl]-1H-[1,2,3] triazole-4-carboxylic acid (1) To a solution of 2-chloro-5-(trifluoromethyl)pyridine (3.0 g) in dimethylsulfoxide (80 ml) was added sodium azide (1.61 g) at room temperature, and stirred at 70° C. for 8.5 hours. After completion of the reaction, to the reaction solution was added ethyl acetate, and washed with water and a saturated aqueous solution of sodium chloride. The organic layer was dried over anhydrous magnesium sulfate, and then the solvent was evaporated to give 2-azide-5-trifluoromethylpyridine (2.22 g) as a yellow solid.

(2) To a solution of 2-azide-5-(trifluoromethyl)pyridine (1.09 g) in ethanol (15 ml) were added 3-oxobutanoic acid ethyl ester (754 mg) and sodium ethoxide (1.18 g) at room temperature, and stirred at 70° C. for 40 minutes. After completion of the reaction, to the reaction solution was added ethyl acetate, and washed with water and a saturated aqueous solution of sodium chloride. The organic layer was dried over anhydrous magnesium sulfate, and then solvent was evaporated. The obtained residue was purified with silica gel column chromatography (hexane:ethyl acetate) to give 5-methyl-1-[5-(trifluoromethyl)pyridin-2-yl]-1H-[1,2,3]triazole-4-carboxylic acid ethyl ester (692 mg) as a white solid.

(3) To a solution of 5-methyl-1-[5-(trifluoromethyl)pyridin-2-yl]-1H-[1,2,3]triazole-4-carboxylic acid ethyl ester (681 mg) in tetrahydrofuran (10 ml) was added 1 N aqueous solution of sodium hydroxide (10 ml) at room temperature, and stirred at 80° C. for 9 hours. After completion of the reaction, 1 N hydrochloric acid aqueous solution (10 ml) was added thereto, and the solvent was evaporated. The obtained residue was washed with water, and dried in vacuo to give the titled compound (396 mg) as a brown solid.

MS (ESI) m/z: 273 (M+H)$^+$.

Reference Example 177

3-Methyl-2-[4-(trifluoromethyl)phenyl]-3H-imidazole-4-carboxylic acid (1) To 2-bromo-3-methyl-3H-imidazole-4-carboxylic acid methyl ester (800 mg) were added 4-(trifluoromethyl)phenylboronic acid (1.04 g), and tetrakis(triphenylphosphine)palladium(0) (422 mg), and tetrahydrofuran (9 ml), saturated sodium carbonate water (3 ml), and water (1.5 ml) as solvents, and stirred at 120° C. for 30 minutes under microwave radiation. After completion of the reaction, to the reaction solution 6 was added water, and extracted with ethyl acetate. The organic layer was dried over anhydrous magnesium sulfate, and then the solvent was evaporated. The obtained residue was purified with silica gel column chromatography (n-hexane/ethyl acetate) to give 3-methyl-2-[4-(trifluoromethyl)phenyl]-3H-imidazole-4-carboxylic acid methyl ester (980 mg) as a yellow solid.

(2) To a solution of 3-methyl-2-[4-(trifluoromethyl)phenyl]-3H-imidazole-4-carboxylic acid methyl ester (962 mg) in tetrahydrofuran (10 ml) was added 1 N aqueous solution of sodium hydroxide (10 ml) at room temperature, and stirred at 80° C. for 1.5 hours. After completion of the reaction, 1 N hydrochloric acid aqueous solution (10 ml) was added thereto, and the solvent was evaporated. The obtained residue was washed with water, and dried in vacuo to give the titled compound (788 mg) as a gray solid.

MS (ESI) m/z: 271 (M+H)$^+$.

Reference Example 178

2-[4-(Trifluoromethyl)phenyl]thiazole-4-carboxylic acid ethyl ester

To a solution of 4-(trifluoromethyl)thiobenzamide (5.24 g) in ethanol (50 ml) was added 90% ethyl bromopyruvate (5.53 g), and stirred at 80° C. for 2.5 hours. After completion of the reaction, the solvent was evaporated, and water was added thereto. The insoluble matter was collected by filtration, and then dried to give the titled compound (7.56 g) as a white solid.

MS (ESI) m/z: 302 (M+H)$^+$.

Reference Example 179

2-[4-(Trifluoromethyl)phenyl]-1H-imidazole-4-carboxylic acid (1) To a solution of 4-(trifluoromethyl)benzonitrile (10 g) in ethanol (100 ml) was added 50% hydroxylamine aqueous solution (11.6 g), and stirred at 80° C. overnight. After completion of the reaction, the solvent was evaporated, and water was added thereto. The insoluble matter was collected by filtration, and then dried to give N-hydroxy-4-(trifluoromethyl)benzamidine (12.6 g).

(2) To a solution of N-hydroxy-4-(trifluoromethyl)benzamidine (3.0 g) in ethanol (30 ml) was added ethyl acetylenecarboxylate (1.44 g), and stirred at 80° C. for 26 hours. After the solvent was evaporated, diphenylether (15 ml) was added thereto, and additionally stirred at 180° C. for 5.5 hours. After completion of the reaction, the mixture was allowed to cool to room temperature, and n-hexane was added thereto. The insoluble matter was collected by filtration, washed with n-hexane, and then dried to give 2-[4-(trifluoromethyl)phenyl]-1H-imidazole-4-carboxylic acid ethyl ester (1.84 g).

(3) To a solution of 2-[4-(trifluoromethyl)phenyl]-1H-imidazole-4-carboxylic acid ethyl ester (300 mg) in methanol (4 ml) was added 1 N aqueous solution of sodium hydroxide (4 ml) at room temperature, and stirred at 80° C. for 6.5 hours. After completion of the reaction, 1 N hydrochloric acid aqueous solution (4 ml) was added thereto, and the solvent was evaporated. The obtained residue was washed with water, and dried in vacuo to give the titled compound (141 mg) as a pale brown solid.

MS (ESI) m/z: 257 (M+H)$^+$.

Reference Example 180

5-Methyl-1-[5-(trifluoromethyl)pyridin-2-yl]-1H-pyrazole-4-carboxylic acid chloride

To a solution of 5-methyl-1-[5-(trifluoromethyl)pyridin-2-yl]-1H-pyrazole-4-carboxylic acid (40.0 g) described in Reference Example 8 in toluene (147 ml) were added N,N-dimethylformamide (catalyst quantity) and thionyl chloride (52.6 g) at room temperature, and stirred at 80° C. for 4.5 hours. After completion of the reaction, the solvent and excessive thionyl chloride were evaporated, azeotropy was performed with toluene twice, and then dried in vacuo to give the titled compound as a pale yellow solid.
$^1$H-NMR (400 MHz, CDCl$_3$) δ: 3.00 (3H, s), 8.08-8.16 (2H, m), 8.20 (1H, s), 8.79 (1H, s).

Reference Example 181

N-(6-Bromo-2-methylpyridin-3-yl)-5-methyl-1-[5-(trifluoromethyl)pyridin-2-yl]-1H-pyrazole-4-carboxamide

To a solution of 5-amino-2-bromo-6-picoline (701 mg) and triethylamine (1.57 ml) in tetrahydrofuran (20 ml) was added 5-methyl-1-[5-(trifluoromethyl)pyridin-2-yl]-1H-pyrazole-4-carboxylic acid chloride (1.34 g) described in Reference Example 180 under ice-cooling, and stirred at room temperature for 1.5 hours. After completion of the reaction, the solvent was evaporated, and saturated sodium bicarbonate water was added thereto. The insoluble matter was collected by filtration, washed with water, and then dried in vacuo to give the titled compound as a pale yellow solid (1.66 g). MS (ESI) m/z: 440 (M+H)$^+$.

Reference Example 182

N-(6-Bromo-4-methylpyridin-3-yl)-5-methyl-1-[5-(trifluoromethyl)pyridin-2-yl]-1H-pyrazole-4-carboxamide

5-Amino-2-bromo-4-methylpyridine (1.02 g) was used, and reacted and treated in the same method as Reference Example 181 to give the titled compound as a white solid (771 mg).
MS (ESI) m/z: 440 (M+H)$^+$.

Reference Example 183

N-(6-Chloro-5-methoxypyridin-3-yl)-5-methyl-1-[5-(trifluoromethyl)pyridin-2-yl]-1H-pyrazole-4-carboxamide

5-Amino-2-chloro-3-methoxypyridine (500 mg) was used, and reacted and treated in the same method as Reference Example 181 to give the titled compound as a white solid (851 mg). MS (ESI) m/z: 412 (M+H)$^+$.

Reference Example 184

N-[6-Chloro-5-(trifluoromethyl)pyridin-3-yl]-5-methyl-1-[5-(trifluoromethyl)pyridin-2-yl]-1H-pyrazole-4-carboxamide

5-Amino-2-chloro-3-trifluoromethylpyridine (1.17 g) was used, and reacted and treated in the same method as Reference Example 181 to give the titled compound as a white solid (569 mg). MS (APCI) m/z: 450 (M+H)$^+$.

Reference Example 185

N-(1,4-Dioxaspiro[4,5]dec-8-yl)-2,2,N-trimethylpropionamide

(1) To a solution of 1,4-dioxaspiro[4,5]decan-8-one (10.0 g) and acetic acid (4.4 ml) in dichloromethane (128 ml) were added methylamine hydrochloride (5.19 g) and sodium triacetoxyborohydride (16.3 g), and stirred at room temperature for 2.5 hours. After completion of the reaction, 4 N aqueous solution of sodium hydroxide (90 ml) was added thereto, and extracted with dichloromethane. The organic layer was dried over sodium sulfate, and then the solvent was evaporated to give (1,4-dioxaspiro[4,5]dec-8-yl)methylamine as an orange oil (11.0 g).

(2) To a solution of (1,4-dioxaspiro[4,5]dec-8-yl)methylamine (11.0 g) in pyridine (64 ml) were added 4-dimethylaminopyridine (catalyst quantity) and pivalic acid anhydride (26.0 ml), and stirred at 90° C. for 2 hours. After completion of the reaction, the solvent was evaporated, ethyl acetate was added thereto, and sequentially washed with 1 N hydrochloric acid aqueous solution, 1 N aqueous solution of sodium hydroxide, and saturated brine. The organic layer was dried over sodium sulfate, then the solvent was evaporated, and the obtained residue was purified with silica gel column chromatography (n-hexane/ethyl acetate) to give the titled compound (12.9 g) as a pale brown oil. MS (ESI) m/z: 256 (M+H)$^+$.

Reference Example 186

2,2,N-Trimethyl-N-(4-oxocyclohexyl)propionamide

To N-(1,4-dioxaspiro[4,5]dec-8-yl)-2,2,N-trimethylpropionamide (12.5 g) was added 6 N hydrochloric acid aqueous solution (50 ml), and stirred at room temperature for 1 hour. After completion of the reaction, 12 N aqueous solution of sodium hydroxide (25 ml) was added thereto, and extracted with ethyl acetate. The organic layer was dried over sodium sulfate, and then the solvent was evaporated. To the obtained residue was added diisopropyl ether, the insoluble matter was collected by filtration, and then dried to give the titled compound (7.25 g) as a white solid. MS (ESI) m/z: 212 (M+H)$^+$.

Reference Example 187

4-[4-(5-Bromo-3-methylpyridin-2-yl)cyclohex-3-en-1-yl]morpholin-3-one

(1) 5-Bromo-2-(1,4-dioxaspiro[4.5]dec-7-en-8-yl)-3-methylpyridine (21.1 g) described in Reference Example 105 was dissolved in concentrated hydrochloric acid (64.5 ml) and water (64.5 ml), and stirred at room temperature. After completion of the reaction, the reaction solution was ice-cooled, 10% sodium carbonate aqueous solution was added thereto to adjust the solution to pH 8, the precipitated solid was collected by filtration, washed with water, and then dried under air blow. The obtained solid was dissolved in ethanol, and the solvent was evaporated. This procedure was repeated twice, then to the obtained residue were added n-hexane and a small amount of ethyl acetate, washed, collected by filtration, and heat-dried in vacuo to give 4-(5-bromo-3-methylpyridin-2-yl)cyclohex-3-en-1-one (8.26 g) as a pale yellow solid. MS (ESI) m/z: 266, 268 (M+H)$^+$.

(2) To a solution of 4-(5-bromo-3-methylpyridin-2-yl)cyclohex-3-en-1-one (2.06 g) in dichloromethane (50 ml) was added 2-aminoethanol (0.463 ml) at room temperature with stirring. Then sodium triacetoxyborohydride (1.64 g) was added thereto, and stirred at the same temperature. After completion of the reaction, to the reaction solution was added 10% sodium carbonate aqueous solution, and extracted with chloroform. The organic layer was dried over anhydrous sodium sulfate, and then the solvent was evaporated. The obtained residue was purified with silica gel column chromatography (chloroform/methanol), and then suspended and washed with a mixed solvent of a small amount of diethyl ether and n-hexane to give 2-[4-(5-bromo-3-methylpyridin-2-yl)cyclohex-3-en-1-yl]amino ethanol (860 mg) as a light brown solid.

MS (ESI) m/z: 311, 313 (M+H)$^+$.

(3) To a solution of 2-[4-(5-bromo-3-methylpyridin-2-yl)cyclohex-3-en-yl]aminoethanol (860 mg) and triethylamine (0.424 ml) in dichloromethane (10 ml) was added chloroacetic acid chloride (0.242 ml) under ice-cooling with stirring. The mixture was stirred at the same temperature for 1 hour, then water was added thereto, and extracted with chloroform. The organic layer was dried over anhydrous sodium sulfate, and then the solvent was evaporated. The obtained residue was dissolved in isopropyl alcohol (10 ml), and hydroxide potassium (129 mg) was added thereto at room temperature with stirring. The mixture was stirred at the same temperature for 8 hours, and then to the reaction solution was added water, and extracted with chloroform. The organic layer was dried over anhydrous sodium sulfate, and then the solvent was evaporated. The obtained residue was purified with silica gel column chromatography (n-hexane/ethyl acetate) to give the titled compound (855 mg) as a white solid.

MS (ESI) m/z: 351, 353 (M+H)$^+$.

Reference Example 188

1-[2,6-Dichloro-4-(trifluoromethyl)phenyl]-5-methyl-1H-pyrazole-4-carboxylic acid (1) [2,6-Dichloro-4-(trifluoromethyl)phenyl]hydrazine (5 g) and ethyl (2-ethoxymethylene)acetoacetate (3.8 g) synthesized according to the method described in J. Chem. Soc. Perkin trans. I, p. 1875 (1988) were added to a mixed solvent of 1 N hydrochloric acid aqueous solution (90 ml) and ethanol (100 ml), and stirred for 4 hours under reflux. After completion of the reaction, the mixture was allowed to cool, ethanol was evaporated, and extracted with ethyl acetate. The organic layer was washed with saturated brine, dried over anhydrous sodium sulfate, and then the solvent was evaporated. The obtained residue was purified with silica gel column chromatography (n-hexane/ethyl acetate) to give 1-[2,6-dichloro-4-(trifluoromethyl)phenyl]-5-methyl-1H-pyrazole-4-carboxylic acid ethyl ester (5.83 g) as a yellow oil. MS (ESI) m/z: 367, 369 (M+H)$^+$.

(2) To a solution of 1-[2,6-dichloro-4-(trifluoromethyl)phenyl]-5-methyl-1H-pyrazole-4-carboxylic acid ethyl ester (5.83 g) in tetrahydrofuran (20 ml) and methanol (20 ml) was added 4 N aqueous solution of sodium hydroxide (30 ml), and stirred at room temperature. After completion of the reaction, the solvent was evaporated, to the aqueous layer was added concentrated hydrochloric acid under ice-cooling to adjust the layer to pH 5, the precipitated solid was collected by filtration, and dried at 60° C. under air blow to give the titled compound (4.89 g) as a white solid. MS (ESI) m/z: 339, 341 (M+H)$^+$.

Reference Example 189

N-(6-Bromo-5-methylpyridin-3-yl)-5-methyl-1-[5-(trifluoromethyl)pyridin-2-yl]-1H-pyrazole-4-carboxamide (1) To a suspension of 2-bromo-3-methyl-5-nitropyridine (10.01 g), isopropanol (130 ml), water (26 ml) and iron (12.9 g) was added acetic acid (5.27 ml), and stirred at 80° C. for 3.5 hours. To the reaction solution was added potassium carbonate (13.37 g), filtered through Celite, then extracted with ethyl acetate, washed with saturated brine, dried over anhydrous sodium sulfate, and the solvent was evaporated in vacuo. The precipitated solid was collected by filtration to give 5-amino-2-bromo-3-methylpyridine (6.66 g) as a gray solid. MS (ESI) m/z: 187, 189 (M+H)$^+$.

(2) To a suspension of 5-methyl-1-[5-(trifluoromethyl)pyridin-2-yl]-1H-pyrazole-4-carboxylic acid (6.51 g) described in Reference Example 8 in toluene (67 ml) were added N,N-dimethylformamide (0.50 ml) and thionyl chloride (4.4 ml), stirred at 80° C. for 2.5 hours, and then the solvent was evaporated in vacuo. To a solution of the residue in pyridine (30 ml) was added a solution of 5-amino-2-bromo-3-methylpyridine (3.74 g) in pyridine (30 ml), and stirred at 40° C. for 3 hours. To the reaction solution was added triethylamine (14 ml), then water was added thereto, and the precipitated solid was washed with ethanol and water to give the titled compound (5.76 g) as a white solid.

MS (ESI) m/z: 440, 442 (M+H)$^+$.

The structural formulae of Reference Examples 139-189 are shown below.

| Reference example No | Structure |
|---|---|
| 139 | 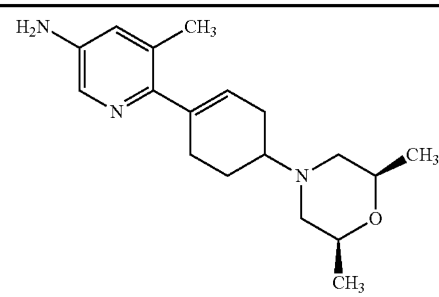 |
| 140 | 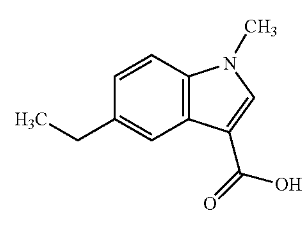 |
| 141 | 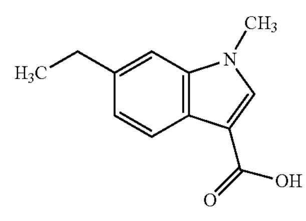 |

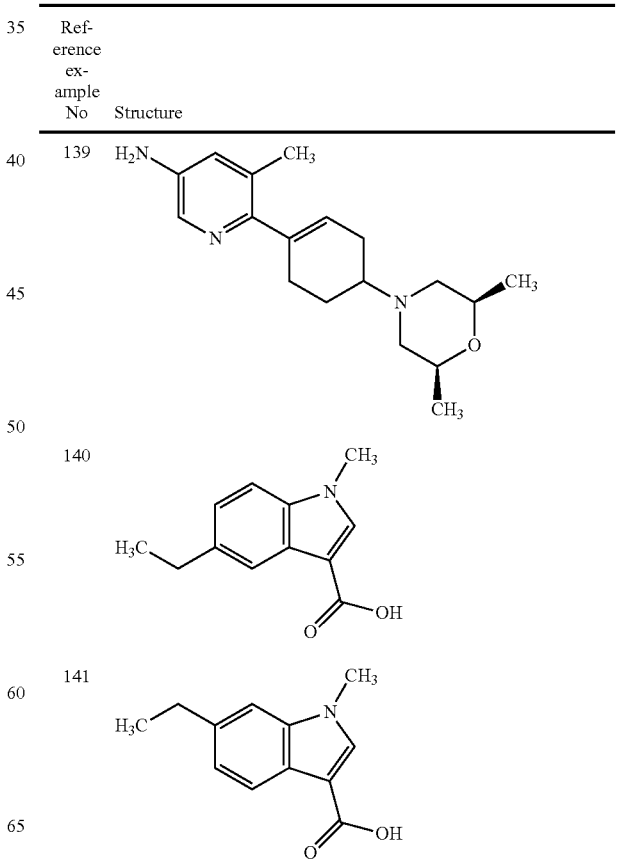

| Reference example No | Structure |
|---|---|
| 142 | (4-aminopyridin-2-yl)cyclohexane with ethyl ester and morpholine substituents |
| 143 | 5-amino-3-methylpyridin-2-yl cyclohexenyl with N-methyl-N-Boc amine |
| 144 | 5-aminopyridin-2-yl cyclohexane with nitrile and O-TBS ether |
| 145 | 5-amino-3-methylpyridin-2-yl cyclohexenyl with N-methyl pivalamide |
| 146 | 5-amino-3-methylpyridin-2-yl cyclohexenyl with N-methyl trifluoroacetamide |
| 147 | 5-amino-3-methylpyridin-2-yl cyclohexenyl with N-methyl isobutyramide |

| Reference example No | Structure |
|---|---|
| 148 | 5-aminopyridin-2-yl cyclohexane with nitrile, OH and CH₃ |
| 149 | 5-aminopyridin-2-yl cyclohexane with nitrile, OH and CH₃ (stereoisomer) |
| 150 | 5-aminopyridin-2-yl cyclohexane with nitrile, OH and vinyl |
| 151 | 5-aminopyridin-2-yl cyclohexane with nitrile, OH and vinyl (stereoisomer) |
| 152 | 5-amino-3-methylpyridin-2-yl cyclohexenyl with N-tert-butyl carboxamide |
| 153 | 5-aminopyridin-2-yl spiro[cyclohexane-dihydrofuran] with nitrile |

| Reference example No | Structure |
|---|---|
| 154 | 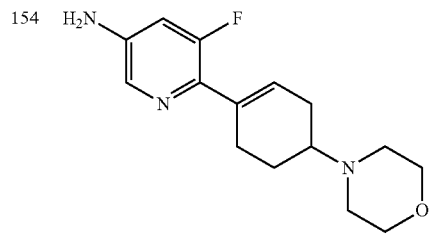 |
| 155 | 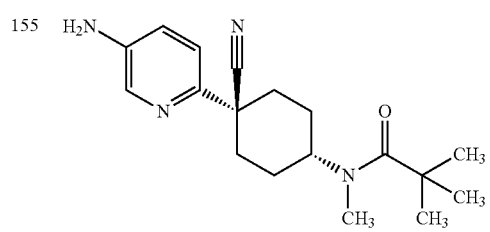 |
| 156 | 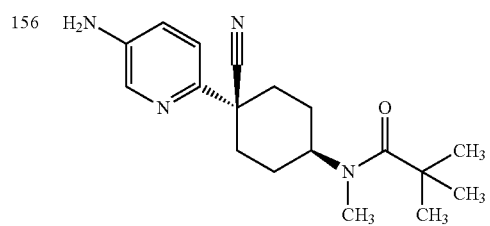 |
| 157 | 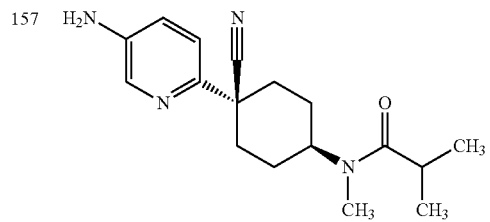 |
| 158 | 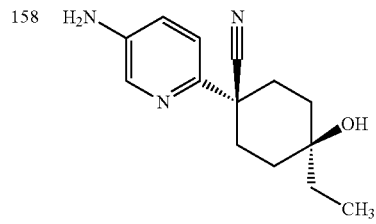 |
| 159 | 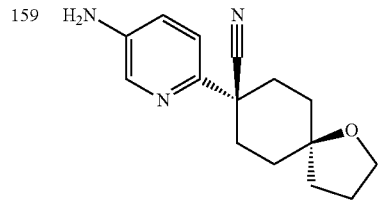 |
| 160 | 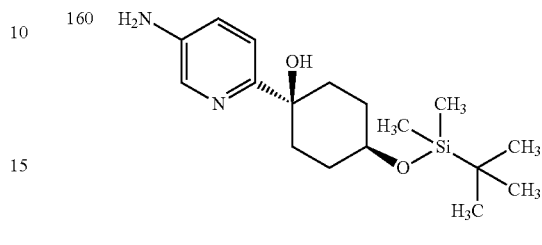 |
| 161 | 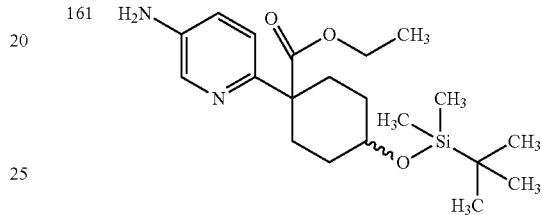 |
| 162 | 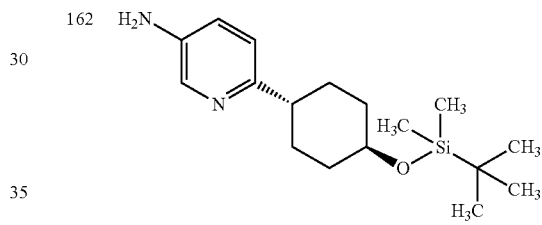 |
| 163 | 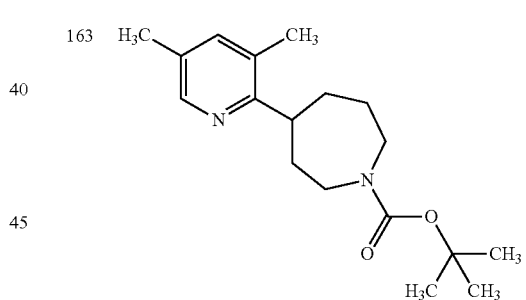 |
| 164 | 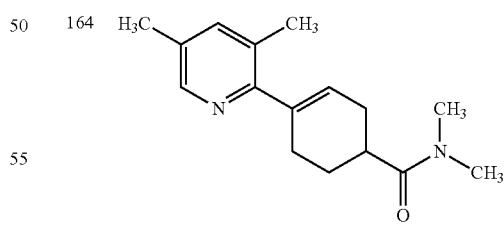 |
| 165 | 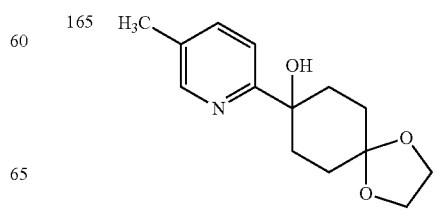 |

| Reference example No | Structure |
|---|---|
| 166 | (pinacol boronate)-cyclohexenyl-morpholine |
| 167 | (pinacol boronate)-cyclohexenyl-N(CH₃)C(O)C(CH₃)₃ |
| 168 | 5-bromo-2-(1-cyano-4-ethoxycyclohexyl)pyridine |
| 169 | 1-(5-(trifluoromethyl)pyridin-2-yl)-5-methyl-N-(6-(4-cyanopiperidin-4-yl)pyridin-3-yl)-1H-pyrazole-4-carboxamide |
| 170 | 1-(5-(trifluoromethyl)pyridin-2-yl)-5-methyl-N-(5-methyl-6-(1,2,3,6-tetrahydropyridin-4-yl)pyridin-3-yl)-1H-pyrazole-4-carboxamide |
| 171 | 1-(5-(trifluoromethyl)pyridin-2-yl)-5-methyl-N-(5-methyl-6-(piperidin-4-yl)pyridin-3-yl)-1H-pyrazole-4-carboxamide |

| Reference example No | Structure |
|---|---|
| 172 | 1-(5-(trifluoromethyl)pyridin-2-yl)-5-methyl-N-(6-(1,2,3,6-tetrahydropyridin-4-yl)pyridin-3-yl)-1H-pyrazole-4-carboxamide |
| 173 | 1-(5-(trifluoromethyl)pyridin-2-yl)-5-methyl-N-(6-(piperidin-4-yl)pyridin-3-yl)-1H-pyrazole-4-carboxamide |
| 174 | 1-(pyridin-2-yl)-5-methyl-1H-pyrazole-4-carboxylic acid |
| 175 | 1-(4-methyl-5-(trifluoromethyl)pyridin-2-yl)-5-methyl-1H-pyrazole-4-carboxylic acid |
| 176 | 1-(5-(trifluoromethyl)pyridin-2-yl)-5-methyl-1H-1,2,3-triazole-4-carboxylic acid |
| 177 | 2-(4-(trifluoromethyl)phenyl)-1-methyl-1H-imidazole-5-carboxylic acid |
| 178 | ethyl 2-(4-(trifluoromethyl)phenyl)thiazole-4-carboxylate |
| 179 | 2-(4-(trifluoromethyl)phenyl)-1H-imidazole-4-carboxylic acid |
| 180 | 1-(5-(trifluoromethyl)pyridin-2-yl)-5-methyl-1H-pyrazole-4-carbonyl chloride |

159
-continued

| Reference example No | Structure |
|---|---|
| 181 | ![structure 181] |
| 182 | ![structure 182] |
| 183 | ![structure 183] |
| 184 | ![structure 184] |
| 185 | ![structure 185] |
| 186 | ![structure 186] |
| 187 | ![structure 187] |
| 188 | ![structure 188] |

160
-continued

| Reference example No | Structure |
|---|---|
| 189 | ![structure 189] |

Example D1

N-{6-[r-1-Cyano-c-4-(morpholin-4-yl)cyclohexyl]pyridin-3-yl}-5-methyl-1-[5-(trifluoromethyl)pyridin-2-yl]-1H-pyrazole-4-carboxamide hydrochloride

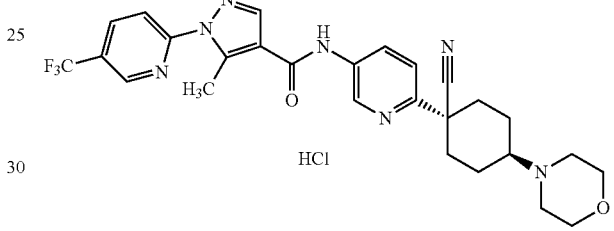

Dimethylformamide (0.05 ml) and thionyl chloride (0.32 g) were added to a suspension of 5-methyl-1-[5-(trifluoromethyl)pyridin-2-yl]-1H-pyrazole-4-carboxylic acid (0.5 g) in toluene (3 ml), and stirred at 80° C. for an hour. The solvent was evaporated in vacuo, a solution of 1-(5-aminopyridin-2-yl)-c-4-(morpholin-4-yl)-r-1-cyclohexanecarbonitrile (0.63 g) in N-methyl-2-pyrrolidone (5 ml) was added to the residue and stirred at 40° C. for two hours. The reaction solution was treated with triethylamine, water (20 ml) was added and the precipitated solid was collected, which was suspended in ethanol and then dissolved by the addition of 2N hydrochloric acid-ethanol at 80° C. The solution was filtered and cooled to give the titled compound (0.43 g).

MS (ESI) m/z: 540 (M+H)$^+$.

Example D2

N-{6-[r-1-Cyano-c-4-(morpholin-4-yl)cyclohexyl]pyridin-3-yl}-5-methyl-1-(4-methylphenyl)-1H-pyrazole-4-carboxamide hydrochloride

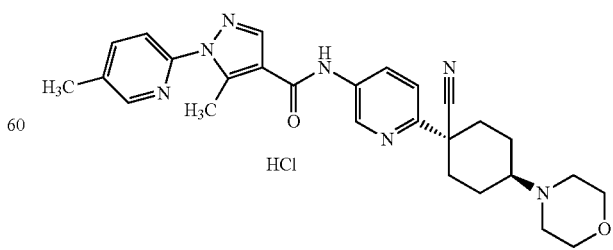

5-Methyl-1-(4-methylphenyl)-1H-pyrazole-4-carboxylic acid described in Reference Example 4 was used in place of 5-methyl-1-[5-(trifluoromethyl)pyridin-2-yl]-1H-pyrazole-carboxylic acid in Example D1, and reacted and treated to give the titled compound.

MS (ESI) m/z: 485 (M+H)+.

Example D3

N-{6-[r-1-Cyano-c-4-(methoxymethoxy)cyclohexyl]pyridin-3-yl}-5-methyl-1-(4-methylphenyl)-1H-pyrazole-4-carboxamide

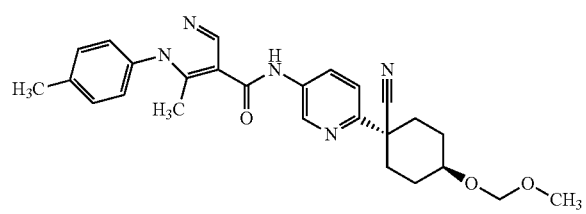

Thionyl chloride (416 mg) and N,N-dimethylformamide (catalytic amounts) were added at room temperature to a solution of 5-methyl-1-(4-methylphenyl)-1H-pyrazole-4-carboxylic acid (473 mg) described in Reference Example 4 in toluene (3.0 ml) and stirred at 80° C. for an hour. The solvent and excess amounts of thioly chloride were evaporated in vacuo. To the reaction mixture, was added N-methylpiperidone (3.6 ml), and then a solution of 1-(5-aminopyridin-2-yl)-c-4-(methoxymethoxy)-r-1-cyclohexanecarbonitrile (600 mg) described in Reference Example 85 in N-methylpiperidone (3.0 ml), and stirred at 45° C. for an hour. After the reaction, triethylamine (0.7 ml) and water were added and extracted with 10% methanol/chloroform. The organic layer was dried over anhydrous sodium sulfate and concentrated. The resulting residue was purified with a silica gel column chromatography (n-hexane/ethyl acetate). Water was added to the purified product, stirred at 40° C. for an hour, cooled to room temperature and the precipitated solid was collected to give the titled compound (781 mg) as a white solid.

MS (ESI) m/z: 460 (M+H)+.

Example D4

8-[5-({[5-Methyl-1-(4-methylphenyl)-1H-pyrazol-4-yl]carbonyl}amino)pyridin-2-yl]-1,4-dioxaspiro[4.5]decane-8-carboxylic acid ethyl ester

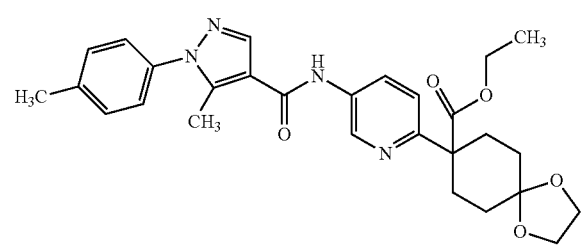 [SMILES: CCOC(=O)C1(c2ccc(NC(=O)c3cnn(-c4ccc(C)cc4)c3C)cn2)CCC2(CC1)OCCO2]

Thionyl chloride (185 mg) and N,N-dimethylformamide (catalytic amounts) were added at room temperature to a solution of 5-methyl-1-(4-methylphenyl)-1H-pyrazole-4-carboxylic acid (210 mg) described in Reference Example 4 in toluene (3.0 ml) and stirred at 80° C. for an hour. The solvent and excess amounts of thionyl chloride were evaporated. The resulting reaction mixture of a pyridine solution (1.5 ml) was added to a solution of 8-(5-aminopyridin-2-yl)-1,4-dioxaspiro[4.5]decane-8-carboxylic acid ethyl ester (312 mg) in pyridine (1.8 ml) and stirred at 40° C. for an hour. After the reaction, the reaction solution was cooled to room temperature, adjusted to pH 4-5 by the addition of 1N hydrochloric acid aqueous solution and extracted with ethyl acetate. The organic layer was washed with 1N hydrochloric acid aqueous solution, dried over anhydrous sodium sulfate and concentrated to give the titled compound (400 mg) as a white solid.

MS (ESI) m/z: 505 (M+H)+.

Example D5

1-(5-Cyclopropylpyridin-2-yl)-5-methyl-N-{6-[4-(morpholin-4-yl)cyclohex-1-en-1-yl]pyridin-3-yl}-1H-pyrazole-4-carboxamide mesylate

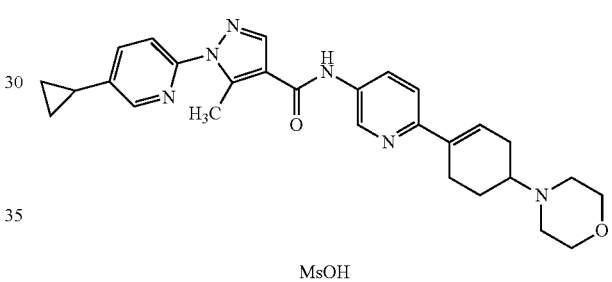

(1) Thionyl chloride (275 mg) and N,N-dimethylformamide (catalytic amounts) were added at room temperature to a solution of 1-(5-cyclopropylpyridin-2-yl)-5-methyl-1H-pyrazole-4-carboxylic acid (206 mg) described in Reference Example 118 in toluene (4.5 ml) and stirred at 80° C. for an hour. The solvent and excess amounts of thionyl chloride were evaporated. Pyridine (4.5 ml) was added to the resulting reaction mixture, a solution of 6-[4-(morpholin-4-yl)cyclohex-1-en-1-yl]pyridine-3-amine (200 mg) in pyridine (4.5 ml), and stirred at 50° C. for an hour. After the reaction, triethylamine (1.5 ml) and water was added and the precipitated solid was filtered. The resulting residue was purified with a silica gel column chromatography (chloroform/methanol) to give 1-(5-cyclopropylpyridin-2-yl)-5-methyl-N-{6-[4-(morpholin-4-yl)cyclohex-1-en-1-yl]pyridin-3-yl}-1H-pyrazole-4-carboxamide (322 mg) as a pink solid.

MS (ESI) m/z: 485 (M+H)+.

(2) Methanesulfonic acid (47 µl) was added at room temperature to a solution of 1-(5-cyclopropylpyridin-2-yl)-5-methyl-N-{6-[4-(morpholin-4-yl)cyclohex-1-en-1-yl]pyridin-3-yl}-1H-pyrazole-4-carboxamide (315 mg) in chloroform (6.3 ml) and methanol (0.7 ml) and stirred at the same temperature for 12 hours. After the reaction, the solvent was evaporated, ethyl acetate was added to the resulting residue and the precipitated solid was filtered to give the titled compound (340 mg) as a white solid.

MS (ESI) m/z: 485 (M+H)+.

Example D6 trans-5-Methyl-N-{6-[4-(morpholin-4-yl)cyclohexyl]pyridin-3-yl}-1-[5-(trifluoromethyl)-pyridin-2-yl]-1H-pyrazole-4-carboxamide mesylate

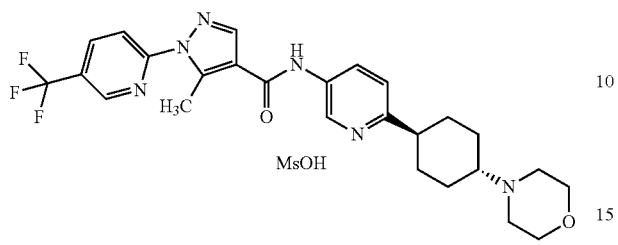

(1) Thionyl chloride (273 mg) and N,N-dimethylformamide (catalytic amounts) were added at room temperature to a solution of 5-methyl-1-[5-(trifluoromethyl)pyridin-2-yl]-5-methyl-1H-pyrazole-4-carboxylic acid (228 mg) described in Reference Example 8 in toluene (8.5 ml) and stirred at 80° C. for an hour, then the solvent and an excess amount of thionyl chloride were evaporated. Pyridine (4.0 ml) was added to the resulting reaction mixture, and a solution of trans-6-(4-(morpholin-4-yl)cyclohexyl)pyridine-3-amine (200 mg) described in Reference Example 80B in pyridine (4.5 ml) and stirred at 50° C. for an hour. After the reaction, triethylamine (1.5 ml) and water was added, the precipitated solid was filtered, and the resulting residue was purified with a silica gel column chromatography (chloroform/methanol) to give trans-5-methyl-N-{6-[4-(morpholin-4-yl)cyclohexyl]pyridin-3-yl}-1-[5-(trifluoromethyl)pyridin-2-yl]-1H-pyrazole-4-carboxamide (336 mg) as a white solid.

MS (ESI) m/z: 515 (M+H)$^+$.

(2) Methanesulfonic acid (46 µl) was added at room temperature to a solution of trans-5-methyl-N-{6-[4-(morpholin-4-yl)cyclohexyl]pyridin-3-yl}-1-[5-(trifluoromethyl)pyridin-2-yl]-1H-pyrazole-4-carboxamide (329 mg) in tetrahydrofuran (12 ml) and ethanol (6.0 ml), and stirred at the same temperature for five hours. After the reaction, the solvent was evaporated, ethyl acetate was added to the resulting residue and the precipitated solid was filtered to give the titled compound (389 mg) as a white solid.

MS (ESI) m/z: 515 (M+H)$^+$.

Example D7

N-{6-[r-1-Cyano-c-4-(morpholin-4-yl)cyclohexyl]pyridin-3-yl}-1-(3,5-dichloropyridin-2-yl)-5-methyl-1H-pyrazole-4-carboxamide hydrochloric acid salt

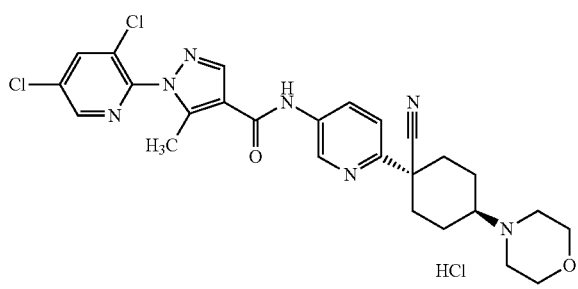 [SMILES: Cc1c(C(=O)Nc2ccc([C@]3(C#N)CC[C@@H](N4CCOCC4)CC3)nc2)cnn1-c1ncc(Cl)cc1Cl ; Cl]

Thionyl chloride (54 µl) was added at room temperature to a solution of 1-(3,5-dichloropyridin-2-yl)-5-methyl-1H-pyrazole-4-carboxylic acid (140 mg) described in Reference Example 22 in toluene (2.5 ml) and N,N-dimethylformamide (catalytic amounts) stirred at 80° C. for an hour, then the solvent was evaporated. To the residue dissolved in pyridine (2.5 ml), was added 1-(5-aminopyridin-2-yl)-c-4-(morpholin-4-yl)-r-1-cyclohexanecarbonitrile (170 mg) described in Reference Example 94 and stirred at 40° C. for three hours. Triethylamine (138 µl) and water were added, the precipitated solid was filtered and washed with ethanol. Ethanol (10 ml) and 2N hydrochloric acid-ethanol (4 ml) were added to the resulting solid and stirred at 40° C. The precipitated solid was washed with ethanol to give the titled compound (120 mg) as a white solid.

MS (ESI) m/z: 540 (M+H)$^+$

Example D8 cis-N-{6-[4-Cyano-1-(2-methyltetrahydrofuran-3-yl)piperidin-4-yl]pyridin-3-yl}-5-methyl-1-[5-(trifluoromethyl)pyridin-2-yl]-1H-pyrazole-4-carboxamide

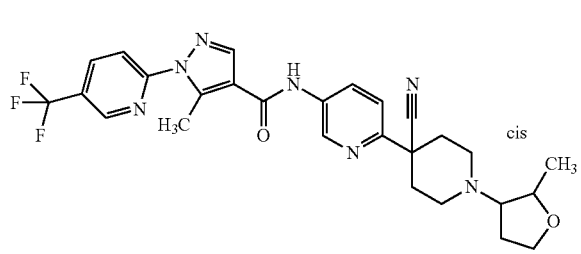 [SMILES: Cc1c(C(=O)Nc2ccc(C3(C#N)CCN(C4CCOC4C)CC3)nc2)cnn1-c1ccc(C(F)(F)F)cn1]

Thionyl chloride (184 µl) was added at room temperature to a mixed solution of 5-methyl-1-[5-(trifluoromethyl)pyridin-2-yl)-1H-pyrazole-4-carboxylic acid (240 mg) described in Reference Example 8 in toluene (2.5 ml) and N,N-dimethylformamide (catalytic amounts) and stirred at 80° C. for an hour, then the solvent was evaporated. A solution of cis-4-(5-aminopyridin-2-yl)-1-(2-methyltetrahydrofuran-3-yl)piperidine-4-carbonitrile (240 ml) described in Reference Example 88 in pyridine (2.5 ml) was added at 40° C. to a solution of the residue in pyridine (3.0 ml) and stirred for two hours. Triethylamine (585 µl) and water were added, the precipitated solid was filtered and washed with ethanol. Ethanol (10 ml) and 2N hydrochloric acid-ethanol (4 ml) were added, stirred at 40° C., the precipitated solid was filtered and washed with ethanol. Ethyl acetate and a saturated aqueous solution of sodium bicarbonate were added to the solid, extracted with ethyl acetate, and the organic layer was dried over anhydrous sodium sulfate. The solvent was evaporated in vacuo and the residue was washed with ethanol to give the titled compound (209 mg) as a white solid.

MS (ESI) m/z: 540 (M+H)$^+$.

Example D9

N-{6-[4-Cyano-1-(2-hydroxy-2-methylpropyl)piperidin-4-yl]pyridin-3-yl}-5-methyl-1-[5-(trifluoromethyl)pyridin-2-yl]-1H-pyrazole-4-carboxamide

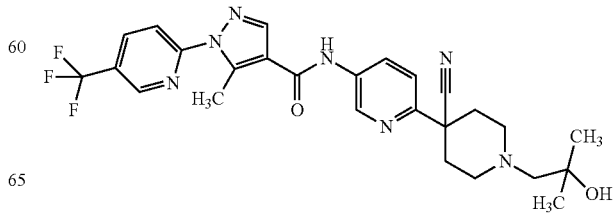

Thionyl chloride (164 μl) was added to a solution of 5-methyl-1-[5-(trifluoromethyl)pyridin-2-yl]-1H-pyrazole-4-carboxylic acid (243 mg) described in Reference Example 8 in toluene (2.5 ml) and N,N-dimethylformamide (catalytic amounts), and stirred at 80° C. for 1.5 hours. The solvent was evaporated and to a solution of the residue in pyridine (2.5 ml), was added a solution of 4-(5-aminopyridin-2-yl)-1-(2-hydroxy-2-methylpropyl)piperidine-4-carbonitrile (205 mg) described in Reference Example 96 in pyridine (2.5 ml) at 40° C. and stirred for 5 hours. Triethylamine (522 μl) and water were added and the precipitated solid was washed with ethyl acetate and ethanol to give the titled compound (343 mg) as a white solid.

MS (ESI) m/z: 528 (M+H)$^+$.

Example D10 cis-N-{6-[4-Cyano-1-(2-methyltetrahydrofuran-3-yl)piperidin-4-yl]pyridin-3-yl}-1-(5-cyclopropylpyridin-2-yl)-5-methyl-1H-pyrazole-4-carboxamide

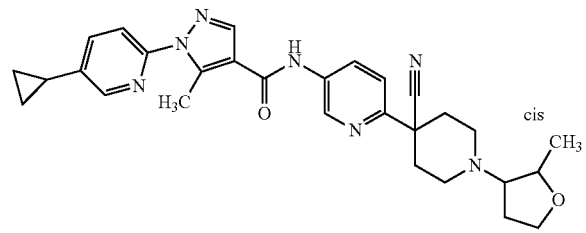 [SMILES: Cc1c(C(=O)Nc2ccc(C3(C#N)CCN(C4CCOC4C)CC3)nc2)cnn1-c1ccc(C2CC2)cn1]

Thionyl chloride (109 μl) was added to a solution of 1-(5-cyclopropylpyridin-2-yl)-5-methyl-1H-pyrazole-4-carboxylic acid (145 mg) described in Reference Example 118 in a mixture of toluene (2.5 ml) and N,N-dimethylformamide (catalytic amounts), stirred at 80° C. for four hours. The solvent was evaporated, the residue was dissolved in pyridine (2.5 ml), a solution of cis-4-(5-aminopyridin-2-yl)-1-(2-methyltetrahydrofuran-3-yl)piperidine-4-carbonitrile (143 mg) described in Reference Example 8 in pyridine (2.5 ml) was added thereto and stirred at 40° C. for 3.5 hours. Triethylamine (350 μl) and water were added and the precipitated solid was washed with a mixed solvent of ethyl acetate and n-hexane (1:2) to give the titled compound (218 mg) as a white solid.

MS (ESI) m/z: 512 (M+H)$^+$.

Example D11 cis-N-{6-[4-Cyano-1-(2-methyltetrahydrofuran-3-yl)piperidin-4-yl]pyridin-3-yl}-5-methyl-1-[4-(trifluoromethyl)phenyl]-1H-pyrazole-4-carboxamide

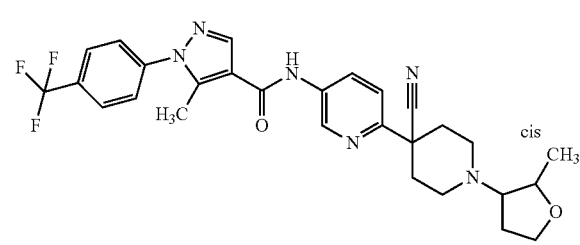 [SMILES: Cc1c(C(=O)Nc2ccc(C3(C#N)CCN(C4CCOC4C)CC3)nc2)cnn1-c1ccc(C(F)(F)F)cc1]

Thionyl chloride (38 μl) was added to a solution of 5-methyl-1-[4-(trifluoromethyl)phenyl]-1H-pyrazole-4-carboxylic acid (57 mg) described in Reference Example 23 in a mixture of toluene (1.5 ml) and N,N-dimethylformamide (catalytic amounts) and stirred at 80° C. for two hours. The solvent was evaporated in vacuo, the residue was dissolved in pyridine (2.5 ml), a solution of cis-4-(5-aminopyridin-2-yl)-1-(2-methyltetrahydrofuran-3-yl)piperidine-4-carbonitrile (50 mg) described in Reference Example 88 in pyridine (2.5 ml) was added at 40° C. therein and stirred for 2.5 hours. Triethylamine (122 μl) and water were added, the precipitated solid was filtered and purified with a silica gel chromatography (chloroform/methanol) to give the titled compound (59 mg) as a white solid.

MS (ESI) m/z: 539 (M+H)$^+$.

Example D12

N-{6-[4-Cyano-1-(2-hydroxy-2-methylpropyl)piperidin-4-yl]pyridin-3-yl}-1-(5-cyclopropylpyridin-2-yl)-5-methyl-1H-pyrazole-4-carboxamide

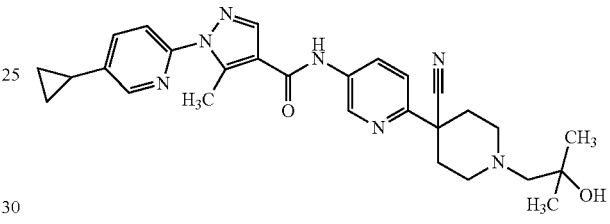

Thionyl chloride (109 μl) was added to a solution of 1-(5-cyclopropylpyridin-2-yl)-5-methyl-1H-pyrazole-4-carboxylic acid (143 mg) described in Reference Example 118 in a mixture of toluene (2.5 ml) and N,N-dimethylformamide (catalytic amounts) and stirred at 80° C. for three hours. The solvent was evaporated in vacuo, a solution of 4-(5-aminopyridin-2-yl)-1-(2-hydroxy-2-methylpropyl) piperidine-4-carbonitrile (137 mg) described in Reference Example 96 was added to a pyridine (2.5 ml) solution of the resulting residue at 40° C. and stirred for five hours. Trithylamine (350 μl) and water was added and the precipitated solid was filtered and purified with a silica gel chromatography (chloroform/methanol) to give the titled compound (198 mg) as a white solid.

MS (ESI) m/z: 500 (M+H)$^+$.

Example D13

N-{6-[r-1-Cyano-c-4-(3-hydroxypyrrolidin-1-yl)cyclohexyl]pyridin-3-yl}-5-methyl-1-[5-(trifluoromethyl)pyridin-2-yl]-1H-pyrazole-4-carboxamide

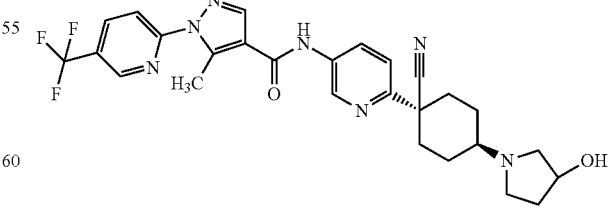

Thionyl chloride (54 μl) was added to a solution of 5-methyl-1-[5-(trifluoromethyl)pyridin-2-yl]-1H-pyrazole-4-carboxylic acid (81 mg) described in Reference Example 8 in a mixture of toluene (2.5 ml) and N,N-dimethylformamide (catalytic amounts) and stirred at 80° C. for 3.5 hours. The solvent was evaporated in vacuo, a solution of 1-(5-aminopyridin-2-yl)-c-4-(3-hydroxypyrrolidin-1-yl)-r-1-cyclohexanecarbonitrile (72 mg) described in Reference Example 132B in pyridine (2.5 ml) was added at 40° C. to a pyridine (2.5 ml) solution of the resulting residue and stirred for three hours. Triethylamine (175 µl) and water were added and the precipitated solid was filtered and purified with a silica gel chromatography (chloroform/methanol) to give the titled compound (18 mg) as a pale yellow solid.

MS (ESI) m/z: 540 (M+H)$^+$.

Example D14

N-{6-[r-1-Cyano-c-4-(morpholin-4-yl)cyclohexyl]pyridin-3-yl}-1-[3-fluoro-5-(trifluoromethyl)pyridin-2-yl]-5-methyl-1H-pyrazole-4-carboxamide

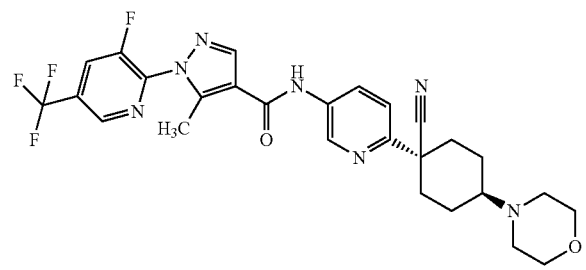 [SMILES: Cc1c(C(=O)Nc2ccc([C@]3(C#N)CC[C@@H](N4CCOCC4)CC3)nc2)cnn1-c1ncc(C(F)(F)F)cc1F]

Thionyl chloride (54 ml) was added to a solution of 1-[3-fluoro-5-(trifluoromethyl)pyridin-2-yl]-5-methyl-1H-pyrazole-4-carboxylic acid (87 mg) to a mixture of toluene (1.5 ml) and N,N-dimethylformamide (catalytic amounts) and stirred at 80° C. for 3.5 hours. The solvent was evaporated in vacuo, a solution of 1-(5-aminopyridin-2-yl)-c-4-(3-hydroxypyrrolidin-1-yl)-r-1-cyclohexanecarbonitrile (72 mg) described in Reference Example 94 in pyridine (2.5 ml) was added at 40° C. to a pyridine (2.5 ml) solution of the residue and stirred at 40° C. for three hours. Triethylamine (175 µl) and water were added and the precipitated solid was purified with a chromatography (chloroform/methanol) to give the titled compound (94 mg) as a white solid.

MS (ESI) m/z: 558 (M+H)$^+$.

Example D15

N-[6-(8-Cyano-1,4-dioxaspiro[4.5]dec-8-yl)pyridin-3-yl]-1-(3,5-dimethylphenyl)-1H-pyrazole-4-carboxamide

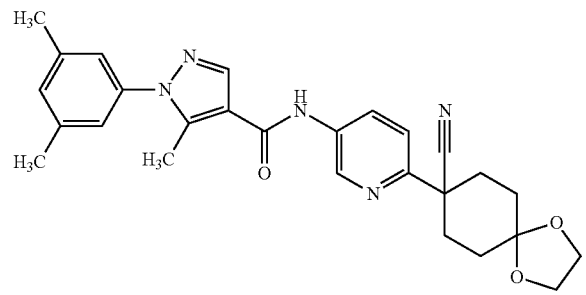 [SMILES: Cc1cc(C)cc(-n2ncc(C(=O)Nc3ccc(C4(C#N)CCC5(CC4)OCCO5)nc3)c2C)c1]

Thionyl chloride (362 mg) and N,N-dimethylformamide (catalytic amounts) were added under ice-cooling to a solution of 1-(3,5-dimethylphenyl)-1H-pyrazole-4-carboxylic acid (438 mg) described in Reference Example 73 in toluene (3 ml) and stirred at 50° C. for an hour. The reaction solvent was evaporated, the residue was dissolved in N-methylmorpholine (2 ml) and added dropwise under ice-cooling to a solution of 8-(5-aminopyridin-2-yl)-1,4-dioxaspiro[4.5]decane-8-carbonitrile (259 mg) described in Reference Example 86 in N-methylmorpholine (1 ml). Triethylamine (1 ml) was added to the reaction solvent and the mixture was reacted at room temperature for six hours. After the reaction, water was added and extracted with ethyl acetate. The organic layer was dried over anhydrous magnesium sulfate and concentrated. The residue was purified with a silica gel column chromatography to give the titled compound (11.7 mg).

MS (ESI) m/z: 458 (M+H)$^+$.

Example D16

N-[6-(8-Cyano-1,4-dioxaspiro[4.5]dec-8-yl)pyridin-3-yl]-1-(5-iodopyridin-2-yl)-1H-pyrazole-4-carboxamide

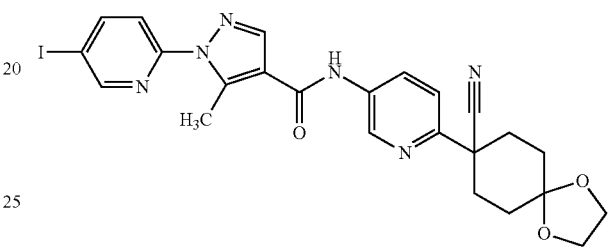

Thionyl chloride (109 mg) and N,N-dimethylformamide (catalytic amounts) were added dropwise under ice-cooling to a solution of 1-(5-iodopyridin-2-yl)-1H-pyrazole-4-carboxylic acid (207 mg) described in Reference Example 74 in toluene (3 ml) and stirred at 50° C. for an hour. The reaction solvent was evaporated, the residue was dissolved in N-methylmorpholine (1 ml) and added dropwise under ice-cooling to a solution of 8-(5-aminopyridin-2-yl)-1,4-dioxaspiro[4.5]decane-8-carbonitrile (259 mg) described in Reference Example 86 in N-methylmorpholine (1 ml). Triethylamine (1 ml) was added to the reaction solvent and the mixture was reacted at room temperature for six hours. After the reaction, water was added and extracted with ethyl acetate. The organic layer was dried over anhydrous magnesium sulfate and concentrated. The residue was purified with a silica gel column chromatography to give the titled compound (4.6 mg).

MS (ESI) m/z: 557 (M+H)$^+$.

Example D17

N-[6-(8-Cyano-1,4-dioxaspiro[4.5]dec-8-yl)pyridin-3-yl]-1-(4-methylphenyl)-1H-indole-3-carboxamide

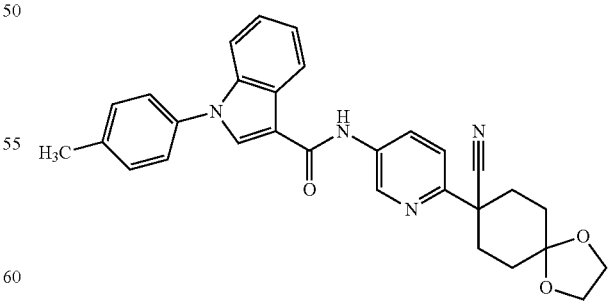

Thionyl chloride (115 mg) and N,N-dimethylformamide (catalytic amounts) were added dropwise under ice-cooling to a solution of 1-(4-methylphenyl)-1H-indole-3-carboxylic acid (184 mg) described in Reference Example 72 in toluene (2 ml) and stirred at 50° C. for an hour. The reaction solvent was evaporated, the residue was dissolved in N-methylmorpholine (2 ml) and added dropwise under ice-cooling to a solution of 8-(5-aminopyridin-2-yl)-1,4-dioxaspiro[4.5]decane-8-carbonitrile (166 mg) described in Reference Example 86 in N-methylmorpholine (2 ml). Triethylamine (1 ml) was added to the reaction solvent and the mixture was reacted at room temperature for six hours. After the reaction, water was added and extracted with ethyl acetate. The organic layer was dried over anhydrous magnesium sulfate and concentrated. The residue was purified with a silica gel column chromatography to give the titled compound (13.8 mg).

MS (ESI) m/z: 493 (M+H)⁺.

Example D18

N-{6-[r-1-Cyano-c-4-methoxycyclohexyl]pyridin-3-yl}-5-methyl-1-(4-methylphenyl)-1H-pyrazole-4-carboxamide

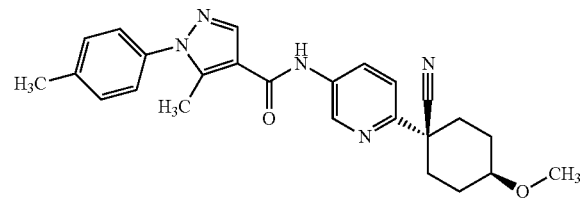

Oxalyl chloride (0.1 ml) and N,N-dimethylformamide (catalytic amounts) were added at room temperature to a solution of 1-(4-methylphenyl)-5-methyl-1H-pyrazole-4-carboxylic acid (126 mg) described in Reference Example 4 in dichloromethane (3.0 ml), stirred at room temperature for an hour and the solvent and an excess amount of oxalyl chloride were evaporated. Toluene (2.0 ml) was added to the reaction mixture, a solution of 1-(5-aminopyridin-2-yl)-c-4-methoxymethoxy-r-1-cyclohexanecarbonitrile (11.2 mg) in pyridine (2.0 ml) was added and stirred at 45° C. for an hour. After the reaction, water was added and extracted with chloroform. The organic layer was dried over anhydrous sodium sulfate and concentrated. The resulting residue was purified with a silica gel column chromatography (n-hexane/ethyl acetate) to give the titled compound (165 mg) as a white solid.

MS (ESI) m/z: 430 (M+H)⁺.

Example D19

1-[5-Chloro-3-fluoropyridin-2-yl]-5-methyl-N-{5-methyl-6-[4-(morpholin-4-yl)cyclohex-1-en-1-yl]pyridin-3-yl}-1H-pyrazole-4-carboxamide

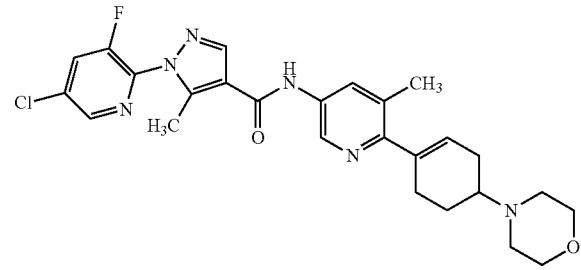 [SMILES: Cc1cc(NC(=O)c2cnn(-c3ncc(Cl)cc3F)c2C)cnc1C1=CCC(N2CCOCC2)CC1]

Oxalyl chloride (0.25 ml) and N,N-dimethylformamide (catalytic amounts) were added to a solution of 1-(5-chloro-3-fluoropyridin-2-yl)-5-methyl-1H-pyrazole-4-carboxylic acid (188 mg) described in Reference Example 124 in dichloromethane (10 ml), and stirred at room temperature for two hours. The solvent and an excess amount of oxalyl chloride was evaporated, the residue was dissolved in toluene (10 ml) and cooled in ice. A solution of 2-(4-(morpholin-4-yl)cyclohex-1-en-1-yl)-3-methyl-5-amino-pyridine (191 mg) in pyridine (10 ml) was added thereto and stirred at room temperature overnight. After the reaction, 1N aqueous solution of sodium hydroxide was added under ice-cooling and extracted with chloroform. The organic layer was dried over anhydrous sodium sulfate, and concentrated in vacuo. The resulting residue was purified with a silica gel column chromatography (chloroform/methanol), washed with ethanol and the resulting solid was dried at 60° C. in vacuo to give the titled compound (184 mg) as a white solid.

MS (ESI) m/z: 511 (M+H)⁺.

Example D20

5-Methyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide mesylate

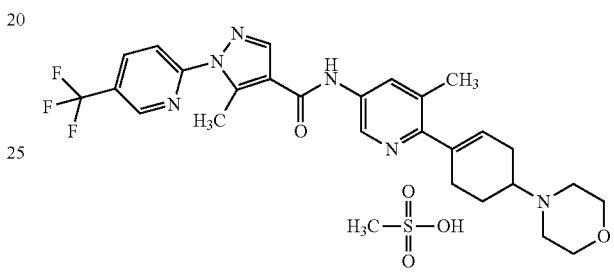

A suspension of 1-(5-trifluoromethylpyridin-2-yl)-5-methyl-1H-pyrazole-4-carboxamide (2.2 g) described in Reference Example 120, 2-(4-(morpholin-4-yl)cyclohex-1-en-1-yl)-3-methyl-5-bromopyridine (2.75 g) described in Reference Example 107, 4,5-bis(diphenylphosphino)-9,9-dimethylxanthene (152 mg), palladium acetate (39 mg) and cesium carbonate (4.01 g) in 1,4-dioxane (30 ml) was stirred at 100° C. After the reaction, the reaction solution was left stand, ice water was added and extracted with chloroform. The organic layer was dried over anhydrous sodium sulfate, and concentrated. The resulting residue was purified with a silica gel column chromatography (chloroform/methanol), washed with ethanol and the resulting solid was filtered and dried at 60° C. in vacuo to give a white solid. Methanesulfonic acid (0.326 ml) was added to a solution of the resulting solid in chloroform (200 ml) and stirred at room temperature for three hours. Then, the solvent was evaporated, ethanol was added and the precipitated solid was filtered and dried at 60° C. in vacuo to give the titled compound (2.9 g) as a white solid.

MS (ESI) m/z: 527 (M+H)⁺.

Example D21

(R)-5-Methyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide

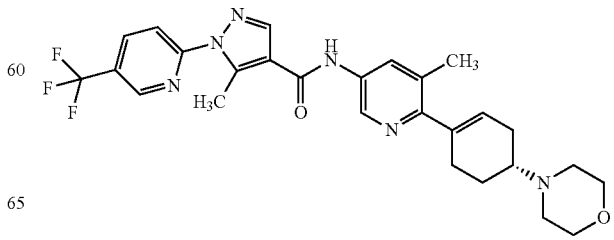

Thionyl chloride (6.6 ml) and N,N-dimethylformamide (catalytic amounts) were added at room temperature to a solution of 5-methyl-1-[5-(trifluoromethyl)pyridin-2-yl]-1H-pyrazole-4-carboxylic acid (8.17 g) described in Reference Example 8 in toluene (150 ml), and stirred at 80° C. for an hour. The solvent and an excess amount of thionyl chloride were evaporated. Pyridine (200 ml) was added to the resulting reaction mixture, and a pyridine (250 ml) solution of (R)-5-methyl-6-[4-(morpholin-4-yl)cyclohex-1-en-1-yl]pyridine-3-amine (7.5 g), which was derived from the first peak fractions when 5-methyl-6-[4-(morpholin-4-yl)cyclohex-1-en-1-yl]pyridine-3-amine of Reference Example 108 was optically fractionated with a chiral column, was added and stirred at 50° C. for two hours. After the reaction, the reaction solution was left stand, triethylamine and water were added and the precipitate was filtered. The resulting solid was dissolved in acetic acid (7.5 ml), water (7.5 ml) and ethanol (750 ml), activated charcoal was added and stirred at 40° C. for an hour. The mixture was filtered through Celite, pH was adjusted to 8 by the addition of 1N aqueous solution of sodium hydroxide and the precipitate was collected by filtration. The resulting solid was washed with water and dried at 60° C. under current of air to give the titled compound (11.4 g) as a white solid.

MS (ESI) m/z: 527 (M+H)+.

The resulting white solid (379 mg) was dissolved in ethanol (120 ml), methanesulfonic acid (0.051 ml) was added and stirred at room temperature for two hours. The solvent was evaporated, the residue was washed with ethanol and then collected by filtration and dried at 60° C. in vacuo to give a white solid. A part of the solid was recrystallized from acetonitrile to give a crystalline, which was analyzed by single-crystal X-ray diffraction and the absolute configuration was determined as "R".

Example D22

(S)-5-Methyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide

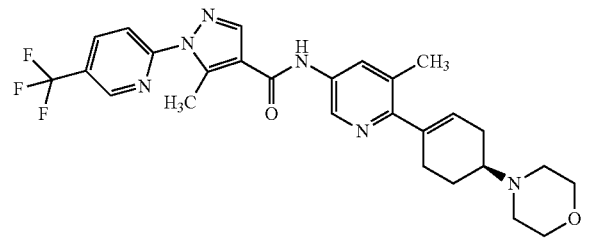 [SMILES: Cc1cc(NC(=O)c2cnn(-c3ccc(C(F)(F)F)cn3)c2C)cnc1C1=CC[C@@H](N2CCOCC2)CC1]

Thionyl chloride (6.6 ml) and N,N-dimethylformamide (catalytic amounts) were added at room temperature to a solution of 5-methyl-1-[5-(trifluoromethyl)pyridin-2-yl]-1H-pyrazole-4-carboxylic acid (8.17 g) described in Reference Example 8 in toluene (150 ml) and stirred at 80° C. for an hour. The solvent and an excess amount of thionyl chloride were evaporated. Pyridine (200 ml) was added to the resulting reaction mixture, and a pyridine (250 ml) solution of (S)-5-methyl-6-[4-(morpholin-4-yl)cyclohex-1-en-1-yl]pyridine-3-amine (7.5 g), which was derived from the second peak fractions when 5-methyl-6-[4-(morpholin-4-yl)cyclohex-1-en-1-yl]pyridine-3-amine of Reference Example 108 was optically fractionated with a chiral column, was added and stirred at 50° C. for two hours. After the reaction, the reaction solution was left stand, triethylamine (40 ml) and water were added and the precipitate was filtered. The resulting solid was dissolved in acetic acid (7.5 ml), water (7.5 ml) and ethanol (750 ml), activated charcoal was added and stirred at 40° C. for an hour. The mixture was filtered through Celite, pH was adjusted to 8 by the addition of 1N aqueous solution of sodium hydroxide and the precipitate was collected by filtration. The resulting solid was washed with water and dried at 60° C. under current of air to give the titled compound (11.3 g) as a white solid.

MS (ESI) m/z: 527 (M+H)+.

Since the configuration of the compound in Example D21 was determined as "R", the configuration of this compound is determined as "S".

Example D23

N-[6-(4-Hydroxycyclohex-1-en-1-yl)-5-methylpyridin-3-yl]-5-methyl-1-[5-(trifluoromethyl)-pyridin-2-yl]-1H-pyrazole-4-carboxamide

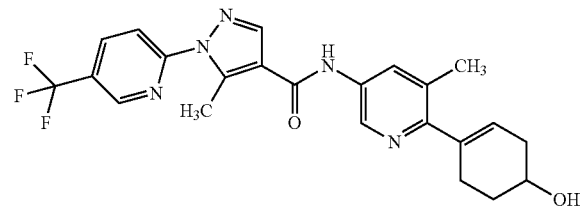 [SMILES: Cc1cc(NC(=O)c2cnn(-c3ccc(C(F)(F)F)cn3)c2C)cnc1C1=CCC(O)CC1]

Oxalyl chloride (0.20 ml) and N,N-dimethylformamide (catalytic amounts) were added at room temperature to a solution of 5-methyl-1-[5-(trifluoromethyl)pyridin-2-yl]-1H-pyrazole-4-carboxylic acid (175 mg) described in Reference Example 8 in dichloromethane (10 ml) and stirred at room temperature for two hours. The solvent and an excess amount of oxalyl chloride were evaporated, and toluene (10 ml) was added to the resulted reaction mixture. Next, a solution of 4-(5-amino-3-methylpyridin-2-yl)cyclohex-3-en-1-ol (120 mg) described in Reference Example 111 in pyridine (10 ml) was added under ice-cooling, and the mixture was stirred at room temperature overnight. After the reaction, 1N aqueous solution of sodium hydroxide was added under ice-cooling and extracted with chloroform. The organic layer was dried over anhydrous sodium sulfate and concentrated. The resulting residue was purified with a silica gel column chromatography (chloroform/methanol), washed with ethanol, the resulting solid was filtered and dried at 60° C. in vacuo to give the titled compound (146 mg) as a white solid.

MS (ESI) m/z: 458 (M+H)+.

Example D24

1-[3-Fluoro-5-(trifluoromethyl)pyridin-2-yl]-5-methyl-N-{5-methyl-6-[4-(morpholin-4-yl)cyclohex-1-en-1-yl]pyridin-3-yl}-1H-pyrazole-4-carboxamide mesylate

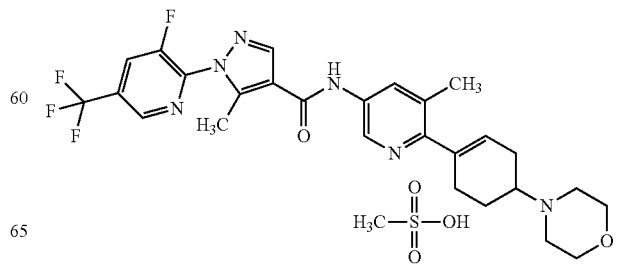

Oxalyl chloride (0.07 ml) and N,N-dimethylformamide (catalytic amounts) were added at room temperature to a solution of 1-[3-fluoro-5-(trifluoromethyl)pyridin-2-yl]-5-methyl-1H-pyrazole-4-carboxylic acid (200 mg) described in Reference Example 130 in dichloromethane (10 ml) and stirred at room temperature for two hours. The solvent and an excess amount of oxalyl chloride were evaporated, and toluene (10 ml) was added to the resulted reaction mixture. Next, a solution of 2-(4-(morpholin-4-yl)cyclohex-1-en-1-yl)-3-methyl-5-aminopyridine (172 mg) described in Reference Example 108 was added under ice-cooling and stirred at room temperature overnight. After the reaction, 1N aqueous solution of sodium hydroxide was added under ice-cooling and extracted with chloroform. The organic layer was dried over anhydrous sodium sulfate and concentrated. The resulting residue was purified with a silica gel column chromatography (chloroform/methanol) to give a white solid. The resulting white solid was dissolved in ethanol (5 ml), methanesulfonic acid (0.03 ml) was added thereto and stirred at room temperature for two hours. Then, the solvent was evaporated, ethyl acetate and a small amount of ethanol were added, and the precipitated solid was collected by filtration and dried at 60° C. in vacuo to give the titled compound (245 mg) as a white solid.

MS (ESI) m/z: 545 (M+H)$^+$.

Example D25

1-[3-Fluoro-5-(trifluoromethyl)pyridin-2-yl]-5-methyl-N-[5-methyl-6-(4-hydroxycyclohex-1-en-1-yl)pyridin-3-yl]-1H-pyrazole-4-carboxamide

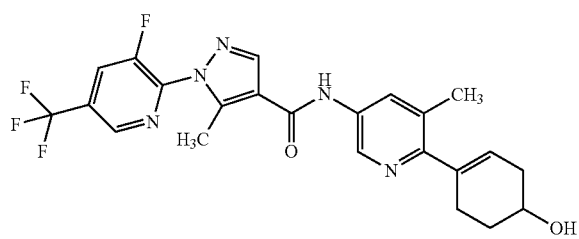 [SMILES: Cc1cc(NC(=O)c2cnn(-c3ncc(C(F)(F)F)cc3F)c2C)cnc1C1=CCC(O)CC1]

Oxalyl chloride (0.14 ml) and N,N-dimethylformamide (catalytic amounts) were added at room temperature to a solution of 1-(3-fluoro-5-trifluoromethylpyridin-2-yl)-5-methyl-1H-pyrazole-4-carboxylic acid (120 mg) described in Reference Example 130 in dichloromethane (5 ml) and stirred at room temperature for two hours. The solvent and an excess amount of oxalyl chloride were evaporated, and toluene (5 ml) was added to the resulted reaction mixture. Next, a solution of 2-(4-hydroxycyclohex-1-en-1-yl)-3-methyl-5-aminopyridine (81 mg) described in Reference Example 111 in pyridine (5 ml) was added thereto and stirred at room temperature overnight. After the reaction, 1N aqueous solution of sodium hydroxide was added under ice-cooling and extracted with chloroform. The organic layer was dried over anhydrous sodium sulfate and concentrated. The resulting residue was purified with a silica gel column chromatography (chloroform/methanol), washed with ethanol and the resulting solid was collected by filtration and dried at 60° C. in vacuo to give the titled compound (107 mg) as a white solid.

MS (ESI) m/z: 476 (M+H)$^+$.

Example D26

N-{6-[r-1-Cyano-c-4-(morpholin-4-yl)cyclohexyl]pyridin-3-yl}-1-(5-isopropylpyridin-2-yl)-5-methyl-1H-pyrazole-4-carboxamide mesylate

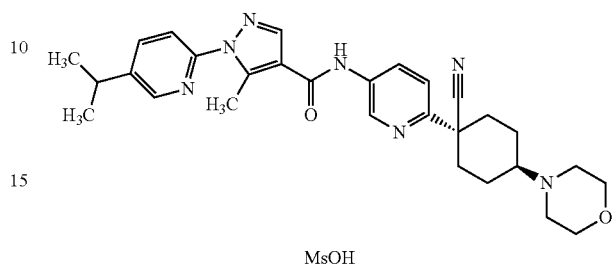

Thionyl chloride (109 µl) was added to a solution of 1-(5-isopropylpyridin-2-yl)-5-methyl-1H-pyrazole-4-carboxylic acid (122 mg) described in Reference Example 30 in a mixture of toluene (2.5 ml) and N,N-dimethylformamide (catalytic amounts) and stirred at 80° C. for 2.5 hours. The solvent was evaporated, and pyridine (2.5 ml) was added to the residue. A solution of 1-(5-aminopyridin-2-yl)-c-4-(morpholin-4-yl)-r-1-cyclohexanecarbonitrile (157 mg) described in Reference Example 94 in pyridine (2.5 ml) was added and stirred at 40° C. for 1.5 hours. Triethylamine (209 µl) and water were added, the precipitated solid was filtered and washed with ethanol. The resulting solid (93 mg) was dissolved in methanol (5 ml) and dichloromethane (3 ml), methanesulfonic acid (12 µl) was added and stirred at room temperature. The solvent was evaporated and the resulting solid was washed with ethyl acetate to give the titled compound (88 mg) as a white solid.

MS (ESI) m/z: 514 (M+H)$^+$.

In a similar manner as a preparation of Examples D1 to D26, the following compounds, Examples D27 to D170, D173 to D214, D216, D217, D220, D222, D224 to D229, D232 to D264, D266 to D277, D279 to D287, D290, D291, D293 to D295, D297 to D299 and D302 to D304, were prepared from the corresponding starting materials.

In addition, Examples D171, D172, D215, D218, D219, D221, D223, D230, D231, D265, D278, D288, D289, D292, D296, D300 and D301 were prepared by the following methods:

Example D171

5-Methyl-N-{5-methyl-6-[4-(morpholin-4-yl)cyclohex-1-en-1-yl]pyridin-3-yl}-1-(5-bromo-2-methoxypyridin-3-yl)-1H-pyrazole-4-carboxamide (1) 4N Aqueous solution of sodium hydroxide (3 ml) and water (3 ml) were added to a solution of 1-(5-bromo-2-chloropyridin-3-yl)-5-methyl-1H-pyrazole-4-carboxylic acid ethyl ester (500 mg) described in Reference Example 29 in methanol (3 ml) and tetrahydrofuran (3 ml), and stirred at room temperature overnight. After the reaction, the organic solvent was evaporated in vacuo, water and diethyl ether were added and the aqueous layer was separated. Concentrated hydrochloric acid was added under ice-cooling to the aqueous solution, pH was adjusted to 5 and the precipitated solid was collected by filtration, washed and dried at 60 C under current of air to give a mixture of 1-(5-bromo-2-chloropyridin-3-yl)-5-methyl-1H-pyrazole-4-carboxylic acid: MS (ESI) m/z: 316, 318 (M+H)$^+$, and 1-(5-bromo-2-methoxypyridin-3-yl)-5-methyl-1H-pyrazole-4-carboxylic acid: MS (ESI) m/z: 312, 314 (M+H)$^+$ (353 mg) as a white solid.

(2) Oxalyl chloride (0.38 ml) and N,N-dimethylformamide (catalytic amounts) were added at room temperature to a solution of the mixture of 1-(5-bromo-2-chloropyridin-3-yl)-5-methyl-1H-pyrazole-4-carboxylic acid and 1-(5-bromo-2-methoxypyridin-3-yl)-5-methyl-1H-pyrazole-4-carboxylic acid (350 mg) in dichloromethane (30 ml) and stirred at room temperature for two hours. The solvent and an excess amount of oxalyl chloride were evaporated, toluene (30 ml) was added to the resulting reaction mixture, and then a solution of 5-methyl-6-(4-(morpholin-4-yl)cyclohex-1-en-1-yl)pyridine-3-amine (290 mg) described in Reference Example 108 in pyridine (30 ml) was added under ice-cooling and stirred at room temperature overnight. After the reaction, 1N aqueous solution of sodium hydroxide was added under ice-cooling and extracted with chloroform. The organic layer was dried over anhydrous sodium sulfate and concentrated. The resulting residue was purified with a preparative HPLC column Capcellpak C18 UG80 5 μM (0.05% trifluoroacetic acid/ acetonitrile: 0.05% trifluoroacetic acid/water) to give the titled compound (49 mg) as a white solid.
MS (ESI) m/z: 567, 569 (M+H)$^+$.

Example D172

5-Methyl-N-{5-methyl-6-[4-(morpholin-4-yl)cyclohex-1-en-1-yl]pyridin-3-yl}-1-(5-bromo-2-chloropyridin-3-yl)-1H-pyrazole-4-carboxamide In a similar manner as Example D171, the titled compound (220 mg) was obtained as a white solid.
MS (ESI) m/z: 573 (M+H)$^+$.

Example D215

N-{6-[4-(N-Isobutyl-N-methylamino)cyclohex-1-en-1-yl]-5-methyl-pyridin-3-yl}-5-methyl-1-[5-(trifluoromethyl)pyridin-2-yl]-1H-pyrazole-4-carboxamide N,N-Dimethylformamide (0.05 ml) and thionyl chloride (0.185 g) were added to a solution of 5-methyl-1-[5-(trifluoromethyl)pyridin-2-yl]-1H-pyrazole-4-carboxylic acid (0.155 g) described in Reference Example 8 in toluene (5.7 ml), and stirred at 80° C. for an hour. The solvent was evaporated in vacuo, a solution of N-[4-(5-amino-3-methylpyridin-2-yl)cyclohex-3-en-1-yl]-N-methyl isobutylamide (0.15 g) described in Reference Example 147 in pyridine (6.5 ml) was added to the residue, and stirred at 50° C. for an hour. The reaction solution was treated with triethylamine, water was added and stirred for two hours. The precipitated solid was filtered to give the titled compound (0.43 g).
MS (ESI) m/z: 541 (M+H)$^+$.

Example D218

N-(6-{4-[N-(2,2-Dimethylpropion-1-yl)-N-methylamino]cyclohex-1-en-1-yl}-5-methylpyridin-3-yl)-5-methyl-1-(pyridin-2-yl)-1H-pyrazole-4-carboxamide N,N-Dimethylformamide (0.05 ml) and thionyl chloride (0.235 g) were added to a solution of 5-methyl-1-(pyridin-2-yl)-1H-pyrazole-4-carboxylic acid (0.148 g) described in Reference Example 174 in toluene (7.3 ml), and stirred at 80° C. for an hour. The solvent was evaporated in vacuo, a solution of N-[4-(5-amino-3-methylpyridin-2-yl)cyclohex-3-en-1-yl]-2,2,N-trimethylpropionic amide (0.2 g) described in Reference Example 145 in pyridine (8.0 ml) was added to the residue, and stirred at 50° C. for an hour. The reaction solution was treated with triethylamine, water (100 ml) was added and stirred for an hour. The precipitated solid was filtered to give the titled compound (0.108 g).
MS (ESI) m/z: 487 (M+H)$^+$.

Example D219

1-(4-Fluorophenyl)-N-{6-[4-(N-isobutyryl-N-methylamino)cyclohex-1-en-1-yl]-5-methylpyridin-3-yl}-5-methyl-1H-pyrazole-4-carboxamide N,N-Dimethylformamide (0.05 ml) and thionyl chloride (0.185 g) were added to a solution of 1-(4-fluorophenyl)-5-methyl-1H-pyrazole-4-carboxylic acid (0.126 g) described in Reference Example 1 in toluene (6.0 ml), and stirred at 80° C. for an hour. The solvent was evaporated in vacuo, a solution of N-[4-(5-amino-3-methylpyridin-2-yl)cyclohex-3-en-1-yl]-N-methyl isobutylamide (0.15 g) described in Reference Example 147 in pyridine (6.0 ml) was added to the residue and stirred at 50° C. for an hour. The reaction solution was treated with triethylamine, water (100 ml) was added and the precipitated solid was filtered to give the titled compound (0.161 g).
MS (ESI) m/z: 490 (M+H)$^+$.

Example D221

N-[6-(4-N,N-Dimethylcarbamoylcyclohex-1-en-1-yl)-5-methylpyridin-3-yl]-5-methyl-1-[5-(trifluoromethyl)pyridin-2-yl]-1H-pyrazole-4-carboxamide N,N-Dimethylformamide (0.05 ml) and thionyl chloride (0.206 g) were added to a solution of 5-methyl-1-[5-(trifluoromethyl)pyridin-2-yl]-1H-pyrazole-4-carboxylic acid (0.172 g) described in Reference Example 8 in toluene (6.0 ml), and stirred at 80° C. for an hour. The solvent was evaporated in vacuo, a solution of N-[4-(5-amino-3-methylpyridin-2-yl)cyclohex-3-en-1-yl]carboxylic acid N,N-dimethylamide (0.15 g) described in Reference Example 164 in pyridine (6.0 ml) was added to the residue and stirred at 50° C. for an hour. The reaction solution was treated with triethylamine, water (100 ml) was added and the precipitated solid was filtered and washed with diethyl ether to give the titled compound (0.12 g).
MS (ESI) m/z: 513 (M+H)$^+$.

Example D223

1-(5-Cyclopropylpyridin-2-yl)-N-[6-(4-N,N-dimethylcarbamoylcyclohex-1-en-1-yl)-5-methylpyridin-3-yl]-5-methyl-1H-pyrazole-4-carboxamide N,N-Dimethylformamide (0.05 ml) and thionyl chloride (0.206 g) were added to a solution of 1-(5-cyclopropylpyridin-2-yl)-5-methyl-1H-pyrazole-4-carboxylic acid (0.155 g) described in Reference Example 118 in toluene (6.0 ml) and stirred at 80° C. for an hour. The solvent was evaporated in vacuo, a solution of N-[4-(5-amino-3-methylpyridin-2-yl)cyclohex-3-en-1-yl]carboxylic acid N,N-dimethylamide (0.15 g) described in Reference Example 164 in pyridine (6.0 ml) was added to the residue and stirred at 50° C. for an hour. The reaction solution was treated with triethylamine, water (100 ml) was added and the precipitated solid was filtered, purified with a silica gel column chromatography (ethyl acetate: methanol) to give the titled compound (0.041 g).

MS (ESI) m/z: 485 (M+H)$^+$.

Example D230

3-Methyl-N-{5-methyl-6-[4-(morpholin-4-yl)cyclohex-1-en-1-yl]pyridin-3-yl}-2-[4-(trifluoromethyl)phenyl]-3H-imidazole-4-carboxamide N,N-Dimethylformamide (catalytic amounts) and thionyl chloride (81.0 µl) were added at room temperature to a solution of 3-methyl-2-[4-(trifluoromethyl)phenyl]-3H-imidazole-4-carboxylic acid (100 mg) described in Reference Example 177 in toluene (2 ml) and stirred at 80° C. for 80 minutes. The solvent and an excess amount of thionyl chloride were evaporated, the resulting residue was dissolved in dichloromethane (2 ml), triethylamine (155 ml) and a solution of 5-methyl-6-[4-(morpholin-4-yl)cyclohex-1-en-1-yl]pyridine-3-amine (121 mg) described in Reference Example 108 was added under ice-cooling and stirred at room temperature for 45 minutes. After the reaction, a saturated aqueous solution of sodium bicarbonate was added and extracted with ethyl acetate. The solvent was evaporated and the resulting residue was purified with a silica gel column chromatography (n-hexane/ethyl acetate) and HPLC preparative column: Capcellpak C18 UG80 20 mm×250 mm (0.05% trifluoroacetic acid/acetonitrile: 0.05% trifluoroacetic acid/water) to give the titled compound (48.8 mg) as a white solid.

MS (ESI) m/z: 526 (M+H)$^+$.

Example D231

N-{5-Methyl-6-[4-(morpholin-4-yl)cyclohex-1-en-1-yl]pyridin-3-yl}-2-[4-(trifluoromethyl)phenyl]thiazole-4-carboxamide 1N Aqueous solution of sodium hydroxide (2 ml) was added at room temperature to a solution of 2-[4-(trifluoromethyl)phenyl]thiazole-4-carboxylic acid ethyl ester (300 mg) described in Reference Example 178 in tetrahydrofuran (2 ml) and stirred at 50° C. for 4.5 hours. After the reaction, 1N aqueous solution of hydrochloric acid (2 ml) was added, the solvent was evaporated and the residue was azeotropically distilled twice with toluene. N,N-Dimethylformamide (catalytic amounts) and thionyl chloride (2 ml) were added to the resulting residue at room temperature, stirred at 80° C. for an hour, and an excess amount of thinly chloride was evaporated. The resulting reaction solution was dissolved in dichloromethane (5 ml), triethylamine (416 µl) and 5-methyl-6-[4-(morpholin-4-yl)cyclohex-1-en-1-yl]pyridine-3-amine (327 mg) were added and stirred at room temperature for 20 minutes. After the reaction, water was added, extracted with chloroform and the solvent was evaporated. The resulting residue was purified with a basic silica gel column chromatography (n-hexane/ethyl acetate) to give the titled compound (321 mg) as a white solid.

MS (ESI) m/z: 529 (M+H)$^+$.

Example D265

5-Methyl-N-(5-methyl-6-{4-[N-methyl-N-(2,2,2-trifluoroacetyl)amino]cyclohex-1-en-1-yl}pyridin-3-yl)-1-[5-(trifluoromethyl)pyridin-2-yl]-1H-pyrazole-4-carboxamide Thionyl chloride (114 mg) and N,N-dimethylformamide (catalytic amounts) were added at room temperature to a solution of 5-methyl-1-[5-(trifluoromethyl)pyridin-2-yl]-1H-pyrazole-4-carboxylic acid (96 mg) described in Reference Example 8 in toluene (4.0 ml) and stirred at 80° C. for an hour. The solvent and an excess amount of thionyl chloride were evaporated, the resulting residue was dissolved in pyridine (2.0 ml), a solution of N-[4-(5-amino-3-methylpyridin-2-yl)cyclohex-3-en-1-yl]-2,2,2-trifluoro-N-methylacetamide (100 mg) described in Reference Example 146 in pyridine (2.0 ml) was added thereto and stirred at 50° C. for an hour. After the reaction, triethylamine (1.0 ml) and water were added and the precipitated solid was filtered. The resulting residue was purified with a silica gel column chromatography (chloroform/methanol) to give the titled compound (141 mg) as a white solid.

MS (ESI) m/z: 567 (M+H)$^+$.

Example D278

N-[6-(c-8-Cyano-r-1-oxaspiro[4.5]decan-8-yl)pyridin-3-yl]-5-methyl-1-[5-(trifluoromethyl)-pyridin-2-yl]-1H-pyrazole-4-carboxamide Thionyl chloride (111 mg) and N,N-dimethylformamide (catalytic amounts) were added at room temperature to a solution of 5-methyl-1-[5-(trifluoromethyl)pyridin-2-yl]-1H-pyrazole-4-carboxylic acid (93 mg) described in Reference Example 8 in toluene (3.5 ml) and stirred at 80° C. for an hour. The solvent and an excess amount of thionyl chloride were evaporated, the resulting residue was dissolved in pyridine (1.5 ml), a solution of 8-(5-aminopyridin-2-yl)-r-1-oxaspiro[4.5]decane-c-8-carbonitrile (80 mg) described in Reference Example 159 in pyridine (2.0 ml) was added and stirred at 50° C. for an hour. After the reaction, triethylamine (1.0 ml) and water were added and the precipitated solid was filtered. The resulting residue was purified with a silica gel column chromatography (chloroform/methanol) to give the titled compound (128 mg) as a white solid.

MS (ESI) m/z: 511 (M+H)$^+$.

Example D288

N-(6-{r-1-Cyano-c-4-[N-(2,2-dimethylpropanoyl)-N-methylamino]cyclohexan-1-yl}pyridin-3-yl)-5-methyl-1-[5-(trifluoromethyl)pyridin-2-yl]-1H-pyrazole-4-carboxamide N-[4-(5-Aminopyridin-2-yl)-c-4-cyanocyclohexan-1-yl]-r-2,2,N-trimethylpropionamide (100 mg) described in Reference Example 156 was added to a solution of 5-methyl-1-[5-(trifluoromethyl)pyridin-2-yl]-1H-pyrazole-4-carboxylic acid chloride (101 mg) described in Reference example 180 in pyridine (4.0 ml) and stirred at 50° C. for an hour. After the reaction, a saturated aqueous solution of sodium bicarbonate was added and the precipitated solid was filtered to give the titled compound (165 mg) as a white solid.

MS (ESI) m/z: 568 (M+H)$^+$.

Example D289

N-{6-[r-1-Cyano-c-4-(N-isobutyryl-N-methylamino)cyclohexan-1-yl]pyridin-3-yl}-5-methyl-1-[5-(trifluoromethyl)pyridin-2-yl]-1H-pyrazole-4-carboxamide N-[4-(5-Aminopyridin-2-yl)-c-4-cyanocyclohexan-1-yl]-r-N-methylisobutyramide (100 mg) described in Reference Example 157 was added to a solution of 5-methyl-1-[5-(trifluoromethyl)pyridin-2-yl]-1H-pyrazole-4-carboxylic acid chloride (106 mg) described in Reference Example 180 in pyridine (4.0 ml) and stirred at 50° C. for an hour. After the reaction, a saturated aqueous solution of sodium bicarbonate was added and the precipitated solid was filtered to give the titled compound (48 mg) as a white solid.
MS (ESI) m/z: 554 (M+H)+.

Example D292

5-Methyl-N-{5-methyl-6-[4-(morpholin-4-yl)cyclohex-1-en-1-yl]pyridin-3-yl}-1-[4-methyl-5-(trifluoromethyl)pyridin-2-yl]-1H-pyrazole-4-carboxamide 5-Methyl-1-[4-methyl-5-(trifluoromethyl)pyridin-2-yl]-1H-pyrazole-4-carboxylic acid (80 mg) described in Reference Example 175 was used in place of 1-(5-chloro-3-fluoropyridin-2-yl)-5-methyl-1H-pyrazole-4-carboxylic acid in Example D19, and reacted and treated in a similar manner to give the titled compound (62 mg) as a white solid.
MS (ESI) m/z: 541 (M+H)+.

Example D296

N-{6-[r-1-Cyano-c-4-(3-hydroxypyrrolidin-1-yl)cyclohexan-1-yl]pyridin-3-yl}-5-methyl-1-[4-(trifluoromethyl)phenyl]-1H-pyrazole-4-carboxamide Thionyl chloride (206 µl) was added to a mixture of 5-methyl-1-[4-(trifluoromethyl)phenyl]-1H-pyrazole-4-carboxylic acid (306 mg) described in Reference Example 23, toluene (3.0 ml) and N,N-dimethylformamide (catalytic amounts) and stirred at 80° C. for 3.5 hours. The solvent was evaporated, the residue was dissolved in pyridine (5.0 ml), a solution of 1-(5-aminopyridin-2-yl)-c-4-(3-hydroxylpyrrolidin-1-yl)-r-1-cyclohexanecarbonitrile (270 mg) described in Reference Example 132B in pyridine (5.0 ml) was added at 40° C. and stirred for three hours. Triethylamine (650 µl) and water were added to the reaction solution, the precipitated solid was filtered and purified with a silica gel chromatography (chloroform/methanol) to give the titled compound (61 mg) as a pale yellow solid.
MS (ESI) m/z: 539 (M+H)+.

Example D300

N-{6-[r-1-Cyano-c-4-(morpholin-4-yl)cyclohexyl]pyridin-3-yl}-5-isopropyl-1-[5-(trifluoromethyl)pyridin-2-yl]-1H-pyrazole-4-carboxamide Thionyl chloride (109 µl) was added to a mixture of 5-isopropyl-1-[5-(trifluoromethyl)pyridin-2-yl]-1H-pyrazole-4-carboxylic acid (180 mg) (commercially available), toluene (2.5 ml) and N,N-dimethylformamide (catalytic amounts) and stirred at 80° C. for 2.5 hours. The solvent was evaporated in vacuo, the residue was dissolved in pyridine (2.5 ml), a solution of 1-(5-aminopyridin-2-yl)-c-4-(morpholin-4-yl)-r-1-cyclohexanecarbonitrile (143 mg) described in Reference Example 94 in pyridine (2.5 ml) was added at 40° C. and stirred for three hours. Triethylamine (350 µl) and water were added to the reaction solution, the precipitated solid was filtered and purified with a silica gel chromatography (chloroform/methanol) to give the titled compound (65 mg) as a white solid.
MS (ESI) m/z: 568 (M+H)+.

Example D301

5-Isopropyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide Thionyl chloride (54 µl) was added to a mixture of 5-isopropyl-1-[5-(trifluoromethyl)pyridin-2-yl]-1H-pyrazole-4-carboxylic acid (90 mg) (commercially available), toluene (1.3 ml) and N,N-dimethylformamide (catalytic amounts) and stirred at 80° C. for three hours. The solvent was evaporated in vacuo, the residue was dissolved in pyridine (1.3 ml), a solution of 5-methyl-6-[4-(morpholin-4-yl)cyclohex-1-en-1-yl]pyridine-3-amine (68 mg) described in Reference Example 108 in pyridine (1.0 ml) was added at 40° C. and stirred for three hours. Triethylamine (275 µl) and water were added to the reaction solution, the precipitated solid was filtered and purified with a silica gel chromatography (chloroform/methanol) to give the titled compound (45 mg) as a white solid.
MS (ESI) m/z: 555 (M+H)+.

| Example No. | Structural formula | Salt | MS(ESI) m/z |
|---|---|---|---|
| D27 | | | 420 |
| D28 | | | 454 |

-continued
| Example No. | Structural formula | Salt | MS(ESI) m/z |
|---|---|---|---|
| D29 | 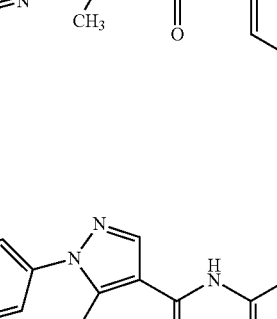 | | 524 |
| D30 | 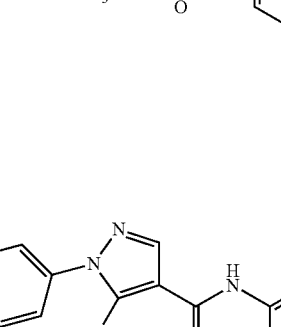 | HCl | 505 |
| D31 | 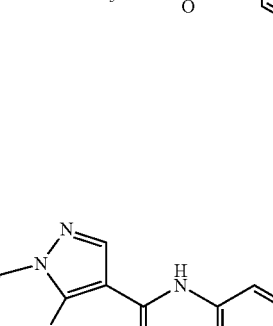 | HCl | 515 |
| D32 | 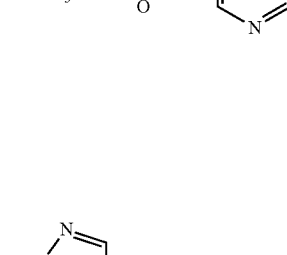 | MsOH | 540 |
| D33 | 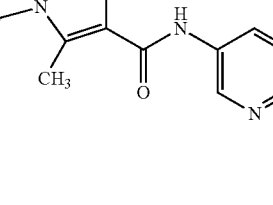 | MsOH | 527 |

-continued

| Example No. | Structural formula | Salt | MS(ESI) m/z |
|---|---|---|---|
| D34 | | | 540 |
| D35 | | MsOH | 527 |
| D36 | | | 527 |
| D37 | | | 527 |
| D38 | | | 541 |

-continued
| Example No. | Structural formula | Salt | MS(ESI) m/z |
|---|---|---|---|
| D39 | 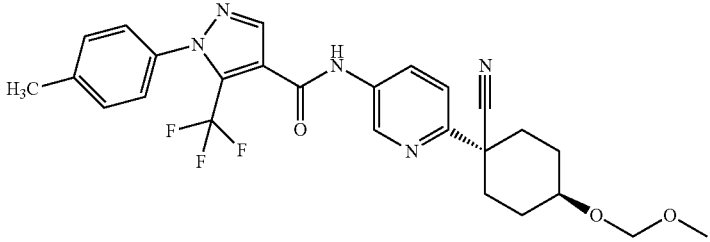 | | 514 |
| D40 | 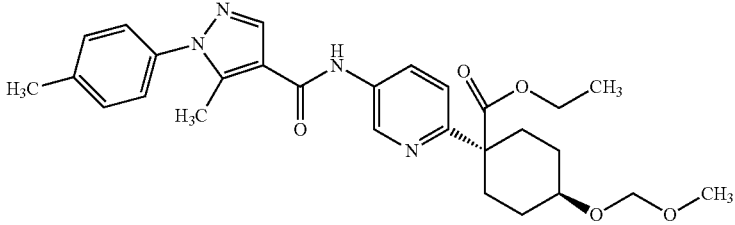 | | 507 |
| D41 | 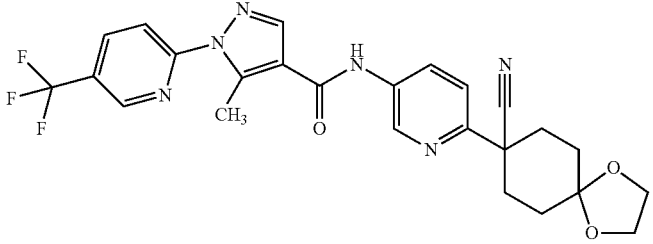 [SMILES: Cc1c(C(=O)Nc2ccc(C3(C#N)CCC4(CC3)OCCO4)nc2)cnn1-c1ccc(C(F)(F)F)cn1] | | 513 |
| D42 | 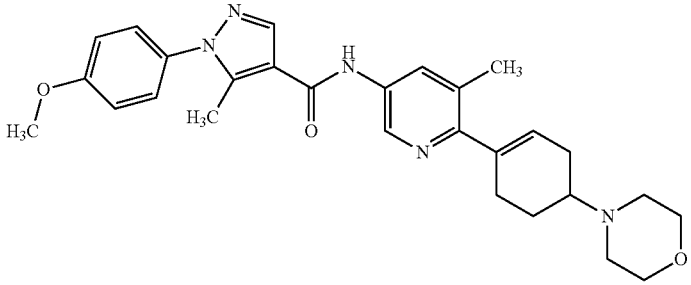 [SMILES: COc1ccc(-n2ncc(C(=O)Nc3cnc(C4=CCC(N5CCOCC5)CC4)c(C)c3)c2C)cc1] | | 488 |
| D43 | 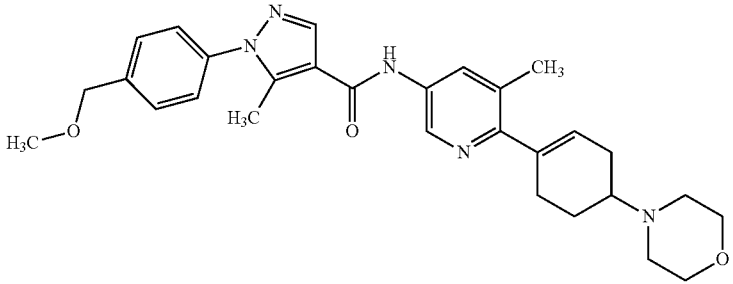 [SMILES: COCc1ccc(-n2ncc(C(=O)Nc3cnc(C4=CCC(N5CCOCC5)CC4)c(C)c3)c2C)cc1] | | 502 |

-continued

| Example No. | Structural formula | Salt | MS(ESI) m/z |
|---|---|---|---|
| D44 | | | 431 |
| D45 | | | 516 |
| D46 | | MsOH | 502 |
| D47 | | MsOH | 509 511 |
| D48 | | | 471 |

| Example No. | Structural formula | Salt | MS(ESI) m/z |
|---|---|---|---|
| D49 | | | 471 |
| D50 | | MsOH | 487 |
| D51 | | MsOH | 503 |
| D52 | | HCl | 531 |
| D53 | | HCl | 530 |

-continued

| Example No. | Structural formula | Salt | MS(ESI) m/z |
|---|---|---|---|
| D54 | | MsOH | 515 |
| D55 | | MsOH | 480 |
| D56 | | HCl | 498 |
| D57 | | MsOH | 508 |
| D58 | | MsOH | 494 |

-continued

| Example No. | Structural formula | Salt | MS(ESI) m/z |
|---|---|---|---|
| D59 | | HCl | 521 |
| D60 | | MsOH | 509 |
| D61 | | MsOH | 495 |
| D62 | | HCl | 522 |
| D63 | | MsOH | 497 |

-continued

| Example No. | Structural formula | Salt | MS(ESI) m/z |
|---|---|---|---|
| D64 | | MsOH | 487 |
| D65 | | MsOH | 505 |
| D66 | | MsOH | 511 |
| D67 | | MsOH | 527 |
| D68 | | HCl | 540 |

| Example No. | Structural formula | Salt | MS(ESI) m/z |
|---|---|---|---|
| D69 | 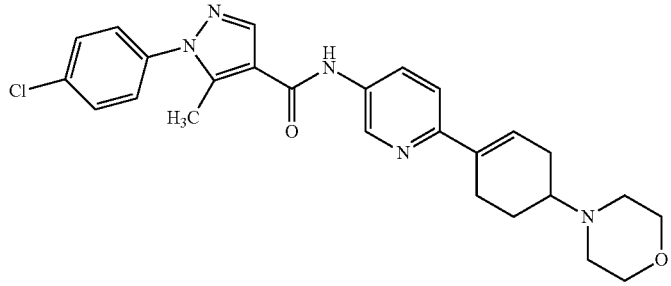 [SMILES: Cc1c(C(=O)Nc2ccc(C3=CCC(N4CCOCC4)CC3)nc2)cnn1-c1ccc(Cl)cc1] | MsOH | 478 |
| D70 | 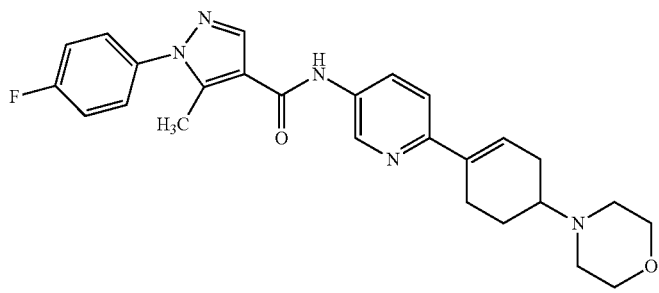 [SMILES: Cc1c(C(=O)Nc2ccc(C3=CCC(N4CCOCC4)CC3)nc2)cnn1-c1ccc(F)cc1] | MsOH | 462 |
| D71 | 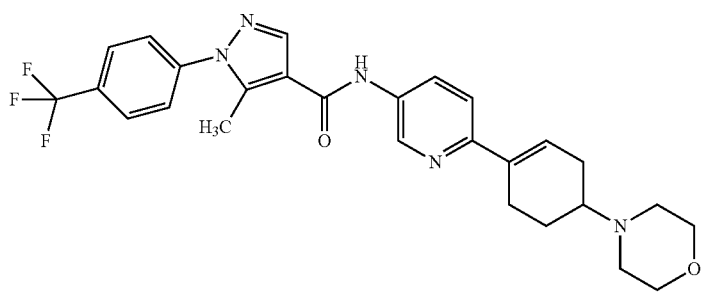 [SMILES: Cc1c(C(=O)Nc2ccc(C3=CCC(N4CCOCC4)CC3)nc2)cnn1-c1ccc(C(F)(F)F)cc1] | MsOH | 512 |
| D72 | 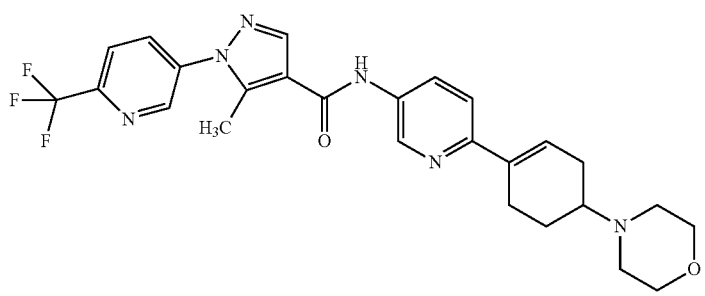 [SMILES: Cc1c(C(=O)Nc2ccc(C3=CCC(N4CCOCC4)CC3)nc2)cnn1-c1ccc(C(F)(F)F)nc1] | MsOH | 513 |
| D73 | 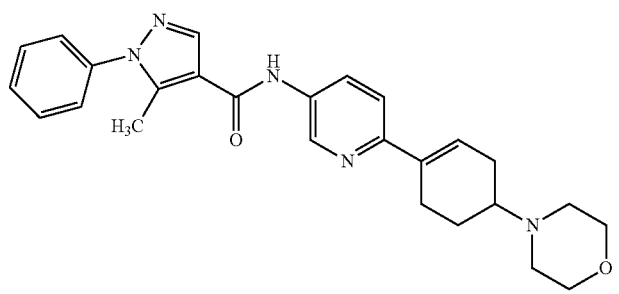 [SMILES: Cc1c(C(=O)Nc2ccc(C3=CCC(N4CCOCC4)CC3)nc2)cnn1-c1ccccc1] | MsOH | 444 |

| Example No. | Structural formula | Salt | MS(ESI) m/z |
|---|---|---|---|
| D74 | 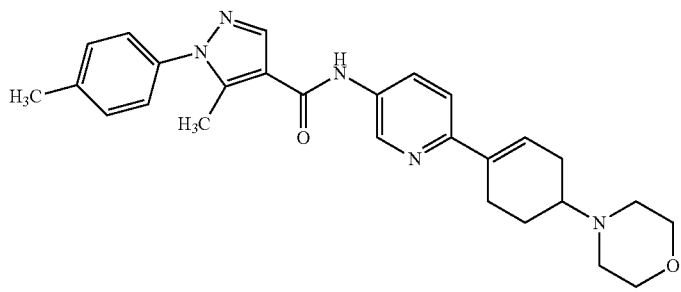 [SMILES: Cc1ccc(-n2ncc(C(=O)Nc3ccc(C4=CCC(N5CCOCC5)CC4)nc3)c2C)cc1] | MsOH | 458 |
| D75 | 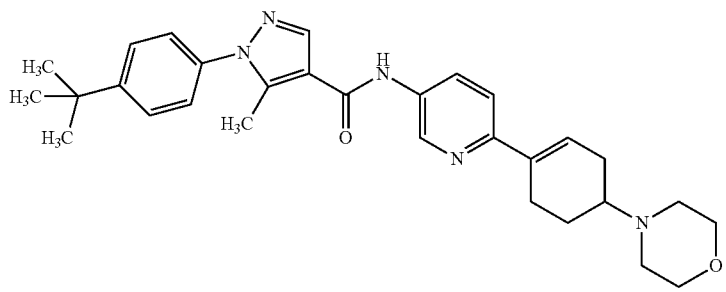 [SMILES: Cc1c(C(=O)Nc2ccc(C3=CCC(N4CCOCC4)CC3)nc2)cnn1-c1ccc(C(C)(C)C)cc1] | MsOH | 500 |
| D76 | 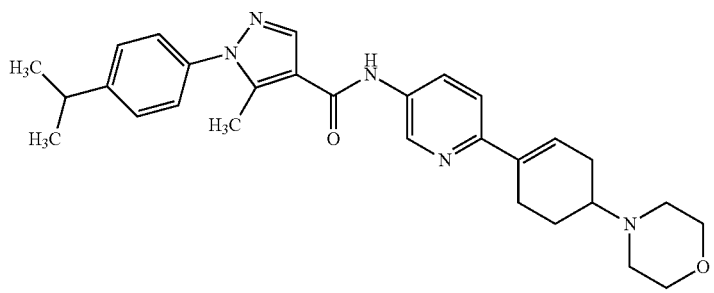 [SMILES: Cc1c(C(=O)Nc2ccc(C3=CCC(N4CCOCC4)CC3)nc2)cnn1-c1ccc(C(C)C)cc1] | MsOH | 486 |
| D77 | 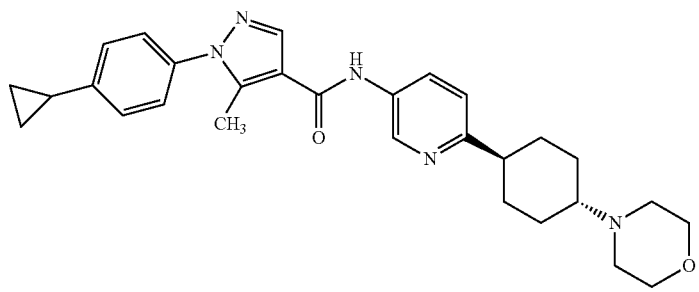 [SMILES: Cc1c(C(=O)Nc2ccc([C@H]3CC[C@H](N4CCOCC4)CC3)nc2)cnn1-c1ccc(C2CC2)cc1] | | 486 |
| D78 | 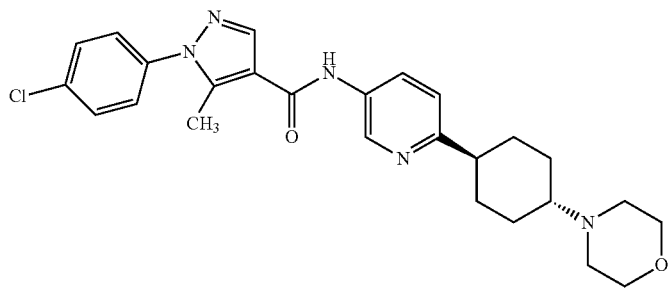 [SMILES: Cc1c(C(=O)Nc2ccc([C@H]3CC[C@H](N4CCOCC4)CC3)nc2)cnn1-c1ccc(Cl)cc1] | | 480 |

-continued

| Example No. | Structural formula | Salt | MS(ESI) m/z |
|---|---|---|---|
| D79 | | | 460 |
| D80 | | | 502 |
| D81 | | | 493 |
| D82 | | | 494 |
| D83 | | | 521 |

-continued

| Example No. | Structural formula | Salt | MS(ESI) m/z |
|---|---|---|---|
| D84 | | HCl | 500 |
| D85 | | HCl | 506 |
| D86 | | HCl | 512 |
| D87 | | HCl | 515 |
| D88 | | HCl | 527 |

-continued
| Example No. | Structural formula | Salt | MS(ESI) m/z |
|---|---|---|---|
| D89 | 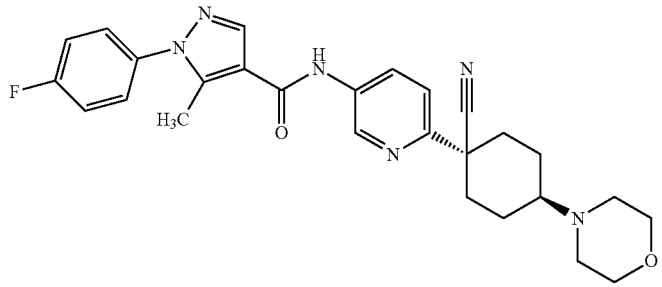 [SMILES: Cc1c(C(=O)Nc2ccc([C@]3(C#N)CC[C@@H](N4CCOCC4)CC3)nc2)cnn1-c1ccc(F)cc1] | HCl | 489 |
| D90 | 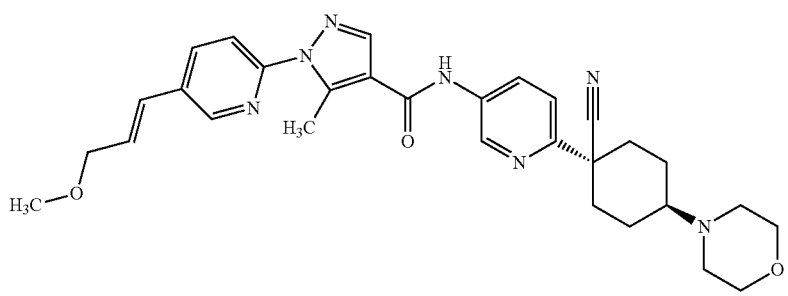 [SMILES: COC/C=C/c1ccc(-n2ncc(C(=O)Nc3ccc([C@]4(C#N)CC[C@@H](N5CCOCC5)CC4)nc3)c2C)nc1] | HCl | 542 |
| D91 | 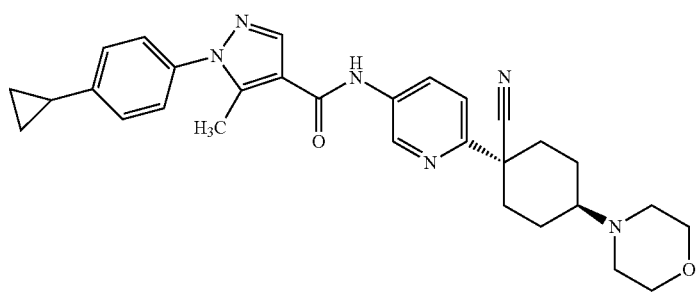 [SMILES: Cc1c(C(=O)Nc2ccc([C@]3(C#N)CC[C@@H](N4CCOCC4)CC3)nc2)cnn1-c1ccc(C2CC2)cc1] | HCl | 511 |
| D92 | 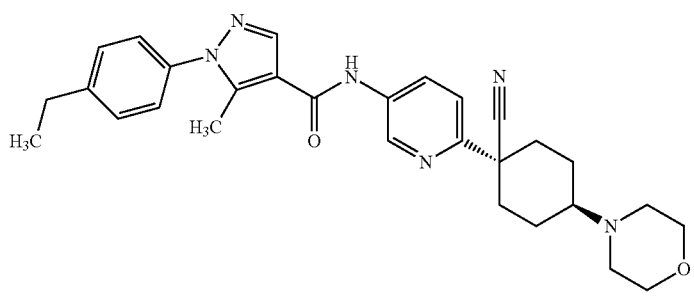 [SMILES: CCc1ccc(-n2ncc(C(=O)Nc3ccc([C@]4(C#N)CC[C@@H](N5CCOCC5)CC4)nc3)c2C)cc1] | HCl | 499 |
| D93 | 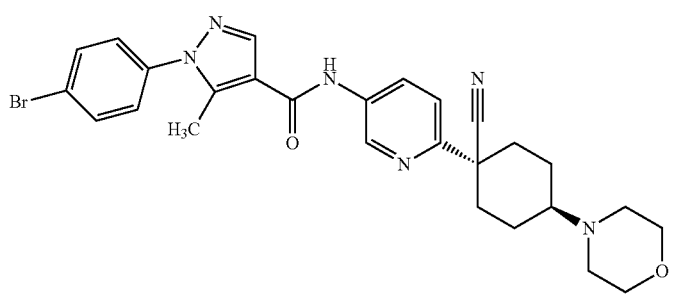 | HCl | 549<br>551 |

-continued

| Example No. | Structural formula | Salt | MS(ESI) m/z |
|---|---|---|---|
| D94 | | HCl | 539 |
| D95 | | HCl | 485 |
| D96 | | MsOH | 478 |
| D97 | | | 472 |
| D98 | | | 529 |

-continued

| Example No. | Structural formula | Salt | MS(ESI) m/z |
|---|---|---|---|
| D99 | | | 501 |
| D100 | | | 529 |
| D101 | | | 501 |
| D102 | | HCl | 473 |
| D103 | | HCl | 530 |

-continued

| Example No. | Structural formula | Salt | MS(ESI) m/z |
|---|---|---|---|
| D104 | | HCl | 528 |
| D105 | | HCl | 507 |
| D106 | | HCl | 494 |
| D107 | | HCl | 526 |
| D108 | | | 526 |

-continued

| Example No. | Structural formula | Salt | MS(ESI) m/z |
|---|---|---|---|
| D109 | | HCl | 539 |
| D110 | | HCl | 520 |
| D111 | | | 539 |
| D112 | | | 514 |
| D113 | | | 514 |

-continued

| Example No. | Structural formula | Salt | MS(ESI) m/z |
|---|---|---|---|
| D114 | | | 527 |
| D115 | | | 459 |
| D116 | | | 493 |
| D117 | | | 527 |
| D118 | | | 477 |

-continued

| Example No. | Structural formula | Salt | MS(ESI) m/z |
|---|---|---|---|
| D119 | | | 473 |
| D120 | | | 539 |
| D121 | | HCl | 570 |
| D122 | | | 512 |
| D123 | | | 526 |

| Example No. | Structural formula | Salt | MS(ESI) m/z |
|---|---|---|---|
| D124 | 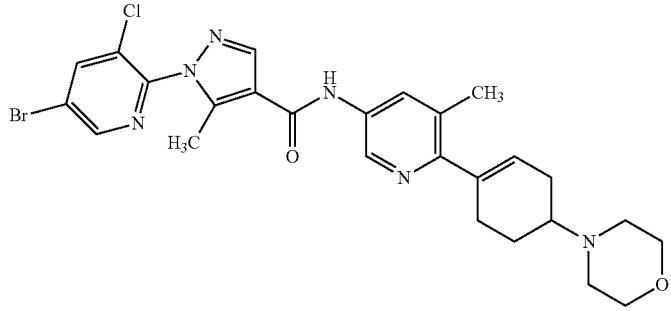 [SMILES: Cc1cc(NC(=O)c2cnn(-c3ccc(Cl)cc3Cl)c2C)cnc1C1=CCC(N2CCOCC2)CC1] | | 573 |
| D125 | 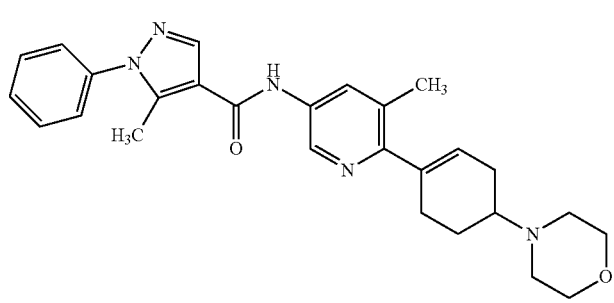 [SMILES: Cc1cc(NC(=O)c2cnn(-c3ccccc3)c2C)cnc1C1=CCC(N2CCOCC2)CC1] | MsOH | 458 |
| D126 | 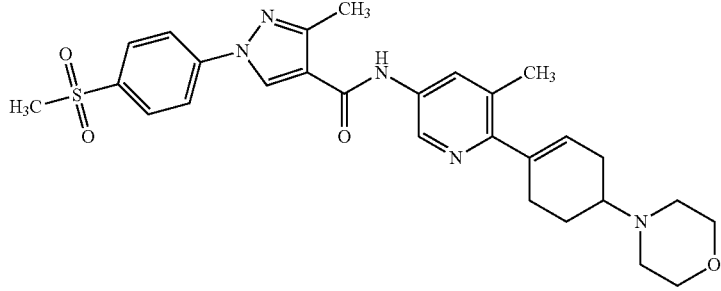 [SMILES: Cc1cc(NC(=O)c2cn(-c3ccc(S(C)(=O)=O)cc3)nc2C)cnc1C1=CCC(N2CCOCC2)CC1] | MsOH | 536 |
| D127 | 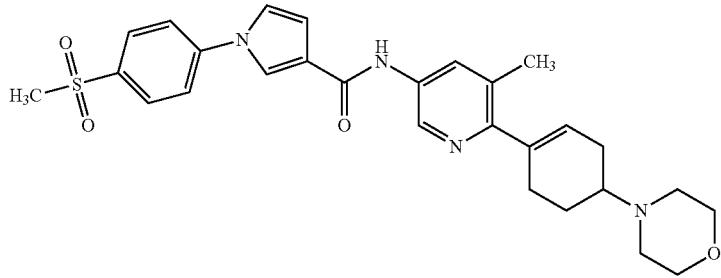 [SMILES: Cc1cc(NC(=O)c2ccn(-c3ccc(S(C)(=O)=O)cc3)c2)cnc1C1=CCC(N2CCOCC2)CC1] | MsOH | 521 |
| D128 | 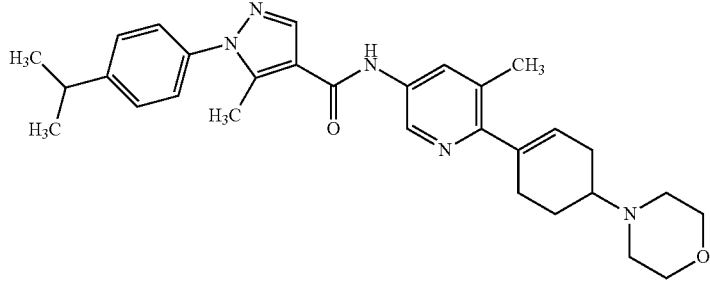 [SMILES: Cc1cc(NC(=O)c2cnn(-c3ccc(C(C)C)cc3)c2C)cnc1C1=CCC(N2CCOCC2)CC1] | MsOH | 500 |

-continued

| Example No. | Structural formula | Salt | MS(ESI) m/z |
|---|---|---|---|
| D129 | | | 533 |
| D130 | | | 507 |
| D131 | | MsOH | 526 |
| D132 | | MsOH | 513 |
| D133 | | MsOH | 472 |

-continued

| Example No. | Structural formula | Salt | MS(ESI) m/z |
|---|---|---|---|
| D134 | | MsOH | 476 |
| D135 | | MsOH | 526 |
| D136 | | MsOH | 513 |
| D137 | | | 521 |
| D138 | | MsOH | 498 |

-continued

| Example No. | Structural formula | Salt | MS(ESI) m/z |
|---|---|---|---|
| D139 | | MsOH | 526 |
| D140 | | | 500 |
| D141 | | | 507 |
| D142 | | | 474 |
| D143 | | | 504 |

-continued

| Example No. | Structural formula | Salt | MS(ESI) m/z |
|---|---|---|---|
| D144 | | | 463 |
| D145 | | | 539 |
| D146 | | | 539 |
| D147 | | | 534 |
| D148 | | | 443 |

| Example No. | Structural formula | Salt | MS(ESI) m/z |
|---|---|---|---|
| D149 | 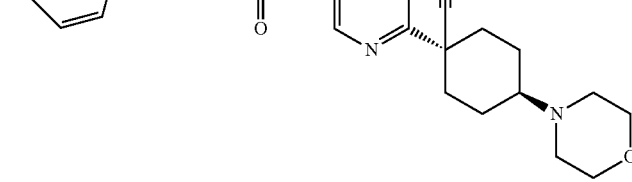 | | 470 |
| D150 | 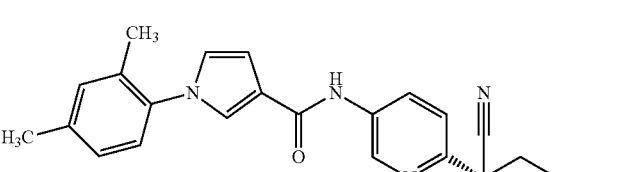 | | 484 |
| D151 |  | | 457 |
| D152 | 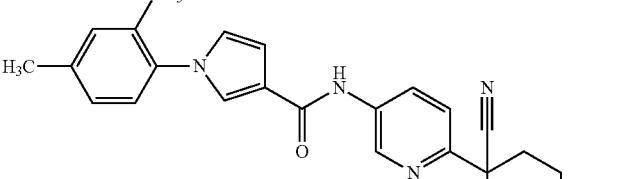 | | 443 |
| D153 |  | | 457 |

-continued

| Example No. | Structural formula | Salt | MS(ESI) m/z |
|---|---|---|---|
| D154 | | | 443 |
| D155 | | | 447 |
| D156 | | | 459 |
| D157 | | | 509 |
| D158 | | | 496 |

-continued

| Example No. | Structural formula | Salt | MS(ESI) m/z |
|---|---|---|---|
| D159 | | | 544 |
| D160 | | | 474 |
| D161 | | | 477 |
| D162 | | | 519 |
| D163 | | | 516 |
| D164 | | | 433 |

-continued

| Example No. | Structural formula | Salt | MS(ESI) m/z |
|---|---|---|---|
| D165 | | | 475 |
| D166 | | | 535 |
| D167 | | MsOH | 499 |
| D168 | | MsOH | 486 |
| D169 | | MsOH | 473 |

| Example No. | Structural formula | Salt | MS(ESI) m/z |
|---|---|---|---|
| D170 | | | 487 |
| D171 | | | 567 569 |
| D172 | | | 573 |
| D173 | | MsOH | 527 |

| Example No. | Structural formula | Salt | MS(ESI) m/z |
|---|---|---|---|
| D174 | | | 533 |
| D175 | | | 561 |
| D176 | | | 499 |
| D177 | | | 517 |
| D178 | | | 527 |

-continued

| Example No. | Structural formula | Salt | MS(ESI) m/z |
|---|---|---|---|
| D179 | | | 499 |
| D180 | | MsOH | 515 |
| D181 | | MsOH | 487 |
| D182 | | | 517 |
| D183 | | | 489 |

-continued

| Example No. | Structural formula | Salt | MS(ESI) m/z |
|---|---|---|---|
| D184 | | | 499 |
| D185 | | | 499 |
| D186 | | | 499 |
| D187 | | | 513 |
| D188 | | | 541 |

| Example No. | Structural formula | Salt | MS(ESI) m/z |
|---|---|---|---|
| D189 | 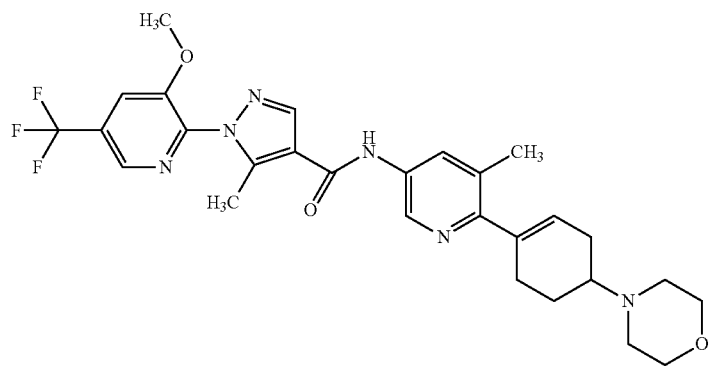 [SMILES: COc1cc(C(F)(F)F)cnc1-n1ncc(C(=O)Nc2cnc(C3=CCC(N4CCOCC4)CC3)c(C)c2)c1C] | | 557 |
| D190 | 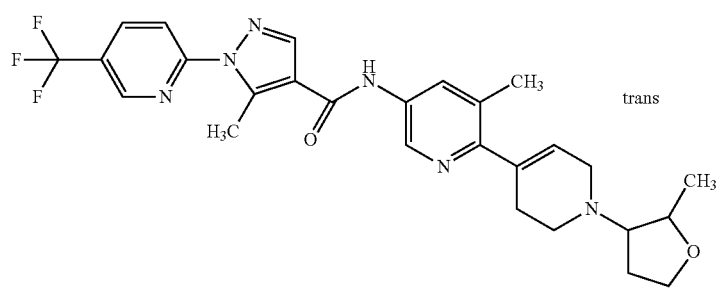 [SMILES: Cc1cc(NC(=O)c2cnn(-c3ccc(C(F)(F)F)cn3)c2C)cnc1C1=CCN(C2CCOC2C)CC1] trans | | 527 |
| D191 | 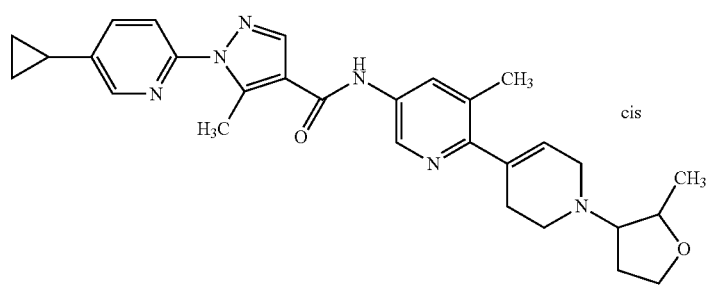 cis | | 499 |
| D192 | 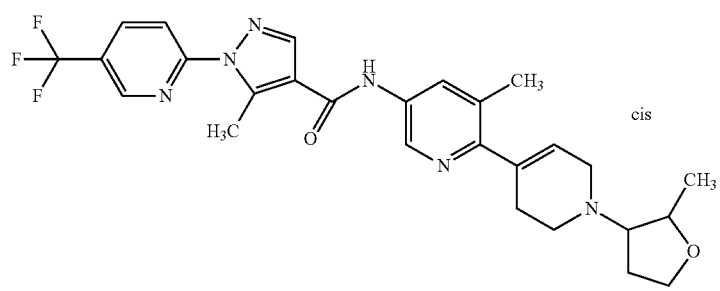 [SMILES: Cc1cc(NC(=O)c2cnn(-c3ccc(C(F)(F)F)cn3)c2C)cnc1C1=CCN(C2CCOC2C)CC1] cis | | 527 |
| D193 | 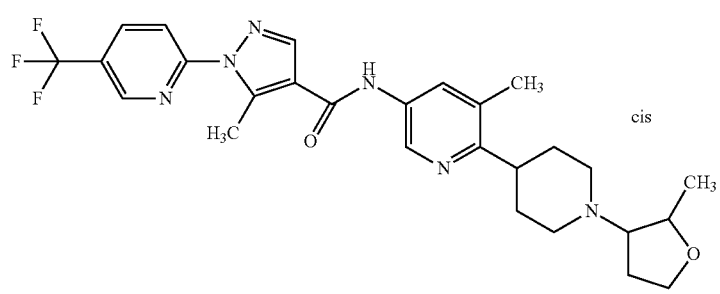 [SMILES: Cc1cc(NC(=O)c2cnn(-c3ccc(C(F)(F)F)cn3)c2C)cnc1C1CCN(C2CCOC2C)CC1] cis | | 529 |

-continued

| Example No. | Structural formula | Salt | MS(ESI) m/z |
|---|---|---|---|
| D194 | | | 501 |
| D195 | | | 472 |
| D196 | | | 520 |
| D197 | | | 532 |
| D198 | | | 536 |

-continued

| Example No. | Structural formula | Salt | MS(ESI) m/z |
|---|---|---|---|
| D199 | | MsOH | 503 |
| D200 | | MsOH | 501 |
| D201 | | MsOH | 489 |
| D202 | | MsOH | 433 |
| D203 | | MsOH | 477 |

-continued

| Example No. | Structural formula | Salt | MS(ESI) m/z |
|---|---|---|---|
| D204 | | HCl | 574 |
| D205 | | HCl | 530 |
| D206 | | HCl | 524 |
| D207 | | HCl | 519 |
| D208 | | HCl | 563 |

US 9,150,555 B2

253                                                                                                                                254

-continued

| Example No. | Structural formula | Salt | MS(ESI) m/z |
|---|---|---|---|
| D209 | | MsOH | 514 |
| D210 | | MsOH | 473 |
| D211 | | | 463 |
| D212 | | | 479 |
| D213 | | | 470 |

-continued
| Example No. | Structural formula | Salt | MS(ESI) m/z |
|---|---|---|---|
| D214 | 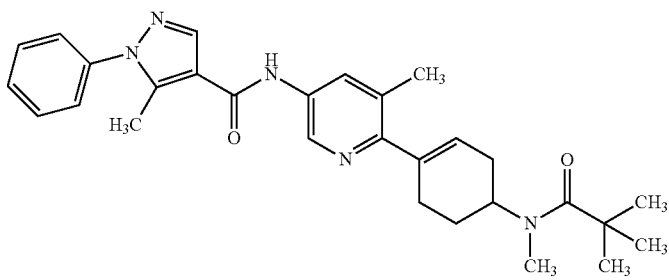 [SMILES: Cc1cc(NC(=O)c2cnn(-c3ccccc3)c2C)cnc1C1=CCC(N(C)C(=O)C(C)(C)C)CC1] | | 486 |
| D215 | 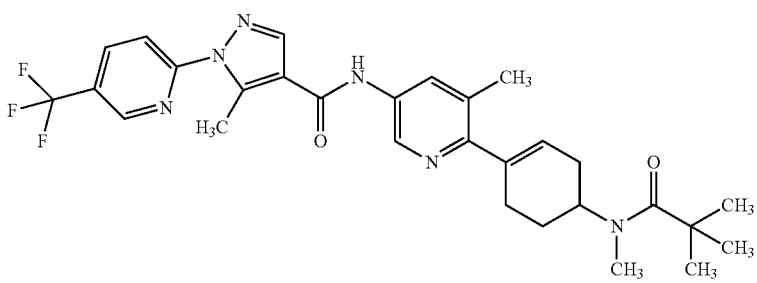 [SMILES: Cc1cc(NC(=O)c2cnn(-c3ccc(C(F)(F)F)cn3)c2C)cnc1C1=CCC(N(C)C(=O)C(C)(C)C)CC1] | | 541 |
| D216 | 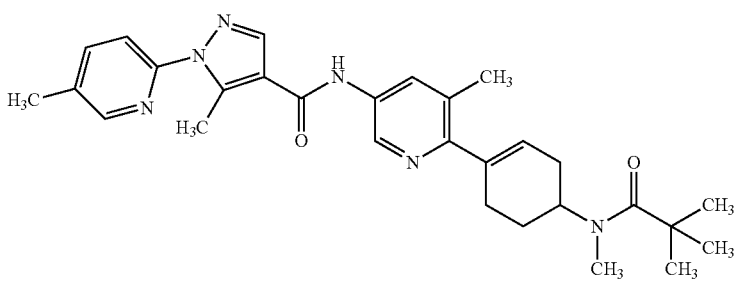 [SMILES: Cc1ccc(-n2ncc(C(=O)Nc3cnc(C4=CCC(N(C)C(=O)C(C)(C)C)CC4)c(C)c3)c2C)nc1] | | 487 |
| D217 | 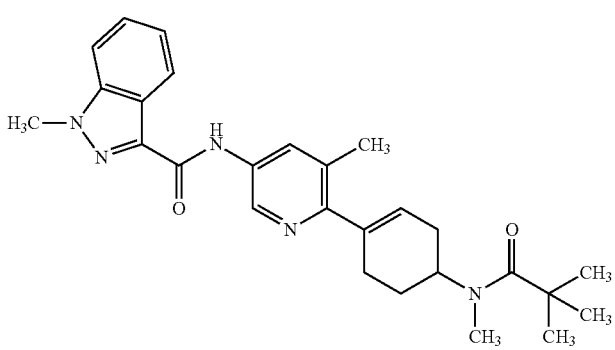 [SMILES: Cc1cc(NC(=O)c2nn(C)c3ccccc23)cnc1C1=CCC(N(C)C(=O)C(C)(C)C)CC1] | | 460 |
| D218 | 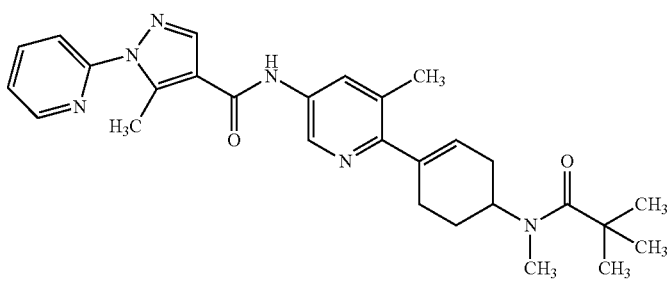 [SMILES: Cc1cc(NC(=O)c2cnn(-c3ccccn3)c2C)cnc1C1=CCC(N(C)C(=O)C(C)(C)C)CC1] | | 487 |

-continued

| Example No. | Structural formula | Salt | MS(ESI) m/z |
|---|---|---|---|
| D219 | | | 490 |
| D220 | | | 486 |
| D221 | | | 513 |
| D222 | | | 484 |
| D223 | | | 485 |

-continued

| Example No. | Structural formula | Salt | MS(ESI) m/z |
|---|---|---|---|
| D224 | | | 541 |
| D225 | | | 499 |
| D226 | | | 472 |
| D227 | | | 506 |
| D228 | | | 543 |

| Example No. | Structural formula | Salt | MS(ESI) m/z |
|---|---|---|---|
| D229 | 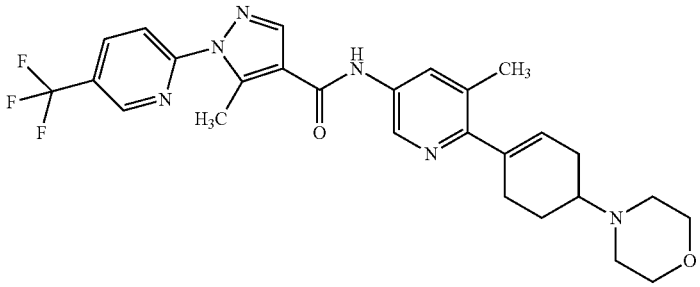 [SMILES: Cc1cc(NC(=O)c2cnn(-c3ccc(C(F)(F)F)cn3)c2C)cnc1C1=CCC(N2CCOCC2)CC1] | | 528 |
| D230 | 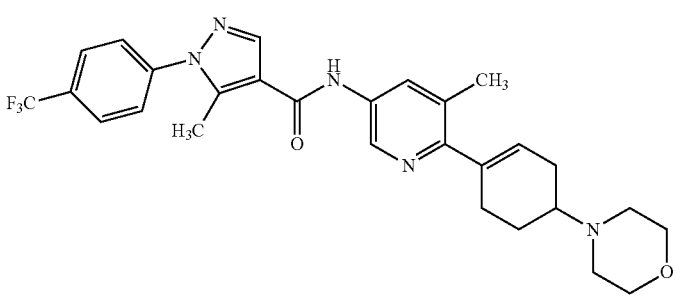 [SMILES: Cc1cc(NC(=O)c2cnn(-c3ccc(C(F)(F)F)cc3)c2C)cnc1C1=CCC(N2CCOCC2)CC1] | | 526 |
| D231 | 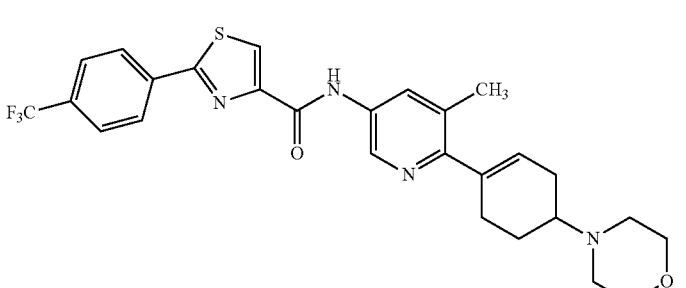 | | 529 |
| D232 | 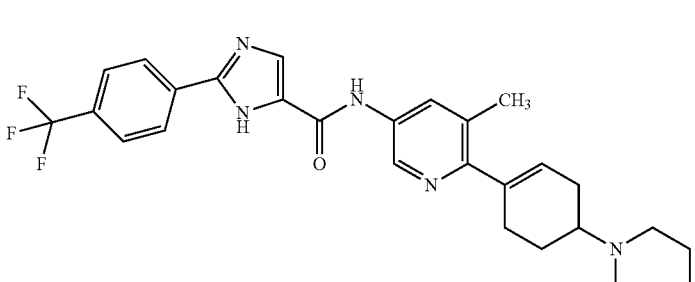 | | 512 |
| D233 | 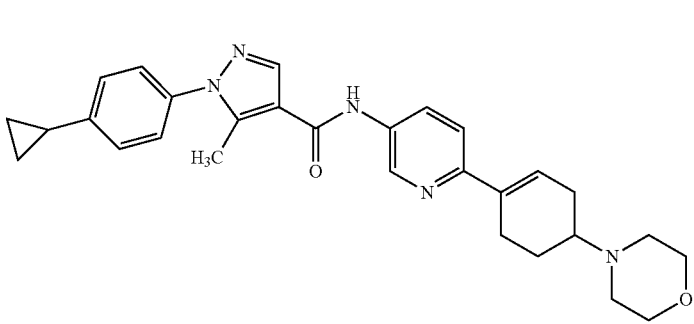 [SMILES: Cc1c(C(=O)Nc2ccc(C3=CCC(N4CCOCC4)CC3)nc2)cnn1-c1ccc(C2CC2)cc1] | MsOH | 484 |

-continued

| Example No. | Structural formula | Salt | MS(ESI) m/z |
|---|---|---|---|
| D234 | | | 500 |
| D235 | | | 555 |
| D236 | | | 527 |
| D237 | | | 488 |
| D238 | | | 502 |

-continued
| Example No. | Structural formula | Salt | MS(ESI) m/z |
|---|---|---|---|
| D239 | 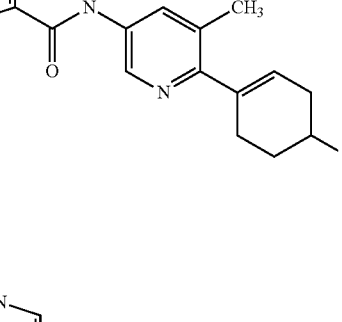 | | 459 |
| D240 | 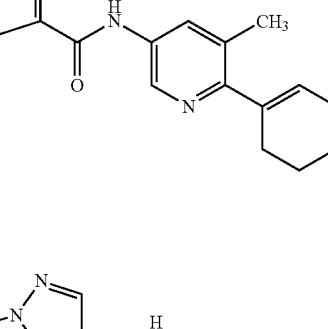 | | 459 |
| D241 | 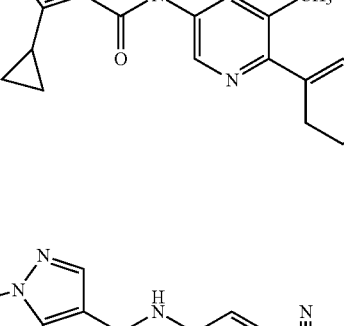 | | 518 |
| D242 | 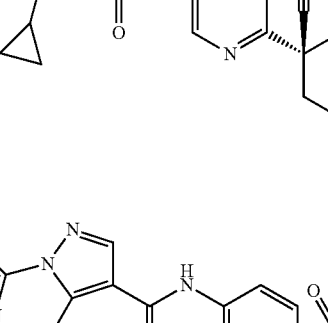 | | 531 |
| D243 | 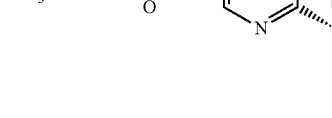 | | 587 |

-continued

| Example No. | Structural formula | Salt | MS(ESI) m/z |
|---|---|---|---|
| D244 | | | 559 |
| D245 | | | 559 |
| D246 | | | 561 |
| D247 | | | 619 |
| D248 | | | 603 |

-continued

| Example No. | Structural formula | Salt | MS(ESI) m/z |
|---|---|---|---|
| D249 | | | 571 |
| D250 | | | 430 |
| D251 | | | 434 |
| D252 | | | 430 |
| D253 | | | 434 |

| Example No. | Structural formula | Salt | MS(ESI) m/z |
|---|---|---|---|
| D254 | | | 485 |
| D255 | | | 485 |
| D256 | | | 442 |
| D257 | | | 446 |
| D258 | | | 446 |

| Example No. | Structural formula | Salt | MS(ESI) m/z |
|---|---|---|---|
| D259 | | | 442 |
| D260 | | | 504 |
| D261 | | | 500 |
| D262 | | | 527 |
| D263 | | | 515 |

-continued

| Example No. | Structural formula | Salt | MS(ESI) m/z |
|---|---|---|---|
| D264 | | | 501 |
| D265 | | | 567 |
| D266 | | | 539 |
| D267 | | | 513 |
| D268 | | | 541 |

-continued

| Example No. | Structural formula | Salt | MS(ESI) m/z |
|---|---|---|---|
| D269 | | | 513 |
| D270 | | | 509 |
| D271 | | | 486 |
| D272 | | | 490 |
| D273 | | | 472 |

| Example No. | Structural formula | Salt | MS(ESI) m/z |
|---|---|---|---|
| D274 | 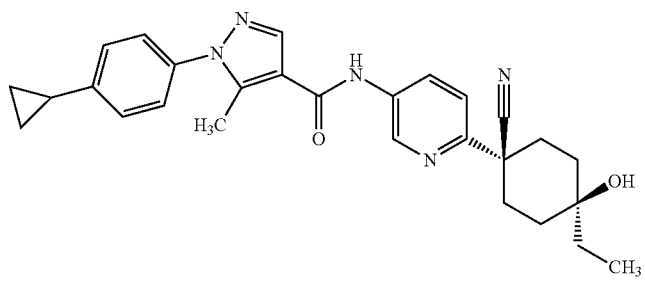 [SMILES: CC[C@]1(O)CC[C@](C#N)(c2ccc(NC(=O)c3cnn(-c4ccc(C5CC5)cc4)c3C)cn2)CC1] | | 470 |
| D275 | 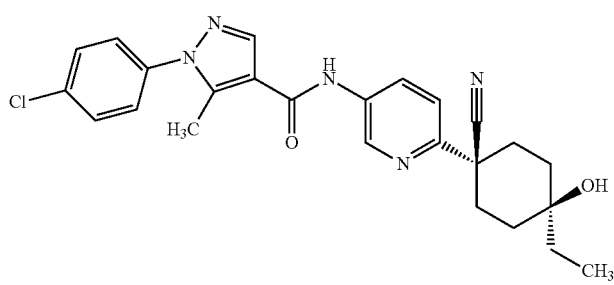 [SMILES: CC[C@]1(O)CC[C@](C#N)(c2ccc(NC(=O)c3cnn(-c4ccc(Cl)cc4)c3C)cn2)CC1] | | 464 |
| D276 | 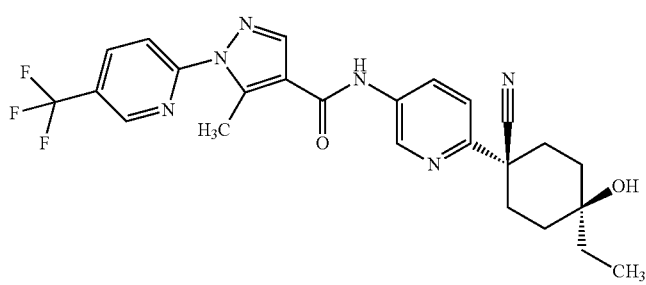 [SMILES: CC[C@]1(O)CC[C@](C#N)(c2ccc(NC(=O)c3cnn(-c4ccc(C(F)(F)F)cn4)c3C)cn2)CC1] | | 499 |
| D277 | 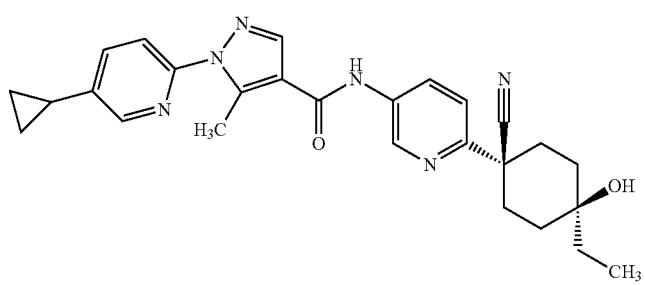 [SMILES: CC[C@]1(O)CC[C@](C#N)(c2ccc(NC(=O)c3cnn(-c4ccc(C5CC5)cn4)c3C)cn2)CC1] | | 471 |
| D278 | 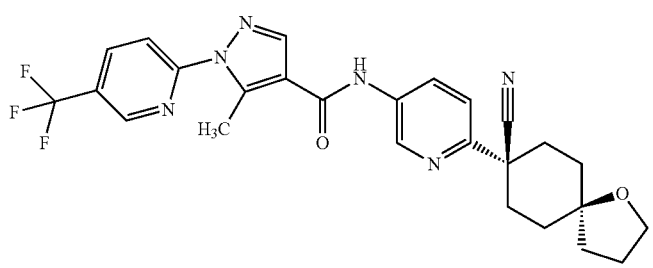 [SMILES: Cc1c(C(=O)Nc2ccc([C@]3(C#N)CC[C@]4(CCCO4)CC3)nc2)cnn1-c1ccc(C(F)(F)F)cn1] | | 511 |

-continued

| Example No. | Structural formula | Salt | MS(ESI) m/z |
|---|---|---|---|
| D279 | | | 456 |
| D280 | | | 476 |
| D281 | | | 482 |
| D282 | | | 531 |
| D283 | | | 503 |

| Example No. | Structural formula | Salt | MS(ESI) m/z |
|---|---|---|---|
| D284 | | | 458 |
| D285 | | | 480 |
| D286 | | | 505 |
| D287 | | | 568 |
| D288 | | | 568 |

-continued

| Example No. | Structural formula | Salt | MS(ESI) m/z |
|---|---|---|---|
| D289 | | | 554 |
| D290 | | | 504 |
| D291 | | | 559 |
| D292 | | | 541 |
| D293 | | | 594 |

-continued
| Example No. | Structural formula | Salt | MS(ESI) m/z |
|---|---|---|---|
| D294 | 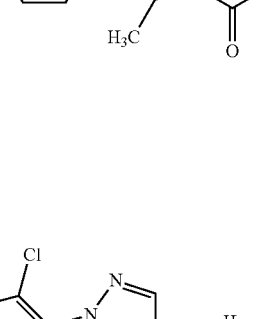 | | 542 |
| D295 | 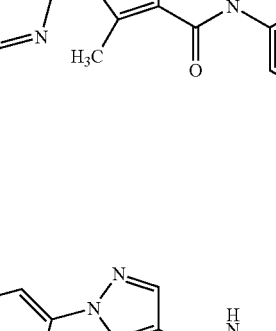 | | 574 |
| D296 | 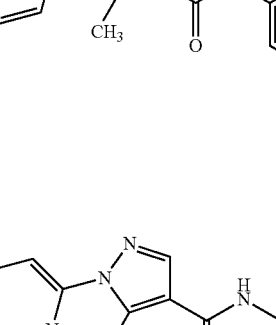 | | 539 |
| D297 | 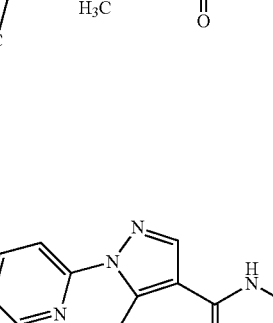 | | 541 |
| D298 |  | | 591 |

| Example No. | Structural formula | Salt | MS(ESI) m/z |
|---|---|---|---|
| D299 | 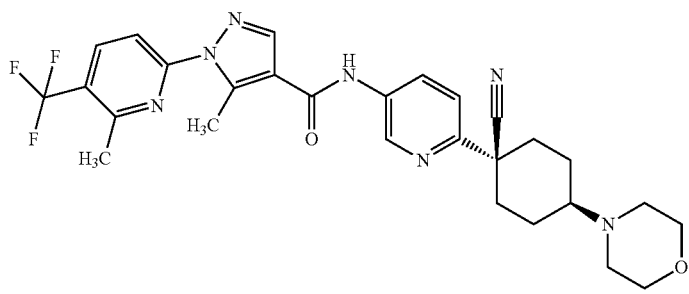 [SMILES: Cc1nc(-n2ncc(C(=O)Nc3ccc([C@]4(C#N)CC[C@@H](N5CCOCC5)CC4)nc3)c2C)ccc1C(F)(F)F] | | 554 |
| D300 | 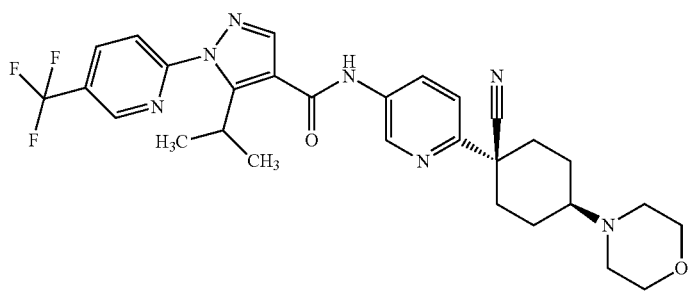 [SMILES: CC(C)c1c(C(=O)Nc2ccc([C@]3(C#N)CC[C@@H](N4CCOCC4)CC3)nc2)cnn1-c1ccc(C(F)(F)F)cn1] | | 568 |
| D301 | 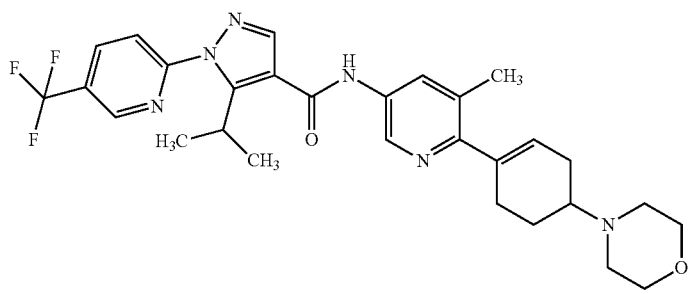 [SMILES: Cc1cc(NC(=O)c2cnn(-c3ccc(C(F)(F)F)cn3)c2C(C)C)cnc1C1=CCC(N2CCOCC2)CC1] | | 555 |
| D302 | 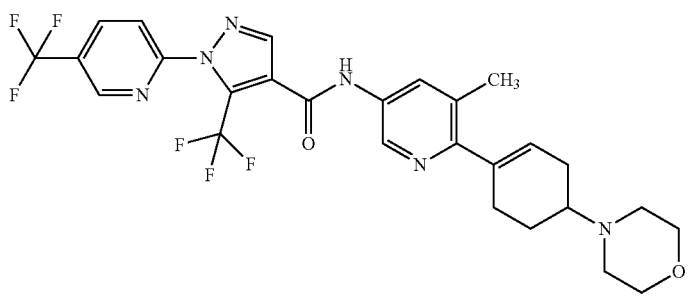 [SMILES: Cc1cc(NC(=O)c2cnn(-c3ccc(C(F)(F)F)cn3)c2C(F)(F)F)cnc1C1=CCC(N2CCOCC2)CC1] | | 581 |
| D303 | 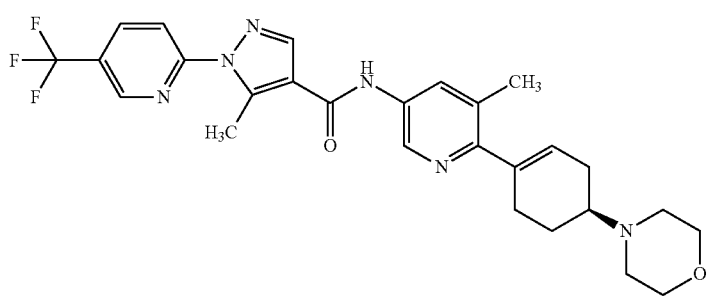 [SMILES: Cc1cc(NC(=O)c2cnn(-c3ccc(C(F)(F)F)cn3)c2C)cnc1C1=CC[C@@H](N2CCOCC2)CC1] | MsOH | 527 |

| Example No. | Structural formula | Salt | MS(ESI) m/z |
|---|---|---|---|
| D304 | | HCl | 539 |

Example E1

5-Methyl-N-{6-[4-(morpholin-4-yl)cyclohex-1-en-1-yl]pyridin-3-yl}-1-[5-(trifluoromethyl)-pyridin-2-yl]-1H-pyrazole-4-carboxamide mesylate

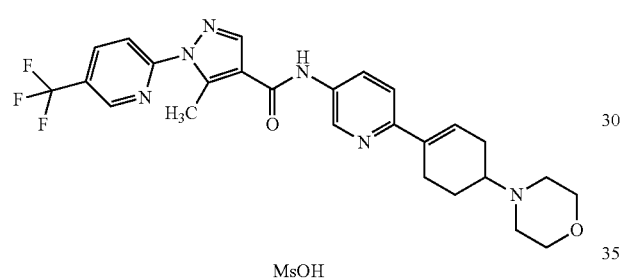

MsOH (1) Thionyl chloride (3.95 g) and N,N-dimethylformamide (catalytic amounts) were added at room temperature to 5-methyl-1-[5-(trifluoromethyl)pyridin-2-yl]-1H-pyrazole-4-carboxylic acid (3.0 g) described in Reference Example 8 in toluene (55 ml), and stirred at 80° C. for an hour. The solvent and an excess amount of thionyl chloride were evaporated, tetrahydrofuran (55 ml) was added to the residue, 25% aqueous ammonia (44 ml) was added under ice-cooling and stirred at room temperature for two hours. After the reaction, 1N aqueous solution of sodium hydroxide was added, and the precipitated solid was filtered to give 5-methyl-1-[5-(trifluoromethyl)pyridin-2-yl]-1H-pyrazole-4-carboxamide (2.9 g) as a white solid.

MS (ESI) m/z: 271 (M+H)⁺.

(2) 4-[4-(5-Bromopyridin-2-yl)cyclohex-3-en-1-yl]morpholine (314 mg) described in Reference Example 77, palladium (II) acetate (20.9 mg), 4,5-bis(diphenylphosphino)-9,9-dimethylxanthene (80.4 mg) and cesium carbonate (422 mg) were added at room temperature to a solution of 5-methyl-1-[5-(trifluoromethylpyridin-2-yl]-1H-pyrazole-4-carboxamide (250 mg) in 1,4-dioxane (9.3 ml), and stirred at 130° C. for an hour. Next, palladium (II) acetate (20.9 mg) and 4,5-bis(diphenylphosphino)-9,9-dimethylxanthene (80.4 mg) were added and stirred at the same temperature for two hours. After the reaction, the reaction mixture was cooled to room temperature, water was added and the precipitated solid was filtered. The resulting residue was purified with a silica gel column chromatography (chloroform/methanol) and washed with ethanol to give 5-methyl-N-{6-[4-(morpholin-4-yl)cyclohex-1-en-1-yl]pyridin-3-yl}-1-[5-(trifluoromethyl)pyridin-2-yl]-1H-pyrazole-4-carboxamide (252 mg) as a pale yellow solid.

MS (ESI) m/z: 513 (M+H)⁺.

(3) Methanesulfonic acid (35 μl) was added at room temperature to a solution of 5-methyl-N-{6-[4-(morpholin-4-yl)cyclohex-1-en-1-yl]pyridin-3-yl}-1-[5-(trifluoromethyl)pyridin-2-yl]-1H-pyrazole-4-carboxamide (245 mg) in chloroform (9.0 ml) and methanol (1.0 ml), and stirred at the same temperature for 12 hours. After the reaction, the solvent was evaporated, ethyl acetate was added to the resulting residue and the precipitated solid was filtered to give the titled compound (265 mg) as a white solid.

MS (ESI) m/z: 513(M+H)⁺.

Example E2

N-{6-[r-1-Hydroxy-c-4-(morpholin-4-yl)cyclohexyl]pyridin-3-yl}-5-methyl-1-[5-(trifluoromethyl)pyridin-2-yl]-1H-pyrazole-4-carboxamide

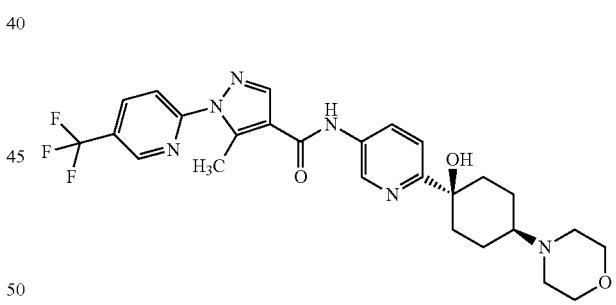

1-(5-Bromopyridin-2-yl)-c-4-(morpholin-4-yl)-r-1-cyclohexanol (332 mg) described in Reference Example 76, palladium (II) acetate (41.5 mg), 4,5-bis(diphenylphosphino)-9,9-dimethylxanthene (161 mg) and cesium carbonate (723 mg) were added at room temperature to a solution of 5-methyl-1-[5-(trifluoromethyl)pyridin-2-yl]-1H-pyrazole-4-carboxamide (250 mg) described in Example E1(1) in 1,4-dioxane (9.3 ml), and stirred at 130° C. for three hours. After the reaction, the reaction solution was cooled to room temperature, water was added and extracted with 10% methanol/chloroform. The organic layer was dried over anhydrous sodium sulfate and concentrated. The resulting residue was purified with a silica gel column chromatography (chloroform/methanol) to give the titled compound (227 mg) as a yellow solid.

MS (ESI) m/z: 531 (M+H)⁺.

Example E3

N-[6-(8-Cyano-1,4-dioxaspiro[4.5]dec-8-yl)pyridin-3-yl]-5-methyl-1-(4-methylphenyl)-1H-pyrazole-4-carboxamide

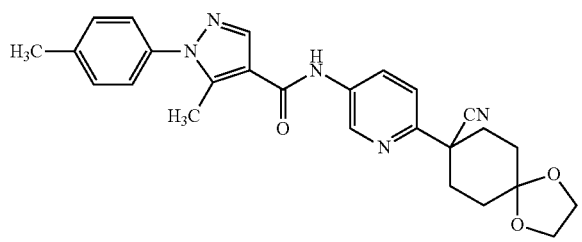 [SMILES: Cc1ccc(-n2ncc(C(=O)Nc3ccc(C4(C#N)CCC5(CC4)OCCO5)nc3)c2C)cc1]

(1) 5-Methyl-1-(4-methylphenyl)-1H-pyrazole-4-carboxamide was prepared from 5-methyl-1-(4-methylphenyl)-1H-pyrazole-4-carboxylic acid in a similar manner as Example E1(1).

(2) 5-Methyl-1-(4-methylphenyl)-1H-pyrazole-4-carboxamide (786 mg) and 8-(5-bromopyridin-2-yl)-1,4-dioxaspiro[4.5]decane-8-carbonitrile (1.12 g) described in Reference Example 82, copper (I) iodide (35 mg), N,N-dimethylethylamine (33 mg) and potassium carbonate in 1,4-dioxane (5 ml) was stirred at 100° C. for six hours. After the reaction, water was added and extracted with ethyl acetate. The organic layer was dried over anhydrous magnesium sulfate and concentrated. The residue was purified with a silica gel column chromatography to give the titled compound (42 mg).

MS (ESI) m/z: 458 (M+H)$^+$.

The next compounds (Examples E4 to E29) were prepared from the corresponding starting material in a similar manner as Examples E1 to E3. Conversions into mesylate or hydrochloride salt was carried out in a similar manner as Examples D1 and D5 etc.

| Example No. | Structural formula | Salt | MS (ESI) m/z |
|---|---|---|---|
| E4 | 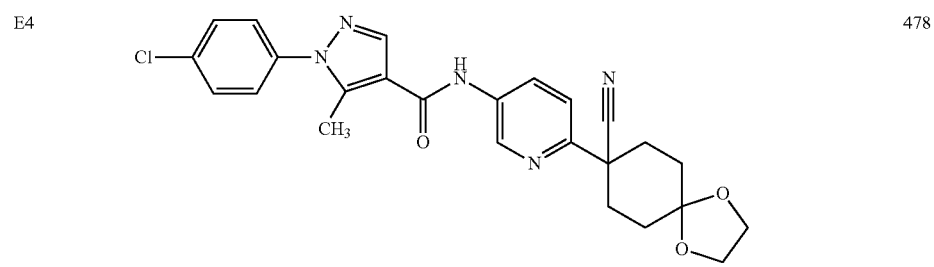 | | 478 |
| E5 | 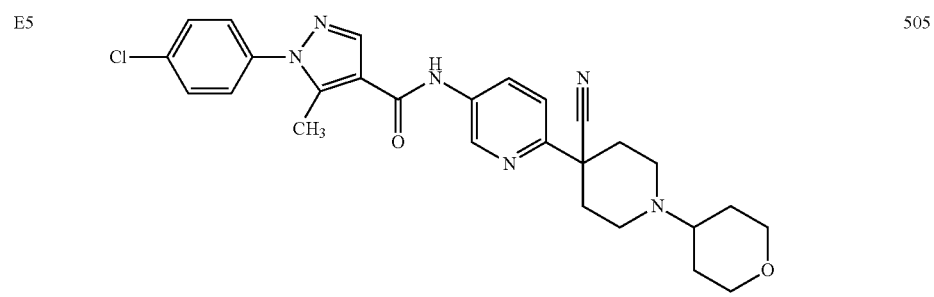 | | 505 |
| E6 | 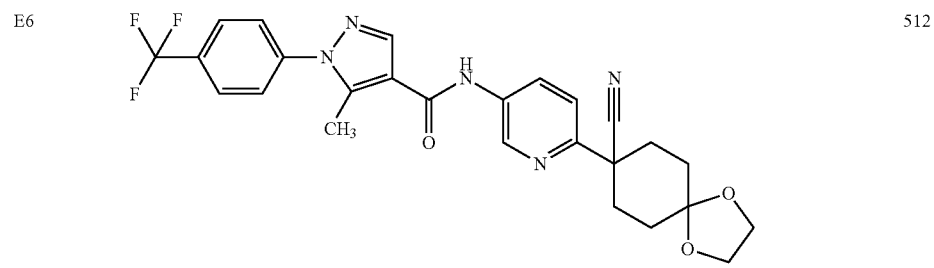 | | 512 |

-continued

| Example No. | Structural formula | Salt | MS (ESI) m/z |
|---|---|---|---|
| E7 | | | 539 |
| E8 | | MsOH | 477 |
| E9 | | MsOH | 461 |
| E10 | | | 462 |
| E11 | | | 480 |

-continued

| Example No. | Structural formula | Salt | MS (ESI) m/z |
|---|---|---|---|
| E12 | | | 513 |
| E13 | | | 409 |
| E14 | | | 443 |
| E15 | | | 528 |
| E16 | | | 480 |

-continued

| Example No. | Structural formula | Salt | MS (ESI) m/z |
|---|---|---|---|
| E17 | | | 480 |
| E18 | | | 464 |
| E19 | | | 459 |
| E20 | | | 444 |
| E21 | | | 411 |

-continued

| Example No. | Structural formula | Salt | MS (ESI) m/z |
|---|---|---|---|
| E22 | | | 389 |
| E23 | | MsOH | 492 |
| E24 | | HCl | 526 |
| E25 | | MsOH | 487 |
| E26 | | | 456 |
| E27 | | | 431 |

| Example No. | Structural formula | Salt | MS (ESI) m/z |
|---|---|---|---|
| E28 | | | 432 |
| E29 | | | 447 |

Example E30

N-[6-(3,6-Dihydro-2H-pyran-4-yl)-5-methylpyridin-3-yl]-5-methyl-1-[4-(trifluoromethyl)-phenyl]-1H-pyrazole-4-carboxamide

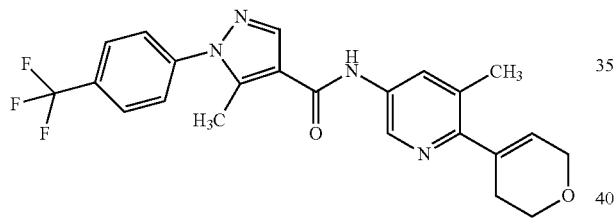

(1) Oxalyl chloride (3.8 ml) and N,N-dimethylformamide (catalytic amounts) were added at room temperature to a solution of 5-methyl-1-[4-(trifluoromethyl)phenyl]-1H-pyrazole-4-carboxylic acid (3.0 g) described in Reference Example 23 in dichloromethane (50 ml) and stirred at room temperature for two hours. The solvent and an excess amount of oxalyl chloride were evaporated, tetrahydrofuran (50 ml) was added to the residue, 28% aqueous ammonia was added under ice-cooling, and stirred at room temperature for two hours. After the reaction, the reaction solution was diluted with water and extracted with ethyl acetate. The resulting organic layer was washed with 1N hydrochloric acid aqueous solution, 4N aqueous solution of sodium hydroxide, water and saturated brine successively, dried over anhydrous sodium sulfate and concentrated to give 5-methyl-1-[4-(trifluoromethyl)phenyl]-1H-pyrazole-4-carboxamide (2.92 g) as a pale brown solid.

MS (ESI) m/z: 270 (M+H)$^+$.

(2) A suspension of 5-methyl-1-[4-(trifluoromethyl)phenyl]-1H-pyrazole-4-carboxamide (212 mg), 5-bromo-2-(3,6-dihydro-2H-pyran-4-yl)-3-methylpyridine (200 mg) described in Reference Example 135, 2-(di-tert-butylphosphino)-3,4,5,6-tetramethyl-2',4',6'-triisopropyl-1,1'-biphenyl (19 mg), tris(dibenzylideneacetone)dipalladium (0) (7.2 mg) and tripotassium phosphate (200 mg) in tert-butanol (3 ml) was stirred at 110° C. After the reaction, the reaction solution was left stand, diluted with chloroform and filtered through Celite. The organic layer was washed with water and saturated brine successively, dried over anhydrous sodium sulfate and concentrated. The resulting residue was purified with a silica gel column chromatography (chloroform/methanol), washed with hot ethanol and the resulting solid was filtered and dried at 60° C. in vacuo to give the titled compound (202 mg) as a white solid.

MS (ESI) m/z: 443 (M+H)$^+$.

Example E31

5-Methyl-N-{5-methyl-6-[4-(3-oxomorpholin-4-yl)cyclohex-1-en-1-yl]pyridin-3-yl}-1-[5-(trifluoromethyl)pyridin-2-yl]-1H-pyrazole-4-carboxamide

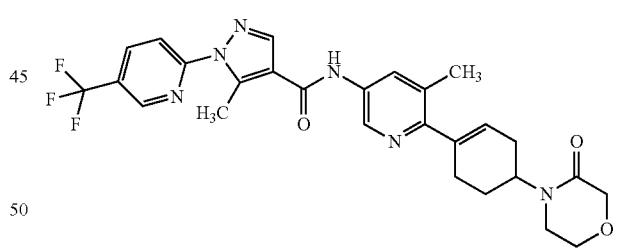

1,4-Dioxane (2 ml) was added to 4-[4-(5-bromo-3-methylpyridin-2-yl)cyclohex-3-en-1-yl]morpholin-3-one (150 mg) described in Reference Example 187, 5-methyl-1-[5-(trifluoromethyl)pyridin-2-yl]-1H-pyrazole-4-carboxamide (115 mg) described in Reference Example 120, palladium (II) acetate (3.8 mg), 4,5-bis(diphenylphosphino)-9,9-dimethylxanthene (14.8 mg) and cesium carbonate (195 mg) and stirred at 110° C. for five hours. After the reaction, the reaction solution was cooled to room temperature, a saturated aqueous solution of ammonium chloride was added and the precipitated solid was filtered. The resulted solid was purified with a silica gel column chromatography (chloroform/methanol), suspended and washed with ethanol to give the titled compound (169 mg) as a white solid.

MS (ESI) m/z: 541 (M+H)$^+$.

Example E32

N-[6-(r-1-Cyano-c-4-ethoxycyclohexan-1-yl)pyridin-3-yl]-5-methyl-1-[5-(trifluoromethyl)-pyridin-2-yl]-1H-pyrazole-4-carboxamide

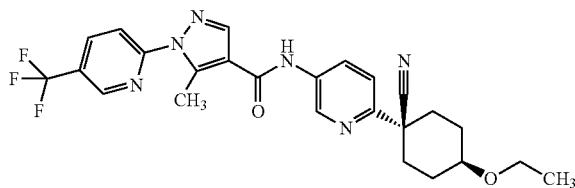 [SMILES: CCO[C@H]1CC[C@](C#N)(c2ccc(NC(=O)c3cnn(-c4ccc(C(F)(F)F)cn4)c3C)cn2)CC1]

(1) Thionyl chloride (2.42 ml) and N,N-dimethylformamide (three drops) were added to a solution of 5-methyl-1-[5-(trifluoromethyl)pyridin-2-yl]-1H-pyrazole-4-carboxylic acid (3.0 g) described in Reference Example 8 in toluene (55 ml) and stirred at 80° C. The reaction solution was concentrated and tetrahydrofuran (55 ml) was added. 28% Aqueous water (44 ml) was added under ice-cooling, stirred for an hour and 1N aqueous solution of NaOH was added. The precipitated solid was filtered, washed with water and dried at 60° C. in vacuo to give 5-methyl-1-[5-(trifluoromethyl)pyridin-2-yl]-1H-pyrazole-4-carboxamide (478 mg).

MS (ESI) m/z: 271 (M+H)⁺.

(2) 1-(5-Bromopyridin-2-yl)-c-4-ethoxy-r-1-cyclohexanecarbonitrile (0.066 g) described in Reference Example 168, palladium acetate (0.001 g), 4,5-bis(diphenylphosphino)-9,9-dimethylxanthene (0.0037 g) and cesium carbonate (0.104 g) were added to a solution of 5-methyl-1-[5-(trifluoromethyl)pyridin-2-yl]-1H-pyrazole-4-carboxamide (0.058 g) in 1,4-dioxane (1.0 ml) and stirred at 80° C. for 12 hours. Then, palladium acetate (0.001 g) and 4,5-bis(diphenylphosphino)-9,9-dimethylxanthene (0.0037 g) were added and stirred at 110° C. for two hours. After the reaction, water was added and extracted with chloroform three times. The organic layer was dried over anhydrous sodium sulfate and concentrated. The resulting residue was purified with a silica gel column chromatography (chloroform/methanol) to give the titled compound (18 mg).

MS (ESI) m/z: 499 (M+H)⁺.

Example F1

4-Hydroxyl-[5-({[5-methyl-1-(4-methylphenyl)-1H-pyrazol-4-yl]carbonyl}amino)pyridin-2-yl]cyclohexanecarboxylic acid ethyl ester

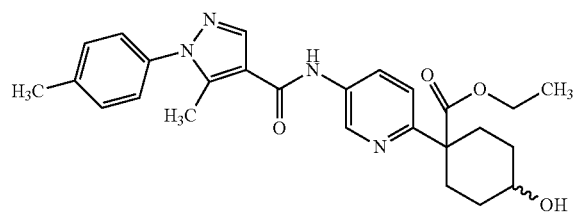 [SMILES: CCOC(=O)C1(c2ccc(NC(=O)c3cnn(-c4ccc(C)cc4)c3C)cn2)CCC(O)CC1]

(1) Trifluoroacetic acid (0.96 ml) was added at room temperature to a solution of 8-[5-({[5-methyl-1-(4-methylphenyl)-1H-pyrazol-4-yl]carbonyl}amino)pyridin-2-yl]-1,4-dioxaspiro[4.5]decane-8-carboxylic acid ethyl ester (1.27 g) described in Example D4 in dichloromethane (2.5 ml) and stirred at the same temperature for six hours. Trifluoroacetic acid (1.9 ml) was added at the same temperature and stirred at the same temperature for 18 hours. After the reaction, the solvent and trifluoroacetic acid were evaporated, a saturated aqueous solution of sodium bicarbonate was added and extracted with ethyl acetate twice. The organic solution was dried over anhydrous magnesium sulfate and concentrated to give 1-[5-({[5-methyl 1-(4-methylphenyl)-1H-pyrazol-4-yl]carbonyl}amino)pyridin-2-yl]-4-oxocyclohexanecarboxylic acid ethyl ester (1.09 g) as a white solid.

MS (ESI) m/z: 461 (M+H)⁺.

(2) Sodium borohydride (131 mg) was added at −78° C. to a solution of 1-[5-({[5-methyl-1-(4-methylphenyl)-1H-pyrazol-4-yl]carbonyl}amino)pyridin-2-yl]-4-oxocyclohexanecarboxylic acid ethyl ester (400 mg) in methanol (6.0 ml) and chloroform (3.0 ml) and stirred at the same temperature for four hours. After the reaction, a saturated aqueous solution of ammonium chloride, the solvent was evaporated and extracted with chloroform three times. The organic solution was dried over anhydrous magnesium sulfate and concentrated. The resulting residue was recrystallized (n-hexane/ethanol) to give the titled compound (284 mg) as a white solid. MS (ESI) m/z: 463 (M+H)⁺.

Example F2

N-[6-(1-Cyano-4-oxocyclohexyl)pyridin-3-yl]-5-methyl-1-[5-(trifluoromethyl)pyridin-2-yl]-1H-pyrazole-4-carboxamide hydrochloride

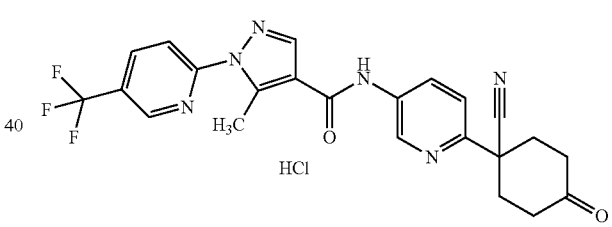

(1) Trifluoroacetic acid (7.0 ml) was added at room temperature to N-[6-(8-cyano-1,4-dioxaspiro[4.5]dec-8-yl)pyridin-3-yl]-5-methyl-1-[5-(trifluoromethyl)pyridin-2-yl]-1H-pyrazolecarboxamide (367 mg), stirred at the same temperature for two hours and at 80° C. for two hours. After the reaction, 4N aqueous solution of sodium hydroxide was added and the precipitated solid was filtered. The resulting residue was purified with a silica gel column chromatography (chloroform/methanol) to give N-[6-(1-cyano-4-oxocyclohexyl)pyridin-3-yl]-5-methyl-1-[5-(trifluoromethyl)pyridin-2-yl]-1H-pyrazole-4-carboxamide (298 mg) as a white solid.

MS (ESI) m/z: 469 (M+H)⁺.

(2) 4N HCl-Ethyl acetate (0.76 ml) was added to a solution of N-[6-(1-cyano-4-oxocyclohexyl)pyridin-3-yl]-5-methyl-1-[5-(trifluoromethyl)pyridin-2-yl]-1H-pyrazole-4-carboxamide (285 mg) in ethyl acetate (60 ml) and stirred at 70° C. for an hour. After the reaction, the solvent was evaporated, ethanol was added, stirred at 70° C. for 0.5 hour and the precipitated solid was filtered to give the titled compound (270 mg) as a white solid.

MS (ESI) m/z: 469 (M+H)⁺.

Example F3

N-[6-(1-Cyano-4-oxocyclohexyl)pyridin-3-yl]-5-methyl-1-(4-methylphenyl)-1H-pyrazole-4-carboxamide

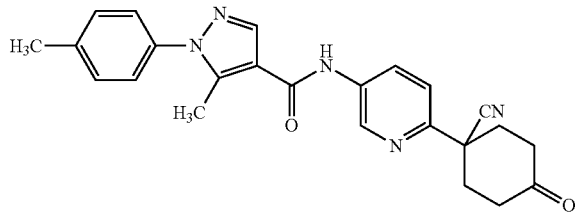 [SMILES: Cc1ccc(-n2ncc(C(=O)Nc3ccc(C4(C#N)CCC(=O)CC4)nc3)c2C)cc1]

A solution of N-[6-(8-cyano-1,4-dioxaspiro[4.5]dec-8-yl)pyridin-3-yl]-5-methyl-1-(4-methylphenyl)-1H-pyrazole-4-carboxamide (181 mg) described in Example E3 in a mixed solvent of acetic acid (2 ml), water (0.5 ml) and 1N hydrochloric acid aqueous solution (0.5 ml) was stirred at 100° C. for two hours. After the reaction, a saturated aqueous solution of potassium carbonate was added and extracted with ethyl acetate. The organic solution was dried over anhydrous magnesium sulfate and concentrated. The residue was purified with a column chromatography to give the titled compound (96 mg).

MS (ESI) m/z: 414 (M+H)+.

The next compounds (Examples F4 to F33 and F35) were prepared from the corresponding starting material in a similar manner as Examples F2 and F3. Conversion into hydrochloride salt was carried out in a similar manner as Examples D1 etc. In addition, Examples F34, F36 and F37 were prepared as follows:

Example F34

1-[3-Fluoro-5-(trifluoromethyl)pyridin-2-yl]-5-methyl-N-[5-methyl-6-(4-oxocyclohexan-1-yl)pyridin-3-yl]-1H-pyrazole-4-carboxamide N-[6-(1,4-Dioxaspiro[4.5]dec-8-yl)-5-methylpyridin-3-yl]-1-[3-fluoro-5-(trifluoromethyl)pyridin-2-yl]-5-methyl-1H-pyrazole-4-carboxamide (274 mg) described in Example D196 was used in place of N-[6-(8-cyano-1,4-dioxaspiro[4.5]dec-8-yl)pyridin-3-yl]-5-methyl-1-[5-(trifluoromethyl)pyridin-2-yl]-1H-pyrazolecarboxamide in Example F2(1), and reacted and treated in a similar manner to give the titled compound (237 mg).

MS (ESI) m/z: 476 (M+H)+.

Example F36

1-[3-Chloro-5-(trifluoromethyl)pyridin-2-yl]-5-methyl-N-[5-methyl-6-(4-oxocyclohexan-1-yl)pyridin-3-yl]-1H-pyrazole-4-carboxamide 1-[3-Chloro-5-(trifluoromethyl)pyridin-2-yl]-N-[6-(1,4-dioxaspiro[4.5]dec-8-yl)-5-methyl-pyridin-3-yl]-5-methyl-1H-pyrazole-4-carboxamide (229 mg) described in Example D 198 was used in place of N-[6-(8-cyano-1,4-dioxaspiro[4.5]dec-8-yl)pyridin-3-yl]-5-methyl-1-[5-(trifluoromethyl)pyridin-2-yl]-1H-pyrazolecarboxamide in Example F2(1), and reacted and treated in a similar manner to give the titled compound (243 mg) as a white solid.

MS (ESI) m/z: 492 (M+H)+.

Example F37

N-[6-(1-Fluoro-4-oxacyclohexan-1-yl)pyridin-3-yl]-5-methyl-1-[5-(trifluoromethyl)pyridin-2-yl]-1H-pyrazole-4-carboxamide 3N Hydrochloric acid aqueous solution (12 ml) was added at room temperature to a solution of N-[6-(8-fluoro-1,4-dioxaspiro[4.5]dec-8-yl)pyridin-3-yl]-5-methyl-1-[5-(trifluoromethyl)pyridin-2-yl]-1H-pyrazole-4-carboxamide (308 mg) described in Example K65 in tetrahydrofuran (12 ml), and stirred at the same temperature for six hours. After the reaction, a saturated aqueous solution of sodium bicarbonate was added, the solvent was evaporated, water was added and the precipitated solid was filtered to give the titled compound (257 mg) as a white solid.

MS (ESI) m/z: 462 (M+H)+.

| Example No. | Structural formula | Salt | MS (ESI) m/z |
|---|---|---|---|
| F4 | | | 434 |
| F5 | | | 468 |

-continued

| Example No. | Structural formula | Salt | MS (ESI) m/z |
|---|---|---|---|
| F6 | | | 418 |
| F7 | | | 436 |
| F8 | | | 469 |
| F9 | | | 484 |
| F10 | | | 436 |
| F11 | | | 454 |

| Example No. | Structural formula | Salt | MS (ESI) m/z |
|---|---|---|---|
| F12 | 5-(4-chlorophenyl)furan-2-carboxamide derivative | | 420 |
| F13 | 1-(4-tert-butylphenyl)-5-methylpyrazole-4-carboxamide derivative | | 456 |
| F14 | 1-(4-methoxyphenyl)-5-methylpyrazole-4-carboxamide derivative | | 430 |
| F15 | 6-isopropylthieno[2,3-b]pyridine-2-carboxamide derivative | | 419 |
| F16 | 1-(5-iodopyridin-2-yl)pyrazole-4-carboxamide derivative | | 513 |
| F17 | 1-(4-methylphenyl)indole-3-carboxamide derivative | | 449 |

-continued

| Example No. | Structural formula | Salt | MS (ESI) m/z |
|---|---|---|---|
| F18 | | | 399 |
| F19 | | | 413 |
| F20 | | | 399 |
| F21 | | | 403 |
| F22 | | | 415 |

-continued

| Example No. | Structural formula | Salt | MS (ESI) m/z |
|---|---|---|---|
| F23 | | | 464 |
| F24 | | | 419 |
| F25 | | | 452 |
| F26 | | | 431 |
| F27 | | | 423 |
| F28 | | | 421 |

-continued

| Example No. | Structural formula | Salt | MS (ESI) m/z |
|---|---|---|---|
| F29 | | | 455 |
| F30 | | | 456 |
| F31 | | | 399 |
| F32 | | | 458 |
| F33 | | | 444 |
| F34 | | | 476 |

| Example No. | Structural formula | Salt | MS (ESI) m/z |
|---|---|---|---|
| F35 | | | 488 |
| F36 | | | 492 |
| F37 | | | 462 |

Example G1

1-(4-Chlorophenyl)-N-[6-(r-1-cyano-c-4-hydroxycyclohexyl)pyridin-3-yl]-5-methyl-1H-pyrazole-4-carboxamide

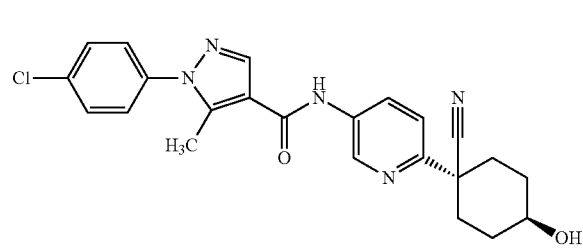 [SMILES: Cc1c(C(=O)Nc2ccc([C@]3(C#N)CC[C@@H](O)CC3)nc2)cnn1-c1ccc(Cl)cc1]

Lithium borohydride (63 mg) was added at −40° C. to a mixture of 1-(4-chlorophenyl)-N-[6-(1-cyano-4-oxocyclohexyl)pyridin-3-yl]-5-methyl-1H-pyrazole-4-carboxamide (520 mg) and tetrahydrofuran (20 ml), and stirred for 0.5 hours and then at room temperature for an hours. Water was added to the reaction solution, extracted with an organic solbent and concentrated in vacuo. The resulting residue was purified with a silica gel chromatography (chloroform/methanol), ethanol (4 ml) was added to the resulting solid (430 mg) and washed to give the titled compound (360 mg).

MS (ESI) m/z: 436 (M+H)$^+$.

Example G2

N-[6-(r-1-Cyano-c-4-hydroxycyclohexyl)pyridin-3-yl]-1-(4-fluorophenyl)-5-methyl-1H-pyrazole-4-carboxamide

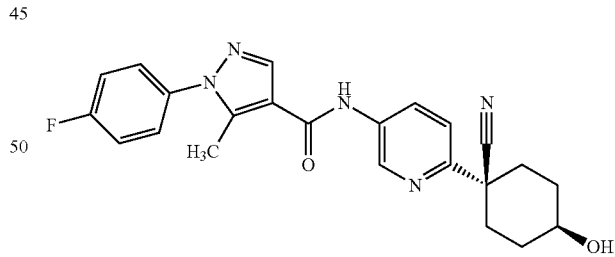

Thionyl chloride (0.40 g) was added to a suspension of 1-(4-fluorophenyl)-5-methyl-1H-pyrazole-4-carboxylic acid (0.34 g) described in Reference Example 1 in toluene (5 ml), and stirred at 70° C. for an hour. The solvent was evaporated in vacuo, a solution of 8-(5-aminopyridin-2-yl)-1,4-dioxaspiro[4.5]decane-8-carbonitrile (0.40 g) described in Reference Example 86 in pyridine (5 ml) was added to the residue, and stirred at 40° C. for two hours. The reaction solution was treated with water, extracted with ethyl acetate and the organic layer was concentrated in vacuo. Trifluoroacetic acid (10 ml) and water (2 ml) were added to the residue and stirred at 40° C. for an hour. The reaction solution was treated with 1N aqueous solution of sodium hydroxide, extracted with ethyl acetate, the organic layer was dried over anhydrous magnesium sulfate and concentrated in vacuo. Sodium borohydride (0.10 g) was added under ice cooling to a solution of the residue in ethanol (1 ml), and stirred at the same temperature for two hours. The reaction solution was treated with water and filtered through Celite. The filtrate was extracted with ethyl acetate. The organic layer was dried over anhydrous magnesium sulfate and concentrated. The residue was purified with a silica gel column chromatography (ethyl acetate/n-hexane=2/1) to give the titled compound (0.38 g).

MS (ESI) m/z: 420 (M+H)+.

Example G3

N-[6-(r-1-Cyano-c-4-hydroxycyclohexyl)pyridin-3-yl]-5-methyl-1-(4-methylphenyl)-1H-pyrazole-4-carboxamide

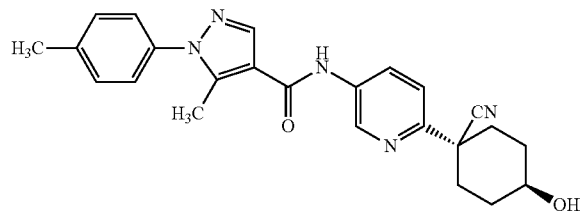 [SMILES: Cc1ccc(-n2ncc(C(=O)Nc3ccc([C@]4(C#N)CC[C@@H](O)CC4)nc3)c2C)cc1]

Lithium borohydride (12 mg) and methanol (1 ml) were added to a solution of N-[6-(1-cyano-4-oxocyclohexyl)pyridin-3-yl]-5-methyl-1-(4-methylphenyl)-1H-pyrazole-4-carboxamide (96 mg) described in Example F3 in tetrahydrofuran (5 ml) and stirred at room temperature for six hours. After the reaction, a saturated aqueous solution of potassium carbonate was added and extracted with ethyl acetate. The organic layer was dried over anhydrous magnesium sulfate and concentrated in vacuo. The residue was purified with a silica gel column chromatography to give the titled compound (3 mg).

MS (ESI) m/z: 416 (M+H)+.

Example G4 trans-1-(4-tert-Butylphenyl)-N-[6-(4-hydroxycyclohexyl)pyridin-3-yl]-5-methyl-1H-pyrazole-4-carboxamide

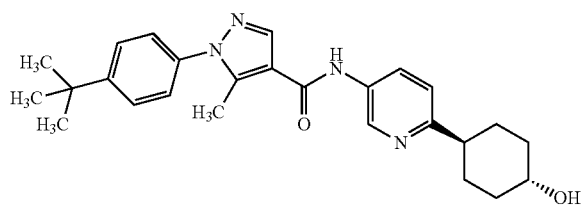 [SMILES: Cc1c(C(=O)Nc2ccc([C@H]3CC[C@H](O)CC3)nc2)cnn1-c1ccc(C(C)(C)C)cc1]

(1) Oxalyl chloride (0.25 ml) and N,N-dimethylformamide (catalytic amounts) were added at room temperature to a solution of 1-(4-tert-butylphenyl)-5-methyl-1H-pyrazole-4-carboxylic acid (222 mg) described in Reference Example 17 in dichloromethane (5 ml) and stirred at room temperature for two hours. The solvent and an excess amount of oxalyl chloride were evaporated. Toluene (5 ml) was added to the resulting reaction mixture, a solution of 6-(1,4-dioxaspiro[4.5]decan-8-yl)pyridine-3-amine (185 mg) described in Reference Example 102 in pyridine (4 ml) was added under ice-cooling, and stirred at room temperature overnight. After the reaction, 1N aqueous solution of sodium hydroxide was added under ice-cooling and extracted with ethyl acetate. The organic layer was dried over anhydrous sodium sulfate, and concentrated. The resulting residue was purified with a silica gel column chromatography (n-hexane/ethyl acetate) and ethanol was added to give 1-(4-tert-butylphenyl)-N-[6-(1,4-dioxaspiro[4.5]decan-8-yl)pyridin-3-yl]-5-methyl-1H-pyrazole-4-carboxamide (242 mg) as a white solid.

MS (ESI) m/z: 475 (M+H)+.

(2) 1-(4-tert-Butylphenyl)-N-[6-(1,4-dioxaspiro[4.5]decan-8-yl)pyridin-3-yl]-5-methyl-1H-pyrazole-4-carboxamide (219 mg) trifluoroacetic acid (3 ml) and water (catalytic amounts) were stirred at room temperature overnight. After the reaction, water was added, the mixture was neutralized by the addition of 1N aqueous solution of sodium hydroxide and extracted with chloroform. The organic layer was dried over anhydrous sodium sulfate, concentrated to give 1-(4-tert-butylphenyl)-5-methyl-N-[6-(4-oxocyclohexyl)pyridin-3-yl]-1H-pyrazole-4-carboxamide as a white solid.

MS (ESI) m/z: 431 (M+H)+.

(3) A solution of 1-(4-tert-butylphenyl)-5-methyl-N-[6-(4-oxocyclohexyl)pyridin-3-yl]-1H-pyrazole-4-carboxamide (136 mg) in ethanol (5 ml) was cooled in ice water, sodium borohydride (48 mg) was added and stirred at the same temperature for an hour. After the reaction, water was added and extracted with chloroform. The organic layer was dried over anhydrous sodium sulfate and concentrated. The resulting residue was purified with a silica gel column chromatography (n-hexane/ethyl acetate), washed with ethanol, the resulting solid was filtered and dried at 60° C. in vacuo to give the titled compound (29 mg) as a white solid.

MS (ESI) m/z: 433 (M+H)+.

Example G5

N-[6-(4-Hydroxycyclohex-1-en-1-yl)-5-methylpyridin-3-yl]-5-methyl-1-[4-(trifluoromethyl)-phenyl]-1H-pyrazole-4-carboxamide

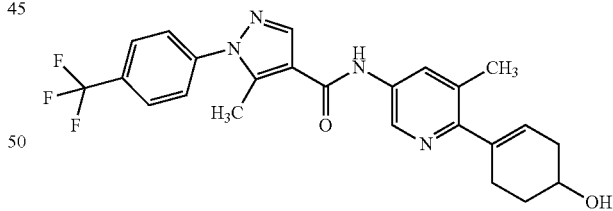

(1) Oxalyl chloride (3.8 ml) and N,N-dimethylformamide (catalytic amounts) were added at room temperature to a solution of 5-methyl-1-[4-(trifluoromethyl)phenyl]-1H-pyrazole-4-carboxylic acid (3.0 g) described in Reference Example 23 in dichloromethane (80 ml) and stirred at room temperature for two hours. The solvent and an excess amount of oxalyl chloride were evaporated. Tetrahydrofuran (50 ml) was added to the reaction mixture, 28% aqueous ammonia solution (50 ml) was added under ice-cooling, and stirred at room temperature for two hours. After the reaction, water was added and extracted with ethyl acetate. The organic layer was washed with 1N hydrochloric acid aqueous solution, 4N aqueous solution of sodium hydroxide, water and saturated brine successively dried over anhydrous sodium sulfate and concentrated to give 5-methyl-1-[4-(trifluoromethyl)]-1H-pyrazole-4-carboxamide (2.92 g) as a pale brown solid.

MS (ESI) m/z: 270 (M+H)$^+$.

(2) A suspension of 5-methyl-1-[4-(trifluoromethyl)phenyl]-1H-pyrazole-4-carboxamide (538 mg), 5-bromo-2-(1,4-dioxaspiro[4.5]decan-7-en-8-yl)-3-methylpyridine (620 mg) described in Reference Example 105, tris(dibenzylideneacetone)dipalladium (0) (18 mg), 2-di-tert-butylphosphino-3,4,5,6-tetramethyl-2',4',6'-triisopropylbiphenyl (48 mg), trisodium phosphate (509 mg) and tert-butanol (10 ml) was stirred at 110° C. After the reaction, the reaction solution was left stand, water was added and extracted with chloroform. The organic layer was dried over anhydrous sodium sulfate and concentrated. The resulting residue was purified with a silica gel column chromatography (chloroform/methanol) to give N-[6-(1,4-dioxaspiro[4.5]decan-7-en-8-yl)-5-methylpyridin-3-yl]-5-methyl-1-[4-(trifluoromethyl)-phenyl]-1H-pyrazole-4-carboxamide (856 mg) as a pale yellow solid.

MS (ESI) m/z: 499 (M+H)$^+$.

(3) N-[6-(1,4-dioxaspiro[4.5]decan-7-en-8-yl)-5-methylpyridin-3-yl]-5-methyl-1-[4-(trifluoromethyl)phenyl]-1H-pyrazole-4-carboxamide (823 mg), trifluoroacetic acid (9 ml) and water (catalytic amounts) was stirred at room temperature overnight. After the reaction, water was added, extracted with chloroform, the aqueous layer was neutralized under cooling by the addition of a saturated aqueous solution of sodium bicarbonate and extracted with chloroform. The organic layer was washed with water and saturated brine respectively and dried over anhydrous sodium sulfate. The solvent was evaporated and the resulting residue was purified with a silica gel column chromatography (chloroform/methanol), washed with ethanol and the resulting solid was dried at 60° C. in vacuo to give N-[5-methyl-6-(4-oxocyclohex-1-en-1-yl)pyridin-3-yl]-1-[4-(trifluoromethyl)phenyl]-1H-pyrazole-4-carboxamide (210 mg) as a white solid.

MS (ESI) m/z: 455 (M+H)$^+$.

(4) Sodium borohydride (19 mg) was added to a solution of N-[5-methyl-6-(4-oxocyclohex-1-en-1-yl)pyridin-3-yl]-1-[4-(trifluoromethyl)phenyl]-1H-pyrazole-4-carboxamide (114 mg) in methanol (15 ml) under ice-cooling and the mixture was stirred at the same temperature for 30 minutes. After the reaction, 1N aqueous solution of sodium hydroxide was added and the organic solvent was evaporated. The precipitated solid was washed with water, filtered and dried at 60° C. under current of air to give the titled compound (110 mg) as a white solid.

MS (ESI) m/z: 457 (M+H)$^+$.

The next compounds (Examples G6 to G28, G30, G31 and G33) were prepared from the corresponding starting material in a similar manner as Examples G1 to G5. In addition, G29, G32 and G34 were prepared by the following methods.

Example G29 trans-1-[3-Fluoro-5-(trifluoromethyl)pyridin-2-yl]-N-[6-(1-hydroxycyclohexan-4-yl)-5-methylpyridin-3-yl]-5-methyl-1H-pyrazole-4-carboxamide Sodium borohydride (116.8 mg) was added under ice-cooling to a solution of 1-[3-fluoro-5-(trifluoromethyl)pyridin-2-yl]-5-methyl-N-[5-methyl-6-(4-oxocyclohexan-1-yl)pyridin-3-yl]-1H-pyrazole-4-carboxamide (211 mg) described in Example F34 in methanol (3 ml) and stirred at the same temperature for 30 minutes. After the reaction, water was added and extracted with chloroform. The organic layer was dried over anhydrous sodium sulfate and concentrated. The resulting residue was fractionated with HPLC (water-acetonitrile:containing 0.05% trifluoroacetic acid). The obtained fraction was neutralized by the addition of 10% sodium carbonate, and the precipitates was filtered and dried at 60° C. under current of air to give the titled compound (92 mg) as a white solid.

MS (ESI) m/z: 478 (M+H)$^+$.

Example G32 trans-1-[3-Chloro-5-(trifluoromethyl)pyridin-2-yl]-N-[6-(1-hydroxycyclohexan-4-yl)-5-methylpyridin-3-yl]-5-methyl-1H-pyrazole-4-carboxamide 1-[3-Chloro-5-(trifluoromethyl)pyridin-2-yl]-5-methyl-N-[5-methyl-6-(4-oxocyclohexan-1-yl)pyridin-3-yl]-1H-pyrazole-4-carboxamide (234 mg) described in Example F36 was used in place of 1-[3-fluoro-5-(trifluoromethyl)pyridin-2-yl]-5-methyl-N-[5-methyl-6-(4-oxocyclohexan-1-yl)pyridin-3-yl]-1H-pyrazole-4-carboxamide in Example 29, and reacted and treated in a similar manner to give the titled compound (72 mg) as a white solid.

MS (ESI) m/z: 494 (M+H)$^+$.

Example G34

N-[6-(c-1-Fluoro-4-hydroxycyclohexan-1-yl)pyridin-3-yl]-5-methyl-1-[5-(trifluoromethyl)-pyridin-2-yl]-1H-pyrazole-4-carboxamide A solution of sodium borohydride (102 mg) in methanol (2.7 ml) was added at −78° C. to a solution of N-[6-(1-fluoro-4-oxocyclohexan-1-yl)pyridin-3-yl]-5-methyl-1-[5-(trifluoromethyl)pyridin-2-yl]-1H-pyrazole-4-carboxamide (312 mg), and stirred at the same temperature for four hours. After the reaction, the reaction solution was extracted with a saturated aqueous solution of ammonium chloride. The organic layer was dried over anhydrous sodium sulfate and concentrated to give the titled compound (295 mg) as a white solid.

MS (ESI) m/z: 464 (M+H)$^+$.

| Example No. | Structural formula | Salt | MS (ESI) m/z |
|---|---|---|---|
| G6 | 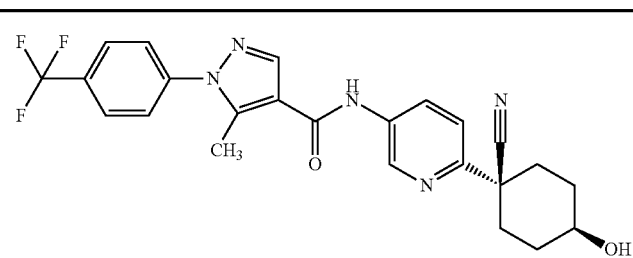 | | 470 |

-continued
| | | |
|---|---|---|
| G7 | 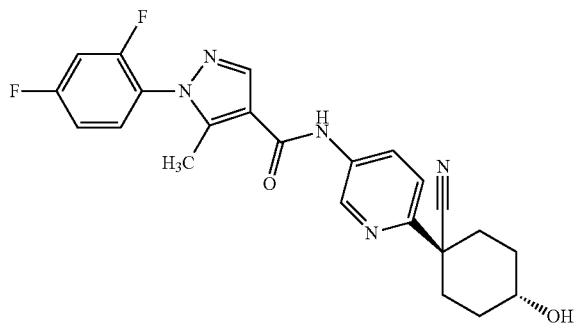 [SMILES: Cc1c(C(=O)Nc2ccc([C@]3(C#N)CC[C@@H](O)CC3)nc2)cnn1-c1ccc(F)cc1F] | 438 |
| G8 | 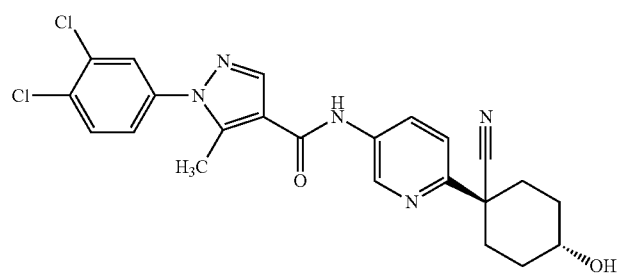 [SMILES: Cc1c(C(=O)Nc2ccc([C@]3(C#N)CC[C@@H](O)CC3)nc2)cnn1-c1ccc(Cl)c(Cl)c1] | 471 |
| G9 | 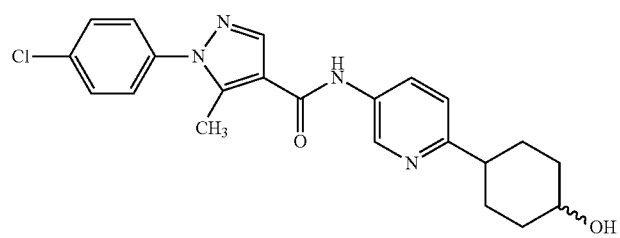 [SMILES: Cc1c(C(=O)Nc2ccc(C3CCC(O)CC3)nc2)cnn1-c1ccc(Cl)cc1] | 411 |
| G10 | 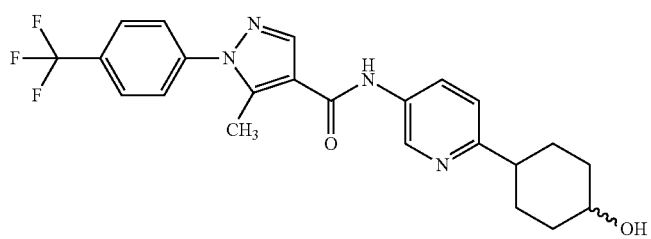 [SMILES: Cc1c(C(=O)Nc2ccc(C3CCC(O)CC3)nc2)cnn1-c1ccc(C(F)(F)F)cc1] | 445 |
| G11 | 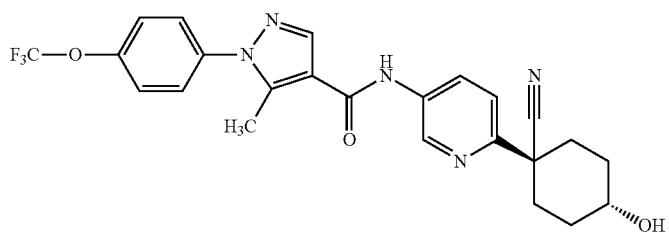 [SMILES: Cc1c(C(=O)Nc2ccc([C@]3(C#N)CC[C@@H](O)CC3)nc2)cnn1-c1ccc(OC(F)(F)F)cc1] | 486 |
| G12 | 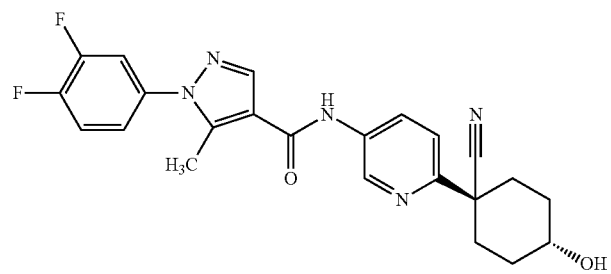 [SMILES: Cc1c(C(=O)Nc2ccc([C@]3(C#N)CC[C@@H](O)CC3)nc2)cnn1-c1ccc(F)c(F)c1] | 438 |

| | | |
|---|---|---|
| G13 | 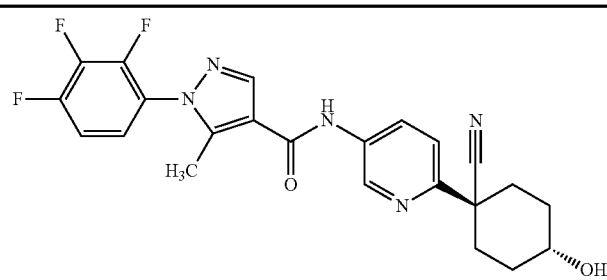 | 456 |
| G14 | 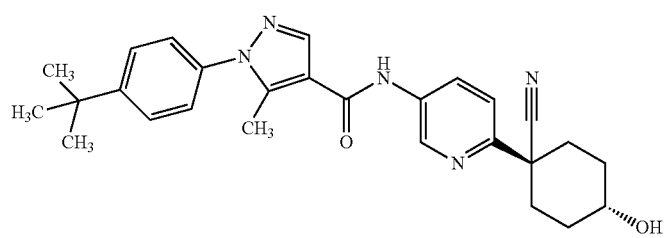 [SMILES: Cc1c(C(=O)Nc2ccc([C@]3(C#N)CC[C@@H](O)CC3)nc2)cnn1-c1ccc(C(C)(C)C)cc1] | 458 |
| G15 | 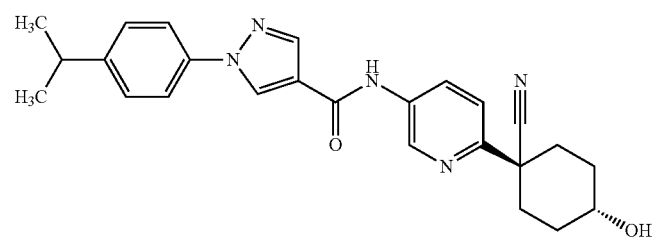 [SMILES: CC(C)c1ccc(-n2cc(C(=O)Nc3ccc([C@]4(C#N)CC[C@@H](O)CC4)nc3)cn2)cc1] | 430 |
| G16 | 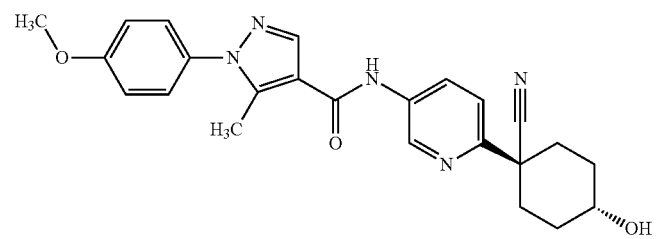 [SMILES: COc1ccc(-n2ncc(C(=O)Nc3ccc([C@]4(C#N)CC[C@@H](O)CC4)nc3)c2C)cc1] | 432 |
| G17 | 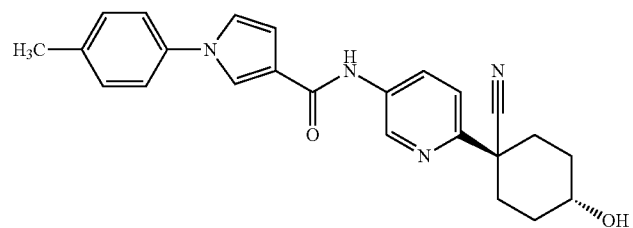 [SMILES: Cc1ccc(-n2ccc(C(=O)Nc3ccc([C@]4(C#N)CC[C@@H](O)CC4)nc3)c2)cc1] | 401 |
| G18 | 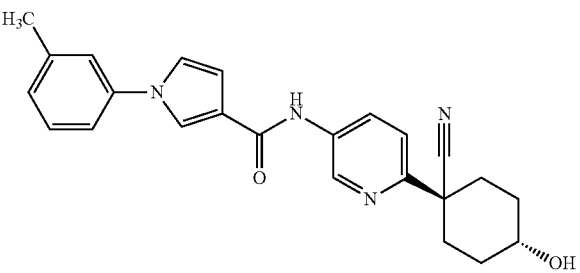 [SMILES: Cc1cccc(-n2ccc(C(=O)Nc3ccc([C@]4(C#N)CC[C@@H](O)CC4)nc3)c2)c1] | 401 |

-continued
| | | |
|---|---|---|
| G19 | 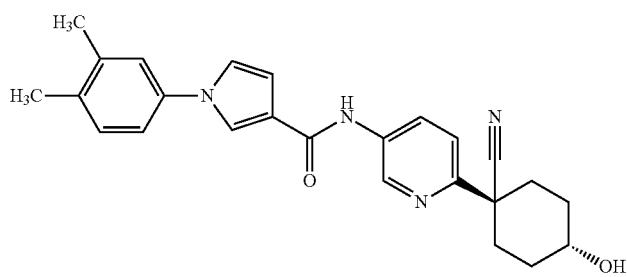 [SMILES: Cc1ccc(-n2ccc(C(=O)Nc3ccc([C@]4(C#N)CC[C@@H](O)CC4)nc3)c2)cc1C] | 415 |
| G20 | 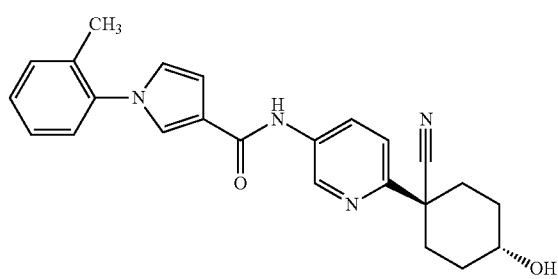 [SMILES: Cc1ccccc1-n1ccc(C(=O)Nc2ccc([C@]3(C#N)CC[C@@H](O)CC3)nc2)c1] | 401 |
| G21 | 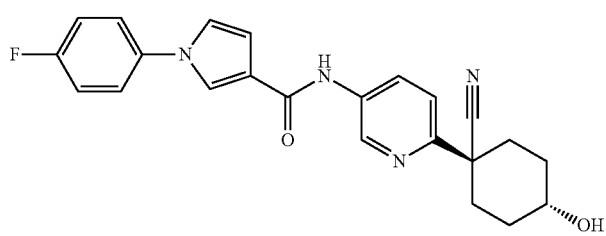 [SMILES: N#C[C@]1(c2ccc(NC(=O)c3ccn(-c4ccc(F)cc4)c3)cn2)CC[C@H](O)CC1] | 405 |
| G22 | 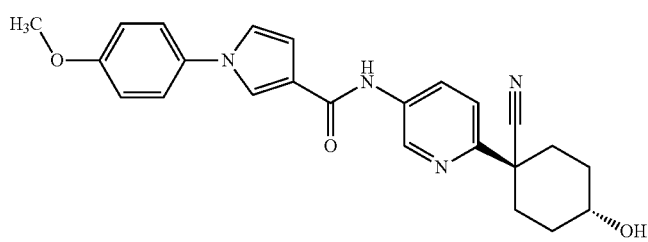 [SMILES: COc1ccc(-n2ccc(C(=O)Nc3ccc([C@]4(C#N)CC[C@@H](O)CC4)nc3)c2)cc1] | 417 |
| G23 | 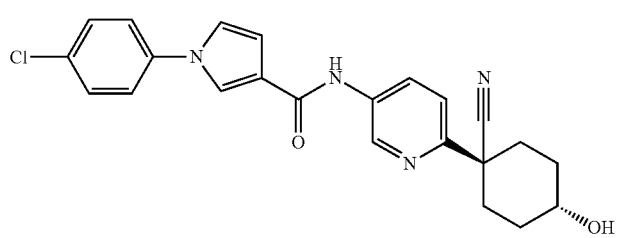 [SMILES: N#C[C@]1(c2ccc(NC(=O)c3ccn(-c4ccc(Cl)cc4)c3)cn2)CC[C@H](O)CC1] | 421 |
| G24 | 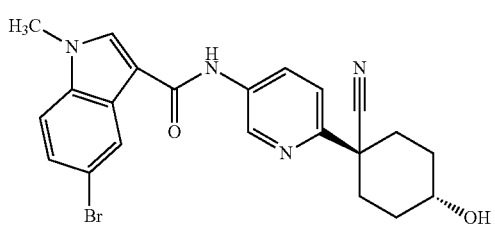 [SMILES: Cn1cc(C(=O)Nc2ccc([C@]3(C#N)CC[C@@H](O)CC3)nc2)c2cc(Br)ccc21] | 454 |

-continued
| | | | MS (ESI) m/z |
|---|---|---|---|
| G25 | 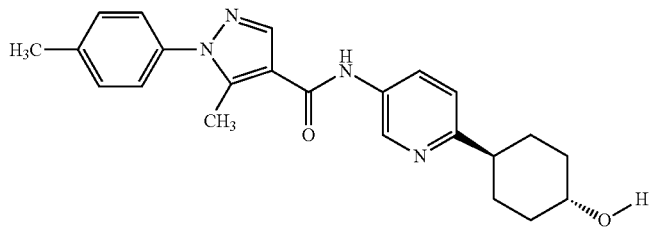 [SMILES: Cc1ccc(-n2ncc(C(=O)Nc3ccc([C@H]4CC[C@H](O)CC4)nc3)c2C)cc1] | | 391 |
| G26 | 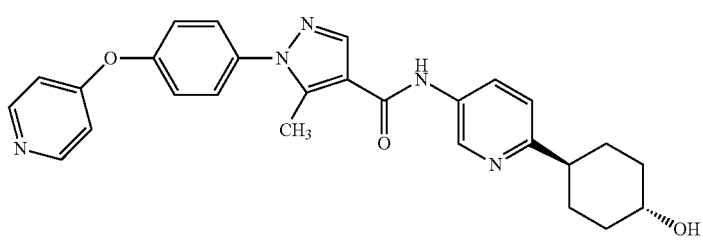 [SMILES: Cc1c(C(=O)Nc2ccc([C@H]3CC[C@H](O)CC3)nc2)cnn1-c1ccc(Oc2ccncc2)cc1] | | 470 |
| G27 | 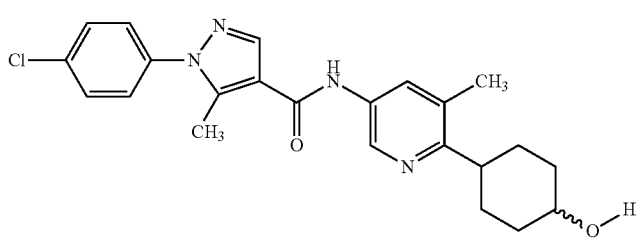 [SMILES: Cc1cc(NC(=O)c2cnn(-c3ccc(Cl)cc3)c2C)cnc1C1CCC(O)CC1] | | 425 |
| G28 | 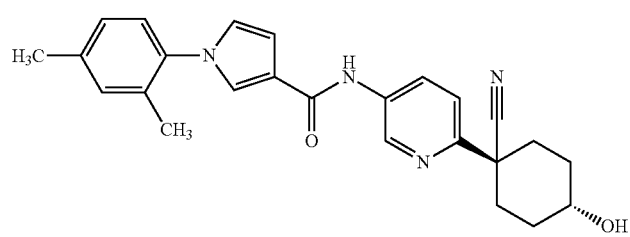 [SMILES: Cc1ccc(-n2ccc(C(=O)Nc3ccc([C@]4(C#N)CC[C@@H](O)CC4)nc3)c2)c(C)c1] | | 415 |
| 実施例 No. | 構造式 | 塩 | MS (ESI) m/z |
|---|---|---|---|
| G29 | 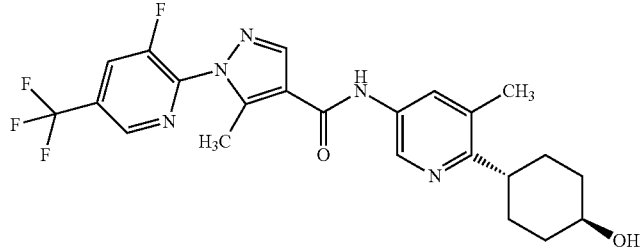 | | 478 |
| G30 | 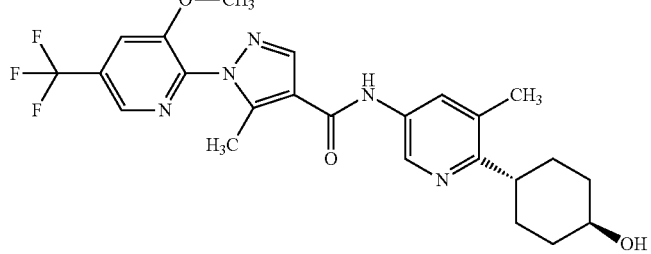 | | 490 |

| | | |
|---|---|---|
| G31 | 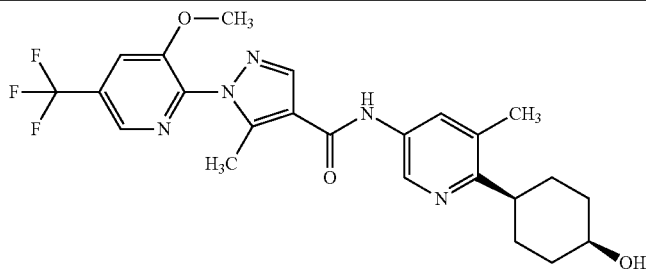 | 490 |
| G32 | 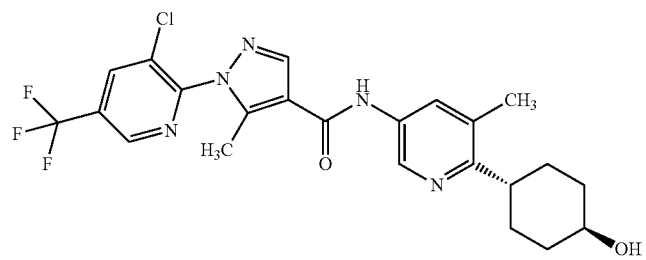 [SMILES: Cc1cc(NC(=O)c2cnn(-c3ncc(C(F)(F)F)cc3F)c2C)cnc1[C@H]1CC[C@H](O)CC1] | 494 |
| G33 | 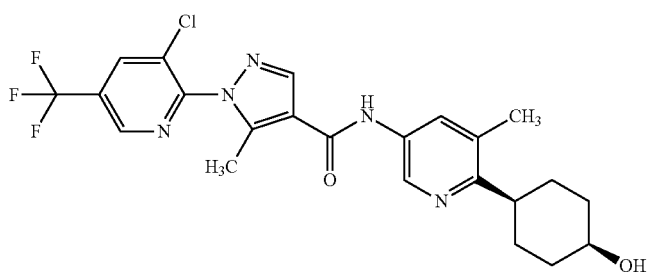 [SMILES: COc1cc(C(F)(F)F)cnc1-n1ncc(C(=O)Nc2cnc([C@H]3CC[C@@H](O)CC3)c(C)c2)c1C] | 494 |
| G34 | 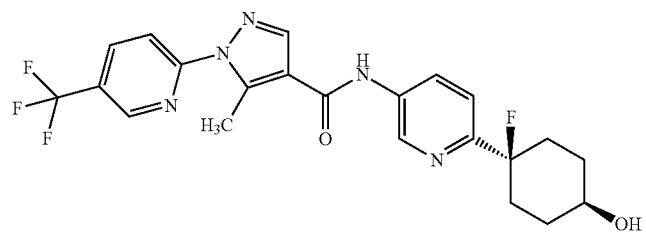 [SMILES: Cc1c(C(=O)Nc2ccc([C@]3(F)CC[C@@H](O)CC3)nc2)cnn1-c1ccc(C(F)(F)F)cn1] | 464 |

Example H1

N-{5-Methyl-6-[4-(morpholin-4-yl)cyclohex-1-en-1-yl]pyridin-3-yl}-1-[5-(trifluoromethyl)-pyridin-2-yl]-1H-pyrrole-3-carboxamide mesylate

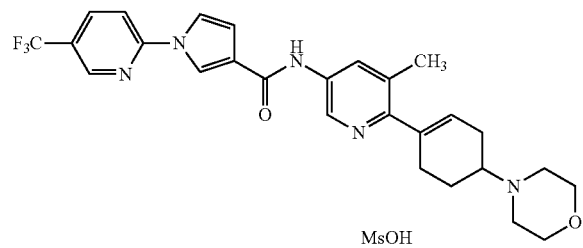 [SMILES: "MsOH" ; Cc1cc(NC(=O)c2ccn(-c3ccc(C(F)(F)F)cn3)c2)cnc1C1=CCC(N2CCOCC2)CC1]

(1) Sodium hydride (60%; 1.02 mg) was added at 0° C. to a solution of 1H-pyrrole-3-carboxylic acid tert-butyl ester (3.57 g) in tetrahydrofuran (71 ml), stirred at room temperature, then p-toluenesulfonic acid chloride (4.47 g) the mixture was stirred all night and all day. Water was added to the reaction solution, extracted with ethyl acetate, washed with saturated brine, and dried over anhydrous sodium sulfate. The organic solution was concentrated in vacuo, dichloromethane (30 ml) and trifluoroacetic acid (15 ml) were added to the resulting residue and stirred at room temperature for four hours. The solvent was evaporated, water was added to the resulting residue and the precipitated solid was washed with water to give 1-[(4-methylphenyl)sulfonyl]-1H-pyrrole-3-carboxylic acid (4.2 g) as a pale yellow solid.

MS (ESI) m/z: 266 (M+H)⁺.

(2) Thionyl chloride (701 µl) was added to a solution of 1-[(4-methylphenyl)sulfonyl]-1H-pyrrole-3-carboxylic acid (1.7 g) in a mixture of toluene (20 ml) and N,N-dimethylformamide (catalytic amounts) and stirred at 80° C. for 1.5 hours. The solvent was evaporated in vacuo, the residue was dissolved in toluene (20 ml) and pyridine (1 ml) and a solution of 5-methyl-6-[4-(morpholin-4-yl)cyclohex-1-en-1-yl]pyridine-3-amine (1.92 g) described in Reference Example 108 in pyridine (20 ml) was added at 0° C. thereto and stirred for 3.5 hours. triethylamine (1.79 ml) and water was added and the precipitated solid was washed with ethanol to give N-{5-methyl-6-[4-(morpholin-4-yl)cyclohex-1-en-1-yl]pyridin-3-yl}-1-[(4-methylphenyl)sulfonyl]-1H-pyrrole-3-carboxamide (2.20 g) as a white solid.

MS (ESI) m/z: 520 (M+H)+.

(3) 1N Aqueous solution of sodium hydroxide (20 ml) was added to a suspension of N-{5-methyl-6-[4-(morpholin-4-yl)cyclohex-1-en-1-yl]pyridin-3-yl}-1-[(4-methylphenyl)sulfonyl]-1H-pyrrole-3-carboxamide (2.07 g) in methanol (20 ml) and tetrahydrofuran (30 ml), and stirred at room temperature for 2.5 hours. 1N Hydrochloric acid aqueous solution was added at 0° C. to the reaction solution and concentrated in vacuo. The precipitated solid was washed with ethanol to give N-{5-methyl-6-[4-(morpholin-4-yl)cyclohex-1-en-1-yl]pyridin-3-yl}-1H-pyrrole-3-carboxamide (1.2 g) as a white solid.

MS (ESI) m/z: 367 (M+H)+.

(4) Sodium hydride (60%: 44 mg) was added at 0° C. to a suspension of N-{5-methyl-6-[4-(morpholin-4-yl)cyclohex-1-en-1-yl]pyridin-3-yl}-1H-pyrrole-3-carboxamide (200 mg) in N,N-dimethylformamide (2.7 ml), then 2-chloro-5-(trifluoromethyl)pyridine (120 mg) was added and stirred at room temperature for 3.5 hours. Water was added to the reaction solution at 0° C., and the precipitated solid was filtered and washed with water. The resulting solid (276 mg) was dissolved in methanol (8 ml), methanesulfonic acid (35 µl) was added and stirred at room temperature. The solvent was evaporated in vacuo, ethanol and ethyl acetate were added to the resulting residue and the precipitated solid was washed with ethanol and ethyl acetate to give the titled compound (207 mg) as an orange solid.

MS (ESI) m/z: 512 (M+H)+.

The next compounds (Examples H2 to H17) were prepared from the corresponding starting material in a similar manner as Example H1. Conversion into mesylate or hydrochloride salt was carried out in a similar manner as Examples D1, D5 etc.

| Example No. | Structural formula | Salt | MS (ESI) m/z |
|---|---|---|---|
| H2 | | | 491 |
| H3 | | | 503 |
| H4 | | HCl | 512 |

-continued

| Example No. | Structural formula | Salt | MS (ESI) m/z |
|---|---|---|---|
| H5 | | HCl | 491 |
| H6 | | HCl | 471 |
| H7 | | MsOH | 458 |
| H8 | | HCl | 457 |
| H9 | | MsOH | 462 |

| Example No. | Structural formula | Salt | MS (ESI) m/z |
|---|---|---|---|
| H10 | | MsOH | 459 |
| H11 | | MsOH | 487 |
| H12 | | MsOH | 459 |
| H13 | | | 458 |
| H14 | | | 458 |

| Example No. | Structural formula | Salt | MS (ESI) m/z |
|---|---|---|---|
| H15 | | MsOH | 458 |
| H16 | | MsOH | 458 |
| H17 | | MsOH | 502 |

Example J1

N-{6-[r-1-Cyano-c-4-(morpholin-4-yl)cyclohexyl]pyridin-3-yl}-1-(4-fluorophenyl)-1H-pyrrole-3-carboxamide

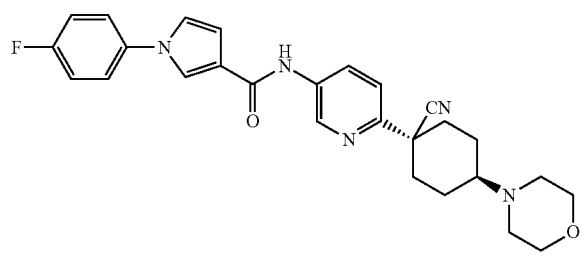 [SMILES: N#C[C@]1(c2ccc(NC(=O)c3ccn(-c4ccc(F)cc4)c3)cn2)CC[C@H](N2CCOCC2)CC1]

Sodium acetoxyborohydride (65 mg) was added under ice-cooling to a solution of N-[6-(1-cyano-4-oxocyclohexyl)pyridin-3-yl]-1-(4-fluorophenyl)-1H-pyrrole-3-carboxamide (100 mg) described in Example F21 and morpholine (65 mg) in tetrahydrofuran (5 ml), and stirred at room temperature for six hours. After the reaction, a saturated aqueous solution of potassium carbonate was added and extracted with ethyl acetate. The organic layer was dried over anhydrous magnesium sulfate and concentrated. The residue was purified with a column chromatography to give the titled compound (93 mg).

MS (ESI) m/z: 474 (M+H)$^+$.

The next compounds (Examples J2 to J6) were prepared from the corresponding starting material in a similar manner as Example J1.

| Example No. | Structural formula | Salt | MS (ESI) m/z |
|---|---|---|---|
| J2 | | | 486 |
| J3 | | | 536 |
| J4 | | | 555 |
| J5 | | | 490 |
| J6 | | | 523 |

Example J7 trans-N-[6-(4-Hydroxycyclohexyl)-5-methylpyridin-3-yl]-5-methyl-1-[5-(trifluoromethyl)-pyridin-2-yl]-1H-pyrazole-4-carboxamide

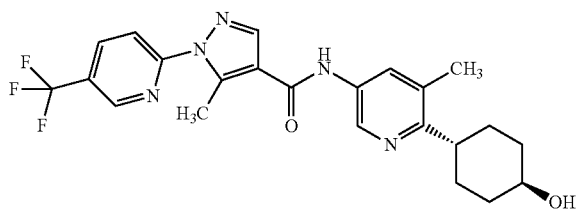 [SMILES: Cc1cc(NC(=O)c2cnn(-c3ccc(C(F)(F)F)cn3)c2C)cnc1[C@H]1CC[C@H](O)CC1]

(1) Oxalyl chloride (0.32 ml) and N,N-dimethylformamide (catalytic amounts) were added at room temperature to a solution of 5-methyl-1-[5-(trifluoromethyl)pyridin-2-yl]-1H-pyrazole-4-carboxylic acid (249 mg) described in Reference Example 8 in dichloromethane (10 ml), and stirred at the room temperature for two hours. The solvent and an excess amount of oxalyl chloride were evaporated, toluene (10 ml) was added to the resulting reaction solution, then, a solution of cis/trans-6-(4-{[tert-butyl(dimethyl)silyl]oxy}cyclohexyl)-5-methylpyridine-3-amine (268 mg) described in Reference Example 114 in pyridine (10 ml) was added under ice-cooling, and stirred at room temperature overnight. After the reaction, 1N aqueous solution of sodium hydroxide was added under ice-cooling and extracted with chloroform. The organic solution was dried over anhydrous sodium sulfate and concentrated. The resulting residue was purified with a silica gel column chromatography (n-hexane/ethyl acetate) to give trans-N-[6-(4-{[tert-butyl(dimethyl)silyl]oxy}cyclohexyl)-5-methylpyridin-3-yl]-5-methyl-1-[5-(trifluoromethyl)pyridin-2-yl]-1H-pyrazole-4-carboxamide (41 mg) as a white solid.

MS (ESI) m/z: 574 (M+H)$^+$.

(2) 1M solution of tetra-n-butylammonium fluoride in tetrahydrofuran (0.2 ml) was added to trans-N-[6-(4-{[tert-butyl(dimethyl)silyl]oxy}cyclohexyl)-5-methylpyridin-3-yl]-5-methyl-1-[5-(trifluoromethyl)pyridin-2-yl]-1H-pyrazole-4-carboxamide (41 mg) and stirred at 85° C. for six hours. After the reaction, the solvent was evaporated and the resulting residue was purified with a silica gel column chromatography (chloroform/methanol). Ethanol was added to the purified product, the precipitated solid was washed with water and dried at 60° C. in vacuo to give the titled compound (29 mg) as a white solid.

MS (ESI) m/z: 460 (M+H)$^+$.

The next compounds (Examples J8 to J24) were prepared from the corresponding starting material in a similar manner as Example J1 or J7. In addition, J25 was prepared by the following method.

Example J25 trans-N-[6-(4-Hydroxcyclohexan-1-yl)pyridin-3-yl]-5-methyl-1-[5-(trifluoromethyl)pyridin-2-yl]-1H-pyrazole-4-carboxamide (1) trans-6-[4-(tert-Butyldimethyl silanyloxy)cyclohexan-1-yl]pyridine-3-amine (150 mg) described in Reference Example 162 was added to a solution of 5-methyl-1-[5-(trifluoromethyl)pyridin-2-yl]-1H-pyrazole-4-carboxylic acid chloride (156 mg) described in Reference Example 180 in pyridine (5.5 ml), and stirred at 50 C for an hour. After the reaction, a saturated aqueous solution of sodium bicarbonate was added and the precipitated solid was filtered to give trans-N-(6-{4-[(tert-Butyldimethylsilanyloxy)cyclohexan-1-yl]pyridin-3-yl}-5-methyl-1-[5-(trifluoromethyl)pyridin-2-yl]-1H-pyrazole-4-carboxamide (263 mg) as a white solid.

MS (ESI) m/z: 560 (M+H)$^+$.

(2) 3N Hydrochloric acid aqueous solution (4.8 ml) was added at room temperature to a solution of trans-N-(6-{4-[(tert-Butyldimethylsilanyloxy)cyclohexan-1-yl]pyridin-3-yl}-5-methyl-1-[5-(trifluoromethyl)pyridin-2-yl]-1H-pyrazole-4-carboxamide (263 mg) in tetrahydrofuran (10 ml), and stirred at room temperature for two hours. The organic layer was dried over anhydrous sodium sulfate and concentrated. The resulting solid was washed with diethyl ether to give the titled compound (191 mg) as a white solid.

MS (ESI) m/z: 446 (M+H)$^+$.

| Example No. | Structural formula | Salt | MS (ESI) m/z |
|---|---|---|---|
| J8 | | | 493 |
| J9 | | | 430 |

-continued

| Example No. | Structural formula | Salt | MS (ESI) m/z |
|---|---|---|---|
| J10 | | | 460 |
| J11 | | | 432 |
| J12 | | | 432 |
| J13 | | | 443 |
| J14 | | | 445 |
| J15 | | | 505 |

-continued

| Example No. | Structural formula | Salt | MS (ESI) m/z |
|---|---|---|---|
| J16 | | | 489 |
| J17 | | | 461 |
| J18 | | | 444 |
| J19 | | | 442 |
| J20 | | | 430 |
| J21 | | | 461 |

-continued

| Example No. | Structural formula | Salt | MS (ESI) m/z |
|---|---|---|---|
| J22 | | | 462 |
| J23 | | | 518 |
| J24 | | | 517 |
| J25 | | | 446 |

Example K1

1-(4-Chlorophenyl)-N-[6-(r-1-cyano-t-4-hydroxycyclohexyl)pyridin-3-yl]-5-methyl-1H-pyrazole-4-carboxamide

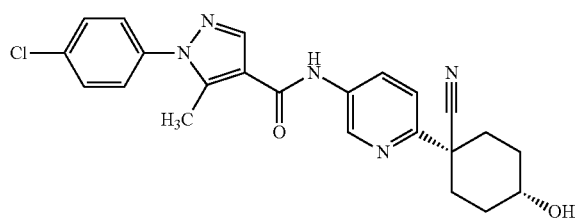 [SMILES: Cc1c(C(=O)Nc2ccc([C@]3(C#N)CC[C@H](O)CC3)nc2)cnn1-c1ccc(Cl)cc1]

(1) Diisopropyl azodicarboxylate (40% toluene solution: 255 mg) was added dropwise to a mixture of 1-(4-chlorophenyl)-N-[6-(r-1-cyano-c-4-hydroxycyclohexyl)pyridin-3-yl]-5-methyl-1H-pyrazole-4-carboxamide (220 mg) described in Example G1, triphenylphosphine (133 mg), tetrahydrofuran (10 ml) and acetic acid (33 mg), and stirred at room temperature. Until the reaction was completed, triphenylphosphine, acetic acid and diisopropyl azodicarboxylate were added each time. After the reaction, water was added to the reaction solution, extracted and concentrated. The resulting residue was purified with a silica gel chromatography (chloroform/methanol) to give N-{6-[t-4-(acetyloxy)cyclohexyl]-r-1-cyanopyridin-3-yl}-1-(4-chlorophenyl)-5-methyl-1H-pyrazole-4-carboxamide (190 mg) as a solid.

(2) Ethanol (4 ml), tetrahydrofuran (4 ml) and 1N aqueous solution of sodium hydroxide (0.8 ml) were added to N-{6-[t-4-(acetyloxy)cyclohexyl]-r-1-cyanopyridin-3-yl}-1-(4-chlorophenyl)-5-methyl-1H-pyrazole-4-carboxamide (185 mg) and stirred at 40° C. for an hour. The solvent was evaporated in vacuo, water was added to the resulting residue and the precipitated solid was filtered and purified with silica gel chromatography (chloroform/methanol). Ethanol (2 ml) was added to the resulting solid (138 mg), which was washed with ethanol to give the titled compound (127 mg).

MS (ESI) m/z: 436 (M+H)+.

Example K2

N-[6-(r-1-Cyano-t-4-hydroxycyclohexyppyridin-3-yl]-5-methyl-1-[4-(trifluoromethyl)phenyl]-1H-pyrazole-4-carboxamide

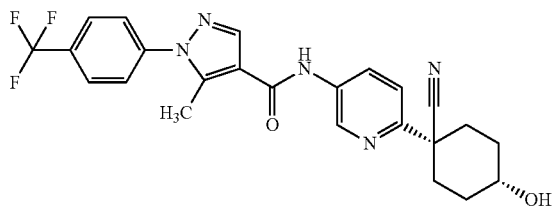 [SMILES: Cc1c(C(=O)Nc2ccc([C@]3(C#N)CC[C@H](O)CC3)nc2)cnn1-c1ccc(C(F)(F)F)cc1]

N-[6-(r-1-Cyano-c-4-hydroxycyclohexyppyridin-3-yl]-5-methyl-1-[4-(trifluoromethyl)-phenyl]-1H-pyrazole-4-carboxamide described in Example G6 was used in place of 1-(4-chlorophenyl)-N-[6-(r-1-cyano-c-4-hydroxycyclohexyl)pyridin-3-yl]-5-methyl-1H-pyrazole-4-carboxamide in Example K1, and reacted and treated in a similar manner to give the titled compound.
MS (ESI) m/z: 470 (M+H)⁺.

Example K3

4-({4-[5-({[1-(4-Chlorophenyl)-5-methyl-1H-pyrazol-4-yl]carbonyl}amino)pyridin-2-yl]-4-cyanocyclohexyl}oxy)-4-oxobutanoic acid

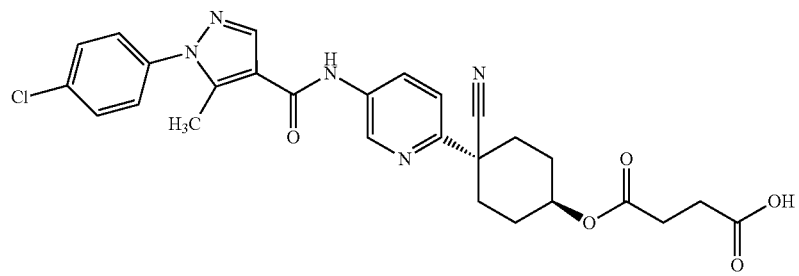 [SMILES: Cc1c(C(=O)Nc2ccc([C@]3(C#N)CC[C@@H](OC(=O)CCC(=O)O)CC3)nc2)cnn1-c1ccc(Cl)cc1]

1-(4-Chlorophenyl)-N-[6-(1-cyano-4-hydroxycyclohexyl)pyridin-3-yl]-5-methyl-1H-pyrazole-4-carboxamide (0.42 g), succinic anhydride (0.11 g) and p-toluenesulfonic acid hydrate (5 mg) were added to 1,2-dichlorobenzene (4 ml) and stirred at 150° C. for seven hours. The reaction solution was treated with water and the precipitated solid was recrystallized from aqueous isopropanol to give the titled compound (0.21 g).
MS (ESI) m/z: 536 (M+H)⁺.

Example K4

1-[5-({[1-(4-Chlorophenyl)-5-methyl-1H-pyrazol-4-yl]carbonyl}amino)pyridin-2-yl]-cyclohexanecarboxylic acid

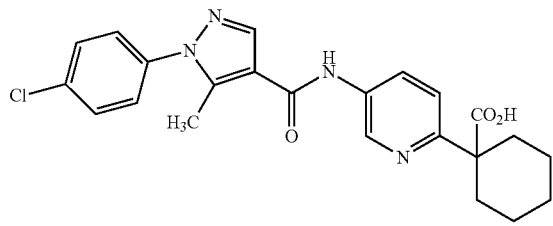 [SMILES: Cc1c(C(=O)Nc2ccc(C3(C(=O)O)CCCCC3)nc2)cnn1-c1ccc(Cl)cc1]

(1) 1M Solution of lithium bis(trimethylailyl)amide (11 ml) was added under ice-cooling to a solution of cyanocyclohxane (1.20 g) in tetrahydrofuran (3 ml) and stirred for an hour. 5-Bromo-2-fluoropyridine (1.76 g) was added at the same temperature, the reaction solution was warmed to room temperature and further stirred for 24 hours. The reaction solution was treated with water, extracted with ethyl acetate and the organic layer was dried over anhydrous magnesium sulfate. The solvent was evaporated, concentrated hydrochloric acid (60 ml) was added to the residue and stirred at 100° C. for 24 hours. Water was evaporated in vacuo, acetone was added to the residue and the precipitated crystalline was suspended in toluene, thionyl chloride (0.94 g) was added and stirred at 70° C. for two hours. The solvent was evaporated in vacuo, ethanol (5 ml) was added to the residue and stirred further for an hour. The reaction mixture was filtered under ice-cooling, the filtrate was concentrated and treated with 1N aqueous solution of sodium hydroxide, then it was extracted with ethyl acetate, the organic layer was dried over anhydrous sodium sulfate and concentrated to give 1-(5-bromopyridin-2-yl)cyclohexanecarboxylic acid ethyl ester (1.13 g).
¹H-NMR (CDCl₃) δ(ppm): 1.20 (3H, t, J=9.9 Hz), 1.27-1.36 (2H, m), 1.47-1.67 (4H, m), 1.87 (2H, ddd, J=3.4, 4.1, 13.1 Hz), 2.37 (2H, d, J=16.7 Hz), 4.14 (2H, q, J=9.9 Hz), 7.23 (1H, d, J=10.9 Hz), 7.74 (1H, dd, J=2.8, 9.9 Hz), 8.60 (1H, d, J=2.8 Hz).

(2) 1-(4-Chlorophenyl)-5-methyl-1H-pyrazole-4-carboxamide was prepared from 1-(4-chlorophenyl)-5-methyl-1H-pyrazole-4-carboxylic acid described in Reference Example 3 in a similar manner as Example E1(1).

(3) 1-(4-Chlorophenyl)-5-methyl-1H-pyrazolecarboxamide (0.43 g), 1-(5-bromopyridin-2-yl)cyclohexanecarboxylic acid ethyl ester (0.83 g), copper (I) iodide (20 mg), 1,2-dimethylethylenediamine (0.13 g) and potassium carbonate (0.42 g) were added to 1,4-dioxane (5 ml), and stirred at 105° C. for six hours. The reaction solution was treated with water, extracted with ethyl acetate and concentrated in vacuo. 1N Aqueous solution of sodium hydroxide (5 ml) and ethanol (5 ml) were added to the residue, and stirred at 75° C. for seven hours. The solvent was evaporated, the residue was purified with a silica gel column chromatography (ethyl acetate:n-hexane=1:1) to give the titled compound (20 mg).
MS (ESI) m/z: 438(M)⁺.

Example K5

4-[(4-Cyano-4-{5-[({5-methyl-1-[4-(trifluoromethyl)phenyl]-1H-pyrazol-4-yl}carbonyl)-amino]pyridin-2-yl}cyclohexyl)oxy]-4-oxobutanoic acid

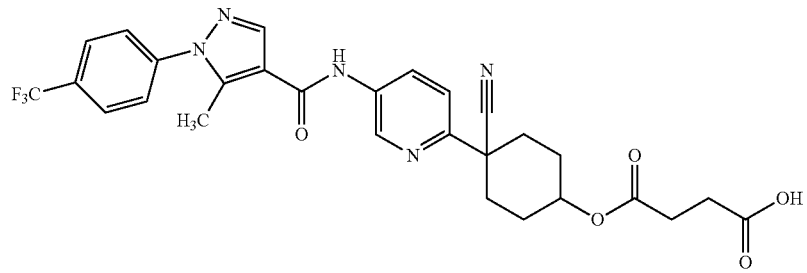 [SMILES: Cc1c(C(=O)Nc2ccc(C3(C#N)CCC(OC(=O)CCC(=O)O)CC3)nc2)cnn1-c1ccc(C(F)(F)F)cc1]

N-[6-(r-1-Cyano-c-4-hydroxycyclohexyl)pyridin-3-yl]-5-methyl-1-[4-(trifluoromethyl)-phenyl]-1H-pyrazole-4-carboxamide (0.47 g), succinic anhydride (0.15 g) and p-toluenesulfonic acid (0.05 g) were added to 1,2-dichlorobenzene (2.5 ml) and stirred at 140° C. for three hours. The reaction solution was treated with water and the precipitated solid was recrystallized from a mixed solvent of ethyl acetate-diisopropyl ether to give the titled compound (0.43 g).

MS (ESI) m/z: 570 (M+H)⁺.

Example K6

N-[6-(r-1-Cyano-c-4-hydroxycyclohexyl)pyridin-3-yl]-5-methyl-1-[5-(trifluoromethyl)pyridin-2-yl]-1H-pyrazole-4-carboxamide

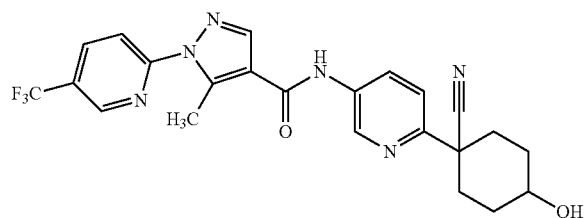 [SMILES: Cc1c(C(=O)Nc2ccc(C3(C#N)CCC(O)CC3)nc2)cnn1-c1ccc(C(F)(F)F)cn1]

5-Methyl-1-[5-(trifluoromethyl)pyridin-2-yl]-1H-pyrazole-4-carboxylic acid was used in place of 1-(4-fluorophenyl)-5-methyl-1H-pyrazole-4-carboxylic acid in Example G2, and reacted and treated in a similar manner to give the titled compound.

MS (ESI) m/z: 471 (M+H)⁺.

Example K7

1-[5-(Ethoxymethyl)pyridin-2-yl]-5-methyl-N-{5-methyl-6-[4-(morpholin-4-yl)cyclohex-1-en-1-yl]pyridin-3-yl}-1H-pyrazole-4-carboxamide

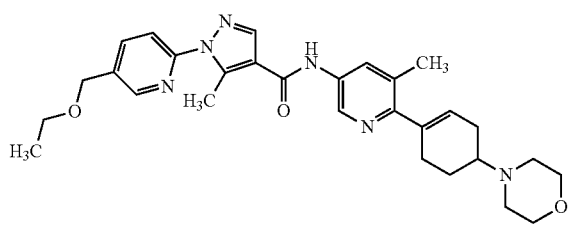 [SMILES: CCOCc1ccc(-n2ncc(C(=O)Nc3cnc(C4=CCC(N5CCOCC5)CC4)c(C)c3)c2C)nc1]

(1) Sodium hydride (175 mg) was added at room temperature to a solution of 1-[5-(hydroxymethyl)pyridin-2-yl]-5-methyl-1H-pyrazole-4-carboxylic acid ethyl ester (935 mg) described in Reference Example 41(3) in N,N-dimethylformamide (18 ml), and stirred at the same temperature for 30 minutes. Ethyl iodide (0.6 ml) was added and the mixture was stirred at 80° C. for two hours. Then, Sodium hydride (175 mg) and ethyl iodide (0.6 ml) were added and stirred at 80° C. for two hours. After the reaction, the reaction solution was cooled to room temperature, water was added and extracted with ethyl acetate four times. The organic layer was dried over anhydrous magnesium sulfate, the solvent was evaporated, and the residue was purified with a silica gel column chromatography (n-hexane/ethyl acetate) to give 1-[5-(ethoxymethyl)pyridin-2-yl]-5-methyl-1H-pyrazole-4-carboxylic acid ethyl ester (223 mg) as a white solid.

(2) 1N Aqueous solution of sodium hydroxide (2.3 ml) was added at room temperature to a solution of 1-[5-(ethoxymethyl)pyridin-2-yl]-5-methyl-1H-pyrazole-4-carboxylic acid ethyl ester (223 mg) in ethanol (16 ml), and stirred at 70° C. for an hour. Then, 1N aqueous solution of sodium hydroxide (4.6 ml) was added and stirred at 70° C. for an hour. After the reaction, ethanol was evaporated, 1N hydrochloric acid aqueous solution was added to adjust the solution to pH 1 to 2 and the precipitated solid was collected by filtration to give 1-[5-(ethoxymethyl)pyridin-2-yl]-5-methyl-1H-pyrazole-4-carboxylic acid (168 mg) as a white solid.

(3) Thionyl chloride (230 mg) and N,N-dimethylformamide (catalytic amounts) were added at room temperature to a solution of 1-[5-(ethoxymethyl)pyridin-2-yl]-5-methyl-1H-pyrazole-4-carboxylic acid (168 mg) in toluene (6.0 ml), and stirred at 80° C. for an hour. The solvent and an excess amount of thionyl chloride were evaporated, pyridine (3.0 ml) was added to the resulting reaction mixture, a solution of 5-methyl-6-[4-(morpholin-4-yl)cyclohex-1-en-1-yl]pyridine-3-amine (176 mg) described in Reference Example 108 in pyridine (3.0 ml) was added and stirred at 50° C. for an hour. After the reaction, triethylamine (1.5 ml) and water were added and the precipitated solid was filtered. The resulting residue was purified with a silica gel column chromatography (chloroform/methanol) to give the titled compound (193 mg) as a white solid.

MS (ESI) m/z: 517 (M+H)⁺.

Example K8

1-(5-Ethoxypyridin-2-yl)-5-methyl-N-{5-methyl-6-[4-(morpholin-4-yl)cyclohex-1-en-1-yl]-pyridin-3-yl}-1H-pyrazole-4-carboxamide

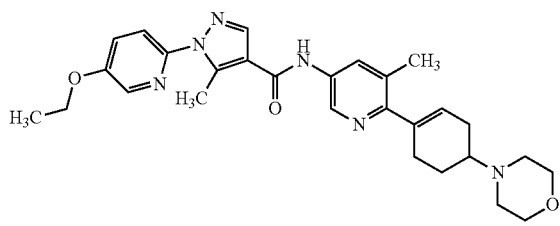 [SMILES: CCOc1ccc(-n2ncc(C(=O)Nc3cnc(C4=CCC(N5CCOCC5)CC4)c(C)c3)c2C)nc1]

(1) Palladium (II) acetate (73 mg), rac-2-(di-tert-butylphosphino)-1,1'-binaphthyl (160 mg), cesium carbonate (2.63 g) and ethanol (1.0 ml) were added at room temperature to a solution of 1-(5-bromopyridin-2-yl)-5-methyl-1H-pyrazole-4-carboxylic acid ethyl ester (1.0 g) described in Reference Example 24(2) in toluene (6.5 ml), and stirred at 70° C. for three hours. After the reaction, the reaction solution was cooled to room temperature, water was added and extracted with ethyl acetate three times. The organic layer was dried over anhydrous magnesium sulfate and concentrated.

(2) The resulting residue was dissolved in ethanol (16 ml), 1N aqueous solution of sodium hydroxide (16 ml) was added at room temperature and stirred at 70° C. for three hours. After the reaction, ethanol was evaporated, 1N hydrochloric acid aqueous solution was added to adjust the solution to pH 1 to 2 and the precipitated solid was filtered.

(3) The resulting residue was dissolved in N,N-dimethylformamide (12 ml), and to the solution were added 5-methyl-6-(4-(morpholin-4-yl)cyclohex-1-en-1-yl)pyridin-3-amine (795 mg) described in Reference Example 108, N-(3-dimethylaminopropyl)-N-ethylcarbodiimide hydrochloride (556 mg) and 4-dimethylaminopyridine (711 mg), and stirred at 80° C. for 24 hours. After the reaction, water was added and the precipitated solid was filtered. The residue was purified with a silica gel column chromatography (chloroform/methanol), and further with preparative HPLC (water:acetonitrile) to give the titled compound (152 mg) as a white solid.

N-{6-[r-1-Cyano-c-4-(morpholin-4-yl)cyclohexyl]pyridin-3-yl}-1-[5-(3-methoxypropyl)-pyridin-2-yl]-5-methyl-1H-pyrazole-4-carboxamide hydrochloride

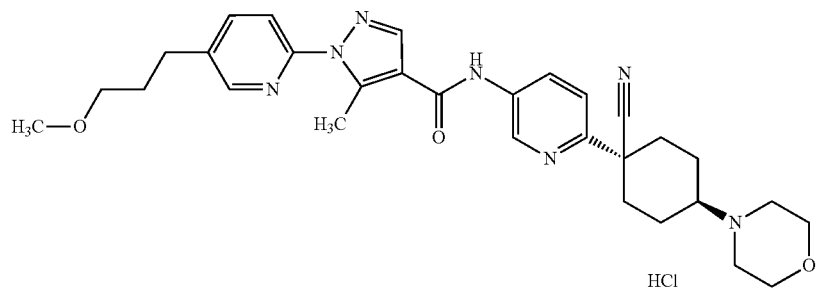 [SMILES: COCCCc1ccc(-n2ncc(C(=O)Nc3ccc([C@]4(C#N)CC[C@@H](N5CCOCC5)CC4)nc3)c2C)nc1 ; Cl]

1-{5-[(1E)-3-Methoxy-1-propenyl]pyridin-2-yl}-5-methyl-1H-pyrazole-4-carboxylic acid (157 mg) described in Reference Example 25 was dissolved in ethanol (10 ml) and methanol (5 ml), 10% palladium-carbon (containing ca. 50% water: 90 mg) was added and stirred at room temperature under hydrogen atmosphere for two hours. The reaction solution was filtered through Celite, washed with methanol and the filtrate was concentrated in vacuo. The precipitated solid was washed with diethyl ether. Thionyl chloride (54 μl) was added to a mixture of the resulting solid (140 mg), toluene (2.5 ml) and N,N-dimethylformamide (catalytic amounts) and stirred at 80° C. for an hour. The solvent was evaporated in vacuo, pyridine (2.5 ml) was added to the residue, a solution of 1-(5-aminopyridin-2-yl)-c-4-(morpholin-4-yl)-r-1-cyclohexanecarbonitrile (170 mg) described in Reference Example 94 in pyridine (2.5 ml) was added and stirred at 40° C. for 1.5 hours. Triethylamine (138 μl) and water were added and the precipitated solid was filtered. The resulting solid was purified with a preparative HPLC (water:acetonitrile). Ethanol (4 ml) and 2N hydrochloric acid-ethanol (1 ml) were added to the resulting solid and stirred at 80° C. The precipitated solid was washed with ethanol to give the titled compound (65 mg) as a white solid.

MS (ESI) m/z: 544 (M+H)+.

Example K10

N-{6-[r-1-Cyano-c-4-(morpholin-4-yl)cyclohexyl]pyridin-3-yl}-1-(4-cyanophenyl)-5-methyl-1H-pyrazole-4-carboxamide hydrochloride

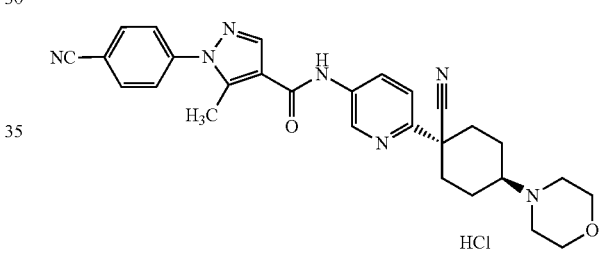

(1) 4-cyanophenylhydrazone hydrochloride was used in place of 4-fluorophenylhydrazine hydrochloride in Reference Example 1, and reacted and treated in a similar manner to give 1-[4-(aminocarbonyl)phenyl]-5-methyl-1H-pyrazole-4-carboxylic acid.

MS (ESI) m/z: 246 (M+H)+.

(2) Thionyl chloride (108 was added to a solution of 1-[4-aminocarbonyl)phenyl]-5-methyl-1H-pyrazole-4-carboxylic acid (123 mg) in toluene (2.5 ml) and N,N-dimethylformamide (catalytic amounts), and stirred at 80° C. for 2.5 hours. The solvent was evaporated in vacuo, the residue was dissolved in pyridine (2.5 ml), 1-(5-aminopyridin-2-yl)-c-4-

(morpholin-4-yl)-r-1-cyclohexanecarbonitrile (170 mg) described in Reference Example 94 was added at 40° C. and stirred for three hours. Triethylamine (138 μl) and water were added, the precipitated solid was filtered and washed with diethyl ether. Ethanol (10 ml) and 2N hydrochloric acid-ethanol (4 ml) were added to the resulting residue and stirred at 80° C. The precipitated solid was washed with ethanol to give the titled compound (159 mg) as a white solid.

MS (ESI) m/z: 496 (M+H)⁺.

Example K11

N-{6-[r-1-Cyano-c-4-(morpholin-4-yl)cyclohexyl]pyridin-3-yl}-1-(5-cyclopropylpyridin-2-yl)-1H-pyrrole-3-carboxamide hydrochloride

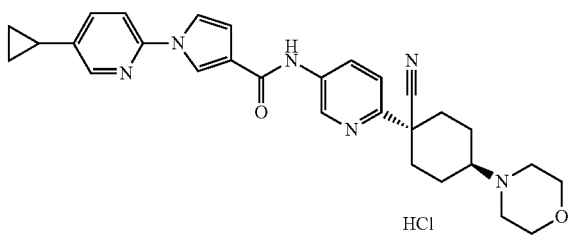 [SMILES: N#C[C@]1(c2ccc(NC(=O)c3ccn(-c4ccc(C5CC5)cn4)c3)cn2)CC[C@H](N2CCOCC2)CC1 ; Cl]

(1) 1-(5-Aminopyridin-2-yl)-c-4-(morpholin-4-yl)-r-1-cyclohexanecarbonitrile described in Reference Example 94 was used in place of 5-methyl-6-(4-(morpholin-4-yl)cyclohex-1-en-1-yl)pyridine-3-amine described in Reference Example 108 in Example H1(1)-(3) to give N-{6-[r-1-cyano-c-4-(morpholin-4-yl)cyclohexyl]pyridin-3-yl}-1H-pyrrole-3-carboxamide.

MS (ESI) m/z: 380 (M+H)⁺.

(2) Copper (I) iodide (214 g), tripotassium phosphate (1.2 g), N,N'-dimethylethylenediamine (360 μl) and 2-bromo-5-chloropyridine (260 mg) were added to a solution of N-{6-[r-1-cyano-c-4-(morpholin-4-yl)cyclohexyl]pyridin-3-yl}-1H-pyrrole-3-carboxamide (600 mg) in 1,4-dioxane (12 ml), and stirred at 120° C. for 8.5 hours. Water was added to the reaction solution, extracted with chloroform, the organic layer was washed with saturated brine, dried over anhydrous sodium sulfate and concentrated in vacuo to give 1-(5-chloropyridin-2-yl)-N-{6-[r-1-cyano-c-4-(morpholin-4-yl)cyclohexyl]pyridin-3-yl}-1H-pyrrole-3-carboxamide (270 mg) as a brown solid.

MS (ESI) m/z: 491 (M+H)⁺.

(3) Tetrahydrofuran (610 μl) was added to a solution of 1-(5-chloropyridin-2-yl)-N-{6-[r-1-cyano-c-4-(morpholin-4-yl)cyclohexyl]pyridin-3-yl}-1H-pyrrole-3-carboxamide (150 mg), palladium (II) acetate (13.6 mg), 2-dicyclohexylphosphino-2',6'-dimethoxybiphenyl (S-Phos) (25 mg), cyclopropylboronic acid (37 mg) and tripotassium phosphate (162 mg), and stirred at 100° C. for 8 hours. Water was added to the reaction solution, and the precipitated solid was purified with silica gel chromatography (chloroform/methanol). To the resulting solid, were added ethanol (6 ml) and 2N hydrochloric acid-ethanol solution and stirred at 80° C. The precipitated solid was washed with ethanol to give the titled compound (93 mg) as a white solid.

MS (ESI) m/z: 497 (M+H)⁺.

Example K12

1-(5-Cyclopropylpyridin-2-yl)-N-{5-methyl-6-[4-(morpholin-4-yl)cyclohex-1-en-1-yl]pyridin-3-yl}-1H-pyrrole-3-carboxamide mesylate

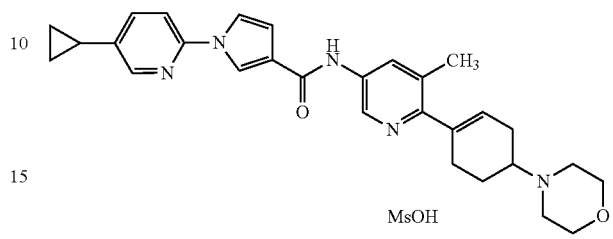

Tetrahydrofuran (1.5 ml) was added to 1-(5-chloropyridin-2-yl)-N-{5-methyl-6-[4-(morpholin-4-yl)cyclohex-1-en-1-yl]pyridin-3-yl}-1H-pyrrole-3-carboxamide (348 mg) of Example D96, palladium (II) acetate (11 mg), 2-dicyclohexylphosphino-2',6'-dimethoxybiphenyl (S-Phos) (20 mg), cyclopropylboronic acid (60 mg) and tripotassium phosphate (264 mg), and stirred at 100° C. for 9 hours. Water was added to the reaction solution, extracted with ethyl acetate, the organic layer was washed with saturated brine, dried over anhydrous sodium sulfate and concentrated in vacuo. The resulting residue was purified with silica gel chromatography (chloroform/methanol). The obtained pale yellow solid (76 mg) was dissolved in methanol (4 ml) and dichloromethane (1 ml), methanesulfonic acid (10 μl) was added, and the mixture was stirred at room temperature and concentrated in vacuo. The precipitated solid was washed with diethyl ether to give the titled compound (62 mg) as a white solid.

MS (ESI) m/z: 484 (M+H)⁺.

N-{[6-(r-1-Cyano-c-4-(morpholin-4-yl)cyclohexyl)-5-methylpyridin-3-yl]}-5-methyl-1-[4-(trifluoromethyl)phenyl]-1H-pyrazole-4-carboxamide

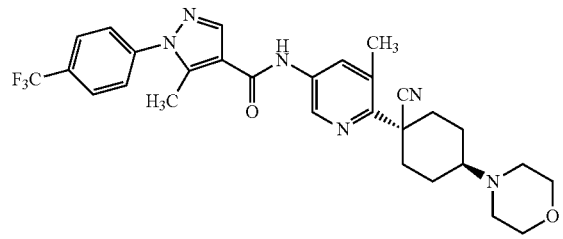 [SMILES: Cc1cc(NC(=O)c2cnn(-c3ccc(C(F)(F)F)cc3)c2C)cnc1[C@]1(C#N)CC[C@@H](N2CCOCC2)CC1]

1-(5-Bromo-3-methylpyridin-2-yl)-4-(morpholin-4-yl)cyclohexanecarbonitrile (0.52 g) of Reference Example 95, which was prepared from 5-methyl-1-[4-(trifluoromethyl)phenyl]-1H-pyrazole-4-amide (0.43 g) described in Reference Example 23 using a method described in Example E1 (1), 1-(5-bromo-3-methylpyridin-2-yl)-4-(morpholin-4-yl)cyclohexanecarbonitrile (0.52 g) described in Reference Example 95, palladium (II) acetate (20 mg), 4,5-bis(diphenylphosphino)-9,9-dimethylxanthene (xantphos) (82 mg) and cesium carbonate (650 mg) were added to 1,4-dioxane (10 ml), and stirred at 100° C. under hydrogen atmosphere for six hours. The reaction solution was treated with water, the organic layer was extracted with ethyl acetate, dried over anhydrous magnesium sulfate and concentrated in vacuo. The residue was purified with silica gel column chromatography (chloroform/methanol=10:1) to give the titled compound (120 mg).

MS (ESI) m/z: 553 (M+H)+.

Example K14 trans-1-(3-Fluoro-5-isopropylpyridin)-2-yl)-5-methyl-N-[5-methyl-6-(4-(morpholin-4-yl)-cyclohexyl)pyridin-3-yl]-1H-pyrazole-4-carboxamide hydrochloride

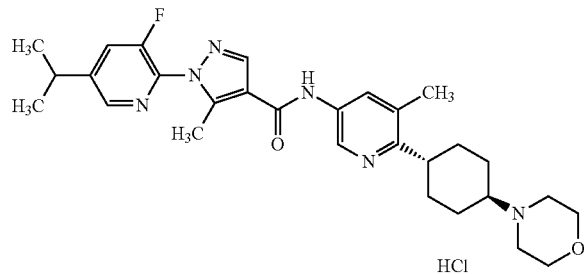 [SMILES: Cc1cc(NC(=O)c2cnn(-c3ncc(C(C)C)cc3F)c2C)cnc1[C@H]1CC[C@H](N2CCOCC2)CC1 ; Cl]

(1) In Example D7,1-(5-chloro-3-fluoropyridin-2-yl)-5-methyl-1H-pyrazole-4-carboxylic acid described in Reference Example 124 was used in place of 1-(3,5-dichloropyridin-2-yl)-5-methyl-1H-pyrazole-4-carboxylic acid, and trans-5-methyl-6-(4-(morpholin-4-yl)cyclohexyl)pyridine-3-amine described in Reference Example 138B was used in place of 1-(5-aminopyridin-2-yl)-c-4-(morpholin-4-yl)-r-1-cyclohexanecarbonitrile, and reacted and treated in a similar manner to give a pale yellow solid (200 mg), to which palladium (II) acetate (8.7 mg), 2-dicyclohexylphosphino-2',6'-dimethoxybiphenyl (S-Phos) (16 mg), tripotassium phosphate (207 mg) and tetrahydrofuran (1.3 ml) were added, and then, isopropenylboronic acid pinacol ester (102 was added and stirred at 100° C. for 4.5 hours. Water was added to the reaction solution, extracted with ethyl acetate, the organic layer was washed with saturated brine, dried over anhydrous sodium sulfate and concentrated in vacuo. The residue was purified with silica gel chromatography (chloroform/methanol) to give N-{6-[r-1-cyano-c-4-(morpholin-4-yl)cyclohexyl]pyridin-3-yl}-1-(3-fluoro-5-isopropenylpyridin-2-yl)-5-methyl-1H-pyrazole-4-carboxamide (160 mg) as a yellow solid.

MS (ESI) m/z: 519 (M+H)+.

(2) 1,4-Dioxane (10 ml) and 10% palladium-carbon (containing ca. 50% water; 150 mg) were added to N-{6-[r-1-cyano-c-4-(morpholin-4-yl)cyclohexyl]pyridin-3-yl}-1-(3-fluoro-5-isopropenylpyridin-2-yl)-5-methyl-1H-pyrazole-4-carboxamide (160 mg), and stirred at room temperature under hydrogen atmosphere for 4.5 hours. The reaction solution was filtered through Celite, the solvent was evaporated in vacuo, and the residue was purified with silica gel chromatography (chloroform/methanol). Ethanol (5 ml) and 2N hydrochloric acid-ethanol (2 ml) were added to the obtained solid, stirred at 40° C. and concentrated in vacuo. Diethyl ether was added to the residue, the precipitated solid was washed with diethyl ether and ethanol to give the titled compound (132 mg) as an orange solid.

MS (ESI) m/z: 521 (M+H)+.

Example K15

N-[6-(8-Cyano-1,4-dioxaspiro[4.5]dec-8-yl)pyridin-3-yl]-5-(4-fluorophenyl)nicotinamide

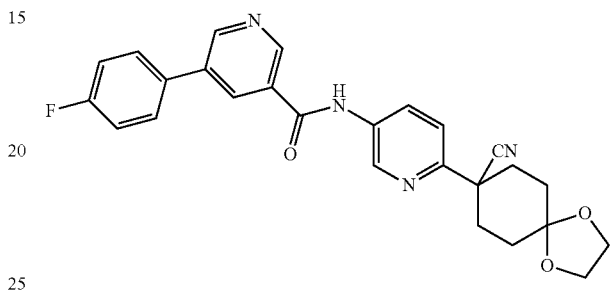

(1) Oxalyl chloride (1.33 ml) and N,N-dimethylformamide (catalytic amounts) were added dropwise under ice-cooling to a solution of 5-bromopyridine-3-carboxylic acid (2.02 g) in dichloromethane, and stirred for an hour. The solvent was evaporated in a evaporator, the residue was dissolved in tetrahydrofuran (10 ml), to which ammonia water (28%; 1 ml) was added dropwise under ice-cooling, and stirred at room temperature for 0.5 hours. After completion of the reaction, water was added to the reaction mixture and extracted with ethyl acetate. The organic layer was dried over anhydrous magnesium sulfate, and concentrated. The residue was purified with column chromatography to give 5-bromopyridine-3-carboxamide (734 mg).

(2) A solution of 5-bromopyridine-3-carboxamide (734 mg), 8-(5-bromopyridin-2-yl)-1,4-dioxaspiro[4.5]decane-8-carbonitrile (1.18 g) described in Reference Example 82, copper (I) iodide (35 mg), N,N-dimethylethylamine (33 mg) and potassium carbonate (1.01 g) in 1,4-dioxane (5 ml) was stirred at 100° C. for six hours. After completion of the reaction, water was added and extracted with ethyl acetate. The organic layer was dried over anhydrous magnesium sulfate and concentrated. The residue was purified with column chromatography to give 5-bromo-N-[6-(8-cyano-1,4-dioxaspiro[4.5]dec-8-yl)pyridin-3-yl]nicotinamide (213 mg).

MS (ESI) m/z: 443 (M+H)+.

(3) A solution of 5-bromo-N-[6-(8-cyano-1,4-dioxaspiro[4.5]dec-8-yl)pyridin-3-yl]nicotinamide (213 mg), 4-fluorophenylboronic acid (63 mg), bis(triphenylphosphine)palladium (II) dichloride (100 mg) and sodium carbonate (636 mg) in a mixture of toluene (5 ml), ethanol (1 ml) and water (1 ml) was stirred at 100° C. for six hours. After completion of the reaction, water was added and extracted with ethyl acetate. The organic layer was dried over anhydrous magnesium sulfate and concentrated. The residue was purified with column chromatography to give the titled compound (31 mg).

MS (ESI) m/z: 459 (M+H)+.

Example K 16

N-[6-(1-Cyano-4-oxocyclohexyl)pyridin-3-yl]-1-(4-ethylphenyl)-1H-pyrazole-4-carboxamide

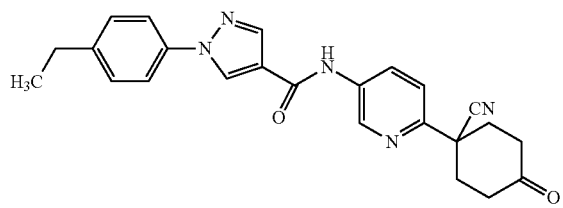 [SMILES: CCc1ccc(-n2cc(C(=O)Nc3ccc(C4(C#N)CCC(=O)CC4)nc3)cn2)cc1]

(1) 4-Ethyl-bromobenzene was reacted and treated in place of 5-iodo-m-xylene in Reference Example 73 to give 1-(4-ethylphenyl)-1H-pyrazole-4-carboxylic acid.

(2) Thionyl chloride (0.052 ml) and N,N-dimethylformamide (catalytic amounts) were added dropwise under ice-cooling to a solution of 1-(4-ethylphenyl)-1H-pyrazole-4-carboxylic acid (102 mg) in toluene (2 ml), and stirred at 50° C. for an hour. The solvent was evaporated with an evaporator, the residue was dissolved in N-methylpyrrolidone (2 ml), the solution was added dropwise under ice-cooling to a solution of 8-(5-aminopyridin-2-yl)-1,4-dioxaspiro[4.5]decane-8-carbonitrile of Reference Example 86 in N-methylpyrrolidone (2 ml). Triethylamine (1 ml) was added to the reaction solution and stirred at room temperature for six hours. After completion of the reaction, water was added and extracted with ethyl acetate. The organic layer was dried over anhydrous magnesium sulfate and concentrated. Acetic acid (8 ml), water (2 ml) and 1N hydrochloric acid aqueous solution (2 ml) were added to the residue and the mixture was stirred at 100° C. for two hours. After completion of the reaction, a saturated aqueous solution of potassium carbonate was added and extracted with ethyl acetate. The organic layer was dried over anhydrous magnesium sulfate and concentrated. The residue was purified with column chromatography to give the titled compound (11 mg).

MS (ESI) m/z: 414 (M+H)⁺.

Example K17

N-[6-(8-Cyano-1,4-dioxaspiro[4.5]dec-8-yl)pyridin-3-yl]-1-(4-isopropylphenyl)-1H-pyrazole-4-carboxamide

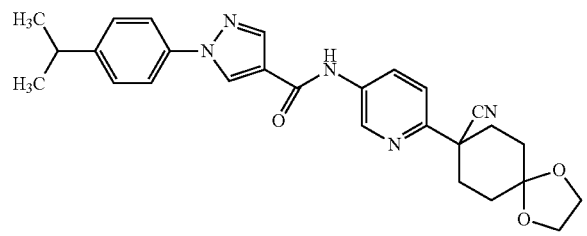 [SMILES: CC(C)c1ccc(-n2cc(C(=O)Nc3ccc(C4(C#N)CCC5(CC4)OCCO5)nc3)cn2)cc1]

(1) 4-Isopropyl-iodobenzene was used in place of 5-iodo-m-xylene in Reference Example 73 and reacted and treated in a similar manner to give 1-(4-iodopropylphenyl)-1H-pyrazole-4-carboxylic acid.

(2) Thionyl chloride (0.11 ml) and N,N-dimethylformamide (catalytic amounts) were added dropwise under ice-cooling to a solution of 1-(4-iodopropylphenyl)-1H-pyrazole-4-carboxylic acid (230 mg) in toluene (3 ml), and stirred at 50° C. for an hour. The solvent was evaporated in an evaporater, the residue was dissolved in N-methylpyrrolidone (2 ml), the solution was added dropwise under ice-cooling to a solution of 8-(5-aminopyridin-2-yl)-1,4-dioxaspiro[4.5]decane-8-carbonitrile (254 mg) of Reference Example 86 in N-methylpyrrolidone (2 ml). Triethylamine (1 ml) was added to the reaction solution and stirred at room temperature for six hours. After completion of the reaction, water was added and extracted with ethyl acetate. The organic layer was dried over anhydrous magnesium sulfate and concentrated. The residue was purified with column chromatography to give the titled compound (254 mg).

MS (ESI) m/z: 472 (M+H)⁺.

Example K18

N-[6-(1-Cyano-4-oxocyclohexyl)pyridin-3-yl]-1-(4-isopropyphenyl)-1H-pyrazole-4-carboxamide

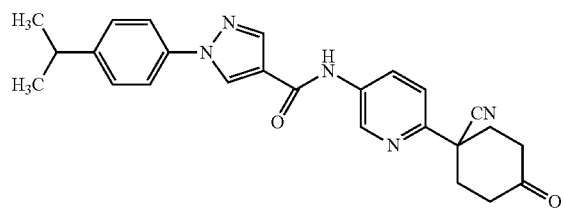 [SMILES: CC(C)c1ccc(-n2cc(C(=O)Nc3ccc(C4(C#N)CCC(=O)CC4)nc3)cn2)cc1]

A solution of N-[6-(8-cyano-1,4-dioxaspiro[4.5]dec-8-yl)pyridin-3-yl]-1-(4-isopropylphenyl)-1H-pyrazole-4-carboxamide (236 mg) in a mixture of acetic acid (5 ml), water (1 ml) and 1N hydrochloric acid aqueous solution (1 ml) was stirred at 100° C. for two hours. After completion of the reaction, a saturated aqueous solution of potassium carbonate was added and extracted with ethyl acetate. The organic layer was dried over anhydrous magnesium sulfate and concentrated. The residue was purified with column chromatography to give the titled compound (216 mg).

MS (ESI) m/z: 428 (M+H)⁺.

Example K19

N-{6-[r-1-cyano-c-4-(2-hydroxyethoxy)cyclohexyl]pyridin-3-yl}-5-methyl-1-(4-methylphenyl)-1H-pyrazole-4-carboxamide

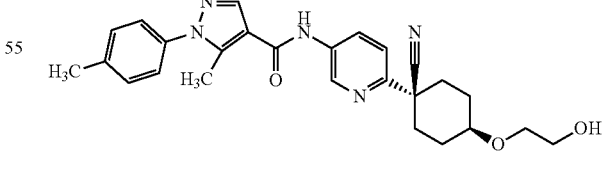

(1) Oxalyl chloride (0.05 ml) and N,N-dimethylformamide (catalytic amounts) were added at room temperature to a solution of 1-(4-methylphenyl)-5-methyl-1H-pyrazole-4-carboxylic acid (33 mg) described in Reference Example 4 in dichloromethane (2 ml), stirred at room temperature for two hours and the solvent and an excess amount of oxalyl chloride were evaporated. Toluene (5 ml) was added to the resulting reaction mixture, a solution of 1-(5-aminopyridin-2-yl)-c-4-[2-(tetrahydro-2H-pyran-2-yloxy)ethoxy]-r-1-cyclohexanecarbonitrile (44 mg) described in Reference Example 99 in pyridine (2 ml) was added under ice-cooling and stirred at room temperature overnight. After completion of the reaction, water was added under ice-cooling, and extracted with ethyl acetate. The organic layer was dried over anhydrous sodium sulfate and concentrated. The resulting residue was purified with silica gel column chromatography (n-hexane/ethyl acetate) to give N-(6-{r-1-cyano-c-4-[2-(tetrahydro-2H-pyran-2-yloxy)ethoxy]cyclohexyl}pyridin-3-yl)-5-methyl-1-(4-methylphenyl)-1H-pyrazole-4-carboxamide (66 mg) as a white solid.

MS (ESI) m/z: 544 (M+H)$^+$.

(2) 1N Hydrochloric acid aqueous solution (3 ml) was added to a solution of N-(6-{r-1-cyano-c-4-[2-(tetrahydro-2H-pyran-2-yloxy)ethoxy]cyclohexyl}pyridin-3-yl)-5-methyl-1-(4-methylphenyl)-1H-pyrazole-4-carboxamide (49 mg) in methanol (3 ml) and stirred at room temperature for two hours. After completion of the reaction, water was added, the organic solvent was evaporated, neutralized by the addition of a saturated aqueous solution of sodium bicarbonate and extracted with chloroform. The resulting organic layer was dried over anhydrous sodium sulfate and concentrated to give the titled compound (41 mg) as a white solid.

MS (ESI) m/z: 460 (M+H)$^+$.

Example K20A 5-(4-Chlorophenyl)-N-[6-(r-1-cyano-c-4-hydroxycyclohexyl)pyridin-3-yl]-2-furamide Example K20B 5-(4-Chlorophenyl)-N-[6-(r-1-cyano-t-4-hydroxycyclohexyl)pyridin-3-yl]-2-furamide

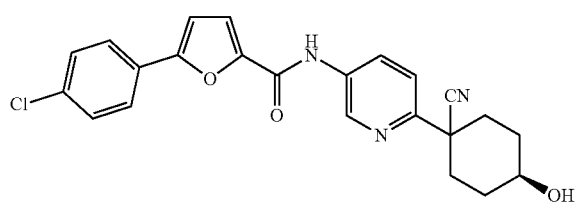

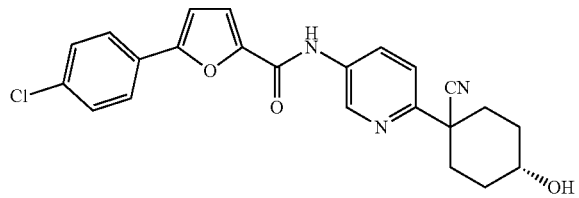

Lithium borohydride (13 mg) and methanol (1 ml) were added to a solution of 5-(4-chlorophenyl)-N-[6-(1-cyano-4-oxocyclohexyl)pyridin-3-yl]-2-furamide (100 mg) of Example F12 in tetrahydrofuran (5 ml) and stirred at room temperature for six hours. After completion of the reaction, a saturated aqueous solution of potassium carbonate was added, and extracted with ethyl acetate. The organic layer was dried over anhydrous magnesium sulfate, and concentrated. The residue was purified with column chromatography to give the titled compound; 5-(4-chlorophenyl)-N-[6-(r-1-cyano-t-4-hydroxycyclohexyppyridin-3-yl]-2-furamide [4 mg; MS (ESI) m/z: 422 (M+H)$^+$] and 5-(4-chlorophenyl)-N-[6-(r-1-cyano-c-4-hydroxycyclohexyl)pyridin-3-yl]-2-furamide [3 mg; MS (ESI) m/z: 422 (M+H)$^+$].

Example K21

N-{6-[r-1-Cyano-c-4-(morpholin-4-yl)cyclohexyl]pyridin-3-yl}-1-(5-propylpyridin-2-yl)-5-methyl-1H-pyrazole-4-carboxamide hydrochloride

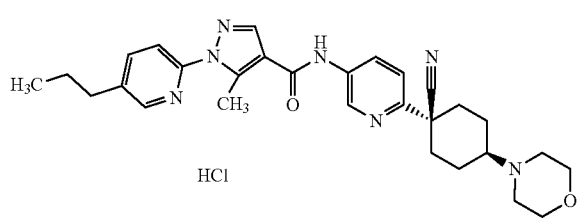 [SMILES: CCCc1ccc(-n2ncc(C(=O)Nc3ccc([C@]4(C#N)CC[C@@H](N5CCOCC5)CC4)nc3)c2C)nc1 ; Cl]

(1) trans-1-Propen-1-ylboronic acid was used in place of vinylboronic acid pinacol ester in Reference Example 28, and reacted and treated in a similar manner to give a white solid (120 mg), which was dissolved in toluene (5.0 ml). Thionyl chloride (97 μl) was added to a mixture of the toluene solution and N,N-dimethylformamide (catalytic amounts), stirred at 80° C. for 3.5 hours and the solvent was evaporated. To a solution of the residue in pyridine (2.5 ml), was added a solution of 1-(5-aminopyridin-2-yl)-c-4-(morpholin-4-yl)-r-1-cyclohexanecarbonitrile (157 mg) described in Reference Example 94 in pyridine (2.5 ml) at 40° C. and stirred for 1.5 hours. Triethylamine (310 μl) and water were added, the precipitated solid was collected by filtration and washed with water. Ethanol (5 ml) and 2N hydrochloric acid-ethanol solution (2 ml) were added to the obtained solid and stirred at 40° C. The precipitated solid was washed with ethanol and ethyl acetate to give the titled compound (151 mg) as a white solid.

MS (ESI) m/z: 514 (M+H)$^+$.

Example K22

N-{6-[r-1-(hydroxymethyl)-c-4-methoxycyclohexyl]pyridin-3-yl}-5-methyl-1-(4-methylphenyl)-1H-pyrazole-4-carboxamide

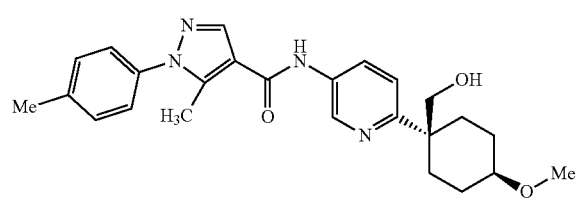 [SMILES: CO[C@H]1CC[C@](CO)(c2ccc(NC(=O)c3cnn(-c4ccc(C)cc4)c3C)cn2)CC1]

Lithium borohydride (8.2 mg) was added under ice-cooling to a solution of 1-[5-({[5-methyl-1-(4-methylphenyl)-1H-pyrazol-4-yl]carbonyl}amino)pyridin-2-yl]-c-4-methoxy-r-1-cyclohexanecarboxylic acid ethyl ester (30 mg) in terahydrofuran (3.0 ml), and stirred under reflux for two hours. After completion of the reaction, water was added under ice-cooling and extracted with ethyl acetate after evaporation of the organic solvent. The organic layer was washed with saturated brine, dried over anhydrous sodium sulfate and concentrated. The residue was purified with silica gel column chromatography (n-hexane/ethyl acetate) to give the titled compound (16 mg) as a white solid.

MS (ESI) m/z: 435 (M+H)⁺.

Example K23

5-Methyl-N-{5-methyl-6-[4-(trifluoromethyl)cyclohex-1-en-1-yl]pyridin-3-yl}-1-[5-(trifluoromethyl)pyridin-2-yl]-1H-pyrazole-4-carboxamide

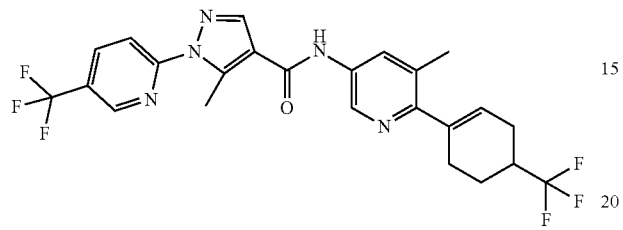

4,4,5,5-Tetramethyl-2-[4-(trifluoromethyl)cyclohex-1-en-1-yl]-[1,3,2] dioxaborolane (163 mg), [1,1'-bis(diphenylphosphino)ferrocene]palladium (II) dichloride dichloromethane complex (37 mg), sodium carbonate (144 mg) and water (1.0 ml) were added at room temperature to a solution of N-(6-bromo-5-methylpyridin-3-yl)-5-methyl-1-[5-(trifluoromethyl)pyridin-2-yl]-1H-pyrazole-4-carboxamide (200 mg) described in Reference Example 189 in 1,4-dioxane (3.0 ml), and stirred at 100° C. under radiation of microwave for an hour. After completion of the reaction, water and ethyl acetate were added, filtered through Celite and the filtrate was extracted with ethyl acetate. The organic layer was dried over anhydrous sodium sulfate and concentrated. The resulting residue was purified with silica gel column chromatography (chloroform/methanol) to give the titled compound (146 mg) as a white solid.

MS (ESI) m/z: 510 (M+H)⁺.

Example K24

5-Methyl-N-{3-methyl-[1-(oxetan-3-yl)piperidin-4-yl]pyridin-5-yl}-1-[5-(trifluoromethyl)-pyridin-2-yl]-1H-pyrazole-4-carboxamide

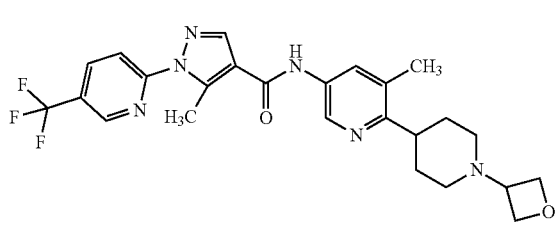 [SMILES: Cc1cc(NC(=O)c2cnn(-c3ccc(C(F)(F)F)cn3)c2C)cnc1C1CCN(C2COC2)CC1]

3-Oxetanone (121 mg) and sodium triacetoxyborohydride (143 mg) were added at room temperature to a solution of 5-methyl-N-[5-methyl-6-(piperidin-4-yl)pyridin-3-yl]-1-[5-(trifluoromethyl)pyridin-2-yl]-1H-pyrazole-4-carboxamide (250 mg) described in Reference Example 171 in dichloromethane (24 ml), and stirred at the same temperature for five hours. After completion of the reaction, water was added and extracted with ethyl acetate. The organic solution was dried over anhydrous sodium sulfate and concentrated. 1N Aqueous solution of sodium hydroxide (20 ml) was added to the resulting residue, solid was collected by filtration purified with silica gel column chromatography (chloroform/methanol) to give the titled compound (100 mg) as a white solid.

MS (ESI) m/z: 501 (M+H)⁺.

Example K25

N-{6-[4-Cyano-1-(oxetan-3-yl)piperidin-4-yl]pyridin-3-yl}-5-methyl-1-[5-(trifluoromethyl)-pyridin-2-yl]-1H-pyrazole-4-carboxamide

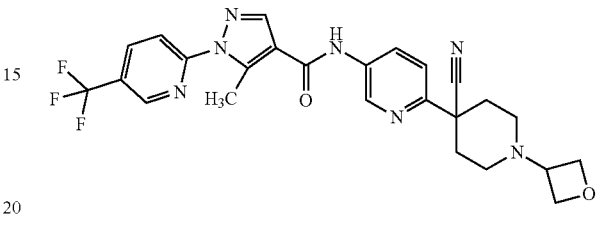

3-Oxetanone (316 mg) and sodium triacetoxyborohydride (112 mg) were added at room temperature to a solution of N-[6-(4-cyanopiperidin-4-yl)pyridin-3-yl]-5-methyl-1-[5-(trifluoromethyl)pyridin-2-yl]-1H-pyrazole-4-carboxamide (200 mg) described in Reference Example 169 in dichloromethane (20 ml) and tetrahydrofuran (20 ml), and stirred at the same temperature for eight hours. Further 3-oxetanone (316 mg) and sodium triacetoxyborohydride (112 mg) were added at room temperature and stirred at the same temperature for six hours. After completion of the reaction, a saturated aqueous solution of sodium bicarbonate was added thereto, and the mixture was extracted with ethyl acetate. The organic layer was dried over anhydrous sodium sulfate, concentrated and the resulting residue was purified with silica gel column chromatography (chloroform/methanol) to give the titled compound (100 mg) as a white solid.

MS (ESI) m/z: 512 (M+H)⁺.

Example K26

5-Methyl-N-[5-methyl-6-(4-methylaminocyclohex-1-en-1-yl)pyridin-3-yl]-1-[5-(trifluoromethyl)pyridin-2-yl]-1H-pyrazole-4-carboxamide

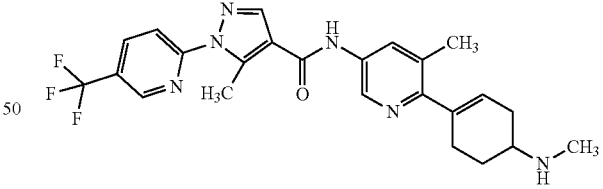

Trifluoroacetic acid (5.0 ml) was added at room temperature to a solution of N-methyl-{4-[3-methyl-5-({5-methyl-1-[5-(trifluoromethyl)pyridin-2-yl]-1H-pyrazole-4-carbonyl}-amino)pyridin-2-yl]cyclohex-3-en-1-yl}carbamoic acid carbamic acid tert-butyl ester (1.47 g) of Example D249 in dichloromethane (25 ml), and stirred at the same temperature for four hours. After completion of the reaction, 4N aqueous solution of sodium hydroxide (15 ml) was added and the solvent was evaporated. Ethanol (15 ml) and water were added to the resulting residue, stirred at room temperature for 30 minutes and the solid was filtered to give the titled compound (1.16 g) as a white solid.

MS (ESI) m/z: 471 (M+H)⁺.

Example K27

N-{6-[4-(N-Acetyl-N-methylamino)cyclohex-1-en-1-yl]-5-methylpyridin-3-yl}-5-methyl-1-[5-(trifluoromethyl)pyridin-2-yl]-1H-pyrazole-4-carboxamide

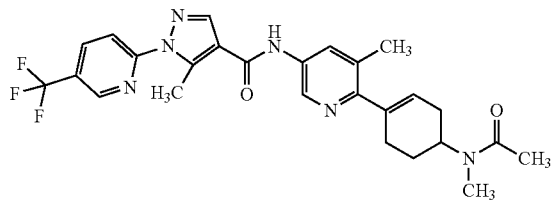 [SMILES: CC(=O)N(C)C1CC=C(c2ncc(NC(=O)c3cnn(-c4ccc(C(F)(F)F)cn4)c3C)cc2C)CC1]

Acetic anhydride (0.5 ml) was added at room temperature to a solution of 5-methyl-N-[5-methyl-6-(4-methylaminocyclohex-1-en-1-yl)pyridin-3-yl]-1-[5-(trifluoromethyl)pyridin-2-yl]-1H-pyrazole-4-carboxamide (200 mg) in pyridine (8.0 ml), and stirred at the same temperature for three hours. After completion of the reaction, water was added and the precipitated solid was filtered. The resulting residue was purified with silica gel column chromatography (chloroform/methanol) to give the titled compound (191 mg) as a white solid.
MS (ESI) m/z: 513 (M+H)⁺.

Example K28

N-(6-{4-[N-(2,2-Dimethylpropion-1-yl)-N-methylamino]cyclohex-1-en-1-yl}-5-methylpyridin-3-yl)-5-methyl-1-[5-(trifluoromethyl)pyridin-2-yl]-1H-pyrazole-4-carboxamide

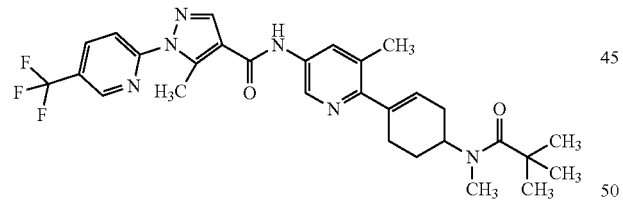

Pivalic anhydride (0.5 ml) and 4-dimethylaminopyridine (16 mg) were added at room temperature to a solution of 5-methyl-N-[5-methyl-6-(4-methylaminocyclohex-1-en-1-yl)pyridin-3-yl]-1-[5-(trifluoromethyl)pyridin-2-yl]-1H-pyrazole-4-carboxamide (200 mg) of Example K26 in pyridine (8.0 ml), and stirred at 70° C. for 10 hours. After completion of the reaction, the reaction solution was cooled to room temperature, water was added and the precipitated solid was filtered. The resulting residue was purified with silica gel column chromatography (chloroform/methanol) to give the titled compound (205 mg) as a white solid.
MS (ESI) m/z: 555 (M+H)⁺.

Example K29

N-{6-[4-(N-Isopropyl-N-methylamino)cyclohex-1-en-1-yl]-5-methylpyridin-3-yl}-5-methyl-1-[5-(trifluoromethyl)pyridin-2-yl]-1H-pyrazole-4-carboxamide

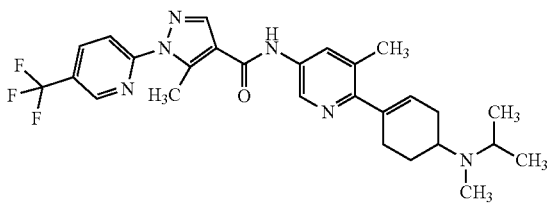 [SMILES: Cc1cc(NC(=O)c2cnn(-c3ccc(C(F)(F)F)cn3)c2C)cnc1C1=CCC(N(C)C(C)C)CC1]

Acetone (0.3 ml) and sodium triacetoxyborohydride (450 mg) were added at room temperature to a solution of 5-methyl-N-[5-methyl-6-(4-methylaminocyclohex-1-en-1-yl)pyridin-3-yl]-1-[5-(trifluoromethyl)pyridin-2-yl]-1H-pyrazole-4-carboxamide (200 mg) of Example K26 in dichloromethane (8.0 ml), and stirred at the same temperature for eight hours. Further, acetone (0.3 ml) and sodium triacetoxyborohydride (450 mg) were added at room temperature and stirred at 40° C. for four hours. After completion of the reaction, the solvent was evaporated, water was added and the precipitated solid was collected by filtration to give the titled compound (198 mg) as a white solid.
MS (ESI) m/z: 513 (M+H)⁺.

Example K30

N-(6-[4-[N-(3,3-Dimethylbutyl)-N-methylamino]cyclohex-1-en-1-yl]-5-methylpyridin-3-yl)-5-methyl-1-[5-(trifluoromethyl)pyridin-2-yl]-1H-pyrazole-4-carboxamide

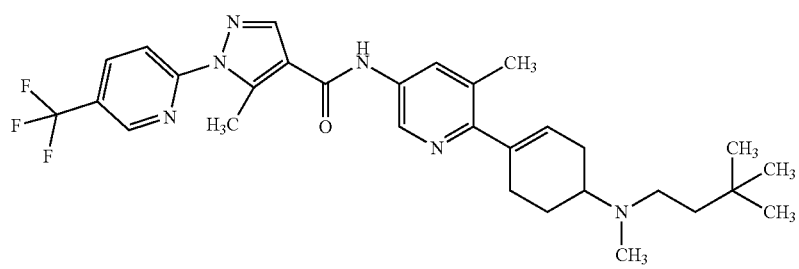 [SMILES: Cc1cc(NC(=O)c2cnn(-c3ccc(C(F)(F)F)cn3)c2C)cnc1C1=CCC(N(C)CCC(C)(C)C)CC1]

3,3-Dimethylbutylaldehyde (1.1 ml) and sodium triacetoxyborohydride (450 mg) were added at room temperature to a solution of 5-methyl-N-[5-methyl-6-(4-methylaminocyclohex-1-en-1-yl)pyridin-3-yl]-1-[5-(trifluoromethyl)pyridin-2-yl]-1H-pyrazole-4-carboxamide (200 mg) of Example K26 in dichloromethane (8.0 ml), and stirred at the same temperature for six hours, and at 40° C. for two hours. After completion of the reaction, the solvent was evaporated, water was added and the precipitated solid was collected by filtration to give the titled compound (168 mg) as a white solid.

MS (ESI) m/z: 555 (M+H)⁺.

Example K31

N-{6-[4-(1-Hydroxy-1-methylethyl)cyclohex-1-en-1-yl]-5-methylpyridin-3-yl}-5-methyl-1-[5-(trifluoromethyl)pyridin-2-yl]-1H-pyrazole-4-carboxamide

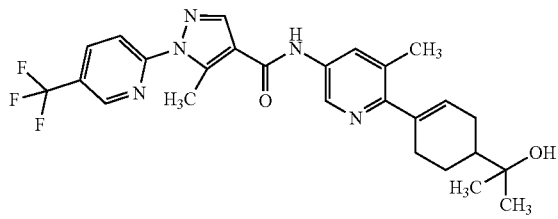 [SMILES: Cc1cc(NC(=O)c2cnn(-c3ccc(C(F)(F)F)cn3)c2C)cnc1C1=CCC(C(C)(C)O)CC1]

(1) 4-(5-Bromo-3-methylpyridin-2-yl)cyclohex-3-ene-1-carboxylic acid ethyl ester (3.34 g) described in Reference Example 152(2) was used in place of 1-(5-bromopyridin-2-yl)-c-4-(tert-butyldimethylsilanyloxy)-r-1-cyclohexanecarbonitrile described in Reference Example 144(2)(3), and reacted and treated in a similar manner to give 4-(5-amino-3-methylpyridin-2-yl)cyclohex-3-ene-1-carboxylic acid ethyl ester (985 mg) as a brown oil.

MS (ESI) m/z: 261 (M+H)⁺.

(2) Thionyl chloride (1.35 g) and N,N-dimethylformamide (catalytic amounts) were added at room temperature to a solution of 5-methyl-1-[5-(trifluoromethyl)pyridin-2-yl]-1H-pyrazole-4-carboxylic acid (1.13 g) described in Reference Example 8 in toluene (14 ml), and stirred at 80° C. for an hour. The solvent and an excess amount of thionyl chloride were evaporated, pyridine (7.0 ml) was added to the resulting residue, a solution of 4-(5-amino-3-methylpyridin-2-yl)cyclohex-3-ene-1-carboxylic acid ethyl ester (985 mg) in pyridine (7.0 ml) was added thereto and the mixture was stirred at 50° C. for an hour. After completion of the reaction, triethylamine (1.5 ml) and water were added and the precipitated solid was collected by filtration. The resulting residue was purified with silica gel column chromatography (chloroform/methanol) to give 4-[3-methyl-5-({5-methyl-1-[5-(trifluoromethyl)pyridin-2-yl]-1H-pyrazole-4-carbonyl}amino)pyridin-2-yl]cyclohex-3-ene-1-carboxylic acid ethyl ester (1.49 g) as a white solid.

MS (ESI) m/z: 514 (M+H)⁺.

(3) 1.0M Tetrahydrofuran-solution (4.6 ml) of methylmagnesium bromide was added at room temperature to a solution of tetrahydrofuran (12 ml) of 4-[3-methyl-5-({5-methyl-1-[5-(trifluoromethyl)pyridin-2-yl]-1H-pyrazole-4-carbonyl}amino)pyridin-2-yl]cyclohex-3-ene-1-carboxylic acid ethyl ester (580 mg), and stirred at 70° C. for 30 minutes. After completion of the reaction, the reaction solution was cooled to room temperature, a saturated aqueous solution of ammonium chloride was added and extracted with 10% methanol/chloroform. The organic layer was dried over anhydrous sodium sulfate and the solvent was evaporated. The resulting residue was purified with silica gel column chromatography (chloroform/methanol) to give the titled compound (281 mg) as a white solid.

MS (ESI) m/z: 500 (M+H)⁺.

N-{6-[4-(1-Hydroxyl-methylethyl)cyclohex-1-en-1-yl]pyridin-3-yl}-5-methyl-1-[5-(trifluoromethyl)pyridin-2-yl]-1H-pyrazole-4-carboxamide

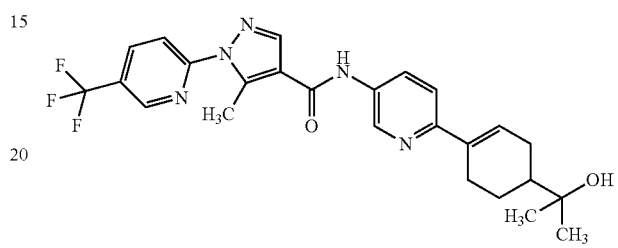

2,5-Dibromopyridine was used in place of 2,5-dibromo-3-methylpyridine in Reference Example 152(1), and reacted and treated in a similar manner as Reference Example 152(1)(2) and Example K3 to give the titled compound as a white solid.

MS (ESI) m/z: 486 (M+H)⁺.

Example K33

N-[6-(r-1-Cyano-4-ethyl-c-4-hydroxycyclohexan-1-yl)pyridin-3-yl]-1-(4-fluorophenyl)-5-methyl-1H-pyrazole-4-carboxamide

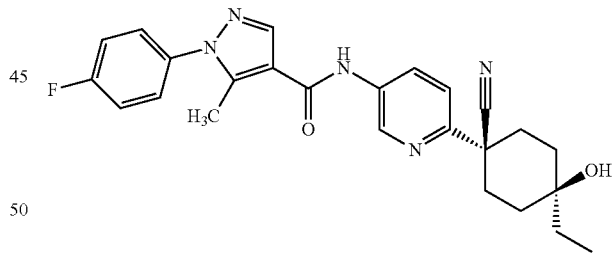

5% Palladium-carbon (containing ca. 50% water; 18 mg) was added at room temperature to a solution of N-[6-(r-1-cyano-c-4-hydroxy-4-vinylcyclohexan-1-yl)pyridin-3-yl]-1-(4-fluorophenyl)-5-methyl-1H-pyrazole-4-carboxamide (88.6 mg) described in Example D258 in methanol (10 ml), and stirred at the same temperature under stream of hydrogen gas for 0.5 hours. After completion of the reaction, the reaction mixture was filtered through Celite, and concentrated. The resulting residue was purified with silica gel column chromatography (chloroform/methanol) to give the titled compound (68.7 mg) as a white solid.

MS (ESI) m/z: 448 (M+H)⁺.

Example K34

N-[6-(r-1-Cyano-4-ethyl-t-4-hydroxycyclohexan-1-yl)pyridin-3-yl]-5-methyl-1-(4-methylphenyl)-1H-pyrazole-4-carboxamide

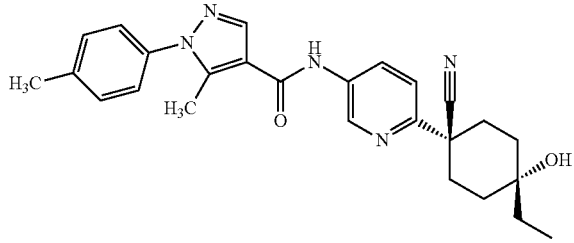 [SMILES: CC[C@]1(O)CC[C@@](C#N)(c2ccc(NC(=O)c3cnn(-c4ccc(C)cc4)c3C)cn2)CC1]

N-[6-(r-1-Cyano-t-4-hydroxy-4-vinylcyclohexan-1-yl)pyridin-3-yl]-5-methyl-1-(4-methylphenyl)-1H-pyrazole-4-carboxamide (129 mg) described in Example D256 was used in place of N-[6-(r-1-cyano-c-4-hydroxy-4-vinylcyclohexan-1-yl)pyridin-3-yl]-1-(4-fluorophenyl)-5-methyl-1H-pyrazole-4-carboxamide in Example K33, and reacted and treated in a similar manner to give the titled compound (121 mg) as a white solid.

MS (ESI) m/z: 444 (M+H)+.

Example K35

N-[6-(r-1-Cyano-4-ethyl-t-4-hydroxycyclohexan-1-yl)pyridin-3-yl]-1-(4-fluorophenyl)-5-methyl-1H-pyrazole-4-carboxamide

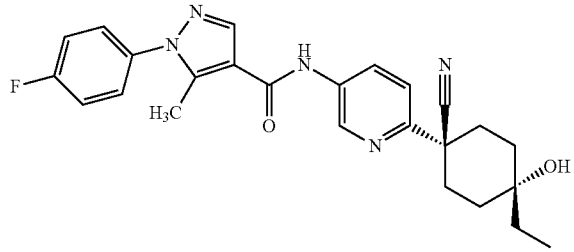 [SMILES: CC[C@]1(O)CC[C@@](C#N)(c2ccc(NC(=O)c3cnn(-c4ccc(F)cc4)c3C)cn2)CC1]

N-[6-(r-1-Cyano-t-4-hydroxy-4-vinylcyclohexan-1-yl)pyridin-3-yl]-1-(4-fluorophenyl)-5-methyl-1H-pyrazole-4-carboxamide (115 mg) of Example D257 was used in place of N-[6-(r-1-cyano-c-4-hydroxy-4-vinylcyclohexan-1-yl)pyridin-3-yl]-1-(4-fluorophenyl)-5-methyl-1H-pyrazole-4-carboxamide in Example K33, and reacted and treated in a similar manner to give the titled compound (110 mg) as a white solid.

MS (ESI) m/z: 448 (M+H)+.

Example K36

N-[6-(r-1-Cyano-4-ethyl-c-4-hydroxycyclohexan-1-yl)pyridin-3-yl]-5-methyl-1-(4-methylphenyl)-1H-pyrazole-4-carboxamide

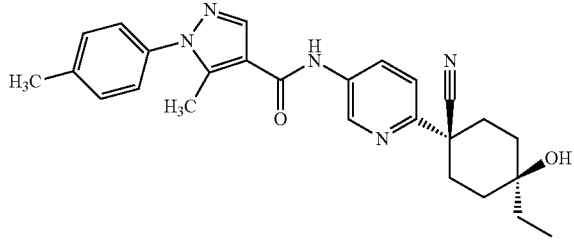 [SMILES: CC[C@]1(O)CC[C@](C#N)(c2ccc(NC(=O)c3cnn(-c4ccc(C)cc4)c3C)cn2)CC1]

N-[6-(r-1-Cyano-c-4-hydroxy-4-vinylcyclohexan-1-yl)pyridin-3-yl]-5-methyl-1-(4-methylphenyl)-1H-pyrazole-4-carboxamide (108 mg) described in Example 259 was used in place of N-[6-(r-1-cyano-c-4-hydroxy-4-vinylcyclohexan-1-yl)pyridin-3-yl]-1-(4-fluorophenyl)-5-methyl-1H-pyrazole-4-carboxamide in Example K33, and reacted and treated in a similar manner to give the titled compound (108 mg) as a white solid.

MS (ESI) m/z: 444 (M+H)+.

Example K37

5-Methyl-N-{5-[4-(morpholin-4-yl)cyclohex-1-en-1-yl]pyrazin-2-yl}-1-[5-(trifluoromethyl)-pyridin-2-yl]-1H-pyrazole-4-carboxamide

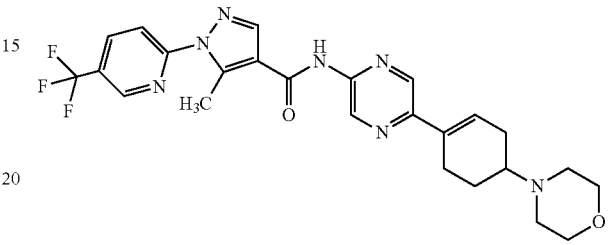

(1) Thionyl chloride (3.28 g) and N,N-dimethylformamide (catalytic amounts) were added at room temperature to a solution of 5-methyl-1-[5-(trifluoromethyl)pyridin-2-yl]-1H-pyrazole-4-carboxylic acid (2.49 g) in toluene (18 ml) and stirred at 80° C. for an hour. The solvent and an excess amount of thionyl chloride were evaporated, pyridine (10 ml) were added to the resulting residue, a solution of 2-amino-5-bromopyrazine (1.6 g) in pyridine (10 ml) was added thereto and stirred at 50° C. for an hour. After completion of the reaction, triethylamine (1.5 ml) and water were added and the precipitated solid was collected by filtration to give N-(5-bromopyrazin-2-yl)-5-methyl-1-[5-(trifluoromethyl)pyridin-2-yl]-1H-pyrazole-4-carboxamide (3.64 g) as a brown solid.

MS (ESI) m/z: 427, 429 (M+H)+.

(2) A mixture of N-(5-bromopyrazin-2-yl)-5-methyl-1-[5-(trifluoromethyl)pyridin-2-yl]-1H-pyrazole-4-carboxamide (300 mg), 4-[4-(4,4,5,5-tetramethyl[1,3,2] dioxaborolan-2-yl)cyclohex-3-en-1-yl]morpholin (185 mg), tetrakis(trophenylphosphine)palladium (0) (81 mg) and sodium carbonate (186 mg) in 1,4-dioxane (7.0 ml) was stirred at 90° C. for four hours. Then, N,N-dimethylformamide (7.0 ml) and bis (diphenylphosphine)ferrocenepalladium (II) dichloride dichloromethane adduct (57 mg) were added at room temperature and stirred at 90° C. for five hours. After completion of the reaction, the reaction solution was cooled to room temperature, water was added, and the precipitated solid was collected by filtration. The resulting residue was purified with silica gel column chromatography (chloroform/methanol) twice to give the titled compound (143 mg) as a white solid.

MS (ESI) m/z: 514 (M+H)+.

Example K38

N-{5-Cyano-6-[4-(morpholin-4-yl)cyclohex-1-en-1-yl]pyridin-3-yl}-5-methyl-1-[5-(trifluoromethyl)pyridin-2-yl]-1H-pyrazole-4-carboxamide

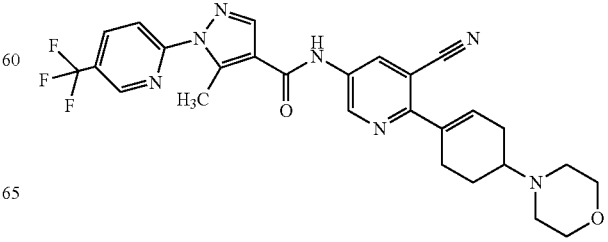

(1) 5-Methyl-1-(5-(trifluoro methyl)pyridin-2-yl)-1H-pyrazole-4-carboxylic acid chloride (200 mg) and 5-amino-2-chloro-3-cyanopyridine (228 mg) were dissolved in pyridine (10 ml) and stirred at room temperature. After completion of the reaction, water was added to the reaction solution, the precipitated solid was collected by filtration and dried under heating and blow to give N-(6-chloro-5-cyanopyridin-3-yl)-5-methyl-1-[5-(trifluoromethyl)pyridin-2-yl]-1H-pyrazole-4-carboxamide (550 mg) as a light brown solid.

MS (ESI) m/z: 407 (M+H)+.

(2) N-(6-Chloro-5-cyanopyridin-3-yl)-5-methyl-1-[5-(trifluoromethyl)pyridin-2-yl]-1H-pyrazole-4-carboxamide (200 mg), 4-[4-(4,4,5,5-tetramethyl-[1,3,2] dioxaborolan-2-yl)cyclohex-3-en-1-yl]morpholine (159 mg) described in Reference Example 166 and tetrakis(triphenylphosphine)palladium (57 mg) were dissolved in a mixture of tetrahydrofuran (1 ml) and 1M aqueous solution of sodium carbonate (0.54 ml), and stirred at 90° C. After completion of the reaction, the reaction solution was left stand, filtered through Celite, washed with chloroform and the filtrate was concentrated. Water was added to the resulting residue and the precipitate was filtered. The obtained solid was refluxed in ethanol, the resulting solution was left stand, the precipitated solid was collected by filtration and dried in vacuo to give the titled compound (143 mg) as a pale yellow solid.

MS (ESI) m/z: 538 (M+H)+.

Example K39

N-{6-[1-Acetyl-1,2,3,6-tetrahydropyridin-4-yl]-5-methylpyridin-3-yl}-5-methyl-1-[5-(trifluoromethyl)pyridin-2-yl]-1H-pyrazole-4-carboxamide

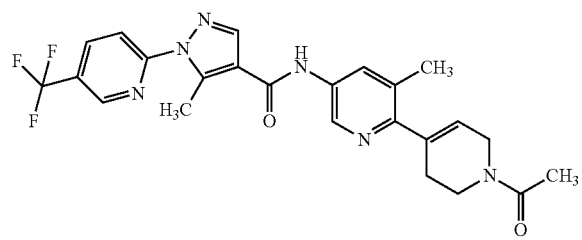 [SMILES: CC(=O)N1CC=C(c2ncc(NC(=O)c3cnn(-c4ccc(C(F)(F)F)cn4)c3C)cc2C)CC1]

Acetyl chloride (50 µl) was added to a solution of 5-methyl-N-[5-methyl-6-(1,2,3,6-tetrahydropyridin-4-yl)pyridin-3-yl]-1-[5-(trifluoromethyl)pyridin-2-yl]-1H-pyrazole-4-carboxamide (300 mg) described in Reference Example 170 in pyridine (3.4 ml), stirred at 40° C. for six hours. Acetyl chloride (50 µl) was added and stirred for two hours, and then, Acetyl chloride (50 µl) was added and stirred for six hours. Water was added to the reaction solution and the precipitated solid was washed with ethanol and water to give the titled compound (283 mg) as a pale yellow solid.

MS (ESI) m/z: 485 (M+H)+.

Example K40

N-{6-[1-Benzoyl-1,2,3,6-tetrahydropyridin-4-yl]-5-methylpyridin-3-yl}-5-methyl-1-[5-(trifluoromethyl)pyridin-2-yl]-1H-pyrazole-4-carboxamide

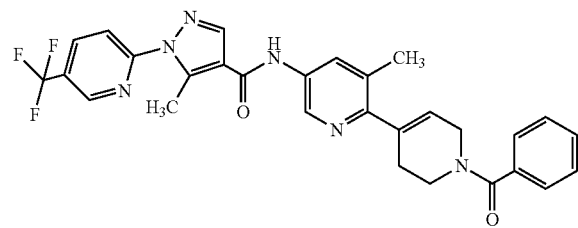 [SMILES: Cc1cc(NC(=O)c2cnn(-c3ccc(C(F)(F)F)cn3)c2C)cnc1C1=CCN(C(=O)c2ccccc2)CC1]

Benzoyl chloride (75 µl) was added to a solution of 5-methyl-N-[5-methyl-6-(1,2,3,6-tetrahydropyridin-4-yl)pyridin-3-yl]-1-[5-(trifluoromethyl)pyridin-2-yl]-1H-pyrazole-4-carboxamide (221 mg) in pyridine (2.5 ml), and stirred at 40° C. for six hours. Water was added to the reaction solution, the precipitated solid was washed with ethanol and water to give the titled compound (218 mg) as a white solid.

MS (ESI) m/z: 547 (M+H)+.

Example K41

N-{6-[1-(2,2-Dimethylpropanoyl)-1,2,3,6-tetrahydropyridin-4-yl]-5-methylpyridin-3-yl}-5-methyl-1-[5-(trifluoromethyl)pyridin-2-yl]-1H-pyrazole-4-carboxamide

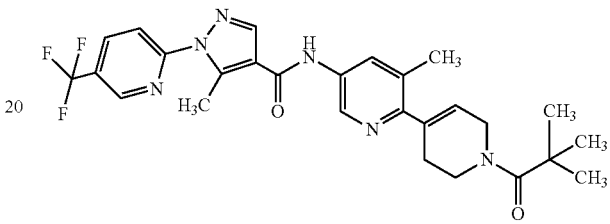

Pivalic anhydride (179 µl) was added to a solution of 5-methyl-N-[5-methyl-6-(1,2,3,6-tetrahydropyridin-4-yl)pyridin-3-yl]-1-[5-(trifluoromethyl)pyridin-2-yl]-1H-pyrazole-4-carboxamide (330 mg) described in Reference Example 170 and 4-dimethylaminopyridine (16 mg) in pyridine (2.3 ml), and stirred at 80° C. for 6.5 hours. Water was added to the reaction solution, the precipitated solid was washed with ethanol and water to give the titled compound (290 mg) as a pale yellow solid.

MS (ESI) m/z: 527 (M+H)+.

Example K42

N-[6-(1-Acetylpiperidin-4-yl)-5-methylpyridin-3-yl]-5-methyl-1-[5-(trifluoromethyl)pyridin-2-yl]-1H-pyrazole-4-carboxamide

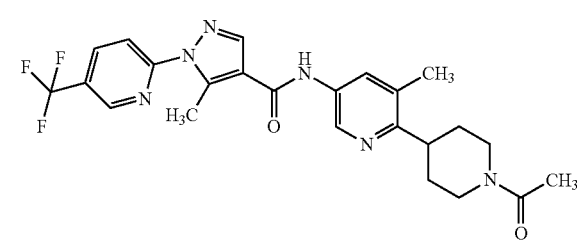 [SMILES: CC(=O)N1CCC(c2ncc(NC(=O)c3cnn(-c4ccc(C(F)(F)F)cn4)c3C)cc2C)CC1]

N-{6-[1-Acetyl-1,2,3,6-tetrahydropyridin-4-yl]-5-methylpyridin-3-yl}-5-methyl-1-[5-(trifluoromethyl)pyridin-2-yl]-1H-pyrazole-4-carboxamide (180 mg) described in Example K39 was dissolved in 1,4-dioxane (2 ml) and ethanol (2 ml), 10% palladium-carbon (containing ca. 50% water; 90 mg) was added, and stirred at room temperature under hydrogen atmosphere for 8.5 hours, then ethanol (1 ml) was added and stirred at 40° C. for two days. The reaction solution was filtered through Celite, washed with chloroform and ethanol and the solvent was evaporated in vacuo. The precipitated solid was washed with ethyl acetate and ethanol to give the titled compound (98 mg) as a white solid.

MS (ESI) m/z: 487 (M+H)+.

Example K43

N-[6-(1-Benzoylpiperidin-4-yl)-5-methylpyridin-3-yl]-5-methyl-1-[5-(trifluoromethyl)pyridin-2-yl]-1H-pyrazole-4-carboxamide

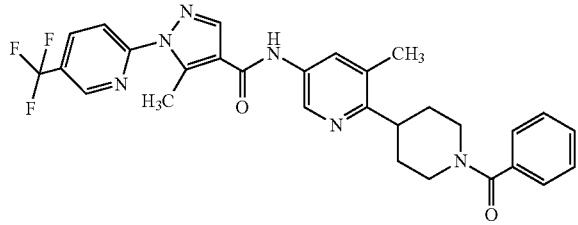 [SMILES: Cc1cc(NC(=O)c2cnn(-c3ccc(C(F)(F)F)cn3)c2C)cnc1C1CCN(C(=O)c2ccccc2)CC1]

N-{6-[1-Benzoyl-1,2,3,6-tetrahydropyridin-4-yl]-5-methylpyridin-3-yl}-5-methyl-1-[5-(trifluoromethyl)pyridin-2-yl]-1H-pyrazole-4-carboxamide (110 mg) described in Example K40 was dissolved in 1,4-dioxane (5 ml) and ethanol (5 ml), 10% palladium-carbon (containing ca. 50% water; 90 mg) was added, and stirred at 40° C. under hydrogen atmosphere for seven hours. The reaction solution was filtered through Celite, washed with chloroform and ethanol and the solvent was evaporated in vacuo. The resulting residue was purified with silica gel chromatography (chloroform/methanol) to give the titled compound (88 mg) as a white solid.
MS (ESI) m/z: 549 (M+H)$^+$.

Example K44

N-{6-[4-Cyano-1-(3,3-dimethyl-2-oxobutyl)piperidin-4-yl]pyridin-3-yl}-5-methyl-1-[5-(trifluoromethyl)pyridin-2-yl]-1H-pyrazole-4-carboxamide

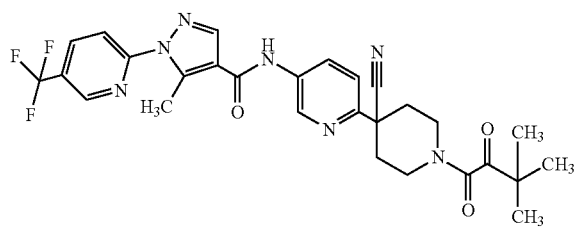 [SMILES: Cc1c(C(=O)Nc2ccc(C3(C#N)CCN(C(=O)C(=O)C(C)(C)C)CC3)nc2)cnn1-c1ccc(C(F)(F)F)cn1]

1-Bromo-3,3-dimethylbutan-2-one (88 μl) was added to a suspension of N-[6-(4-cyanopiperidin-4-yl)pyridin-3-yl]-5-methyl-1-[5-(trifluoromethyl)pyridin-2-yl]-1H-pyrazole-4-carboxamide (227 mg) and potassium carbonate (138 mg) in N,N-dimethylformamide (1.7 ml), and stirred at room temperature for 8.5 hours. Water was added to the reaction solution, the precipitated solid was filtered, and washed with water and ethanol to give the titled compound (271 mg) as a white solid.
MS (ESI) m/z: 554 (M+H)$^+$.

Example K45

5-Methyl-N-{5-methyl-6-[1-(propane-2-sulfonyl)-1,2,3,6-tetrahydropyridin-4-yl]pyridin-3-yl}-1-[5-(trifluoromethyl)pyridin-2-yl]-1H-pyrazole-4-carboxamide

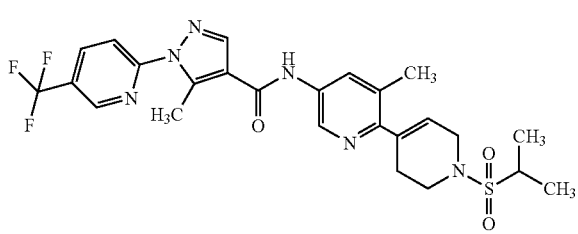 [SMILES: Cc1cc(NC(=O)c2cnn(-c3ccc(C(F)(F)F)cn3)c2C)cnc1C1=CCN(S(=O)(=O)C(C)C)CC1]

Isopropylsulfonyl chloride (72 μl) was added to a suspension of 5-methyl-N-[5-methyl-6-(1,2,3,6-tetrahydropyridin-4-yl)pyridin-3-yl]-1-[5-(trifluoromethyl)pyridin-2-yl]-1H-pyrazole-4-carboxamide (221 mg) described in Reference Example 170 and potassium carbonate (138 mg) in N,N-dimethylformamide (1.7 ml), and stirred at room temperature for 5 hours. Water was added and the precipitated solid was purified with silica gel chromatography (chloroform/methanol) to give the titled compound (62 mg) as a white solid.
MS (ESI) m/z: 540 (M+H)$^+$.

Example K46

N-{6-[1-(3,3-Dimethyl-2-oxobutyl)-1,2,3,6-tetrahydropyridin-4-yl]-5-methylpyridin-3-yl}-5-methyl-1-[5-(trifluoromethyl)pyridin-2-yl]-1H-pyrazole-4-carboxamide

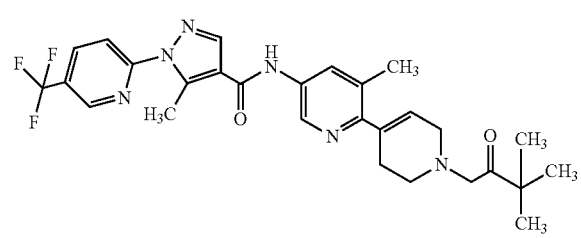 [SMILES: Cc1cc(NC(=O)c2cnn(-c3ccc(C(F)(F)F)cn3)c2C)cnc1C1=CCN(CC(=O)C(C)(C)C)CC1]

5-Methyl-N-[5-methyl-6-(1,2,3,6-tetrahydropyridin-4-yl)pyridin-3-yl]-1-[5-(trifluoromethyl)pyridin-2-yl]-1H-pyrazole-4-carboxamide described in Reference Example 170 was used in place of N-[6-(4-cyanopiperidin-4-yl)pyridin-3-yl]-5-methyl-1-[5-(trifluoromethyl)pyridin-2-yl]-1H-pyrazole-4-carboxamide in Example K44, and reacted and treated in a similar manner to give the titled compound as a pale yellow solid.
MS (ESI) m/z: 541 (M+H)$^+$.

Example K47

5-Methyl-N-[5-methyl-6-(1,2,3,6-tetrahydro-1-trifluoroacetylpyridin-4-yl)pyridin-3-yl]-1-[5-(trifluoromethyl)pyridin-2-yl]-1H-pyrazole-4-carboxamide

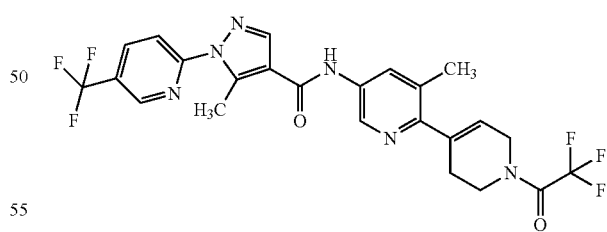

Trifluoroacetic anhydride (136 μl) was added to a mixture of 5-methyl-N-[5-methyl-6-(1,2,3,6-tetrahydropyridin-4-yl)pyridin-3-yl]-1-[5-(trifluoromethyl)pyridin-2-yl]-1H-pyrazole-4-carboxamide (330 mg), 4-dimethylaminopyridine (16 mg) in pyridine (2.3 ml), and stirred at 80° C. for an hour. Triethylamine (285 μl) was added to the reaction solution, water and ethanol were added and the precipitated solid was purified with silica gel chromatography (chloroform/methanol) to give the titled compound (209 mg) as a white solid.
MS (ESI) m/z: 539 (M+H)$^+$.

Example K48

N-{6-[4-Cyano-1-(1,1-dimethyl-2-hydroxyethyl)piperidin-4-yl]pyridin-3-yl}-5-methyl-1-[5-(trifluoromethyl)pyridin-2-yl]-1H-pyrazole-4-carboxamide

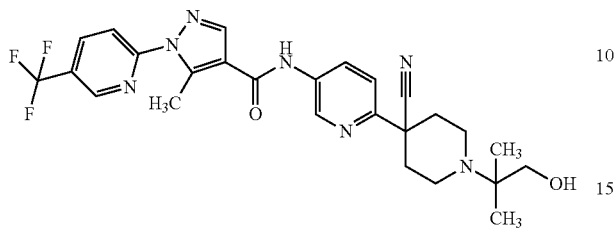

2-Bromo-2-methylpropanoic acid ethyl ester (193 μl) was added to a suspension of N-[6-(4-cyanopiperidin-4-yl)pyridin-3-yl]-5-methyl-1-[5-(trifluoromethyl)pyridin-2-yl]-1H-pyrazole-4-carboxamide (455 mg) described in Reference Example 169 and potassium carbonate (276 mg) in N,N-dimethylformamide (3.3 ml) and stirred at 50° C. for 12 hours. Then, 2-bromo-2-methylpropanoic acid ethyl ester (100 μl) and potassium carbonate (276 mg) were added and stirred at 50° C. for 5 hours and at 80° C. for 3 hours. Further, 2-bromo-2-methylpropanoic acid ethyl ester (100 μl) was added and stirred at 80° C. for 3 hours. Water was added to the reaction solution, the precipitated solid was purified with silica gel chromatography (chloroform/methanol) to give 2-{4-cyano-4-[5-({5-methyl-1-[5-(trifluoromethyl)pyridin-2-yl]-1H-pyrazole-4-carbonyl}amino)pyridin-2-yl]piperidin-1-yl}-2-methylpropanoic acid ethyl ester (320 mg) as a white solid. MS (ESI) m/z: 570 (M+H)$^+$. (2) Lithium borohydride (25 mg) was added to a solution of 2-{4-cyano-4-[5-({5-methyl-1-[5-(trifluoromethyl)pyridin-2-yl]-1H-pyrazole-4-carbonyl}amino)pyridin-2-yl]piperidin-1-yl}-2-methylpropanoic acid ethyl ester (320 mg) in tetrahydrofuran (3.7 ml) and stirred at room temperature for 1.5 hours. Then, lithium borohydride (25 mg) was added and stirred at 80° C. for 2 hours. To the reaction solution, were added methanol (1.5 ml) and sodium borohydride (85 mg), and stirred at room temperature for an hour. A saturated aqueous solution of ammonium chloride was added to the reaction solution, extracted with dichloromethane, and the organic layer was dried over anhydrous sodium sulfate and concentrated in vacuo. The resulting residue was purified with silica gel chromatography (chloroform/methanol) to give the titled compound (35 mg) as a white solid.
MS (ESI) m/z: 528 (M+H)$^+$.

Example K49

N-{6-[1-(Dimethylcarbamoyl)-1,2,3,6-tetrahydropyridin-4-yl]-5-methylpyridin-3-yl}-5-methyl-1-[5-(trifluoromethyl)pyridin-2-yl]-1H-pyrazole-4-carboxamide

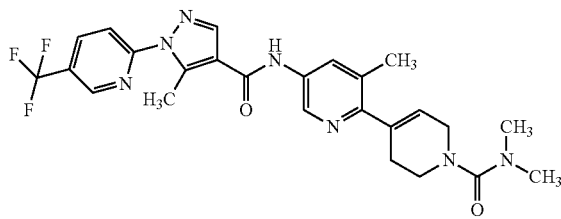 [SMILES: Cc1cc(NC(=O)c2cnn(-c3ccc(C(F)(F)F)cn3)c2C)cnc1C1=CCN(C(=O)N(C)C)CC1]

Triethylamine (33 μl) and dimethylcarbamoyl chloride (22 μl) were added to a mixture of 5-methyl-N-[5-methyl-6-(1,2,3,6-tetrahydropyridin-4-yl)pyridin-3-yl]-1-[5-(trifluoromethyl)pyridin-2-yl]-1H-pyrazole-4-carboxamide (100 mg) and dichloromethane (4.6 ml) and stirred at room temperature for two hours. Triethylamine (95 μl), water and ethanol were added to the reaction solution and the solvent was evaporated in vacuo. The precipitated solid was washed with water and ethanol to give the titled compound (66 mg) as a white solid.
MS (ESI) m/z: 514 (M+H)$^+$.

Example K50

5-Methyl-N-{5-methyl-6-[1-(4-morpholinecarbamoyl)-1,2,3,6-tetrahydropyridin-4-yl]pyridin-3-yl}-1-[5-(trifluoromethyl)pyridin-2-yl]-1H-pyrazole-4-carboxamide

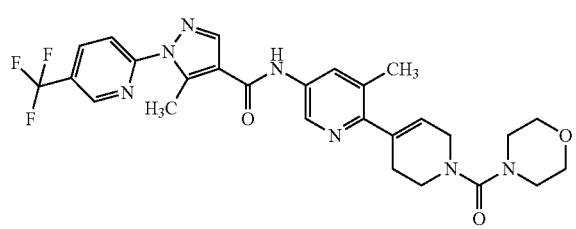 [SMILES: Cc1cc(NC(=O)c2cnn(-c3ccc(C(F)(F)F)cn3)c2C)cnc1C1=CCN(C(=O)N2CCOCC2)CC1]

4-Morpholinecarbamoyl chloride was used in place of dimethylcarbamoyl chloride in Example K49, and reacted and treated in a similar manner to give the titled compound as a white solid.
MS (ESI) m/z: 556 (M+H)$^+$.

Example K51

N-{6-[4-Cyano-1-(propane-2-sulfonyl)piperidin-4-yl]pyridin-3-yl}-5-methyl-1-[5-(trifluoromethyl)pyridin-2-yl]-1H-pyrazole-4-carboxamide

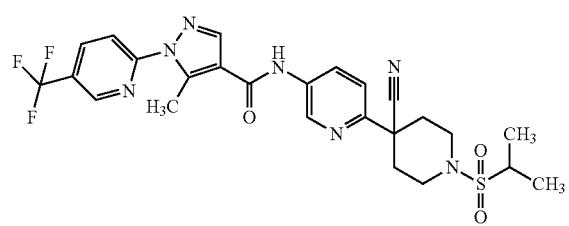 [SMILES: Cc1c(C(=O)Nc2ccc(C3(C#N)CCN(S(=O)(=O)C(C)C)CC3)nc2)cnn1-c1ccc(C(F)(F)F)cn1]

Isopropylsulfonyl chloride (72 μl) was added to a suspension of N-[6-(4-cyanopiperidin-4-yl)pyridin-3-yl]-5-methyl-1-[5-(trifluoromethyl)pyridin-2-yl]-1H-pyrazole-4-carboxamide (227 mg) described in Reference Example 169 and potassium carbonate (138 mg) in N,N-dimethylformamide (1.7 ml) and stirred at room temperature for six hours. Then, potassium carbonate (276 mg) and isopropylsulfonyl chloride (144 μl) were added and stirred at room temperature for 0.5 hours. Water was added to the reaction solution and the precipitated solid was washed with water, ethanol and ethyl acetate to give the titled compound (151 mg) as a white solid.
MS (ESI) m/z: 562 (M+H)$^+$.

Example K52

5-Methyl-N-{5-methyl-1-(pyrrolidin-1-ylcarbonyl)-6-[1,2,3,6-tetrahydropyridin-4-yl]pyridin-3-yl}-1-[5-(trifluoromethyl)pyridin-2-yl]-1H-pyrazole-4-carboxamide

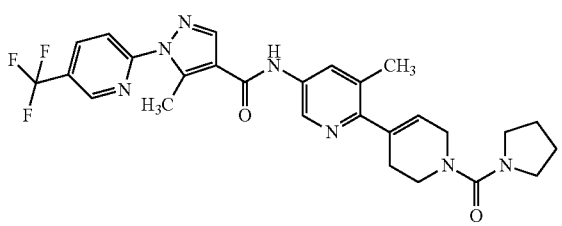 [SMILES: Cc1cc(NC(=O)c2cnn(-c3ccc(C(F)(F)F)cn3)c2C)cnc1C1=CCN(C(=O)N2CCCC2)CC1]

Triethylamine (38 μl) and 1-pyrrolidinecarbonyl chloride (30 μl) were added to a mixture of 5-methyl-N-[5-methyl-6-(1,2,3,6-tetrahydropyridin-4-yl)pyridin-3-yl]-1-[5-(trifluoromethyl)pyridin-2-yl]-1H-pyrazole-4-carboxamide (100 mg) described in Reference Example 170 and dichloromethane (4.6 ml), and stirred at room temperature for six hours. Then, triethylamine (380 μl) and 1-pyrrolidinecarbonyl chloride (300 μl) were added and stirred at room temperature all night and all day. Triethylamine (95 μl) and water was added to the reaction solution, dichloromethane was evaporated in vacuo, and the precipitated solid was washed with ethanol to give the titled compound (99 mg) as a pale yellow solid.

MS (ESI) m/z: 540 (M+H)$^+$.

Example K53

N-{6-[4-Cyano-1-(trifluoroacetyl)piperidin-4-yl]pyridin-3-yl}-5-methyl-1-[5-(trifluoromethyl)-pyridin-2-yl]-1H-pyrazole-4-carboxamide

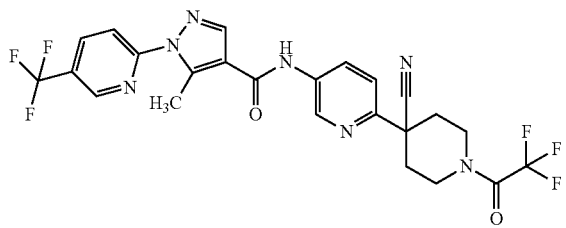 [SMILES: Cc1c(C(=O)Nc2ccc(C3(C#N)CCN(C(=O)C(F)(F)F)CC3)nc2)cnn1-c1ccc(C(F)(F)F)cn1]

N-[6-(4-Cyanopiperidin-4-yl)pyridin-3-yl]-5-methyl-1-[5-(trifluoromethyl)pyridin-2-yl]-1H-pyrazole-4-carboxamide described in Reference Example 169 was used in place of 5-methyl-N-[5-methyl-6-(1,2,3,6-tetrahydropyridine-4-)pyridin-3-yl]-1-[5-(trifluoromethyl)-pyridin-2-yl]-1H-pyrazole-4-carboxamide in Example K47, and reacted and treated in a similar manner to give the titled compound as a pale yellow solid.

MS (ESI) m/z: 552 (M+H)$^+$.

Example K54

N-{6-[1-(2,2-dimethylpropanoyl)-5-methylpiperidin-4-yl]pyridin-3-yl}-5-methyl-1-[5-(trifluoromethyl)pyridin-2-yl]-1H-pyrazole-4-carboxamide

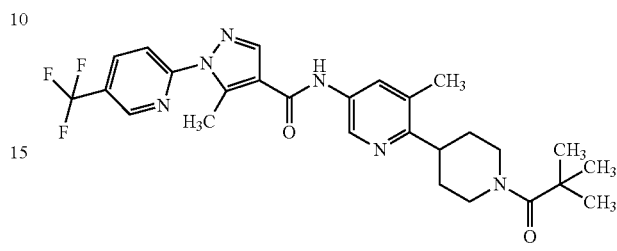

5-Methyl-N-[5-methyl-6-(piperidin-4-yl)pyridin-3-yl]-1-[5-(trifluoromethyl)pyridin-2-yl]-1H-pyrazole-4-carboxamide described in Reference Example 171 was used in place of 5-methyl-N-[5-methyl-6-(1,2,3,6-tetrahydropyridin-4-yl)pyridin-3-yl]-1-[5-(trifluoromethyl)-pyridin-2-yl]-1H-pyrazole-4-carboxamide in Example K41, and reacted and treated in a similar manner to give the titled compound as a white solid.

MS (ESI) m/z: 529 (M+H)$^+$.

Example K55

5-Methyl-N-{5-methyl-6-[1-(propane-2-sulfonyl)piperidin-4-yl]pyridin-3-yl}-1-[5-(trifluoromethyl)pyridin-2-yl]-1H-pyrazole-4-carboxamide

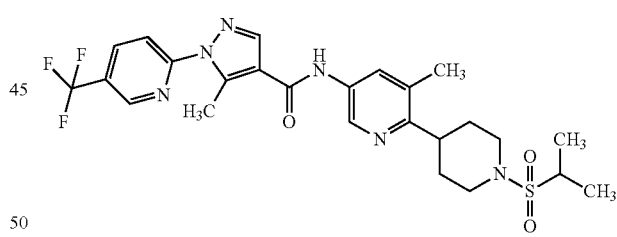

Isopropylsulfonyl chloride (72 μl) was added to a suspension of 5-methyl-N-[5-methyl-6-(piperidin-4-yl)pyridin-3-yl]-1-[5-(trifluoromethyl)pyridin-2-yl]-1H-pyrazole-4-carboxamide (222 mg) described in Reference Example 171 and potassium carbonate (138 mg) in N,N-dimethylformamide (1.7 ml) and stirred at room temperature for an hour. Then, isopropylsulfonyl chloride (36 μl) was added and stirred at room temperature for two hours. Triethylamine (350 μl) and water were added and the precipitated solid was washed with ethanol and water. The resulting solid was purified with silica gel chromatography (chloroform/methanol) to give the titled compound (103 mg) as a white solid.

MS (ESI) m/z: 551 (M+H)$^+$.

Example K56

N-{6-[4-Cyano-1-(ethane sulfonylpiperidin-4-yl]pyridin-3-yl}-5-methyl-1-[5-(trifluoromethyl)-pyridin-2-yl]-1H-pyrazole-4-carboxamide

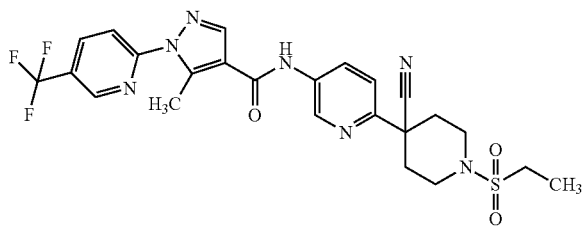 [SMILES: CCS(=O)(=O)N1CCC(C#N)(c2ccc(NC(=O)c3cnn(-c4ccc(C(F)(F)F)cn4)c3C)cn2)CC1]

Ethanesulfonyl chloride was used in place of isopropylsulfonyl chloride in Example K51, and reacted and treated in a similar manner to give the titled compound as a white solid.
MS (ESI) m/z: 548 (M+H)+.

Example K57

N-{6-[4-Cyano-1-(cyclopropanesulfonyl)piperidin-4-yl]pyridin-3-yl}-5-methyl-1-[5-(trifluoromethyl)pyridin-2-yl]-1H-pyrazole-4-carboxamide

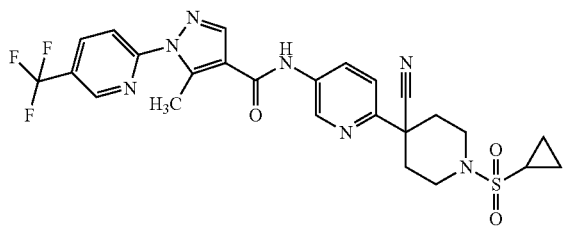 [SMILES: Cc1c(C(=O)Nc2ccc(C3(C#N)CCN(S(=O)(=O)C4CC4)CC3)nc2)cnn1-c1ccc(C(F)(F)F)cn1]

Cyclopropanesulfonyl chloride (66 μl) was added to a suspension of N-[6-(4-cyanopiperidine-4-yl)pyridin-3-yl]-5-methyl-1-[5-(trifluoromethyl)pyridin-2-yl]-1H-pyrazole-4-carboxamide (227 mg) described in Reference Example 169 and potassium carbonate (207 mg) in N,N-dimethylformamide (1.7 ml), and stirred at room temperature for 5.5 hours. Water was added to the reaction solution and the precipitated solid was purified with silica gel chromatography (chloroform/methanol) to give the titled compound (242 mg) as a white solid.
MS (ESI) m/z: 560 (M+H)+.

Example K58

N-{6-[4-Cyano-1-(methanesulfonyl)piperidin-4-yl]pyridin-3-yl}-5-methyl-1-[5-(trifluoromethyl)pyridin-2-yl]-1H-pyrazole-4-carboxamide

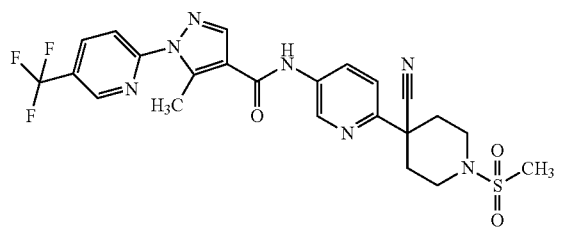 [SMILES: Cc1c(C(=O)Nc2ccc(C3(C#N)CCN(S(C)(=O)=O)CC3)nc2)cnn1-c1ccc(C(F)(F)F)cn1]

Methanesulfonyl chloride was used in place of isopropylsulfonyl chloride in Example K51, and reacted and treated in a similar manner to give the titled compound as a white solid.
MS (ESI) m/z: 534 (M+H)+.

Example K59

N-{6-[4-Cyano-1-(dimethylsulfamoyl)piperidin-4-yl]pyridin-3-yl}-5-methyl-1-[5-(trifluoromethyl)pyridin-2-yl]-1H-pyrazole-4-carboxamide

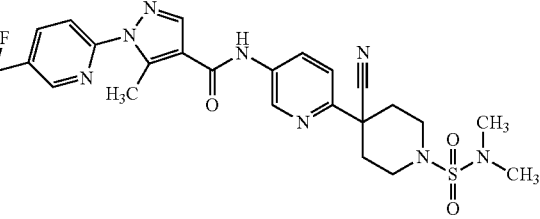

Triethylamine (48 μl) and dimethylsulfamoyl chloride (37 μl) were added to a mixture of N-[6-(4-cyanopiperidin-4-yl)pyridin-3-yl]-5-methyl-1-[5-(trifluoromethyl)pyridin-2-yl]-1H-pyrazole-4-carboxamide (150 mg) described in Reference Example 169 and dichloromethane (6.6 ml) and stirred at room temperature for two days. Water was added to the reaction solution, extracted with chloroform, the organic layer was washed with saturated brine, dried over anhydrous sodium sulfate and concentrated in vacuo. The resulting residue was purified with silica gel chromatography (chloroform/methanol) to give the titled compound (135 mg) as a white solid.
MS (ESI) m/z: 463 (M+H)+.

Example K60

5-Methyl-N-{5-methyl-6-[1-(trifluoroacetyl)piperidin-4-yl]pyridin-3-yl}-1-[5-(trifluoromethyl)pyridin-2-yl]-1H-pyrazole-4-carboxamide

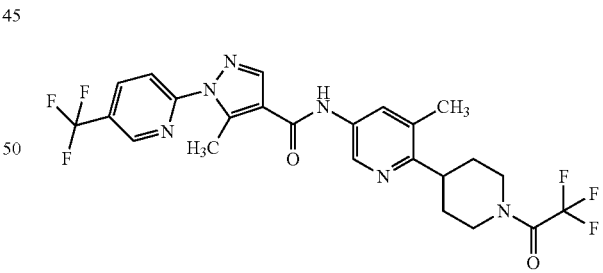

Trifluoroacetic anhydride (91 μl) was added to a mixture of 5-methyl-N-[5-methyl-6-(piperidin-4-yl)pyridin-3-yl]-1-[5-(trifluoromethyl)pyridin-2-yl]-1H-pyrazole-4-carboxamide (222 mg) described in Reference Example 171, 4-dimethylaminopyridine (12 mg) in pyridine (1.7 ml), and stirred at 80° C. for 6.5 hours. After the addition of triethylamine (350 μl) to the reaction solution, water and ethanol were added, the precipitated solid was purified with silica gel chromatography (chloroform/methanol) to give the titled compound (142 mg) as a white solid.
MS (ESI) m/z: 541 (M+H)+.

Example K61

5-Methyl-N-{5-methyl-6-[1-(2-methylpropanoyl)piperidin-4-yl]pyridin-3-yl}-1-[5-(trifluoromethyl)pyridin-2-yl]-1H-pyrazole-4-carboxamide

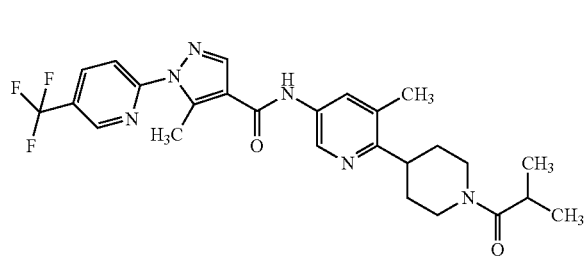 [SMILES: Cc1cc(NC(=O)c2cnn(-c3ccc(C(F)(F)F)cn3)c2C)cnc1C1CCN(C(=O)C(C)C)CC1]

2-Methylpropanoylchloride (79 μl) was added to a mixture of 5-methyl-N-[5-methyl-6-(piperidin-4-yl)pyridin-3-yl]-1-[5-(trifluoromethyl)pyridin-2-yl]-1H-pyrazole-4-carboxamide (222 mg) described in Reference Example 171 and pyridine (2.5 ml), and stirred at 40° C. for five hours. Triethylamine (350 μl), water and ethanol were added to the reaction solution, and the precipitated solid was washed with water to give the titled compound (220 mg) as a white solid.

MS (ESI) m/z: 515 (M+H)$^+$.

Example K62

5-Methyl-N-{5-methyl-6-[1-(2-methylpropanoyl)-1,2,3,6-tetrahydropyridin-4-yl]pyridin-3-yl}-1-[5-(trifluoromethyl)pyridin-2-yl]-1H-pyrazole-4-carboxamide

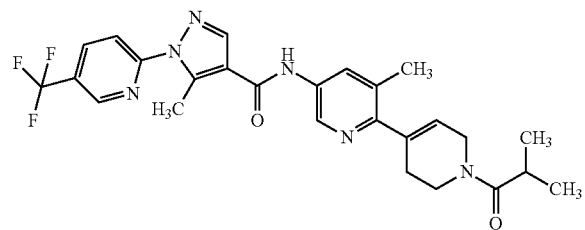 [SMILES: Cc1cc(NC(=O)c2cnn(-c3ccc(C(F)(F)F)cn3)c2C)cnc1C1=CCN(C(=O)C(C)C)CC1]

5-Methyl-N-[5-methyl-6-(1,2,3,6-tetrahydropyridin-4-yl)pyridin-3-yl]-1-[5-(trifluoromethyl)pyridin-2-yl]-1H-pyrazole-4-carboxamide described in Reference Example 170 in place of 5-methyl-N-[5-methyl-6-(piperidin-4-yl)pyridin-3-yl]-1-[5-(trifluoromethyl)-pyridin-2-yl]-1H-pyrazole-4-carboxamide in Example K61, and reacted and treated in a similar manner to give the titled compound as a pale yellow solid.

MS (ESI) m/z: 513 (M+H)$^+$.

Example K63

N-[6-(4-Cyano-1-trifluoromethanesulfonylpiperidin-4-yl)pyridin-3-yl]-5-methyl-1-[5-(trifluoromethyl)pyridin-2-yl]-1H-pyrazole-4-carboxamide

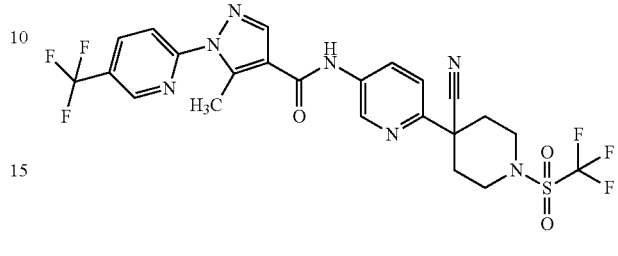

A solution of trifluoromethanesulfonic acid anhydride (110 μl) in dichloromethane (1 ml) was added dropwise under ice-cooling to a solution of N-[6-(4-cyanopiperidin-4-yl)pyridin-3-yl]-5-methyl-1-[5-(trifluoromethyl)pyridin-2-yl]-1H-pyrazole-4-carboxamide (227 mg) described in Reference Example 169 and triethylamine (140 μl) in dichloromethane (4.0 ml), and stirred at room temperature for seven hours. Water was added to the reaction solution, extracted with chloroform, the organic layer was washed with saturated brine, dried over anhydrous sodium sulfate and concentrated in vacuo. The resulting residue was purified with silica gel chromatography (chloroform/methanol) to give the titled compound (73 mg) as a white solid.

MS (ESI) m/z: 588 (M+H)$^+$.

Example K64

N-(5-{4-[N-(2,2-Dimethylpropion-1-yl)-N-methylamino]cyclohex-1-en-1-yl}pyrazin-2-yl)-5-methyl-1-[5-(trifluoromethyl)pyridin-2-yl]-1H-pyrazole-4-carboxamide

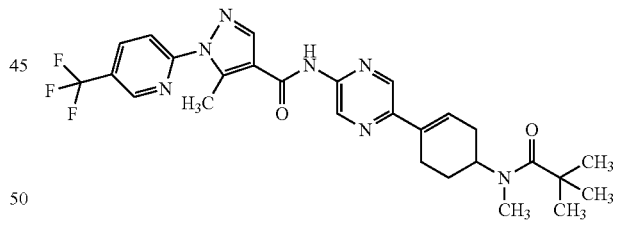

A mixture of N-(5-bromopyrazin-2-yl)-5-methyl-1-[5-(trifluoromethyl)pyridin-2-yl]-1H-pyrazole-4-carboxamide (213 mg) described in Example K37(1), 2,2,N-trimethyl-N-[4-(4,4,5,5-tetramethyl[1,3,2]dioxaborolan-2-yl)cyclohex-3-en-1-yl]propionamide (200 mg), bis(diphenylphosphino)ferrocene]palladium (II) dichloride dichloromethane adduct (21 mg) and sodium carbonate (132 mg) in 1,4-dioxane (3.6 ml) and water (1.2 ml) was stirred at 120° C. under radiation of microwave for 20 minutes. After completion of the reaction, the reaction solution was cooled to room temperature, water was added therein and the precipitated solid was filtered. The resulting solid was purified with silica gel column chromatography (chloroform/methanol) to give the titled compound (121 mg) as a pale yellow solid.

MS (ESI) m/z: 542 (M+H)$^+$.

Example K65

N-[6-(8-Fluoro-1,4-dioxaspiro[4.5]dec-8-yl)pyridin-3-yl]-5-methyl-1-[5-(trifluoromethyl)-pyridin-2-yl]-1H-pyrazole-4-carboxamide

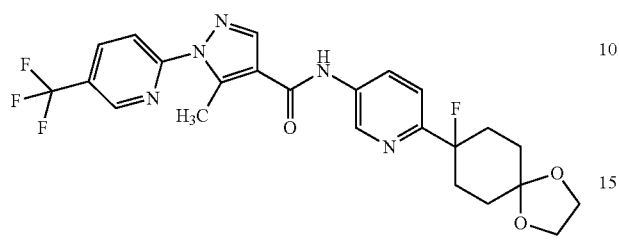

Diethylaminosulfur trifluoride (0.2 ml) was added at −78° C. to a solution of N-[6-(8-hydroxy-1,4-dioxaspiro[4.5]dec-8-yl)-5-methyl-1-[5-(trifluoromethyl)pyridin-2-yl]-1H-pyrazole-4-carboxamide (500 mg) described in Example D290 in tetrahydrofuran (20 ml), and the mixture was warmed up to 0° C. over two hours. Then, it was cooled to −78° C., diethylaminosulfur trifluoride (0.2 ml) was added and warmed up to 0° C. over 1.5 hours. After completion of the reaction, a saturated aqueous solution of sodium bicarbonate was added and extracted with ethyl acetate. The organic layer was dried over anhydrous sodium sulfate and concentrated. The resulting residue was purified with silica gel column chromatography (n-hexane/ethyl acetate) to give the titled compound (335 mg) as a white solid.

MS (ESI) m/z: 506 (M+H)+.

Example K66

N-{6-[1-(2,2-Dimethylpropanoyl)azepan-4-yl]-5-methylpyridin-3-yl}-5-methyl-1-[5-(trifluoromethyl)pyridin-2-yl]-1H-pyrazole-4-carboxamide

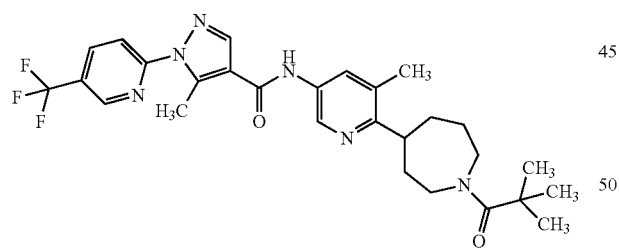

(1) Trifluoroacetic acid (4.0 ml) was added at room temperature to a solution of 4-[3-ethyl-5-({5-methyl-1-[5-(trifluoromethyl)pyridin-2-yl]-1H-pyrazole-4-carbonyl}amino)pyridin-2-yl]azepan-1-carboxylic acid tert-butyl ester (1.1 g) described in Example D291 in dichloromethane (20 ml), and stirred at the same temperature for 4 hours. After completion of the reaction, 4N aqueous solution of sodium hydroxide was added to adjust the solution to pH 11 and extracted with ethyl acetate. The organic layer was dried over anhydrous sodium sulfate, and concentrated to give N-[6-(azepan-4-yl)-5-methylpyridin-3-yl]-5-methyl-1-[5-(trifluoromethyl)pyridin-2-yl]-1H-pyrazole-4-carboxamide as a pale yellow oil.

MS (ESI) m/z: 459 (M+H)+.

(2) Pivaloyl anhydride (0.21 ml) and 4-dimethylaminopyridine (14 mg) were added at room temperature to a solution of N-[6-(azepan-4-yl)-5-methylpyridin-3-yl]-5-methyl-1-[5-(trifluoromethyl)pyridin-2-yl]-1H-pyrazole-4-carboxamide (250 mg) in pyridine (5.5 ml), and stirred at 60° C. for three hours. After completion of the reaction, the reaction solution was cooled to room temperature, water was added and extracted with ethyl acetate. The organic layer was washed with saturated brine, dried over anhydrous sodium sulfate and concentrated. The resulting residue was purified with silica gel column chromatography (chloroform/methanol) to give the titled compound (74 mg) as a white solid.

MS (ESI) m/z: 543 (M+H)+.

Example K67

N-[6-(1-Dimethylsulfamoylazepan-4-yl)-5-methylpyridin-3-yl]-5-methyl-1-[5-(trifluoromethyl)pyridin-2-yl]-1H-pyrazole-4-carboxamide

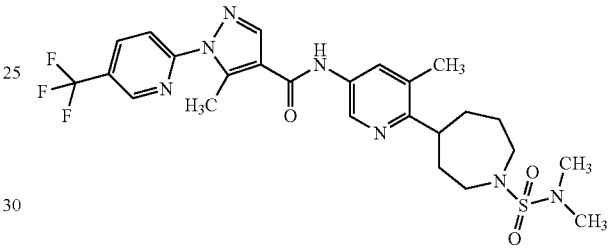

Triethylamine (0.16 ml) and dimethylsulfamoyl chloride (157 mg) were added at room temperature to a solution of N-[6-(azepan-4-yl)-5-methylpyridin-3-yl]-5-methyl-1-[5-(trifluoromethyl)pyridin-2-yl]-1H-pyrazole-4-carboxamide (250 mg) described in Example K66(1) in tetrahydrofuran (5.5 ml) and N,N-dimethylformamide (5.5 ml), and stirred at 60° C. for three hours. After completion of the reaction, the reaction solution was cooled to room temperature, saturated aqueous solution of sodium bicarbonate was added and extracted with ethyl acetate. The organic layer was dried over anhydrous sodium sulfate and concentrated. The resulting residue was purified with silica gel column chromatography (chloroform/methanol) to give the titled compound (133 mg) as a white solid.

MS (ESI) m/z: 566 (M+H)+.

Example K68

N-(6-{4-[N-(2,2-Dimethylpropion-1-yl)-N-methylamino]cyclohex-1-en-1-yl}-2-methylpyridin-3-yl)-5-methyl-1-[5-(trifluoromethyl)pyridin-2-yl]-1H-pyrazole-4-carboxamide

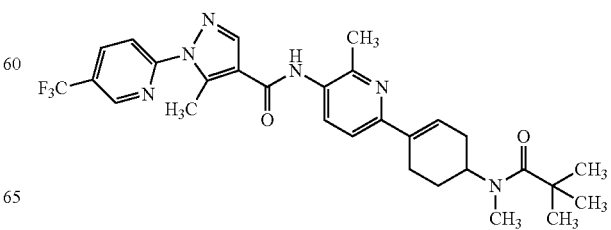

2,2,N-Trimethyl-N-{4-(4,4,5,5-tetramethyl-[1,3,2] dioxaborolan-2-yl)cyclohex-3-en-1-yl}propionamide (76.6 mg), tetrakis(triphenylphosphine)palladium (13.1 mg), tetrahydrofuran (2 ml), saturated aqueous solution of sodium carbonate (1 ml) and water (0.5 ml) were added to N-(6-bromo-2-methylpyridin-3-yl)-5-methyl-1-[5-(trifluoromethyl)pyridin-2-yl]-1H-pyrazole-4-carboxamide (100 mg), and stirred at 150° C. under radiation of microwave for 15 minutes. After completion of the reaction, extracted with ethyl acetate, the organic layer was dried over anhydrous magnesium sulfate and concentrated. Ethyl acetate was added to the resulting residue, an insoluble materials were filtered off and dried in vacuo to give the titled compound (80.4 mg)

MS (ESI) m/z: 555 (M+H)⁺.

Example K69

N-(6-{4-[N-(2,2-Dimethylpropion-1-yl)-N-methylamino]cyclohex-1-en-1-yl}-5-methoxypyridin-3-yl)-5-methyl-1-[5-(trifluoromethyl)pyridin-2-yl]-1H-pyrazole-4-carboxamide

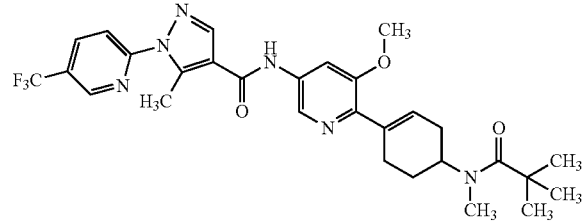 [SMILES: COc1cc(NC(=O)c2cnn(-c3ccc(C(F)(F)F)cn3)c2C)cnc1C1=CCC(N(C)C(=O)C(C)(C)C)CC1]

2,2,N-Trimethyl-N-{4-(4,4,5,5-tetramethyl-[1,3,2] dioxaborolan-2-yl)cyclohex-3-en-1-yl}propionamide (81.9 mg) described in Reference Example 167, 1,1-bis(diphenylphosphino)ferrocene-palladium (II) dichloride-dichloromethane complex (2.0 mg), cesium carbonate (237 mg), 1,4-dioxane (2 ml) and water (1 ml) were added to N-(2-chloro-3-methoxypyridin-5-yl)-5-methyl-1-[5-(trifluoromethyl)pyridin-2-yl]-1H-pyrazole-4-carboxamide (100 mg) described in Reference Example 183, and stirred at 120° C. for 15 minutes, and at 150° C. for 30 minutes under radiation of microwave. After completion of the reaction, water and ethyl acetate were added to the reaction solution, and insoluble materials was filtered off. The resulting residue was purified with silica gel column chromatography (n-hexane/ethyl acetate) to give the titled compound (18.9 mg) as a white solid.

MS (APCI) m/z: 571 (M+H)⁺.

Example K70

N-{5-Methoxy-6-[4-(morpholin-4-yl)cyclohex-1-en-1-yl]pyridin-3-yl}-5-methyl-1-[5-(trifluoromethyl)pyridin-2-yl]-1H-pyrazole-4-carboxamide

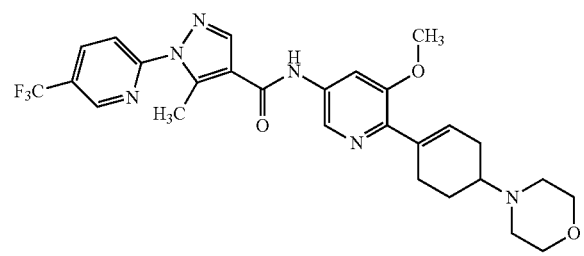 [SMILES: COc1cc(NC(=O)c2cnn(-c3ccc(C(F)(F)F)cn3)c2C)cnc1C1=CCC(N2CCOCC2)CC1]

4-[4-(4,4,5,5-Tteramethyl-[1,3,2]dioxaborolan-2-yl)cyclohex-3-en-1-yl]morpholine (74.8 mg) described in Reference Example 166, 1,1-bis(diphenylphosphino)ferrocene-palladium (II) dichloride-dichloromethane complex (9.9 mg), cesium carbonate (237 mg), 1,4-dioxane (2 ml) and water (1 ml) were added to N-(2-chloro-3-methoxypyridin-5-yl)-5-methyl-1-[5-(trifluoromethyl)pyridin-2-yl]-1H-pyrazole-4-carboxamide (100 mg) described in Reference Example 183, and stirred at 150° C. under radiation of microwave for 30 minutes.

After completion of the reaction, water was added, extracted with ethyl acetate and concentrated. The resulting residue was purified with silica gel column chromatography (chloroform/methanol) to give the titled compound (52.6 mg) as a white solid.

MS (APCI) m/z: 543 (M+H)⁺.

Example K71

5-Methyl-N-{5-trifluoromethyl-6-[4-(morpholin-4-yl)cyclohex-1-en-1-yl]pyridin-3-yl}-1-[5-(trifluoromethyl)pyridin-2-yl]-1H-pyrazole-4-carboxamide

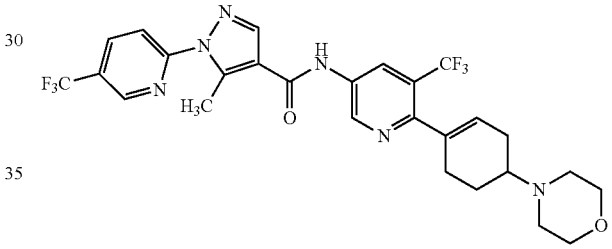

The titled compound (50.2 mg) was prepared as a white solid from N-(6-chloro-5-trifluoromethylpyridin-3-yl)-5-methyl-1-[5-(trifluoromethyl)pyridin-2-yl]-1H-pyrazole-4-carboxamide (100 mg) described in Reference Example 184 in a similar manner as Example K70.

MS (APCI) m/z: 581 (M+H)⁺.

Example K72

N-(6-{4-[N-(2,2-Dimethylpropion-1-yl)-N-methylamino]cyclohex-1-en-1-yl}-4-methylpyridin-3-yl)-5-methyl-1-[5-(trifluoromethyl)pyridin-2-yl]-1H-pyrazole-4-carboxamide

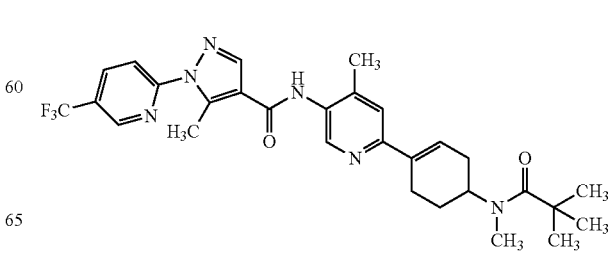

2,2,N-Trimethyl-N-{4-(4,4,5,5-tetramethyl-[1,3,2] dioxaborolan-2-yl)cyclohex-3-en-1-yl}propionamide (76.6 mg) described in Reference Example 167, 1,1-bis(diphenylphosphino)ferrocene-palladium (II) dichloride-dichloromethane complex (9.3 mg), cesium carbonate (222 mg), 1,4-dioxane (2 ml) and water (1 ml) were added to N-(6-bromo-4-methylpyridin-3-yl)-5-methyl-1-[5-(trifluoromethyl)pyridin-2-yl]-1H-pyrazole-4-carboxamide (100 mg) described in Reference Example 182, and stirred at 120° C. for 15 minutes under radiation of microwave. After completion of the reaction, insoluble materials were filtered off. Ethyl acetate was added to the resulting residue, and insoluble materials were collected by filtration and dried in vacuo to give the titled compound (83.8 mg) as a yellow solid.

MS (APCI) m/z: 555 (M+H)+.

Example 73

N-(6-{4-[N-(2,2-Dimethylpropion-1-yl)-N-methylamino]cyclohex-1-en-1-yl}-5-(trifluoromethyl)pyridin-3-yl)-5-methyl-1-[5-(trifluoromethyl)pyridin-2-yl]-1H-pyrazole-4-carboxamide

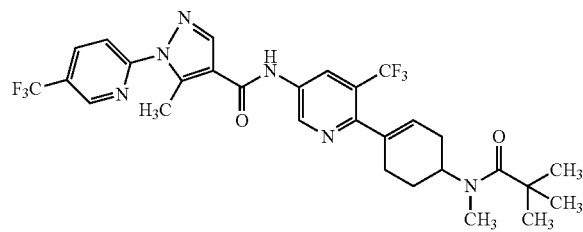 [SMILES: Cc1c(C(=O)Nc2cnc(C3=CCC(N(C)C(=O)C(C)(C)C)CC3)c(C(F)(F)F)c2)cnn1-c1ccc(C(F)(F)F)cn1]

The titled compound (70.7 mg) was prepared as a white solid from N-(6-chloro-5-trifluoromethylpyridin-3-yl)-5-methyl-1-[5-(trifluoromethyl)pyridin-2-yl]-1H-pyrazole-4-carboxamide (100 mg) described in Reference Example 184 in a similar manner as Example K72.

MS (APCI) m/z: 609 (M+H)+.

Example K74

5-Methyl-N-{5-methyl-6-[1-(trifluoromethanesulfonyl)piperidin-4-yl]pyridin-3-yl}-1-[5-(trifluoromethyl)pyridin-2-yl]-1H-pyrazole-4-carboxamide

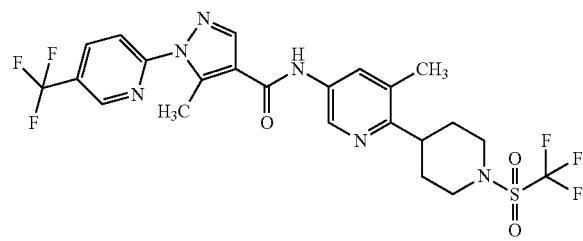 [SMILES: Cc1cc(NC(=O)c2cnn(-c3ccc(C(F)(F)F)cn3)c2C)cnc1C1CCN(S(=O)(=O)C(F)(F)F)CC1]

5-Methyl-N-[5-methyl-6-(piperidin-4-yl)pyridin-3-yl]-1-[5-(trifluoromethyl)pyridin-2-yl]-1H-pyrazole-4-carboxamide described in Reference Example 171 was used in place of N-[6-(4-cyanopiperidin-4-yl)pyridin-3-yl]-5-methyl-1-[5-(trifluoromethyl)pyridin-2-yl]-1H-pyrazole-4-carboxamide in Example K63, and reacted and treated in a similar manner to give the titled compound as a pale yellow solid.

MS (ESI) m/z: 577 (M+H)+.

Example K75

5-Methyl-N-{5-methyl-6-[1,2,3,6-tetrahydro-1-(trifluoromethanesulfonyl)pyridin-4-yl]pyridin-3-yl}-1-[5-(trifluoromethyl)pyridin-2-yl]-1H-pyrazole-4-carboxamide

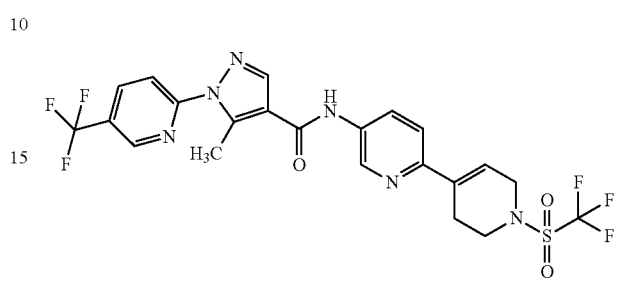

5-Methyl-N-[6-(1,2,3,6-tetrahydropyridin-4-yl)pyridin-3-yl]-1-[5-(trifluoromethyl)-pyridin-2-yl]-1H-pyrazole-4-carboxamide described in Reference Example 172 was used in place of N-[6-(4-cyanopiperidin-4-yl)pyridin-3-yl]-5-methyl-1-[5-(trifluoromethyl)pyridin-2-yl]-1H-pyrazole-4-carboxamide in Example K63, and reacted and treated in a similar manner to give the titled compound as a white solid.

MS (ESI) m/z: 561 (M+H)+.

Example K76

N-{6-[1-(Dimethylsulfamoyl)piperidin-4-yl]-5-methylpyridin-3-yl}-5-methyl-1-[5-(trifluoromethyl)pyridin-2-yl]-1H-pyrazole-4-carboxamide

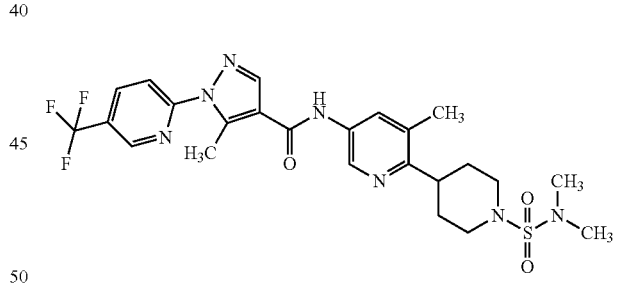

Triethylamine (73 μl) and dimethylsulfamoyl chloride (56 μl) were added to a mixture of 5-methyl-N-[5-methyl-6-(piperidin-4-yl)pyridin-3-yl]-1-[5-(trifluoromethyl)pyridin-2-yl]-1H-pyrazole-4-carboxamide (222 mg) described in Reference Example 171 and dichloromethane (10 ml), stirred at room temperature for 6.5 hours, triethylamine (146 μl) and dimethylsulfamoyl chloride (56 μl) were added and stirred at room temperature for 7.5 hours. Water was added to the reaction solution, extracted with chloroform, the organic layer was washed with saturated brine, dried over anhydrous sodium sulfate and concentrated in vacuo. The precipitated solid was washed with ethyl acetate and ethanol to give the titled compound (122 mg) as a white solid.

MS (ESI) m/z: 552 (M+H)+.

Example K77

N-{6-[1-(Dimethylsulfamoyl)-1,2,3,6-tetrahydropyridin-4-yl]pyridin-3-yl}-5-methyl-1-[5-(trifluoromethyl)pyridin-2-yl]-1H-pyrazole-4-carboxamide

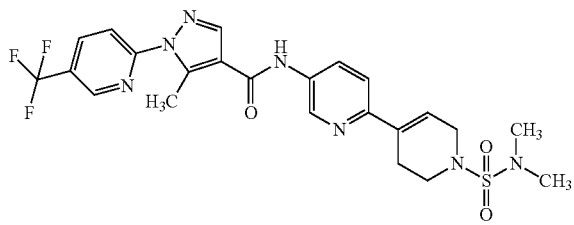 [SMILES: Cc1c(C(=O)Nc2ccc(C3=CCN(S(=O)(=O)N(C)C)CC3)nc2)cnn1-c1ccc(C(F)(F)F)cn1]

5-Methyl-N-[6-(1,2,3,6-tetrahydropyridin-4-yl)pyridin-3-yl]-1-[5-(trifluoromethyl)-pyridin-2-yl]-1H-pyrazole-4-carboxamide described in Reference Example 172 was used in place of 5-methyl-N-[5-methyl-6-(piperidin-4-yl)pyridin-3-yl]-1-[5-(trifluoromethyl)pyridin-2-yl]-1H-pyrazole-4-carboxamide in Example K76, and reacted and treated in a similar manner to give the titled compound as a pale yellow solid.

MS (ESI) m/z: 536 (M+H)$^+$.

Example K78

5-Methyl-N-{6-[1-(propane-2-sulfonyl)piperidin-4-yl]pyridin-3-yl}-1-[5-(trifluoromethyl)-pyridin-2-yl]-1H-pyrazole-4-carboxamide

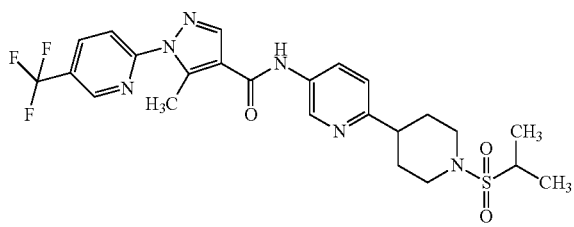 [SMILES: Cc1c(C(=O)Nc2ccc(C3CCN(S(=O)(=O)C(C)C)CC3)nc2)cnn1-c1ccc(C(F)(F)F)cn1]

Isopropylsulfonyl chloride (167 μl) was added at room temperature to a suspension of 5-methyl-N-[6-(piperidin-4-yl)pyridin-3-yl]-1-[5-(trifluoromethyl)pyridin-2-yl]-1H-pyrazole-4-carboxamide (215 mg) described in Reference Example 173 and potassium carbonate (237 mg) in N,N-dimethylformamide (1.7 ml), and stirred at room temperature for 4.5 hours. Water was added to the reaction solution, the precipitated solid was washed with ethyl acetate. The resulting solid was purified with a preparative HPLC (water:acetonitrile) to give the titled compound (44 mg) as a white solid.

MS (ESI) m/z: 537 (M+H)$^+$.

Example K79

5-Methyl-N-{6-[1-(propane-2-sulfonyl)-1,2,3,6-tetrahydropyridin-4-yl]pyridin-3-yl}-1-[5-(trifluoromethyl)pyridin-2-yl]-1H-pyrazole-4-carboxamide

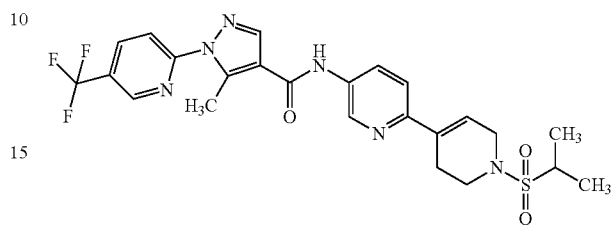

5-Methyl-N-[6-(1,2,3,6-tetrahydropyridin-4-yl)pyridin-3-yl]-1-[5-(trifluoromethyl)-pyridin-2-yl]-1H-pyrazole-4-carboxamide described in Reference Example 172 was used in place of 5-methyl-N-[6-(piperidin-4-yl)pyridin-3-yl]-1-[5-(trifluoromethyl)pyridin-2-yl]-1H-pyrazole-4-carboxamide in Example K78, and reacted and treated in a similar manner to give the titled compound as a pale yellow solid.

MS (ESI) m/z: 535 (M+H)$^+$.

Example K80

5-Methyl-N-{6-[1-(trifluoromethanesulfonyl)piperidin-4-yl]pyridin-3-yl}-1-[5-(trifluoromethyl)pyridin-2-yl]-1H-pyrazole-4-carboxamide

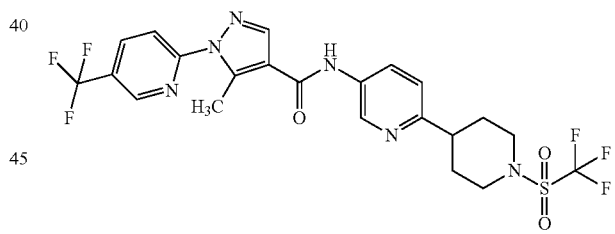

A solution of trifluoromethanesulfonic acid anhydride (110 μl) in dichloromethane (1.0 ml) was added under ice-cooling to a solution of 5-methyl-N-[6-(piperidin-4-yl)pyridin-3-yl]-1-[5-(trifluoromethyl)pyridin-2-yl]-1H-pyrazole-4-carboxamide (215 mg) described in Reference Example 173 and triethylamine (140 μl) in dichloromethane (5.0 ml) and stirred at room temperature for 4 hours. Then, trifluoromethanesulfonic acid anhydride (25 μl) was added and further stirred for 4.5 hours. Water was added to the reaction solution, extracted with chloroform, the organic layer was washed with saturated brine, dried over anhydrous sodium sulfate and concentrated in vacuo. The resulting residue was purified with silica gel chromatography (chloroform/methanol) to give the titled compound (70 mg) as a pale yellow solid.

MS (ESI) m/z: 563 (M+H)$^+$.

Example K81

N-(2-{4-[N-(2,2-Dimethylpropion-1-yl)-N-methylamino]cyclohex-1-en-1-yl}-pyrimidin-5-yl)-5-methyl-1-[5-(trifluoromethyl)pyridin-2-yl]-1H-pyrazole-4-carboxamide

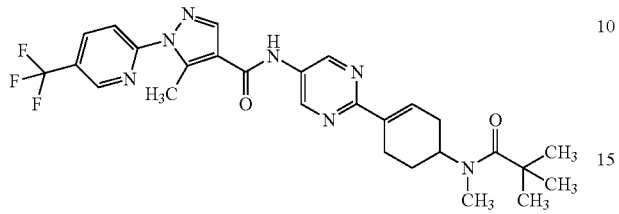

(1) Toluene (5 ml) was added to 5-methyl-1-[5-(trifluoromethyl)pyridin-2-yl]-1H-pyrazole-4-carboxylic acid chloride (500 mg) described in Reference Example 180, pyridine (5 ml) and 5-amino-2-chloropyridine (198 mg) were added thereto with stirring, and the mixture was stirred at 80° C. for two hours. After completion of the reaction, water was added to the reaction solution and extracted with chloroform. The organic layer was dried over anhydrous sodium sulfate and concentrated. The resulting residue was purified with silica gel column chromatography (chloroform/methanol) to give N-(2-chloropyrimidin-5-yl)-5-methyl-1-[5-(trifluoromethyl)pyridin-2-yl]-1H-pyrazole-4-carboxamide (410 mg) as a white solid.

MS (ESI) m/z: 383 (M+H)$^+$.

(2) A suspension of N-(2-chloropyrimidin-5-yl)-5-methyl-1-[5-(trifluoromethyl)pyridin-2-yl]-1H-pyrazole-4-carboxamide (100 mg), 2,2,N-trimethyl-N-[4-(4,4,5,5-tetramethyl[1,3,2]dioxaborolan-2-yl)cyclohex-3-en-1-yl]propionamide (101 mg), bis(diphenylphosphine)ferrocenepalladium (II) dichloride dichloromethane adduct (21.4 mg) and cesium carbonate (238 mg) in 1,4-dioxane (1.5 ml) and water (0.5 ml) was stirred at 120° C. under nitrogen atmosphere for 40 minutes. After completion of the reaction, the reaction solution was cooled to room temperature, water was added and extracted with chloroform. The resulting organic layer was dried over anhydrous sodium sulfate and concentrated. The resulting solid was purified with silica gel column chromatography (chloroform/methanol) to give the titled compound (116 mg) as a yellow solid.

MS (ESI) m/z: 542 (M+H)$^+$.

Example K82

N-(6-{4-[N-(2,2-Dimethylpropion-1-yl)-N-methylamino]cyclohex-1-en-1-yl}pyridin-3-yl)-5-methyl-1-[5-(trifluoromethyl)pyridin-2-yl]-1H-pyrazole-4-carboxamide

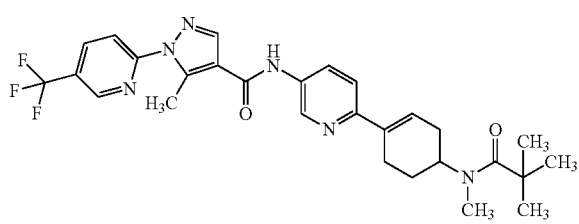 [SMILES: Cc1c(C(=O)Nc2ccc(C3=CCC(N(C)C(=O)C(C)(C)C)CC3)nc2)cnn1-c1ccc(C(F)(F)F)cn1]

1,4-Dioxane (3 ml) and water (1 ml) were added to N-(6-bromopyridin-3-yl)-5-methyl-1-[5-(trifluoromethyl)pyridin-2-yl]-1H-pyrazole-4-carboxamide (213 mg) described in Reference Example 172(1), cesium carbonate (456 mg), [1,1'-bis(diphenylphosphino)-ferrocene]palladium (II) dichloride dichloromethane complex (20 mg) and 2,2,N-trimethyl-N-{4-(4,4,5,5-tetramethyl[1,3,2]diborolan-2-yl)cyclohex-3-en-1-yl}propionamide (209 mg) described in Reference Example 167, and stirred at 110° C. for four hours. Water and ethanol were added to the reaction solution, and the obtained solid was washed with ethyl acetate and methanol to give the titled compound (162 mg) as a yellow solid.

MS (ESI) m/z: 541 (M+H)$^+$.

Example K83

5-Chloro-N-(6-{4-[N-(2,2-dimethylpropion-1-yl)-N-methylamino]cyclohex-1-en-1-yl}-5-methylpyridin-3-yl)-1-[5-(trifluoromethyl)pyridin-2-yl]-1H-pyrazole-4-carboxamide

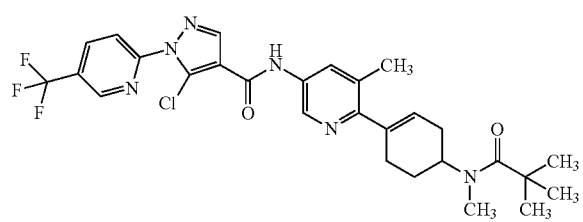 [SMILES: Cc1cc(NC(=O)c2cnn(-c3ccc(C(F)(F)F)cn3)c2Cl)cnc1C1=CCC(N(C)C(=O)C(C)(C)C)CC1]

(1) Sodium carbonate (2.8 g), water (20 ml) and ethanol (20 ml) were added to 5-trifluoromethylpyridin-2-ylhydrazine hydrochloride (7.0 g) and ethyl 2-ethoxymethylene cyanoacetate (5.54 g), and stirred at refluxing temperature for three hours. Water was added to the reaction solution and the precipitated solid was collected by filtration to give 5-amino-1-[5-(trifluoromethyl)pyridin-2-yl]-1H-pyrazole-4-carboxylic acid ethyl ester (8.30 g).

(2) tert-Butyl nitrite (154 mg) was added slowly dropwise to a solution of 5-amino-1-[5-(trifluoromethyl)pyridin-2-yl]-1H-pyrazole-4-carboxylic acid ethyl ester (300 mg) and N-chlorosuccinimide (200 mg) in dichloromethane (10 ml) and stirred at room temperature for three hours. The reaction solution was concentrated while keeping not dried up, and the residue was purified with silica gel chromatography (ethyl acetate/n-hexane) to give 5-chloro-1-[5-(trifluoromethyl)pyridin-2-yl]-1H-pyrazole-4-carboxylic acid ethyl ester (140 mg) as a white solid.

MS (ESI) m/z: 320 (M+H)$^+$.

(3) A mixture of 12N aqueous solution of sodium hydroxide (0.5 ml), water (2 ml) and ethanol (4 ml) was added to 5-chloro-1-[5-(trifluoromethyl)pyridin-2-yl]-1H-pyrazole-4-carboxylic acid ethyl ester (120 mg), and stirred at 80° C. for four hours. After the reaction, 1N hydrochoric acid aqueous solution was added under ice-cooling, the precipitated solid was washed with ethyl acetate to give 5-chloro-1-[5-(trifluoromethyl)pyridin-2-yl]-1H-pyrazole-4-carboxylic acid (50 mg).

MS (ESI) m/z: 292 (M+H)$^+$.

(4) N,N-Dimethylformamide (catalytic amounts) and thionyl chloride (0.86 ml) were added to a solution of 5-chloro-1-[5-(trifluoromethyl)pyridin-2-yl]-1H-pyrazole-4-carboxylic acid (50 mg) in toluene (0.86 ml), stirred at 80° C. for five hours and concentrated in vacuo. The residue was dissolved in pyridine (0.86 ml), N-[4-(5-amino-3-methylpyridin-2-yl)cyclohex-3-en-1-yl]-2,2,N-trimethylpromionic acid amide (67 mg) described in Reference Example 145 was added thereto and stirred at 60° C. for four hours. Triethylamine (0.12 ml) and water was added and the precipitated solid was purified with silica gel chromatography (chloroform/methanol) to give the titled compound (60 mg) as a pale yellow solid.

MS (ESI) m/z: 575 (M+H)$^+$.

Example K84

N-{6-[1-(Dimethylsulfamoyl)-5-methyl-1,2,3,6-tetrahydropyridin-4-yl]pyridin-3-yl}-5-methyl-1-[5-(trifluoromethyl)pyridin-2-yl]-1H-pyrazole-4-carboxamide

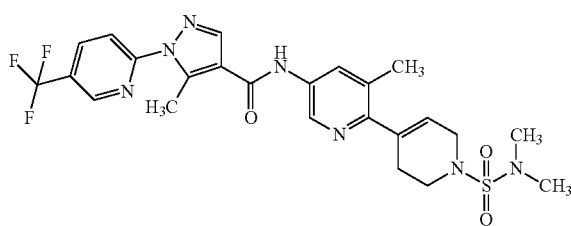

5-Methyl-N-[5-methyl-6-(1,2,3,6-tetrahydropyridin-4-yl)pyridin-3-yl]-1-[5-(trifluoromethyl)pyridin-2-yl]-1H-pyrazole-4-carboxamide described in Reference Example 170 was used in place of N-[6-(4-cyanopiperidin-4-yl)pyridin-3-yl]-5-methyl-1-[5-(trifluoromethyl)pyridin-2-yl]-1H-pyrazole-4-carboxamide in Example K59, and reacted and treated in a similar manner to give the titled compound as a white solid.

MS (ESI) m/z: 550 (M+H)$^+$.

Example K85

N-{6-[1-(Dimethylsulfamoyl)piperidin-4-yl]pyridin-3-yl}-5-methyl-1-[5-(trifluoromethyl)-pyridin-2-yl]-1H-pyrazole-4-carboxamide

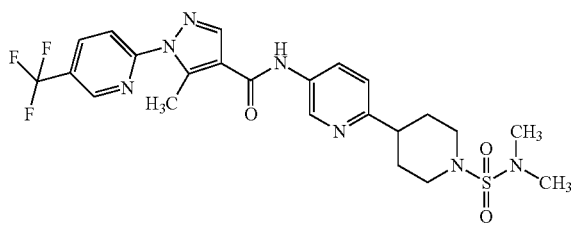 [SMILES: Cc1c(C(=O)Nc2ccc(C3CCN(S(=O)(=O)N(C)C)CC3)nc2)cnn1-c1ccc(C(F)(F)F)cn1]

5-Methyl-N-[6-(piperidin-4-yl)pyridin-3-yl]-1-[5-(trifluoromethyl)pyridin-2-yl]-1H-pyrazole-4-carboxamide described in Reference Example 173 was used in place of N-[6-(4-cyanopiperidin-4-yl)pyridin-3-yl]-5-methyl-1-[5-(trifluoromethyl)pyridin-2-yl]-1H-pyrazole-4-carboxamide in Example K59, and reacted and treated in a similar manner to give the titled compound as a white solid.

MS (ESI) m/z: 538 (M+H)$^+$.

Example K86

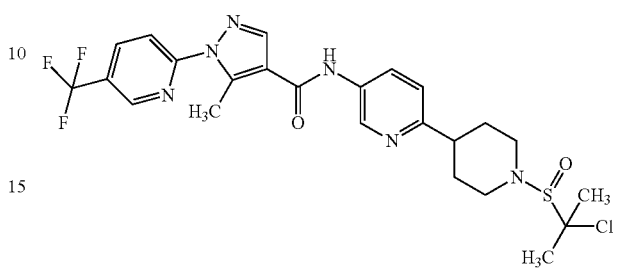

The titled compound (21 mg) was obtained as a white solid in the reaction described in Example K80.

MS (ESI) m/z: 555 (M+H)$^+$.

Example K87

N-[6-(r-1-Cyano-t-4-hydroxycyclohexyl)pyridin-3-yl]-1-(4-fluorophenyl)-5-methyl-1H-pyrazole-4-carboxamide

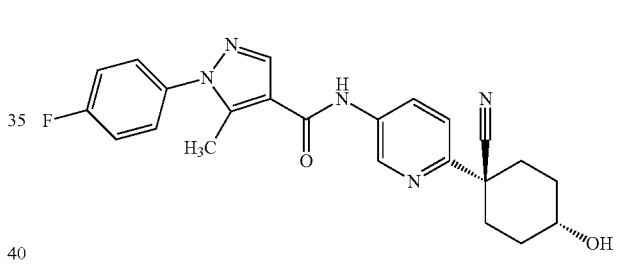

(1) Triphenylphosphine (375 mg), acetic acid (82 μl) and 1.9M diisopropyl azodicarboxylate solution in toluene (0.75 ml) were added at room temperature to a solution of N-[6-(r-1-cyano-c-4-hydroxycyclohexyl)pyridin-3-yl]-1-(4-fluorophenyl)-5-methyl-1H-pyrazole-4-carboxamide (400 mg) described in Example G2 in tetrahydrofuran (10 ml), and stirred at the same temperature for six hours. Next, triphenylphosphine (375 mg), acetic acid (82 μl) and 1.9M diisopropyl azodicarboxylate solution in toluene (0.75 ml) were added and stirred at the same temperature for 18 hours. Further, triphenylphosphine (375 mg), acetic acid (82 μl) and 1.9M diisopropyl azodicarboxylate solution in toluene (0.75 ml) were added and stirred at the same temperature for 20 hours. After completion of the reaction, water was added and extracted with ethyl acetate. The organic layer was dried over anhydrous sodium sulfate and concentrated. The resulting residue was purified with basic silica gel column chromatography (n-hexane/ethyl acetate) and silica gel column chromatography (chloroform/methanol) to give r-4-cyano-4-({[1-(4-fluorophenyl)-5-methyl-1H-pyrazole-4-carbonyl]amino}pyridin-2-yl)cyclohexane-t-1-acetic acid ester (377 mg) as a white solid.

MS (ESI) m/z: 462 (M+H)$^+$.

(2) 1N Aqueous solution of sodium hydroxide was added at room temperature to a solution of r-4-cyano-4-({[1-(4-fluorophenyl)-5-methyl-1H-pyrazole-4-carbonyl]

amino}pyridin-2-yl)cyclohexane-t-1-acetic acid ester (357 mg) in ethanol (8.0 ml) and tetrahydrofuran (8.0 ml), and stirred at 40° C. for two hours. After completion of the reaction, the solvent was evaporated, water was added and the precipitated solid was collected by filtration. The resulting residue was purified with silica gel column chromatography (chloroform/methanol) to give the titled compound (251 mg) as a white solid.

MS (ESI) m/z: 420 (M+H)$^+$.

Example K88

4-({r-4-Cyano-4-(5-{[1-(4-fluorophenyl)-5-methyl-1H-pyrazole-4-carbonyl]amino}pyridin-2-yl)cyclohexyl}-c-1-oxy)-4-oxobutanoic acid

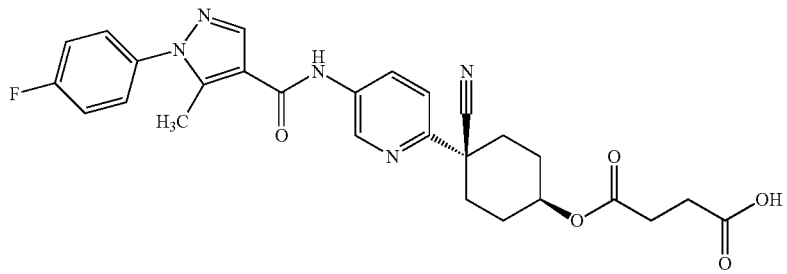 [SMILES: Cc1c(C(=O)Nc2ccc([C@]3(C#N)CC[C@@H](OC(=O)CCC(=O)O)CC3)nc2)cnn1-c1ccc(F)cc1]

p-Toluenesulfonic acid hydrate (41 mg) and succinic acid anhydride (358 mg) were added at room temperature to a suspension of N-[6-(r-1-cyano-c-4-hydroxycyclohexyl)pyridin-3-yl]-1-(4-fluorophenyl)-5-methyl-1H-pyrazole-4-carboxamide (1.0 g) described in Example G2 in 1,2-dichlorobenzene (6.0 ml), and stirred at 160° C. for three hours. After completion of the reaction, the reaction solution was cooled to room temperature, ethyl acetate was added and the precipitated solid was collected by filtration. The resulting residue was purified with silica gel column chromatography (chloroform/methanol) and the resulting solid was suspended in and washed with ethyl acetate to give the titled compound (609 mg) as a white solid.

MS (ESI) m/z: 462 (M+H)$^+$.

Example K89

N-[6-(r-4-Hydroxy-c-1-methylcyclohexyl)pyridin-3-yl]-5-methyl-1-[5-(trifluoromethyl)-pyridin-2-yl]-1H-pyrazole-4-carboxamide

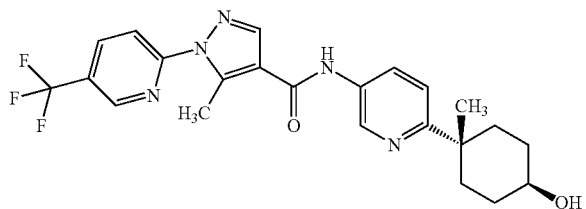 [SMILES: Cc1c(C(=O)Nc2ccc([C@]3(C)CC[C@@H](O)CC3)nc2)cnn1-c1ccc(C(F)(F)F)cn1]

(1) Lithium borohydride (1.71 g) was added at room temperature to a solution of 8-(5-bromopyridin-2-yl)-1,4-dioxaspiro[4.5]decane-8-carboxylic acid ethyl ester (7.26 g) described in Reference Example 81(2) in tetrahydrofuran (100 ml) and stirred at the same temperature for 39 hours.

Then, lithium borohydride (855 mg) was added and stirred at the same temperature for 24 hours. After completion of the reaction, a saturated aqueous solution of ammonium chloride was added thereto, and the mixture was extracted with ethyl acetate. The organic layer was dried over anhydrous sodium sulfate and concentrated. The resulting residue was purified with silica gel column chromatography (n-hexane/ethyl acetate) to give [8-(5-bromopyridin-2-yl)-1,4-dioxaspiro[4.5]dec-8-yl]methanol (5.17 g) as a colorless transparent oil.

MS (ESI) m/z: 328, 330 (M+H)$^+$.

(2) Triethylamine (3.3 ml) and methanesulfonyl chloride (1.32 g) was added at room temperature to a solution of [8-(5-bromopyridin-2-yl)-1,4-dioxaspiro[4.5]dec-8-yl]methanol (3.16 g) in tetrahydrofuran (32 ml) and stirred at the same temperature for 18 hours. After completion of the reaction, water was added and extracted with ethyl acetate. The organic layer was dried over anhydrous sodium sulfate and concentrated. The resulting residue was purified with basic silica gel column chromatography (n-hexane/ethyl acetate) to give [8-(5-bromopyridin-2-yl)-1,4-dioxaspiro[4.5]dec-8-yl]-8-methanesulfonic acid ester (3.68 g) as a colorless transparent oil.

MS (ESI) m/z: 406, 408 (M+H)$^+$.

(3) [8-(5-Bromopyridin-2-yl)-1,4-dioxaspiro[4.5]dec-8-yl]-8-methanesulfonic acid ester (3.55 g) was used in place of 1-(5-bromopyridin-2-yl)-c-4-(tert-butyldimethylsilanyloxy)-r-1-cyclohexanecarbonitrile in Reference Example 144 (2) and (3), and reacted and treated in a similar manner to give [8-(5-aminopyridin-2-yl)-1,4-dioxaspiro[4.5]dec-8-yl]-8-methanesulfonic acid ester (978 mg) as a white solid.

MS (ESI) m/z: 343 (M+H)$^+$.

(4) A solution of [8-(5-aminopyridin-2-yl)-1,4-dioxaspiro[4.5]dec-8-yl]-8-methanesulfonic acid ester (700 mg) in tetrahydrofuran (20 ml) was added dropwise under ice-cooling to a suspension of lithium aluminium hydride (233 mg) in tetrahydrofuran (20 ml), and stirred at room temperature for an hour. After completion of the reaction, 1N aqueous solution of sodium hydroxide was added dropwise, and then ethyl acetate and Celite were added and stirred for an hour. Next, the mixture was filtered and the filtrate was concentrated. The resulting residue was purified with basic silica gel column chromatography (n-hexane/ethyl acetate) to give [6-(8-methyl-1,4-dioxaspiro[4.5]dec-8-yl)pyridin-3-yl]amine (362 mg) as a colorless transparent oil.

MS (ESI) m/z: 249 (M+H)$^+$.

(5) [6-(8-Methyl-1,4-dioxaspiro[4.5]dec-8-yl)pyridin-3-yl]amine (340 mg) was added to a solution of 5-methyl-1-[5-(trifluoromethyl)pyridin-2-yl]-1H-pyrazole-4-carboxylic acid chloride (491 mg) described in Reference Example 180 in pyridine (7.0 ml) and stirred at 50° C. for an hour. After completion of the reaction, triethylamine (1.5 ml) and water was added and the precipitated solid was collected by filtration to give 5-methyl-N-[6-(8-methyl-1,4-dioxaspiro[4.5]

dec-8-yl)pyridin-3-yl]-1-[5-(trifluoromethyl)pyridin-2-yl]-1H-pyrazole-4-carboxamide (618 mg) as a white solid.

MS (ESI) m/z: 502 (M+H)$^+$.

(6) 5-Methyl-N-[6-(8-methyl-1,4-dioxaspiro[4.5]dec-8-yl)pyridin-3-yl]-1-[5-(trifluoromethyl)pyridin-2-yl]-1H-pyrazole-4-carboxamide (595 mg) was used in place of N-[6-(8-fluoro-1,4-dioxaspiro[4.5]dec-8-yl)pyridin-3-yl]-5-methyl-1-[5-(trifluoromethyl)pyridin-2-yl]-1H-pyrazole-4-carboxamide described in Example F37, and reacted and treated in a similar manner to give 5-methyl-N-[6-(1-methyl-4-oxocyclohexan-1-yl)pyridin-3-yl]-1-[5-(trifluoromethyl)pyridin-2-yl]-1H-pyrazole-4-carboxamide (504 mg) as a white solid.

MS (ESI) m/z: 458 (M+H)$^+$.

(7) A solution of sodium borohydride (156 mg) in methanol (4.0 ml) was added dropwise at −78° C. to a solution of 5-methyl-N-[6-(1-methyl-4-oxocyclohexan-1-yl)pyridin-3-yl]-1-[5-(trifluoromethyl)pyridin-2-yl]-1H-pyrazole-4-carboxamide (471 mg) in a mixture of tetrahydrofuran (40 ml) and methanol (40 ml), and stirred at the same temperature for an hour. After completion of the reaction, a saturated aqueous solution of ammonium chloride was added thereto, and the mixture was concentrated. The resulting residue was washed with ethyl acetate, suspended in and washed with ethanol to give the titled compound (229 mg) as a white solid.

MS (ESI) m/z: 460 (M+H)$^+$.

Test Example 1

Effect on Production of IL-17 Induced when Mouse Spleen Cells were Stimulated by Recombinant Mouse Interleukin-23 (rm-IL-23)

An RPMI1640 (Sigma-Aldrich) was used as a medium, to which penicillin G potassium (50 units/mL; Gibco), streptomycin (50 μg/mL; Gibco) and 2-mercaptoethanol (50 μmol/l; Sigma-Aldrich) were added, and then 10% of fetal calf serum (FCS; Cell Culture Technology) inactivated at 56° C. for 30 minutes was added and used in the Test. The test compound was dissolved in dimethylsulfoxide and diluted with 10% FCS-containing RPMI1640 medium to a desired concentration and used in the test. The spleens were aseptically taken out from 6-7 week-old male DBA/1J mice (Charles River Japan, Inc.) and a single cell suspension of spleen cells was prepared and hemolyzed by hypotonic treatment with a mixture of 0.83% aqueous solution of ammonium chloride and Tris-HCl buffer of pH 7.65 (9:1). A cell suspension prepared by 10% FCS-containing RPMI1640 medium was added to flat-bottomed 96 well microtestplate at 2×10$^5$ cells/well. Test compounds and rm-IL-23 (R&D systems) were diluted with a medium to 1 to 1,000 nmol/L, and 1 nmol/L of the final concentration respectively, which were added and cultured at 37° C., 5% carbon dioxide and 95% air for 72 hours. After completion of the culture, culture supernatant was sampled and an amount of IL-17 production was determined by ELISA method. After sampling the supernatant, WST-8 (Seikagaku Corporation) was added at 10 μl/well and cultured at 37° C., 5% carbon dioxide and 95% air for 4 hours. Then, absorbance (O.D.: Optical Density) at 450 nm was measured by a microplate reader and the value was adopted as an index of cell survivability. An inhibition rate (%) was calculated according to the following formula on the basis of an average of an amount of IL-17 production and a O.D. values of the well containing a test compound of each concentration.

$$(\%)\ \text{inhibition} = \left(1 - \frac{\text{average value of well with addition of test compound}}{\text{average value of well without addition of test compound}}\right) \times 100$$

Based on the dose-response curve obtained by plotting the inhibition rate in the longitudinal axis and concentration in the horizontal axis, the concentration of the compound which inhibits the level to 50% of the value of the control group (IC50; nmol/L) was determined by linear regression analysis. The results was shown in the next Table 1

Test Example 2

Effects on hERG Current

Dimethylsulfoxide was used as a vehicle and hERG-expressed HEK 293 cells (Cytomyx) were used as test cells. Test cells were once cultured and subdivided and were stored under frozen condition in liquid nitrogen. In the study, thawed and subcultured cells having less than 30 of the passage number were used. Test cells were cultured in a carbon dioxide incubator BNP-110M (Tabai Espec Corp.) at 37±1° C., and 5.0±0.5% of carbon dioxide concentration. The component of culture medium was MEM (Minimum Essential Medium) supplemented with 10 vol % fetal bovine serum (non-activated), 1 mmol/L sodium pyruvate, 0.1 mmol/L non-essential amino acid, 100 U/mL penicillin with 100 μg/mL streptomycin. To select gene-expressing cells, 400 μg/mL G418 Sulphate (Invitrogen) was added to the culture medium. In the dishes for the measurement, the medium which not contain G418 Sulphate (Invitrogen) was used. A manufacturer of the culture solution is Invitrogen Corporation.

As to seeding of cells for measurement, subcultured cells which became confluent were treated with 0.25% trypsin-solution containing 1 mmol/L EDTA (Invitrogen) to remove from the plate, and seeded on sterilized collagen-coated cover glass (Iwaki, AGC Techno Glass Co., LTD). The medium was exchanged appropriately, including the day of measurement.

A perfusion method was applied to the experiment. Test cells were perfused (perfusion speed: approximately 4 mL/min) with an external solution containing specified concentrations of test compounds (component of external solution: 137 mmol/L of sodium chloride, 4 mmol/L of potassium chloride, 10 mmol/L of HEPES, 1.8 mmol/L of calcium chloride, 1 mmol/L of magnesium chloride and 10 mmol/L of glucose; adjusted to pH 7.4±0.1 with sodium hydroxide aqueous solution). When no effects were observed until 4 minutes after perfusion of a test compound, the next different concentration of the test compound was perfused. When effects were observed, the perfusion was continued until the maximum response was observed. The maximum perfusion time for the lowest concentration of test compound was set for 10 minutes even when effects were observed. The data were obtained from one experiment or more and the cells which were incubated in a carbon dioxide incubator after seeding and attached to cover slips were used for the measurement.

A whole-cell clamping method was applied to the measurement. Test cells were perfused (perfusion speed: approximately 4 mL/min) with an external solution (component of external solution: 137 mmol/L of sodium chloride, 4 mmol/L of potassium chloride, 10 mmol/L of HEPES, 1.8 mmol/L of calcium chloride, 1 mmol/L of magnesium chloride and 10 mmol/L of glucose; adjusted to pH 7.4±0.1 with sodium hydroxide aqueous solution). A glass electrode with a resistance of 2 to 6 MΩ, filled with an internal solution (component: 130 mmol/L of potassium chloride, 1 mmol/L of magnesium chloride, 5 mmol/L of EGTA, 10 mmol/L of HEPES and 5 mmol/L of ATP adjusted to pH 7.2±0.1 with sodium hydroxide aqueous solution) was used. After rupturing cell membrane with glass electrode, the cell membrane voltage was held at −80 mV via a patch clamp software (pCLAMP9 [Axon CNS], Molecular Devices) using patch clamp amplifier (EPC8, HEKA). As illustrated in FIG. 1, a test pulse of +20 mV for 1.5 seconds and −40 mV for 1.5 seconds was given every 15 seconds. After obtaining 500 pA or higher peak value of the tail currents stably for at least 1 minute, test compounds were applied. Test cells and the cell-attached cover glass were changed every treatment. Temperature of the fluid in a perfusion fluid tank was 24±2° C.

The obtained current was recorded on a computer via a patch clamp amplifier using patch clamp software. An evaluation item was a tail peak current.

A tail peak current was analyzed using analyzing software (Clampfit 9 [Axon CNS], MolecularDevices). Each 2 pulses of before and after perfusion of test compound for each concentration was analyzed, and a peak values of the tail current on the pulses were determined. The inhibition ratio was determined according to the following equation:

$$(\%)\ \text{Inhibition} = 100 - \frac{\text{Peak tail current after perfusion}}{\text{Peak tail current before perfusion}} \times 100$$

An inhibition ratio of each test compound at 1 μM of concentration is shown in the Table 1 below.

TABLE 1

IC50 (nmol/L) and hERG inhibition rate (%) of each Example compound

| Example No. | IC50 (nmol/L) | hERG inhibition rate (%) (1 μM) |
|---|---|---|
| D1 | 78.9 | 22.6 |
| D2 | 193 | 43.4 |
| D3 | 182 | 7.2 |
| D5 | 119 | 15.1 |
| D6 | 63.3 | 24.5 |
| D7 | 208 | 24.7 |
| D8 | 114 | 15.8 |
| D9 | 76.7 | 42.1 |
| D10 | 120 | 6.7 |
| D11 | 53.4 | 21 |
| D12 | 117 | 29.2 |
| D13 | 154 | 22 |
| D14 | 162 | 6.4 |
| D18 | 251 | 7.2 |
| D19 | 92 | 35.1 |
| D20 | 56.4 | 32.2 |
| D21 | 39.5 | 14.3 |
| D22 | 36.2 | 31 |
| D23 | 105 | 20.2 |
| D24 | 40.3 | 20.9 |
| D25 | 148 | 4.2 |
| D26 | 125 | 26.4 |
| D29 | 86.9 | 27.7 |
| D41 | 32.8 | 26.4 |
| D53 | 169 | 25.1 |
| D63 | 207 | 40.4 |
| D64 | 160 | 27.9 |
| D65 | 139 | 5.5 |
| D71 | 62.5 | 16.5 |
| D88 | 52.6 | 43 |
| D89 | 183 | 44.4 |
| D104 | 212 | 13.8 |
| D116 | 129 | 41.2 |

TABLE 1-continued

IC50 (nmol/L) and hERG inhibition rate (%) of each Example compound

| Example No. | IC50 (nmol/L) | hERG inhibition rate (%) (1 μM) |
|---|---|---|
| D117 | 57 | 35.6 |
| D146 | 46.6 | 47.2 |
| D153 | 55.1 | 47.6 |
| D165 | 44 | 8.9 |
| D175 | 49.8 | 31.7 |
| D177 | 66 | 13 |
| D188 | 86.3 | 40 |
| D191 | 58.4 | 47.6 |
| D196 | 54.6 | 13.6 |
| D197 | 123 | 0.8 |
| D200 | 58.4 | 47.6 |
| D214 | 18.7 | 10 |
| D215 | 20.3 | 16.6 |
| D216 | 118 | 21 |
| D217 | 84.4 | 26.7 |
| D219 | 59.5 | 11.4 |
| D221 | 31.4 | 20.1 |
| D224 | 141 | 19.5 |
| D230 | 161 | 46.1 |
| D234 | 55.6 | 5.6 |
| D237 | 50.3 | 3.6 |
| D238 | 49.1 | 5 |
| D249 | 131 | 36.9 |
| D254 | 146 | 6.6 |
| D260 | 4.02 | 16.8 |
| D264 | 17.4 | 7.5 |
| D265 | 4.91 | 35.9 |
| D268 | 155 | 9.8 |
| D269 | 207 | 14.1 |
| D270 | 55.8 | 0.5 |
| D275 | 55.3 | 14.4 |
| D276 | 71.2 | 8.9 |
| D278 | 50.2 | 13.6 |
| D279 | 112 | 12.8 |
| D282 | 174 | 11.9 |
| D288 | 5.38 | 5.9 |
| D289 | 87.2 | 11.6 |
| D299 | 112 | 40.6 |
| D300 | 182 | 26.1 |
| D303 | 48 | 22.7 |
| E1 | 62.3 | 34.7 |
| E2 | 179 | 24.4 |
| E6 | 28.5 | 36.9 |
| E7 | 349 | 21.1 |
| E13 | 109.3 | 10.3 |
| E18 | 50.4 | 8.8 |
| E21 | 179.8 | 8.3 |
| E22 | 327.8 | 2.7 |
| E30 | 149 | 10.7 |
| F2 | 53.4 | 22.4 |
| F6 | 107 | 6.8 |
| F8 | 61.6 | 15.4 |
| F10 | 278 | 8 |
| F26 | 321 | 8.1 |
| F32 | 146 | 17.9 |
| G1 | 118.1 | 25.8 |
| G2 | 194 | 15.2 |
| G3 | 91.8 | 4.4 |
| G4 | 48 | 5.2 |
| G5 | 86.6 | 11.7 |
| G6 | 73.9 | 26 |
| G7 | 197.6 | 5.2 |
| G8 | 56.4 | 1.9 |
| G9 | 145.1 | 0.8 |
| G10 | 118 | 5.1 |
| G11 | 84.6 | 12.2 |
| G12 | 260.3 | 6.5 |
| G29 | 133 | 6.7 |
| G30 | 147 | 3.2 |
| G32 | 105 | 7.9 |
| J7 | 67.5 | 7.9 |
| J8 | 53 | 11.3 |
| J12 | 149 | 10.8 |
| J13 | 242 | 10.7 |
| J15 | 438 | 8.2 |

TABLE 1-continued

IC50 (nmol/L) and hERG inhibition rate (%) of each Example compound

| Example No. | IC50 (nmol/L) | hERG inhibition rate (%) (1 μM) |
|---|---|---|
| J16 | 305 | 13.5 |
| J17 | 275 | 2.4 |
| J18 | 137 | 17.8 |
| J19 | 132 | 18.5 |
| J20 | 90 | 18.1 |
| K4 | 127.3 | 17.2 |
| K6 | 148 | 40 |
| K19 | 148 | 2.4 |
| K26 | 376 | 14.3 |
| K27 | 242 | 9.7 |
| K28 | 8.11 | 5.1 |
| K30 | 368 | 79.6 |
| K31 | 4.27 | 15.8 |
| K32 | 6.32 | 11.3 |
| K33 | 206 | 8 |
| K34 | 154 | 0.5 |
| K36 | 124 | 8.1 |
| K38 | 58.1 | 44.1 |
| K41 | 161 | 25.6 |
| K45 | 46.2 | 21.1 |
| K51 | 37.3 | 43.7 |
| K52 | 160 | 31.5 |
| K55 | 46.4 | 29.5 |
| K60 | 47.2 | 22.8 |
| K64 | 157 | 2.3 |
| K69 | N.D. | 1.3 |

Test Example 3

Effect on Type II Collagen-Induced Arthritis in DBA/1J Mice

An emulsion was prepared by mixing bovine II collagen (100-200 μg purchased from collagen Gijyutsu Kenshuukai) and Freund's complete adjuvant (Sigma Aldrich) containing killed *Mycobacterium tuberculosis* H37Ra. Arthritis was induced by immunization through subcutaneous administration of the emulsion to the tail of 6-7 week-old male DBA/1J mouse (Charles River Japan, Inc.), followed by booster immunization three weeks later by administration of an emulsion prepared by mixing bovine II collagen with Freund's incomplete adjuvant (Sigma-Aldrich). Test compound was suspended or dissolved in 0.5% carboxymethylcellulose (Sigma-Aldrich) and repeatedly administered orally once a day at a dose of 0.1 to 10 mg/kg body weight using an oralsonde for three weeks from the day of booster immunization. In this model, the symptom of arthritis of the limbs was each evaluated according to the following evaluation criteria of 0 to 4 scores: 0, No change; 1, edema in only one joint; 2, edema in two or more joints, or light edema of the entire limb; 3, severe edema of the entire limb; 4, severe edema of the entire limb and ankylosis and immovability of joint. The score of arthritis of each mouse was expressed as the total of the scores of the limbs (Maximum: 16 points). On the next day of the last administration, soft X-ray photograph of the limbs was taken with soft X-ray equipment (Omic), and the level of joint destruction was evaluated by observation under a microscope. In each finger of the limbs the score of joint destruction was judged as 0 when no joint destruction was found, and as 1 when one or more destruction was found, and the score of joint destruction of a mouse was expressed as the total of scores for each finger of limb (Maximum: 20). The arthritis score and joint destruction score were expressed as the average value and standard error for each group (n=6-8). Only a vehicle was administered in a control group, and statistical analysis was performed by Dunnett's multiple comparison test, in which the case was judged as significant when the p value was less than 0.05. The typical compounds showed a significant inhibitory effect on arthritis in a dose of Table 2 or more.

TABLE 2

Effective dose showing arthritis-inhibiting activity of each example

| Example No. | Effective Dose |
|---|---|
| D146 | 0.1 mg/kg |
| D20 | 1 mg/kg |
| E13 | 1 mg/kg |
| E24 | 1 mg/kg |
| G1 | 3 mg/kg |
| G2 | 1 mg/kg |
| G3 | 1 mg/kg |
| G6 | 10 mg/g |
| G7 | 0.3 mg/kg |
| K2 | 10 mg/kg |

INDUSTRIAL APPLICABILITY

The compound (I) of the present invention or the pharmaceutically acceptable salt or solvate thereof has a superior inhibitory activity on production of cytokines in T-cell and is useful as an agent for the prophylaxis or treatment of various diseases, especially rheumatoid arthritis, an autoimmune disease, inflammation and/or allergy disease.

The invention claimed is:

1. An amide derivative of formula (I):

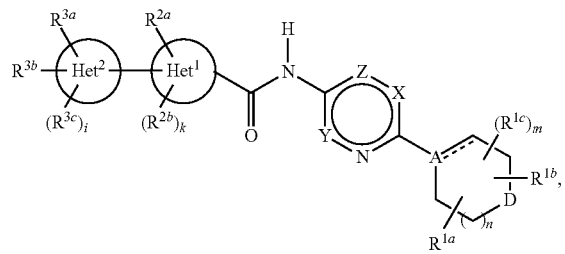

wherein:
$R^{1a}$, $R^{1b}$ and $R^{1c}$ each independently represent hydrogen atom, halogen atom, cyano group, hydroxy group, amino group, alkylamino group, optionally substituted alkyl group, or optionally substituted alkoxy group;
n represents an integer of 0 to 3;
m represents an integer of 0 to 3;
$Het^1$ represents thiazolyl group, isothiazolyl group, isoxazolyl group, thiadiazolyl group, oxadiazolyl group, furyl group, thienyl group, pyrrolyl group, pyrazolyl group, imidazolyl group, triazolyl group, pyridyl group, pyridazinyl group, pyrimidinyl group, pyrazinyl group, triazinyl group, cycloalkyl group, indolyl group, indazolyl group, benzimidazolyl group, benzisoxazolyl group, benzisothiazolyl group, benzoxazolyl group, benzothiazolyl group, quinolyl group, quinazolyl group, isoquinolyl group, quinoxalyl group, cinnolyl group, pyrrolopyrimidinyl group, pyrrolopyridyl group, imidazopyridyl group, or imidazopyrimidyl group;
$Het^2$ represents cycloalkyl group, aryl group, heterocycle group, or heteroaryl group;

$R^{2a}$, $R^{2b}$, $R^{3a}$, $R^{3b}$ and $R^{3c}$ each independently represent hydrogen atom, halogen atom, cyano group, hydroxy group, optionally substituted alkyl group, optionally substituted alkenyl group, optionally substituted alkynyl group, optionally substituted cycloalkyl group, optionally substituted heterocycle group, optionally substituted aryl group, optionally substituted heteroaryl group, —O—$R^{4a}$, —$NR^{4a}R^{4b}$, CO—$R^{4a}$, —CO—O—$R^{4a}$, —NHCO—$R^{4a}$, —SO—$R^{4a}$, —S—$R^{4a}$, —$SO_2$—$R^{4a}$, —$CONR^{4a}R^{4b}$, —NH—CO—$NR^{4a}R^{4b}$, —NH—CO—O—$R^{4b}$, or —O—CO—$NR^{4a}R^{4b}$;

$R^{4a}$ and $R^{4b}$ each independently represent hydrogen atom, alkyl group, alkoxyalkyl group, hydroxyalkyl group, haloalkyl group, aminoalkyl group, optionally substituted cycloalkyl group, optionally substituted aryl group, optionally substituted heterocycle group, or optionally substituted heteroaryl, or $R^{4a}$ and $R^{4b}$ are combined together to form an optionally substituted heterocycle group;

i represents an integer of 0 to 3;
k represents an integer of 0 to 2;
X represents N or C—$R^5$;
$R^5$ represents hydrogen atom, halogen atom, hydroxy group, cyano group, optionally substituted alkyl group, optionally substituted alkenyl group, optionally substituted alkynyl group, optionally substituted cycloalkyl group, optionally substituted aryl group, optionally substituted heterocycle group, optionally substituted heteroaryl group, —O—$R^{6a}$, —$NR^{6a}R^{6b}$, —CO—$R^{6a}$, —CO—O—$R^{6a}$, —$N(R^{6c})$—CO—$R^{6a}$, —$SO_2$—$R^{6a}$, —S—$R^{6a}$, —SO—$R^{6a}$, —CO—$NR^{6a}R^{6b}$, —$N(R^{6c})$—CO—$NR^{6a}R^{6b}$, or —$N(R^{6c})$—CO—O—$R^{6a}$;

$R^{6a}$, $R^{6b}$ and $R^{6c}$ each independently represent hydrogen atom, alkyl group, haloalkyl group, aminoalkyl group, hydroxyalkyl group, alkenyl group, alkynyl group, optionally substituted cycloalkyl group, optionally substituted heterocycle group, optionally substituted cycloalkylalkyl group, or optionally substituted heterocyclic alkyl group, or $R^{6a}$ and $R^{6b}$ are combined together to form an optionally substituted heterocycle group;

Y and Z each independently represent N or C—$R^7$;
$R^7$ represents hydrogen atom, halogen atom, cyano group, optionally substituted alkyl group, or optionally substituted alkoxy group;
═══ represents a single bond or a double bond;
A represents carbon atom or C—$R^8$;
$R^8$ represents hydrogen atom, halogen atom, hydroxy group, cyano group, optionally substituted alkyl group, optionally substituted alkenyl group, optionally substituted alkynyl group, optionally substituted cycloalkyl group, optionally substituted aryl group, optionally substituted heterocycle group, optionally substituted heteroaryl group, —O—$R^{9a}$, —$NR^{9a}R^{9b}$, —CO—$R^{9a}$, —CO—O—$R^{9a}$, —$NR^{9c}$—CO—$R^{9a}$, —$SO_2$—$R^{9a}$, —S—$R^{9a}$, —SO—$R^{9a}$, —CO—$NR^{9a}R^{9b}$, —$NR^{9c}$—CO—$NR^{9a}R^{9b}$, or —$NR^{9c}$—CO—O—$R^{9a}$;

$R^{9a}$, $R^{9b}$ and $R^{9c}$ each independently represent hydrogen atom, alkyl group, haloalkyl group, aminoalkyl group, hydroxyalkyl group, alkenyl group, alkynyl group, optionally substituted cycloalkyl group, optionally substituted heterocycle group, optionally substituted cycloalkylalkyl group or optionally substituted heterocyclic alkyl group, or $R^{9a}$ and $R^{9b}$ are combined together to form an optionally substituted heterocycle group;

D represents one of the following:

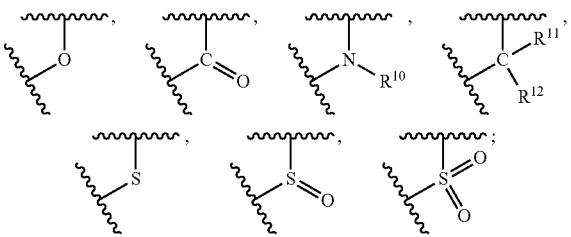

$R^{10}$ represents hydrogen atom, alkyl group, haloalkyl group, alkoxyalkyl group, hydroxyalkyl group, carboxyalkyl group, aminoalkyl group, -$L^{1a}$-$R^{13}$, -$L^{1b}$-O—$R^{14}$, -$L^{1b}$-O—CO—$R^{14}$, -$L^{1b}$-O—Si($R^{15}R^{16}$)—$R^{14}$, -$L^{1a}$-$SO_2$—$R^{14}$, -$L^{1a}$-$SO_2$—$NR^{14}R^{15}$, -$L^{1a}$-SO—$R^{14}$, -$L^{1b}$-S—$R^{14}$, -$L^{1b}$-$NR^{14}R^{15}$, -$L^{1b}$-$N(R^{16})$—CO—$R^{14}$, -$L^{1a}$-CO—$R^{14}$, -$L^{1a}$-CO—O—$R^{14}$, -$L^{1a}$-CO—$NR^{14}R^{15}$, -$L^{1b}$-$N(R^{16})$—CO—O—$R^{14}$, -$L^{1b}$-O—CO—$NR^{14}R^{15}$, or -$L^{1b}$-$N(R^{16})$—CO—$NR^{14}R^{15}$;

$R^{13}$ represents optionally substituted cycloalkyl group, optionally substituted aryl group, optionally substituted heterocycle group, or optionally substituted heteroaryl group;

$L^{1a}$ represents a bond, or —$(CR_AR_B)_j$—;
j represents an integer of 1-4;
$R_A$ and $R_B$ each independently represent hydrogen atom or alkyl group;
$L^{1b}$ represents —$(CR_AR_B)_j$—, wherein j, $R_A$ and $R_B$ are defined as above;
$R^{14}$, $R^{15}$ and $R^{16}$ each independently represent hydrogen atom, alkyl group, alkoxyalkyl group, hydroxyalkyl group, haloalkyl group, aminoalkyl group, optionally substituted cycloalkyl group, optionally substituted aryl group, optionally substituted heterocycle group, hydroxyalkyloxyalkyl group, haloalkyloxyalkyl group, carboxylalkyl group, alkyloxycarbonylalkyl group, alkylcarbonylalkyl group, alkylaminoalkyl group, amidealkyl group, alkylamidealkyl group, alkylcarbonylaminoalkyl group, alkylsulfonylalkyl group, alkylsulfoxyalkyl group, alkylsulfidealkyl group, optionally substituted cycloalkyloxyalkyl group, optionally substituted heterocyclic oxyalkyl group, optionally substituted cycloalkylalkoxyalkyl group, or optionally substituted heterocyclic alkoxyalkyl group, or $R^{14}$ and $R^{15}$ are combined together to form an optionally substituted heterocycle group; and $R^{11}$ and $R^{12}$ each independently represent hydrogen atom, halogen atom, hydroxy group, alkyl group, haloalkyl group, alkoxyalkyl group, hydroxyalkyl group, carboxylalkyl group, aminoalkyl group, alkenyl group, -$L^{1a}$-$R^{13}$, -$L^{1a}$-O—$R^{14}$, -$L^{1a}$-O—CO—$R^{14}$, -$L^{1a}$-O—Si($R^{15}R^{16}$)—$R^{14}$, $L^{1a}$-O—CO—$NR^{14}R^{15}$, -$L^{1a}$-CO—$R^{14}$, -$L^{1a}$-CO—O—$R^{14}$, -$L^{1a}$-CO—$NR^{14}R^{15}$, -$L^{1a}$-$SO_2$—$R^{14}$, -$L^{1a}SO_2$—$NR^{14}R^{15}$, -$L^{1a}$-SO—$R^{14}$, -$L^{1a}$-S—$R^{14}$, -$L^{1a}$-$NR^{14}R^{15}$, -$L^{1a}$-$N(R^{16})$—CO—$R^{14}$, -$L^{1a}$-$N(R^{16})$—CO—O—$R^{14}$, or -$L^{1a}$-$N(R^{16})$—CO—$NR^{14}R^{15}$, or $R^{11}$ and $R^{12}$ are combined together to form an optionally substituted cycloalkyl group, or optionally substituted heterocycle group, or a pharmacologically acceptable salt thereof, wherein $L^{1a}$, $L^{1b}$, $R^{14}$, $R^{13}$, $R^{15}$ and $R^{16}$ are defined as above.

2. The amide derivative of claim 1, wherein $Het^1$ represents thiazolyl group, furyl group, thienyl group, pyrrolyl group, pyrazolyl group, imidazolyl group, triazolyl group, pyridyl group, or indolyl group, or a pharmacologically acceptable salt thereof.

3. The amide derivative of claim 2, wherein Y and Z represents C—R⁷, or a pharmacologically acceptable salt thereof.

4. The amide derivative of claim 3, wherein X represents C—R⁵, or a pharmacologically acceptable salt thereof.

5. The amide derivative of claim 4, wherein Het² represents aryl group or heteroaryl group, or a pharmacologically acceptable salt thereof.

6. The amide derivative of claim 5, wherein:
    ---- represents a single bond; and
    A represents C—R⁸,
or a pharmacologically acceptable salt thereof.

7. The amide derivative of claim 5, wherein
    ---- represents a double bond; and
    A represents carbon atom,
or a pharmacologically acceptable salt thereof.

8. A compound selected from the group consisting of:
N-{6-[1-cyano-4-(morpholin-4-yl)cyclohexyl]pyridin-3-yl}-5-methyl-1-[5-(trifluoromethyl)pyridin-2-yl]-1H-pyrazole-4-carboxamide;
N-{6-[1-cyano-4-(morpholin-4-yl)cyclohexyl]pyridin-3-yl}-5-methyl-1-(4-methylphenyl)-1H-pyrazole-4-carboxamide;
N-{6-[1-cyano-4-(methoxymethoxy)cyclohexyl]pyridin-3-yl}-5-methyl-1-(4-methylphenyl)-1H-pyrazole-4-carboxamide;
5-methyl-N-{6-[4-(morpholin-4-yl)cyclohexyl]pyridin-3-yl}-1-[5-(trifluoromethyl)pyridin-2-yl]-1H-pyrazole-4-carboxamide;
N-{6-[1-cyano-4-(morpholin-4-yl)cyclohexyl]pyridin-3-yl}-1-(3,5-dichloropyridin-2-yl)-5-methyl-1H-pyrazole-4-carboxamide;
N-{6-[4-cyano-1-(2-methyltetrahydrofuran-3-yl)piperidin-4-yl]pyridin-3-yl}-5-methyl-1-[5-(trifluoromethyl)pyridin-2-yl]-1H-pyrazole-4-carboxamide;
N-{6-[4-cyano-1-(2-methyltetrahydrofuran-3-yl)piperidin-4-yl]pyridin-3-yl}-1-(5-cyclopropylpyridin-2-yl)-5-methyl-1H-pyrazole-4-carboxamide;
N-{6-[4-cyano-1-(2-methyltetrahydrofuran-3-yl)piperidin-4-yl]pyridin-3-yl}-5-methyl-1-[4-(trifluoromethyl)phenyl]-1H-pyrazole-4-carboxamide;
N-{6-[1-cyano-4-(3-hydroxypyrrolidin-1-yl)cyclohexyl]pyridin-3-yl}-5-methyl-1-[5-(trifluoromethyl)pyridin-2-yl]-1H-pyrazole-4-carboxamide;
N-{6-[1-cyano-4-(morpholin-4-yl)cyclohexyl]pyridin-3-yl}-1-[3-fluoro-5-(trifluoromethyl)pyridin-2-yl]-5-methyl-1H-pyrazole-4-carboxamide;
N-{6-[1-cyano-4-methoxycyclohexyl]pyridin-3-yl}-5-methyl-1-(4-methylphenyl)-1H-pyrazole-4-carboxamide;
5-methyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide;
N-{6-[1-cyano-4-(morpholin-4-yl)cyclohexyl]pyridin-3-yl}-1-(5-isopropylpyridin-2-yl)-5-methyl-1H-pyrazole-4-carboxamide;
N-{6-[1-hydroxy-4-(morpholin-4-yl)cyclohexyl]pyridin-3-yl}-5-methyl-1-[5-(trifluoromethyl)pyridin-2-yl]-1H-pyrazole-4-carboxamide;
1-(4-chlorophenyl)-N-[6-(1-cyano-4-hydroxycyclohexyl)pyridin-3-yl]-5-methyl-1H-pyrazole-4-carboxamide;
N-[6-(1-cyano-4-hydroxycyclohexyl)pyridin-3-yl]-1-(4-fluorophenyl)-5-methyl-1H-pyrazole-4-carboxamide;
N-[6-(1-cyano-4-hydroxycyclohexyl)pyridin-3-yl]-5-methyl-1-(4-methylphenyl)-1H-pyrazole-4-carboxamide;
1-(4-tert-butylphenyl)-N-[6-(4-hydroxycyclohexyl)pyridin-3-yl]-5-methyl-1H-pyrazole-4-carboxamide;
N-[6-(4-hydroxycyclohexyl)-5-methylpyridin-3-yl]-5-methyl-1-[5-(trifluoromethyl)pyridin-2-yl]-1H-pyrazole-4-carboxamide;
N-{6-[1-cyano-4-(2-hydroxyethoxy)cyclohexyl]pyridin-3-yl}-5-methyl-1-(4-methylphenyl)-1H-pyrazole-4-carboxamide;
N-[6-(8-cyano-1-oxaspiro[4.5]dec-8-yl)pyridin-3-yl]-5-methyl-1-[5-(trifluoromethyl)pyridin-2-yl]-1H-pyrazole-4-carboxamide;
N-(6-{1-cyano-4-[N-(2,2-dimethylpropanoyl)-N-methylamino]cyclohexan-1-yl}pyridin-3-yl)-5-methyl-1-[5-(trifluoromethyl)pyridin-2-yl]-1H-pyrazole-4-carboxamide;
N-{6-[1-cyano-4-(N-isobutyryl-N-methylamino)cyclohexan-1-yl]pyridin-3-yl}-5-methyl-1-[5-(trifluoromethyl)pyridin-2-yl]-1H-pyrazole-4-carboxamide;
N-{6-[1-cyano-4-(3-hydroxypyrrolidin-1-yl)cyclohex-1-yl]pyridin-3-yl}-5-methyl-1-[4-(trifluoromethyl)phenyl]-1H-pyrazole-4-carboxamide;
N-{6-[1-cyano-4-(morpholin-4-yl)cyclohexyl]pyridin-3-yl}-5-isopropyl-1-[5-(trifluoromethyl)pyridin-2-yl]-1H-pyrazole-4-carboxamide;
N-[6-(1-cyano-4-ethoxycyclohex-1-yl)pyridin-3-yl]-5-methyl-1-[5-(trifluoromethyl)pyridin-2-yl]-1H-pyrazole-4-carboxamide;
1-[3-fluoro-5-(trifluoromethyl)pyridin-2-yl]-N-[6-(1-hydroxycyclohexan-4-yl)-5-methylpyridin-3-yl]-5-methyl-1H-pyrazole-4-carboxamide;
1-[3-chloro-5-(trifluoromethyl)pyridin-2-yl]-N-[6-(1-hydroxycyclohexan-4-yl)-5-methylpyridin-3-yl]-5-methyl-1H-pyrazole-4-carboxamide;
N-[6-(1-fluoro-4-hydroxycyclohexan-1-yl)pyridin-3-yl]-5-methyl-1-[5-(trifluoromethyl)pyridin-2-yl]-1H-pyrazole-4-carboxamide;
N-[6-(4-hydroxycyclohexan-1-yl)pyridin-3-yl]-5-methyl-1-[5-(trifluoromethyl)pyridin-2-yl]-1H-pyrazole-4-carboxamide; and
N-[6-(1-cyano-4-ethyl-4-hydroxycyclohexan-1-yl)pyridin-3-yl]-1-(4-fluorophenyl)-5-methyl-1H-pyrazole-4-carboxamide, or a pharmacologically acceptable salt thereof.

9. A compound selected from the group consisting of:
N-{6-[r-1-cyano-c-4-(morpholin-4-yl)cyclohexyl]pyridin-3-yl}-5-methyl-1-[5-(trifluoromethyl)pyridin-2-yl]-1H-pyrazole-4-carboxamide;
N-{6-[r-1-cyano-c-4-(morpholin-4-yl)cyclohexyl]pyridin-3-yl}-5-methyl-1-(4-methylphenyl)-1H-pyrazole-4-carboxamide;
N-{6-[r-1-cyano-c-4-(methoxymethoxy)cyclohexyl]pyridin-3-yl}-5-methyl-1-(4-methylphenyl)-1H-pyrazole-4-carboxamide;
1-(5-cyclopropylpyridin-2-yl)-5-methyl-N-{6-[4-(morpholin-4-yl)cyclohex-1-en-1-yl]pyridin-3-yl}-1H-pyrazole-4-carboxamide;
trans-5-methyl-N-{6-[4-(morpholin-4-yl)cyclohexyl]pyridin-3-yl}-1-[5-(trifluoromethyl)pyridin-2-yl]-1H-pyrazole-4-carboxamide;
N-{6-[r-1-cyano-c-4-(morpholin-4-yl)cyclohexyl]pyridin-3-yl}-1-(3,5-dichloropyridin-2-yl)-5-methyl-1H-pyrazole-4-carboxamide;
cis-N-{ 6-[4-cyano-1-(2-methyltetrahydrofuran-3-yl)piperidin-4-yl]pyridin-3-yl}-5-methyl-1-[5-(trifluoromethyl)pyridin-2-yl]-1H-pyrazole-4-carboxamide;

N-{6-[4-cyano-1-(2-hydroxy-2-methylpropyl)piperidin-4-yl]pyridin-3-yl}-5-methyl-1-[5-(trifluoromethyl)pyridin-2-yl]-1H-pyrazole-4-carboxamide;
cis-N-{6-[4-cyano-1-(2-methyltetrahydrofuran-3-yl)piperidin-4-yl]pyridin-3-yl}-1-(5-cyclopropylpyridin-2-yl)-5-methyl-1H-pyrazole-4-carboxamide;
cis-N-{6-[4-cyano-1-(2-methyltetrahydrofuran-3-yl)piperidin-4-yl]pyridin-3-yl}-5-methyl-1-[4-(trifluoromethyl)phenyl]-1H-pyrazole-4-carboxamide;
N-{6-[4-cyano-1-(2-hydroxy-2-methylpropyl)piperidin-4-yl]pyridin-3-yl}-1-(5-cyclopropylpyridin-2-yl)-5-methyl-1H-pyrazole-4-carboxamide;
N-{6-[r-1-cyano-c-4-(3-hydroxypyrrolidin-1-yl)cyclohexyl]pyridin-3-yl}-5-methyl-1-[5-(trifluoromethyl)pyridin-2-yl]-1H-pyrazole-4-carboxamide;
N-{6-[r-1-cyano-c-4-(morpholin-4-yl)cyclohexyl]pyridin-3-yl}-1-[3-fluoro-5-(trifluoromethyl)pyridin-2-yl]-5-methyl-1H-pyrazole-4-carboxamide;
N-{6-[r-1-cyano-c-4-methoxycyclohexyl]pyridin-3-yl}-5-methyl-1-(4-methylphenyl)-1H-pyrazole-4-carboxamide;
1-[5-chloro-3-fluoropyridin-2-yl]-5-methyl-N-{5-methyl-6-[4-(morpholin-4-yl)cyclohex-1-en-1-yl]pyridin-3-yl}-1H-pyrazole-4-carboxamide;
5-methyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide;
(R)-5-methyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide;
(S)-5-methyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide;
N-[6-(4-hydroxycyclohex-1-en-1-yl)-5-methyl-pyridin-3-yl]-5-methyl-1-[5-(trifluoromethyl)pyridin-2-yl]-1H-pyrazole-4-carboxamide;
1-[3-fluoro-5-(trifluoromethyl)pyridin-2-yl]-5-methyl-N-{5-methyl-6-[4-(morpholin-4-yl)cyclohex-1-en-1-yl]pyridin-3-yl}-1H-pyrazole-4-carboxamide;
1-[3-fluoro-5-(trifluoromethyl)pyridin-2-yl]-5-methyl-N-[5-methyl-6-(4-hydroxycyclohex-1-en-1-yl)pyridin-3-yl]-1H-pyrazole-4-carboxamide;
N-{6-[r-1-cyano-c-4-(morpholin-4-yl)cyclohexyl]pyridin-3-yl}-1-(5-isopropylpyridin-2-yl)-5-methyl-1H-pyrazole-4-carboxamide;
5-methyl-N-{6-[4-(morpholin-4-yl)cyclohex-1-en-1-yl]pyridin-3-yl}-1-[5-(trifluoromethyl)pyridin-2-yl]-1H-pyrazole-4-carboxamide;
N-{6-[r-1-hydroxy-e-4-(morpholin-4-yl)cyclohexyl]pyridin-3-yl}-5-methyl-1-[5-(trifluoromethyl)pyridin-2-yl]-1H-pyrazole-4-carboxamide;
N-[6-(1-cyano-4-oxocyclohexyl)pyridin-3-yl]-5-methyl-1-[5-(trifluoromethyl)pyridin-2-yl]-1H-pyrazole-4-carboxamide;
1-(4-chlorophenyl)-N-[6-(r-1-cyano-c-4-hydroxycyclohexyl)pyridin-3-yl]-5-methyl-1H-pyrazole-4-carboxamide;
N-[6-(r-1-cyano-c-4-hydroxycyclohexyl)pyridin-3-yl]-1-(4-fluorophenyl)-5-methyl-1H-pyrazole-4-carboxamide;
N-[6-(r-1-cyano-c-4-hydroxycyclohexyl)pyridin-3-yl]-5-methyl-1-(4-methylphenyl)-1H-pyrazole-4-carboxamide;
trans-1-(4-tert-butylphenyl)-N-[6-(4-hydroxycyclohexyl)pyridin-3-yl]-5-methyl-1H-pyrazole-4-carboxamide;
N-[6-(4-hydroxycyclohex-1-en-1-yl)-5-methylpyridin-3-yl]-5-methyl-1-[4-(trifluoromethyl)phenyl]-1H-pyrazole-4-carboxamide;
trans-N-[6-(4-hydroxycyclohexyl)-5-methylpyridin-3-yl]-5-methyl-1-[5-(trifluoromethyl)pyridin-2-yl]-1H-pyrazole-4-carboxamide;
N-{6-[r-1-cyano-c-4-(2-hydroxyethoxyl)cyclohexyl]pyridin-3-yl}-5-methyl-1-(4-methylphenyl)-1H-pyrazole-4-carboxamide;
N-[6-(3,6-dihydro-2H-pyran-4-yl)-5-methylpyridin-3-yl]-5-methyl-1-[4-(trifluoromethyl)phenyl]-1H-pyrazole-4-carboxamide;
N-{6-[4-(N-isobutyryl-N-methylamino)cyclohex-1-en-1-yl]-5-methylpyridin-3-yl}-5-methyl-1-[5-(trifluoromethyl)pyridin-2-yl]-1H-pyrazole-4-carboxamide;
N-(6-{4-[N-(2,2-dimethylpropion-1-yl)-N-methylamino]cyclohex-1-en-1-yl}-5-methylpyridin-3-yl)-5-methyl-1-(pyridin-2-yl)-1H-pyrazole-4-carboxamide;
1-(4-fluorophenyl)-N-{6-[4-(N-isobutyryl-N-methylamino)cyclohex-1-en-1-yl]-5-methylpyridin-3-yl}-5-methyl-1H-pyrazole-4-carboxamide;
N-[6-(4-N,N-dimethylcarbamoylcyclohex-1-en-1-yl)-5-methylpyridin-3-yl]-5-methyl-1-[5-(trifluoromethyl)pyridin-2-yl]-1H-pyrazole-4-carboxamide;
1-(5-cyclopropylpyridin-2-yl)-N-[6-(4-N,N-dimethylcarbamoylcyclohex-1-en-1-yl)-5-methylpyridin-3-yl]-5-methyl-1H-pyrazole-4-carboxamide;
3-methyl-N-{5-methyl-6-[4-(morpholin-4-yl)cyclohex-1-en-1-yl]pyridin-3-yl}-2-[4-(trifluoromethyl)phenyl]-3H-imidazole-4-carboxamide;
N-{5-methyl-6-[4-(morpholin-4-yl)cyclohex-1-en-1-yl]pyridin-3-yl}-2-[4-(trifluoromethyl)phenyl]thiazole-4-carboxamide;
5-methyl-N-(5-methyl-6-{4-[N-methyl-N-(2,2,2-trifluoroacetyl)amino]cyclohex-1-en-1-yl}pyridin-3-yl)-1-[5-(trifluoromethyl)pyridin-2-yl]-1H-pyrazole-4-carboxamide;
N-[6-(c-8-cyano-r-1-oxaspiro[4.5]dec-8-yl)pyridin-3-yl]-5-methyl-1-[5-(trifluoromethyl)pyridin-2-yl]-1H-pyrazole-4-carboxamide;
N-(6-{r-1-cyano-c-4-[N-(2,2-dimethylpropanoyl)-N-methylamino]cyclohexan-1-yl}pyridin-3-yl)-5-methyl-1-[5-(trifluoromethyl)pyridin-2-yl]-1H-pyrazole-4-carboxamide;
N-{6-[r-1-cyano-c-4-(N-isobutyryl-N-methylamino)cyclohexan-1-yl]pyridin-3-yl}-5-methyl-1-[5-(trifluoromethyl)pyridin-2-yl]-1H-pyrazole-4-carboxamide;
5-methyl-N-{5-methyl-6-[4-(morpholin-4-yl)cyclohex-1-en-1-yl]pyridin-3-yl}-1-[4-methyl-5-(trifluoromethyl)pyridin-2-yl]-1H-pyrazole-4-carboxamide;
N-{6-[r-1-cyano-c-4-(3-hydroxypyrrolidin-1-yl)cyclohex-1-yl]pyridin-3-yl}-5-methyl-1-[4-(trifluoromethyl)phenyl]-1H-pyrazole-4-carboxamide;
N-{6-[r-1-cyano-c-4-(morpholin-4-yl)cyclohexyl]pyridin-3-yl}-5-isopropyl-1-[5-(trifluoromethyl)pyridin-2-yl]-1H-pyrazole-4-carboxamide;
5-isopropyl-N-{5-methyl-6-[4-(morpholin-4-yl)cyclohex-1-en-1-yl]pyridin-3-yl}-1-[5-(trifluoromethyl)pyridin-2-yl]-1H-pyrazole-4-carboxamide;
5-methyl-N-{5-methyl-6-[4-(3-oxomorpholin-4-yl)cyclohex-1-en-1-yl]pyridin-3-yl}-1-[5-(trifluoromethyl)pyridin-2-yl]-1H-pyrazole-4-carboxamide;
N-[6-(r-1-cyano-c-4-ethoxycyclohex-1-yl)pyridin-3-yl]-5-methyl-1-[5-(trifluoromethyl)pyridin-2-yl]-1H-pyrazole-4-carboxamide;

1-[3-fluoro-5-(trifluoromethyl)pyridin-2-yl]-5-methyl-N-[5-methyl-6-(4-oxocyclohex-1-yl)pyridin-3-yl]-1H-pyrazole-4-carboxamide;

1-[3-chloro-5-(trifluoromethyl)pyri din-2-yl]-5-methyl-N-[5-methyl-6-(4-oxocyclohex-1-yl)pyridin-3-yl]-1H-pyrazole-4-carboxamide;

N-[6-(1-fluoro-4-oxocyclohexan-1-yl)pyridin-3-yl]-5-methyl-1-[5-(trifluoromethyl)pyridin-2-yl]-1H-pyrazole-4-carboxamide;

trans-1-[3-fluoro-5-(trifluoromethyl)pyridin-2-yl]-N-[6-(1-hydroxycyclohexan-4-yl)-5-methylpyridin-3-yl]-5-methyl-1H-pyrazole-4-carboxamide;

trans-1-[3-chloro-5-(trifluoromethyl)pyridin-2-yl]-N-[6-(1-hydroxycyclohexan-4-yl)-5-methylpyridin-3-yl]-5-methyl-1H-pyrazole-4-carboxamide;

N-[6-(c-1-fluoro-r-4-hydroxycyclohexan-1-yl)pyridin-3-yl]-5-methyl-1-[5-(trifluoromethyl)pyridin-2-yl]-1H-pyrazole-4-carboxamide;

trans-N-[6-(4-hydroxycyclohexan-1-yl)pyridin-3-yl]-5-methyl-1-[5-(trifluoromethyl)pyridin-2-yl]-1H-pyrazole-4-carboxamide;

N-(6-{4-[N-(2,2-dimethylpropion-1-yl)-N-methylamino]cyclohex-1-en-1-yl}-5-methylpyridin-3-yl)-5-methyl-1-[5-(trifluoromethyl)pyridin-2-yl]-1H-pyrazole-4-carboxamide;

N-{6-[4-(1-hydroxy-1-methylethyl)cyclohex-1-en-1-yl]-5-methylpyridin-3-yl}-5-methyl-1-[5-(trifluoromethyl)pyridin-2-yl]-1H-pyrazole-4-carboxamide;

N-[6-(r-1-cyano-4-ethyl-c-4-hydroxycyclohexan-1-yl)pyridin-3-yl]-1-(4-fluorophenyl)-5-methyl-1H-pyrazole-4-carboxamide;

5-methyl-N-{5-[4-(morpholin-4-yl)cyclohex-1-en-1-yl]pyrazin-2-yl}-1-[5-(trifluoromethyl)pyridin-2-yl]-1H-pyrazole-4-carboxamide;

N-{5-cyano-6-[4-(morpholin-4-yl)cyclohex-1-en-1-yl]pyridin-3-yl}-5-methyl-1-[5-(trifluoromethyl)pyridin-2-yl]-1H-pyrazole-4-carboxamide;

N-{6-[1-(2,2-dimethylpropanoyl)-1,2,3,6-tetrahydropyridin-4-yl]-5-methylpyridin-3-yl}-5-methyl-1-[5-(trifluoromethyl)pyridin-2-yl]-1H-pyrazole-4-carboxamide;

5-methyl-N-{5-methyl-6-[1-(propane-2-sulfonyl)-1,2,3,6-tetrahydropyridin-4-yl]pyridin-3-yl}-1-[5-(trifluoromethyl)pyridin-2-yl]-1H-pyrazole-4-carboxamide;

5-methyl-N-[5-methyl-6-(1,2,3,6-tetrahydro-1-trifluoroacetylpyridin-4-yl)pyridin-3-yl]-1-[5-(trifluoromethyl)pyridin-2-yl]-1H-pyrazole-4-carboxamide;

N-{6-[4-cyano-1-(propane-2-sulfonyl)piperidin-4-yl]pyridin-3-yl}-5-methyl-1-[5-(trifluoromethyl)pyridin-2-yl]-1H-pyrazole-4-carboxamide;

5-methyl-N-{5-methyl-1-(pyrrolidin-1-ylcarbonyl)-6-[1,2,3,6-tetrahydropyridin-4-yl]pyridin-3-yl}-1-[5-(trifluoromethyl)pyridin-2-yl]-1H-pyrazole-4-carboxamide;

5-methyl-N-{5-methyl-6-[1-(propane-2-sulfonyl)piperidin-4-yl]pyridin-3-yl}-1-[5-(trifluoromethyl)pyridin-2-yl]-1H-pyrazole-4-carboxamide;

N-{6-[4-cyano-1-(cyclopropanesulfonyl)piperidin-4-yl]pyridin-3-yl}-5-methyl-1-[5-(trifluoromethyl)pyridin-2-yl]-1H-pyrazole-4-carboxamide;

N-{6-[4-cyano-1-(dimethylsulfamoyl)piperidin-4-yl]pyridin-3-yl}-5-methyl-1-[5-(trifluoromethyl)pyridin-2-yl]-1H-pyrazole-4-carboxamide;

5-methyl-N-{5-methyl-6-[1-(trifluoroacetyl)piperidin-4-yl]pyridin-3-yl}-1-[5-(trifluoromethyl)pyridin-2-yl]-1H-pyrazole-4-carboxamide;

N-[6-(4-cyano-1-trifluoromethanesulfonylpiperidin-4-yl)pyridin-3-yl]-5-methyl-1-[5-(trifluoromethyl)pyridin-2-yl]-1H-pyrazole-4-carboxamide;

N-(5-{4-[N-(2,2-dimethylpropion-1-yl)-N-methylamino]cyclohex-1-en-1-yl}pyrazin-2-yl)-5-methyl-1-[5-(trifluoromethyl)pyridin-2-yl]-1H-pyrazole-4-carboxamide;

N-(6-{4-[N-(2,2-dimethylpropion-1-yl)-N-methylamino]cyclohex-1-en-1-yl}-5-methoxypyridin-3-yl)-5-methyl-1-[5-(trifluoromethyl)pyridin-2-yl]-1H-pyrazole-4-carboxamide;

N-{5-methoxy-6-[4-(morpholin-4-yl)cyclohex-1-en-1-yl]pyridin-3-yl}-5-methyl-1-[5-(trifluoromethyl)pyridin-2-yl]-1H-pyrazole-4-carboxamide;

N-(6-{4-[N-(2,2-dimethylpropion-1-yl)-N-methylamino]cyclohex-1-en-1-yl}-5-(trifluoromethyl)pyridin-3-yl)-5-methyl-1-[5-(trifluoromethyl)pyridin-2-yl]-1H-pyrazole-4-carboxamide;

N-{6-[1-(dimethylsulfamoyl)piperidin-4-yl]-5-methylpyridin-3-yl}-5-methyl-1-[5-(trifluoromethyl)pyridin-2-yl]-1H-pyrazole-4-carboxamide;

5-methyl-N-{6-[1-(propane-2-sulfonyl)piperidin-4-yl]pyridin-3-yl}-1-[5-(trifluoromethyl)pyridin-2-yl]-1H-pyrazole-4-carboxamide; and 5-methyl-N-{6-[1-(trifluoromethanesulfonyl)piperidin-4-yl]pyridin-3-yl}-1-[5-(trifluoromethyl)pyridin-2-yl]-1H-pyrazole-4-carboxamide, or a pharmacologically acceptable salt thereof.

10. A method for inhibiting IL-17 production, comprising: administering an effective amount of the amide derivative of claim 1 or a pharmacologically acceptable salt thereof to a patient in need thereof.

11. A method for treating multiple sclerosis, systemic lupus erythematosus, psoriasis, inflammatory bowel disease, or asthma, comprising:
administering an effective amount of the amide derivative of claim 1 or a pharmacologically acceptable salt thereof to a patient in need thereof.

12. A method for treating rheumatoid arthritis, comprising:
administering an effective amount of the amide derivative of claim 1 or a pharmacologically acceptable salt thereof to a patient in need thereof.

\* \* \* \* \*